(12) United States Patent
Yasuma et al.

(10) Patent No.: US 7,786,165 B2
(45) Date of Patent: Aug. 31, 2010

(54) AMINOPHENYLPROPANOIC ACID DERIVATIVE

(75) Inventors: Tsuneo Yasuma, Osaka (JP); Nobuyuki Negoro, Osaka (JP); Shinobu Sasaki, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 380 days.

(21) Appl. No.: 10/592,789

(22) PCT Filed: Mar. 14, 2005

(86) PCT No.: PCT/JP2005/004872

§ 371 (c)(1),
(2), (4) Date: Sep. 14, 2006

(87) PCT Pub. No.: WO2005/087710

PCT Pub. Date: Sep. 22, 2005

(65) Prior Publication Data

US 2008/0269220 A1 Oct. 30, 2008

(30) Foreign Application Priority Data

Mar. 15, 2004 (JP) ............................. 2004-073576
Aug. 26, 2004 (JP) ............................. 2004-247339

(51) Int. Cl.
*A61K 31/335* (2006.01)
(52) U.S. Cl. ...................................................... 514/450
(58) Field of Classification Search ...................... None
See application file for complete search history.

(56) References Cited

U.S. PATENT DOCUMENTS

| 6,710,089 B2 * | 3/2004 | Sikorski et al. ............. 514/654 |
| 2002/0002203 A1 | 1/2002 | Rahbar |
| 2006/0258722 A1 * | 11/2006 | Yasuma et al. ............... 514/367 |

FOREIGN PATENT DOCUMENTS

| JP | 6-239817 | | 8/1994 |
| WO | 89/05294 | | 6/1989 |
| WO | WO 96/03380 | * | 2/1996 |
| WO | 02/26732 | | 4/2002 |
| WO | 02/053547 | | 7/2002 |
| WO | 03/072100 | | 9/2003 |
| WO | 03/072102 | | 9/2003 |
| WO | 03/099793 | | 12/2003 |
| WO | 2004/026823 | | 4/2004 |
| WO | 2004/032848 | | 4/2004 |
| WO | 2004/041266 | | 5/2004 |
| WO | 2004/106276 | | 12/2004 |
| WO | WO 2004/106276 | * | 12/2004 |
| WO | 2005/058834 | | 6/2005 |
| WO | 2005/058844 | | 6/2005 |
| WO | 2005/063725 | | 7/2005 |
| WO | 2005/063729 | | 7/2005 |

OTHER PUBLICATIONS

Montori et al (BMJ 334:882-884, 2007).*
Williams et al (Foye's Principles of Medicinal Chemistry, pp. 59-62, 2002).*
Patani et al (Chem. Rev. 96:3147-3176, 1996).*
U. Maitra et al., "Design and Synthesis of New Bile Acid-Based Macrocycles", J. Chem. Soc. Perkin Trans., vol. 1, pp. 83-88, 1995.

* cited by examiner

*Primary Examiner*—Brandon J Fetterolf
*Assistant Examiner*—Craig Ricci
(74) *Attorney, Agent, or Firm*—Wenderoth, Lind & Ponack, LLP.

(57) ABSTRACT

A compound represented by the formula (1):

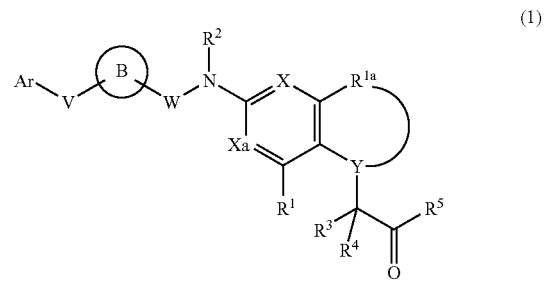

wherein each symbol is as defined in the specification, and a salt thereof and a prodrug thereof unexpectedly have superior GPR40 receptor agonist activity, superior in the properties as a pharmaceutical product such as stability and the like, and can be a safe and useful pharmaceutical agent as a drug for the prophylaxis or treatment of GPR40 receptor related pathology or diseases such as diabetes and the like.

8 Claims, No Drawings

AMINOPHENYLPROPANOIC ACID DERIVATIVE

This application is a U.S. national stage of International Application No. PCT/JP2005/004872 filed Mar. 14, 2005.

TECHNICAL FIELD

The present invention relates to a novel compound having a GPR40 receptor function modulating action, which is useful as an agent for the prophylaxis or treatment of diabetes.

BACKGROUND ART

It has been reported in recent years that a ligand of GPR40, which is one of the G Protein-Coupled Receptors (GPCR), is fatty acid and GPR40 in pancreatic β cell is deeply involved in insulin secretion action (Nature, 2003, vol. 422, pages 173-176). Thus, a GPR40 agonist promotes insulin secretion, a GPR40 antagonist inhibits insulin secretion, and the agonist and the antagonist are useful as an agent for the prophylaxis or treatment of type 2 diabetes, obesity, impaired glucose tolerance, insulin resistance, neurodegenerative diseases (Alzheimer's disease) and the like (WO02/057783).

There are many compounds reported to be useful as agents for the prophylaxis or treatment of diabetes.

For example, WO03/072102 discloses that a PPAR transcription modulator represented by the formula:

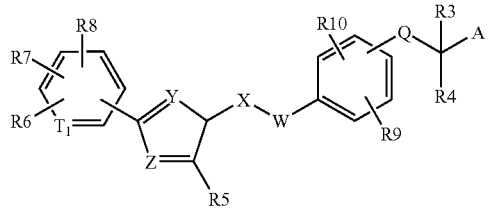

wherein

R3, R4: H and the like; R9, R10: H, $(C_1\text{-}C_4)$alkyl, halo, $(C_1\text{-}C_4)$alkoxy and the like; Q: $CH_2$; W: $(CH_2)_rN(R20)(CH_2)k$ (r, k: 0; R20: H, $C_1\text{-}C_3$ alkyl etc.) and the like; X: $C_mH_{2m}$ (m: 0, 1, 2) and the like; A: carboxyl, carboxamide and the like; Y, Z: N, S, O; R5: $(C_1\text{-}C_6)$alkyl and the like; R6: $(C_1\text{-}C_4)$alkyl and the like; R7, R8: $(C_1\text{-}C_6)$alkyl and the like; $T_1$: N, O, is useful as an agent for the prophylaxis or treatment of syndrome X, type 2 diabetes and the like.

WO02/026732 discloses that a PPAR transcription modulator represented by the formula:

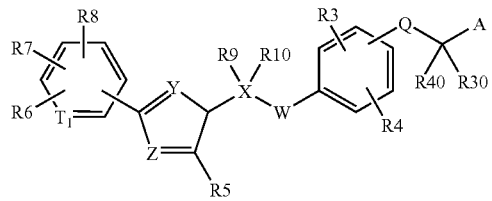

wherein

R3, R4: H and the like; R30, R40: H; R9: $C_1\text{-}C_3$ alkyl; R10: H, $C_1\text{-}C_5$ alkyl; Q: O, $CH_2$; W: N(R21) (R21: $C_1\text{-}C_2$ alkyl); X: C, $CH_2C$, $CCH_2$; A: carboxyl, carboxamide; Y, Z: N, S, O; R5: $(C_1\text{-}C_6)$alkyl and the like; R6: $(C_1\text{-}C_4)$alkyl and the like; R7, R8: $(C_1\text{-}C_4)$alkyl and the like; $T_1$: N, CH, is useful as an agent for the prophylaxis or treatment of syndrome X, type 2 diabetes and the like.

US2002/0002203 discloses that a compound represented by the formula:

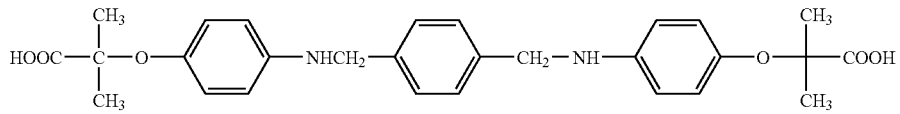

is useful for diabetes, arteriosclerosis, Alzheimer's disease, rheumatism-like arthritis.

However, it has not been disclosed at all that these known therapeutic drugs for diabetes have a GPR40 receptor function modulating action, and there is no report on a compound having a GPR40 receptor function modulating action (compound useful as a GPR40 agonist or GPR40 antagonist). Under the circumstances, development of a compound having a GPR40 receptor function modulating action has been desired.

DISCLOSURE OF THE INVENTION

The present invention aims at providing a novel compound having a GPR40 receptor function modulating action, which is useful as an insulin secretagogue or an agent for the prophylaxis or treatment of diabetes and the like.

The present inventors have intensively conducted various studies and found that the compounds represented by the following formulas (1) and (1') unexpectedly have a superior GPR40 receptor agonist activity, show superior properties as pharmaceutical products such as stability and the like, and can be safe and useful pharmaceutical agents for the prophylaxis or treatment of GPR40 receptor related disease state or diseases in mammals, and completed the present invention.

Accordingly, the present invention provides the following.

[1] a compound represented by the formula (I):

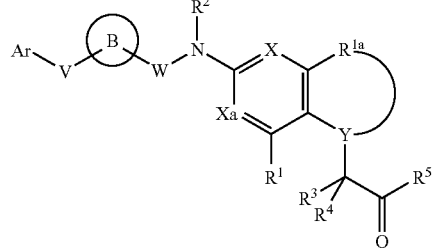

(1)

wherein

Ar is an optionally substituted cyclic group, provided that the cyclic group is not a 4-piperidinyl group, ring B is an optionally substituted ring, provided that the ring is not a thiazole ring and an oxazole ring, V is a bond or a spacer having 1 to 3 atoms in the main chain, except —N=N—, W is a bond or a $C_{1-6}$ alkylene group optionally substituted by $C_{1-6}$ alkoxy group(s)

X and Xa are the same or different and each is CH or N,

Y is O or $CR^6R^7$,
wherein $R^6$ and $R^7$ are the same or different and each is a hydrogen atom, a halogen atom, a $C_{1-6}$ alkyl group or an optionally substituted hydroxy group, or $R^7$ is bonded to $R^{1a}$ to form a 4- to 8-membered ring, $R^1$ and $R^{1a}$ are the same or different and each is a hydrogen atom, a halogen atom, a $C_{1-6}$ alkyl group or a $C_{1-6}$ alkoxy group, $R^2$ is a hydrogen atom, a $C_{1-6}$ alkyl group or an optionally substituted acyl group, $R^3$ and $R^4$ are the same or different and each is a hydrogen atom or a halogen atom, and $R^5$ is an optionally substituted hydroxy group or an optionally substituted amino group, provided that when W is a bond, then ring B should be an optionally substituted non-aromatic ring condensed with a benzene ring, not being an optionally substituted tetrahydroquinoline ring, or a salt thereof (hereinafter sometimes to be abbreviated as compound (1)), with the proviso that methyl 3-[4-[[3-(tetrahydropyran-2-yloxy)benzyl]-(2,4,6-trimethyl-benzenesulfonyl)amino]phenyl]propionate is excluded.

[2] Compound (1) wherein the partial structural formula:

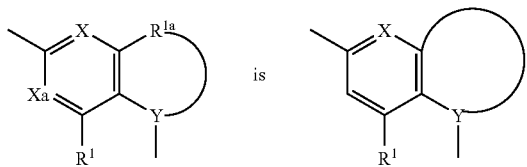

wherein

X and $R^1$ are as defined in the above-mentioned [1], and

Y is O or $CR^6R^7$
wherein $R^6$ and $R^7$ are the same or different and each is a hydrogen atom, a halogen atom, a $C_{1-6}$ alkyl group or an optionally substituted hydroxy group, or $R^7$ is bonded to the methine group adjacent to X to form a 4- to 8-membered ring.

[3] Compound (1) of the above-mentioned [2], wherein W is a $C_{1-6}$ alkylene group optionally substituted by $C_{1-6}$ alkoxy group(s).

[4] A prodrug of compound (1).

[5] Compound (1) wherein $R^5$ is a hydroxy group.

[6] Compound (1) wherein the cyclic group for Ar is phenyl, naphthyl, thiazolyl, pyrazolyl, indolyl or dihydroquinolinyl.

[7] Compound (1) wherein the ring for ring B is a benzene ring, a pyrazole ring or an indane ring.

[8] Compound (1) wherein V is a bond; —O—; —CH=N—; or —CH$_2$—, —CH$_2$CH$_2$—, —CH$_2$O—, —NH—CH$_2$—, —CH$_2$—NH— or —CH$_2$—NH—CH$_2$—, each of which optionally has substituent(s) selected from a $C_{1-6}$ alkyl group, a $C_{7-16}$ aralkyl group and a $C_{6-14}$ aryl group.

[9] Compound (1) wherein $R^2$ is a hydrogen atom.

[10] Compound (1) which is 6-({[4'-(2-ethoxyethoxy)-2',6'-dimethylbiphenyl-3-yl]methyl}amino)-2,3-dihydro-1-benzofuran-3-yl]acetic acid;

3-{4-[({4'-[2-(ethylsulfonyl)ethoxy]-2',6'-dimethylbiphenyl-3-yl}methyl)amino]-2-fluorophenyl}propanoic acid;

3-{4-[({2',6'-dimethyl-4'-[3-(2-oxopyrrolidin-1-yl)propoxy]biphenyl-3-yl}methyl)amino]-2-fluorophenyl}propanoic acid;

3-{2-fluoro-4-[({4'-[(4-hydroxy-1,1-dioxidotetrahydro-2H-thiopyran-4-yl)methoxy]-2',6'-dimethylbiphenyl-3-yl}methyl)amino]phenyl}propanoic acid;

3-{4-[({4'-[(1,1-dioxidotetrahydro-2H-thiopyran-4-yl)oxy]-2',6'-dimethylbiphenyl-3-yl}methyl)amino]-2-fluorophenyl}propanoic acid;

3-[4-({[4'-(2-ethoxyethoxy)-2',3',5',6'-tetramethylbiphenyl-3-yl]methyl}amino)-2-fluorophenyl]propanoic acid;

3-{4-[(4-{4-[2-(ethylsulfonyl)ethoxy]-2,6-dimethylphenyl}-2,3-dihydro-1H-inden-1-yl)amino]-2-fluorophenyl}propanoic acid;

3-[2-fluoro-4-({4-[((3-methylbutyl){4-[4-(trifluoromethyl)phenyl]-1,3-thiazol-2-yl}amino)methyl]benzyl}amino)phenyl]propanoic acid;

3-[4-({4-[(3,5-diphenyl-1H-pyrazol-1-yl)methyl]-3-isopropoxybenzyl}amino)-2,6-difluorophenyl]propanoic acid;

3-{2-fluoro-4-[({4'-[(4-hydroxy-1,1-dioxidotetrahydro-2H-thiopyran-4-yl)methoxy]-2',6'-trimethylbiphenyl-3-yl}methyl)amino]phenyl}propanoic acid;

or a salt thereof.

[11] An insulin secretagogue comprising a compound represented by the formula (1'):

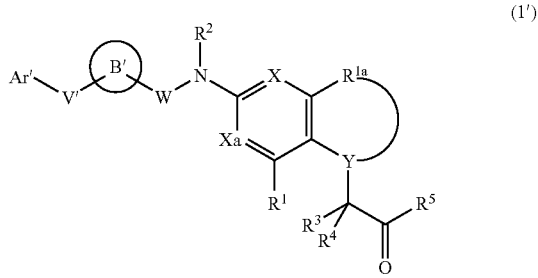

wherein

Ar' is an optionally substituted cyclic group, ring B' is an optionally substituted ring, V' is a bond or a spacer having 1 to 3 atoms in the main chain, W is a bond or a $C_{1-6}$ alkylene group optionally substituted by $C_{1-6}$ alkoxy group(s), X and Xa are the same or different and each is CH or N, Y is O or $CR^6R^7$ wherein $R^6$ and $R^7$ are the same or different and each is a hydrogen atom, a halogen atom, a $C_{1-6}$ alkyl group or an optionally substituted hydroxy group, or, $R^7$ is bonded to $R^{1a}$ to form a 4- to 8-membered ring, $R^1$ and $R^{1a}$ are the same or different and each is a hydrogen atom, a halogen atom, a $C_{1-6}$ alkyl group or a $C_{1-6}$ alkoxy group, $R^2$ is a hydrogen atom, a $C_{1-6}$ alkyl group or an optionally substituted acyl group, $R^3$ and $R^4$ are the same or different and each is a hydrogen atom or a halogen atom, and $R^5$ is an optionally substituted hydroxy group or an optionally substituted amino group, or a salt thereof (hereinafter sometimes to be abbreviated compound (1')) or a prodrug thereof.

[12] The insulin secretagogue of the above-mentioned [11], wherein the partial structural formula:

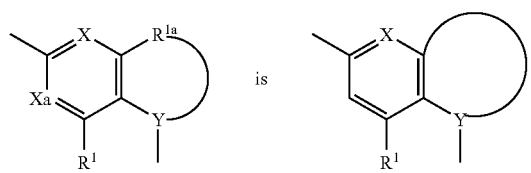

wherein

X and $R^1$ are as defined in the above-mentioned [11], and

Y is O or $CR^6R^7$ wherein $R^6$ and $R^7$ are the same or different and each is a hydrogen atom, a halogen atom, a $C_{1-6}$ alkyl group or an optionally substituted hydroxy group, or $R^7$ is bonded to the methine group adjacent to X to form a 4- to 8-membered ring.

[13] The insulin secretagogue of the above-mentioned [12], wherein W is a $C_{1-6}$ alkylene group optionally substituted by $C_{1-6}$ alkoxy group(s).

[14] A GPR40 receptor function modulator comprising compound (1') or a prodrug thereof.

[15] The GPR40 receptor function modulator of the above-mentioned [14], wherein the partial structural formula:

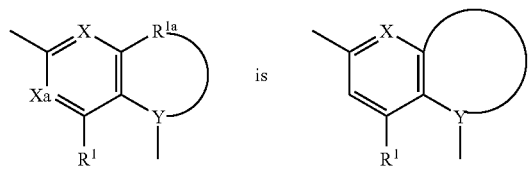

wherein each symbol is as defined in the above-mentioned [12].

[16] The GPR40 receptor function modulator of the above-mentioned [15], wherein W is a $C_{1-6}$ alkylene group optionally substituted by $C_{1-6}$ alkoxy group(s).

[17] A pharmaceutical agent comprising compound (I) or a prodrug thereof.

[18] The pharmaceutical agent of the above-mentioned [17], which is an agent for the prophylaxis or treatment of diabetes.

[19] Use of compound (1') or a prodrug thereof for the production of a GPR40 receptor function modulator.

[20] Use of compound (1') or a prodrug thereof for the production of an insulin secretagogue.

[21] Use of compound (I) or a prodrug thereof for the production of an agent for the prophylaxis or treatment of diabetes.

[22] A method of modulating a GPR40 receptor function in a mammal, which comprises administering an effective amount of compound (1') or a prodrug thereof to the mammal.

[23] A method of promoting insulin secretion in a mammal, which comprises administering an effective amount of compound (1') or a prodrug thereof to the mammal.

[24] A method for the prophylaxis or treatment of diabetes in a mammal, which comprises administering an effective amount of compound (1) or a prodrug thereof to the mammal.

The compound of the present invention has a superior GPR40 receptor function modulating action, and can be used as an agent for the prophylaxis or treatment of diabetes and the like, or as an insulin secretagogue.

DETAILED DESCRIPTION OF THE INVENTION

Best Mode for Embodying the Invention

Unless otherwise specified, as the "halogen atom" in the present specification, a fluorine atom, a chlorine atom, a bromine atom and an iodine atom can be mentioned.

Unless otherwise specified, as the "optionally substituted hydrocarbon group" in the present specification, for example, an "optionally substituted $C_{1-6}$ alkyl group", an "optionally substituted $C_{2-6}$ alkenyl group", an "optionally substituted $C_{2-6}$ alkynyl group", an "optionally substituted $C_{3-8}$ cycloalkyl group", an "optionally substituted $C_{6-14}$ aryl group", an "optionally substituted $C_{7-16}$ aralkyl group" and the like can be mentioned.

Unless otherwise specified, as the "$C_{1-6}$ alkyl group" in the present specification, for example, methyl, ethyl, propyl, isopropyl, butyl, isobutyl, sec-butyl, tert-butyl, pentyl, isopentyl, neopentyl, hexyl and the like can be mentioned.

Unless otherwise specified, as the "$C_{2-6}$ alkenyl group" in the present specification, for example, vinyl, propenyl, isopropenyl, 2-buten-1-yl, 4-penten-1-yl, 5-hexen-1-yl and the like can be mentioned.

Unless otherwise specified, as the "$C_{2-6}$ alkynyl group" in the present specification, for example, 2-butyn-1-yl, 4-pentyn-1-yl, 5-hexyn-1-yl and the like can be mentioned.

Unless otherwise specified, as the "$C_{3-8}$ cycloalkyl group" in the present specification, for example, cyclopropyl, cyclobutyl, cyclopentyl, cyclohexyl and the like can be mentioned.

Unless otherwise specified, as the "$C_{6-14}$ aryl group" in the present specification, for example, phenyl, 1-naphthyl, 2-naphthyl, 2-biphenylyl, 3-biphenylyl, 4-biphenylyl, 2-anthryl and the like can be mentioned. The $C_{6-14}$ aryl may be saturated partially, and as the partially saturated $C_{6-14}$ aryl, for example, tetrahydronaphthyl and the like can be mentioned.

Unless otherwise specified, as the "$C_{7-16}$ aralkyl group" in the present specification, for example, benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, 4-biphenylylmethyl and the like can be mentioned.

Unless otherwise specified, as the "optionally substituted hydroxy group" in the present specification, for example, a "hydroxy group", an "optionally substituted $C_{1-10}$ alkoxy group", an "optionally substituted heterocyclyloxy group", an "optionally substituted $C_{6-14}$ aryloxy group", an "optionally substituted $C_{7-16}$ aralkyloxy group", a "tri-$C_{1-6}$ alkyl-silyloxy group", an "optionally substituted $C_{1-6}$ alkylsulfonyloxy group", an "optionally substituted heterocyclylsulfonyloxy group" and the like can be mentioned.

Unless otherwise specified, as the "$C_{1-6}$ alkoxy group" in the present specification, for example, methoxy, ethoxy, propoxy, isopropoxy, butoxy, isobutoxy, tert-butoxy, pentyloxy, hexyloxy and the like can be mentioned. As the "$C_{1-10}$ alkoxy group" in the present specification, heptyloxy, octyloxy, nonyloxy, decyloxy and the like can be mentioned besides the above-mentioned $C_{1-6}$ alkoxy group.

Unless otherwise specified, as the "$C_{1-6}$ alkoxy-$C_{1-6}$ alkoxy group" in the present specification, for example, methoxymethoxy, methoxyethoxy, ethoxymethoxy, ethoxyethoxy and the like can be mentioned.

As the "heterocyclyloxy group" in the present specification, a hydroxy group substituted by a "heterocyclic group" below can be mentioned. As preferable examples of the heterocyclyloxy group, tetrahydropyranyloxy, thiazolyloxy, pyridyloxy, pyrazolyloxy, oxazolyloxy, thienyloxy, furyloxy, tetrahydrothiopyranyloxy, 1,1-dioxidotetrahydrothiopyranyloxy, 1-oxidotetrahydrothiopyranyloxy and the like can be mentioned.

Unless otherwise specified, as the "$C_{6-14}$ aryloxy group" in the present specification, for example, phenoxy, 1-naphthyloxy, 2-naphthyloxy and the like can be mentioned.

Unless otherwise specified, as the "$C_{7-16}$ aralkyloxy group" in the present specification, for example, benzyloxy, phenethyloxy and the like can be mentioned.

As the "$C_{1-6}$ alkylsulfonyloxy group" in the present specification, for example, methylsulfonyloxy, ethylsulfonyloxy and the like can be mentioned.

Unless otherwise specified, as the "tri-$C_{1-6}$ alkyl-silyloxy group" in the present specification, for example, trimethylsilyloxy, tert-butyl(dimethyl)silyloxy and the like can be mentioned.

Unless otherwise specified, as the "optionally substituted mercapto group" in the present specification, for example, a "mercapto group", an "optionally substituted $C_{1-10}$ alkylthio group", an "optionally substituted heterocyclylthio group", an "optionally substituted $C_{6-14}$ arylthio group", an "optionally substituted $C_{7-16}$ aralkylthio group" and the like can be mentioned.

Unless otherwise specified, as the "$C_{1-6}$ alkylthio group" in the present specification, for example, methylthio, ethylthio, propylthio, isopropylthio, butylthio, sec-butylthio, tert-butylthio and the like can be mentioned. As the "$C_{1-10}$ alkylthio group" in the present specification, heptylthio, octylthio, nonylthio, decylthio and the like can be mentioned besides the above-mentioned $C_{1-6}$ alkylthio group.

Unless otherwise specified, as the "heterocyclylthio group" in the present specification, a mercapto group substituted by a "heterocyclic group" below can be mentioned. As preferable examples of the heterocyclylthio group, tetrahydropyranylthio, thiazolylthio, pyridylthio, pyrazolylthio, oxazolylthio, thienylthio, furylthio and the like can be mentioned.

Unless otherwise specified, as the "$C_{6-14}$ arylthio group" in the present specification, for example, phenylthio, 1-naphthylthio, 2-naphthylthio and the like can be mentioned.

Unless otherwise specified, as the "$C_{7-16}$ aralkylthio group" in the present specification, for example, benzylthio, phenethylthio and the like can be mentioned.

Unless otherwise specified, as the "heterocyclic group" in the present specification, for example, a 5- to 14-membered (monocyclic, bicyclic or tricyclic) heterocyclic group containing, as a ring-constituting atom besides carbon atoms, one or two kinds of 1 to 4 hetero atoms selected from a nitrogen atom, a sulfur atom and an oxygen atom, preferably (i) a 5- to 14-membered (preferably 5- to 10-membered) aromatic heterocyclic group, (ii) a 4- to 10-membered non-aromatic heterocyclic group and the like can be mentioned. Of these, a 5- or 6-membered aromatic heterocyclic group is preferable. Specifically, aromatic heterocyclic groups such as thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl, 5-oxazolyl), quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), pyridazinyl (e.g., 3-pyridazinyl, 4-pyridazinyl), isothiazolyl (e.g., 3-isothiazolyl, 4-isothiazolyl, 5-isothiazolyl), isoxazolyl (e.g., 3-isoxazolyl, 4-isoxazolyl, 5-isoxazolyl), indolyl (e.g., 1-indolyl, 2-indolyl, 3-indolyl), 2-benzothiazolyl, 2-benzoxazolyl, benzimidazolyl (e.g., 1-benzimidazolyl, 2-benzimidazolyl), benzo[b]thienyl (e.g., 2-benzo[b]thienyl, 3-benzo[b]thienyl), benzo[b]furanyl (e.g., 2-benzo[b]furanyl, 3-benzo[b]furanyl) and the like; non-aromatic heterocyclic groups such as pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., 1-piperidinyl, 2-piperidinyl, 3-piperidinyl, 4-piperidinyl), piperazinyl (e.g., 1-piperazinyl, 2-piperazinyl), morpholinyl (e.g., 2-morpholinyl, 3-morpholinyl, 4-morpholinyl), thiomorpholinyl (e.g., 2-thiomorpholinyl, 3-thiomorpholinyl, 4-thiomorpholinyl), tetrahydropyranyl (e.g., 2-tetrahydropyranyl, 3-tetrahydropyranyl, 4-tetrahydropyranyl), oxetanyl (e.g., 2-oxetanyl, 3-oxetanyl), oxopyrrolidinyl (e.g., 2-oxopyrrolidin-1-yl, 2-oxopyrrolidin-3-yl, 2-oxopyrrolidin-4-yl, 2-oxopyrrolidin-5-yl, 3-oxopyrrolidin-1-yl), dioxopyrrolidinyl (e.g., 2,5-dioxopyrrolidin-1-yl, 2,5-dioxopyrrolidin-3-yl), tetrahydrothiopyranyl (e.g., 2-tetrahydrothiopyranyl, 3-tetrahydrothiopyranyl, 4-tetrahydrothiopyranyl), 1,1-dioxidotetrahydrothiopyranyl (e.g., 1,1-dioxidotetrahydrothiopyran-2-yl, 1,1-dioxidotetrahydrothiopyran-3-yl, 1,1-dioxidotetrahydrothiopyran-4-yl), dihydrobenzofuranyl (e.g., 2,3-dihydro-1-benzofuran-4-yl, 2,3-dihydro-1-benzofuran-5-yl, 2,3-dihydro-1-benzofuran-6-yl, 2,3-dihydro-1-benzofuran-7-yl), dihydroquinolinyl (e.g., 1,2-dihydroquinolin-1-yl), tetrahydroquinolinyl (e.g., 1,2,3,4-tetrahydroquinolin-1-yl), 1-oxidotetrahydrothiopyranyl (e.g., 1-oxidotetrahydrothiopyran-2-yl, 1-oxidotetrahydrothiopyran-3-yl, 1-oxidotetrahydrothiopyran-4-yl) and the like, and the like can be mentioned.

Unless otherwise specified, as the "$C_{1-6}$ alkylsulfonyl group" in the present specification, for example, methylsulfonyl, ethylsulfonyl and the like can be mentioned.

Unless otherwise specified, as the "$C_{1-6}$ alkylsulfinyl group" in the present specification, for example, methylsulfinyl, ethylsulfinyl and the like can be mentioned.

Unless otherwise specified, as the "$C_{6-14}$ arylsulfonyl group" in the present specification, for example, phenylsulfonyl, 1-naphthylsulfonyl, 2-naphthylsulfonyl and the like can be mentioned.

Unless otherwise specified, as the "$C_{6-14}$ arylsulfinyl group" in the present specification, for example, phenylsulfinyl, 1-naphthylsulfinyl, 2-naphthylsulfinyl and the like can be mentioned.

Unless otherwise specified, as the "optionally esterified carboxyl group" in the present specification, for example, a carboxyl group, a $C_{1-6}$ alkoxy-carbonyl group (e.g., methoxycarbonyl, ethoxycarbonyl, propoxycarbonyl, tert-butoxycarbonyl etc.), a $C_{6-14}$ aryloxy-carbonyl group (e.g., phenoxycarbonyl etc.), a $C_{7-16}$ aralkyloxy-carbonyl group (e.g., benzyloxycarbonyl, phenethyloxycarbonyl etc.) and the like can be mentioned.

Unless otherwise specified, as the "optionally halogenated $C_{1-6}$ alkyl group" in the present specification, the above-mentioned "$C_{1-6}$ alkyl group" optionally substituted by 1 to 5 above-mentioned "halogen atoms" can be mentioned. For example, methyl, ethyl, propyl, isopropyl, butyl, tert-butyl, isobutyl, trifluoromethyl and the like can be mentioned.

Unless otherwise specified, as the "optionally halogenated $C_{1-6}$ alkoxy group" in the present specification, the above-mentioned "$C_{1-6}$ alkoxy group" optionally substituted by 1 to 5 above-mentioned "halogen atoms" can be mentioned. For example, methoxy, ethoxy, isopropoxy, tert-butoxy, trifluoromethoxy and the like can be mentioned.

Unless otherwise specified, as the "mono- or di-$C_{1-6}$ alkyl-amino group" in the present specification, an amino group mono- or di-substituted by the above-mentioned "$C_{1-6}$ alkyl group(s)" can be mentioned. For example, methylamino, ethylamino, propylamino, dimethylamino, diethylamino and the like can be mentioned.

Unless otherwise specified, as the "mono- or di-$C_{6-14}$ aryl-amino group" in the present specification, an amino group mono- or di-substituted by the above-mentioned "$C_{6-14}$ aryl group(s)" can be mentioned. For example, phenylamino, diphenylamino, 1-naphthylamino, 2-naphthylamino and the like can be mentioned.

Unless otherwise specified, as the "mono- or di-$C_{7-16}$ aralkyl-amino group" in the present specification, an amino group mono- or di-substituted by the above-mentioned "$C_{7-16}$ aralkyl group(s)" can be mentioned. For example, benzylamino, phenethylamino and the like can be mentioned.

Unless otherwise specified, as the "N—$C_{1-6}$ alkyl-N—$C_{6-14}$ aryl-amino group" in the present specification, an amino group substituted by the above-mentioned "$C_{1-6}$ alkyl group" and the above-mentioned "$C_{6-14}$ aryl group" can be mentioned. For example, N-methyl-N-phenylamino, N-ethyl-N-phenylamino and the like can be mentioned.

Unless otherwise specified, as the "N—$C_{1-6}$ alkyl-N—$C_{7-16}$ aralkyl-amino group" in the present specification, an amino group substituted by the above-mentioned "$C_{1-6}$ alkyl group" and the above-mentioned "$C_{7-16}$ aralkyl group" can be mentioned. For example, N-methyl-N-benzylamino, N-ethyl-N-benzylamino and the like can be mentioned.

Unless otherwise specified, as the "N—$C_{1-6}$ alkyl-N—$C_{1-6}$ alkyl-carbonyl-amino group" in the present specification, an amino group substituted by the above-mentioned "$C_{1-6}$ alkyl group" and a $C_{1-6}$ alkyl-carbonyl group (e.g., acetyl, isobutanoyl, isopentanoyl) can be mentioned. For example, N-methyl-N-acetylamino, N-ethyl-N-acetylamino and the like can be mentioned.

Unless otherwise specified, as the "mono- or di-$C_{1-6}$ alkyl-carbamoyl group" in the present specification, a carbamoyl group mono- or di-substituted by the above-mentioned "$C_{1-6}$ alkyl group(s)" can be mentioned. For example, methylcarbamoyl, ethylcarbamoyl, dimethylcarbamoyl, diethylcarbamoyl, ethylmethylcarbamoyl and the like can be mentioned.

Unless otherwise specified, as the "mono- or di-$C_{6-14}$ aryl-carbamoyl group" in the present specification, a carbamoyl group mono- or di-substituted by the above-mentioned "$C_{6-14}$ aryl group(s)" can be mentioned. For example, phenylcarbamoyl, 1-naphthylcarbamoyl, 2-naphthylcarbamoyl and the like can be mentioned.

Unless otherwise specified, as the "mono- or di-5- to 7-membered heterocyclyl-carbamoyl group" in the present specification, a carbamoyl group mono- or di-substituted by 5- to 7-membered heterocyclic group(s) can be mentioned. As the 5- to 7-membered heterocyclic group, a heterocyclic group containing, as a ring-constituting atom besides carbon atoms, one or two kinds of 1 to 4 hetero atoms selected from a nitrogen atom, a sulfur atom and an oxygen atom can be mentioned. As preferable examples of the "mono- or di-5 to 7-membered heterocyclyl-carbamoyl group", 2-pyridylcarbamoyl, 3-pyridylcarbamoyl, 4-pyridylcarbamoyl, 2-thienylcarbamoyl, 3-thienylcarbamoyl and the like can be mentioned.

Unless otherwise specified, as the "mono- or di-$C_{1-6}$ alkylsulfamoyl group" in the present specification, a sulfamoyl group mono- or di-substituted by the above-mentioned "$C_{1-6}$ alkyl group(s)" can be used, for example, methylsulfamoyl, ethylsulfamoyl, dimethylsulfamoyl, diethylsulfamoyl and the like can be mentioned.

Unless otherwise specified, as the "mono- or di-$C_{6-14}$ arylsulfamoyl group" in the present specification, a sulfamoyl group mono- or di-substituted by the above-mentioned "$C_{6-14}$ aryl group(s)" can be used, for example, phenylsulfamoyl, diphenylsulfamoyl, 1-naphthylsulfamoyl, 2-naphthylsulfamoyl and the like can be mentioned.

Unless otherwise specified, as the "optionally substituted $C_{1-6}$ alkyl group", "optionally substituted $C_{2-6}$ alkenyl group", "optionally substituted $C_{2-6}$ alkynyl group", "optionally substituted $C_{1-10}$ alkoxy group (containing optionally substituted $C_{1-6}$ alkoxy group)", "optionally substituted $C_{1-6}$ alkylsulfonyloxy group" and "optionally substituted $C_{1-10}$ alkylthio group (containing optionally substituted $C_{1-6}$ alkylthio group)" in the present specification, for example, a "$C_{1-6}$ alkyl group", a "$C_{2-6}$ alkenyl group", a "$C_{2-6}$ alkynyl group", a "$C_{1-10}$ alkoxy group (containing $C_{1-6}$ alkoxy group)", a "$C_{1-6}$ alkylsulfonyloxy group" and a "$C_{1-10}$ alkylthio group (containing $C_{1-6}$ alkylthio group)", each of which optionally has 1 to 5 substituents at substitutable position(s) selected from (1) a halogen atom;

(2) a hydroxy group;

(3) an amino group;

(4) a nitro group;

(5) a cyano group;

(6) a heterocyclic group (preferably furyl, pyridyl, thienyl, pyrazolyl, thiazolyl, oxazolyl, isoxazolyl, isothiazolyl, oxetanyl, morpholinyl, thiomorpholinyl, pyrrolidinyl, oxopyrrolidinyl, dioxopyrrolidinyl, tetrahydropyranyl, tetrahydrothiopyranyl, 1,1-dioxidotetrahydrothiopyranyl, 1-oxidotetrahydrothiopyranyl) optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;

(7) a mono- or di-$C_{1-6}$ alkyl-amino group;

(8) a mono- or di-$C_{6-14}$ aryl-amino group;

(9) a mono- or di-$C_{7-16}$ aralkyl-amino group;

(10) an N—$C_{1-6}$ alkyl-N—$C_{6-14}$ aryl-amino group;

(11) an N—$C_{1-6}$ alkyl-N—$C_{7-16}$ aralkyl-amino group;

(12) a $C_{3-8}$ cycloalkyl group;

(13) an optionally halogenated $C_{1-6}$ alkoxy group;

(14) a $C_{1-6}$ alkylthio group optionally substituted by $C_{1-6}$ alkoxy group(s);

(15) a $C_{1-6}$ alkylsulfinyl group optionally substituted by $C_{1-6}$ alkoxy group(s);

(16) a $C_{1-6}$ alkylsulfonyl group optionally substituted by $C_{1-6}$ alkoxy group(s);

(17) an optionally esterified carboxyl group;

(18) a carbamoyl group;

(19) a thiocarbamoyl group;

(20) a mono- or di-$C_{1-6}$ alkyl-carbamoyl group;

(21) a mono- or di-$C_{6-14}$ aryl-carbamoyl group;

(22) a mono- or di-5- to 7-membered heterocyclyl-carbamoyl group;

(23) a $C_{1-6}$ alkyl-carbonylamino group (e.g., acetylamino, propionylamino) optionally substituted by carboxyl group(s);

(24) a $C_{6-14}$ aryloxy group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;

(25) a $C_{6-14}$ aryl group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;

(26) a heterocyclyloxy group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;

(27) a sulfamoyl group;

(28) a mono- or di-$C_{1-6}$ alkyl-sulfamoyl group;

(29) a mono- or di-$C_{6-14}$ aryl-sulfamoyl group;

(30) a $C_{7-16}$ aralkyloxy group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;

(31) a $C_{1-6}$ alkylsulfonyloxy group;

(32) a tri-$C_{1-6}$ alkyl-silyloxy group;

(33) a nitrogen-containing heterocyclyl-carbonyl group (e.g., pyrrolidinylcarbonyl, piperidinocarbonyl, morpholinocarbonyl, thiomorpholinocarbonyl);

(34) an N—$C_{1-6}$ alkyl-N—$C_{1-6}$ alkyl-carbonylamino group;

(35) a mono- or di-$C_{1-6}$ alkylphosphono group (e.g., dimethylphosphono, diethylphosphono);

and the like, can be mentioned.

As the "optionally substituted $C_{3-8}$ cycloalkyl group", "optionally substituted $C_{6-14}$ aryl group", "optionally substituted $C_{7-16}$ aralkyl group", "optionally substituted heterocyclic group", "optionally substituted heterocyclyloxy group", "optionally substituted $C_{6-14}$ aryloxy group", "optionally substituted $C_{7-16}$ aralkyloxy group", "optionally substituted heterocyclylsulfonyloxy group", "optionally substituted heterocyclylthio group", "optionally substituted $C_{6-14}$ arylthio group" and "optionally substituted $C_{7-16}$ aralkylthio group" in the present specification, for example, a "$C_{3-8}$ cycloalkyl group", a "$C_{6-14}$ aryl group", a "$C_{7-16}$ aralkyl group", a "heterocyclic group", a "heterocyclyloxy group", a "$C_{6-14}$ aryloxy group", a "$C_{7-16}$ aralkyloxy group", a "heterocyclylsulfonyloxy group", a "heterocyclylthio group", a "$C_{6-14}$ arylthio group" and a "$C_{7-16}$ aralkylthio group", each of which optionally has 1 to 5 substituents at substitutable position(s) selected from (1) a halogen atom;

(2) a hydroxy group;

(3) an amino group;

(4) a nitro group;

(5) a cyano group;

(6) an optionally substituted $C_{1-6}$ alkyl group;

(7) an optionally substituted $C_{2-6}$ alkenyl group;

(8) an optionally substituted $C_{2-6}$ alkynyl group;

(9) a $C_{6-14}$ aryl group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;

(10) a $C_{6-14}$ aryloxy group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;

(11) a $C_{7-16}$ aralkyloxy group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;

(12) a heterocyclic group (preferably furyl, pyridyl, thienyl, pyrazolyl, thiazolyl, oxazolyl, isoxazolyl, isothiazolyl, oxetanyl, morpholinyl, thiomorpholinyl, pyrrolidinyl, oxopyrrolidinyl, dioxopyrrolidinyl, tetrahydropyranyl, tetrahydrothiopyranyl, 1,1-dioxidotetrahydrothiopyranyl, 1-oxidotetrahydrothiopyranyl) optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;

(13) a mono- or di-$C_{1-6}$ alkyl-amino group;

(14) a mono- or di-$C_{6-14}$ aryl-amino group;

(15) a mono- or di-$C_{7-16}$ aralkyl-amino group;

(16) an N—$C_{1-6}$ alkyl-N—$C_{6-14}$ aryl-amino group;

(17) an N—$C_{1-6}$ alkyl-N—$C_{7-16}$ aralkyl-amino group;

(18) a $C_{3-8}$ cycloalkyl group;

(19) an optionally substituted $C_{1-6}$ alkoxy group;

(20) a $C_{1-6}$ alkylthio group optionally substituted by $C_{1-6}$ alkoxy group(s);

(21) a $C_{1-6}$ alkylsulfinyl group optionally substituted by $C_{1-6}$ alkoxy group(s);

(22) a $C_{1-6}$ alkylsulfonyl group optionally substituted by $C_{1-6}$ alkoxy group(s);

(23) an optionally esterified carboxyl group;

(24) a carbamoyl group;

(25) a thiocarbamoyl group;

(26) a mono- or di-$C_{1-6}$ alkyl-carbamoyl group;

(27) a mono- or di-$C_{6-14}$ aryl-carbamoyl group;

(28) a mono- or di-5- to 7-membered heterocyclyl-carbamoyl group;

(29) a sulfamoyl group;

(30) a mono- or di-$C_{1-6}$ alkyl-sulfamoyl group;

(31) a mono- or di-$C_{6-14}$ aryl-sulfamoyl group;

(32) a $C_{1-6}$ alkylsulfonyloxy group;

(33) a tri-$C_{1-6}$ alkyl-silyloxy group;

(34) a nitrogen-containing heterocyclyl-carbonyl group (e.g., pyrrolidinylcarbonyl, piperidinocarbonyl, morpholinocarbonyl, thiomorpholinocarbonyl);

(35) a heterocyclyloxy group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;

(36) a $C_{1-6}$ alkyl-carbonylamino group (e.g., acetylamino, propionylamino);

and the like, can be mentioned.

Unless otherwise specified, as the "optionally substituted amino group" in the present specification, an amino group optionally substituted by 1 or 2 substituents selected from (1) an optionally substituted $C_{1-6}$ alkyl group;

(2) an optionally substituted $C_{2-6}$ alkenyl group;

(3) an optionally substituted $C_{2-6}$ alkynyl group;

(4) an optionally substituted $C_{3-8}$ cycloalkyl group;

(5) an optionally substituted $C_{6-14}$ aryl group;

(6) an optionally substituted $C_{1-6}$ alkoxy group;

(7) an optionally substituted acyl group;

(8) an optionally substituted heterocyclic group (preferably furyl, pyridyl, thienyl, pyrazolyl, thiazolyl, oxazolyl);

(9) a sulfamoyl group;

(10) a mono- or di-$C_{1-6}$ alkyl-sulfamoyl group;

(11) a mono- or di-$C_{6-14}$ aryl-sulfamoyl group;

and the like, can be mentioned. When the "optionally substituted amino group" is an amino group substituted by 2 substituents, these substituents may form a nitrogen-containing heterocycle together with the adjacent nitrogen atom. As the "nitrogen-containing heterocycle", for example, a 5- to 7-membered nitrogen-containing heterocycle containing, as a ring-constituting atom besides carbon atoms, at least one nitrogen atom and optionally further containing 1 or 2 hetero atoms selected from an oxygen atom, a sulfur atom and a nitrogen atom can be mentioned. As preferable examples of the nitrogen-containing heterocycle, pyrrolidine, imidazolidine, pyrazolidine, piperidine, piperazine, morpholine, thiomorpholine, thiazolidine, oxazolidine and the like can be mentioned.

Unless otherwise specified, as the "optionally substituted acyl group" in the present specification, groups represented by the formula: —$COR^8$, —CO—$OR^8$, —$SO_2R^8$, —$SOR^8$, —$PO(OR^8)(OR^9)$, —CO—$NR^{8a}R^{9a}$ and CS—$NR^{8a}R^{9a}$, wherein $R^8$ and $R^9$ are the same or different and each is a hydrogen atom, an optionally substituted hydrocarbon group or an optionally substituted heterocyclic group, and $R^{8a}$ and $R^{9a}$ are the same or different and each is a hydrogen atom, an optionally substituted hydrocarbon group or an optionally substituted heterocyclic group, or $R^{8a}$ and $R^{9a}$ may form an optionally substituted nitrogen-containing heterocycle together with the adjacent nitrogen atom, and the like can be mentioned.

As the "nitrogen-containing heterocycle" of the "optionally substituted nitrogen-containing heterocycle" which $R^{8a}$ and $R^{9a}$ form together with the adjacent nitrogen atom, for example, a 5- to 7-membered nitrogen-containing heterocycle containing, as a ring-constituting atom besides carbon atoms, at least one nitrogen atom and optionally further containing 1 to 2 hetero atoms selected from an oxygen atom, a sulfur atom and a nitrogen atom can be mentioned. As preferable examples of the "nitrogen-containing heterocycle", pyrrolidine, imidazolidine, pyrazolidine, piperidine, piperazine, morpholine, thiomorpholine, thiazolidine, oxazolidine and the like can be mentioned.

The nitrogen-containing heterocycle optionally has 1 to 2 substituents at substitutable position(s). As these substituents, a hydroxy group, an optionally halogenated $C_{1-6}$ alkyl group, a $C_{6-14}$ aryl group, a $C_{7-16}$ aralkyl group and the like can be mentioned.

As preferable examples of the "optionally substituted acyl group", a formyl group;

a carboxyl group;

a carbamoyl group;

a $C_{1-6}$ alkyl-carbonyl group (e.g., acetyl, isobutanoyl, isopentanoyl) optionally substituted by 1 to 3 halogen atoms;

a $C_{1-6}$ alkoxy-carbonyl group (e.g., methoxycarbonyl, ethoxycarbonyl, propoxycarbonyl, tert-butoxycarbonyl) optionally substituted by 1 to 3 halogen atoms;

a $C_{3-8}$ cycloalkyl-carbonyl group (e.g., cyclopentylcarbonyl, cyclohexylcarbonyl);

a $C_{6-14}$ aryl-carbonyl group (e.g., benzoyl, 1-naphthoyl, 2-naphthoyl);

a $C_{7-16}$ aralkyl-carbonyl group (e.g., phenylacetyl, 2-phenylpropanoyl);

a $C_{6-14}$ aryloxy-carbonyl group (e.g., phenyloxycarbonyl, naphthyloxycarbonyl);

a $C_{7-16}$ aralkyloxy-carbonyl group (e.g., benzyloxycarbonyl, phenethyloxycarbonyl);

a mono- or di-$C_{1-6}$ alkylcarbamoyl group;

a mono- or di-$C_{6-14}$ aryl-carbamoyl group;

a $C_{3-8}$ cycloalkyl-carbamoyl group (e.g., cyclopropylcarbamoyl);

a $C_{7-16}$ aralkyl-carbamoyl group (e.g., benzylcarbamoyl);

a $C_{1-6}$ alkylsulfonyl group optionally substituted by 1 to 3 halogen atoms;

a $C_{6-14}$ arylsulfonyl group (e.g., phenylsulfonyl) optionally substituted by nitro group(s);

a nitrogen-containing heterocyclyl-carbonyl group (e.g., pyrrolidinylcarbonyl, piperidinocarbonyl, morpholinocarbonyl, thiomorpholinocarbonyl);

a $C_{1-6}$ alkylsulfinyl group optionally substituted by 1 to 3 halogen atoms;

a $C_{6-14}$ arylsulfinyl group;

a thiocarbamoyl group;

and the like can be mentioned.

Each symbol in the formula (1) and the formula (1') is described in detail in the following.

Ar and Ar' are each an optionally substituted cyclic group. As used herein, as the "cyclic group", for example, a $C_{3-8}$ cycloalkyl group, a $C_{6-14}$ aryl group, a heterocyclic group and the like can be mentioned. Of these, phenyl, naphthyl, thiazolyl, pyrazolyl, pyridyl, indolyl, dihydroquinolinyl, tetrahydroquinolinyl, 1-piperidinyl and the like are preferable, and phenyl, naphthyl, thiazolyl, pyrazolyl, indolyl, dihydroquinolinyl and the like are more preferable.

The cyclic group for Ar is not a 4-piperidinyl group.

The cyclic group for Ar or Ar' optionally has 1 to 5 substituents, preferably 1 to 3 substituents, at substitutable position(s). As the "substituent", those exemplarily recited as the substituents of the aforementioned "optionally substituted $C_{3-8}$ cycloalkyl group" can be used. When the cyclic group has two or more substituents, respective substituents may be the same or different.

The substituents are preferably, (1) an optionally substituted $C_{1-6}$ alkyl group (preferably an $C_{1-6}$ alkyl group optionally substituted by 1 to 3 substituents selected from a halogen atom, an optionally halogenated $C_{1-6}$ alkoxy group, a $C_{6-14}$ aryl group, a $C_{6-14}$ aryloxy group and the like);

(2) a $C_{6-14}$ aryl group optionally substituted by 1 to 3 substituents selected from a halogen atom, an optionally halogenated $C_{1-6}$ alkyl group and the like;

(3) a $C_{7-16}$ aralkyloxy group;

(4) an optionally substituted $C_{1-6}$ alkoxy group (preferably a $C_{1-6}$ alkoxy group optionally substituted by 1 to 3 substituents selected from
   (a) an optionally halogenated $C_{1-6}$ alkoxy group;
   (b) a $C_{3-8}$ cycloalkyl group;
   (c) a carboxyl group;
   (d) a mono- or di-$C_{1-6}$ alkyl-carbamoyl group;
   (e) a nitrogen-containing heterocyclyl-carbonyl group (preferably morpholinocarbonyl);
   (f) a $C_{1-6}$ alkylthio group;
   (g) a $C_{1-6}$ alkylsulfonyl group;
   (h) a heterocyclic group (preferably furyl, pyridyl, thienyl, pyrazolyl, thiazolyl, oxazolyl, isoxazolyl, isothiazolyl, oxetanyl, morpholinyl, thiomorpholinyl, pyrrolidinyl, oxopyrrolidinyl, dioxopyrrolidinyl, tetrahydropyranyl, tetrahydrothiopyranyl, 1,1-dioxidotetrahydrothiopyranyl, 1-oxidotetrahydrothiopyranyl) optionally substituted by 1 to 3 substituents selected from a hydroxy group, a $C_{1-6}$ alkyl group, a $C_{1-6}$ alkoxy group and the like;
   (i) an N—$C_{1-6}$ alkyl-N—$C_{1-6}$ alkyl-carbonyl-amino group;
   (j) a mono- or di-$C_{1-6}$ alkylphosphono group; and the like);

(5) a hydroxy group;

(6) a $C_{1-6}$ alkylsulfonyloxy group;

(7) a tri-$C_{1-6}$ alkyl-silyloxy group;

(8) a heterocyclyloxy group (preferably pyridyloxy, tetrahydropyranyloxy, tetrahydrothiopyranyloxy, 1,1-dioxidotetrahydrothiopyranyloxy, 1-oxidotetrahydrothiopyranyloxy) optionally substituted by 1 to 3 substituents selected from a $C_{1-6}$ alkyl group, a $C_{1-6}$ alkoxy group and the like;

(9) a $C_{1-6}$ alkylsulfonyl group optionally substituted by $C_{1-6}$ alkoxy group(s);

(10) a $C_{6-14}$ aryloxy group optionally substituted by 1 to 3 $C_{1-6}$ alkyl groups;

and the like.

Ring B and ring B' are each an optionally substituted ring. As used herein, as the "ring", for example, aromatic rings such as an aromatic hydrocarbon, an aromatic heterocycle and the like; non-aromatic rings such as an alicyclic hydrocarbon, an non-aromatic heterocycle and the like can be mentioned.

As the aromatic hydrocarbon, for example, an aromatic hydrocarbon having 6 to 14 carbon atoms can be mentioned. As preferable examples of the aromatic hydrocarbon, benzene, naphthalene, anthracene, phenanthrene, acenaphthylene and the like can be mentioned.

As the aromatic heterocycle, for example, a 5- to 7-membered monocyclic aromatic heterocycle containing, as a ring-constituting atom besides carbon atoms, 1 to 4 hetero atoms selected from an oxygen atom, a sulfur atom and a nitrogen atom, or a fused aromatic heterocycle can be mentioned. As the fused aromatic heterocycle, for example, a ring wherein the 5- to 7-membered monocyclic aromatic heterocycle and a 6-membered ring containing 1 or 2 nitrogen atoms, a benzene ring or a 5-membered ring containing one sulfur atom are condensed, and the like can be mentioned.

As preferable examples of the aromatic heterocycle, furan, thiophene, pyridine, pyrimidine, pyridazine, pyrazine, pyrrole, imidazole, pyrazole, isoxazole, isothiazole, oxazole, thiazole, oxadiazole, thiadiazole, triazole, tetrazole, quinoline, quinazoline, quinoxaline, benzofuran, benzothiophene, benzoxazole, benzothiazole, benzimidazole, indole, 1H-indazole, 1H-pyrrolo[2,3-b]pyrazine, 1H-pyrrolopyridine, 1H-imidazopyridine, 1H-imidazopyrazine, triazine, isoquinoline, benzothiadiazole and the like can be mentioned.

As the alicyclic hydrocarbon, a saturated or unsaturated alicyclic hydrocarbon having 3 to 12 carbon atoms, for example, a cycloalkane, a cycloalkene, a cycloalkadiene and the like can be mentioned. The alicyclic hydrocarbon is optionally condensed with a benzene ring, and as the alicyclic hydrocarbon condensed with a benzene ring, for example, indane and the like can be mentioned.

As preferable examples of the cycloalkane, a cycloalkane having 3 to 10 carbon atoms, for example, cyclopropane, cyclobutane, cyclopentane, cyclohexane, cycloheptane, cyclooctane, bicyclo[2.2.1]heptane, bicyclo[2.2.2]octane, bicyclo[3.2.1]octane, bicyclo[3.2.2]nonane, bicyclo[3.3.1]nonane, bicyclo[4.2.1]nonane, bicyclo[4.3.1]decane and the like can be mentioned.

As preferable examples of the cycloalkene, a cycloalkene having 3- to 10 carbon atoms, for example, cyclobutene, cyclopentene, cyclohexene and the like can be mentioned.

As preferable examples of the cycloalkadiene, a cycloalkadiene having 4 to 10 carbon atoms, for example, 2,4-cyclopentadiene, 2,4-cyclohexadiene, 2,5-cyclohexadiene and the like can be mentioned.

As the non-aromatic heterocycle, for example, a 5- to 7-membered monocyclic non-aromatic heterocycle containing, as a ring-constituting atom besides carbon atoms, 1 to 4 hetero atoms selected from an oxygen atom, a sulfur atom and a nitrogen atom, or a fused non-aromatic heterocycle can be mentioned. As the fused non-aromatic heterocycle, for example, a ring wherein the 5- to 7-membered monocyclic non-aromatic heterocycle and a 6-membered ring containing 1 or 2 nitrogen atoms, a benzene ring or a 5-membered ring containing one sulfur atom are condensed, and the like can be mentioned.

As preferable examples of the non-aromatic heterocycle, monocyclic non-aromatic heterocycles such as pyrrolidine, pyrroline, pyrazolidine, piperidine, piperazine, morpholine, thiomorpholine, hexamethyleneimine, oxazolidine, thiazolidine, imidazolidine, imidazoline, tetrahydrofuran, dihydrofuran, tetrahydrothiophene, dihydrothiophene, azepane, tetrahydropyridine and the like; a non-aromatic heterocycle condensed with a benzene ring, such as dihydrobenzofuran, dihydrobenzothiophene and the like, and the like can be mentioned.

Of the above-mentioned rings, a benzene ring, a pyrazole ring, an indane ring and the like are preferable, and a benzene ring is particularly preferable.

The ring for ring B is not a thiazole ring and an oxazole ring.

When W is a bond, then ring B should be an optionally substituted non-aromatic ring condensed with a benzene ring (the ring is not a tetrahydroquinoline ring). As used herein, as the non-aromatic ring condensed with a benzene ring, the aforementioned alicyclic hydrocarbon condensed with a benzene ring and non-aromatic heterocycle condensed with a benzene ring can be mentioned. The non-aromatic ring condensed with a benzene ring is preferably an indane ring, a dihydrobenzofuran ring and the like, particularly preferably an indane ring.

The ring for ring B or ring B' optionally has 1 to 5 substituents, preferably 1 to 3 substituents, at substitutable position(s). As the "substituent", those exemplarily recited as the substituents of the aforementioned "optionally substituted $C_{3-8}$ cycloalkyl group" can be used. When the ring has two or more substituents, respective substituents may be the same or different.

The substituents are preferably, (1) a $C_{6-14}$ aryl group optionally substituted by 1 to 3 substituents selected from a $C_{1-6}$ alkoxy-$C_{1-6}$ alkoxy group and the like;

(2) a $C_{7-16}$ aralkyloxy group;

(3) a $C_{1-6}$ alkoxy group optionally substituted by $C_{3-8}$ cycloalkyl group(s);

(4) a $C_{1-6}$ alkyl group;

(5) a $C_{2-6}$ alkenyl group;

(6) a $C_{1-6}$ alkylsulfonyloxy group;

(7) a $C_{1-6}$ alkyl-carbonylamino group;

and the like.

V is a bond or a spacer having 1 to 3 atoms in the main chain (excluding —N═N—). As used herein, the "main chain" is a divalent straight chain connecting Ar and ring B, and the atom number of the main chain is counted such that the number of atoms in the main chain will be minimum. The "main chain" consists of 1 to 3 atoms selected from a carbon atom and a hetero atom (e.g., oxygen atom, sulfur atom, nitrogen atom and the like), and may be saturated or unsaturated. Sulfur atom may be oxidized and —N═N— is excluded.

Specific examples of the "spacer having 1 to 3 atoms in the main chain" include a saturated chain such as —$(CH_2)_k$— (k=an integer of 1 to 3); —$(CH_2)_{k11}$—O—$(CH_2)_{k12}$— (k11 and k12 are each independently an integer of 0 to 2 and k11+k12=an integer of 1 or 2) (e.g., —$OCH_2$—, —$CH_2O$— etc.); —$(CH_2)_{k21}$—$S(O)_{k23}$—$(CH_2)_{k22}$— (k21 and k22 are each independently an integer of 0 to 2 and k21+k22=an integer of 1 or 2, and k23 is an integer of 0 to 2); —$(CH_2)_{k31}$—$(NH)_{k32}$—$(CH_2)_{k33}$— (k31 and k33 are each independently an integer of 0 to 2, k32 is an integer of 1 or 2, and k31+k32+k33=an integer of 1 to 3); and the like, and a chain derived from said saturated chain, which has been partly or entirely unsaturated (e.g., —CH═CH—, —N═CH—, —CH═N— etc.). The carbon atom and nitrogen atom constituting the main chain optionally has one or more substituents at substitutable position(s). When the number of the substituents is not less than 2, respective substituents may be the same or different. As the "substituent", those exemplarily recited as the substituents of the aforementioned "optionally substituted $C_{3-8}$ cycloalkyl group" can be used. Of these, an optionally substituted $C_{1-6}$ alkyl group (preferably, a $C_{1-6}$ alkyl group, a $C_{7-16}$ aralkyl group and the like) and a $C_{6-14}$ aryl group are preferable, and a $C_{1-6}$ alkyl group, a $C_{7-16}$ aralkyl group and a $C_{6-14}$ aryl group are particularly preferable.

V is preferably a bond; —O—; —CH═N—; —$CH_2$—, —$CH_2CH_2$—, —$CH_2O$—, —NH—$CH_2$—, —$CH_2$—NH— or —$CH_2$—NH—$CH_2$—, each of which optionally has substituent(s) selected from a $C_{1-6}$ alkyl group, a $C_{7-16}$ aralkyl group and a $C_{6-14}$ aryl group; and the like.

W is a bond or a $C_{1-6}$ alkylene group optionally substituted by $C_{1-6}$ alkoxy group(s). The "$C_{1-6}$ alkylene group" is a linear or branched chain, for example, methylene, ethylene, 1-methylethylene, propylene, 1-ethylethylene, 1-methylpropylene, 2-methylpropylene, butylene, pentylene, hexylene and the like can be mentioned. The "$C_{1-6}$ alkylene group" optionally has, for example 1 to 3, preferably 1 or 2 "$C_{1-6}$ alkoxy groups" at substitutable position(s).

W is preferably a $C_{1-6}$ alkylene group optionally substituted by $C_{1-6}$ alkoxy group(s), more preferably methylene.

X and Xa are the same or different and each is CH or N, preferably CH.

Y is O or $CR^6R^7$. As used herein, $R^6$ and $R^7$ are the same or different and each is a hydrogen atom, a halogen atom, a $C_{1-6}$ alkyl group or an optionally substituted hydroxy group, or $R^7$ is bonded to $R^{1a}$ to form a 4- to 8-membered ring. When $R^7$ is bonded to $R^{1a}$ to form a 4- to 8-membered ring, then $R^6$ should be a hydrogen atom, a halogen atom, a $C_{1-6}$ alkyl group or an optionally substituted hydroxy group.

As the "optionally substituted hydroxy group", a hydroxy group, a $C_{1-6}$ alkoxy group and the like are preferable.

As the "4- to 8-membered ring" formed by $R^7$ bonded to $R^{1a}$, for example, 4- to 8-membered rings among the rings exemplified for ring B can be mentioned. Of these, benzene, a 5- to 7-membered monocyclic aromatic heterocycle (preferably, furan, thiophene), a 5- to 7-membered monocyclic non-aromatic heterocycle (preferably, dihydrofuran, dihydrothiophene), a cycloalkene having 4 to 8 carbon atoms, a cycloalkadiene having 4 to 8 carbon atoms and the like are preferable. Particularly, a 5- to 7-membered monocyclic aromatic heterocycle (preferably, furan, thiophene) and a 5- to 7-membered monocyclic non-aromatic heterocycle (preferably, dihydrofuran, dihydrothiophene) are preferable.

The partial structural formula:

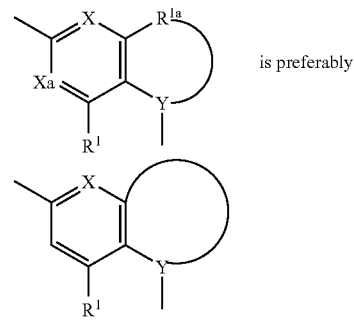

is preferably wherein

X and $R^1$ are as defined above, and

Y is O or $CR^6R^7$ wherein $R^6$ and $R^7$ are the same or different and each is a hydrogen atom, a halogen atom, a $C_{1-6}$ alkyl group or an optionally substituted hydroxy group, or $R^7$ is bonded to the methine group adjacent to X to form a 4- to 8-membered ring.

As the "4- to 8-membered ring" formed by $R^7$ bonded to the methine group adjacent to X, those recited as the aforementioned "4- to 8-membered ring" formed by $R^7$ bonded to $R^{1a}$ can be mentioned.

$R^6$ and $R^7$ are preferably the same or different and each is a hydrogen atom or a hydroxy group, more preferably a hydrogen atom.

$R^1$ and $R^{1a}$ are the same or different and each is a hydrogen atom, a halogen atom, a $C_{1-6}$ alkyl group or a $C_{1-6}$ alkoxy group, preferably a hydrogen atom, a $C_{1-6}$ alkyl group or a halogen atom, particularly preferably a hydrogen atom or a halogen atom (preferably a fluorine atom).

$R^2$ is a hydrogen atom, a $C_{1-6}$ alkyl group or an optionally substituted acyl group. As the "optionally substituted acyl group", a $C_{1-6}$ alkyl-carbonyl group; a $C_{6-14}$ arylsulfonyl group optionally substituted by nitro groups; and the like are preferable.

$R^2$ is preferably a hydrogen atom.

$R^3$ and $R^4$ are the same or different and each is a hydrogen atom or a halogen atom, preferably a hydrogen atom.

$R^5$ is an optionally substituted hydroxy group or an optionally substituted amino group, preferably a hydroxy group or a $C_{1-6}$ alkoxy group, more preferably a hydroxy group.

Compound (1) or a salt thereof does not comprise methyl 3-[4-[[3-(tetrahydropyran-2-yloxy)benzyl]-(2,4,6-trimethyl-benzenesulfonyl)amino]phenyl]propionate.

Compound (1') is preferably compound (1).

As preferable examples of compound (1), the following compounds can be mentioned.

[Compound A]

A compound wherein

Ar is phenyl, naphthyl, thiazolyl, pyrazolyl, indolyl or dihydroquinolinyl, each of which optionally has 1 to 3 substituents selected from an optionally substituted $C_{1-6}$ alkyl group (preferably a $C_{1-6}$ alkyl group optionally substituted by 1 to 3 substituents selected from an optionally halogenated $C_{1-6}$ alkoxy group, a $C_{6-14}$ aryl group and the like);

a $C_{6-14}$ aryl group optionally substituted by 1 to 3 substituents selected from a halogen atom and the like;

a $C_{7-16}$ aralkyloxy group; and an optionally substituted $C_{1-6}$ alkoxy group (preferably a $C_{1-6}$ alkoxy group optionally substituted by 1 to 3 substituents selected from an optionally halogenated $C_{1-6}$ alkoxy group, a $C_{3-8}$ cycloalkyl group and the like);

ring B is a benzene ring or a pyrazole ring, each of which optionally has 1 to 3 substituents selected from a $C_{6-14}$ aryl group optionally substituted by 1 to 3 substituents selected from a $C_{1-6}$ alkoxy-$C_{1-6}$ alkoxy group and the like;

a $C_{7-16}$ aralkyloxy group; and a $C_{1-6}$ alkoxy group;

V is a bond; —$CH_2$—; —$CH_2O$—; —NH—$CH_2$— or —$CH_2$—NH—, each of which optionally has substituent(s) selected from a $C_{1-6}$ alkyl group and a $C_{7-16}$ aralkyl group; or —CH=N—;

W is a $C_{1-6}$ alkylene group (preferably methylene);

X is CH or N;

Xa is CH;

Y is O or $CR^6R^7$ wherein $R^6$ and $R^7$ are the same or different and each is a hydrogen atom or a hydroxy group;

$R^1$ is a hydrogen atom or a halogen atom;

$R^{1a}$ is a hydrogen atom;

$R^2$ is a hydrogen atom; a $C_{1-6}$ alkyl group; a $C_{1-6}$ alkyl-carbonyl group; or a $C_{6-14}$ arylsulfonyl group optionally substituted by nitro group(s);

$R^3$ and $R^4$ are the same or different and each is a hydrogen atom or a halogen atom; and $R^5$ is a hydroxy group or a $C_{1-6}$ alkoxy group (preferably a hydroxy group).

[Compound B]

A compound wherein

Ar is phenyl, naphthyl, thiazolyl, pyrazolyl, indolyl or dihydroquinolinyl, each of which optionally has 1 to 3 substituents selected from (1) an optionally substituted $C_{1-6}$ alkyl group (preferably a $C_{1-6}$ alkyl group optionally substituted by 1 to 3 substituents selected from an optionally halogenated $C_{1-6}$ alkoxy group, a $C_{6-14}$ aryl group, a $C_{6-14}$ aryloxy group and the like);

(2) a $C_{6-14}$ aryl group optionally substituted by 1 to 3 substituents selected from a halogen atom, an optionally halogenated $C_{1-6}$ alkyl group and the like;

(3) a $C_{7-16}$ aralkyloxy group;

(4) an optionally substituted $C_{1-6}$ alkoxy group (preferably a $C_{1-6}$ alkoxy group optionally substituted by 1 to 3 substituents selected from
    (a) an optionally halogenated $C_{1-6}$ alkoxy group;
    (b) a $C_{3-8}$ cycloalkyl group;
    (c) a carboxyl group;
    (d) a mono- or di-$C_{1-6}$ alkyl-carbamoyl group;
    (e) a nitrogen-containing heterocyclyl-carbonyl group (preferably morpholinocarbonyl);
    (f) a $C_{1-6}$ alkylthio group;
    (g) a $C_{1-6}$ alkylsulfonyl group;
    (h) a heterocyclic group (preferably furyl, pyridyl, thienyl, pyrazolyl, thiazolyl, oxazolyl, isoxazolyl, isothiazolyl, oxetanyl, morpholinyl, thiomorpholinyl, pyrrolidinyl, oxopyrrolidinyl, dioxopyrrolidinyl, tetrahydropyranyl, tetrahydrothiopyranyl, 1,1-dioxidotetrahydrothiopyranyl) optionally substituted by 1 to 3 substituents selected from a hydroxy group, a $C_{1-6}$ alkyl group, a $C_{1-6}$ alkoxy group and the like;
    (i) an N—$C_{1-6}$ alkyl-N—$C_{1-6}$ alkyl-carbonyl-amino group; and the like);

(5) a hydroxy group;

(6) a $C_{1-6}$ alkylsulfonyloxy group;

(7) a tri-$C_{1-6}$ alkyl-silyloxy group;

(8) a heterocyclyloxy group (preferably pyridyloxy, tetrahydropyranyloxy, tetrahydrothiopyranyloxy, 1,1-dioxidotetrahydrothiopyranyloxy) optionally substituted by 1 to 3 substituents selected from a $C_{1-6}$ alkyl group, a $C_{1-6}$ alkoxy group and the like; and (9) a $C_{1-6}$ alkylsulfonyl group optionally substituted by $C_{1-6}$ alkoxy group(s);

ring B is a benzene ring or a pyrazole ring, each of which optionally has 1 to 3 substituents selected from (1) a $C_{6-14}$ aryl group optionally substituted by 1 to 3 substituents selected from a $C_{1-6}$ alkoxy-$C_{1-6}$ alkoxy group and the like;

(2) a $C_{7-16}$ aralkyloxy group;

(3) a $C_{1-6}$ alkoxy group;

(4) a $C_{1-6}$ alkyl group; and (5) a $C_{2-6}$ alkenyl group;

V is a bond; —$CH_2$—; —O—; —$CH_2O$—; —NH—$CH_2$—, —$CH_2$—NH— or —$CH_2$—NH—$CH_2$—, each of which optionally has substituent(s) selected from a $C_{1-6}$ alkyl group and a $C_{7-16}$ aralkyl group; or —CH=N—;

Y is O or $CR^6R^7$, wherein $R^6$ and $R^7$ are the same or different and each is a hydrogen atom or a hydroxy group, or $R^7$ is bonded to $R^{1a}$ to form a 4- to 8-membered ring (preferably a 5- to 7-membered monocyclic aromatic heterocycle (preferably furan, thiophene) or a 5- to 7-membered monocyclic non-aromatic heterocycle (preferably dihydrofuran, dihydrothiophene));

R¹ is a hydrogen atom, a $C_{1-6}$ alkyl group or a halogen atom;
R¹ᵃ is a hydrogen atom; and
W, X, Xa, R², R³, R⁴ and R⁵ are as defined in the aforementioned [Compound A].

[Compound C]

A compound wherein
ring B is an indane ring which optionally has 1 to 3 substituents selected from (1) a $C_{6-14}$ aryl group optionally substituted by 1 to 3 substituents selected from a $C_{1-6}$ alkoxy-$C_{1-6}$ alkoxy group and the like;

(2) a $C_{7-16}$ aralkyloxy group;

(3) a $C_{1-6}$ alkoxy group;

(4) a $C_{1-6}$ alkyl group; and (5) a $C_{2-6}$ alkenyl group;
W is a bond; and
Ar, V, X, Xa, Y, R¹, R¹ᵃ, R², R³, R⁴ and R⁵ are as defined in the aforementioned [Compound B].

[Compound D]

A compound wherein
Ar is phenyl, naphthyl, thiazolyl, pyrazolyl, pyridyl, indolyl, dihydroquinolinyl, tetrahydroquinolinyl or 1-piperidinyl, each of which optionally has 1 to 3 substituents selected from (1) an optionally substituted $C_{1-6}$ alkyl group (preferably a $C_{1-6}$ alkyl group optionally substituted by 1 to 3 substituents selected from a halogen atom, an optionally halogenated $C_{1-6}$ alkoxy group, a $C_{6-14}$ aryl group, a $C_{6-14}$ aryloxy group and the like);

(2) a $C_{6-14}$ aryl group optionally substituted by 1 to 3 substituents selected from a halogen atom, an optionally halogenated $C_{1-6}$ alkyl group and the like;

(3) a $C_{7-16}$ aralkyloxy group;

(4) an optionally substituted $C_{1-6}$ alkoxy group (preferably a $C_{1-6}$ alkoxy group optionally substituted by 1 to 3 substituents selected from
  (a) an optionally halogenated $C_{1-6}$ alkoxy group;
  (b) a $C_{3-8}$ cycloalkyl group;
  (c) a carboxyl group;
  (d) a mono- or di-$C_{1-6}$ alkyl-carbamoyl group;
  (e) a nitrogen-containing heterocyclyl-carbonyl group (preferably morpholinocarbonyl);
  (f) a $C_{1-6}$ alkylthio group;
  (g) a $C_{1-6}$ alkylsulfonyl group;
  (h) a heterocyclic group (preferably furyl, pyridyl, thienyl, pyrazolyl, thiazolyl, oxazolyl, isoxazolyl, isothiazolyl, oxetanyl, morpholinyl, thiomorpholinyl, pyrrolidinyl, oxopyrrolidinyl, dioxopyrrolidinyl, tetrahydropyranyl, tetrahydrothiopyranyl, 1,1-dioxidotetrahydrothiopyranyl, 1-oxidotetrahydrothiopyranyl) optionally substituted by 1 to 3 substituents selected from a hydroxy group, a $C_{1-6}$ alkyl group, a $C_{1-6}$ alkoxy group and the like;
  (i) an N—$C_{1-6}$ alkyl-N—$C_{1-6}$ alkyl-carbonyl-amino group;
  (j) a mono- or di-$C_{1-6}$ alkylphosphono group;
  and the like);

(5) a hydroxy group;

(6) a $C_{1-6}$ alkylsulfonyloxy group;

(7) a tri-$C_{1-6}$ alkyl-silyloxy group;

(8) a heterocyclyloxy group (preferably pyridyloxy, tetrahydropyranyloxy, tetrahydrothiopyranyloxy, 1,1-dioxidotetrahydrothiopyranyloxy, 1-oxidotetrahydrothiopyranyloxy) optionally substituted by 1 to 3 substituents selected from a $C_{1-6}$ alkyl group, a $C_{1-6}$ alkoxy group and the like;

(9) a $C_{1-6}$ alkylsulfonyl group optionally substituted $C_{1-6}$ alkoxy group(s); and

(10) a $C_{6-14}$ aryloxy group optionally substituted 1 to 3 $C_{1-6}$ alkyl groups;
ring B is a benzene ring or a pyrazole ring, each of which optionally has 1 to 3 substituents selected from (1) a $C_{6-14}$ aryl group optionally substituted by 1 to 3 substituents selected from a $C_{1-6}$ alkoxy-$C_{1-6}$ alkoxy group and the like;

(2) a $C_{7-16}$ aralkyloxy group;

(3) a $C_{1-6}$ alkoxy group optionally substituted by $C_{3-8}$ cycloalkyl group(s);

(4) a $C_{1-6}$ alkyl group;

(5) a $C_{2-6}$ alkenyl group;

(6) a $C_{1-6}$ alkylsulfonyloxy group; and (7) a $C_{1-6}$ alkyl-carbonylamino group;
V is a bond; —O—; —CH=N—; or —CH₂—, —CH₂CH₂—, —CH₂O—, —NH—CH₂—, —CH₂—NH— or —CH₂—NH—CH₂—, each of which optionally has substituent(s) selected from a $C_{1-6}$ alkyl group, a $C_{7-16}$ aralkyl group and a $C_{6-14}$ aryl group;
X and Xa are the same or different and each is CH or N;
R¹ᵃ is a hydrogen atom or a halogen atom; and
W, Y, R¹, R², R³, R⁴ and R⁵ are as defined in the aforementioned [Compound B].

[Compound E]
A compound wherein
ring B is an indane ring which optionally has 1 to 3 substituents selected from (1) a $C_{6-14}$ aryl group optionally substituted by 1 to 3 substituents selected from a $C_{1-6}$ alkoxy-$C_{1-6}$ alkoxy group and the like;

(2) a $C_{7-16}$ aralkyloxy group;

(3) a $C_{1-6}$ alkoxy group optionally substituted by $C_{3-8}$ cycloalkyl group(s);

(4) a $C_{1-6}$ alkyl group;

(5) a $C_{2-6}$ alkenyl group;

(6) a $C_{1-6}$ alkylsulfonyloxy group; and (7) a $C_{1-6}$ alkyl-carbonylamino group;

W is a bond; and

Ar, V, X, Xa, Y, R¹, R¹ᵃ, R², R³, R⁴ and R⁵ are as defined in the aforementioned [Compound D].

[Compound F]
[6-({[4'-(2-ethoxyethoxy)-2',6'-dimethylbiphenyl-3-yl]methyl}amino)-2,3-dihydro-1-benzofuran-3-yl]acetic acid hydrochloride (Example 86);

3-{4-[({4'-[2-(ethylsulfonyl)ethoxy]-2',6'-dimethylbiphenyl-3-yl}methyl)amino]-2-fluorophenyl}propanoic acid methanesulfonate (Example 146);

3-{4-[({2',6'-dimethyl-4'-[3-(2-oxopyrrolidin-1-yl)propoxy]biphenyl-3-yl}methyl)amino]-2-fluorophenyl}propanoic acid benzenesulfonate (Example 149);

3-{2-fluoro-4-[({4'-[(4-hydroxy-1,1-dioxidotetrahydro-2H-thiopyran-4-yl)methoxy]-2',6'-dimethylbiphenyl-3-yl}methyl)amino]phenyl}propanoic acid (Example 188);

3-{4-[({4'-[(1,1-dioxidotetrahydro-2H-thiopyran-4-yl)oxy]-2',6'-dimethylbiphenyl-3-yl}methyl)amino]-2-fluorophenyl}propanoic acid methanesulfonate (Example 204);

3-[4-({[4'-(2-ethoxyethoxy)-2',3',5',6'-tetramethylbiphenyl-3-yl]methyl}amino)-2-fluorophenyl]propanoic acid hydrochloride (Example 231);

3-{4-[(4-(4-[2-(ethylsulfonyl)ethoxy]-2,6-dimethylphenyl)-2,3-dihydro-1H-inden-1-yl)amino]-2-fluorophenyl}propanoic acid hydrochloride (Example 268);

3-[2-fluoro-4-({4-[((3-methylbutyl){4-[4-(trifluoromethyl)phenyl]-1,3-thiazol-2-yl}amino)methyl]benzyl}amino)phenyl]propanoic acid (Example 274);

3-[4-({4-[(3,5-diphenyl-1H-pyrazol-1-yl)methyl]-3-isopropoxybenzyl}amino)-2,6-difluorophenyl]propanoic acid (Example 284); and 3-{2-fluoro-4-[({4'-[(4-hydroxy-1,1-dioxidotetrahydro-2H-thiopyran-4-yl)methoxy]-2',6,6'-trimethylbiphenyl-3-yl}methyl)amino]phenyl}propanoic acid calcium salt (Example 314).

As a salt of compound (1) and compound (1') (unless otherwise specified, these are referred to as compound (I)) used in the present invention, for example, metal salts, an ammonium salt, salts with organic bases, salts with inorganic acids, salts with organic acids, salts with basic or acidic amino acids and the like.

Here, preferable examples of the metal salt include alkali metal salts such as sodium salt, potassium salt and the like; alkaline earth metal salts such as calcium salt, magnesium salt, barium salt and the like. Preferable examples of the salt with organic base include a salt with trimethylamine, triethylamine, pyridine, picoline, 2,6-lutidine, ethanolamine, diethanolamine, triethanolamine, cyclohexylamine, dicyclohexylamine, N,N-dibenzylethylenediamine and the like. Preferable examples of the salt with inorganic acid include a salt with hydrochloric acid, hydrobromic acid, nitric acid, sulfuric acid, phosphoric acid and the like. Preferable examples of the salt with organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include a salt with arginine, lysin, ornithine and the like. Preferable examples of the salt with acidic amino acid include a salt with aspartic acid, glutamic acid and the like.

Of these, a pharmacologically acceptable salt is preferable. For example, when compound (I) has an acidic functional group, metal salts such as alkali metal salts, alkaline earth metal salts and the like; an ammonium salt and the like are preferable, and when compound (I) has basic functional group, salts with inorganic acid and salts with organic acid are preferable.

A prodrug of compound (I) is a compound that converts to compound (I) due to the reaction by enzyme, gastric acid and the like under the physiological conditions in the body; that is, a compound that converts to compound (I) by enzymatic oxidation, reduction; hydrolysis and the like, and a compound that converts to compound (I) by hydrolysis and the like by gastric acid and the like.

Examples of a prodrug of compound (I) include a compound herein an amino group of compound (I) is acylated, alkylated or phosphorylated (e.g., compound wherein amino group of compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated or tert-butylated, and the like); a compound wherein a hydroxy group of compound (I) is acylated, alkylated, phosphorylated or borated (e.g., a compound wherein a hydroxy group of compound (I) is acetylated, palmitoylated, propanoylated, pivaloylated, succinylated, fumarylated, alanylated or dimethylaminomethylcarbonylated, and the like); a compound wherein a carboxyl group of compound (I) is esterified or amidated (e.g., a compound wherein a carboxyl group of compound (I) is $C_{1-6}$ alkyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified or methylamidated, and the like) and the like. Of these, a compound wherein a carboxyl group of compound (I) is esterified by $C_{1-6}$ alkyl group such as methyl, ethyl, tert-butyl and the like is preferable. These compounds can be produced from compound (I) by a method known per se.

A prodrug of compound (I) may be a compound that converts to compound (I) under physiological conditions as described in Development of Pharmaceutical Products, vol. 7, Molecule Design, 163-198, Hirokawa Shoten (1990).

Hereinafter the production methods of the compound (I) are explained.

Each symbol of the compounds in the schematic drawings of the following schemes is as defined above unless particularly described. Each compound described in the schemes may form a salt as long as it does not inhibit the reaction, and as such salt, those similar to the salts of compound (I) can be mentioned.

The compound obtained in each step can also be used as a crude product in the form of a reaction mixture in the next reaction, or can be isolated from the reaction mixture according to a conventional method, and further purified easily by a separation method such as recrystallization, distillation, chromatography and the like.

Compound (I) (e.g., compounds represented by the formulas (Ia), (Ia'), (Ib') and (Ic') (to be abbreviated as compound (Ia), compound (Ia'), compound (Ib') and compound (Ic'), respectively)) can be produced, for example, according to the method as shown in the following Scheme 1 or a method analogous thereto.

Scheme 1

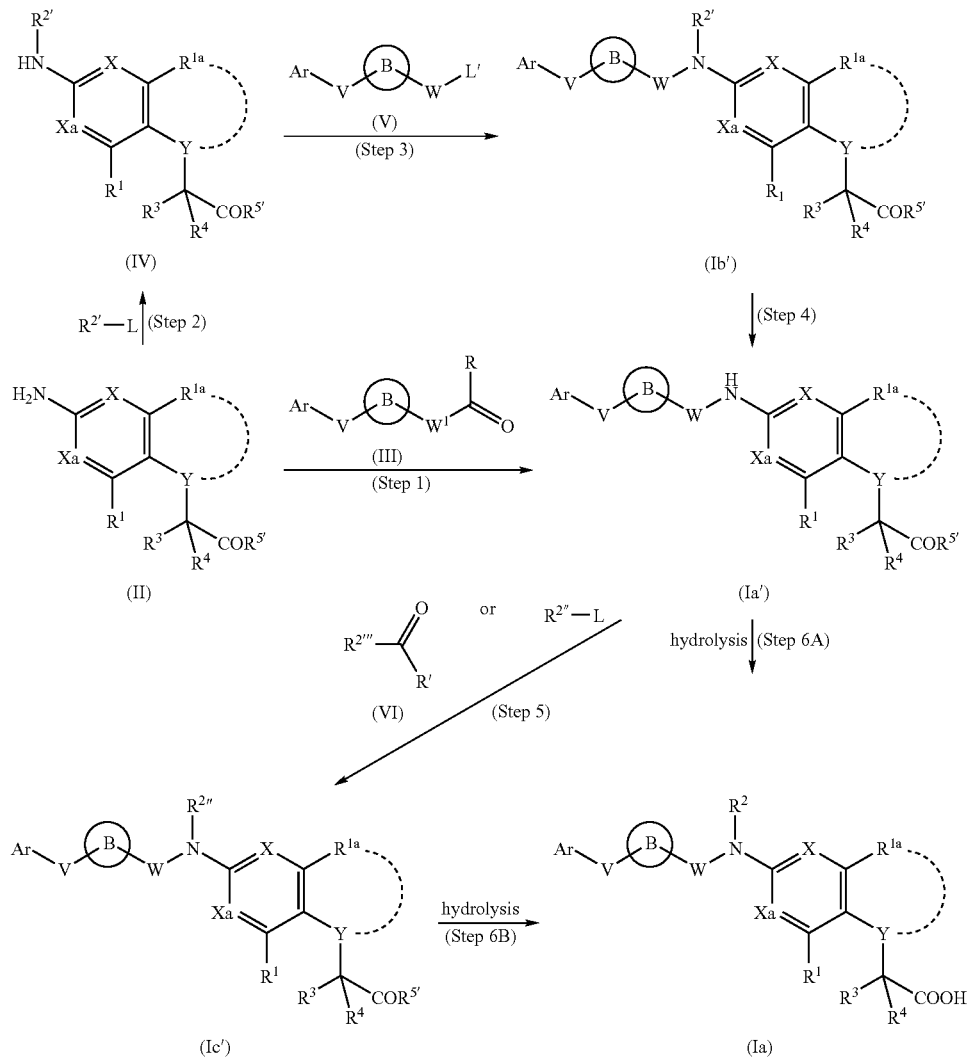

<Step 1>

Compound (Ia') can be produced by reacting a compound represented by the formula (II) with a compound represented by the formula (III) (to be abbreviated compound (II) and compound (III), respectively).

When W in compound (Ia') is a bond, this step is performed using a compound represented by formula:

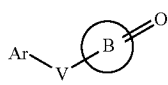         (III'')

(to be abbreviated compound (III'')) instead of compound (III).

In Step 1, $R^{5'}$ is an optionally substituted $C_{1-6}$ alkoxy group, $W^1$ is a bond or a $C_{1-5}$ alkylene group, R is a hydrogen atom or a $C_{1-5}$ alkyl group, and the other symbols are as defined above.

As the $C_{1-5}$ alkylene group for $W^1$, of the $C_{1-6}$ alkylene groups exemplarily recited for W, one having 1 to 5 carbon atoms can be mentioned.

As the $C_{1-5}$ alkyl group for R, for example, methyl, ethyl, propyl, isopropyl, butyl, isobutyl, sec-butyl, tert-butyl, pentyl, isopentyl, neopentyl and the like can be mentioned.

Compound (Ia') can be produced by subjecting compound (II) and compound (III) to a reductive amination reaction (for example, the methods described in Jikken Kagaku Kouza, the 4th Edition, vol. 20, pages 282-284 and 366-368 (The Chemical Society of Japan ed.); Journal of the American Chemical Society, vol. 93, pages 2897-2904, 1971; Synthesis, page 135, 1975, and the like). In the reductive amination reaction, compound (II) and compound (III) are subjected to a dehydration reaction to give an imine form, and the imine form is subjected to a reduction reaction to give compound (Ia').

The dehydration reaction is promoted by the addition of a dehydrating agent (e.g., molecular sieve and the like), or a catalyst (e.g., zinc chloride, phosphoryl chloride, boron trifluoride, titanium tetrachloride and the like) to the reaction system.

The reduction reaction is generally carried out using a reducing agent according to a conventional method. As the reducing agent, for example, metal hydrides such as aluminum hydride, diisobutyl aluminum hydride, tributyltin hydride and the like; metal hydride complex compounds such as sodium cyanoborohydride, sodium triacetoxyborohydride, sodium borohydride, lithium aluminum hydride and the like; borane complex such as borane-tetrahydrofuran complex, borane-dimethylsulfide complex and the like; alkylboranes such as thexylborane, disiamylborane and the like; diborane; metals such as zinc, aluminum, tin, iron and the like; alkali metals (e.g., sodium, lithium and the like)/liquid ammonia (Birch reduction) and the like can be mentioned. The amount of the reducing agent to be used is appropriately determined depending on the kind of the reducing agent. For example, the amount of the metal hydride, metal hydride complex compound, borane complex, alkyl boran or diborane to be used is about 0.25 to about 10 mol, preferably about 0.5 to about 5 mol, per 1 mol of compound (II), respectively, and the amount of the metal (containing alkali metal used for Birch reduction) to be used is about 1 to about 20 mol, preferably about 1 to about 5 mol, per 1 mol of compound (II).

The reduction reaction can also be carried out by a hydrogenation reaction. In this case, for example, catalysts such as palladium carbon, palladium black, platinum dioxide, Raney-nickel, Raney-cobalt and the like can be used. The amount of the catalyst to be used is about 5 to about 1000 wt %, preferably about 10 to about 300 wt %, per 1 mol of compound (II). The hydrogenation reaction can also be carried out using various hydrogen sources instead of gaseous hydrogen. As the hydrogen source, for example, formic acid, ammonium formate, triethylammonium formate, sodium phosphinate, hydrazine and the like can be mentioned. The amount of the hydrogen source to be used is about 1 to about 10 mol, preferably about 1 to about 5 mol, per 1 mol of compound (II).

This reaction is advantageously carried out using a solvent inert to the reaction. While the solvent is not particularly limited as long as the reaction proceeds, for example, solvents such as alcohols (e.g., methanol, ethanol, 1-propanol, 2-propanol, tert-butanol and the like); ethers (e.g., diethyl ether, diisopropyl ether, diphenyl ether, tetrahydrofuran, 1,4-dioxane, 1,2-dimethoxyethane and the like); aromatic hydrocarbons (e.g., benzene, toluene and the like); saturated hydrocarbons (e.g., cyclohexane, hexane and the like); amides (e.g., N,N-dimethylformamide, N,N-dimethylacetamide, hexamethylphosphoramide and the like); organic acids (e.g., formic acid, acetic acid, propanoic acid, trifluoroacetic acid, methanesulfonic acid and the like), and the like, a mixed solvent thereof and the like are preferable.

While the reaction time varies depending on the reagent and solvent to be used, it is generally about 10 min to about 100 hr, preferably about 30 min to about 50 hr. The reaction temperature is generally about −20 to about 100° C., preferably about 0 to about 80° C.

The amount of compound (III) to be used is about 0.5 to about 5 mol, preferably about 1 to about 2 mol, per 1 mol of compound (II).

The reaction of compound (II) with compound (III″) is carried out in the same manner as in the reaction of compound (II) with compound (III).

<Step 2>

A compound represented by the formula (IV) (to be abbreviated compound (IV)) can be produced by reacting compound (II) with a compound represented by formula: $R^{2'}$—La (to be abbreviated compound $R^{2'}$-L).

In Step 2, $R^{2'}$ is an acyl group, L is a leaving group, and the other symbols are as defined above.

As the acyl group for $R^{2'}$, for example, a substituted sulfonyl group (e.g., 2-nitrobenzenesulfonyl, 4-nitrobenzenesulfonyl, 2,4-dinitrobenzenesulfonyl, methanesulfonyl, ethanesulfonyl, benzenesulfonyl, p-toluenesulfonyl and the like), a substituted carbonyl group (e.g., trichloroacetyl, trifluoroacetyl and the like), and the like can be mentioned.

As the leaving group for L, for example, a halogen atom (e.g., fluorine, chlorine, bromine, iodine), an optionally halogenated $C_{1-6}$ alkylsulfonyloxy group (e.g., methanesulfonyloxy, ethanesulfonyloxy, trichloromethanesulfonyloxy, trifluoromethanesulfonyloxy), a $C_{6-10}$ arylsulfonyloxy group optionally having substituent(s) (e.g., a $C_{6-10}$ arylsulfonyloxy group (e.g., phenylsulfonyloxy, naphthylsulfonyloxy) optionally having 1 to 3 substituents selected from a $C_{1-6}$ alkyl group (e.g., methyl, ethyl), a $C_{1-6}$ alkoxy group (e.g., methoxy, ethoxy) and nitro, and the like; as specific examples, phenylsulfonyloxy group, m-nitrophenylsulfonyloxy group, p-toluenesulfonyloxy group and the like), an acyloxy group (e.g., trichloroacetoxy, trifluoroacetoxy and the like), and the like can be mentioned.

Compound (IV) can be produced according to a method known per se, for example, by reacting compound (II) with compound $R^{2'}$-L in the presence of a base.

As the base, for example, alkali metal hydroxides such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate, cesium carbonate and the like; organic bases such as trimethylamine, triethylamine, diisopropylethylamine, pyridine, picoline, lutidine, 4-dimethylaminopyridine, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like, and the like can be mentioned.

This reaction is advantageously carried out using a solvent inert to the reaction. While the solvent is not particularly limited as long as the reaction proceeds, for example, solvents such as ethers (e.g., diethyl ether, diisopropyl ether, diphenyl ether, tetrahydrofuran, 1,4-dioxane, 1,2-dimethoxyethane and the like); aromatic hydrocarbons (e.g., benzene, toluene and the like); saturated hydrocarbons (e.g., cyclohexane, hexane and the like); amides (e.g., N,N-dimethylformamide, N,N-dimethylacetamide, hexamethylphosphoramide and the like); halogenated hydrocarbons (e.g., dichloromethane, chloroform, carbon tetrachloride, 1,2-dichloroethane and the like); nitriles (e.g., acetonitrile, propionitrile and the like); ketones (e.g., acetone, ethyl methyl ketone and the like); sulfoxides (e.g., dimethyl sulfoxide and the like), and the like, a mixed solvent thereof and the like are preferable.

While the reaction time varies depending on the reagent and solvent to be used, it is generally about 10 min to about 100 hr, preferably about 30 min to about 50 hr. The reaction temperature is generally about −30 to about 100° C., preferably about 0 to about 80° C.

The amount of compound $R^{2'}$-L to be used is about 0.5 to about 5 mol, preferably about 1 to about 3 mol, per 1 mol of compound (II). The amount of the base to be used is about 1 to about 10 mol, preferably about 1 to about 3 mol, per 1 mol of compound (II).

<Step 3>

Compound (Ib') can be produced by reacting compound (IV) with a compound represented by the formula (V) (to be abbreviated compound (V)).

In Step 3, L' is a leaving group or a hydroxy group, and the other symbols are as defined above. As the leaving group for L', those exemplarily recited for L can be used.

(i) When L' is a hydroxy group, compound (Ib') can be produced by subjecting compound (IV) and compound (V) to the Mitsunobu reaction (for example, described in Synthesis, pages 1-27, 1981; Tetrahedron Lett., vol. 36, pages 6373-6374, 1995; Tetrahedron Lett., vol. 38, pages 5831-5834, 1997, and the like). In the reaction, compound (IV) is reacted with compound (V) in the presence of an azodicarboxylate (e.g., diethyl azodicarboxylate, diisopropyl azodicarboxylate, 1,1'-(azodicarbonyl)dipiperidine and the like) and a phosphine (e.g., triphenylphosphine, tributylphosphine and the like).

This reaction is advantageously carried out using a solvent inert to the reaction. As the solvent, those exemplarily recited in Step 2 can be used.

The reaction time is generally 5 min to 100 hr, preferably 30 min to 72 hr. The reaction temperature is generally −20 to 200° C., preferably 0 to 100° C.

The amount of compound (V) to be used is about 1 to about 5 mol, preferably about 1 to about 2 mol, per 1 mol of compound (IV).

The amount of each of the azodicarboxylate and phosphine to be used is about 1 to about 5 mol, preferably about 1 to about 2 mol, per 1 mol of compound (IV).

(ii) When L' is a leaving group, compound (Ib') can be produced by reacting compound (IV) with compound (V) in the presence of a base.

As the base, for example, alkali metal hydroxides such as lithium hydroxide, sodium hydroxide, potassium hydroxide and the like; alkaline earth metal hydroxides such as barium hydroxide and the like; alkali metal carbonates such as sodium carbonate, potassium carbonate, cesium carbonate and the like; alkali metal hydrogencarbonates such as sodium hydrogencarbonate and the like; acetates such as sodium acetate, ammonium acetate and the like; aromatic amines such as pyridine, lutidine and the like; tertiary amines such as triethylamine, tripropylamine, tributylamine, N-ethyldiisopropylamine, cyclohexyldimethylamine, 4-dimethylaminopyridine, N,N-dimethylaniline, N-methylpiperidine, N-methylpyrrolidine, N-methylmorpholine and the like; alkali metal hydrides such as sodium hydride, potassium hydride and the like; metal amides such as sodium amide, lithium diisopropylamide, lithium hexamethyldisilazide and the like; alkali metal alkoxides having 1 to 6 carbon atoms, such as sodium methoxide, sodium ethoxide, sodium tert-butoxide, potassium tert-butoxide and the like, and the like can be mentioned.

This reaction is advantageously carried out using a solvent inert to the reaction. As the solvent, those exemplarily recited in Step 2 can be used.

The amount of compound (V) to be used is about 0.8 to about 10 mol, preferably about 0.9 to about 2 mol, per 1 mol of compound (IV). The amount of the base to be used is about 1 to about 10 mol, preferably about 1 to about 3 mol, per 1 mol of compound (IV).

The reaction time is generally 10 min to 12 hr, preferably 20 min to 6 hr. The reaction temperature is generally −70 to 150° C., preferably −20 to 100° C.

<Step 4>

Compound (Ia') can be produced by eliminating $R^{2'}$ of compound (Ib').

Compound (Ia') can be produced, for example, according to the methods described in Tetrahedron Lett., vol. 36, pages 6373-6374, 1995; Tetrahedron Lett., vol. 38, pages 5831-5834, 1997; Journal of Synthetic Organic Chemistry, Japan, vol. 59, pages 779-789, 2001; and the like, or a method analogous thereto, or by deprotection known per se.

For example, when $R^{2'}$ is a 2-nitrobenzenesulfonyl group, a 4-nitrobenzenesulfonyl group or a 2,4-dinitrobenzenesulfonyl group, compound (Ib') is reacted with a thiol (e.g., thiophenol, benzylmercaptan, mercaptoacetic acid, 2-mercaptoethanol and the like) in the presence of a base, or reacted with a large excess amount of an amine (e.g., methylamine, ethylamine, propylamine, butylamine and the like).

As the base, those exemplarily recited in Step 2 can be used.

This reaction is advantageously carried out using a solvent inert to the reaction. As the solvent, those exemplarily recited in Step 2 can be used. As the preferable solvent in this step, for example, amides (e.g., N,N-dimethylformamide, N,N-dimethylacetamide, hexamethylphosphoramide and the like); halogenated hydrocarbons (e.g., dichloromethane, chloroform, carbon tetrachloride, 1,2-dichloroethane and the like); nitrites (e.g. acetonitrile, propionitrile and the like), and the like can be mentioned.

The amount of the thiol to be used is about 1 to about 10 mol, preferably about 1 to about 3 mol, per 1 mol of compound (Ib'). The amount of the base to be used is about 1 to about 10 mol, preferably about 2 to about 6 mol, per 1 mol of compound (Ib').

The amount of the amine to be used is about 5 to about 100 mol, preferably about 10 to about 30 mol, per 1 mol of compound (Ib').

The reaction time is generally 1 min to 24 hr, preferably 5 min to 6 hr. The reaction temperature is generally −20 to 150° C., preferably −10 to 100° C.

<Step 5>

Compound (Ic') can be produced by reacting compound (Ia') with a compound represented by the formula: $R^{2''}$-L (to be abbreviated compound $R^{2''}$-L) or a compound represented by the formula (VI) (to be abbreviated compound (VI)).

In Step 5, in the formula, $R^{2''}$ is a $C_{1-6}$ alkyl group or an optionally substituted acyl group, $R^{2'''}$ is a $C_{1-5}$ alkyl group, R' is a hydrogen atom or a $C_{1-4}$ alkyl group, and the other symbols are as defined above.

As the $C_{1-5}$ alkyl group for $R^{2'''}$, those exemplarily recited for R can be used.

As the $C_{1-4}$ alkyl group for R', for example, methyl, ethyl, propyl, isopropyl, butyl, isobutyl, sec-butyl, tert-butyl and the like can be mentioned.

Compound (Ic') wherein $R^{2''}$ is a $C_{1-6}$ alkyl group can be produced by reacting compound (Ia') with compound $R^{2''}$-L in the same manner as in the reaction, as shown in Step 3, of compound (IV) with compound (V) wherein L' is a leaving group, or by reacting compound (Ia') with compound (VI) in the same manner as in the reductive amination reaction, as shown in Step 1, of compound (II) and compound (III).

Compound (Ic') wherein $R^{2''}$ is an acyl group can be produced by reacting compound (Ia') with compound $R^{2''}$-L in the same manner as in Step 2.

<Step 6A>

Compound (Ia) wherein $R^2$ is a hydrogen atom can be produced by subjecting compound (Ia') to hydrolysis.

The hydrolysis is carried out using an acid or a base according to a conventional method.

As the acid, for example, mineral acids such as hydrochloric acid, sulfuric acid and the like; Lewis acids such as boron trichloride, boron tribromide and the like; organic acids such as trifluoroacetic acid, p-toluenesulfonic acid and the like, and the like can be mentioned. The Lewis acid can be used in combination with a thiol or a sulfide.

As the base, for example, alkali metal hydroxides such as lithium hydroxide, sodium hydroxide, potassium hydroxide, and the like; alkaline earth metal hydroxides such as barium hydroxide and the like; alkali metal carbonates such as sodium carbonate, potassium carbonate and the like; alkali metal alkoxides having 1 to 6 carbon atoms, such as sodium methoxide, sodium ethoxide, potassium tert-butoxide and the like; organic bases (including hydrates thereof) such as triethylamine, imidazole, formamidine and the like, and the like can be mentioned. The amount of the acid or base to be used is about 0.5 to about 10 mol, preferably about 0.5 to about 6 mol, per 1 mol of compound (Ia').

The hydrolysis is carried out without a solvent or in a solvent inert to the reaction. While the solvent is not particularly limited as long as the reaction proceeds, for example, solvents such as alcohols (e.g., methanol, ethanol, propanol and the like); aromatic hydrocarbons (e.g., benzene, toluene and the like); saturated hydrocarbons (e.g., cyclohexane, hexane and the like); organic acids (e.g., formic acid, acetic acid and the like); ethers (e.g., tetrahydrofuran, 1,4-dioxane, 1,2-dimethoxyethane and the like); amides (e.g., N,N-dimethylformamide, N,N-dimethylacetamide and the like); halogenated hydrocarbons (e.g., dichloromethane, chloroform, carbon tetrachloride, 1,2-dichloroethane and the like); nitriles (e.g., acetonitrile, propionitrile and the like); ketones (e.g., acetone, methyl ethyl ketone and the like); sulfoxides (e.g., dimethyl sulfoxide and the like); water and the like, a mixed solvent thereof and the like are preferable.

The reaction time is generally 10 min to 100 hr, preferably 10 min to 24 hr. The reaction temperature is generally −10 to 200° C., preferably 0 to 120° C.

<Step 6B>

Compound (Ia) wherein $R^2$ is $R^{2'''}$, i.e., a $C_{1-6}$ alkyl group or an optionally substituted acyl group can be produced by subjecting compound (Ic') to hydrolysis.

The hydrolysis can be carried out in the same manner as in Step 6A, or according to a method analogous thereto.

Compounds (II), (III), (III''), (V), (VI), $R^{2'}$-L and $R^{2'''}$-L, which are used in Scheme 1, are easily commercially available, or can also be produced according to a method known per se or a method analogous thereto.

For example, compound (II'), which is compound (II) wherein Y is $CHR^6$ and $R^4$ is a hydrogen atom, for example, can be produced according to a method as shown in Scheme 2A or a method analogous thereto.

Scheme 2A

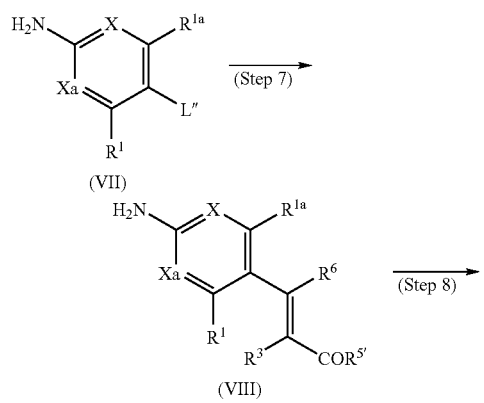

(VII)

(VIII)

-continued

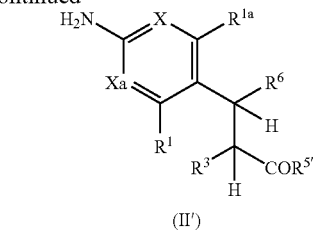

(II')

wherein L'' is a leaving group, and the other symbols are as defined above.

<Step 7>

A compound represented by the formula (VIII) (compound (VIII) to be abbreviated) can be produced by subjecting a compound represented by the formula (VII) (compound (VII) to be abbreviated) to the Heck reaction.

As the leaving group for L'', those exemplarily recited for L can be used. As preferable leaving group in this step, a halogen atom, trifluoromethanesulfonyloxy group and the like can be mentioned.

Compound (VIII) can be produced using compound (VII) according to method known per se, for example, the method described in Org. Reactions, vol. 27, pages 345-390, 1982, or a method analogous thereto. Compound (VIII) can be produced, for example, by reacting compound (VII) with an α,β-unsaturated ester in the presence of a palladium catalyst and a base.

As the α,β-unsaturated ester, for example, methyl acrylate, ethyl acrylate, butyl acrylate, methyl crotonate and the like can be used.

As the palladium catalyst, palladium(II) acetate, palladium (II) chloride, dichlorobis(triphenylphosphine)palladium(II), dibromobis(triphenylphosphine)palladium(II), diiodobis (triphenylphosphine)palladium(II), dichlorobis(tritolylphosphine)palladium(II), chlorophenylbis(triphenylphosphine) palladium(II) and the like can be used.

The amount of the palladium catalyst to be used is about 0.000001 to about 5 mol, preferably about 0.0001 to about 1 mol, per 1 mol of compound (VII).

This reaction may be advantageously carried out in the co-presence of a phosphine ligand in an amount of about 1 to 50 mol, preferably about 2 to 20 mol, relative to the palladium catalyst. As the phosphine ligand, for example, triarylphosphines such as triphenylphosphine, tris(2-methylphenyl) phosphine and the like; bis(diarylphosphino)alkyl analogues such as 1,2-bis(diphenylphosphino)ethane, 1,3-bis(diphenylphosphino)propane, 1,4-bis(diphenylphosphino)butane and the like, and the like can be used.

As the base, for example, secondary amines such as diethylamine, dicyclohexylamine and the like; tertiary amines such as triethylamine, tributylamine, tetramethylethylenediamine and the like; carbonates such as sodium carbonate, potassium carbonate, sodium hydrogencarbonate and the like, and the like can be used.

This reaction is advantageously carried out using a solvent inert to the reaction. As the solvent, those exemplarily recited in Step 2 can be used. As the preferable solvent in this step, amides such as N,N-dimethylformamide, N-methylpyrrolidinone, hexamethylphosphoramide and the like; nitrites such as acetonitrile, propionitrile and the like, and the like can be mentioned.

This reaction is preferably carried out in an inert gas (e.g., argon and the like).

The amount of each of the acrylate and base to be used is generally about 1 to about 10 mol, preferably about 1 to about 3 mol, per 1 mol of compound (VII).

While the reaction time varies depending on the amount and kind of the reagent, catalyst, base and reaction solvent to be used and the reaction temperature, it is generally 1 to 100 hr, preferably 5 to 80 hr. The reaction temperature is generally 10 to 200° C., preferably 20 to 150° C.

<Step 8>

Compound (II') can be produced by subjecting compound (VIII) to a hydrogenation reaction.

The hydrogenation reaction can be carried out in the same manner as in the hydrogenation reaction as shown in Step 1.

Compound (II''), which is compound (II) wherein Y is $CHR^7$, can be produced, for example, according to the method as shown in Scheme 2B, or a method analogous thereto.

a triphenylphosphine ylide, as a single E- or Z-configurational isomer or a configurational isomer mixture of E form and Z form.

This step can be performed according to a method known per se, for example, the methods described in J. Chem. Soc. Perkin Trans. 1, pages 2895-2900, 1996, and the like, or a method analogous thereto.

As the alkylphosphonic acid diester or triphenylphosphine ylide, for example, ethyl diethylphosphonoacetate, tert-butyl diethylphosphonoacetate, ethyl diethylphosphono-2-fluoro-acetate, (carboethoxymethylene)triphenylphosphorane, (tert-butoxycarbonylmethylene)triphenylphosphorane and the like can be used.

The amount of the alkylphosphonic acid diester or triphenylphosphine ylide to be used is about 1 to about 3 mol, preferably about 1 to about 2 mol, per 1 mol of compound (IX).

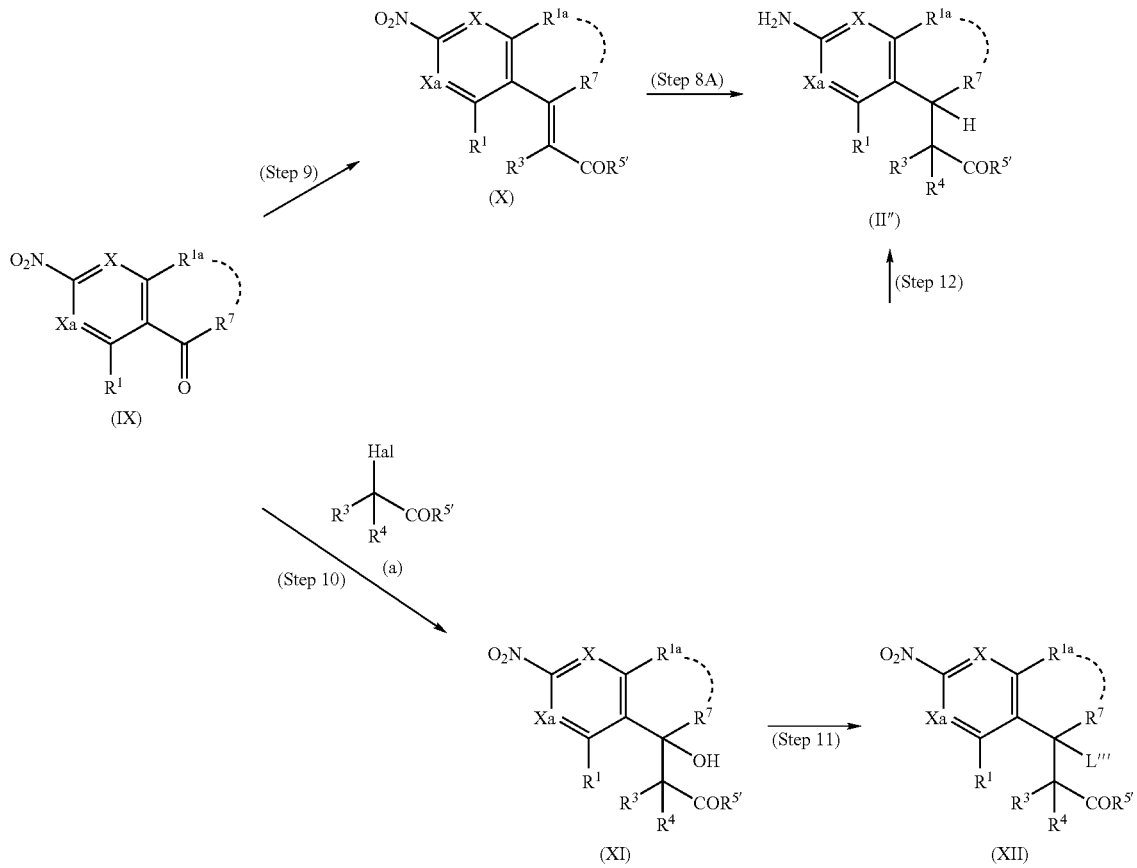

wherein L''' is a leaving group, and the other symbols are as defined above.

<Step 9>

A compound represented by the formula (X) (to be abbreviated compound (X)) can be produced by reacting a compound represented by the formula (IX) (to be abbreviated compound (IX)) with (i) a phosphonato carbanion produced by treating an alkylphosphonic acid diester with a base, or (ii)

As the base, for example, alkali metal hydrides such as sodium hydride, potassium hydride and the like; alkali metal hydroxides such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate and the like; alkali metal hydrogencarbonates such as sodium hydrogencarbonate, potassium hydrogencarbonate and the like; alkali metal alkoxides having 1 to 6 carbon atoms, such as sodium methoxide, sodium ethoxide, sodium tert-butoxide and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like; organic lithiums such as methyllithium, n-butyllithium, sec-butyllithium, tert-butyllithium and the like; lithium amides (including hydrates thereof) such as lithium diisopropylamide and the like, and the like can be mentioned.

The amount of the base to be used is about 1 to about 5 mol, preferably about 1 to about 2 mol, per 1 mol of compound (IX).

This reaction is advantageously carried out using a solvent inert to the reaction. As the solvent, those exemplarily recited in Step 2 can be used.

The reaction time is generally 1 hr to 50 hr, preferably 1 hr to 10 hr. The reaction temperature is generally −78 to 200° C., preferably 0 to 150° C.

<Step 8A>

Compound (II″) wherein $R^4$ is a hydrogen atom can be produced by subjecting compound (X) to a hydrogenation reaction.

pages 878-881, 1974, and the like, or a method analogous thereto.

<Step 12>

Compound (II″) can be produced by eliminating L‴ of compound (XII) under the conditions for a catalytic reduction reaction.

This step is performed according to a method known per se, for example, the methods described in J. Org. Chem., vol. 39, pages 878-881, 1974, and the like, or a method analogous thereto.

Compound (II) wherein Y is O can be produced according to method known per se, for example, the methods described in J. Med. Chem., vol. 43, pages 3052-3066, 2000, and the like, or a method analogous thereto.

Compound (III′), which is compound (III) wherein V is $V^1$ ($V^1$ is a bond, an optionally substituted $C_{1-3}$ alkylene group, $—W^3—N(R^4)—W^2—$, $—W^3—O—W^2—$ or $—W^3—S(O)_{k23}—W^2—$) can be produced, for example, according to the method as shown in Scheme 3 or a method analogous thereto.

As the "optionally substituted $C_{1-3}$ alkylene group" for $V^1$, for example, methylene, ethylene or propylene, each of which optionally has 1 or 2 substituents exemplarily recited as the substituents of V, can be mentioned.

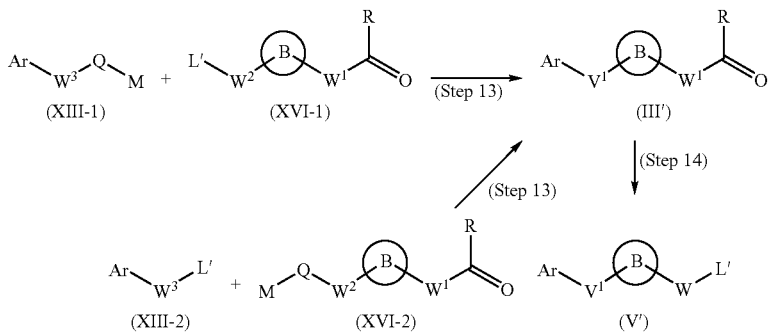

Scheme 3

The hydrogenation reaction can be carried out in the same manner as in the hydrogenation reaction as shown in Step 1.

<Step 10>

A compound represented by the formula (XI) (to be abbreviated compound (XI)) can be produced by subjecting compound (IX) and a compound represented by the formula (a) (to be abbreviated compound (a)) to the Reformatsky reaction.

Hal is a halogen atom (e.g., chlorine, bromine).

The Reformatsky reaction can be carried out according to a method known per se, for example, the methods described in J. Med. Chem., vol. 41, pages 3008-3014, 1998, and the like, or a method analogous thereto.

<Step 11>

A compound represented by the formula (XII) (to be abbreviated compound (XII)) can be produced by converting the hydroxyl group of compound (XI) to a leaving group L‴.

As the leaving group L‴, those exemplarily recited for L can be used. As preferable leaving group in this step, arylsulfonyloxy groups such as benzenesulfonyloxy group, p-toluenesulfonyloxy group and the like can be mentioned.

This step is performed according to a method known per se, for example, the methods described in J. Org. Chem., vol. 39, wherein $W^2$ and $W^3$ are the same or different and each is a bond or an optionally substituted $C_{1-2}$ alkylene group, Q is $—N(R^4)—$, $—O—$ or $—S(O)_{k23}—$, $R^4$ is an optionally substituted $C_{1-6}$ alkyl group or an optionally substituted acyl group, k23 is as defined above, M is a hydrogen atom or a metal (e.g., potassium, sodium, lithium, magnesium, copper, mercury, zinc, thallium, boron, tin and the like, these may be complexed), and the other symbols are as defined above.

As the "optionally substituted $C_{1-2}$ alkylene group" for $W^2$ or $W^3$, for example, methylene or ethylene, each of which optionally has 1 or 2 substituents exemplarily recited as the substituents of V, can be mentioned.

<Step 13>

Compound (III′) can be produced by reacting (i) compound (XIII-1) with compound (XVI-1), or (ii) compound (XIII-2) with compound (XVI-2). Unless otherwise specified, compound (XIII-1) and compound (XIII-2) are generally referred to as compound (XIII), and unless otherwise specified, compound (XVI-1) and compound (XVI-2) are generally referred to as compound (XVI).

The reaction of compound (XIII) with compound (XVI) is generally carried out in the presence of a base. As the base, for example, alkali metal hydrides such as sodium hydride, potassium hydride and the like; alkali metal hydroxides such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate and the like; alkali metal hydrogencarbonates such as sodium hydrogencarbonate, potassium hydrogencarbonate and the like; alkali metal alkoxides having 1 to 6 carbon atoms, such as sodium methoxide, sodium ethoxide, sodium tert-butoxide and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like; organic lithiums such as methyllithium, n-butyllithium, sec-butyllithium, tert-butyllithium and the like; lithium amides (including hydrates thereof) such as lithium diisopropylamide and the like, and the like can be mentioned.

The reaction of compound (XIII) with compound (XVI) is advantageously carried out using a solvent inert to the reaction. While the solvent is not particularly limited as long as the reaction proceeds, for example, solvents such as alcohols (e.g., methanol, ethanol, propanol, isopropanol, butanol, tert-butanol and the like); ethers (e.g., 1,4-dioxane, tetrahydrofuran, diethyl ether, tert-butyl methyl ether, diisopropyl ether, 1,2-dimethoxyethane and the like); esters (e.g., ethyl formate, ethyl acetate, n-butyl acetate and the like); halogenated hydrocarbons (e.g., dichloromethane, chloroform, carbon tetrachloride, trichloroethylene and the like); hydrocarbons (e.g., n-hexane, benzene, toluene and the like); amides (e.g., N,N-dimethylformamide, N,N-dimethylacetamide and the like); nitriles (e.g., acetonitrile, propionitrile and the like); sulfoxides (e.g., dimethyl sulfoxide and the like); sulforane; hexamethylphosphoramide; water, and the like, a mixed solvent thereof and the like are preferable.

The reaction of compound (XIII) with compound (XVI) can be generally promoted by the use of a metal catalyst. As the metal catalyst, metal complexes having various ligands can be used and, for example, palladium compounds [e.g., palladium(II) acetate, tetrakis(triphenylphosphine)palladium (0), bis(triphenylphosphine)palladium(II) chloride, dichlorobis(triethylphosphine)palladium(II), tris(dibenzylideneacetone)dipalladium-2,2'-bis(diphenylphosphino)-1,1'-binaphthyl, a complex of palladium(II) acetate and 1,1'-bis (diphenylphosphino)ferrocene, and the like]; nickel compounds [e.g., tetrakis(triphenylphosphine)nickel (0), bis (triethylphosphine)nickel (II) chloride, bis(triphenylphosphine)nickel (II) chloride and the like]; rhodium compounds [e.g.: tris(triphenylphosphine)rhodium (III) chloride and the like]; cobalt compounds; copper compounds [e.g., copper oxide, copper(II) chloride and the like]; platinum compounds and the like can be mentioned. Of these, palladium compounds, nickel compounds and copper compounds are preferable. The amount of the metal catalyst to be used is about 0.000001 to about 5 mol, preferably about 0.0001 to about 1 mol, per 1 mol of compound (XIII). When a metal catalyst unstable to oxygen is used in this reaction, the reaction is preferably carried out in an inert gas (e.g., argon gas or nitrogen gas) stream.

The amount of compound (XVI) to be used is about 0.1 to about 10 mol, preferably about 0.5 to about 2 mol, per 1 mol of compound (XIII). The amount of the base to be used is about 1 to about 20 mol, preferably about 1 to about 5 mol, per 1 mol of compound (XIII).

The reaction temperature is −10 to 250° C., preferably 0 to 150° C. While the reaction time varies depending on the kind of compound (XIII), compound (XVI), metal catalyst, base and solvent, the reaction temperature and the like, it is generally 1 min to 200 hr, preferably 5 min to 100 hr.

<Step 14>

Compound (V') can be produced from compound (III').

Compound (V') wherein L' is a hydroxy group can be produced by subjecting compound (III') to a reduction reaction. The reduction reaction can be carried out using a reducing agent exemplarily recited in Step 1, according to a conventional method.

Compound (V') wherein L' is a leaving group can be produced by reacting compound (V') wherein L' is a hydroxy group (hereinafter sometimes to be abbreviated as compound (V")) with a halogenating agent or a sulfonylating agent.

As the halogenating agent, for example, thionyl chloride, phosphorus tribromide and the like can be used. In this case, compound (V') wherein L' is a halogen atom (e.g., chlorine, bromine and the like), can be produced.

The reaction of compound (V") with the halogenating agent is generally carried out using a solvent inert to the reaction. As the solvent inert to the reaction, for example, halogenated hydrocarbons (e.g., dichloromethane, chloroform, carbon tetrachloride and the like); aromatic hydrocarbons (e.g., benzene, toluene, xylene and the like); ethers (e.g., diethyl ether, diisopropyl ether, tert-butyl methyl ether, tetrahydrofuran, 1,4-dioxane, 1,2-dimethoxyethane and the like); esters (e.g., methyl acetate, ethyl acetate, n-butyl acetate, tert-butyl acetate and the like) and the like can be mentioned. In addition, an excess amount of a halogenating agent may be used as a solvent.

The amount of the halogenating agent to be used is generally about 1 to about 10 mol per 1 mol of compound (V"). The reaction temperature is generally −20 to 100° C. The reaction time is generally 0.5 to 24 hr.

As the sulfonylating agent, for example, methanesulfonyl chloride, benzenesulfonyl chloride, p-toluenesulfonyl chloride and the like can be used. In this case, for example, compound (V') wherein L' is methanesulfonyloxy, benzenesulfonyloxy, p-toluenesulfonyloxy or the like, can be produced.

The reaction of compound (V") with the sulfonylating agent is generally carried out using a solvent inert to the reaction in the presence of a base. As the solvent inert to the reaction, for example, solvents such as halogenated hydrocarbons (e.g., dichloromethane, chloroform, carbon tetrachloride and the like); aromatic hydrocarbons (e.g., benzene, toluene, xylene and the like); ethers (e.g., diethyl ether, diisopropyl ether, tert-butyl methyl ether, tetrahydrofuran, 1,4-dioxane, 1,2-dimethoxyethane and the like); esters (e.g., methyl acetate, ethyl acetate, n-butyl acetate, tert-butyl acetate and the like) and the like can be mentioned.

The amount of the sulfonylating agent to be used is generally about 1 to about 10 mol per 1 mol of compound (V").

As the base, for example, amines such as triethylamine, N-methylmorpholine and the like; alkali metal salts such as sodium hydrogencarbonate, potassium hydrogencarbonate, potassium carbonate and the like, and the like can be mentioned. The amount of the base to be used is generally about 1 to about 10 mol per 1 mol of compound (V"). The reaction temperature is generally −20 to 100° C. The reaction time is generally 0.5 to 24 hr.

Compound (III") can also be produced according to the method similar to the method as shown in Scheme 3.

In each of the above-mentioned reaction steps, where desired, compound (I) can be also synthesized by further using a known hydrolysis, deprotection, acylation, alkylation, hydrogenation, oxidation, reduction, carbon chain elongation and substituent exchange reaction alone or the combination of two or more thereof. For these reactions, for example, the methods described in Jikken Kagaku Koza, Vols. 14 and 15, (The Chemical Society Japan ed.) and the like are employed.

In addition, in each of the aforementioned reactions, when the starting compound has amino group, carboxyl group, hydroxy group or mercapto group as a substituent, a protecting group generally used in peptide chemistry and the like may be introduced into these groups. By removing the protecting group as necessary after the reaction, the objective compound can be obtained.

As the amino-protecting group, for example, formyl group; $C_{1-6}$ alkyl-carbonyl group (e.g., acetyl, ethylcarbonyl and the like), phenylcarbonyl group, $C_{1-6}$ alkoxy-carbonyl group (e.g., methoxycarbonyl, ethoxycarbonyl, tert-butoxycarbonyl (Boc) and the like), allyloxycarbonyl group (Alloc), phenyloxycarbonyl group, fluorenylmethyloxycarbonyl group (Fmoc), $C_{7-10}$ aralkyl-carbonyl group (e.g., benzylcarbonyl and the like), $C_{7-10}$ aralkyloxy-carbonyl group (e.g., benzyloxycarbonyl (Z) and the like), $C_{7-10}$ aralkyl group (e.g., benzyl and the like), trityl group, phthaloyl group, dithiasuccinoyl group, N,N-dimethylaminomethylene group, each optionally having substituent(s), and the like can be mentioned. As the substituent(s), for example, phenyl group, halogen atom, $C_{1-6}$ alkyl-carbonyl group (e.g., acetyl, ethylcarbonyl, buthylcarbonyl and the like), $C_{1-6}$ alkoxy group optionally substituted by halogen atom(s) (e.g., methoxy, ethoxy, trifluoromethoxy and the like), nitro group and the like are used. The number of the substituent(s) is 1 to 3.

As the carboxyl-protecting group, for example, $C_{1-6}$ alkyl group, allyl group, benzyl group, phenyl group, trityl group, trialkylsilyl group, each optionally having substituent(s), and the like can be mentioned. As the substituent(s), for example, halogen atom, formyl group, $C_{1-6}$ alkyl-carbonyl group (e.g., acetyl, ethylcarbonyl, butylcarbonyl and the like), $C_{1-6}$ alkoxy group optionally substituted by halogen atom(s) (e.g., methoxy, ethoxy, trifluoromethoxy and the like), nitro group and the like are used. The number of the substituent(s) is 1 to 3.

As the hydroxy-protecting group, for example, $C_{1-6}$ alkyl group, $C_{7-20}$ aralkyl group (e.g., benzyl, trityl and the like), formyl group, $C_{1-6}$ alkyl-carbonyl group (e.g., acetyl, ethylcarbonyl and the like), benzoyl group, $C_{7-10}$ aralkyl-carbonyl group (e.g., benzylcarbonyl and the like), 2-tetrahydropyranyl group, tetrahydrofuranyl group, trialkylsilyl group (e.g., trimethylsilyl, tert-butyldimethylsilyl, diisopropylethylsilyl and the like), each optionally having substituent(s), and the like can be mentioned. As the substituent(s), for example, halogen atom, $C_{1-6}$ alkyl group, phenyl group, $C_{7-10}$ aralkyl group (e.g., benzyl and the like), $C_{1-6}$ alkoxy group, nitro group and the like are used. The number of the substituent(s) is 1 to 4.

As the mercapto-protecting group, for example, $C_{1-6}$ alkyl group, $C_{7-20}$ aralkyl group (e.g., benzyl, trityl), each optionally having substituent(s), and the like can be mentioned. As the substituent(s), for example, halogen atom, $C_{1-6}$ alkyl group, phenyl group, $C_{7-10}$ aralkyl group (e.g., benzyl and the like), $C_{1-6}$ alkoxy group, $C_{1-6}$ alkyl-carbonyl group (e.g., acetyl, ethylcarbonyl and the like), nitro group and the like are used. The number of the substituent(s) is 1 to 4.

For elimination of the protecting group, a method known per se or a method analogous thereto is used. For example, treatments with acid, base, reduction, ultraviolet rays, hydrazine, phenylhydrazine, sodium N-methyldithiocarbamate, tetrabutylammonium fluoride, palladium acetate and the like are used.

Compound (I) obtained in this manner, other reaction intermediates and starting material compounds thereof can be isolated or purified from the reaction mixture by a method known per se, such as extraction, concentration, neutralization, filtration, distillation, recrystallization, column chromatography, thin layer chromatography, preparative high pressure liquid chromatography (preparative HPLC), intermediate pressure preparative liquid chromatography (intermediate pressure preparative LC) and the like.

The salt of compound (I) can be produced according to a method known per se. For example, when compound (I) is a basic compound, the salt can be produced by adding an inorganic acid or an organic acid, or when compound (I) is an acidic compound, by adding an organic base or an inorganic base.

When compound (I) has optical isomers, these respective optical isomers and mixtures thereof are naturally encompassed in the scope of the present invention, and where desired, these isomers can be also subjected to optical resolution or individually produced according to a method known per se.

When the compound (I) is present as a configurational isomer, diastereomer, conformer or the like, each can be isolated by the above separation and purification methods on demand. In addition, when the compound (I) is in the form of racemates, they can be separated into S- and R-forms by any conventional optical resolution.

When the compound (I) includes stereoisomers, both the isomers alone and mixtures of each isomers are included in the scope of the present invention.

In addition, the compound (I) may be a hydrate or non-hydrate.

The compound (I) may be labeled with an isotope (e.g., $^3H$, $^{14}C$, $^{35}S$) or the like.

Since the compound (I) and a prodrug thereof (hereinafter, sometimes to be abbreviated to as a compound of the present invention) have a GPR40 receptor function modulating action (GPR40 receptor agonist activity and GPR40 receptor antagonist activity) particularly, a GPR40 receptor agonist activity, show low toxicity and fewer side effects (e.g.: acute toxicity, chronic toxicity, genetic toxicity, reproductive toxicity, cardiotoxicity, drug interaction, carcinogenicity), they are useful as safe GPR40 receptor function modulators, preferably GPR40 agonists.

A pharmaceutical agent containing the compound of the present invention shows a superior GPR40 receptor function modulating action in mammals (e.g., mouse, rat, hamster, rabbit, cat, dog, bovine, sheep, monkey, human etc.), and are useful as modulators of physiological function in which GPR40 receptor is involved or agents for the prophylaxis or treatment of disease state or disease in which GPR40 receptor is involved.

To be specific, a pharmaceutical agent containing the compound of the present invention is useful as insulin secretion modulators (preferably insulin secretagogues), hypoglycemic drugs and pancreatic β cell protectors.

Moreover, a pharmaceutical agent containing the compound of the present invention is useful as agents for the prophylaxis or treatment of diseases such as diabetes, impaired glucose tolerance, ketosis, acidosis, diabetic neuropathy, diabetic nephropathy, diabetic retinopathy, macular edema, hyperlipidemia, genital disorder, skin disease, arthropathy, osteopenia, arteriosclerosis, thrombotic disease, dyspepsia, memory and learning disorder, depression, depression and mania, schizophrenia, attention deficit hyperactivity disorder, visual disorder, appestat disorder (e.g., hyperorexia), obesity, hypoglycemia, hypertension, edema, insulin resistance, unstable diabetes, fatty atrophy, insulin allergy, insulinoma, lipotoxicity, pancreatic fatigue, hyperinsulinemia, cancers breast cancer), metabolic syndrome, immune diseases (e.g., immunodeficiency), inflammatory disease (e.g., enteritis, arthritis, allergy), multiple sclerosis, acute kidney failure and the like; particularly, diseases such as diabetes, impaired glucose tolerance, ketosis, acidosis, diabetic neuropathy, diabetic nephropathy, diabetic retinopathy, macular edema, hyperlipidemia, genital disorder, skin disease, arthropathy, osteopenia, arteriosclerosis, thrombotic disease, dyspepsia, memory and learning disorder and the like. Here, diabetes includes type I diabetes, type II diabetes and gestational diabetes. In addition, hyperlipidemia includes hypertriglyceridemia, hypercholesterolemia, hypo-high-density-lipoproteinemia, postprandial hyperlipidemia and the like.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) reported new diagnostic criteria of diabetes in 1997 and WHO in 1998.

According to these reports, diabetes is a condition showing a fasting blood glucose level (glucose concentration of intravenous plasma) of not less than 126 mg/dl and a 75 g oral glucose tolerance test 2 h level (glucose concentration of intravenous plasma) of not less than 200 mg/dl.

According to the above-mentioned reports, impaired glucose tolerance is a condition showing a fasting blood glucose level (glucose concentration of intravenous plasma) of less than 126 mg/dl and a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). On the other hand, according to the report of WHO, among the IFG (Impaired Fasting Glucose), a condition showing a 75 g oral glucose tolerance test 2 h level (glucose concentration of intravenous plasma) of less than 140 mg/dl is called IFG (Impaired Fasting Glycemia).

The compound of the present invention can be also used as an agent for the prophylaxis or treatment of diabetes, borderline type, impaired glucose tolerance, IFG (Impaired Fasting Glucose) and IFG (Impaired Fasting Glycemia), as determined according to the above-mentioned new diagnostic criteria. Moreover, the compound of the present invention can prevent progress of borderline type, impaired glucose tolerance, IFG (Impaired Fasting Glucose) or IFG (Impaired Fasting Glycemia) into diabetes.

Since the compound of the present invention has a superior insulin secretion promoting effect, it can be preferably used as an agent for treating insulin secretion deficient diabetes in patients with insulin secretion deficient diabetes.

The compound of the present invention is also useful as a therapeutic agent for diabetes with sulfonylurea secondary failure and affords a superior insulin secretion effect and a hypoglycemic effect for diabetic patients for whom sulfonylurea compounds and fast-acting insulin secretagogues fail to provide an insulin secretion effect, and therefore, fail to provide a sufficient hypoglycemic effect.

As the sulfonylurea compound here, a compound having a sulfonylurea skeleton or a derivative thereof (e.g., tolbutamide, glibenclamide, gliclazide, chlorpropamide, tolazamide, acetohexamide, glyclopyramide, glimepiride, glipizide, glybuzole and the like) can be mentioned.

As the fast-acting insulin secretagogue, a compound that promotes insulin secretion from pancreatic β cell in the same manner as a sulfonylurea compound, though it does not have a sulfonylurea skeleton, such as glinide compounds (e.g., repaglinide, senaglinide, nateglinide, mitiglinide, a calcium salt hydrate thereof etc.), and the like, can be mentioned.

A pharmaceutical agent containing the compound of the present invention show low toxicity, and can be safely administered orally or parenterally (e.g., topical, rectal, intravenous administration etc.) in the form of the compound of the present invention as it is or after admixing with a pharmacologically acceptable carrier to give a pharmaceutical preparation according to a method known per se employed for general production methods for pharmaceutical preparations.

The dosage form of the aforementioned pharmaceutical preparation is, for example, an oral agent such as tablets (inclusive of sublingual tablets and orally disintegrable tablets), capsules (inclusive of soft capsules and micro capsules), granules, powders, troches, syrups, emulsions, suspensions and the like; or a parenteral agent such as injections (e.g., subcutaneous injections, intravenous injections, intramuscular injections, intraperitoneal injections, drip infusions etc.), external agents (e.g., transdermal preparations, ointments etc.), suppositories (e.g., rectal suppositories, vaginal suppositories etc.), pellets, nasal preparations, pulmonary preparations (inhalations), ophthalmic preparations and the like.

These agents may be controlled-release preparations such as rapid-release preparations and sustained-release preparations (e.g., sustained-release microcapsules).

The content of the compound of the present invention in a pharmaceutical preparation is about 0.01 to about 100% by weight relative to the whole preparation. While the dose of the compound of the present invention varies depending on the administration subject, administration route, diseases, condition and the like, for example, the compound of the present invention can be administered to an adult patient with diabetes (body weight about 60 kg) in about 0.01 to about 30 mg/kg body weight per day, preferably about 0.1 to about 20 mg/kg body weight per day, more preferably about 1 to about 20 mg/kg body weight per day, which may be given at once or in several portions a day.

As the above-mentioned pharmacologically acceptable carrier, various organic or inorganic carrier substances conventionally used as a preparation material can be mentioned. For example, excipient, lubricant, binder and disintegrant for solid preparations, solvent, dissolution aids, suspending agent, isotonicity agent, buffer and soothing agent for liquid preparations and the like can be mentioned. Where necessary, additives such as preservatives, antioxidants, coloring agents, sweetening agents, adsorbing agents, wetting agents and the like can be used.

As the excipient, for example, lactose, sucrose, D-mannitol, starch, corn starch, crystalline cellulose, light anhydrous silicic acid and the like can be mentioned.

As the lubricant, for example, magnesium stearate, calcium stearate, talc, colloidal silica and the like can be mentioned.

As the binder, for example, crystalline cellulose, sucrose, D-mannitol, dextrin, hydroxypropylcellulose, hydroxypropylmethylcellulose, polyvinylpyrrolidone, starch, saccharose, gelatin, methylcellulose, carboxymethylcellulose sodium and the like can be mentioned.

As the disintegrant, for example, starch, carboxymethylcellulose, carboxymethylcellulose calcium, carboxymethylstarch sodium, L-hydroxypropylcellulose and the like can be mentioned.

As the solvent, for example, water for injection, alcohol, propylene glycol, macrogol, sesame oil, corn oil, olive oil and the like can be mentioned.

As the dissolution aids, for example, polyethylene glycol, propylene glycol, D-mannitol, benzyl benzoate, ethanol, trisaminomethane, cholesterol, triethanolamine, sodium carbonate, sodium citrate and the like can be mentioned.

As the suspending agent, for example, surfactants such as stearyltriethanolamine, sodium lauryl sulfate, lauryl aminopropionate, lecithin, benzalkonium chloride, benzethonium chloride, glycerol monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like, and the like can be mentioned.

As the isotonicity agent, for example, glucose, D-sorbitol, sodium chloride, glycerin, D-mannitol and the like can be mentioned.

As the buffer, for example, buffers such as phosphate, acetate, carbonate, citrate and the like, and the like can be mentioned.

As the soothing agent, for example, benzyl alcohol and the like can be mentioned.

As the preservative, for example, p-hydroxybenzoates, chlorobutanol, benzyl alcohol, phenethyl alcohol, dehydroacetic acid, sorbic acid and the like can be mentioned.

As the antioxidant, for example, sulfite, ascorbic acid, α-tocopherol and the like can be mentioned.

As the coloring agent, for example, water-soluble edible tar pigments (e.g., foodcolors such as Food Color Red Nos. 2 and 3, Food Color Yellow Nos. 4 and 5, Food Color Blue Nos. 1 and 2 and the like), water insoluble lake pigments (e.g., aluminum salt of the aforementioned water-soluble edible tar pigment), natural pigments (e.g., β-carotene, chlorophil, red iron oxide) and the like can be mentioned.

As the sweetening agent, for example, saccharin sodium, dipotassium glycyrrhizinate, aspartame, stevia and the like can be mentioned.

The compound of the present invention can be used in combination with drugs such as therapeutic agents for diabetes, therapeutic agents for diabetic complications, therapeutic agents for hyperlipidemia, antihypertensive agents, antiobesity agents, diuretics, chemotherapeutic agents, immunotherapeutic agents, antiinflammatory agents, antithrombotic agents, therapeutic agents for osteoporosis, vitamins, antidementia agents, therapeutic agents for pollakiuria or urinary incontinence, therapeutic agents for dysuria and the like (hereinafter, sometimes to be abbreviated to as drug X).

As the above-mentioned therapeutic agents for diabetes, insulin preparations (e.g., animal insulin preparations extracted from pancreas of bovine and swine; human insulin preparations genetically synthesized using *Escherichia coli*, yeast; zinc insulin; protamine zinc insulin; fragment or derivative of insulin (e.g., INS-1 etc.), oral insulin preparation and the like), insulin sensitizers (e.g., pioglitazone or a salt thereof (preferably hydrochloride), rosiglitazone or a salt thereof (preferably maleate), Reglixane (JTT-501), Netoglitazone (MCC-555), GI-262570, FK-614, Rivoglitazone (CS-011), Muraglitazar (BMS-298585), compounds described in WO99/58510 (e.g., (E)-4-[4-(5-methyl-2-phenyl-4-oxazolylmethoxy)benzyloxyimino]-4-phenylbutyric acid), compounds described in WO01/38325, Tesaglitazar (AZ-242), BM-13-1258, LM-4156, MBX-102, LY-519818, MX-6054, LY-510929, Balaglitazone (N,N-2344), T-131 or a salt thereof, THR-0921), α-glucosidase inhibitors (e.g., voglibose, acarbose, miglitol, emiglitate etc.), biguanides (e.g., phenformin, metformin, buformin or a salt thereof (e.g., hydrochloride, fumarate, succinate) etc.), insulin secretagogues [sulfonylurea (e.g., tolbutamide, glibenclamide, gliclazide, chlorpropamide, tolazamide, acetohexamide, glyclopyramide, glimepiride etc.), repaglinide, senaglinide, mitiglinide or calcium salt hydrate thereof, nateglinide etc.], GLP-1 receptor agonists [e.g., GLP-1, GLP-1MR agent, N,N-2211, AC-2993 (exendin-4), BIM-51077, Aib(8, 35)hGLP-1 (7, 37)NH$_2$, CJC-1131 etc.], dipeptidyl peptidase IV inhibitors (e.g., NVP-DPP-278, PT-100, P32/98, P93/01, NVP-DPP-728, LAF237, TS-021 etc.), β3 agonists (e.g., CL-316243, SR-58611-A, UL-TG-307, AJ-9677, AZ40140 etc.), amylin agonists (e.g., pramlintide etc.), phosphotyrosine phosphatase inhibitors (e.g., sodium vanadate etc.), gluconeogenesis inhibitors (e.g., glycogen phosphorylase inhibitors, glucose-6-phosphatase inhibitors, glucagon antagonists etc.), SGLT (sodium-glucose cotransporter) inhibitors (e.g., T-1095 etc.), 11β-hydroxysteroid dehydrogenase inhibitors (e.g., BVT-3498 etc.), adiponectin or agonists thereof, IKK inhibitors (e.g., AS-2868 etc.), leptin resistance improving drugs, somatostatin receptor agonists (compounds described in WO01/25228, WO03/42204, WO98/44921, WO98/45285, WO99/22735 etc.), glucokinase activators (e.g., Ro-28-1675) and the like can be mentioned.

Examples of the therapeutic agents for diabetic complications include aldose reductase inhibitors (e.g., Tolrestat, Epalrestat, Zenarestat, Zopolrestat, Fidarestat (SNK-860), AS-3201, Minalrestat (ARI-509), CT-112 etc.), neurotrophic factors and increasing drugs thereof (e.g., NGF, NT-3, BDNF, neurotrophin production-secretion promoters described in WO01/14372 (e.g., 4-(4-chlorophenyl)-2-(2-methyl-1-imidazolyl)-5-[3-(2-methylphenoxy)propyl]oxazole etc.) and the like), protein kinase C (PKC) inhibitors (e.g., ruboxistaurin mesylate; LY-333531 etc.), AGE inhibitors (e.g., ALT-945, pimagedine, pyratoxanthine, N-phenacylthiazolium bromide (ALT-766), EXO-226, ALT-711, Pyridorin, Pyridoxamine etc.), active oxygen scavengers (e.g., thioctic acid etc.), cerebral vasodilators (e.g., tiapuride etc.), somatostatin receptor agonist (BIM23190), apoptosis signal regulating kinase-1 (ASK-1) inhibitors and the like.

Examples of the therapeutic agents for hyperlipidemia include HMG-COA reductase inhibitors (e.g., pravastatin, simvastatin, lovastatin, atorvastatin, fluvastatin, pitavastatin, rosuvastatin or a salt thereof (e.g., sodium salt, calcium salt etc.) etc.), squalene synthase inhibitors (e.g., compounds described in WO97/10224, such as N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid and the like), fibrate compounds (e.g., bezafibrate, clofibrate, simfibrate, clinofibrate etc.), antioxidants (e.g., lipoic acid, probucol) and the like.

Examples of the antihypertensive agents include angiotensin converting enzyme inhibitors (e.g., captopril, enalapril, delapril etc.), angiotensin II receptor antagonists (e.g., losartan, candesartan cilexetil, eprosartan, valsartan, telmisartan, irbesartan, olmesartan medoxomil, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid etc.), calcium antagonists (e.g., manidipine, nifedipine, amlodipine, efonidipine, nicardipine etc.), clonidine and the like.

Examples of the antiobesity agents include antiobesity agents acting on the central nervous system (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compounds described in WO01/82925 and WO01/87834 etc.); neuropeptide Y antagonists (e.g., CP-422935 etc.); cannabinoid receptor antagonists (e.g., SR-141716, SR-147778 etc.); ghrelin antagonists; 11β-hydroxysteroid dehydrogenase inhibitors (e.g., BVT-3498 etc.) and the like), pancreatic lipase inhibitors (e.g., orlistat, ATL-962 etc.), β3 agonists (e.g., CL-316243, SR-58611-A, UL-TG-307, AJ-9677, AZ40140 etc.), peptide anorexiants (e.g., leptin, CNTF (Ciliary Neurotropic Factor) etc.), cholecystokinin agonists (e.g., lintitript, FPL-15849 etc.), feeding deterrent (e.g., P-57 etc.) and the like.

Examples of the diuretics include xanthine derivatives (e.g., sodium salicylate and theobromine, calcium salicylate and theobromine etc.), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide etc.), antialdosterone preparations (e.g., spironolactone, triamterene etc.), carbonate dehydratase inhibitors (e.g., acetazolamide and the like), chlorobenzenesulfonamide preparations (e.g., chlortalidone, mefruside, indapamide etc.), azosemide, isosorbide, etacrynic acid, piretanide, bumetanide, furosemide and the like.

Examples of the chemotherapeutic agents include alkylating agents (e.g., cyclophosphamide, ifosfamide etc.), metabolic antagonists (e.g., methotrexate, 5-fluorouracil and a derivative thereof etc.), antitumor antibiotics (e.g., mitomycin, adriamycin etc.), plant-derived antitumor agent (e.g., vincristine, vindesine, Taxol etc.), cisplatin, carboplatin, etoposide and the like. Of these, Furtulon or NeoFurtulon, which are 5-fluorouracil derivatives, and the like are preferable.

Examples of the immunotherapeutic agents include microorganism or bacterial components (e.g., muramyl dipeptide derivative, Picibanil etc.), polysaccharides having immunity potentiating activity (e.g., lentinan, schizophyllan, krestin etc.), cytokines obtained by genetic engineering techniques (e.g., interferon, interleukin (IL) etc.), colony stimulating factors (e.g., granulocyte colony stimulating factor, erythropoietin etc.) and the like, with preference given to interleukins such as IL-1, IL-2, IL-12 and the like.

Examples of the antiinflammatory agents include non-steroidal antiinflammatory agents such as aspirin, acetaminophen, indomethacin and the like.

Examples of the antithrombotic agents include heparin (e.g., heparin sodium, heparin calcium, dalteparin sodium etc.), warfarin (e.g., warfarin potassium etc.), anti-thrombin drugs (e.g., aragatroban etc.), thrombolytic agents (e.g., urokinase, tisokinase, alteplase, nateplase, monteplase, pamiteplase etc.), platelet aggregation inhibitors (e.g., ticlopidine hydrochloride, cilostazol, ethyl icosapentate, beraprost sodium, sarpogrelate hydrochloride etc.) and the like.

Examples of the therapeutic agents for osteoporosis include alfacalcidol, calcitriol, elcatonin, calcitonin salmon, estriol, ipriflavone, risedronate disodium, pamidronate disodium, alendronate sodium hydrate, incadronate disodium and the like.

Examples of the vitamins include vitamin $B_1$, vitamin $B_{12}$ and the like.

Examples of the antidementia agents include tacrine, donepezil, rivastigmine, galanthamine and the like.

Examples of the therapeutic agents for pollakiuria or urinary incontinence include flavoxate hydrochloride, oxybutynin hydrochloride, propiverine hydrochloride and the like.

Examples of the therapeutic agents for dysuria include acetylcholine esterase inhibitors (e.g., distigmine) and the like.

Furthermore, drugs having a cachexia-ameliorating action established in animal models and clinical situations, such as cyclooxygenase inhibitors (e.g., indomethacin etc.), progesterone derivatives (e.g., megestrol acetate), glucosteroids (e.g., dexamethasone etc.), metoclopramide agents, tetrahydrocannabinol agents, fat metabolism improving agents (e.g., eicosapentanoic acid etc.), growth hormones, IGF-1, or antibodies to a cachexia-inducing factor such as TNF-α, LIF, IL-6, oncostatin M and the like, can be used in combination with the compound of the present invention.

Furthermore, glycosylation inhibitors (e.g., ALT-711, etc.), nerve regeneration promoting drugs (e.g., Y-128, VX853, prosaptide, etc.), antidepressants (e.g., desipramine, amitriptyline, imipramine, etc.), antiepileptics (e.g., lamotrigine, Trileptal, Keppra, Zonegran, Pregabalin, Harkoseride and carbamazepine), antiarrhythmic agents (e.g., mexiletine), acetylcholine receptor ligands (e.g., ABT-594), endothelin receptor antagonists (e.g., ABT-627), monoamine uptake inhibitors (e.g., tramadol), narcotic analgesics (e.g., morphine), GABA receptor agonists (e.g., gabapentin and gabapentin MR agents), α2 receptor agonists (e.g., clonidine), local analgesics (e.g., capsaicin), antianxiety drugs (e.g., benzothiazepines), phosphodiesterase inhibitors (e.g., sildenafil), dopamine receptor agonists (e.g., apomorphine) and the like can be also used in combination with the compound of the present invention.

The above-mentioned drug X may be used in a mixture of two or more kinds thereof at an appropriate ratio.

By combining the compound of the present invention with drug X, superior effects such as (1) decreased dose of the compound of the present invention and/or drug X as compared to single administration of the compound of the present invention or drug X, (2) possible setting of a long treatment period by selecting drug X having different mechanism of action from those of the compound of the present invention, (3) possible designing of a sustained treatment effect by selecting drug X having different mechanism of action from those of the compound of the present invention, (4) a synergistic effect afforded by a combined use of the compound of the present invention and drug X, and the like can be achieved.

When the compound of the present invention and drug X are used in combination, the administration time of the compound of the present invention and the drug X is not restricted, and the compound of the present invention and the drug X can be administered to an administration subject simultaneously, or may be administered at staggered times. The dosage of the drug X may be determined according to the dose clinically used, and can be appropriately selected depending on an administration subject, administration route, disease, combination and the like.

The administration mode of the compound of the present invention and the drug X is not particularly restricted, and it is sufficient that the compound of the present invention and the drug X are combined in administration. As such administration mode, the following methods can be mentioned: (1) The compound of the present invention and the drug X are simultaneously formulated to give a single preparation which is administered. (2) The compound of the present invention and the drug X are separately formulated to give two kinds of preparations which are administered simultaneously by the same administration route. (3) The compound of the present invention and the drug X are separately formulated to give two kinds of preparations which are administered by the same administration route at staggered times. (4) The compound of the present invention and the drug X are separately formulated to give two kinds of preparations which are administered simultaneously by the different administration routes. (5) The compound of the present invention and the drug X are separately formulated to give two kinds of preparations which are administered by the different administration routes at staggered times (for example, the compound of the present invention and the drug X are administered in this order, or in the reverse order), and the like.

EXAMPLES

The present invention is further explained in detail by referring to the following Reference Examples, Examples, Formulation Examples and Experimental Example, which are mere working examples not to be construed as limitative and may be changed without departing from the scope of the present invention.

The term "room temperature" in the following Reference Examples and Examples indicates the range of generally from about 10° C. to about 35° C. As for "%", the yield is in mol/mol %, the solvent used for chromatography is in % by volume and other "%" is in "%" by weight. OH proton, NH proton etc. that could not be confirmed due to broad peak by proton NMR spectrum are not included in the data.

The other symbols used herein mean the following:

s: singlet d: doublet t: triplet q: quartet m: multiplet br: broad

J: coupling constant

Hz: Hertz $CDCl_3$: deuterated chloroform

DMSO-$d_6$: deuterated dimethylsulfoxide $^1$H NMR: proton nuclear magnetic resonance In the following Reference Examples and Examples, mass spectrum (MS) and nuclear magnetic resonance spectrum (NMR) were measured under the following conditions.

MS measurement tools: ZMD manufactured by Waters Corporation, ZQ2000 manufactured by Waters Corporation or platform II manufactured by Micromass Ltd.

ionization method: Electron Spray Ionization (ESI) or Atmospheric Pressure Chemical Ionization (APCI). Unless specifically indicated, ESI was used.

NMR measurement tools: Varian Gemini 200 (200 MHz) manufactured by Varian, Varian Gemini 300 (300 MHz) manufactured by Varian, AVANCE 300 manufactured by Bruker BioSpin Corp.

In Reference Examples and Examples, purification by preparative HPLC was performed under the following conditions. preparative HPLC tools: high through-put purification system manufactured by Gilson, Inc.

column: YMC Combiprep ODS-A S-5 μm, 20×50 mm solvent:
   Solution A; 0.1% trifluoroacetic acid-containing water,
   Solution B; 0.1% trifluoroacetic acid-containing acetonitrile gradient cycle A: 0.00 min (Solution A/Solution B=90/10), 1.20 min (Solution A/Solution B=90/10), 4.75 min (Solution A/Solution B=0/100), 7.30 min (Solution A/Solution B=0/100), 7.40 min (Solution A/Solution B=90/10), 7.50 min (Solution A/Solution B=90/10).

gradient cycle B: 0.00 min (Solution A/Solution B=95/5), 1.00 min (Solution A/Solution B=95/5), 5.20 min (Solution A/Solution B=5/95), 6.40 min (Solution A/Solution B=5/95), 6.50 min (Solution A/Solution B=95/5), 6.60 min (Solution A/Solution B=95/5).

flow rate: 25 ml/min, detection method: UV 220 nm

In the present specification, the melting point (m.p.) refers to that measured using, for example, micromelting point measuring apparatus (Büchi, B-545) and the like.

In general, melting points vary depending on measurement apparatuses, measurement conditions and the like. The crystal in the present specification may show a different melting point from that described in the present specification, as long as it is within general error range.

Reference Example 1 methyl 3-(4-aminophenyl)propanoate

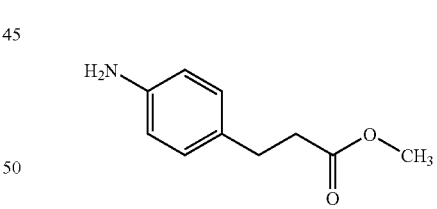

Under ice-cooling, thionyl chloride (15 mL, 206 mmol) was added dropwise to methanol (60 mL), and the mixture was stirred for 10 min. 3-(4-Aminophenyl)propanoic acid (10.1 g, 61.1 mmol) was added to the reaction mixture, and the mixture was stirred at room temperature for 18 hr. The solvent and excess thionyl chloride were evaporated under reduced pressure, and water and saturated aqueous sodium hydrogencarbonate were added. The mixture was extracted with ethyl acetate. The extract was washed with saturated brine, dried over anhydrous sodium sulfate, and concentrated under reduced pressure. The obtained solid was washed with hexane to give the title compound (10.9 g, yield 99%) as pale-brown prism crystals.

MS m/z 180 (MH$^+$).

Reference Example 2

2',6'-dimethylbiphenyl-3-carbaldehyde

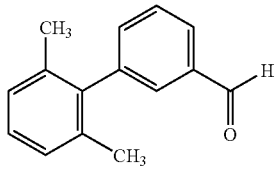

3-Bromobenzaldehyde (18.5 g, 100 mmol) and 2,6-dimethylphenylboronic acid (21.0 g, 140 mmol) were dissolved in a mixture of 1 M aqueous sodium carbonate solution (200 mL), ethanol (100 mL) and toluene (200 mL). The air was substituted with argon gas, and tetrakis(triphenylphosphine) palladium(0) (5.78 g, 5.00 mmol) was added. The reaction mixture was stirred under an argon atmosphere at 80° C. for 20 hr. After cooling the reaction mixture, water was added and the mixture was diluted with ethyl acetate. The insoluble material was filtered off through celite. The organic layer in the filtrate was washed with saturated brine, dried over anhydrous magnesium sulfate, and concentrated under reduced pressure. The residue was purified by silica gel column chromatography (hexane-10% ethyl acetate/hexane) to give the title compound (20.4 g, yield 97%) as a colorless oil.

MS m/z 211 (MH$^+$).

Reference Example 3 methyl 3-(4-{[(2-nitrophenyl)sulfonyl]amino}phenyl)propanoate

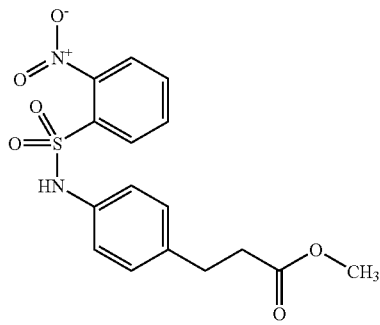

To a solution of methyl 3-(4-aminophenyl)propanoate (2.69 g, 15.0 mmol) in pyridine (20 mL) was added 2-nitrobenzenesulfonyl chloride (3.99 g, 18.0 mmol) by small portions, and the mixture was stirred at room temperature for 45 hr. The solvent was evaporated under reduced pressure, and water and ethyl acetate were added to the obtained residue. The mixture was stirred with heating at 80° C. for 15 min and filtrated through celite. The organic layer was washed with saturated brine, dried over anhydrous magnesium sulfate, and concentrated under reduced pressure. The residue was purified by silica gel column chromatography (30%-60% ethyl acetate/hexane) to give the title compound (3.39 g, yield 62%) as yellow prism crystals.

MS m/z 365 (MH$^+$).

Reference Example 4 methyl 4-[(2-phenyl-1H-indol-1-yl)methyl]benzoate

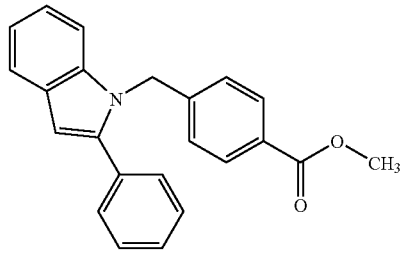

A solution of 2-phenylindole (4.2 g, 21.7 mmol) and sodium hydride (60% in oil, 0.96 g, 24 mmol) in tetrahydrofuran (90 mL) and N,N-dimethylformamide (10 mL) was stirred under ice-cooling for 20 min. To the reaction mixture was added methyl 4-bromomethylbenzoate (5.0 g, 21.8 mmol), and the mixture was stirred at room temperature for 18 hr. An aqueous citric acid solution was added to the reaction mixture, and the mixture was extracted with ethyl acetate. The extract was washed with aqueous sodium chloride solution, dried over anhydrous magnesium sulfate, and concentrated under reduced pressure. The obtained residue was subjected to silica gel column chromatography (ethyl acetate:hexane=1:10-1:5-1:2) to give the title compound (2.8 g, yield 38%) as a pale-yellow oil.

MS m/z 342 (MH$^+$).

Reference Example 5

{4-[(2-phenyl-1H-indol-1-yl)methyl]phenyl}methanol

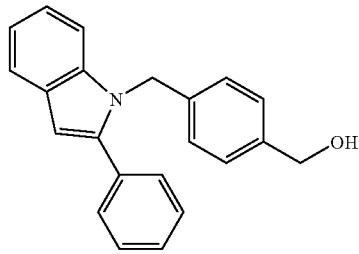

Methyl 4-[(2-phenyl-1H-indol-1-yl)methyl]benzoate (2.8 g, 8.20 mmol) was dissolved in anhydrous tetrahydrofuran (100 mL), and the solution was ice-cooled. To this solution was added dropwise a solution (13.5 mL, 20.3 mmol) of 1.5 mol/L diisobutylaluminum hydride in toluene. This solution was stirred under ice-cooling for 4 hr. An aqueous citric acid solution was added to the reaction mixture, and the mixture was extracted with ethyl acetate. The extract was washed with aqueous sodium chloride solution, dried over anhydrous magnesium sulfate, and concentrated under reduced pressure. The obtained residue was subjected to silica gel column chromatography (ethyl acetate:hexane=1:4-1:2) to give the title compound (2.25 g, yield 88%) as a colorless oil.

MS m/z 314 (MH$^+$).

Reference Example 6 methyl 3-(4-{[4-(chloromethyl)benzyl][(2-nitrophenyl)sulfonyl]amino}phenyl)propanoate

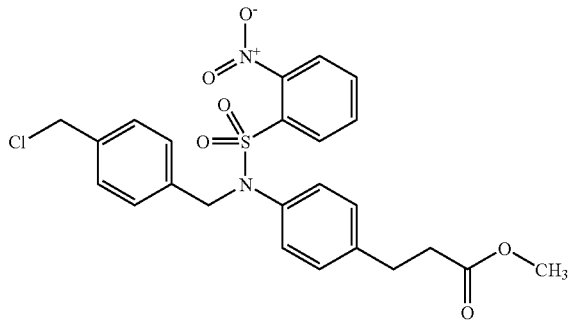

A solution of methyl 3-(4-{[(2-nitrophenyl)sulfonyl]amino}phenyl)propanoate (2.78 g, 7.63 mmol), 4-chloromethylbenzyl alcohol (1.21 g, 7.70 mmol) and triphenylphosphine (3.93 g, 15.4 mmol) in toluene (150 mL) was stirred under ice-cooling. Diethyl azodicarboxylate (40% toluene solution, 6.98 μmL, 15.4 mmol) was added, and the mixture was allowed to warm to room temperature and stirred for 72 hr. The reaction mixture was concentrated under reduced pressure, and the residue was purified by silica gel column chromatography (20%-60% ethyl acetate/hexane). Hexane-ethyl acetate was added to the obtained residue, and the resultant insoluble material was filtered off. The filtrate was concentrated to give the title compound (3.65 g, yield 95%) as a red oil.

MS m/z 503 (MH+).

Reference Example 7 methyl 4-{[(2-phenylethyl)(4-phenyl-1,3-thiazol-2-yl)amino]methyl}benzoate

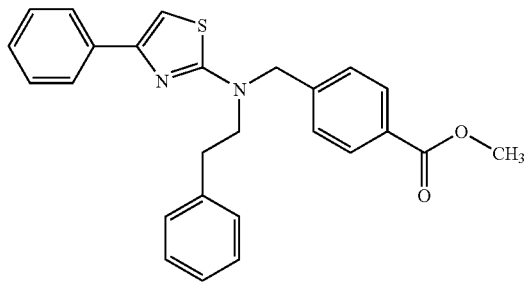

To a solution of 4-phenyl-N-(2-phenylethyl)-1,3-thiazole-2-amine (4.63 g, 16.5 mmol) in N,N-dimethylformamide (50 mL) was added sodium hydride (60% in oil, 990 mg, 24.8 mmol) and the mixture was stirred for 30 min. Methyl 4-(bromomethyl)benzoate (4.54 g, 19.8 mmol) was added and the mixture was stirred at room temperature for 2 hr. Water was added to the reaction mixture, and the mixture was extracted with ethyl acetate. The extract was washed with water, and concentrated under reduced pressure. The residue was purified by silica gel column chromatography (5%-50% ethyl acetate/hexane) to give the title compound (3.39 g, yield 48%) as a yellow oil.

$^1$H NMR (CDCl$_3$) δ: 3.00 (2H, t, J=7.8 Hz), 3.69 (2H, t, J=7.8 Hz), 3.90 (3H, s), 4.71 (2H, s), 6.76 (1H, s), 7.18-7.41 (10H, m), 7.86-7.88 (2H, m), 7.98-8.00 (2H, m).

Reference Example 8

(4-{[(2-phenylethyl)(4-phenyl-1,3-thiazol-2-yl)amino]methyl}phenyl)methanol

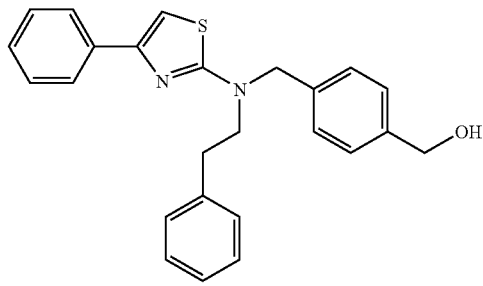

In the same manner as in Reference Example 5, the title compound was obtained as a colorless oil from methyl 4-{[(2-phenylethyl)(4-phenyl-1,3-thiazol-2-yl)amino]methyl}benzoate. yield 81%.

$^1$H NMR (CDCl$_3$) δ: 2.99 (2H, t, J=8.1 Hz), 3.68 (2H, t, J=8.1 Hz), 4.65-4.69 (4H, m), 6.74 (1H, s), 7.19-7.41 (12H, m), 7.87-7.90 (2H, m).

Reference Example 9 methyl 4-{[(4-phenyl-1,3-thiazol-2-yl)(propyl)amino]methyl}benzoate

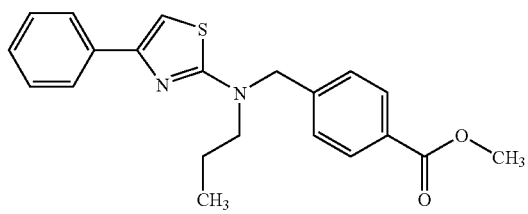

In the same manner as in Reference Example 7, the title compound was obtained as a colorless oil from 4-phenyl-N-propyl-1,3-thiazole-2-amine. yield 75%.

$^1$H NMR (CDCl$_3$) δ: 0.93 (3H, t, J=7.7 Hz), 1.64-1.74 (2H, m), 3.40 (2H, t, J=7.7 Hz), 3.91 (3H, s), 4.85 (2H, s), 6.72 (1H, s), 7.23-7.42 (5H, m), 7.82-7.85 (2H, m), 7.99-8.01 (2H, m).

Reference Example 10

(4-{[(4-phenyl-1,3-thiazol-2-yl)(propyl)amino]methyl}phenyl)methanol

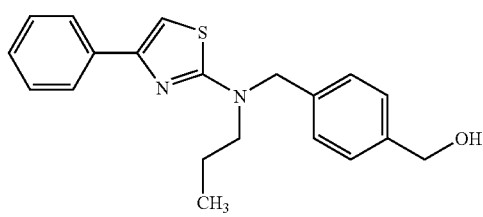

In the same manner as in Reference Example 5, the title compound was obtained as a colorless oil from methyl 4-{[(4-phenyl-1,3-thiazol-2-yl)(propyl)amino]methyl}benzoate. yield 67%.

¹H NMR (CDCl₃) δ: 0.93 (3H, t, J=7.4 Hz), 1.62 (1H, t, J=5.8 Hz), 1.64-1.74 (2H, m), 3.40 (2H, t, J=7.7 Hz), 4.69 (2H, d, J=5.8 Hz), 4.79 (2H, s), 6.70 (1H, s), 7.24-7.39 (7H, m), 7.84-7.87 (2H, m).

Reference Example 11

3-(2-methyl-1-naphthyl)benzaldehyde

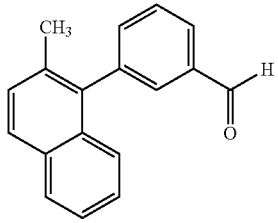

In the same manner as in Reference Example 2, the title compound was obtained as a pale-yellow oil from 1-bromo-2-methylnaphthalene and (3-formylphenyl)boronic acid. yield 65%.
MS m/z 247 (MH⁺).

Reference Example 12

[3-(2-methyl-1-naphthyl)phenyl]methanol

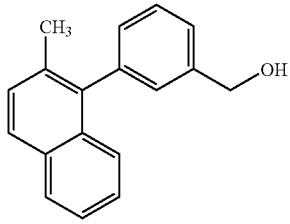

3-(2-Methyl-1-naphthyl)benzaldehyde (2.39 g, 9.70 mmol) was dissolved in a mixture of 1,2-dimethoxyethane (10 mL) and tetrahydrofuran (10 mL), and sodium borohydride (0.189 g, 5.00 mmol) was added under ice-cooling. The mixture was stirred at the same temperature for 3 hr. Dilute hydrochloric acid was added to the reaction mixture, and the mixture was extracted with ethyl acetate. The extract was washed with saturated brine, dried over anhydrous magnesium sulfate, and concentrated under reduced pressure. The residue was purified by silica gel column chromatography (5%-30% ethyl acetate/hexane) to give the title compound (1.96 g, yield 81%) as a colorless viscous oil.
¹H NMR (CDCl₃) δ: 1.66 (1H, t, J=5.9 Hz), 2.03 (6H, s), 4.74 (2H, d, J=5.9 Hz), 7.07-7.19 (5H, m), 7.35 (1H, d, J=7.5 Hz), 7.43 (1H, t, J=7.5 Hz).

Reference Example 13

4'-hydroxy-2',6'-dimethylbiphenyl-3-carbaldehyde

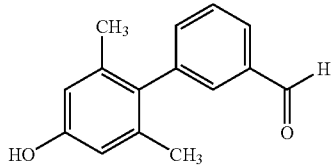

4-Bromo-3,5-dimethylphenol (10.3 g, 51.0 mmol) and (3-formylphenyl)boronic acid (7.67 g, 51.2 mmol) were dissolved in a mixture of 1 M aqueous sodium carbonate solution (150 mL), ethanol (50 mL) and toluene (150 mL), and the air was substituted with argon gas. Tetrakis(triphenylphosphine)palladium(0) (2.95 g, 2.55 mmol) was added and the mixture was stirred under an argon atmosphere at 80° C. for 24 hr. After cooling the reaction mixture, water was added and the mixture was diluted with ethyl acetate. The insoluble material was filtered off through celite. The organic layer in the filtrate was washed with saturated brine, dried over anhydrous magnesium sulfate, and concentrated under reduced pressure. The residue was purified by silica gel column chromatography (10%-40% ethyl acetate/hexane) to give the title compound (9.53 g, yield 83%) as pale-yellow crystals.
MS m/z 227 (MH⁺).

Reference Example 14

4'-(benzyloxy)-2',6'-dimethylbiphenyl-3-carbaldehyde

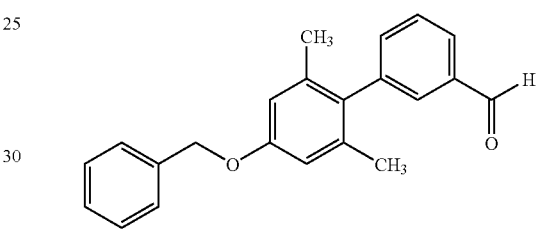

To a solution of 4'-hydroxy-2',6'-dimethylbiphenyl-3-carbaldehyde (2.26 g, 10.0 mmol) and benzyl bromide (3.42 g, 20.0 mmol) in N,N-dimethylformamide (10 mL) was added potassium carbonate (2.76 g, 20.0 mmol), and the mixture was stirred at 70° C. for 2 hr. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (hexane-10% ethyl acetate/hexane) to give the title compound (2.90 g, yield 92%) as a colorless oil.
MS m/z 317 (MH⁺).

Reference Example 15

[4'-(benzyloxy)-2',6'-dimethylbiphenyl-3-yl]methanol

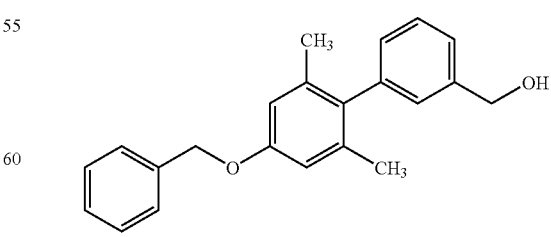

In the same manner as in Reference Example 12, the title compound was obtained as a colorless oil from 4'-(benzyloxy)-2',6'-dimethylbiphenyl-3-carbaldehyde. yield 95%.

$^1$H NMR (CDCl$_3$) δ: 1.65 (1H, t, J=5.9 Hz), 2.01 (6H, s), 4.73 (2H, d, J=5.9 Hz), 5.07 (2H, s), 6.75 (2H, s), 7.07 (1H, d, J=7.3 Hz), 7.13 (1H, s), 7.30-7.48 (7H, m).

Reference Example 16

4'-(cyclopropylmethoxy)-2',6'-dimethylbiphenyl-3-carbaldehyde

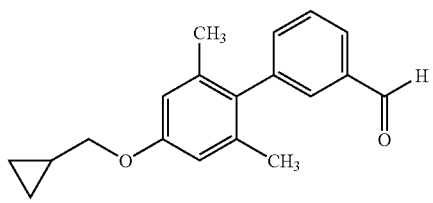

In the same manner as in Reference Example 14, the title compound was obtained as a colorless oil from 4'-hydroxy-2',6'-dimethylbiphenyl-3-carbaldehyde and cyclopropylmethyl bromide. yield 78%.
MS m/z 281 (MH$^+$).

Reference Example 17

[4'-(cyclopropylmethoxy)-2',6'-dimethylbiphenyl-3-yl]methanol

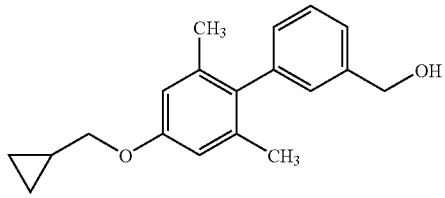

In the same manner as in Reference Example 12, the title compound was obtained as a colorless oil from 4'-(cyclopropylmethoxy)-2',6'-dimethylbiphenyl-3-carbaldehyde. yield 98%.
$^1$H NMR (CDCl$_3$) δ: 0.32-0.39 (2H, m), 0.62-0.69 (2H, m), 1.22-1.36 (1H, m), 1.66 (1H, t, J=5.9 Hz), 2.00 (6H, s), 3.81 (2H, d, J=7.0 Hz), 4.73 (2H, d, J=5.9 Hz), 6.67 (2H, s), 7.04-7.09 (1H, m), 7.11-7.14 (1H, m), 7.31-7.36 (1H, m), 7.40 (1H, t, J=7.5 Hz).

Reference Example 18

4'-(2-ethoxyethoxy)-2',6'-dimethylbiphenyl-3-carbaldehyde

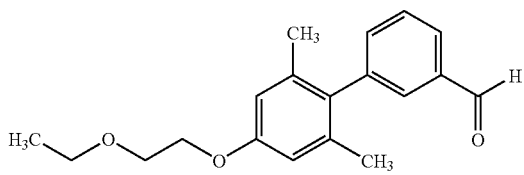

To a solution of 4'-hydroxy-2',6'-dimethylbiphenyl-3-carbaldehyde (8.52 g, 37.7 mmol) and 2-chloroethyl ethyl ether (6.15 g, 56.6 mmol) in N,N-dimethylformamide (40 mL) were added potassium carbonate (6.25 g, 45.2 mmol) and potassium iodide (1.25 g, 7.54 mmol), and the mixture was stirred at 80° C. for 18 hr. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (5%-25% ethyl acetate/hexane) to give the title compound (10.0 g, yield 89%) as a colorless oil.
MS m/z 299 (MH$^+$).

Reference Example 19

[4'-(2-ethoxyethoxy)-2',6'-dimethylbiphenyl-3-yl]methanol

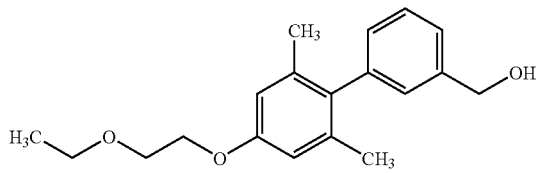

4'-(2-Ethoxyethoxy)-2',6'-dimethylbiphenyl-3-carbaldehyde (2.39 g, 9.70 mmol) was dissolved in a mixture of 1,2-dimethoxyethane (20 mL) and tetrahydrofuran (20 mL), sodium borohydride (0.227 g, 6.00 mmol) was added under ice-cooling, and the mixture was stirred at the same temperature for 3 hr. Aqueous ammonium chloride solution was added to the reaction mixture, and the mixture was extracted with ethyl acetate. The extract was washed with saturated brine, dried over anhydrous magnesium sulfate, and concentrated under reduced pressure. The residue was purified by silica gel column chromatography (20%-50% ethyl acetate/hexane) to give the title compound (3.55 g, yield 98%) as colorless crystals.
MS m/z 301 (MH$^+$).

Reference Example 20 ethyl(2E)-3-(4-amino-2-fluorophenyl)acrylate

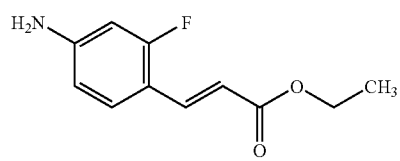

4-Bromo-3-fluoroaniline (13.3 g, 70.0 mmol), ethyl acrylate (9.48 mL, 87.5 mmol) and tris(2-methylphenyl)phosphine (8.52 g, 28.0 mmol) were dissolved in N,N-diisopropylethylamine (50 mL) and N,N-dimethylformamide (50 mL), palladium(II) acetate (0.786 g, 3.50 mmol) was added, and the mixture was stirred under an argon atmosphere at 110° C. for 5 hr. After cooling the reaction mixture, the solvent was evaporated under reduced pressure. Water and ethyl acetate were added to the residue, and the insoluble material was removed by filtering through celite. The organic layer in the filtrate was washed with saturated brine, dried over anhydrous magnesium sulfate, and concentrated under reduced pressure. The residue was purified by silica gel column chromatography (20%-60% ethyl acetate/hexane) to give the title compound (14.0 g, yield 96%). A part thereof was recrystallized to give yellow prism crystals.

MS m/z 210 (MH+).

Reference Example 21 ethyl 3-(4-amino-2-fluorophenyl)propanoate

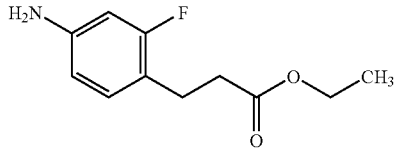

Ethyl(2E)-3-(4-amino-2-fluorophenyl)acrylate (12.4 g, 59.3 mmol) was dissolved in ethanol (120 mL), and 10% palladium-carbon (50% water-containing product, 4.0 g) was added. The mixture was stirred under a hydrogen atmosphere (balloon pressure) at room temperature for 12 hr. The catalyst was filtered off, and the filtrate was concentrated under reduced pressure. The residue was purified by silica gel column chromatography (20%-50% ethyl acetate/hexane) to give the title compound (9.89 g, yield 79%) as a pale-brown oil.

MS m/z 212 (MH+).

Reference Example 22 ethyl 3-(2-fluoro-4-{[(2-nitrophenyl)sulfonyl]amino}phenyl)propanoate

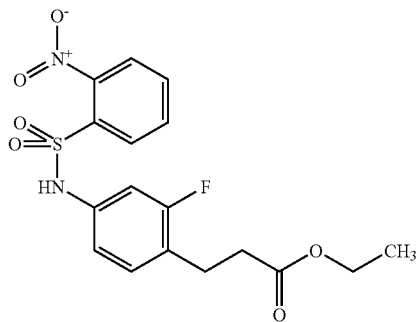

To a solution of ethyl 3-(4-amino-2-fluorophenyl)propanoate (9.89 g, 46.8 mmol) in pyridine (70 mL) was added 2-nitrobenzenesulfonyl chloride (11.4 g, 51.5 mmol) by small portions, and the mixture was stirred at room temperature for 70 hr. The solvent was evaporated under reduced pressure, and water and ethyl acetate were added to the obtained residue. The mixture was stirred with heating at 80° C. for 15 min and filtrated through celite. The organic layer in the filtrate was washed with saturated brine, dried over anhydrous magnesium sulfate, and concentrated under reduced pressure. The residue was purified by silica gel column chromatography (20%-50% ethyl acetate/hexane) to give the title compound (14.2 g, yield 76%) as pale-yellow prism crystals.

MS m/z 397 (MH+).

Reference Example 23

3-bromo-1-(2-ethoxyethyl)-2-phenyl-1H-indole

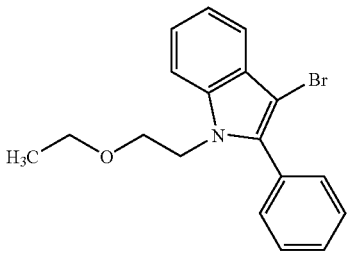

Under ice-cooling, sodium hydride (60% in oil, 0.48 g, 12.0 mmol) was added to a solution of 3-bromo-2-phenyl-1H-indole (2.72 g, 10.0 mmol) in N,N-dimethylformamide (10 mL) by small portions, and the mixture was stirred under a nitrogen atmosphere at the same temperature for 30 min. To the reaction mixture was added 2-chloroethyl ethyl ether (1.65 mL, 15.0 mmol), and the mixture was stirred at 70° C. for 3 hr. Water was added to the reaction mixture, and the mixture was extracted with ethyl acetate. The extract was washed with saturated brine, dried over anhydrous magnesium sulfate, and concentrated under reduced pressure. The obtained residue was purified by silica gel column chromatography (hexane-25% ethyl acetate/hexane) to give the title compound (2.60 g, yield 76%) as a red oil.

MS m/z 344 (MH+).

Reference Example 24

3-[1-(2-ethoxyethyl)-2-phenyl-1H-indol-3-yl]benzaldehyde

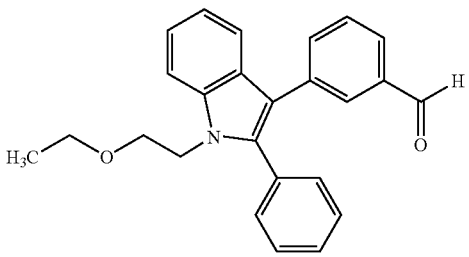

In the same manner as in Reference Example 2, the title compound was obtained as a yellow oil from 3-bromo-1-(2-ethoxyethyl)-2-phenyl-1H-indole and (3-formylphenyl)boronic acid. yield 30%.

MS m/z 370 (MH+).

Reference Example 25

{3-[1-(2-ethoxyethyl)-2-phenyl-1H-indol-3-yl]phenyl}methanol

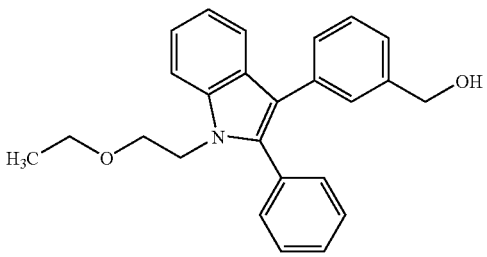

In the same manner as in Reference Example 12, the title compound was obtained as a colorless oil from 3-[1-(2-ethoxyethyl)-2-phenyl-1H-indol-3-yl]benzaldehyde. yield 97%.

MS m/z 372 (MH⁺).

Reference Example 26

{4-[(3,5-diphenyl-1H-pyrazol-1-yl)methyl]phenyl}methanol

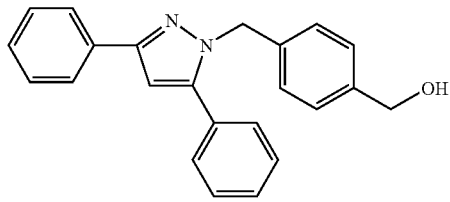

A mixture of 3,5-diphenylpyrazole (7.32 g, 33 mmol), [4-(chloromethyl)phenyl]methanol (5.00 g, 32 mmol), potassium carbonate (6.90 g, 50 mmol) and N,N-dimethylformamide (50 mL) was stirred at 120° C. for 1 hr. The reaction mixture was poured into 1 N hydrochloric acid and the mixture was extracted with ethyl acetate. The ethyl acetate layer was washed with saturated brine, dried over anhydrous magnesium sulfate, and concentrated under reduced pressure to give the title compound (7.10 g, yield 63%) as colorless crystals.

¹H NMR (CDCl₃) δ: 1.59-1.68 (1H, m), 4.66 (2H, d, J=5.8 Hz), 5.39 (2H, s), 6.67 (1H, s), 7.10 (2H, d, J=8.1 Hz), 7.24-7.47 (10H, m), 7.84-7.90 (2H, m).

Reference Example 27 methyl 4-{[5-(4-fluorophenyl)-1-methyl-1H-pyrazol-4-yl]methoxy}benzoate

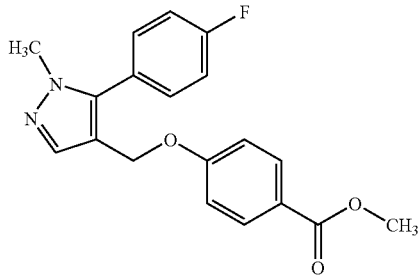

To a solution of 5-(4-fluorophenyl)-1-methyl-1H-pyrazole-4-carbaldehyde (1.02 g, 5.0 mmol) in tetrahydrofuran (10 mL) was added lithium aluminum hydride (200 mg, 5.27 mmol) at 0° C., and the mixture was stirred at 0° C. for 1 hr. Sodium sulfate decahydrate (1.0 g) was added to the reaction mixture, and the mixture was allowed to warm to room temperature and stirred for 30 min. The insoluble material was filtered off, and the filtrate was concentrated to give a colorless oil. To this oil were added methyl 4-hydroxybenzoate (910 mg, 6.0 mmol), tributylphosphine (1.61 g, 8.0 mmol) and tetrahydrofuran (10 mL), and 1,1'-(azodicarbonyl)dipiperidine (1.50 g, 5.94 mmol) was added at room temperature. The mixture was stirred at room temperature for 1 hr. The reaction mixture was concentrated under reduced pressure, and the residue was purified by silica gel column chromatography (10%-65% ethyl acetate/hexane) to give the title compound (925 mg, yield 54%, 2 steps) as a yellow oil.

¹H NMR (CDCl₃) δ: 3.81 (3H, s), 3.88 (3H, s), 4.83 (2H, s), 6.90 (2H, d, J=8.9 Hz), 7.17 (2H, t, J=8.7 Hz), 7.34-7.41 (2H, m), 7.67 (1H, s), 7.97 (2H, d, J=8.9 Hz).

Reference Example 28

(4-{[5-(4-fluorophenyl)-1-methyl-1H-pyrazol-4-yl]methoxy}phenyl)methanol

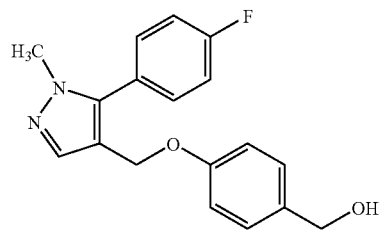

To a solution of methyl 4-{[5-(4-fluorophenyl)-1-methyl-1H-pyrazol-4-yl]methoxy}benzoate (920 mg, 2.70 mmol) in tetrahydrofuran (10 mL) was added lithium aluminum hydride (200 mg, 5.27 mmol) at 0° C., and the mixture was stirred at 0° C. for 1 hr. Sodium sulfate decahydrate (1.0 g) was added to the reaction mixture, and the mixture was allowed to warm to room temperature and stirred for 30 min. The insoluble material was filtered off, and the filtrate was concentrated to give the title compound (680 mg, yield 80%) as a yellow oil.

MS m/z 313 (MH⁺).

Reference Example 29

5-(2-phenylethyl)-3-[4-(trifluoromethyl)phenyl]-1H-pyrazole

3-[4-(Trifluoromethyl)phenyl]-1H-pyrazole-5-carbaldehyde (1.20 g, 5.0 mmol) was dissolved in N,N-dimethylformamide (10 mL), and benzyltriphenylphosphonium bromide (3.25 g, 7.5 mmol) and potassium carbonate (2.76 g, 20.0 mmol) were added. The mixture was stirred at room temperature for 14 hr. The reaction mixture was poured into water, and the mixture was extracted with ethyl acetate. The ethyl acetate layer was dried over anhydrous magnesium sulfate and concentrated. The residue was purified by silica gel column chromatography (10%-65% ethyl acetate/hexane) to give colorless crystals. The colorless crystals were dissolved in tetrahydrofuran (30 mL) and ethanol (30 mL), and 10% palladium-carbon (50% water-containing product, 500 mg) was added. Under an atmospheric hydrogen atmosphere, the mixture was stirred at room temperature for 2 hr. The catalyst was filtered off, and the filtrate was concentrated to give the title compound (880 mg, yield 56%, 2 steps) as colorless crystals.

MS m/z 317 (MH+).

Reference Example 30

[4-({5-(2-phenylethyl)-3-[4-(trifluoromethyl)phenyl]-1H-pyrazol-1-yl}methyl)phenyl]methanol

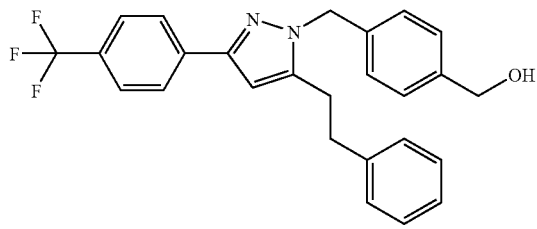

A mixture of 5-(2-phenylethyl)-3-[4-(trifluoromethyl)phenyl]-1H-pyrazole (318 mg, 1.01 mmol), [4-(chloromethyl)phenyl]methanol (240 mg, 1.53 mmol), potassium carbonate (276 mg, 2.0 mmol) and N,N-dimethylformamide (10 mL) was stirred at 120° C. for 1 hr. The reaction mixture was poured into 1 N hydrochloric acid, and the mixture was extracted with ethyl acetate. The ethyl acetate layer was dried using a Presep Dehydration tube (manufactured by Wako Pure Chemical Industries, Ltd.) and concentrated. The residue was purified by silica gel column chromatography (10%-80% ethyl acetate/hexane) to give the title compound (220 mg, yield 50%) as a yellow oil.

$^1$H NMR (CDCl$_3$) δ: 1.63 (1H, t, J=5.8 Hz), 2.78-2.94 (4H, m), 4.66 (2H, d, J=5.8 Hz), 5.24 (2H, s), 6.46 (1H, s), 7.06-7.13 (3H, m), 7.20-7.33 (6H, m), 7.62 (2H, d, J=8.2 Hz), 7.90 (2H, d, J=8.5 Hz).

Reference Example 31

(4-{[(1E)-(4-phenyl-1,3-thiazol-2-yl)methylene]amino}phenyl)methanol

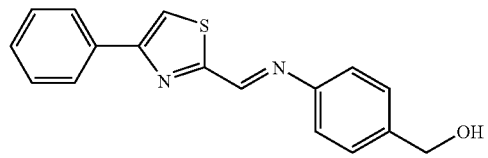

A mixture of 4-phenyl-1,3-thiazole-2-carbaldehyde (1.10 g, 5.81 mmol), (4-aminophenyl)methanol (615 mg, 5.0 mmol), acetic acid (0.4 mL) and 1,2-dichloroethane (10 mL) was stirred at room temperature for 30 min. The reaction mixture was diluted with hexane. The precipitated solid was collected by filtration, washed with hexane, and dried to give the title compound (1.30 g, yield 88%) as yellow crystals.

$^1$H NMR (DMSO-d$_6$) δ: 4.54 (2H, d, J=5.7 Hz), 5.25 (1H, t, J=5.7 Hz), 7.36-7.55 (7H, m), 7.99-8.08 (2H, m), 8.39 (1H, s), 8.92 (1H, s).

Reference Example 32 methyl(2E)-3-(6-aminopyridin-3-yl)acrylate

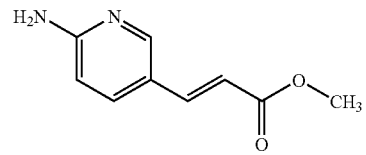

2-Amino-5-bromopyridine (13.5 g, 78.0 mmol), methyl acrylate (10.1 g, 117 mmol) and tris(2-methylphenyl)phosphine (4.75 g, 15.6 mmol) were dissolved in acetonitrile (200 mL), palladium(II) acetate (1.75 g, 7.8 mmol) was added and the mixture was stirred overnight under an argon atmosphere at 100° C. After cooling the reaction mixture, the insoluble material was removed by filtering through celite and the solvent was evaporated under reduced pressure. The residue was dissolved in saturated aqueous sodium hydrogencarbonate and chloroform, and he mixture was extracted with ethyl acetate. The organic layer was washed with saturated brine, dried over anhydrous magnesium sulfate, and concentrated under reduced pressure. The residue was purified by silica gel column chromatography (chloroform, then 0%-5% methanol/ethyl acetate), and recrystallized from ethyl acetate-hexane to give the title compound (3.81 g, yield 27%) as yellow crystals.

$^1$H NMR (CDCl$_3$) δ: 3.79 (3H, s), 4.79 (2H, s), 6.26 (1H, d, J=16.0 Hz), 6.51 (1H, d, J=8.5 Hz), 7.59 (1H, d, J=16.0 Hz), 7.64 (1H, dd, J=8.7, 2.5 Hz), 8.19 (1H, d, J=2.3 Hz).

Reference Example 33 methyl 3-(6-aminopyridin-3-yl)propanoate

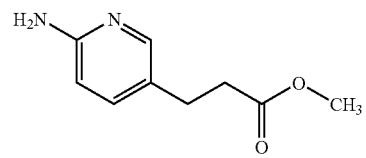

Methyl(2E)-3-(6-Aminopyridin-3-yl)acrylate (1.5 g, 8.42 mmol) was dissolved in methanol (15 mL), and 10% palladium-carbon (50% water-containing product, 0.30 g) was added. The mixture was stirred under a hydrogen atmosphere (balloon pressure) at room temperature for 16 hr. The catalyst was filtered off, and the filtrate was concentrated under reduced pressure. The residue was purified by silica gel column chromatography (0%-10% methanol/ethyl acetate) to give the title compound (1.26 g, yield 83%) as a white powder.

$^1$H NMR (CDCl$_3$) δ: 2.57 (2H, t, J=7.6 Hz), 2.81 (2H, t, J=7.6 Hz), 3.66 (3H, s), 4.36 (2H, s), 6.42-6.48 (1H, m), 7.25-7.32 (1H, m), 7.92 (1H, d, J=1.9 Hz).

Reference Example 34 methyl 3-(6-{[(2-nitrophenyl)sulfonyl]amino}pyridin-3-yl)propanoate

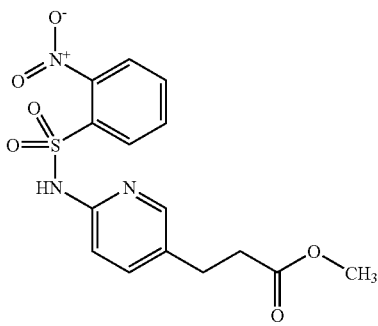

To a solution of methyl 3-(6-aminopyridin-3-yl)propanoate (500 mg, 2.78 mmol) in pyridine (5 mL) was added 2-nitrobenzenesulfonyl chloride (924 mg, 4.17 mmol), and the mixture was stirred at room temperature for 16 hr. Water was added to the reaction mixture, and the mixture was extracted with ethyl acetate. The extract was washed with saturated brine, dried over anhydrous magnesium sulfate, and concentrated under reduced pressure. The residue was crystallized from ethyl acetate-hexane to give the title compound (365 mg, yield 36%) as yellow crystals.

MS m/z 366 (MH$^+$).

Reference Example 35 ethyl(2Z)-2-fluoro-3-(4-nitrophenyl)acrylate

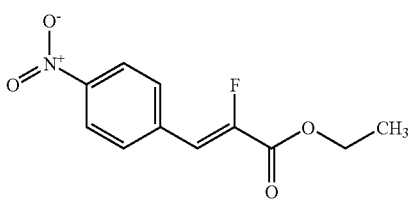

A solution of ethyl diethylphosphono-2-fluoroacetate (4.90 g, 20.2 mmol) in tetrahydrofuran (40 mL) was stirred under a nitrogen atmosphere at 0° C. and 1.6 M n-butyllithium/hexane solution (13.1 mL, 21.0 mmol) was added dropwise. The reaction mixture was stirred at 0° C. for 30 min, and a solution of 4-nitrobenzaldehyde (3.05 g, 20.2 mmol) in tetrahydrofuran (40 mL) was added dropwise. The mixture was stirred at room temperature for 16 hr, and ice-cooled aqueous ammonium chloride solution was added. The mixture was extracted with ethyl acetate, and the extract was washed with saturated brine, dried over anhydrous magnesium sulfate, and concentrated under reduced pressure. The residue was purified by silica gel column chromatography (3%-40% ethyl acetate/hexane) to give the title compound (3.46 g, yield 72%) as a yellow powder.

$^1$H NMR (CDCl$_3$) δ: 1.26 (3H, t, J=7.2 Hz), 4.26 (2H, q, J=7.2 Hz), 6.92 (1H, d, J=20.5 Hz), 7.57-7.65 (2H, m), 8.18-8.28 (2H, m).

Reference Example 36 ethyl 3-(4-aminophenyl)-2-fluoropropanoate

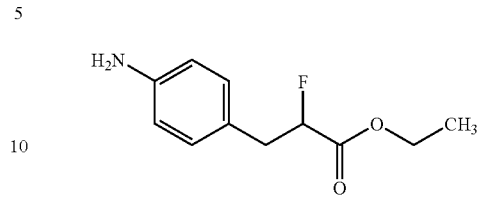

In the same manner as in Reference Example 33, the title compound was obtained as a pale-yellow oil from ethyl(2Z)-2-fluoro-3-(4-nitrophenyl)acrylate. yield 53%.

$^1$H NMR (CDCl$_3$) δ: 1.26 (3H, t, J=7.1 Hz), 2.95-3.21 (2H, m), 3.62 (2H, s), 4.22 (2H, q, J=7.1 Hz), 4.89-5.12 (1H, m), 6.60-6.66 (2H, m), 7.03 (2H, d, J=8.1 Hz).

Reference Example 37 ethyl 2,2-difluoro-3-hydroxy-3-(4-nitrophenyl)propanoate

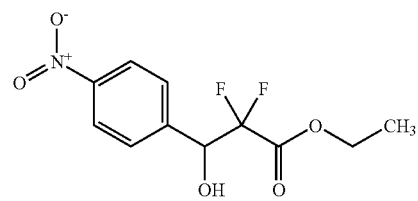

A suspension of ethyl bromodifluoroacetate (20.3 g, 100 mmol) and zinc powder (6.5 g, 100 mmol) in tetrahydrofuran (100 mL) was heated under reflux for 10 min, and 4-nitrobenzaldehyde (8.4 g, 55.8 mmol) was added dropwise. The reaction mixture was refluxed for 4 hr and allowed to cool to room temperature. Aqueous sodium hydrogensulfate solution was added, and the mixture was extracted with ethyl acetate. The extract was washed with saturated brine, dried over anhydrous magnesium sulfate, and concentrated under reduced pressure. The residue was purified by silica gel column chromatography (5%-40% ethyl acetate/hexane) to give the title compound (4.80 g, yield 20%) as a yellow oil.

$^1$H NMR (CDCl$_3$) δ: 1.34 (3H, t, J=7.1 Hz), 2.96 (1H, d, J=5.1 Hz), 4.35 (2H, q, J=7.1 Hz), 5.27-5.38 (1H, m), 7.63-7.69 (2H, m, J=8.3 Hz), 8.23-8.29 (2H, m).

Reference Example 38 ethyl 3-(4-aminophenyl)-2,2-difluoro-3-hydroxypropanoate

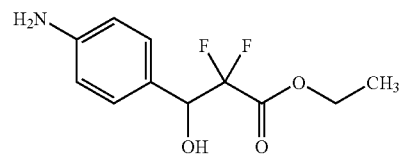

In the same manner as in Reference Example 33, the title compound was obtained as a yellow powder from ethyl 2,2-difluoro-3-hydroxy-3-(4-nitrophenyl)propanoate. yield 75%.

$^1$H NMR (CDCl$_3$) δ: 1.24-1.35 (3H, m), 3.40 (3H, br s), 4.29 (2H, q, J=7.2 Hz), 5.02 (1H, dd, J=15.5, 8.5 Hz), 6.65 (2H, d, J=8.3 Hz), 7.20 (2H, d, J=8.3 Hz).

Reference Example 39

4-{[(2-phenylethyl)(4-phenyl-1,3-thiazol-2-yl)amino]methyl}benzaldehyde

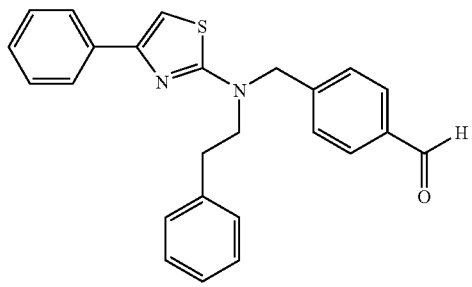

To a solution of (4-{[(2-phenylethyl)(4-phenyl-1,3-thiazol-2-yl)amino]methyl}phenyl)methanol (3.0 g, 7.49 mmol) in tetrahydrofuran (50 mL) was added manganese dioxide (1.95 g, 22.5 mmol), and the mixture was stirred at room temperature for 3 hr. The insoluble material was filtered off and the filtrate was concentrated. The residue was purified by silica gel column chromatography (5%-50% ethyl acetate/hexane) to give the title compound (2.02 g, yield 68%) as a colorless oil.

$^1$H NMR (CDCl$_3$) δ: 2.97-3.05 (2H, m), 3.66-3.74 (2H, m), 4.73 (2H, s), 6.77 (1H, s), 7.17-7.48 (10H, m), 7.81-7.89 (4H, m), 9.99 (1H, s).

Reference Example 40 ethyl(4-nitrophenoxy)acetate

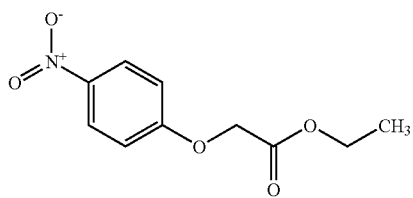

A solution of 4-nitrophenol (10 g, 71.9 mmol), ethyl bromoacetate (13.5 g, 80.8 mmol) and potassium carbonate (12.0 g, 86.8 mmol) in N,N-dimethylformamide (100 mL) was stirred at room temperature for 18 hr. The reaction solution was concentrated under reduced pressure, and the residue was diluted with ethyl acetate, washed successively with water and brine, dried over magnesium sulfate, and concentrated under reduced pressure. The obtained crystals were washed with diethyl ether-hexane to give the title compound (16.0 g, yield 99%) as colorless needle crystals.

$^1$H NMR (CDCl$_3$) δ: 1.31 (3H, t, J=7.0 Hz), 4.29 (2H, q, J=7.0 Hz), 4.72 (2H, s), 6.97 (2H, d, J=9.0 Hz), 8.22 (2H, d, J=9.0 Hz).

Reference Example 41 ethyl(4-aminophenoxy)acetate

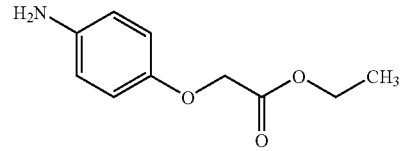

Ethyl(4-nitrophenoxy)acetate (10.0 g, 44.4 mmol) and 10% palladium-carbon (50% water-containing product, 3.0 g) were added to a mixed solution of tetrahydrofuran (50 mL) and ethanol (50 mL), and the mixture was stirred at room temperature for 18 hr in a hydrogen stream. The catalyst was filtered off, and the filtrate was concentrated under reduced pressure. The obtained residue was subjected to silica gel column chromatography (ethyl acetate:hexane=1:2-2:3-1:1), and the obtained crystals were recrystallized from ethyl acetate-hexane to give the title compound (6.4 g, yield 74%) as pale-pink prism crystals.

$^1$H NMR (CDCl$_3$) δ: 1.29 (3H, t, J=7.0 Hz), 3.46 (2H, br s), 4.26 (2H, q, J=7.0 Hz), 4.54 (2H, s), 6.63 (2H, d, J=9.0 Hz), 6.77 (2H, d, J=9.0 Hz).

Reference Example 42 methyl 6-(benzyloxy)-4'-hydroxybiphenyl-3-carboxylate

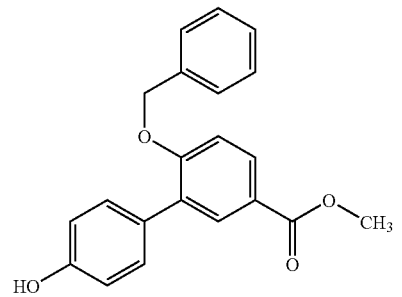

(4-Hydroxyphenyl)boronic acid (5.0 g, 36.3 mmol), methyl 4-benzyloxy-3-bromobenzoate (7.0 g, 21.8 mmol) and cesium carbonate (18.0 g, 55.2 mmol) were added to a mixed solution of methanol (50 mL) and toluene (100 mL), the air was substituted with argon gas, and tetrakis(triphenylphosphine)palladium(0) (0.45 g, 0.39 mmol) was added. The reaction mixture was stirred under an argon atmosphere at 70° C. for 2 days. After cooling the reaction mixture, the insoluble material was filtered off through celite, and the filtrate was concentrated under reduced pressure. The obtained residue was subjected to silica gel column chromatography (ethyl acetate:hexane=1:5-2:1), and the obtained crystals were recrystallized from ethyl acetate-hexane to give the title compound (5.0 g, yield 69%) as colorless prism crystals.

MS m/z 335 (MH$^+$).

Reference Example 43 methyl 6-(benzyloxy)-4'-(2-ethoxyethoxy)biphenyl-3-carboxylate

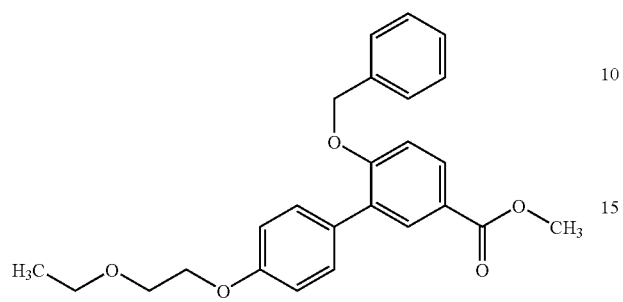

A solution of methyl 6-(benzyloxy)-4'-hydroxybiphenyl-3-carboxylate (5.0 g, 15.0 mmol), 2-chloroethyl ethyl ether (2.1 mL, 19.1 mmol) and potassium carbonate (3.1 g, 22.4 mmol) in N,N-dimethylformamide (50 mL) was stirred at 60° C. for 24 hr. 2-Chloroethyl ethyl ether (2.0 mL, 18.2 mmol) and potassium carbonate (3.0 g, 21.8 mmol) were further added to the reaction solution, and the mixture was stirred at 60° C. for 2 days. The reaction solution was diluted with ethyl acetate, washed successively with water and brine, dried over magnesium sulfate, and concentrated under reduced pressure. The obtained residue was subjected to silica gel column chromatography (ethyl acetate:hexane=1:10-1:3) to give the title compound (6.0 g, yield 99%) as a colorless oil.

MS m/z 407 (MH$^+$).

Reference Example 44

[6-(benzyloxy)-4'-(2-ethoxyethoxy)biphenyl-3-yl]methanol

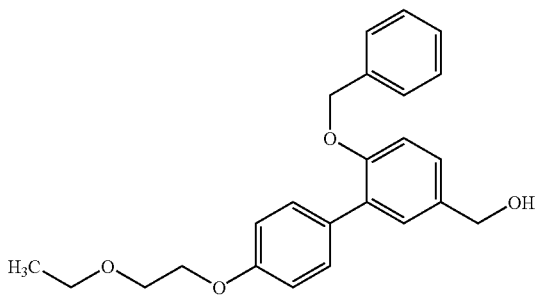

To a solution (40 mL) of methyl 6-(benzyloxy)-4'-(2-ethoxyethoxy)biphenyl-3-carboxylate (2.0 g, 4.92 mmol) in anhydrous tetrahydrofuran was added lithium aluminum hydride (0.19 g, 5.01 mmol) under ice-cooling, and the mixture was stirred at room temperature for 3 hr. The reaction solution was ice-cooled, and sodium sulfate decahydrate (3.0 g, 5.74 mmol) was added. The mixture was stirred at room temperature for 1 hr. The precipitated insoluble material was filtered off through celite, and the filtrate was concentrated under reduced pressure. The obtained residue was subjected to silica gel column chromatography (ethyl acetate:hexane=1:2-1:1), and the obtained crystals were recrystallized from ethyl acetate-hexane to give the title compound (1.7 g, yield 91%) as colorless needle crystals.

$^1$H NMR (CDCl$_3$) δ: 1.26 (3H, t, J=6.9 Hz), 1.57 (1H, t, J=6.0 Hz), 3.62 (2H, q, J=6.9 Hz), 3.82 (2H, t, J=4.8 Hz), 4.16 (2H, t, J=4.8 Hz), 4.65 (2H, d, J=6.0 Hz), 5.07 (2H, s), 6.94-7.34 (10H, m), 7.50 (2H, d, J=8.7 Hz).

Reference Example 45

4'-(2-ethoxyethoxy)-6-methoxybiphenyl-3-carbaldehyde

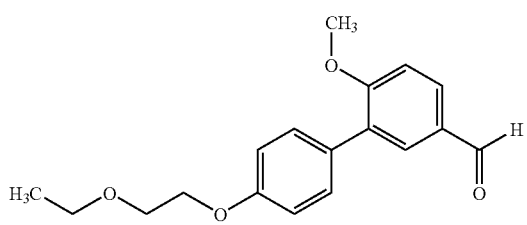

In the same manner as in Reference Example 42, the title compound was obtained as a pale-yellow oil from 1-bromo-4-(2-ethoxyethoxy)benzene and 5-formyl-2-methoxyphenylboronic acid. yield 70%.

MS m/z 301 (MH$^+$).

Reference Example 46 ethyl 5-hydroxy-1-(2-methylphenyl)-1H-pyrazole-3-carboxylate

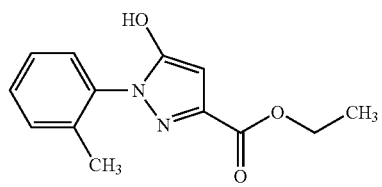

To a mixture of diethyl oxalacetate sodium salt (10.5 g, 50 mmol), acetic acid (100 mL) and toluene (50 mL) was added an aqueous solution (50 mL) of (2-methylphenyl)hydrazine hydrochloride (7.93 g, 50 mmol) under stirring at room temperature, and the mixture was heated under reflux for 3 hr. After cooling, the reaction mixture was partitioned. The organic layer was washed with water and saturated brine, dried, and concentrated under reduced pressure. The residue was purified by silica gel column chromatography (hexane/ethyl acetate=10/1-3/1) to give yellow crystals. This product was dissolved in acetic acid (36 mL), and the mixture was heated under reflux for 2 hr. After cooling, the reaction mixture was concentrated under reduced pressure, and recrystallized from hexane-ethyl acetate to give the title compound (2.69 g, yield 22%) as colorless crystals.

$^1$H NMR (CDCl$_3$) δ: 1.30 (3H, t, J=7.2 Hz), 2.02 (3H, s), 3.74 (1H, s), 4.33 (2H, q, J=7.2 Hz), 5.94 (1H, s), 7.13-7.36 (4H, m).

Reference Example 47 ethyl 5-isobutoxy-1-(2-methylphenyl)-1H-pyrazole-3-carboxylate

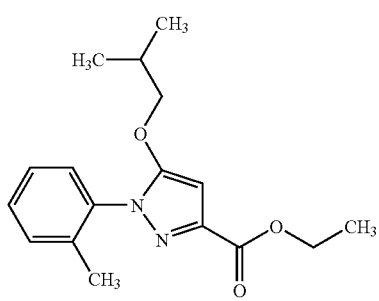

To a mixture of ethyl 5-hydroxy-1-(2-methylphenyl)-1H-pyrazole-3-carboxylate (1.0 g, 4.06 mmol), potassium carbonate (0.84 g, 6.09 mmol) and N,N-dimethylformamide (10 mL) was added isobutyl bromide (0.49 mL, 4.47 mmol) under stirring at room temperature, and the mixture was stirred at the same temperature for 16 hr. The reaction mixture was diluted with ethyl acetate, washed with water and 5% aqueous potassium hydrogensulfate solution, dried, and concentrated under reduced pressure. The residue was purified by silica gel column chromatography (hexane/ethyl acetate=10/1-4/1) to give the title compound (1.07 g, yield 87%) as pale-yellow crystals.

$^1$H NMR (CDCl$_3$) δ: 0.90 (6H, d, J=6.9 Hz), 1.40 (3H, t, J=7.2 Hz), 2.02 (1H, m), 2.13 (3H, s), 3.84 (2H, d, J=6.6 Hz), 4.41 (2H, q, J=7.2 Hz), 6.17 (1H, s), 7.21-7.41 (4H, m).

Reference Example 48

[5-isobutoxy-1-(2-methylphenyl)-1H-pyrazol-3-yl]methanol

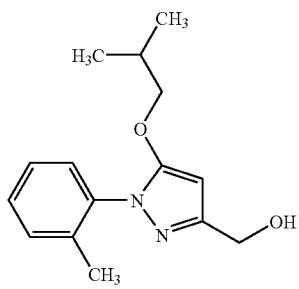

To a solution (10 mL) of ethyl 5-isobutoxy-1-(2-methylphenyl)-1H-pyrazole-3-carboxylate (1.07 g, 3.54 mmol) in anhydrous tetrahydrofuran was added lithium aluminum hydride (0.13 g, 3.54 mmol) under stirring at 0° C., and the mixture was stirred at the same temperature for 2 hr. After completion of the reaction, sodium sulfate decahydrate (2.28 g, 7.08 mmol) was added to the reaction system and the mixture was stirred at room temperature for 2 hr. The precipitated insoluble material was filtered off, and the filtrate was concentrated under reduced pressure. The residue was purified by silica gel column chromatography (hexane/ethyl acetate=4/1-1/1) to give the title compound (0.85 g, yield 92%) as a pale-yellow oil.

$^1$H NMR (CDCl$_3$) δ: 0.90 (6H, d, J=6.6 Hz), 1.92-2.12 (2H, m), 2.16 (3H, s), 3.80 (2H, d, J=6.9 Hz), 4.65 (2H, d, J=5.7 Hz), 5.64 (1H, s), 7.23-7.36 (4H, m).

Reference Example 49

3-(chloromethyl)-4-isobutoxybenzaldehyde

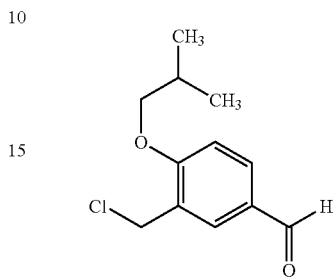

To a mixture of 4-isobutoxybenzaldehyde (6.9 g, 38.7 mmol), aluminum chloride (12.9 g, 96.8 mmol) and nitromethane (39 mL) was added methoxyacetyl chloride (4.1 mL, 44.5 mmol) under stirring at 0° C., and the mixture was stirred at the same temperature for 3 hr. After completion of the reaction, the reaction mixture was poured into ice water, and the mixture was extracted with ethyl acetate. The organic layer was dried over magnesium sulfate, and concentrated under reduced pressure. The residue was purified by silica gel column chromatography (hexane/ethyl acetate=10/1-4/1) to give the title compound (5.22 g, yield 60%) as colorless crystals.

$^1$H NMR (CDCl$_3$) δ: 1.08 (6H, d, J=6.9 Hz), 2.19 (1H, m), 3.89 (2H, d, J=6.0 Hz), 4.68 (2H, s), 6.98 (1H, d, J=8.4 Hz), 7.84 (1H, dd, J=8.4, 2.1 Hz), 7.91 (1H, d, J=2.1 Hz), 9.89 (1H, s).

Reference Example 50

4-isobutoxy-3-{[(2-phenylethyl)(4-phenyl-1,3-thiazol-2-yl)amino]methyl}benzaldehyde

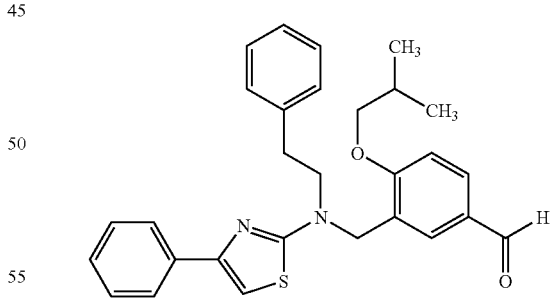

To a solution of 4-phenyl-N-(2-phenylethyl)-1,3-thiazole-2-amine (0.95 g, 3.40 mmol) in N,N-dimethylformamide (7 mL) was added sodium hydride (60% in oil, 0.14 g, 3.40 mmol) under stirring at 0° C., and the mixture was stirred at the same temperature for 5 min. Then, 3-(chloromethyl)-4-isobutoxybenzaldehyde (0.70 g, 3.09 mmol) and sodium iodide (0.51 g, 3.40 mmol) were added to the reaction mixture, and the mixture was stirred at room temperature for 16 hr. The reaction mixture was diluted with ethyl acetate, washed with water and saturated brine, dried, and concentrated under reduced pressure. The residue was purified by silica gel column chromatography (hexane/ethyl acetate=10/1-3/1) to give the title compound (1.43 g, yield 99%) as a pale-yellow oil.

$^1$H NMR (CDCl$_3$) δ: 1.03 (6H, d, J=6.6 Hz), 2.12 (1H, m), 3.03 (2H, t, J=7.5 Hz), 3.76 (2H, t, J=7.5 Hz), 3.85 (2H, d, J=6.6 Hz), 4.68 (2H, s), 6.74 (1H, s), 6.97 (1H, d, J=8.4 Hz), 7.17-7.34 (6H, m), 7.34-7.43 (2H, m), 7.74-7.83 (2H, m), 7.84-7.91 (2H, m), 9.82 (1H, s).

Reference Example 51

(4-isobutoxy-3-{[(2-phenylethyl)(4-phenyl-1,3-thiazol-2-yl)amino]methyl}phenyl)methanol

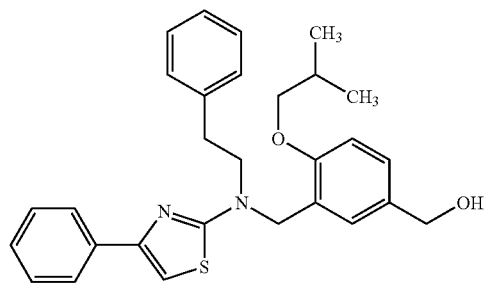

To a mixture of 4-isobutoxy-3-{[(2-phenylethyl)(4-phenyl-1,3-thiazol-2-yl)amino]methyl}benzaldehyde (1.43 g, 3.04 mmol), methanol (5 mL) and tetrahydrofuran (10 mL) was added sodium borohydride (58 mg, 1.52 mmol) under stirring at 0° C., and the mixture was stirred at the same temperature for 2 hr. The reaction mixture was diluted with ethyl acetate, washed with water and saturated brine, dried, and concentrated under reduced pressure. The residue was purified by silica gel column chromatography (hexane/ethyl acetate=10/1-1/1) to give the title compound (1.28 g, yield 88%) as colorless crystals.

$^1$H NMR (CDCl$_3$) δ: 1.01 (6H, d, J=6.6 Hz), 1.47 (1H, t, J=5.4 Hz), 2.09 (1H, m), 3.02 (2H, t, J=7.5 Hz), 3.70-3.80 (4H, m), 4.55 (2H, d, J=4.8 Hz), 4.67 (2H, s), 6.72 (1H, s), 6.85 (1H, d, J=9.0 Hz), 7.16-7.34 (8H, m), 7.35-7.43 (2H, m), 7.86-7.93 (2H, m).

Reference Example 52

N-(3-hydroxyphenyl)-2-nitrobenzenesulfonamide

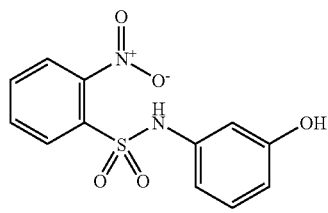

In the same manner as in Reference Example 3, the title compound was obtained as pale-brown crystals from 3-aminophenol. yield 77%.

MS m/z 295 (MH$^+$).

Reference Example 53

N-[4-(chloromethyl)-2-oxo-2H-chromen-7-yl]-2-nitrobenzenesulfonamide

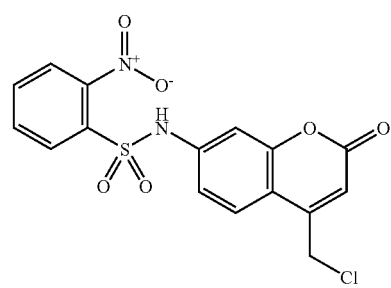

To a suspension of N-(3-hydroxyphenyl)-2-nitrobenzenesulfonamide (21.0 g, 71.4 mmol) in concentrated sulfuric acid (8 mL) was added ethyl 4-chloroacetacetate (12.0 mL, 85.6 mmol) by small portions and the mixture was stirred at room temperature for 18 hr. The reaction mixture was poured into ice water, and the resulting solid was collected by filtration, washed with water and air-dried to give the title compound (14.3 g, yield 51%).

MS m/z 282 (MH$^+$).

Reference Example 54

(6-{[(2-nitrophenyl)sulfonyl]amino}-1-benzofuran-3-yl)acetic acid

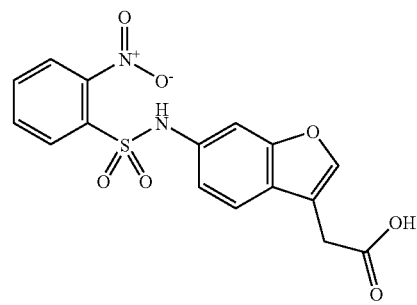

A mixture of N-[4-(chloromethyl)-2-oxo-2H-chromen-7-yl]-2-nitrobenzenesulfonamide (14.3 g, 36.2 mmol) and 1 M aqueous sodium hydroxide solution (120 mL) was stirred at room temperature for 24 hr. The reaction mixture was acidified with 1 M hydrochloric acid, and the mixture was extracted with a mixed solvent of ethyl acetate and tetrahydrofuran. The extract was washed with saturated brine, dried over anhydrous magnesium sulfate, and concentrated under reduced pressure to give the title compound (13.6 g, quant.) as pale-brown crystals.

MS m/z 377 (MH$^+$).

Reference Example 55 methyl(6-{[(2-nitrophenyl)sulfonyl]amino}-1-benzofuran-3-yl)acetate

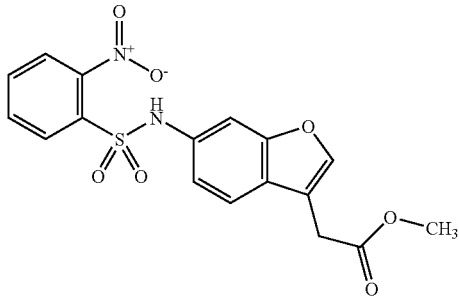

(6-{[(2-Nitrophenyl)sulfonyl]amino}-1-benzofuran-3-yl)acetic acid (2.84 g, 7.55 mmol) was suspended in methanol (8 mL), and thionyl chloride (2 mL, 27.4 mmol) was added dropwise under ice-cooling. After completion of the dropwise addition, the mixture was stirred at room temperature for 2.5 hr. The reaction mixture was concentrated under reduced pressure. Water was added and the mixture was extracted with ethyl acetate. The extract was washed with saturated brine, dried over anhydrous magnesium sulfate, and concentrated under reduced pressure. The residue was purified by silica gel column chromatography (20%-60% ethyl acetate/hexane), and the obtained solid was recrystallized from ethyl acetate-hexane to give the title compound (1.82 g, yield 62%) as yellow prism crystals.

MS m/z 391 (MH$^+$).

Reference Example 56

N,N-diethyl-2-[(3'-formyl-2,6-dimethylbiphenyl-4-yl)oxy]acetamide

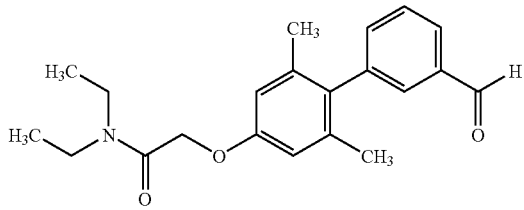

To a solution of 4'-hydroxy-2',6'-dimethylbiphenyl-3-carbaldehyde (0.905 g, 4.00 mmol) and 2-chloro-N,N-diethylacetamide (0.748 g, 5.00 mmol) in acetone (10 mL) was added potassium carbonate (0.663 g, 4.80 mmol), and the mixture was heated under reflux for 2 hr under a nitrogen atmosphere. The reaction mixture was concentrated under reduced pressure, water was added and the mixture was extracted with ethyl acetate. The extract was washed with saturated brine, dried over anhydrous magnesium sulfate, and concentrated under reduced pressure. The residue was purified by silica gel column chromatography (30%-70% ethyl acetate/hexane) to give the title compound (0.729 g, yield 54%) as a yellow oil.

MS m/z 340 (MH$^+$).

Reference Example 57

2',6'-dimethyl-4'-(2-morpholin-4-yl-2-oxoethoxy)biphenyl-3-carbaldehyde

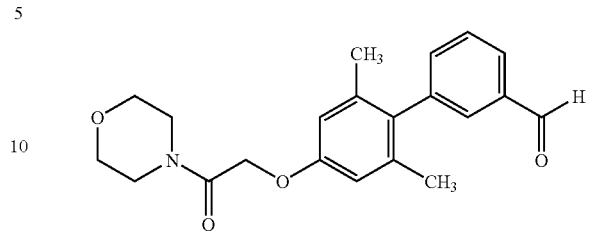

In the same manner as in Reference Example 56, the title compound was obtained as a colorless oil from 4'-hydroxy-2',6'-dimethylbiphenyl-3-carbaldehyde and 4-(chloroacetyl)morpholine. yield 71%.

MS m/z 354 (MH$^+$).

Reference Example 58

3-bromo-1-(2-ethoxyethyl)-2-methyl-1H-indole

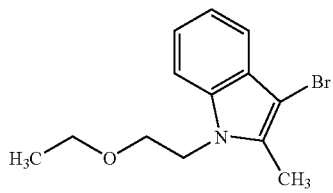

Under ice-cooling, sodium hydride (60% in oil, 1.44 g, 36.0 mmol) was added to a solution of 3-bromo-2-methyl-1H-indole (6.30 g, 30.0 mmol) in N,N-dimethylformamide (30 mL) by small portions, and the mixture was stirred under a nitrogen atmosphere at the same temperature for 1 hr. To the reaction mixture were added 2-bromoethyl ethyl ether (5.07 mL, 45.0 mmol) and sodium iodide (0.747 g, 4.50 mmol), and the mixture was stirred at 70° C. for 6 hr. The reaction mixture was concentrated under reduced pressure, water was added and the mixture was extracted with ethyl acetate. The extract was washed with saturated brine, dried over anhydrous magnesium sulfate, and concentrated under reduced pressure. The residue was purified by silica gel column chromatography (hexane-25% ethyl acetate/hexane) to give the title compound (6.30 g, yield 74%) as dark-purple oil.

MS m/z 282 (MH$^+$).

Reference Example 59

3-[1-(2-ethoxyethyl)-2-methyl-1H-indol-3-yl]benzaldehyde

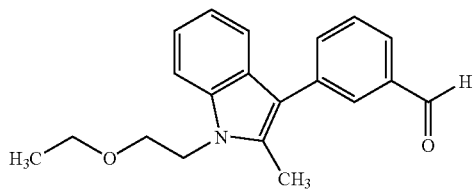

In the same manner as in Reference Example 2, the title compound was obtained as a yellow oil from 3-bromo-1-(2-ethoxyethyl)-2-methyl-1H-indole and (3-formylphenyl)boronic acid. yield 13%.

MS m/z 308 (MH⁺).

Reference Example 60 methyl 3-(benzyloxy)-5-hydroxybenzoate

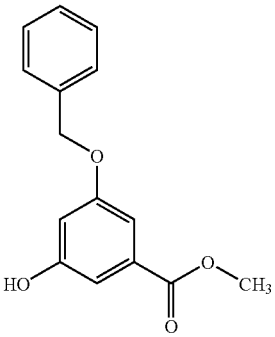

To a solution of methyl 3,5-dihydroxybenzoate (8.41 g, 50.0 mmol) and benzyl bromide (3.57 mL, 30.0 mmol) in N,N-dimethylformamide (30 mL) was added potassium carbonate (4.15 g, 30.0 mmol), and the mixture was stirred under a nitrogen atmosphere at 70° C. for 16 hr. The reaction mixture was concentrated under reduced pressure, and water was added. The mixture was extracted with ethyl acetate. The extract was washed with saturated brine, dried over anhydrous magnesium sulfate, and concentrated under reduced pressure. The residue was purified by silica gel column chromatography (5%-30% ethyl acetate/hexane) and recrystallized from ethyl acetate-hexane to give the title compound (3.56 g, yield 46%) as colorless prism crystals.

MS m/z 259 (MH⁺).

Reference Example 61 methyl 5-(benzyloxy)-2',6'-dimethylbiphenyl-3-carboxylate

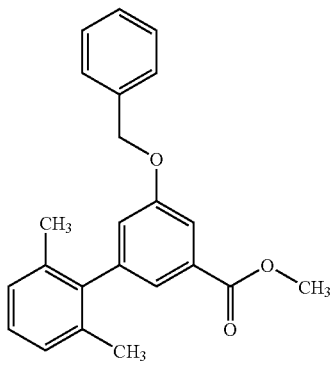

To a solution of methyl 3-(benzyloxy)-5-hydroxybenzoate (3.10 g, 12.0 mmol) and N-ethyldiisopropylamine (2.51 mL, 14.4 mmol) in dichloromethane (30 mL) was added dropwise trifluoromethanesulfonic anhydride (2.22 mL, 13.2 mmol) under ice-cooling, and the mixture was stirred at the same temperature for 1 hr. The reaction mixture was washed with water, dried over anhydrous magnesium sulfate, and concentrated under reduced pressure. The obtained residue was dissolved in 1,2-dimethoxyethane (40 mL), and 2,6-dimethylphenylboronic acid (2.25 g, 15.0 mmol), tripotassium phosphate (3.82 g, 18.0 mmol), and tetrakis(triphenylphosphine)palladium(0) (0.693 g, 0.600 mmol) were added. The reaction mixture was stirred under an argon atmosphere at 80° C. for 15 hr. The reaction mixture was concentrated under reduced pressure, and water was added to the residue. The mixture was extracted with ethyl acetate. The extract was washed with saturated brine, dried over anhydrous magnesium sulfate, and concentrated under reduced pressure. The residue was purified by silica gel column chromatography (hexane-20% ethyl acetate/hexane) to give the title compound (3.60 g, yield 87%) as a yellow oil.

MS m/z 347 (MH⁺).

Reference Example 62

[5-(benzyloxy)-2',6'-dimethylbiphenyl-3-yl]methanol

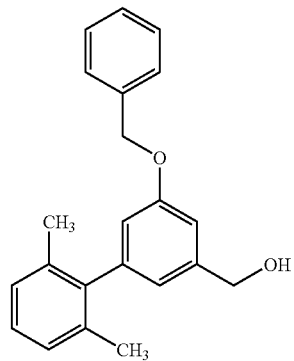

To a solution of methyl 5-(benzyloxy)-2',6'-dimethylbiphenyl-3-carboxylate (1.04 g, 3.00 mmol) in tetrahydrofuran (10 mL) was added lithium aluminum hydride (0.114 g, 3.00 mmol) by small portions, and the mixture was stirred under a nitrogen atmosphere at room temperature for 2 hr. Sodium sulfate decahydrate (0.967 g, 3.00 mmol) was added to the reaction mixture, and the mixture was stirred at room temperature for 1 hr. The precipitated insoluble material was filtered off through celite, and the filtrate was concentrated under reduced pressure to give the title compound (0.934 g, yield 98%) as a colorless oil.

¹H NMR (CDCl₃) δ: 1.68 (1H, t, J=5.7 Hz), 2.02 (6H, s), 4.71 (2H, d, J=5.7 Hz), 5.09 (2H, s), 6.67-6.75 (2H, m), 6.99-7.19 (4H, m), 7.28-7.47 (5H, m).

Reference Example 63

{4-[(3-tert-butyl-5-phenyl-1H-pyrazol-1-yl)methyl]phenyl}methanol

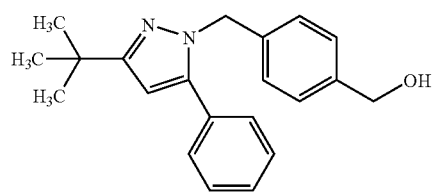

A mixture of 3-tert-butyl-5-phenyl-1H-pyrazole (2.0 g, 10 mmol), 4-(chloromethyl)benzyl alcohol (1.70 g, 10.8 mmol), potassium carbonate (2.76 g, 20 mmol) and N,N-dimethylformamide (20 mL) was stirred at 120° C. for 2 hr. The reaction mixture was poured into water, and the mixture was extracted with ethyl acetate. The ethyl acetate layer was dried over anhydrous magnesium sulfate and concentrated. The residue was purified by silica gel column chromatography (5%-80% ethyl acetate/hexane) to give the title compound (640 mg, yield 20%) as a yellow oil.

$^1$H NMR (CDCl$_3$) δ: 1.37 (9H, s), 1.68 (1H, t, J=5.9 Hz), 4.65 (2H, d, J=5.7 Hz), 5.27-5.35 (2H, m), 6.20 (1H, s), 7.00 (2H, d, J=8.3 Hz), 7.23-7.37 (7H, m).

Reference Example 64

4-({5-(2-phenylethyl)-3-[4-(trifluoromethyl)phenyl]-1H-pyrazol-1-yl}methyl)benzaldehyde

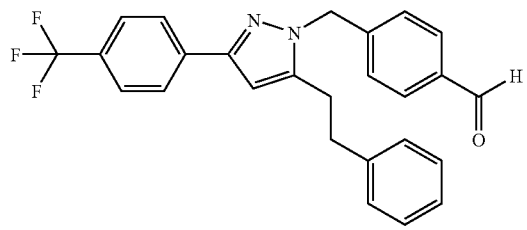

A mixture of [4-({5-(2-phenylethyl)-3-[4-(trifluoromethyl)phenyl]-1H-pyrazol-1-yl}methyl)phenyl]methanol (2.00 g, 4.58 mmol), manganese dioxide (7.00 g, 80.5 mmol) and tetrahydrofuran (50 mL) was stirred at room temperature for 2 hr. The insoluble material was filtered off and the filtrate was concentrated to give the title compound (1.70 g, yield 86%) as colorless crystals.

$^1$H NMR (CDCl$_3$) δ: 2.79-2.87 (2H, m), 2.88-2.97 (2H, m), 5.30 (2H, s), 6.51 (1H, s), 7.07-7.13 (2H, m), 7.18-7.33 (5H, m), 7.65 (2H, d, J=8.3 Hz), 7.79-7.85 (2H, m), 7.91 (2H, d, J=8.1 Hz), 9.98 (1H, s).

Reference Example 65

3-tert-butyl-1H-pyrazole-5-carbaldehyde

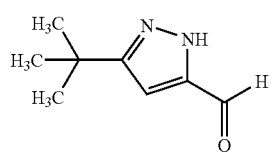

To a mixture of ethyl 3-tert-butyl-1H-pyrazole-5-carboxylate (4.00 g, 20.4 mmol) and tetrahydrofuran (50 mL) was added lithium aluminum hydride (800 mg, 21.1 mmol) by small portions under ice-cooling, and the mixture was stirred at the same temperature for 1 hr. Sodium sulfate decahydrate (7.6 g) was added to the reaction mixture, and the insoluble material was filtered off. The filtrate was concentrated and a mixture of the obtained residue, manganese dioxide (10 g, 115 mmol) and tetrahydrofuran (100 mL) was stirred at room temperature for 3 hr. The insoluble material was filtered off, and the filtrate was concentrated to give the title compound (2.13 g, yield 69%) as colorless crystals.

$^1$H NMR (CDCl$_3$) δ: 1.37 (9H, s), 6.65 (1H, s), 9.95 (1H, s).

Reference Example 66

3-tert-butyl-5-(2-phenylethyl)-1H-pyrazole

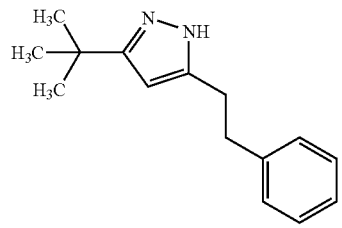

In the same manner as in Reference Example 29, the title compound was obtained as colorless crystals from 3-tert-butyl-1H-pyrazole-5-carbaldehyde. yield 83%.

$^1$H NMR (CDCl$_3$) δ: 1.31 (9H, s), 2.90-2.99 (4H, m), 5.89 (1H, s), 7.18-7.33 (5H, m).

Reference Example 67 methyl 4-{[3-tert-butyl-5-(2-phenylethyl)-1H-pyrazol-1-yl]methyl}benzoate

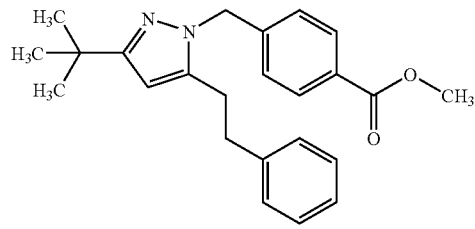

To a mixture of 3-tert-butyl-5-(2-phenylethyl)-1H-pyrazole (1.57 g, 6.87 mmol), sodium hydride (60% in oil, 280 mg, 7 mmol), and N,N-dimethylformamide (15 mL) was added methyl 4-(bromomethyl)benzoate (2.29 g, 10.0 mmol) at room temperature, and the mixture was stirred at room temperature for 2 hr. The reaction mixture was poured into 1 M hydrochloric acid, and the mixture was extracted with ethyl acetate. The ethyl acetate layer was dried over anhydrous magnesium sulfate, and concentrated under reduced pressure. The residue was purified by silica gel column chromatography (5%-40% ethyl acetate/hexane) to give the title compound (1.75 g, yield 68%) as a yellow oil.

$^1$H NMR (CDCl$_3$) δ: 1.33 (9H, s), 2.66-2.74 (2H, m), 2.77-2.87 (2H, m), 3.89 (3H, s), 5.24 (2H, s), 6.00 (1H, s), 7.00-7.09 (4H, m), 7.18-7.30 (3H, m), 7.93-7.98 (2H, m)

Reference Example 68 methyl 4-{[5-tert-butyl-3-(2-phenylethyl)-1H-pyrazol-1-yl]methyl}benzoate

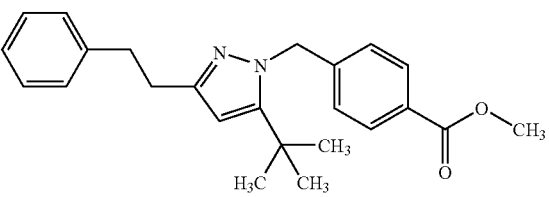

As a by-product of Reference Example 67, the title compound (240 mg, yield 9%) was obtained as a yellow oil.

$^1$H NMR (CDCl$_3$) δ: 1.26 (9H, s), 2.86-3.00 (4H, m), 3.89 (3H, s), 5.49 (2H, s), 5.90 (1H, s), 6.91 (2H, d, J=8.8 Hz), 7.17-7.30 (5H, m), 7.91-7.96 (2H, m).

Reference Example 69

4-{[3-tert-butyl-5-(2-phenylethyl)-1H-pyrazol-1-yl]methyl}benzaldehyde

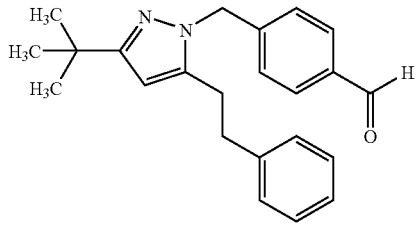

1-Methylpiperazine (10.7 g, 107 mmol) was added dropwise to sodium dihydridobis(2-methoxyethoxy)aluminate (70% toluene solution, 25 g, 86.6 mmol) at 0° C. To the obtained solution was added methyl 4-{[3-tert-butyl-5-(2-phenylethyl)-1H-pyrazol-1-yl]methyl}benzoate (1.65 g, 4.38 mmol) at 0° C. by small portions, and the mixture was further stirred at the same temperature for 1 hr. The reaction mixture was poured into 2 M hydrochloric acid, and the mixture was extracted with ethyl acetate. The extract was dried over anhydrous magnesium sulfate, and concentrated under reduced pressure to give the title compound (1.40 g, yield 92%) as a yellow oil.

$^1$H NMR (CDCl$_3$) δ: 1.33 (9H, s), 2.67-2.75 (2H, m), 2.78-2.90 (2H, m), 5.26 (2H, s), 6.01 (1H, s), 6.97-7.33 (7H, m), 7.77-7.84 (2H, m), 9.97 (1H, s).

Reference Example 70

4-{[5-tert-butyl-3-(2-phenylethyl)-1H-pyrazol-1-yl]methyl}benzaldehyde

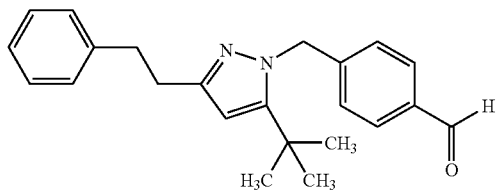

In the same manner as in Reference Example 69, the title compound was obtained as a yellow oil from methyl 4-{[5-tert-butyl-3-(2-phenylethyl)-1H-pyrazol-1-yl]methyl}benzoate. yield 72%.

$^1$H NMR (CDCl$_3$) δ: 1.27 (9H, s), 2.87-3.02 (4H, m), 5.53 (2H, s), 5.92 (1H, s), 7.01 (2H, d, J=8.1 Hz), 7.13-7.34 (5H, m), 7.79 (2H, d, J=8.1 Hz), 9.97 (1H, s).

Reference Example 71 ethyl 2,2-difluoro-3-{[(4-methylphenyl)sulfonyl]oxy}-3-(4-nitrophenyl)propanoate

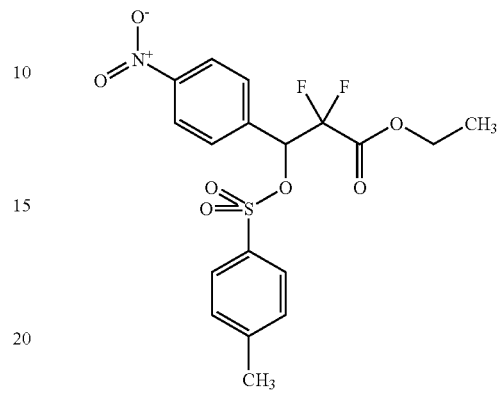

To a solution of ethyl 2,2-difluoro-3-hydroxy-3-(4-nitrophenyl)propanoate (800 mg, 2.91 mmol) in pyridine (20 mL) was added dropwise p-toluenesulfonyl chloride (665 mg, 3.49 mmol), and the mixture was stirred at room temperature for 3 days. The reaction mixture was diluted with ethyl acetate, washed with saturated aqueous sodium hydrogencarbonate and saturated brine, dried over anhydrous magnesium sulfate, and concentrated under reduced pressure. The residue was purified by silica gel column chromatography (5%-40% ethyl acetate/hexane) to give the title compound (1.09 g, yield 99%) as a colorless oil.

$^1$H NMR (CDCl$_3$) δ: 1.34 (3H, t, J=7.2 Hz), 2.40 (3H, s), 4.25-4.36 (2H, m), 5.98 (1H, dd, J=15.8, 6.2 Hz), 7.20-7.30 (2H, m), 7.51 (2H, d, J=8.5 Hz), 7.62 (2H, d, J=8.3 Hz), 8.15 (2H, d, J=8.7 Hz).

Reference Example 72 ethyl 3-(4-aminophenyl)-2,2-difluoropropanoate

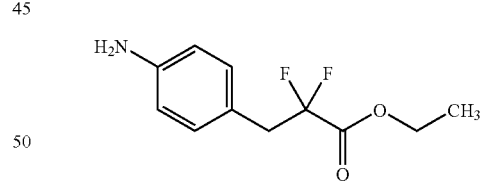

To a solution of ethyl 2,2-difluoro-3-{[(4-methylphenyl)sulfonyl]oxy}-3-(4-nitrophenyl)propanoate (1.06 g, 2.80 mmol) in ethyl acetate (30 mL) was added 10% palladium-carbon (50% water-containing product, 0.50 g), and the mixture was stirred at room temperature for 16 hr under a hydrogen atmosphere (balloon pressure). To the reaction mixture was added saturated aqueous sodium hydrogencarbonate, and the mixture was extracted with ethyl acetate. The extract was washed with saturated brine, dried over anhydrous magnesium sulfate, and concentrated under reduced pressure. The residue was purified by silica gel column chromatography (10%-50% ethyl acetate/hexane) to give the title compound (255 mg, yield 40%) as a pale-yellow oil.

MS m/z 230 (MH$^+$).

Reference Example 73 ethyl(2E)-3-(4-amino-2-methylphenyl)acrylate

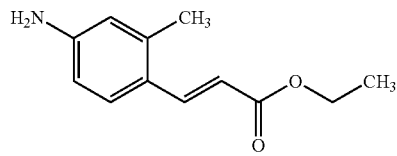

In the same manner as in Reference Example 20, the title compound was obtained as a pale-brown oil from 4-bromo-3-methylaniline. yield 44%. MS m/z 206 (MH+).

Reference Example 74 methyl 4'-hydroxy-6-isopropoxybiphenyl-3-carboxylate

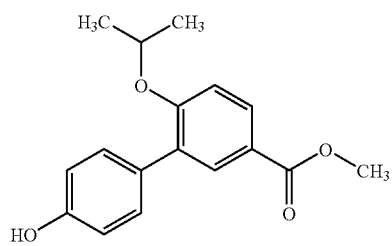

In the same manner as in Reference Example 42, the title compound was obtained as a colorless needle crystals from methyl 3-bromo-4-isopropoxybenzoate and (4-hydroxyphenyl)boronic acid. yield 64%.
MS m/z 287 (MH+).

Reference Example 75 methyl 4'-(2-ethoxyethoxy)-6-isopropoxybiphenyl-3-carboxylate

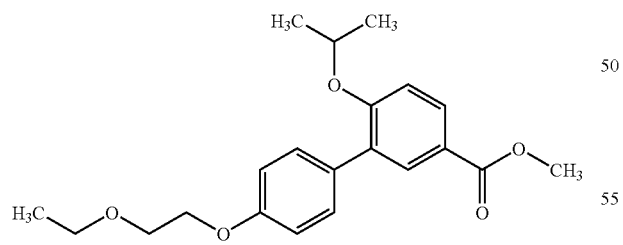

In the same manner as in Reference Example 43, the title compound was obtained as a pale-brown oil from methyl 4'-hydroxy-6-isopropoxybiphenyl-3-carboxylate and 2-chloroethyl ethyl ether. yield 89%.

$^1$H NMR (CDCl$_3$) δ: 1.26 (3H, t, J=7.0 Hz), 1.31 (6H, d, J=6.0 Hz), 3.63 (2H, q, J=7.0 Hz), 3.82 (2H, t, J=5.0 Hz), 3.89 (3H, s), 4.17 (2H, t, J=5.0 Hz), 4.54-4.70 (1H, m), 6.96 (2H, d, J=8.8 Hz), 7.15-7.25 (1H, m), 7.47 (2H, d, J=8.8 Hz), 7.96 (1H, dd, J=2.2, 8.8 Hz), 8.00 (1H, d, J=2.2 Hz).

Reference Example 76

[4'-(2-ethoxyethoxy)-6-isopropoxybiphenyl-3-yl]methanol

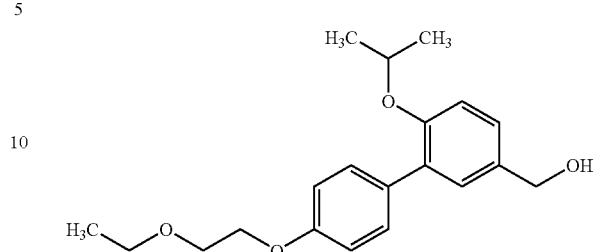

In the same manner as in Reference Example 44, the title compound was obtained as a colorless oil from methyl 4'-(2-ethoxyethoxy)-6-isopropoxybiphenyl-3-carboxylate. yield 87%.

$^1$H NMR (CDCl$_3$) δ: 1.24 (6H, d, J=6.0 Hz), 1.26 (3H, t, J=6.9 Hz), 1.57 (1H, t, J=6.0 Hz), 3.63 (2H, q, J=6.9 Hz), 3.82 (2H, t, J=5.1 Hz), 4.17 (2H, t, J=5.1 Hz), 4.36-4.50 (1H, m), 4.66 (2H, d, J=6.0 Hz), 6.96 (2H, d, J=9.0 Hz), 6.97 (1H, d, J=8.1 Hz), 7.23-7.30 (1H, m), 7.32 (1H, d, J=2.1 Hz), 7.48 (2H, d, J=9.0 Hz).

Reference Example 77

4'-(2-ethoxyethoxy)-6-isopropoxybiphenyl-3-carbaldehyde

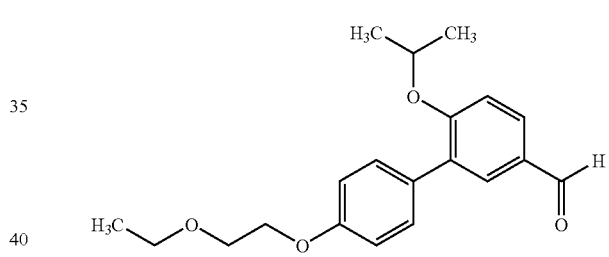

A solution of [4'-(2-ethoxyethoxy)-6-isopropoxybiphenyl-3-yl]methanol (0.90 g, 2.72 mmol) and manganese dioxide (2.7 g, 31.1 mmol) in tetrahydrofuran (40 mL) was stirred at room temperature for 2 hr. The insoluble material was filtered off, and the filtrate was concentrated under reduced pressure. The residue was subjected to silica gel column chromatography (ethyl acetate:hexane=1:19-3:7) to give the title compound (725 mg) as colorless needle crystals. yield 81%.
MS m/z 329 (MH+).

Reference Example 78 methyl 3-bromo-4-hydroxy-5-(2-methylprop-2-en-1-yl)benzoate and ethyl 4-hydroxy-5-(2-methylprop-2-en-1-yl)benzoate

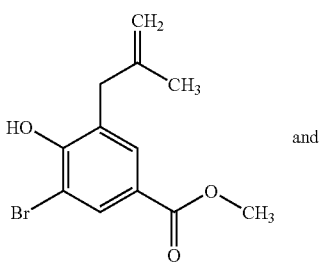

and

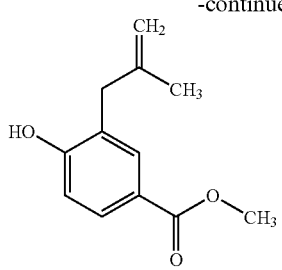

A mixture of methyl 3-bromo-4-[(2-methylprop-2-en-1-yl)oxy]benzoate (12.5 g, 43.8 mmol) and N,N-diethylaniline (15 mL, 94.3 mmol) was stirred at 240° C. for 2.5 hr. The reaction solution was diluted with ethyl acetate, washed successively with dilute hydrochloric acid, water and aqueous sodium chloride solution, dried over anhydrous magnesium sulfate, and concentrated under reduced pressure. The residue was subjected to silica gel column chromatography (ethyl acetate:hexane=1:19-1:4) to give the title compound.

methyl 3-bromo-4-hydroxy-5-(2-methylprop-2-en-1-yl)benzoate pale-brown oil (4.1 g, yield 33%).

$^1$H NMR (CDCl$_3$) δ: 1.74 (3H, s), 3.42 (2H, s), 3.89 (3H, s), 4.72 (1H, br s), 4.87 (1H, br s), 6.01 (1H, s), 7.78 (1H, d, J=2.0 Hz), 8.07 (1H, d, J=2.0 Hz).

methyl 4-hydroxy-5-(2-methylprop-2-en-1-yl)benzoate pale-brown oil (1.25 g, yield 14%).

MS m/z 207 (MH$^+$).

Reference Example 79 methyl 4-[(4-methylbenzyl)oxy]-3-(2-methylprop-2-en-1-yl)benzoate

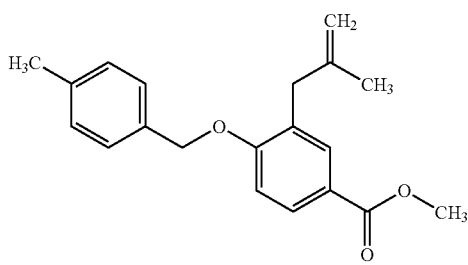

In the same manner as in Reference Example 47, the title compound was obtained as a pale-yellow oil from methyl 4-hydroxy-5-(2-methylprop-2-en-1-yl)benzoate and 4-methylbenzyl bromide. yield 88%. MS m/z 311 (MH$^+$).

Reference Example 80

[4-[(4-methylbenzyl)oxy]-3-(2-methylprop-2-en-1-yl)phenyl]methanol

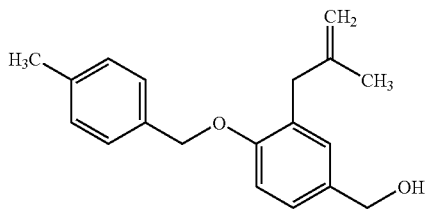

In the same manner as in Reference Example 44, the title compound was obtained as a pale-yellow oil from methyl 4-[(4-methylbenzyl)oxy]-3-(2-methylprop-2-en-1-yl)benzoate. yield 73%.

$^1$H NMR (CDCl$_3$) δ: 1.49 (1H, t, J=5.8 Hz), 1.72 (3H, s), 2.36 (3H, s), 3.39 (2H, s), 4.60 (2H, d, J=5.8 Hz), 4.67 (1H, br s), 4.79 (1H, br s), 5.04 (2H, s), 6.90 (1H, d, J=9.2 Hz), 7.15-7.40 (6H, m).

Reference Example 81

4'-(methoxymethoxy)-2',6'-dimethylbiphenyl-3-carbaldehyde

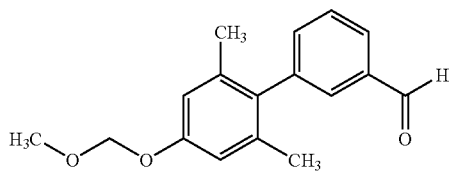

In the same manner as in Reference Example 18, the title compound was obtained as a colorless oil from 4'-hydroxy-2',6'-dimethylbiphenyl-3-carbaldehyde and chloromethyl methyl ether. yield 32%.

MS m/z 271 (MH$^+$).

Reference Example 82 methyl 7-bromo-2,2-dimethyl-2,3-dihydro-1-benzofuran-5-carboxylate

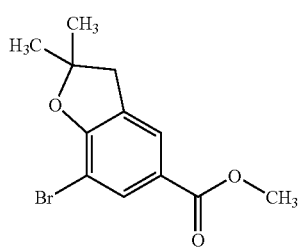

A solution of methyl 3-bromo-4-hydroxy-5-(2-methylprop-2-en-1-yl)benzoate (4.1 g, 14.4 mmol) and boron trifluoride diethyl ether complex (2.0 mL, 15.8 mmol) in toluene (30 mL) was stirred at 100° C. for 90 min. After cooling, the reaction solution was diluted with ethyl acetate, washed successively with water, aqueous sodium hydrogencarbonate solution and aqueous sodium chloride solution, dried over anhydrous magnesium sulfate, and concentrated under reduced pressure. The residue was subjected to silica gel column chromatography (ethyl acetate:hexane=3:97-15:85) to give the title compound (3.05 g, yield 74%) as colorless prism crystals.

MS m/z 286 (MH$^+$).

Reference Example 83 methyl 7-[4-(2-ethoxyethoxy)phenyl]-2,2-dimethyl-2,3-dihydro-1-benzofuran-5-carboxylate

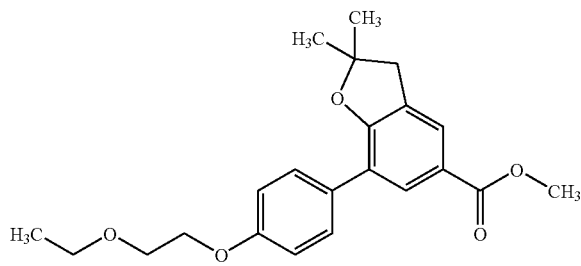

In the same manner as in Reference Example 42, the title compound was obtained as colorless needle crystals from methyl 7-bromo-2,2-dimethyl-2,3-dihydro-1-benzofuran-5-carboxylate and [4-(2-ethoxyethoxy)phenyl]boronic acid. yield 79%.

MS m/z 371 (MH$^+$).

Reference Example 84

{7-[4-(2-ethoxyethoxy)phenyl]-2,2-dimethyl-2,3-dihydro-1-benzofuran-5-yl}methanol

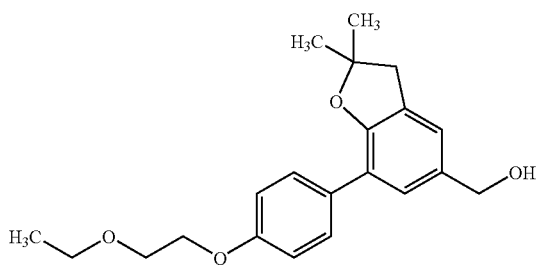

In the same manner as in Reference Example 44, the title compound was obtained as colorless needle crystals from methyl 7-[4-(2-ethoxyethoxy)phenyl]-2,2-dimethyl-2,3-dihydro-1-benzofuran-5-carboxylate. yield 98%.

$^1$H NMR (CDCl$_3$) δ: 1.25 (3H, t, J=7.0 Hz), 1.50 (6H, s), 3.04 (2H, s), 3.62 (2H, q, J=7.0 Hz), 3.81 (2H, t, J=5.0 Hz), 4.16 (2H, t, J=5.0 Hz), 4.62 (2H, br s), 6.97 (2H, d, J=8.8 Hz), 7.11 (1H, br s), 7.24 (1H, br s), 7.65 (2H, d, J=8.8 Hz).

Reference Example 85

7-[4-(2-ethoxyethoxy)phenyl]-2,2-dimethyl-2,3-dihydro-1-benzofuran-5-carbaldehyde

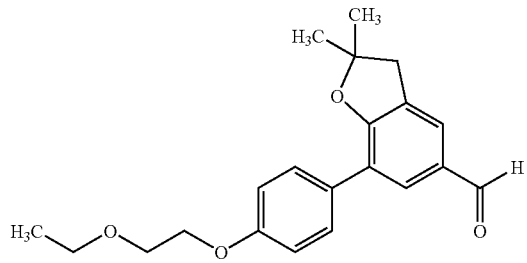

In the same manner as in Reference Example 77, the title compound was obtained as a pale-yellow oil from {7-[4-(2-ethoxyethoxy)phenyl]-2,2-dimethyl-2,3-dihydro-1-benzofuran-5-yl}methanol. yield 89%.

MS m/z 341 (MH$^+$).

Reference Example 86

3-[(dibenzylamino)methyl]-4-isobutoxybenzaldehyde

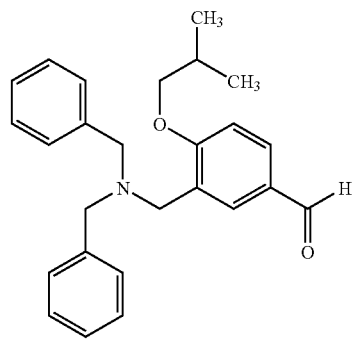

In the same manner as in Reference Example 50, the title compound was obtained as a yellow oil from dibenzylamine and 3-(chloromethyl)-4-isobutoxybenzaldehyde. yield 72%.

$^1$H NMR (CDCl$_3$) δ: 1.04 (6H, d, J=6.6 Hz), 2.11 (1H, m), 3.61 (4H, s), 3.65 (2H, s), 3.79 (2H, d, J=6.6 Hz), 6.90 (1H, d, J=8.4 Hz), 7.17-7.36 (6H, m), 7.37-7.45 (4H, m), 7.73 (1H, dd, J=2.1, 8.4 Hz), 8.15 (1H, d, J=2.1 Hz), 9.90 (1H, s).

Reference Example 87

{3-[(dibenzylamino)methyl]-4-isobutoxyphenyl}methanol

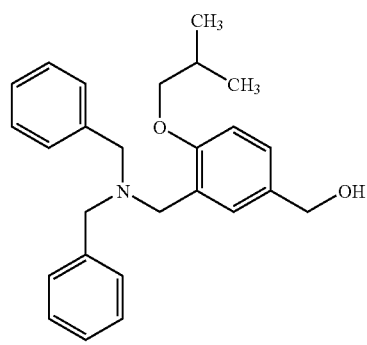

In the same manner as in Reference Example 51, the title compound was obtained as a colorless oil from 3-[(dibenzylamino)methyl]-4-isobutoxybenzaldehyde. yield 86%.

$^1$H NMR (CDCl$_3$) δ: 1.03 (6H, d, J=6.6 Hz), 1.47 (1H, t, J=5.7 Hz), 2.09 (1H, m), 3.59 (4H, s), 3.64 (2H, s), 3.70 (2H, d, J=6.3 Hz), 4.62 (2H, d, J=5.4 Hz), 6.79 (1H, d, J=8.1 Hz), 7.14-7.34 (7H, m), 7.38-7.44 (4H, m), 7.58 (1H, d, J=2.4 Hz).

Reference Example 88

3-[(2,2-dimethylquinolin-1(2H)-yl)methyl]-4-isobutoxybenzaldehyde

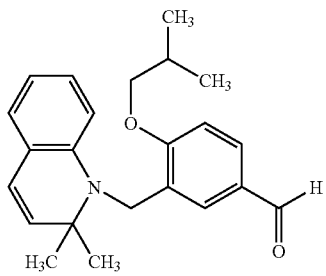

In the same manner as in Reference Example 50, the title compound was obtained as yellow crystals from 2,2-dimethyl-1,2-dihydroquinoline and 3-(chloromethyl)-4-isobutoxybenzaldehyde. yield 83%.

$^1$H NMR (CDCl$_3$) δ: 1.12 (6H, d, J=6.6 Hz), 1.39 (6H, s), 2.23 (1H, m), 3.92 (2H, d, J=6.6 Hz), 4.48 (2H, s), 5.47 (1H, d, J=9.9 Hz), 6.10 (1H, d, J=8.1 Hz), 6.32 (1H, d, J=9.9 Hz), 6.54 (1H, m), 6.82-6.92 (2H, m), 6.98 (1H, d, J=8.1 Hz), 7.72-7.81 (2H, m), 9.77 (1H, s).

Reference Example 89

{3-[(2,2-dimethylquinolin-1(2H)-yl)methyl]-4-isobutoxyphenyl}methanol

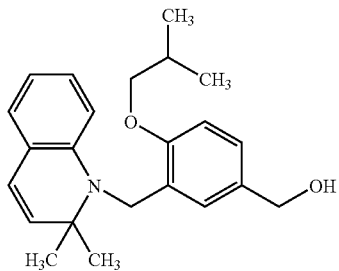

In the same manner as in Reference Example 51, the title compound was obtained as a pale-yellow oil from 3-[(2,2-dimethylquinolin-1(2H)-yl)methyl]-4-isobutoxybenzaldehyde. yield 91%.

$^1$H NMR (CDCl$_3$) δ: 1.09 (6H, d, J=6.6 Hz), 1.38 (6H, s), 1.42 (1H, m), 2.18 (1H, m), 3.83 (2H, d, J=6.6 Hz), 4.47 (2H, s), 4.49 (2H, d, J=4.5 Hz), 5.45 (1H, d, J=9.6 Hz), 6.15 (1H, d, J=8.7 Hz), 6.30 (1H, d, J=9.6 Hz), 6.52 (1H, m), 6.81-6.92 (3H, m), 7.17-7.24 (2H, m).

Reference Example 90

3-[(3,5-di-tert-butyl-1H-pyrazol-1-yl)methyl]-4-isobutoxybenzaldehyde

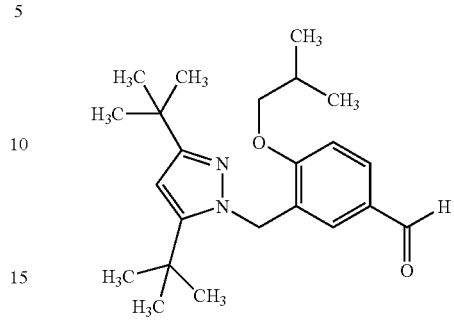

In the same manner as in Reference Example 50, the title compound was obtained as colorless crystals from 3,5-di-tert-butyl-1H-pyrazole and 3-(chloromethyl)-4-isobutoxybenzaldehyde. yield 90%.

MS (ESI+): 371 (M+H).

Reference Example 91

2-(4-bromo-3,5-dimethylphenoxy)-6-methylpyridine

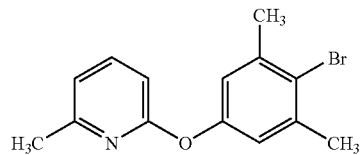

To a solution of sodium hydroxide (0.23 g, 5.81 mmol) in methanol (50 mL) was added 4-bromo-3,5-dimethylphenol (1.17 g, 5.81 mmol), and the mixture was stood at room temperature for 10 min and concentrated to dryness to give 4-bromo-3,5-dimethylphenol sodium salt (1.30 g). Then, a mixture of the product, 2-bromo-6-methylpyridine (1.0 g, 5.81 mmol) and copper powder (11 mg, 0.17 mmol) was stirred at 185° C. for 1 hr. After cooling, the reaction mixture was diluted with ethyl acetate, washed with water and saturated brine, dried, and concentrated under reduced pressure. The residue was purified by silica gel column chromatography (hexane-hexane/ethyl acetate=5/1) to give the title compound (1.25 g, yield 74%) as a pale-yellow oil.

MS (ESI+): 292 (M+H), 294.

Reference Example 92

2',6'-dimethyl-4'-[(6-methylpyridin-2-yl)oxy]biphenyl-3-carbaldehyde

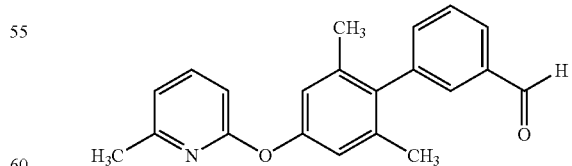

In the same manner as in Reference Example 2, the title compound was obtained as a colorless oil from 2-(4-bromo-3,5-dimethylphenoxy)-6-methylpyridine and (3-formylphenyl)boronic acid. yield 94%.

MS (ESI+): 318 (M+H).

Reference Example 93

2-bromo-5-(2-ethoxyethoxy)-1,3-dimethylbenzene

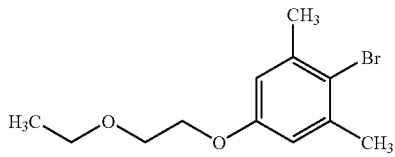

In the same manner as in Reference Example 18, the title compound was obtained as a colorless oil from 4-bromo-3,5-dimethylphenol and 2-chloroethyl ethyl ether. yield 98%.
MS (ESI+): 274 (M+H).

Reference Example 94

[4-(2-ethoxyethoxy)-2,6-dimethylphenyl]boronic acid

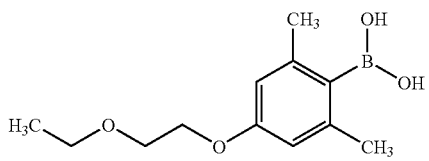

To a solution of 2-bromo-5-(2-ethoxyethoxy)-1,3-dimethylbenzene (10.0 g, 36.6 mmol) in tetrahydrofuran (100 mL) was added n-butyllithium hexane solution (1.6 M, 25.1 mL, 40.2 mmol) under stirring at −78° C. The reaction mixture was stirred at the same temperature for 30 min and triisopropyl borate (10.5 mL, 45.5 mmol) was added. The mixture was allowed to warm to room temperature, and the mixture was stirred for 3 hr. To the reaction mixture were added 5 M hydrochloric acid (20 mL), ethyl acetate and water to allow partitioning, and the organic layer was dried over anhydrous magnesium sulfate, and concentrated under reduced pressure. The residue was washed with hexane/diethyl ether and dried to give the title compound (5.9 g, yield 68%) as pale-yellow crystals.
$^1$H NMR (CDCl$_3$) δ: 1.24 (3H, t, J=7.0 Hz), 2.36 (6H, s), 3.60 (2H, q, J=7.0 Hz), 3.77 (2H, t, J=5.0 Hz), 4.09 (2H, t, J=5.0 Hz), 4.52 (2H, s), 6.58 (2H, s).

Reference Example 95 methyl 4'-(2-ethoxyethoxy)-6-methoxy-2',6'-dimethylbiphenyl-3-carboxylate

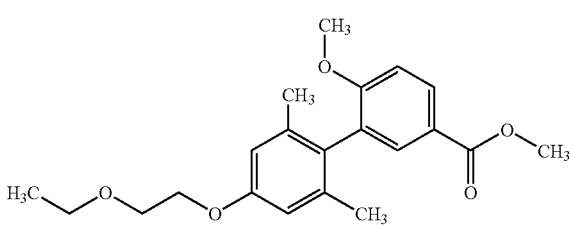

A mixture of methyl 3-bromo-4-methoxybenzoate (0.90 g, 3.67 mmol), [4-(2-ethoxyethoxy)-2,6-dimethylphenyl]boronic acid (0.87 g, 3.67 mmol), tris(dibenzylideneacetone)dipalladium(0) (0.13 g, 0.15 mmol), 2-(dicyclohexylphosphino)biphenyl (79 mg, 0.22 mmol), tripotassium phosphate (1.56 g, 7.34 mmol) and toluene (20 mL) was stirred under a nitrogen atmosphere at 90° C. for 18 hr. After cooling the reaction mixture, the insoluble material was filtered off, and the filtrate was concentrated under reduced pressure. The residue was purified by silica gel column chromatography (hexane/ethyl acetate=9/1-hexane/ethyl acetate=1/1) to give the title compound (0.71 g, yield 54%) as a yellow oil.
MS (ESI+): 359 (M+H).

Reference Example 96

[4'-(2-ethoxyethoxy)-6-methoxy-2',6'-dimethylbiphenyl-3-yl]methanol

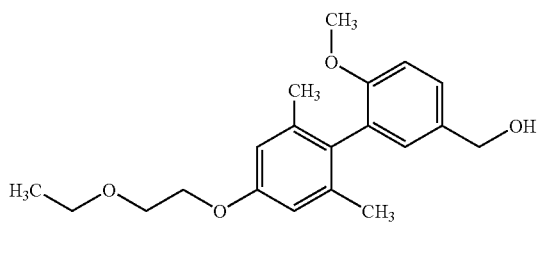

In the same manner as in Reference Example 28, the title compound was obtained as a colorless oil from methyl 4'-(2-ethoxyethoxy)-6-methoxy-2',6'-dimethylbiphenyl-3-carboxylate. yield 100%.
MS (ESI+): 331 (M+H).

Reference Example 97

2-(4-bromo-3,5-dimethylphenoxy)-6-methoxypyridine

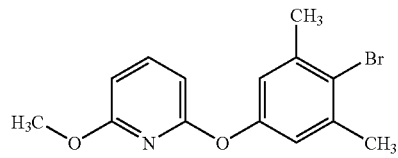

In the same manner as in Reference Example 91, the title compound was obtained as a yellow oil from 4-bromo-3,5-dimethylphenol and 2-bromo-6-methoxypyridine. yield 73%.
MS (ESI+): 309 (M+H), 311.

Reference Example 98

4'-[(6-methoxypyridin-2-yl)oxy]-2',6'-dimethylbiphenyl-3-carbaldehyde

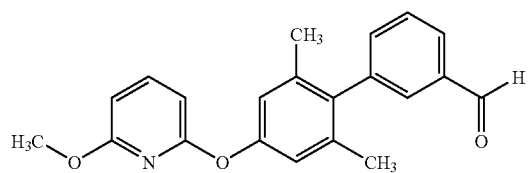

In the same manner as in Reference Example 2, the title compound was obtained as a colorless oil from 2-(4-bromo-3,5-dimethylphenoxy)-6-methoxypyridine and (3-formylphenyl)boronic acid. yield 74%.

MS (ESI+): 334 (M+H).

Reference Example 99

4'-{[tert-butyl(dimethyl)silyl]oxy}-2',6'-dimethylbiphenyl-3-carbaldehyde

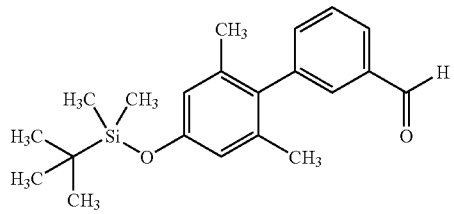

To a solution of 4'-hydroxy-2',6'-dimethylbiphenyl-3-carbaldehyde (9.0 g, 39.8 mmol) and imidazole (2.98 g, 43.8 mmol) in N,N-dimethylformamide (100 mL) was added tert-butyldimethylchlorosilane (6.6 g, 43.8 mmol) under stirring at room temperature and the mixture was stirred at room temperature for 4 hr. The reaction mixture was diluted with ethyl acetate, washed with water and saturated brine, dried, and concentrated under reduced pressure. The residue was purified by silica gel column chromatography (hexane/ethyl acetate=10/1-hexane/ethyl acetate=4/1) to give the title compound (10.5 g, yield 77%) as a yellow oil.

$^1$H NMR (CDCl$_3$) δ: 0.25 (6H, s), 1.02 (9H, s), 1.97 (6H, s), 6.62 (2H, s), 7.44 (1H, dt, J=1.5, 7.5 Hz), 7.59 (1H, t, J=7.5 Hz), 7.68 (1H, t, J=1.5 Hz), 7.86 (1H, dt, J=1.5, 7.5 Hz), 10.06 (1H, s).

Reference Example 100

(4'-{[tert-butyl(dimethyl)silyl]oxy}-2',6'-dimethylbiphenyl-3-yl)methanol

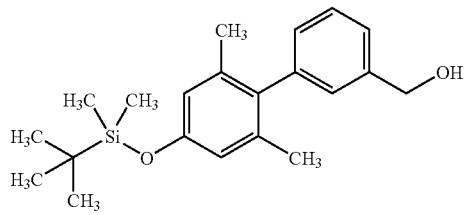

In the same manner as in Reference Example 51, the title compound was obtained as colorless crystals from 4'-{[tert-butyl(dimethyl)silyl]oxy}-2',6'-dimethylbiphenyl-3-carbaldehyde. yield 89%.

$^1$H NMR (CDCl$_3$) δ: 0.23 (6H, s), 1.00 (9H, s), 1.96 (6H, s), 4.73 (2H, s), 6.58 (2H, s), 7.07 (1H, d, J=7.5 Hz), 7.13 (1H, s), 7.32 (1H, d, J=7.5 Hz), 7.40 (1H, t, J=7.5 Hz).

Reference Example 101 tert-butyl (2E)-3-(4-amino-2-fluorophenyl)acrylate

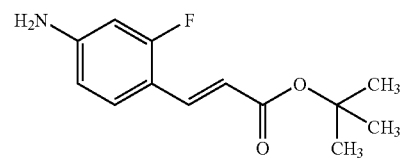

In the same manner as in Reference Example 20, the title compound was obtained as yellow crystals from 4-bromo-3-fluoroaniline and tert-butyl acrylate. yield 80%.

$^1$H NMR (CDCl$_3$) δ: 1.52 (9H, s), 3.99 (2H, s), 6.26 (1H, d, J=16.2 Hz), 6.31-6.45 (2H, m), 7.30 (1H, t, J=8.4 Hz), 7.62 (1H, d, J=16.2 Hz).

Reference Example 102 tert-butyl 3-(4-amino-2-fluorophenyl)propanoate

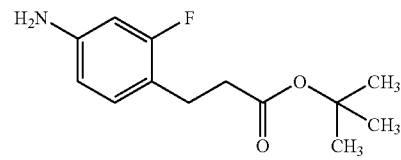

In the same manner as in Reference Example 21, the title compound was obtained as pale-yellow crystals from tert-butyl (2E)-3-(4-amino-2-fluorophenyl)acrylate. yield 98%.

MS (ESI+): 240 (M+H).

Reference Example 103 tert-butyl 3-(2-fluoro-4-{[(2-nitrophenyl)sulfonyl]amino}phenyl)propanoate

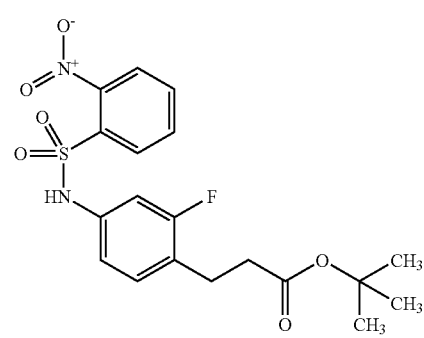

In the same manner as in Reference Example 22, the title compound was obtained as beige crystals from tert-butyl 3-(4-amino-2-fluorophenyl)propanoate. yield 77%.

$^1$H NMR (CDCl$_3$) δ: 1.38 (9H, s), 2.48 (2H, t, J=7.8 Hz), 2.85 (2H, t, J=7.8 Hz), 6.86 (1H, dd, J=2.1, 8.1 Hz), 6.98 (1H, dd, J=2.1, 10.8 Hz), 7.10 (1H, t, J=8.1 Hz), 7.61 (1H, m), 7.71 (1H, m), 7.87 (2H, dd, J=1.5, 7.8 Hz).

Reference Example 104 ethyl 3-tert-butyl-1-{4-[(methoxymethoxy)methyl]benzyl}-1H-pyrazole-5-carboxylate

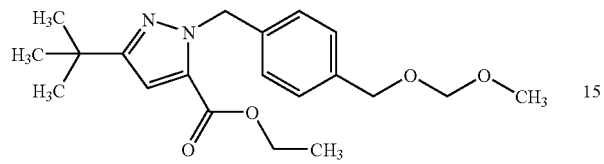

A mixture of ethyl 3-tert-butyl-1H-pyrazole-5-carboxylate (3.00 g, 15.3 mmol), [4-(chloromethyl)phenyl]methanol (2.50 g, 16.0 mmol), potassium carbonate (2.11 g, 15.3 mmol) and N,N-dimethylformamide (40 mL) was stirred at 70° C. for 3 hr. Water was added to the reaction mixture, and the mixture was extracted with ethyl acetate. The extract was washed with saturated brine, dried over anhydrous magnesium sulfate, and concentrated under reduced pressure to give a yellow oil. To a solution of the obtained oil and N-ethyldiisopropylamine (8.0 mL, 46 mmol) in tetrahydrofuran (50 mL) was added chloromethyl methyl ether (4.40 mL, 46.3 mmol) at 0° C., and the mixture was stirred overnight at room temperature. The reaction mixture was concentrated, and the residue was purified by silica gel column chromatography (30% ethyl acetate/hexane) to give the title compound (1.95 g, yield 35%) as a colorless oil.

$^1$H NMR (CDCl$_3$) δ: 1.31 (3H, t, J=7.1 Hz), 1.32 (9H, s), 3.39 (3H, s), 4.26 (2H, q, J=7.1 Hz), 4.54 (2H, s), 4.68 (2H, s), 5.70 (2H, s), 6.71 (1H, s), 7.15-7.33 (4H, m).

Reference Example 105

(3-tert-butyl-1-{4-[(methoxymethoxy)methyl]benzyl}-1H-pyrazol-5-yl)methanol

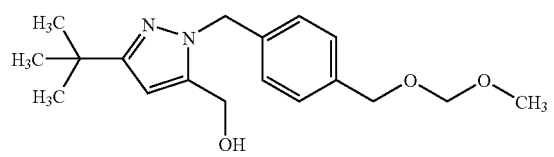

To a solution of ethyl 3-tert-butyl-1-{4-[(methoxymethoxy)methyl]benzyl}-1H-pyrazole-5-carboxylate (1.95 g, 5.41 mmol) in tetrahydrofuran (20 mL) was added lithium aluminum hydride (0.26 g, 5.5 mmol) at 0° C., and the mixture was stirred at room temperature for 30 min. Ethanol (10 mL) and saturated aqueous ammonium chloride solution (1.0 mL) were added to the reaction mixture, and the precipitated solid was filtered off. The filtrate was concentrated and the residue was purified by silica gel column chromatography (50% ethyl acetate/hexane) to give the title compound (1.45 g, yield 84%) as a colorless oil.

$^1$H NMR (CDCl$_3$) δ: 1.32 (9H, s), 1.57 (1H, t, J=6.0 Hz), 3.39 (3H, s), 4.49 (2H, d, J=6.2 Hz), 5.55 (2H, s), 4.68 (2H, s), 5.36 (2H, s), 6.10 (1H, s), 7.05-7.13 (2H, m), 7.24-7.33 (2H, m).

Reference Example 106

(4-{[3-tert-butyl-5-(phenoxymethyl)-1H-pyrazol-1-yl]methyl}phenyl)methanol

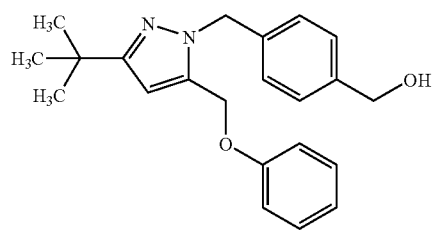

To a solution of (3-tert-butyl-1-{4-[(methoxymethoxy)methyl]benzyl}-1H-pyrazol-5-yl)methanol (1.45 g, 4.55 mmol), phenol (0.47 g, 5.0 mmol) and tributylphosphine (2.27 mL, 9.11 mmol) in tetrahydrofuran (70 mL) was added 1,1'-(azodicarbonyl)dipiperidine (2.30 g, 9.12 mmol), and the mixture was stirred at room temperature for 2 hr. The reaction solution was concentrated, and diisopropyl ether was added to the residue. The resultant insoluble material was filtered off. The filtrate was concentrated and the residue was purified by silica gel column chromatography (30% ethyl acetate/hexane) to give a colorless oil (1.66 g).

A mixture of the obtained oil (1.66 g), concentrated hydrochloric acid (0.2 mL) and methanol (20 mL) was heated under reflux overnight. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (50% ethyl acetate/hexane) to give the title compound (1.35 g, yield 85%) as a colorless oil.

$^1$H NMR (CDCl$_3$) δ: 1.34 (9H, s), 4.65 (2H, s), 4.83 (2H, s), 5.37 (2H, s), 6.21 (1H, s), 6.80-7.10 (5H, m), 7.20-7.34 (4H, m).

Reference Example 107 methyl 4-[(3-tert-butyl-5-{[4-(methoxycarbonyl)benzyl]oxy}-1H-pyrazol-1-yl)methyl]benzoate

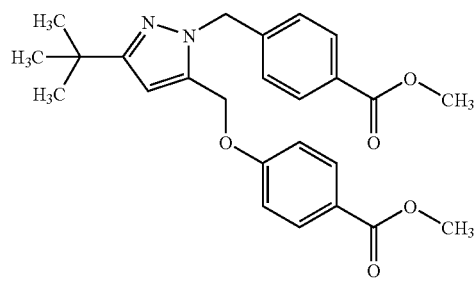

A mixture of 3-tert-butyl-5-hydroxy-1H-pyrazole (5.00 g, 35.7 mmol), methyl 4-(bromomethyl)benzoate (17.2 g, 74.9 mmol), potassium carbonate (10.5 g, 76.0 mmol) and N,N-dimethylformamide (50 mL) was stirred overnight at 60° C. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (30% ethyl acetate/hexane) to give the title compound (6.90 g, yield 44%) as colorless crystals. mp 93-94° C.

Reference Example 108 methyl 4-[(3-tert-butyl-5-hydroxy-1H-pyrazol-1-yl)methyl]benzoate

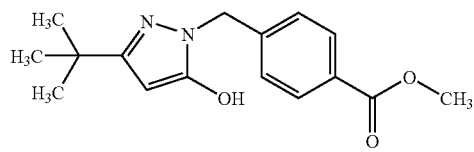

A mixture of methyl 4-[(3-tert-butyl-5-{[4-(methoxycarbonyl)benzyl]oxy}-1H-pyrazol-1-yl)methyl]benzoate (6.90 g, 15.8 mmol), 10% palladium-carbon (50% water-containing product, 0.35 g) and tetrahydrofuran (50 mL) was stirred overnight at room temperature under a hydrogen atmosphere (balloon pressure). The catalyst was filtered off, and the obtained filtrate was concentrated under reduced pressure to give the title compound (3.70 g, yield 81%) as colorless crystals.

mp 161-162° C.

Reference Example 109 methyl 4-{[5-(benzyloxy)-3-tert-butyl-1H-pyrazol-1-yl]methyl}benzoate

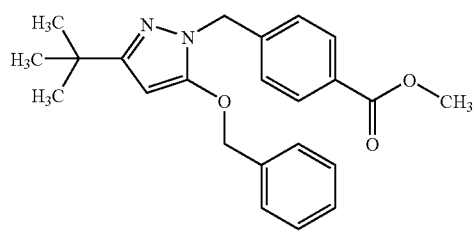

A mixture of methyl 4-[(3-tert-butyl-5-hydroxy-1H-pyrazol-1-yl)methyl]benzoate (2.00 g, 6.94 mmol), benzyl bromide (0.91 mL, 7.7 mmol), potassium carbonate (0.96 g, 6.9 mmol) and N,N-dimethylformamide (25 mL) was stirred overnight at room temperature. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (30% ethyl acetate/hexane) to give the title compound (2.14 g, yield 81%) as a yellow oil.

$^1$H NMR (CDCl$_3$) δ: 1.29 (9H, s), 3.90 (3H, s), 5.01 (2H, s), 5.19 (2H, s), 5.49 (1H, s), 7.00-7.37 (7H, m), 7.92-8.00 (2H, m).

Reference Example 110

(4-{[5-(benzyloxy)-3-tert-butyl-1H-pyrazol-1-yl]methyl}phenyl)methanol

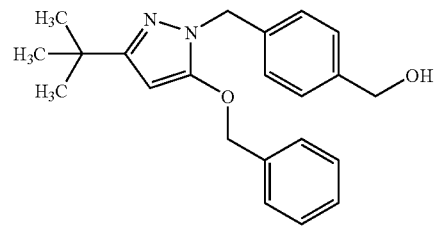

To a solution of methyl 4-{[5-(benzyloxy)-3-tert-butyl-1H-pyrazol-1-yl]methyl}benzoate (2.14 g, 5.65 mmol) in tetrahydrofuran (20 mL) was added lithium aluminum hydride (0.27 g, 5.7 mmol) at 0° C., and the mixture was stirred at room temperature for 30 min. Ethanol (10 mL) and saturated aqueous ammonium chloride solution (1.0 mL) were added to the reaction mixture, and the precipitated solid was filtered off. The filtrate was concentrated and the residue was purified by silica gel column chromatography (50% ethyl acetate/hexane) to give the title compound (1.97 g, yield 99%) as a colorless oil.

$^1$H NMR (CDCl$_3$) δ: 1.28 (9H, s), 1.77 (1H, brt), 4.62-4.70 (2H, m), 5.00 (2H, s), 5.13 (2H, s), 5.47 (1H, s), 7.08-7.38 (9H, m).

Reference Example 111

(3-methoxy-1-methyl-1H-pyrazol-5-yl)methanol

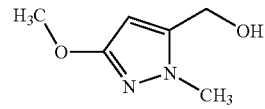

To a solution of methyl 3-methoxy-1-methyl-1H-pyrazole-5-carboxylate (2.03 g, 11.9 mmol) in tetrahydrofuran (20 mL) was added lithium aluminum hydride (0.57 g, 12 mmol) at 0° C., and the mixture was stirred at room temperature for 30 min. Ethanol (10 mL) and saturated aqueous ammonium chloride solution (2.0 mL) were added to the reaction mixture, and the precipitated solid was filtered off. The filtrate was concentrated and the residue was purified by silica gel column chromatography (ethyl acetate) to give the title compound (1.67 g, yield 98%) as a colorless oil.

$^1$H NMR (CDCl$_3$) δ: 1.94 (1H, br t), 3.74 (3H, s), 3.85 (3H, s), 4.57 (2H, d, J=4.6 Hz), 5.60 (1H, s).

Reference Example 112 methyl 4-[(3,5-di-tert-butyl-1H-pyrazol-1-yl)methyl]benzoate

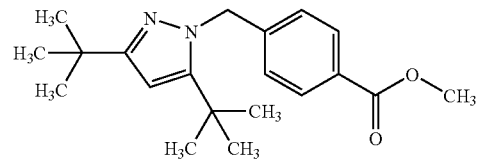

To a solution of 3,5-di-tert-butyl-1H-pyrazole (1.00 g, 5.55 mmol) in N,N-dimethylformamide (15 mL) was added sodium hydride (60% in oil, 0.27 g, 6.8 mmol) under ice-cooling. After completion of hydrogen generation, methyl 4-(bromomethyl)benzoate (1.40 g, 6.11 mmol) was added, and the mixture was stirred overnight at room temperature. Water was added to the reaction mixture, and the precipitated solid was collected by filtration, washed with water, and dried to give the title compound (1.78 g, yield 98%) as colorless crystals.

mp 135-136° C.

Reference Example 113

{4-[(3,5-di-tert-butyl-1H-pyrazol-1-yl)methyl]phenyl}methanol

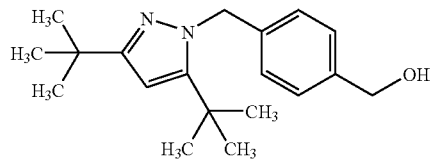

To a solution of methyl 4-[(3,5-di-tert-butyl-1H-pyrazol-1-yl)methyl]benzoate (1.72 g, 5.24 mmol) in tetrahydrofuran (35 mL) was added lithium aluminum hydride (0.25 g, 5.3 mmol) at 0° C., and the mixture was stirred at room temperature for 30 min. Ethanol (10 mL) and saturated aqueous ammonium chloride solution (1.0 mL) were added to the reaction mixture, and the precipitated solid was filtered off. The filtrate was concentrated and the residue was purified by silica gel column chromatography (50% ethyl acetate/hexane) to give the title compound (1.28 g, yield 81%) as colorless crystals.

mp 121-122° C.

Reference Example 114

2-[(3,5-dimethylphenyl)thio]ethyl ethyl ether

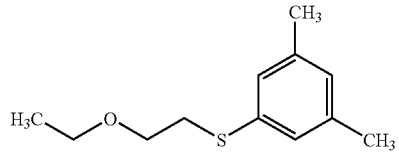

To a solution of 1-chloro-2-ethoxyethane (5.90 mL, 54.3 mmol) and 3,5-dimethylbenzenethiol (5.00 g, 36.2 mmol) in N,N-dimethylformamide (140 mL) were added potassium carbonate (5.50 g, 39.8 mmol) and potassium iodide (0.90 g, 5.43 mmol) under stirring at room temperature, and the mixture was stirred at 80° C. for 5 hr. The reaction mixture was concentrated under reduced pressure, and water was added to the residue. The mixture was extracted with diethyl ether. The extract was dried over anhydrous sodium sulfate, and concentrated under reduced pressure. The residue was purified by silica gel column chromatography (hexane-hexane/ethyl acetate=10/1) to give the title compound (5.80 g, yield 76%) as a colorless oil.

$^1$H NMR (CDCl$_3$) δ: 1.20 (3H, t, J=7.0 Hz), 2.28 (6H, s), 3.09 (2H, t, J=7.0 Hz), 3.51 (2H, q, J=7.0 Hz), 3.61 (2H, t, J=7.0 Hz), 6.81 (1H, s), 6.99 (2H, s).

Reference Example 115

2-[(4-bromo-3,5-dimethylphenyl)thio]ethyl ethyl ether

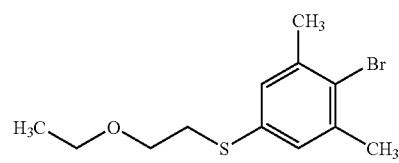

To a solution of 2-[(3,5-dimethylphenyl)thio]ethyl ethyl ether (2.69 g, 12.8 mmol) in acetic acid (60 mL) was slowly added dropwise a solution of bromine (0.68 mL, 13.2 mmol) in acetic acid (30 mL) under stirring at room temperature. The reaction mixture was stirred at the same temperature for 2 hr, poured into cold water, and the mixture was extracted with diethyl ether. The extract was washed with water and saturated brine, dried over anhydrous sodium sulfate, and concentrated under reduced pressure. The residue was purified by silica gel column chromatography (hexane-hexane/ethyl acetate=20/1) to give the title compound (2.41 g, yield 65%) as a pale-yellow oil.

$^1$H NMR (CDCl$_3$) δ: 1.20 (3H, t, J=7.0 Hz), 2.38 (6H, s), 3.08 (2H, t, J=7.0 Hz), 3.51 (2H, q, J=7.0 Hz), 3.60 (2H, t, J=7.0 Hz), 7.08 (2H, s).

Reference Example 116

4'-[(2-ethoxyethyl)thio]-2',6'-dimethylbiphenyl-3-carbaldehyde

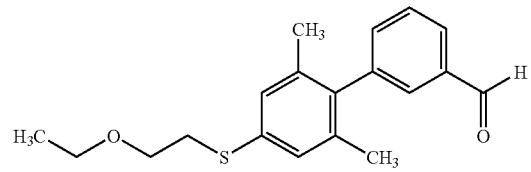

2-[(4-Bromo-3,5-dimethylphenyl)thio]ethyl ethyl ether (2.41 g, 8.33 mmol) and (3-formylphenyl)boronic acid (1.37 g, 9.16 mmol) were dissolved in a mixture of 2 M aqueous sodium carbonate solution (24 mL), ethanol (8 mL) and toluene (24 mL), the air was substituted with argon gas, and tetrakis(triphenylphosphine)palladium(0) (0.48 g, 0.42 mmol) was added. The reaction mixture was stirred under an argon atmosphere at 80° C. for 16 hr. After cooling the reaction mixture, saturated brine was added and the mixture was extracted with diethyl ether. The organic layer was dried over anhydrous magnesium sulfate, and concentrated under reduced pressure. The residue was purified by silica gel column chromatography (hexane/ethyl acetate=10/1-hexane/ethyl acetate=5/1) to give the title compound (1.00 g, yield 38%) as a colorless oil.

$^1$H NMR (CDCl$_3$) δ: 1.23 (3H, t, J=7.0 Hz), 1.99 (6H, s), 3.15 (2H, t, J=7.0 Hz), 3.55 (2H, q, J=7.0 Hz), 3.67 (2H, t,

J=7.0 Hz), 7.13 (2H, s), 7.38-7.46 (1H, m), 7.61 (1H, t, J=7.6 Hz), 7.64-7.70 (1H, m), 7.84-7.92 (1H, m), 10.06 (1H, s).

Reference Example 117

{4'-[(2-ethoxyethyl)thio]-2',6'-dimethylbiphenyl-3-yl}methanol

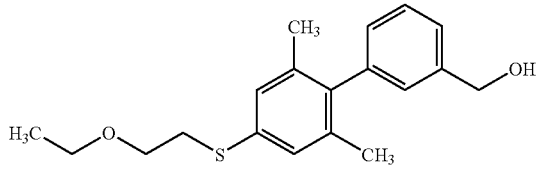

To a solution of 4'-[(2-ethoxyethyl)thio]-2',6'-dimethylbiphenyl-3-carbaldehyde (0.97 g, 3.10 mmol) in a mixture of tetrahydrofuran (4 mL) and methanol (2 mL) was added sodium borohydride (0.07 g, 1.59 mmol) under stirring at 0° C., and the mixture was stirred at the same temperature for 10 min. The reaction solution was concentrated under reduced pressure, the residue was diluted with ammonium chloride solution, and the mixture was extracted with ethyl acetate. The organic layer was dried over anhydrous sodium sulfate, and concentrated under reduced pressure. The residue was purified by silica gel column chromatography (hexane/ethyl acetate=4/1-hexane/ethyl acetate=5/1) to give the title compound (0.94 g, yield 96%) as a colorless oil.

$^1$H NMR (CDCl$_3$) δ: 1.22 (3H, t, J=7.0 Hz), 1.72 (1H, s), 1.99 (6H, s), 3.13 (2H, t, J=7.0 Hz), 3.54 (2H, q, J=7.0 Hz), 3.66 (2H, t, J=7.0 Hz), 4.73 (2H, s), 6.99-7.16 (4H, m), 7.30-7.46 (2H, m).

Reference Example 118

1-oxa-6-thiaspiro[2.5]octane

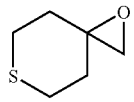

Under a nitrogen atmosphere at room temperature, to a suspension of trimethylsulfoxonium iodide (37.1 g, 165.1 mmol) in dimethylsulfoxide (120 mL) was slowly added sodium hydride (60% in oil, 6.10 g, 152.4 mmol) and the mixture was stirred for 1 hr. A solution of tetrahydro-4H-thiopyran-4-one (14.8 g, 127.0 mmol) in dimethylsulfoxide (60 mL) was added dropwise over 20 min. The reaction solution was further stirred at room temperature for 14 hr, diluted with water and extracted with diethyl ether. The organic layer was washed with water and saturated brine, dried over anhydrous sodium sulfate, and concentrated under reduced pressure. The residue was stood at room temperature and the obtained crystals were washed with a small amount of hexane and dried to give the title compound (8.22 g, yield 50%) as colorless needle crystals.

$^1$H NMR (CDCl$_3$) δ: 1.69-1.82 (2H, m), 1.93-2.09 (2H, m), 2.56-2.73 (4H, m), 2.85-3.01 (2H, m).

Reference Example 119

4'-[(4-hydroxytetrahydro-2H-thiopyran-4-yl)methoxy]-2',6'-dimethylbiphenyl-3-carbaldehyde

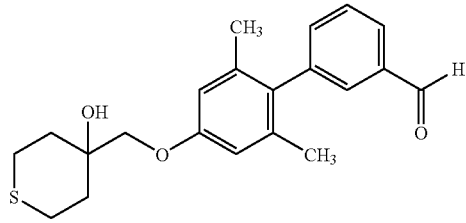

To a solution of 1-oxa-6-thiaspiro[2.5]octane (6.33 g, 48.6 mmol) and 4'-hydroxy-2',6'-dimethylbiphenyl-3-carbaldehyde (10.0 g, 44.2 mmol) in N,N-dimethylformamide (150 mL) was added potassium carbonate (6.11 g, 44.2 mmol) under stirring at room temperature, and the mixture was stirred at 100° C. stirred for 12 hr. The reaction mixture was concentrated under reduced pressure, and the residue was neutralized with 1 M hydrochloric acid. The mixture was extracted with ethyl acetate, and the extract was dried over anhydrous sodium sulfate and concentrated under reduced pressure. Diisopropyl ether was added to the obtained oil to allow crystallization and the crystals were collected by filtration to give the title compound (12.3 g yield 78%) as colorless crystals.

$^1$H NMR (CDCl$_3$) δ: 1.77-1.91 (2H, m), 2.00 (6H, s), 2.06-2.16 (2H, m), 2.19 (1H, s), 2.42-2.53 (2H, m), 3.04-3.18 (2H, m), 3.81 (2H, s), 6.69 (2H, s), 7.41 (1H, dt, J=7.5, 1.5 Hz), 7.59 (1H, t, J=7.5 Hz), 7.66 (1H, t, J=1.5 Hz), 7.87 (1H, dt, J=7.5, 1.5 Hz), 10.05 (1H, s).

Reference Example 120

4-({[3'-(hydroxymethyl)-2,6-dimethylbiphenyl-4-yl]oxy}methyl)tetrahydro-2H-thiopyran-4-ol

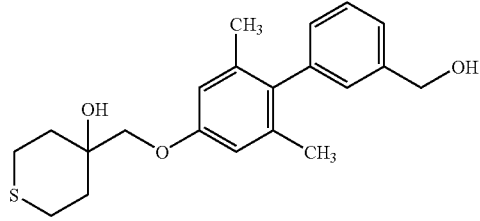

In the same manner as in Reference Example 117, the title compound was obtained as colorless crystals from 4'-[(4-hydroxytetrahydro-2H-thiopyran-4-yl)methoxy]-2',6'-dimethylbiphenyl-3-carbaldehyde. yield 100%.

$^1$H NMR (CDCl$_3$) δ: 1.70 (1H, t, J=5.8 Hz), 1.76-1.90 (2H, m), 2.01 (6H, s), 2.05-2.16 (2H, m), 2.20 (1H, s), 2.40-2.53 (2H, m), 3.03-3.18 (2H, m), 3.80 (2H, s), 4.73 (2H, d, J=5.8 Hz), 6.67 (2H, s), 7.02-7.09 (1H, m), 7.12 (1H, s), 7.31-7.37 (1H, m), 7.41 (1H, t, J=7.4 Hz).

Reference Example 120A 5-(2,6-dimethylphenyl)indan-1-one

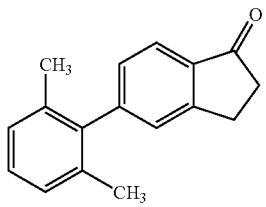

A mixture of 5-bromoindan-1-one (1.20 g, 5.69 mmol), 2,6-dimethylphenylboronic acid (1.02 g, 6.82 mmol), tetrakis(triphenylphosphine)palladium(0) (328 mg, 0.285 mmol), sodium carbonate (1.81 g, 17.1 mmol), methanol (8 mL), water (8 mL) and toluene (25 mL) was heated under reflux overnight under an argon atmosphere. After cooling, the reaction mixture was diluted with ethyl acetate, washed with water, dried and concentrated under reduced pressure. The residue was purified by silica gel column chromatography (5%-50% ethyl acetate/hexane) to give the title compound (0.73 g, yield 54%) as a colorless oil.

$^1$H NMR (CDCl$_3$) δ: 2.02 (6H, s), 2.72-2.80 (2H, m), 3.15-3.23 (2H, m), 7.09-7.23 (4H, m), 7.25-7.30 (1H, m), 7.82 (1H, d, J=7.7 Hz).

Reference Example 121

5-phenoxyindan-1-one

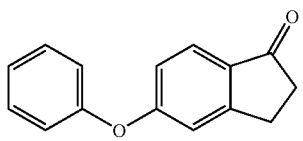

To a solution of 5-hydroxyindan-1-one (2.00 g, 13.5 mmol) in N,N-dimethylformamide (25 mL) was added sodium hydride (60% in oil, 0.596 mg, 14.9 mmol) and the mixture was stirred at 90° C. for 1 hr. Diphenyliodonium chloride (4.72 g, 14.9 mmol) was added to the mixture, and the mixture was stirred at the same temperature for 16 hr. After cooling, the reaction mixture was diluted with ethyl acetate, washed with water, dried and concentrated under reduced pressure. The residue was purified by silica gel column chromatography (5%-40% ethyl acetate/hexane) to give the title compound (1.63 g, yield 54%) as a pale-yellow oil.

$^1$H NMR (CDCl$_3$) δ: 2.64-2.73 (2H, m), 3.03-3.10 (2H, m), 6.93 (1H, br s), 6.96-7.00 (1H, m), 7.05-7.12 (2H, m), 7.18-7.26 (1H, m), 7.37-7.46 (2H, m), 7.72 (1H, d, J=8.5 Hz).

Reference Example 122

5-(benzyloxy)indan-1-one

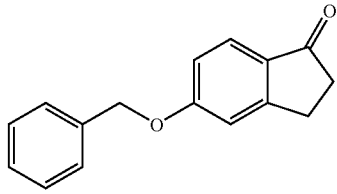

A solution of 5-hydroxyindan-1-one (1.00 q, 6.17 mmol), benzyl alcohol (800 mg, 7.40 mmol) and tributylphosphine (1.70 g, 8.40 mmol) in tetrahydrofuran (80 mL) was stirred at room temperature, 1,1'-(azodicarbonyl)dipiperidine (2.12 g, 8.40 mmol) was added, and the mixture was stirred for 24 hr. Hexane was added to the reaction mixture, the precipitated insoluble material was filtered off, and the filtrate was concentrated under reduced pressure. The residue was purified by silica gel column chromatography (5%-40% ethyl acetate/hexane) to give the title compound (1.14 g, yield 78%) as pale-yellow crystals.

$^1$H NMR (CDCl$_3$) δ: 2.64-2.70 (2H, m), 3.05-3.11 (2H, m), 5.15 (2H, s), 6.95-7.01 (2H, m), 7.28-7.47 (5H, m), 7.70 (1H, d, J=9.2 Hz).

Reference Example 123

4-(benzyloxy)indan-1-one

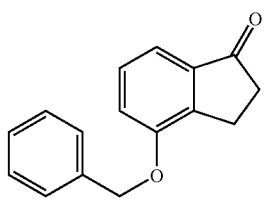

In the same manner as in Reference Example 122, the title compound was obtained as colorless crystals from 4-hydroxyindan-1-one and benzyl alcohol. yield 94%.

MS m/z 239 (MH$^+$).

Reference Example 124

4-phenoxyindan-1-one

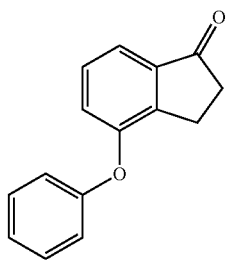

In the same manner as in Reference Example 121, the title compound was obtained as colorless crystals from 4-hydroxyindan-1-one. yield 28%.

$^1$H NMR (CDCl$_3$) δ: 2.67-2.74 (2H, m), 3.01-3.09 (2H, m), 7.01 (2H, d, J=8.3 Hz), 7.08-7.17 (2H, m), 7.29-7.42 (3H, m), 7.54 (1H, d, J=7.5 Hz).

Reference Example 125

1-oxo-2,3-dihydro-1H-inden-4-yl trifluoromethanesulfonate

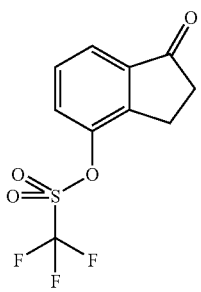

To an ice-cooled solution of 4-hydroxyindan-1-one (15.0 g, 101 mmol) in pyridine (150 mL) was added dropwise trifluoromethanesulfonic anhydride (34.3 g, 121 mmol). The mixture was stirred at room temperature for 16 hr, water was added, and the mixture was extracted with ethyl acetate. The extract was washed with saturated brine, dried over anhydrous magnesium sulfate, and concentrated under reduced pressure. The residue was purified by silica gel column chromatography (5%-45% ethyl acetate/hexane) to give the title compound (26.0 g, yield 92%) as a colorless oil.

$^1$H NMR (CDCl$_3$) δ: 2.74-2.82 (2H, m), 3.24-3.28 (2H, m), 7.45-7.56 (2H, m), 7.75-7.86 (1H, m).

Reference Example 126

4-(2,6-dimethylphenyl)indan-1-one

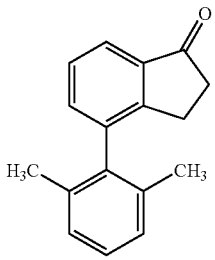

A mixture of 1-oxo-2,3-dihydro-1H-inden-4-yl trifluoromethanesulfonate (10.0 g, 35.7 mmol), 2,6-dimethylphenylboronic acid (6.96 g, 46.4 mmol), 2-(dicyclohexylphosphino)biphenyl (750 mg, 2.14 mmol), tris(dibenzylideneacetone)dipalladium(0) (1.31 mg, 1.43 mmol), tripotassium phosphate (15.2 g, 71.4 mmol) and toluene (200 mL) was heated under reflux under an argon atmosphere at 90° C. for 16 hr. After cooling the reaction mixture, the insoluble material was filtered off, and the filtrate was concentrated under reduced pressure. The residue was purified by silica gel column chromatography (5%-45% ethyl acetate/hexane) to give the title compound (7.21 g, yield 85%) as pale-yellow crystals.

MS m/z 237 (MH$^+$).

Reference Example 127

4-(2,6-dimethylphenyl)indan-1-ol

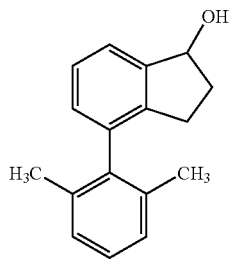

4-(2,6-Dimethylphenyl)indan-1-one (2.00 g, 8.47 mmol) was dissolved in a mixture of tetrahydrofuran (20 mL) and methanol (10 mL), sodium borohydride (449 mg, 11.9 mmol) was added, and the mixture was stirred at room temperature for 2 hr. Water was added to the reaction mixture, and the mixture was extracted with ethyl acetate. The extract was dried, and concentrated under reduced pressure. The residue was purified by silica gel column chromatography (5%-60% ethyl acetate/hexane) to give the title compound (1.54 g, yield 76%) as a colorless oil.

$^1$H NMR (CDCl$_3$) δ: 1.85-1.92 (1H, m), 1.94 (3H, s), 1.98 (3H, s), 2.34-2.52 (2H, m), 2.56-2.67 (1H, m), 5.33 (1H, q, J=6.5 Hz), 7.00-7.04 (1H, m), 7.07-7.20 (3H, m), 7.32 (1H, t, J=7.4 Hz), 7.42 (1H, d, J=7.5 Hz).

Reference Example 128

4-[4-(2-ethoxyethoxy)-2,6-dimethylphenyl]indan-1-one

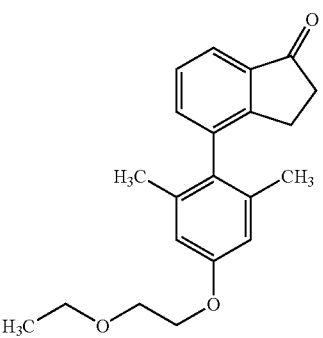

In the same manner as in Reference Example 126, the title compound was obtained as a pale-yellow oil from 1-oxo-2,3-dihydro-1H-inden-4-yl trifluoromethanesulfonate and [4-(2-ethoxyethoxy)-2,6-dimethylphenyl]boronic acid. yield 51%.

MS m/z 325 (MH$^+$).

Reference Example 129

3-bromo-4-isopropoxybenzaldehyde

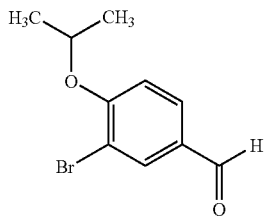

To a mixture of 3-bromo-4-hydroxybenzaldehyde (2.5 g, 12.4 mmol), potassium carbonate (2.57 g, 18.6 mmol), potassium iodide (0.21 g, 1.24 mmol) and N,N-dimethylformamide (30 mL) was added 2-bromopropane (1.46 mL, 15.5 mmol) under stirring at room temperature, and the mixture was stirred at 70° C. for 18 hr. The reaction mixture was diluted with ethyl acetate, washed with water and saturated brine, dried over anhydrous magnesium sulfate, and concentrated. under reduced pressure. The residue was purified by silica gel column chromatography (hexane/ethyl acetate=10/1-3/1) to give the title compound (1.77 g, yield 59%) as a pale-yellow oil.

MS (ESI+): 243 (M+H), 245.

Reference Example 130

3-bromo-4-propoxybenzaldehyde

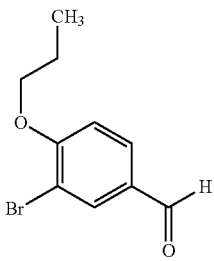

In the same manner as in Reference Example 129, the title compound was obtained as pale-yellow crystals from 3-bromo-4-hydroxybenzaldehyde and 1-bromopropane. yield 92%.

MS (ESI+): 243 (M+H), 245.

Reference Example 131

3-bromo-4-(cyclopropylmethoxy)benzaldehyde

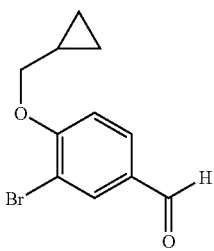

In the same manner as in Reference Example 129, the title compound was obtained as pale-yellow crystals from 3-bromo-4-hydroxybenzaldehyde and cyclopropylmethyl bromide. yield 85%.

MS (ESI+): 255 (M+H), 257.

Reference Example 132

3-[(3,5-diphenyl-1H-pyrazol-1-yl)methyl]-4-isobutoxybenzaldehyde

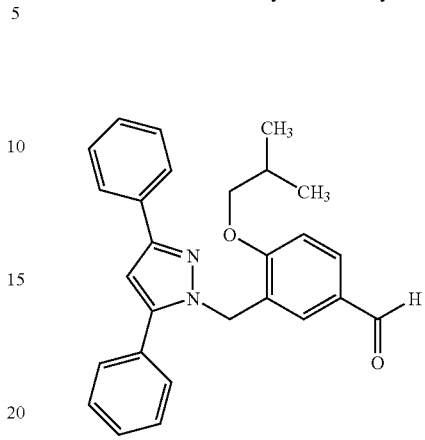

In the same manner as in Reference Example 50, the title compound was obtained as colorless crystals from 3,5-diphenyl-1H-pyrazole and 3-(chloromethyl)-4-isobutoxybenzaldehyde. yield 99%.

MS (ESI+): 411 (M+H).

Reference Example 133 methyl 3-isopropoxy-4-methylbenzoate

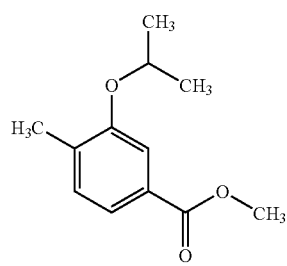

To a mixture of methyl 3-hydroxy-4-methylbenzoate (5.28 g, 31.8 mmol), potassium carbonate (6.59 g, 47.7 mmol) and N,N-dimethylformamide (50 mL) were added 2-bromopropane (3.58 mL, 38.2 mmol) and potassium iodide (0.53 g, 3.18 mmol) under stirring at room temperature, and the mixture was stirred at 80° C. for 7 hr. To the reaction mixture were added 2-bromopropane (1.79 mL, 19.1 mmol) and potassium iodide (0.27 g, 1.59 mmol), and the mixture was further stirred at 80° C. for 15 hr. The reaction mixture was allowed to cool, diluted with ethyl acetate, washed with water and saturated brine, dried over anhydrous magnesium sulfate, and concentrated under reduced pressure. The residue was purified by silica gel column chromatography (hexane/ethyl acetate=19/1-hexane/ethyl acetate=4/1) to give the title compound (6.3 g, yield 96%) as a colorless oil.

MS (ESI+): 209 (M+H).

Reference Example 134 methyl 4-(bromomethyl)-3-isopropoxybenzoate

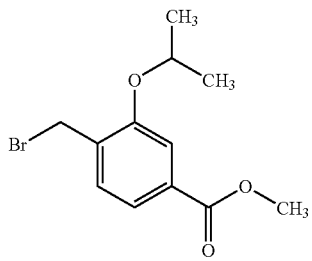

To a solution of methyl 3-isopropoxy-4-methylbenzoate (1.0 g, 4.8 mmol) in ethyl acetate (20 mL) were added N-bromosuccinimide (0.92 g, 5.19 mmol) and 2,2'-azobis(isobutyronitrile) (3 mg), and the mixture was heated under reflux for 6 hr. The reaction mixture was allowed to cool, washed with water and saturated brine, dried over anhydrous magnesium sulfate, and concentrated under reduced pressure. The residue was purified by silica gel column chromatography (hexane/ethyl acetate=10/1-hexane/ethyl acetate=4/1) to give the title compound (0.89 g, yield 64%) as a colorless oil.

MS (ESI+): 287 (M+H), 289.

Reference Example 135 methyl 4-[(3,5-diphenyl-1H-pyrazol-1-yl)methyl]-3-isopropoxybenzoate

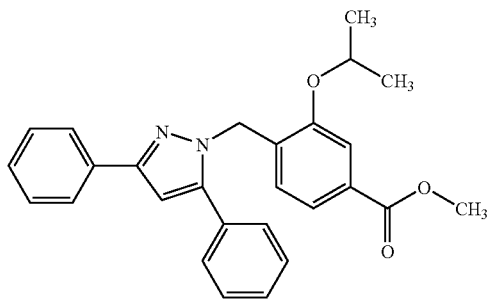

To a solution of 3,5-diphenyl-1H-pyrazole (0.36 g, 1.65 mmol) in N,N-dimethylformamide (8.6 mL) was added sodium hydride (60% in oil, 66 mg, 1.65 mmol) under stirring at room temperature, and the mixture was stirred at the same temperature for 30 min. To the reaction mixture was added sodium iodide (22 mg, 0.15 mmol) and a solution of methyl 4-(bromomethyl)-3-isopropoxybenzoate (0.43 g, 1.50 mmol) in N,N-dimethylformamide (4.3 mL), and the mixture was stirred at room temperature for 3 hr. The reaction mixture was diluted with ethyl acetate, washed with water and saturated brine, dried over anhydrous magnesium sulfate, and concentrated under reduced pressure. The residue was purified by silica gel column chromatography (hexane/ethyl acetate=10/1-hexane/ethyl acetate=4/1) to give the title compound (0.59 g, yield 92%) as a colorless oil.

MS (ESI+): 427 (M+H).

Reference Example 136

{4-[(3,5-diphenyl-1H-pyrazol-1-yl)methyl]-3-isopropoxyphenyl}methanol

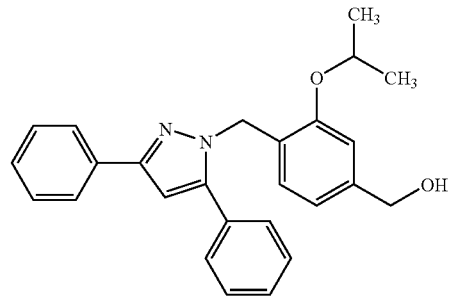

To a solution of methyl 4-[(3,5-diphenyl-1H-pyrazol-1-yl)methyl]-3-isopropoxybenzoate (0.59 g, 1.38 mmol) in tetrahydrofuran (12 mL) was added lithium aluminum hydride (52 mg, 1.38 mmol) under stirring at 0° C., and the mixture was stirred at the same temperature for 2.5 hr. After completion of the reaction, sodium sulfate decahydrate (0.89 g, 2.76 mmol) was added to the reaction mixture, and the mixture was stirred at room temperature for 2 hr. The insoluble material was filtered off, and the filtrate was concentrated under reduced pressure. The residue was purified by silica gel column chromatography (hexane/ethyl acetate=5/1-hexane/ethyl acetate=1/1) to give the title compound (0.50 g, yield 92%) as a colorless oil.

MS (ESI+): 399 (M+H).

Reference Example 137

4-[(3,5-diphenyl-1H-pyrazol-1-yl)methyl]-3-isopropoxybenzaldehyde

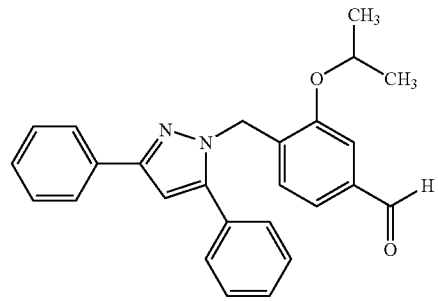

In the same manner as in Reference Example 77, the title compound was obtained as a colorless oil from {4-[(3,5-diphenyl-1H-pyrazol-1-yl)methyl]-3-isopropoxyphenyl}methanol. yield 75%.

MS (ESI+): 397 (M+H).

Reference Example 138

1-(2-ethoxyethoxy)-2,3,5-trimethylbenzene

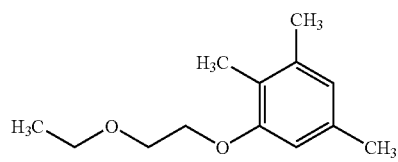

To a solution of 2,3,5-trimethylphenol (3.0 g, 22.0 mmol), potassium carbonate (3.65 g, 26.4 mmol) and potassium iodide (0.55 g, 3.3 mmol) in N,N-dimethylformamide (50 mL) was added 2-chloroethyl ethyl ether (3.59 g, 33.3 mmol) under stirring at room temperature, and the mixture was stirred at 70° C. for 24 hr. To the reaction mixture were added reagents (potassium carbonate, potassium iodide and 2-chloroethyl ethyl ether) in the same amount as mentioned above, and the mixture was further stirred at 70° C. for 24 hr. The reaction mixture was diluted with ethyl acetate, washed successively with water and saturated brine, dried over anhydrous magnesium sulfate, and concentrated under reduced pressure. The residue was purified by silica gel column chromatography (hexane/ethyl acetate=49/1-hexane/ethyl acetate=4/1) to give the title compound (4.1 g, yield 90%) as a colorless oil.

MS (ESI+): 209 (M+H).

Reference Example 139

2-bromo-5-(2-ethoxyethoxy)-1,3,4-trimethylbenzene

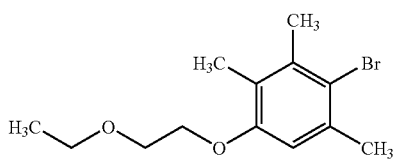

To a mixture of 1-(2-ethoxyethoxy)-2,3,5-trimethylbenzene (1.0 g, 4.08 mmol), pyridine (0.097 mL, 1.20 mmol) and dichloromethane (10 mL) was added a solution of bromine (0.66 g, 4.12 mmol) in dichloromethane (1 mL) under stirring at 0° C., and the mixture was stirred at the same temperature for 1 hr. The reaction mixture was washed successively with saturated aqueous sodium hydrogencarbonate solution and saturated brine, dried over anhydrous magnesium sulfate, and concentrated under reduced pressure. The residue was purified by silica gel column chromatography (hexane/ethyl acetate=49/1-hexane/ethyl acetate=4/1) to give the title compound (1.2 g, yield 99%) as a colorless oil.

$^1$H NMR (CDCl$_3$) δ: 1.24 (3H, t, J=6.9 Hz), 2.20 (3H, s), 2.37 (3H, s), 2.38 (3H, s), 3.60 (2H, q, J=6.9 Hz), 3.76-3.81 (2H, m), 4.04-4.09 (2H, m), 6.63 (1H, s).

Reference Example 140

4'-(2-ethoxyethoxy)-2',3',6'-trimethylbiphenyl-3-carbaldehyde

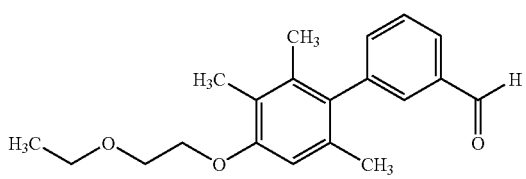

A mixture of 2-bromo-5-(2-ethoxyethoxy)-1,3,4-trimethylbenzene (1.16 g, 4.04 mmol), 3-formylphenylboronic acid (0.67 g, 4.44 mmol), tetrakis(triphenylphosphine)palladium (0) (0.23 g, 0.20 mmol), cesium carbonate (3.2 g, 9.7 mmol), water (4.8 mL) and 1,2-dimethoxyethane (15 mL) was stirred under a nitrogen atmosphere at 90° C. for 64 hr. The reaction mixture was diluted with ethyl acetate, washed successively with water and saturated brine, dried, and concentrated under reduced pressure. The residue was purified by silica gel column chromatography (hexane/ethyl acetate=10/1-hexane/ethyl acetate=2/1) to give the title compound (0.35 g, yield 28%) as a colorless oil.

MS (ESI+): 313 (M+H).

Reference Example 141

3-(2-ethoxyethoxy)-1,2,4,5-tetramethylbenzene

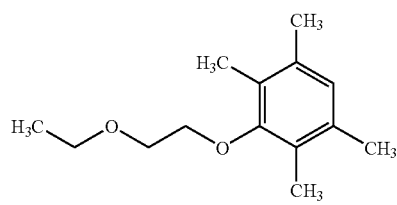

The title compound was obtained as a pale-yellow oil from 2,3,5,6-tetramethylphenol synthesized according to the method described in Tetrahedron Lett., 1989, vol. 30, p. 5215 and 2-chloroethyl ethyl ether. yield 73%.

MS (ESI+): 223 (M+H).

Reference Example 142

1-bromo-4-(2-ethoxyethoxy)-2,3,5,6-tetramethylbenzene

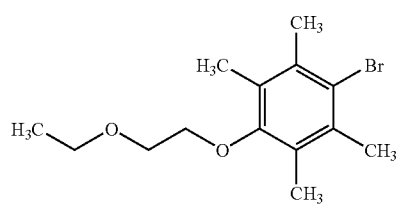

In the same manner as in Reference Example 139, the title compound was obtained as a pale-yellow oil from 3-(2-ethoxyethoxy)-1,2,4,5-tetramethylbenzene. yield 86%.

$^1$H NMR (CDCl$_3$) δ: 1.27 (3H, t, J=6.9 Hz), 2.27 (6H, s), 2.38 (6H, s), 3.62 (2H, q, J=6.9 Hz), 3.73-3.78 (2H, m), 3.80-3.86 (2H, m).

Reference Example 143

4'-(2-ethoxyethoxy)-2',3',5',6'-tetramethylbiphenyl-3-carbaldehyde

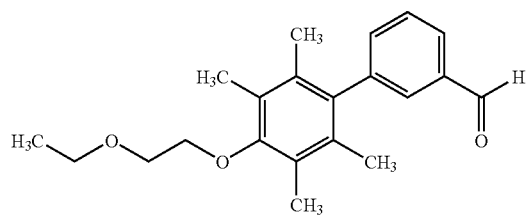

In the same manner as in Reference Example 140, the title compound was obtained as a yellow oil from 1-bromo-4-(2-ethoxyethoxy)-2,3,5,6-tetramethylbenzene and 3-formylphenylboronic acid. yield 18%.

MS (ESI+): 327 (M+H).

Reference Example 144 methyl 4-[(2,2-dimethylquinolin-1(2H)-yl)methyl]-3-isopropoxybenzoate

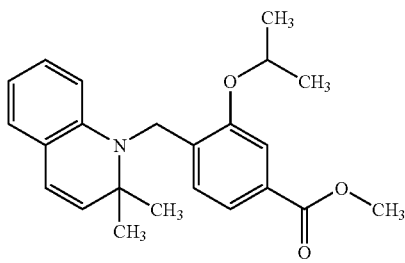

In the same manner as in Reference Example 135, the title compound was obtained as a green oil from 2,2-dimethyl-1,2-dihydroquinoline synthesized according to the method described in J. Med. Chem., 1998, vol. 41, p. 623, and methyl 4-(bromomethyl)-3-isopropoxybenzoate. yield 38%.
MS (ESI+): 366 (M+H).

Reference Example 145

{4-[(2,2-dimethylquinolin-1(2H)-yl)methyl]-3-isopropoxyphenyl}methanol

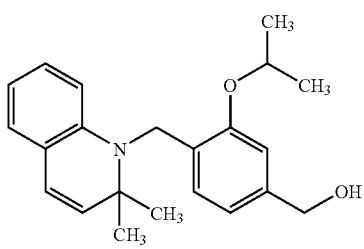

In the same manner as in Reference Example 136, the title compound was obtained as a yellow oil from methyl 4-[(2,2-dimethylquinolin-1(2H)-yl)methyl]-3-isopropoxybenzoate. yield 86%.
MS (ESI+): 338 (M+H).

Reference Example 146

4-[(2,2-dimethylquinolin-1(2H)-yl)methyl]-3-isopropoxybenzaldehyde

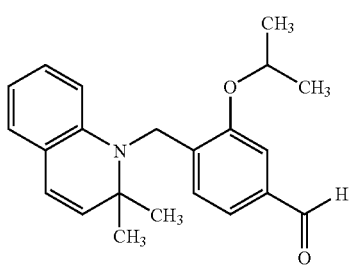

In the same manner as in Reference Example 77, the title compound was obtained as a yellow oil from {4-[(2,2-dimethylquinolin-1(2H)-yl)methyl]-3-isopropoxyphenyl}methanol. yield 78%.
MS (ESI+): 336 (M+H).

Reference Example 147 methyl 3-isopropoxy-4-[(2-methyl-3,4-dihydroquinolin-1(2H)-yl)methyl]benzoate

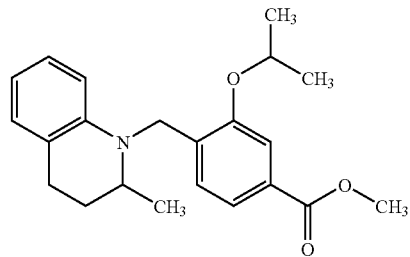

In the same manner as in Reference Example 135, the title compound was obtained as a colorless oil from methyl 4-(bromomethyl)-3-isopropoxybenzoate and 2-methyl-1,2,3,4-tetrahydroquinoline. yield 42%.
MS (ESI+): 354 (M+H).

Reference Example 148

{3-isopropoxy-4-[(2-methyl-3,4-dihydroquinolin-1(2H)-yl)methyl]phenyl}methanol

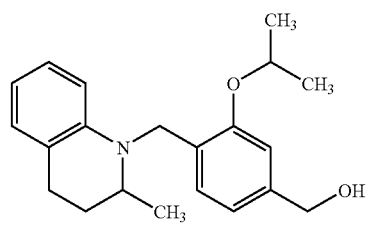

In the same manner as in Reference Example 136, the title compound was obtained as a yellow oil from methyl 3-isopropoxy-4-[(2-methyl-3,4-dihydroquinolin-1(2H)-yl)methyl]benzoate. yield 100%.
MS (ESI+): 326 (M+H).

Reference Example 149

3-isopropoxy-4-[(2-methyl-3,4-dihydroquinolin-1(2H)-yl)methyl]benzaldehyde

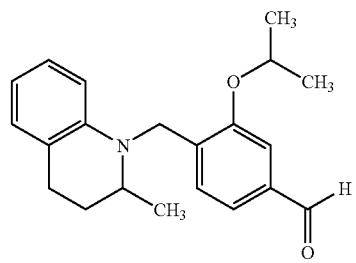

In the same manner as in Reference Example 77, the title compound was obtained as a colorless oil from {3-isopropoxy-4-[(2-methyl-3,4-dihydroquinolin-1(2H)-yl)methyl]phenyl}methanol. yield 76%.

MS (ESI+): 324 (M+H).

Reference Example 150 methyl 4-[(4-hydroxypiperidin-1-yl)methyl]-3-isopropoxybenzoate

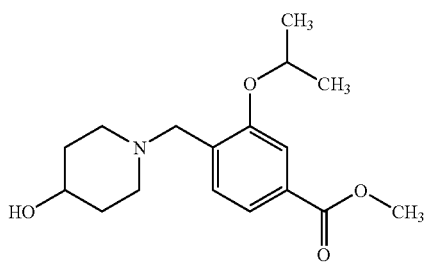

A mixture of methyl 4-(bromomethyl)-3-isopropoxybenzoate (2.0 g, 6.96 mmol), 4-hydroxypiperidine (1.06 g, 10.4 mmol), potassium carbonate (1.44 g, 10.4 mmol) and N,N-dimethylformamide (20 mL) was stirred at 70° C. for 20 hr. The reaction mixture was diluted with ethyl acetate, washed with water and saturated brine, dried over anhydrous magnesium sulfate, and concentrated under reduced pressure. The residue was purified by silica gel column chromatography (basic silica gel, hexane/ethyl acetate=10/1-hexane/ethyl acetate=1/2) to give the title compound (1.77 g, yield 83%) as a pale-yellow oil.

MS (ESI+): 308 (M+H).

Reference Example 151 methyl 4-{[4-(2,6-dimethylphenoxy)piperidin-1-yl]methyl}-3-isopropoxybenzoate

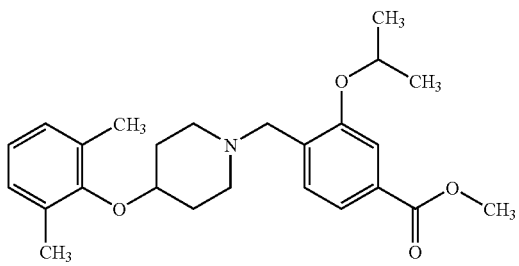

To a solution of methyl 4-[(4-hydroxypiperidin-1-yl)methyl]-3-isopropoxybenzoate (0.72 g, 2.34 mmol), 2,6-dimethylphenol (0.43 g, 3.51 mmol) and tributylphosphine (0.88 mL, 3.51 mmol) in anhydrous tetrahydrofuran (14 mL) was added 1,1'-(azodicarbonyl)dipiperidine (0.89 g, 3.51 mmol), and the mixture was stirred at room temperature for 12 hr. To the reaction mixture were added reagents (2,6-dimethylphenol, tributylphosphine and 1,1'-(azodicarbonyl)dipiperidine) in the same amount as mentioned above, and the mixture was further stirred for 12 hr. Diethyl ether (40 mL) was added to the reaction solution, the precipitate was filtered off, and the filtrate was concentrated under reduced pressure. The residue was purified by silica gel column chromatography (hexane/ethyl acetate=10/1-hexane/ethyl acetate=2/1) to give the title compound (0.35 g, yield 36%) as a colorless oil.

MS (ESI+): 412 (M+H).

Reference Example 152

(4-{[4-(2,6-dimethylphenoxy)piperidin-1-yl]methyl}-3-isopropoxyphenyl)methanol

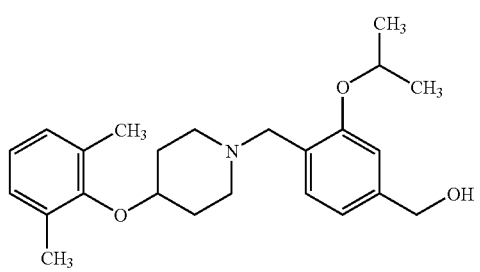

In the same manner as in Reference Example 136, the title compound was obtained as a colorless oil from methyl 4-{[4-(2,6-dimethylphenoxy)piperidin-1-yl]methyl}-3-isopropoxybenzoate. yield 100%.

MS (ESI+): 384 (M+H).

Reference Example 153

4-{[4-(2,6-dimethylphenoxy)piperidin-1-yl]methyl}-3-isopropoxybenzaldehyde

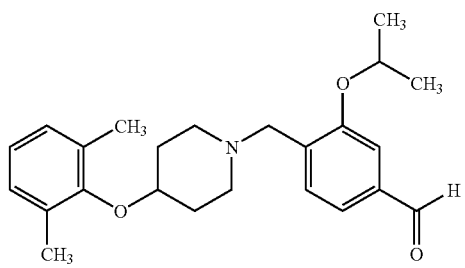

In the same manner as in Reference Example 77, the title compound was obtained as a yellow oil from (4-{[4-(2,6-dimethylphenoxy)piperidin-1-yl]methyl}-3-isopropoxyphenyl)methanol. yield 100%.

MS (ESI+): 382 (M+H).

Reference Example 154 methyl 3-isopropoxy-4-[(2-methyl-1H-indol-1-yl)methyl]benzoate

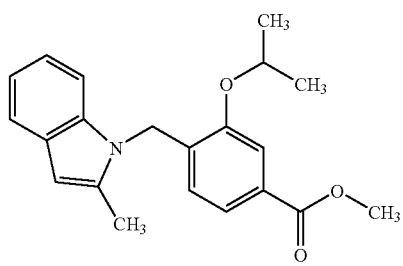

In the same manner as in Reference Example 135, the title compound was obtained as pale-yellow crystals from methyl 4-(bromomethyl)-3-isopropoxybenzoate and 2-methylindole. yield 29%.

MS (ESI+): 338 (M+H).

Reference Example 155

{3-isopropoxy-4-[(2-methyl-1H-indol-1-yl)methyl]phenyl}methanol

In the same manner as in Reference Example 136, the title compound was obtained as a pale-yellow oil from methyl 3-isopropoxy-4-[(2-methyl-1H-indol-1-yl)methyl]benzoate. yield 88%.

MS (ESI+): 310 (M+H).

Reference Example 156

3-isopropoxy-4-[(2-methyl-1H-indol-1-yl)methyl]benzaldehyde

In the same manner as in Reference Example 77, the title compound was obtained as a yellow oil from {3-isopropoxy-4-[(2-methyl-1H-indol-1-yl)methyl]phenyl}methanol. yield 72%.

MS (ESI+): 308 (M+H).

Reference Example 157 methyl 4-methyl-3-[(methylsulfonyl)oxy]benzoate

To a solution of methyl 3-hydroxy-4-methylbenzoate (3.0 g, 18.1 mmol) in pyridine (20 mL) was added methanesulfonyl chloride (2.80 mL, 36.1 mmol) under stirring at 0° C., and the mixture was stirred at room temperature for 3 hr. The solvent was evaporated under reduced pressure, and the residue was partitioned between ethyl acetate and 1 N hydrochloric acid. The organic layer was washed with saturated brine, dried over anhydrous magnesium sulfate, and concentrated under reduced pressure. The residue was purified by silica gel column chromatography (hexane/ethyl acetate=9/1-hexane/ethyl acetate=1/1) to give the title compound (4.11 g, yield 93%) as a yellow oil.

MS (ESI+): 245 (M+H).

Reference Example 158 methyl 4-(bromomethyl)-3-[(methylsulfonyl)oxy]benzoate

In the same manner as in Reference Example 134, the title compound was obtained as a pale-yellow oil from methyl 4-methyl-3-[(methylsulfonyl)oxy]benzoate. yield 69%.

$^1$H NMR (CDCl$_3$) δ: 3.35 (3H, s), 3.94 (3H, s), 4.58 (2H, s), 7.58 (1H, d, J=7.8 Hz), 7.98 (1H, dd, J=1.8, 7.8 Hz), 8.02 (1H, d, J=1.8 Hz).

Reference Example 159 methyl 4-[(2-methyl-3,4-dihydroquinolin-1(2H)-yl)methyl]-3-[(methylsulfonyl)oxy]benzoate A mixture of methyl 4-(bromomethyl)-3-[(methylsulfonyl)oxy]benzoate (0.70 g, 2.2 mmol), 2-methyl-1,2,3,4-tetrahydroquinoline (0.39 g, 2.6 mmol), potassium carbonate (0.60 g, 4.3 mmol) and N,N-dimethylformamide (14 mL) was stirred at 70° C. for 23 hr. The reaction mixture was diluted with ethyl acetate, washed with water and saturated brine, dried over anhydrous magnesium sulfate, and concentrated under reduced pressure. The residue was purified by silica gel column chromatography (hexane/ethyl acetate=10/1-2/1) to give the title compound (0.63 g, yield 75%) as a pale-yellow oil.

MS (ESI+): 389 (M+H).

Reference Example 160

5-(hydroxymethyl)-2-[(2-methyl-3,4-dihydroquino-lin-1(2H)-yl)methyl]phenyl methanesulfonate

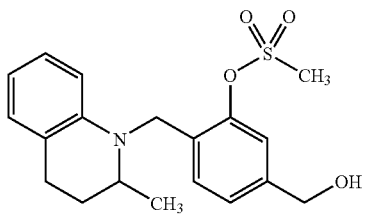

In the same manner as in Reference Example 136, the title compound was obtained as a yellow oil from methyl 4-[(2-methyl-3,4-dihydroquinolin-1(2H)-yl)methyl]-3-[(methylsulfonyl)oxy]benzoate. yield 80%.

MS (ESI+): 362 (M+H).

Reference Example 161 methyl 4-[(3,5-diphenyl-1H-pyrazol-1-yl)methyl]-3-methoxybenzoate

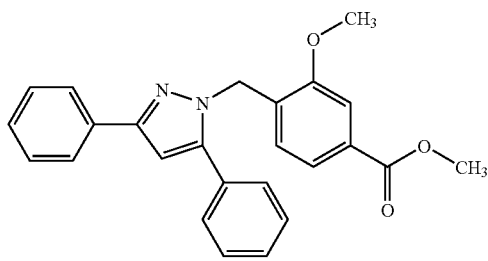

In the same manner as in Reference Example 159, the title compound was obtained as a colorless powder from methyl 4-(bromomethyl)-3-methoxybenzoate and 3,5-diphenyl-1H-pyrazole. yield 71%.

MS (ESI+): 399 (M+H).

Reference Example 162

{4-[(3,5-diphenyl-1H-pyrazol-1-yl)methyl]-3-methoxyphenyl}methanol

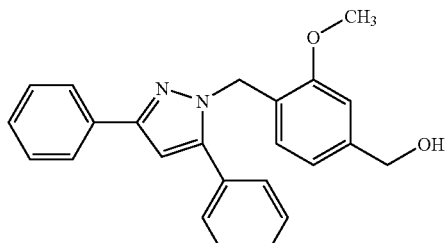

In the same manner as in Reference Example 136, the title compound was obtained as a pale-yellow powder from methyl 4-[(3,5-diphenyl-1H-pyrazol-1-yl)methyl]-3-methoxybenzoate. yield 90%.

MS (ESI+): 371 (M+H).

Reference Example 163 methyl 4-hydroxy-3-isobutylbenzoate

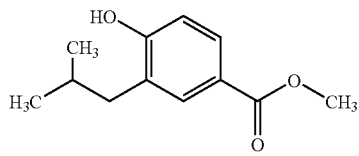

Methyl 3-bromo-4-hydroxy-5-(2-methylprop-2-en-1-yl)benzoate (5.0 g, 24.2 mmol) and 10% palladium-carbon (50% water-containing product, 1.5 g) were added to a mixed solvent of tetrahydrofuran (70 mL) and methanol (70 mL), and the mixture was stirred under a hydrogen atmosphere at room temperature for 5 hr. The catalyst was filtered off, and the filtrate was concentrated to give the title compound (4.8 g, yield 95%) as colorless needle crystals.

$^1$H NMR (CDCl$_3$) δ: 0.93 (6H, d, J=6.6 Hz), 1.82-2.04 (1H, m), 2.51 (2H, d, J=7.4 Hz), 3.88 (3H, s), 5.00-5.30 (1H, m), 6.78 (1H, d, J=8.8 Hz), 7.75-7.84 (2H, m).

Reference Example 164 methyl 4-(diphenylmethoxy)-3-isobutylbenzoate

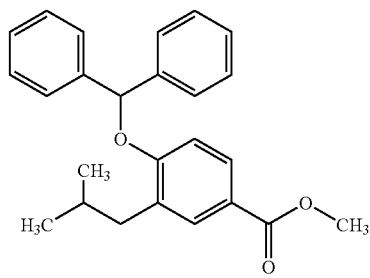

A solution of methyl 4-hydroxy-3-isobutylbenzoate (0.80 g, 3.84 mmol), diphenylmethyl bromide (1.05 g, 4.25 mmol) and potassium carbonate (0.69 g, 4.99 mmol) in N,N-dimethylformamide (20 mL) was stirred at room temperature for 3 days. The reaction solution was poured into ice water, and the mixture was extracted with ethyl acetate. The extract was washed with aqueous citric acid solution, dried over anhydrous magnesium sulfate, and concentrated under reduced pressure. The residue was subjected to silica gel column chromatography (ethyl acetate/hexane=3/97-15/85) to give the title compound (450 mg, yield 31%) as a colorless oil.

$^1$H NMR (CDCl$_3$) δ: 0.94 (6H, d, J=6.6 Hz), 1.95-2.18 (1H, m), 2.64 (2H, d, J=6.8 Hz), 3.83 (3H, s), 6.26 (1H, s), 6.78 (1H, d, J=8.8 Hz), 7.20-7.84 (11H, m).

Reference Example 165

[4-(diphenylmethoxy)-3-isobutylphenyl]methanol

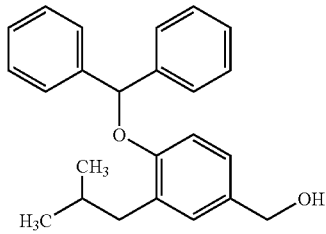

To a solution of methyl 4-(diphenylmethoxy)-3-isobutylbenzoate (0.45 g, 1.20 mmol) in tetrahydrofuran (20 mL) was added lithium aluminum hydride (60 mg, 1.58 mmol) by small portions under ice-cooling. The mixture was stirred under ice-cooling for 2 hr, sodium sulfate decahydrate (1.2 g, 2.30 mmol) was added to the reaction solution by small portions, and the mixture was stirred at room temperature for 1 hr. The insoluble material was filtered off, and the filtrate was concentrated to give the title compound (420 mg, yield 100%) as a colorless oil.

$^1$H NMR (CDCl$_3$) δ: 0.93 (6H, d, J=6.6 Hz), 1.47 (1H, t, J=5.7 Hz), 1.96-2.12 (1H, m), 2.60 (2H, d, J=6.9 Hz), 4.54 (2H, d, J=5.7 Hz), 6.17 (1H, s), 6.72 (1H, d, J=5.7 Hz), 6.99 (1H, dd, J=2.4, 8.4 Hz), 7.10 (1H, d, J=2.4 Hz), 7.15-7.25 (10H, m).

Reference Example 166

4-butyrylphenyl trifluoromethanesulfonate

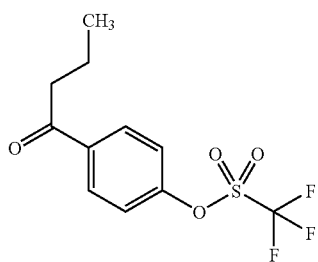

To an ice-cooled solution of ice-cooled 1-(4-hydroxyphenyl)butan-1-one (15.0 g, 91.4 mmol) in pyridine (100 mL) was added dropwise trifluoromethanesulfonic anhydride (30.9 g, 110 mmol). The mixture was stirred at room temperature for 3 hr, diluted with water, and the mixture was extracted with ethyl acetate. The extract was washed with saturated brine, dried over anhydrous magnesium sulfate, and concentrated under reduced pressure. The residue was purified by silica gel column chromatography (ethyl acetate/hexane=5/95-40/60) to give the title compound (27.1 g, yield 100%) as a pale-yellow oil.

$^1$H NMR (CDCl$_3$) δ: 1.01 (3H, t, J=7.4 Hz), 1.71-1.85 (2H, m), 2.95 (2H, t, J=7.3 Hz), 7.34-7.41 (2H, m), 8.02-8.09 (2H, m).

Reference Example 167 methyl 4-butyrylbenzoate

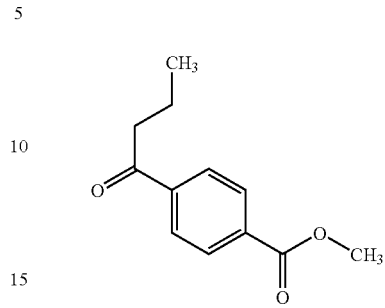

A mixture of 4-butyrylphenyl trifluoromethanesulfonate (27.14 g, 91.7 mmol), palladium acetate (1.24 g, 5.50 mmol), 1,3-bis(diphenylphosphino)propane (2.45 g, 6.05 mmol), triethylamine (23.2 g, 229 mmol), methanol (200 mL) and dimethyl sulfoxide (100 mL) was heated under reflux under a carbon monoxide atmosphere at 80° C. for 8 hr. After cooling the reaction mixture, 0.5 N hydrochloric acid was added, and the mixture was extracted with ethyl acetate. The extract was washed with saturated brine, dried over anhydrous magnesium sulfate, and concentrated under reduced pressure. The residue was purified by silica gel column chromatography (ethyl acetate/hexane=3/97-30/70) and recrystallized from ethyl acetate-hexane to give the title compound (9.24 g, yield 49%) as colorless crystals.

MS: m/z 207 (MH$^+$).

Reference Example 168

(4-{1-[(4-phenyl-1,3-thiazol-2-yl)methyl]butyl}phenyl)methanol

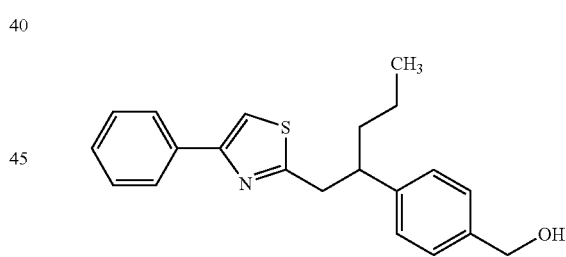

To a suspension of triphenyl[(4-phenyl-1,3-thiazol-2-yl)methyl]phosphonium bromide (1.00 g, 1.94 mmol) synthesized according to the method described in Liebigs Annalen der Chemie, 1981, vol. 4, pp. 623-632 and benzene (20 mL) was added potassium tert-butoxide (239 mg, 2.13 mmol), and the mixture was stirred under an argon atmosphere at room temperature for 3 hr. A solution of methyl 4-butyrylbenzoate (319 mg, 1.55 mmol) in benzene (20 mL) was added dropwise to the reaction solution, and the mixture was stirred at room temperature for 3 hr, and further heated under reflux for 16 hr. The reaction mixture was allowed to cool to room temperature, poured into water, and the mixture was extracted with ethyl acetate. The extract was washed with saturated brine, dried over anhydrous magnesium sulfate, and concentrated under reduced pressure. The residue was purified by silica gel column chromatography (ethyl acetate:hexane=5:95-20:80) to give a yellow oil. A mixture of the obtained oil, tetrahydrofuran (20 mL), methanol (10 mL) and 10% palladium-carbon (50% water-containing product, 200 mg) was stirred under a hydrogen atmosphere at room temperature for 2 days. The catalyst was filtered off, and the obtained filtrate was concentrated to give a colorless oil. To a solution of the obtained oil in tetrahydrofuran (10 mL) was added dropwise 1.0 M diisobutylaluminum hydride toluene solution (10 mL, 10 mmol) under ice-cooling. The reaction mixture was stirred at room temperature for 2 hr, sodium sulfate decahydrate was added and the mixture was further stirred at room temperature for 1 hr. The insoluble material was filtered off, the filtrate was concentrated, and the residue was purified by silica gel column chromatography (ethyl acetate/hexane=10/90-60/40) to give the title compound (250 mg, yield 48%) as a colorless oil.

MS: m/z 338 (MH$^+$).

Reference Example 169

4-{[tert-butyl(dimethyl)silyl]oxy}indan-1-ol

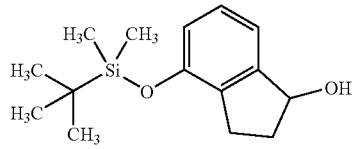

In the same manner as in Reference Example 127, the title compound was obtained as a colorless oil from 4-{[tert-butyl(dimethyl)silyl]oxy}indan-1-one. yield 93%.

$^1$H NMR (CDCl$_3$) δ: 0.20 (6H, d, J=1.1 Hz), 1.00 (9H, s), 1.72 (1H, d, J=7.2 Hz), 1.85-1.99 (1H, m), 2.40-2.53 (1H, m), 2.67-2.79 (1H, m), 2.94-3.06 (1H, m), 5.20-5.27 (1H, m), 6.71 (1H, d, J=7.6 Hz), 7.03 (1H, d, J=7.6 Hz), 7.13 (1H, t, J=7.6 Hz).

Reference Example 170 ethyl 3-(2-fluoro-4-{(4-hydroxy-2,3-dihydro-1H-inden-1-yl)[(2-nitrophenyl)sulfonyl]amino}phenyl)propanoate

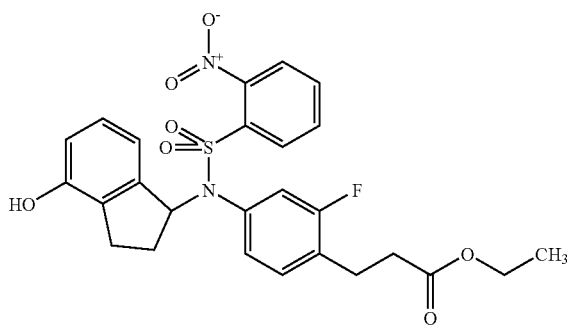

A solution of ethyl 3-(2-fluoro-4-{[(2-nitrophenyl)sulfonyl]amino}phenyl)propanoate (20.0 g, 50.5 mmol), 4-{[tert-butyl(dimethyl)silyl]oxy}indan-1-ol (14.7 g, 55.6 mmol) and triphenylphosphine (14.6 g, 55.6 mmol) in tetrahydrofuran (300 mL) was stirred under ice-cooling, and diethyl azodicarboxylate (40% toluene solution, 25.3 mL, 55.6 mmol) was added. The mixture was allowed to warm to room temperature and stirred for 16 hr. To the reaction mixture were added reagents (4-{[tert-butyl(dimethyl)silyl]oxy}indan-1-ol, triphenylphosphine and diethyl azodicarboxylate) in a half amount of the above, and the mixture was further stirred for 4 hr. The reaction mixture was concentrated, and diethyl ether and hexane were added to the residue. The resultant insoluble material was filtered off and the filtrate was concentrated under reduced pressure. The residue was purified by silica gel column chromatography (hexane/ethyl acetate=95/5-hexane/ethyl acetate=30/70) to give a yellow oil. To a solution of the obtained oil in tetrahydrofuran (250 mL) was added tetrabutylammonium fluoride (1 M THF solution, 61.1 mL, 61.1 mmol) under stirring under ice cooling and the mixture was stirred at the same temperature for 3 hr. Ethyl acetate was added to the reaction mixture, and the mixture was washed with saturated brine, dried over anhydrous magnesium sulfate, and concentrated under reduced pressure. The residue was purified by silica gel column chromatography (hexane/ethyl acetate=70/30-hexane/ethyl acetate=30/70) to give the title compound (21.5 g, yield 81%, 2 steps) as a yellow oil.

MS m/z 551 ((M+Na)$^+$).

Reference Example 171 ethyl 3-{2-fluoro-4-[[(2-nitrophenyl)sulfonyl](4-{[(trifluoromethyl)sulfonyl]oxy}-2,3-dihydro-1H-inden-1-yl)amino]phenyl}propanoate

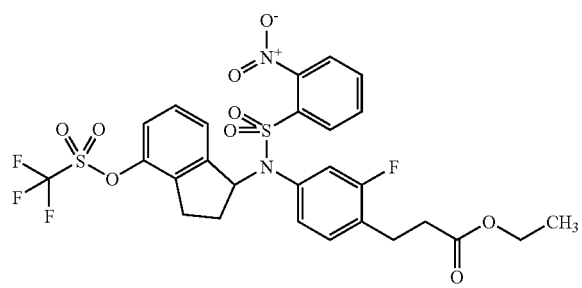

In the same manner as in Reference Example 125, the title compound was obtained as a yellow oil from ethyl 3-(2-fluoro-4-{(4-hydroxy-2,3-dihydro-1H-inden-1-yl)[(2-nitrophenyl)sulfonyl]amino}phenyl)propanoate. yield 96%.

MS m/z 661 ((M+Na)$^+$).

Reference Example 172 methyl(2E)-3-(6-amino-2-methylpyridin-3-yl)acrylate

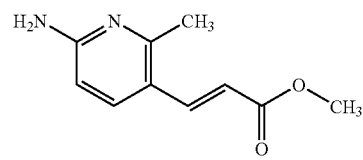

In the same manner as in Reference Example 20, the title compound was obtained as yellow crystals from 5-bromo-6-ethylpyridine-2-amine. yield 11%.

MS m/z 193 (MH$^+$).

Reference Example 173 methyl 3-(6-amino-2-methylpyridin-3-yl)propanoate

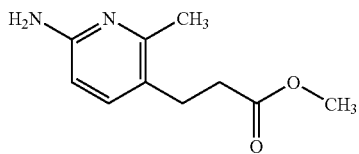

In the same manner as in Reference Example 21, the title compound was obtained as yellow crystals from methyl(2E)-3-(6-amino-2-methylpyridin-3-yl)acrylate. yield 73%.

MS m/z 195 (MH$^+$).

Reference Example 174 methyl(2E)-3-(2-aminopyrimidin-5-yl)acrylate

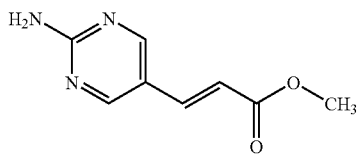

In the same manner as in Reference Example 20, the title compound was obtained as yellow crystals from 2-amino-5-bromopyrimidine. yield 28%.

$^1$H NMR (DMSO-d$_6$) δ: 3.69 (3H, s), 6.52 (1H, d, J=16.2 Hz), 7.49 (1H, d, J=16.2 Hz), 8.61 (2H, s).

Reference Example 175 methyl 3-(2-aminopyrimidin-5-yl)propanoate

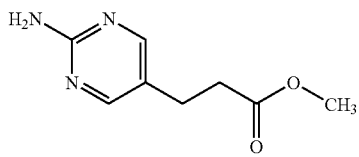

In the same manner as in Reference Example 21, the title compound was obtained as colorless crystals from methyl (2E)-3-(2-aminopyrimidin-5-yl)acrylate. yield 17%.

MS m/z 182 (MH$^+$).

Reference Example 176

N-(3-methylbutyl)-4-[4-(trifluoromethyl)phenyl]-1,3-thiazole-2-amine

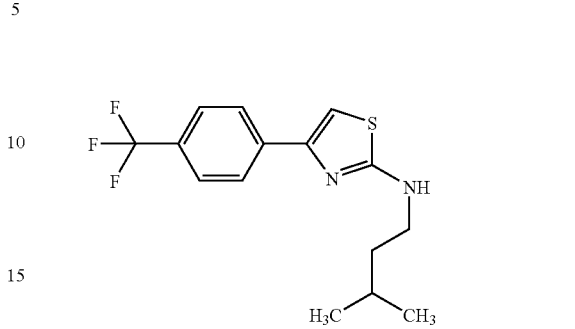

A solution of N-(3-methylbutyl)thiourea (3.00 g, 20.5 mmol), 2-bromo-1-[4-(trifluoromethyl)phenyl]ethanone (5.45 g, 20.5 mmol), sodium acetate (2.19 g, 26.7 mmol) in ethanol (50 mL) was stirred at 90° C. for 4 hr. The reaction mixture was poured into water, and the mixture was extracted with ethyl acetate. The extract was dried over anhydrous sodium sulfate, and concentrated under reduced pressure. The obtained solid was recrystallized from dichloromethane-hexane to give the title compound (1.76 g, yield 27%) as pale-yellow crystals.

$^1$H NMR (CDCl$_3$) δ: 0.95 (6H, d, J=6.5 Hz), 1.55 (2H, q, J=7.0 Hz), 1.63-1.79 (1H, m), 3.24-3.36 (2H, m), 5.29 (1H, br s), 6.80 (1H, s), 7.61 (2H, d, J=8.5 Hz), 7.90 (2H, d, J=8.2 Hz).

Reference Example 177 methyl 4-[((3-methylbutyl){4-[4-(trifluoromethyl)phenyl]-1,3-thiazol-2-yl}amino)methyl]benzoate

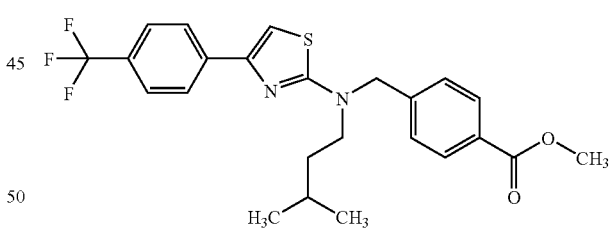

To a solution of N-(3-methylbutyl)-4-[4-(trifluoromethyl)phenyl]-1,3-thiazole-2-amine (1.20 g, 3.82 mmol) in N,N-dimethylformamide (20 mL) was added sodium hydride (60% in oil, 229 mg, 5.73 mmol) and the mixture was stirred for 30 min. Methyl 4-(bromomethyl)benzoate (1.05 g, 4.58 mmol) was added and the mixture was stirred at 60° C. for 1.5 hr. Water was added to the reaction mixture, and the mixture was extracted with ethyl acetate. The extract was washed with saturated brine, and concentrated under reduced pressure. The residue was purified by silica gel column chromatography (hexane/ethyl acetate=97/3-hexane/ethyl acetate=60/40) to give the title compound (1.34 g, yield 76%) as a yellow oil.

MS m/z 463 (MH$^+$).

Reference Example 178

{4-[((3-methylbutyl){4-[4-(trifluoromethyl)phenyl]-1,3-thiazol-2-yl}amino)methyl]phenyl}methanol

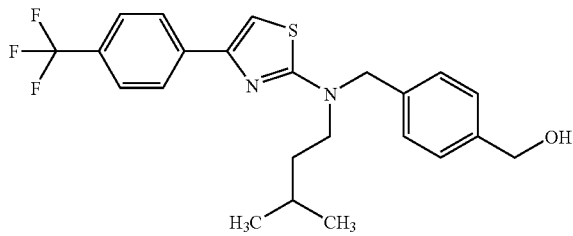

To a solution of methyl 4-[((3-methylbutyl){4-[4-(trifluoromethyl)phenyl]-1,3-thiazol-2-yl}amino)methyl]benzoate (1.34 g, 2.90 mmol) in tetrahydrofuran (10 mL) was added dropwise 1.0 M diisobutylaluminum hydride toluene solution (6.38 mL, 6.38 mmol) under ice-cooling. The reaction mixture was stirred at room temperature for 2 hr, sodium sulfate decahydrate was added and the mixture was further stirred at room temperature for 1 hr. The insoluble material was filtered off, and the filtrate was concentrated. The residue was purified by silica gel column chromatography (ethyl acetate/hexane=10/90-60/40) to give the title compound (950 mg, yield 75%) as a colorless oil.
MS m/z 435 (MH$^+$).

Reference Example 179 ethyl(2E)-3-[4-(dibenzylamino)-2,6-difluorophenyl]acrylate

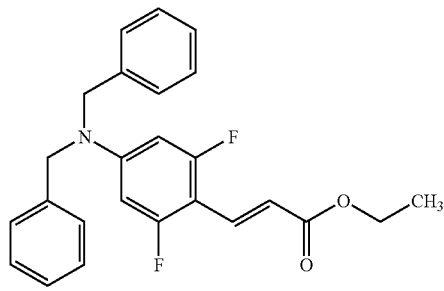

To an ice-cooled solution of ethyl diethylphosphonoacetate (7.71 g, 34.4 mmol) in tetrahydrofuran (80 mL) was added sodium hydride (60% in oil, 1.38 g, 34.4 mmol) and the mixture was stirred for 30 min. A solution of 4-(dibenzylamino)-2,6-difluorobenzaldehyde (9.28 g, 27.5 mmol) synthesized according to the method described in European Journal of Medicinal Chemistry, 1999, vol. 34, pp. 137-151 in tetrahydrofuran (100 mL) was added dropwise. The mixture was stirred at room temperature for 1 hr, water was added, and the mixture was extracted with ethyl acetate. The extract was washed with saturated brine, dried over anhydrous magnesium sulfate, and concentrated under reduced pressure. The residue was purified by silica gel column chromatography (hexane/ethyl acetate=97/3-hexane/ethyl acetate=60/40) to give the title compound (9.57 g, yield 85%) as a yellow oil.
MS m/z 408 (MH$^+$).

Reference Example 180 ethyl 3-(4-amino-2,6-difluorophenyl)propanoate

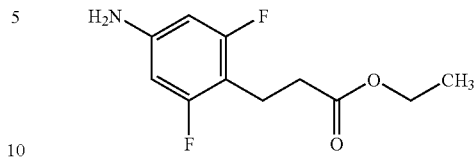

To a solution of ethyl(2E)-3-[4-(dibenzylamino)-2,6-difluorophenyl]acrylate (5.00 g, 12.3 mmol) in acetic acid (100 mL) was added 10% palladium-carbon (50% water-containing product, 0.50 g), and the mixture was stirred under a hydrogen atmosphere at 50° C. for 16 hr. The catalyst was filtered off, and the obtained filtrate was concentrated. The residue was diluted with ethyl acetate, washed with saturated aqueous sodium hydrogencarbonate and saturated brine, dried over anhydrous magnesium sulfate, and concentrated under reduced pressure. The residue was purified by silica gel column chromatography (hexane/ethyl acetate=95/5-hexane/ethyl acetate=50/50) to give the title compound (2.63 g, yield 93%) as a yellow oil.
MS m/z 230 (MH$^+$).

Reference Example 181 ethyl 3-(2,6-difluoro-4-{[(2-nitrophenyl)sulfonyl]amino}phenyl)propanoate

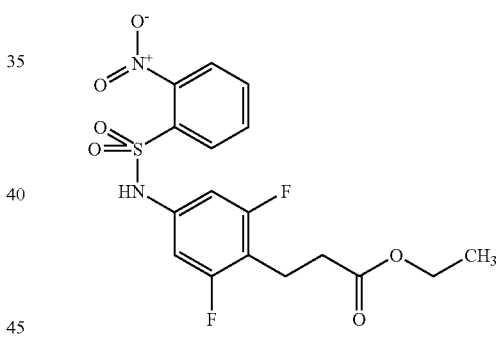

In the same manner as in Reference Example 34, the title compound was obtained as a yellow oil from ethyl 3-(4-amino-2,6-difluorophenyl)propanoate. yield 88%.
$^1$H NMR (CDCl$_3$) δ: 1.18-1.30 (3H, m), 2.53 (2H, t, J=7.7 Hz), 2.90 (2H, t, J=7.7 Hz), 4.06-4.17 (2H, m), 6.73-6.85 (2H, m), 7.63-7.70 (1H, m), 7.71-7.78 (1H, m), 7.89 (1H, dd, J=7.8, 1.4 Hz), 7.96 (1H, dd, J=7.7, 1.5 Hz).

Reference Example 182

4-(2,6-dimethylphenoxy)indan-1-one

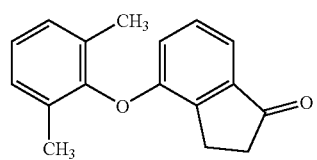

A mixture of 2-bromo-1,3-dimethylbenzene (15.0 g, 81.1 mmol), 4-hydroxyindan-1-one (10.0 g, 67.5 mmol), copper (II) oxide (9.13 g, 114 mmol), potassium carbonate (18.7 g, 135 mmol), pyridine (200 mL) and o-xylene (100 mL) was stirred under a nitrogen atmosphere at 130° C. for 18 hr. After cooling the reaction mixture, a mixed solvent of toluene and methanol was added. The insoluble material was filtered off, and the filtrate was concentrated. Water was added to the residue, and the mixture was extracted with ethyl acetate. The organic layer was washed with 1 M hydrochloric acid, water and saturated brine, dried over anhydrous magnesium sulfate, and concentrated under reduced pressure. Chloroform was added to the residue, the insoluble material was filtered off and the filtrate was purified by silica gel column chromatography (hexane/ethyl acetate=90/10-hexane/ethyl acetate=0/100) to give the title compound (0.373 g, yield 2%) as a yellow oil.

MS m/z 253 (MH$^+$).

Reference Example 183

4-(2,6-dimethylphenoxy)indan-1-ol

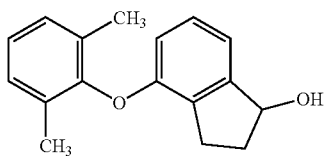

In the same manner as in Reference Example 127, the title compound was obtained as a colorless oil from 4-(2,6-dimethylphenoxy)indan-1-one. yield 70%.

$^1$H NMR (CDCl$_3$) δ: 1.80 (1H, d, J=6.6 Hz), 1.97-2.09 (1H, m), 2.10-2.14 (6H, m), 2.51-2.68 (1H, m), 2.86-3.01 (1H, m), 3.14-3.29 (1H, m), 5.29-5.35 (1H, m), 6.17-6.27 (1H, m), 6.98-7.14 (5H, m).

Reference Example 184

4-{[5-(trifluoromethyl)pyridin-2-yl]oxy}indan-1-one

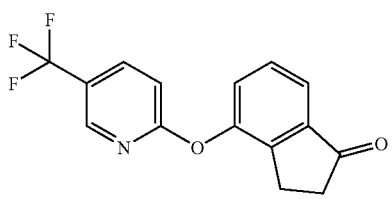

A mixture of 4-hydroxyindan-1-one (2.94 g, 19.8 mmol), 2-chloro-5-(trifluoromethyl)pyridine (3.00 g, 16.5 mmol), potassium-carbonate (6.84 g, 49.5 mmol) and N,N-dimethylformamide (40 mL) was stirred under a nitrogen atmosphere at 100° C. for 8 hr. After cooling, the reaction mixture was diluted with ethyl acetate, washed with water, dried, and concentrated under reduced pressure. The residue was purified by silica gel column chromatography (hexane/ethyl acetate=95/5-hexane/ethyl acetate=60/40) to give the title compound (2.74 g, yield 69%) as pale-yellow crystals.

$^1$H NMR (CDCl$_3$) δ: 2.65-2.74 (2H, m), 2.92-2.99 (2H, m), 7.13 (1H, d, J=8.7 Hz), 7.35-7.42 (1H, m), 7.47 (1H, t, J=7.6 Hz), 7.70 (1H, d, J=7.5 Hz), 7.96 (1H, dd, J=8.6, 2.2 Hz), 8.41 (1H, s).

Reference Example 185

4-{[5-(trifluoromethyl)pyridin-2-yl]oxy}indan-1-ol

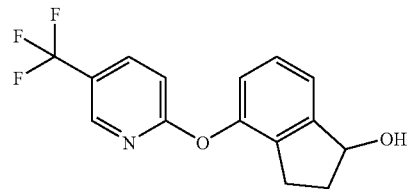

In the same manner as in Reference Example 127, the title compound was obtained as a yellow oil from 4-{[5-(trifluoromethyl)pyridin-2-yl]oxy}indan-1-one. yield 89%.

MS m/z 296 (MH$^+$).

Reference Example 186

4-(4-methoxy-2,6-dimethylphenyl)indan-1-one

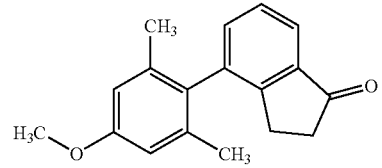

In the same manner as in Reference Example 126, the title compound was obtained as a yellow powder from 1-oxo-2,3-dihydro-1H-inden-4-yl trifluoromethanesulfonate and (2,6-dimethyl-4-methoxyphenyl)boronic acid. yield 85%.

MS m/z 237 (MH$^+$).

Reference Example 187

4-(4-methoxy-2,6-dimethylphenyl)indan-1-ol

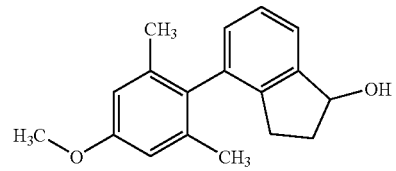

In the same manner as in Reference Example 127, the title compound was obtained as a yellow powder from 4-(4-methoxy-2,6-dimethylphenyl)indan-1-one. yield 31%.

¹H NMR (CDCl₃) δ: 1.77-1.89 (1H, m), 1.92 (3H, s), 1.96 (3H, s), 2.34-2.51 (2H, m), 2.54-2.70 (1H, m), 3.82 (3H, s), 5.27-5.37 (1H, m), 6.66 (2H, s), 7.00 (1H, d, J=7.4 Hz), 7.27-7.47 (2H, m).

Reference Example 188 methyl 3-bromo-4-hydroxybenzoate

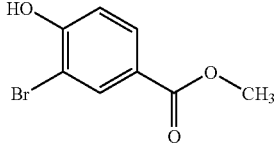

A solution of 3-bromo-4-hydroxybenzoic acid (50.4 g, 232 mmol) and concentrated sulfuric acid (17 mL) in methanol (330 mL) was heated under reflux for 24 hr. The reaction mixture was neutralized with aqueous sodium hydroxide solution, methanol was evaporated under reduced pressure, and the mixture was extracted with ethyl acetate. The extract was washed with aqueous sodium bicarbonate solution and saturated brine, dried over anhydrous sodium sulfate, and concentrated under reduced pressure. The obtained crystals were washed with diethyl ether/hexane to give the title compound (45.5 g, yield 85%) as pale-pink crystals.

MS m/z 231 (MH⁺).

Reference Example 189 methyl 3-bromo-4-isopropoxybenzoate

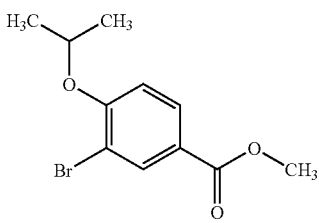

To a solution of methyl 3-bromo-4-hydroxybenzoate (15.0 g, 64.9 mmol), 2-bromopropane (7.68 mL, 77.9 mmol) and potassium iodide (1.0 g, 6.49 mmol) in N,N-dimethylformamide (200 mL) was added potassium carbonate (13.5 g, 97.4 mmol), and the mixture was stirred at 80° C. for 2 hr. The reaction mixture was concentrated under reduced pressure, brine was added to the obtained residue, and the mixture was extracted with ethyl acetate. The extract was dried over anhydrous sodium sulfate, and concentrated under reduced pressure. The residue was purified by silica gel chromatography (hexane-hexane/ethyl acetate=9/1) to give the title compound (14.6 g, yield 83%) as a colorless oil.

¹H NMR (CDCl₃) δ: 1.41 (6H, d, J=6.0 Hz), 3.89 (3H, s), 4.59-4.75 (1H, m), 6.90 (1H, d, J=8.8 Hz), 7.94 (1H, dd, J=8.8, 2.1 Hz), 8.23 (1H, d, J=2.1 Hz).

Reference Example 190

(4-bromo-3,5-dimethylphenoxy)(tert-butyl)dimethylsilane

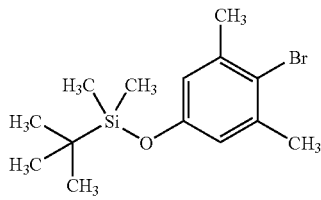

To a solution of 4-bromo-3,5-dimethylphenol (25.4 g, 126.2 mmol) and imidazole (9.5 g, 138.9 mmol) in N,N-dimethylformamide (300 mL) was added tert-butyldimethylchlorosilane (20.9 g, 138.9 mmol) under stirring at 0° C., and the mixture was stirred at room temperature for 5 hr. The reaction mixture was diluted with ethyl acetate, washed with water and saturated brine, dried over anhydrous sodium sulfate, and concentrated under reduced pressure. The residue was purified by silica gel column chromatography (hexane-hexane/ethyl acetate=10/1) to give the title compound (38.7 g, yield 97%) as a colorless oil.

¹H NMR (CDCl₃) δ: 0.18 (6H, s), 0.97 (9H, s), 2.34 (6H, s), 6.57 (2H, s).

Reference Example 191

(4-{[tert-butyl(dimethyl)silyl]oxy}-2,6-dimethylphenyl)boronic acid

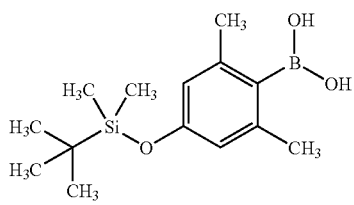

To a solution (250 mL) of (4-bromo-3,5-dimethylphenoxy)(tert-butyl)dimethylsilane (39.2 g, 124 mmol) in tetrahydrofuran was added n-butyllithium hexane solution (1.6 M, 90.0 mL, 144 mmol) under stirring at −78° C. The reaction mixture was stirred at the same temperature for 2 hr, and triisopropyl borate (40.0 mL, 173 mmol) was added. The mixture was allowed to warm to room temperature and stirred for 3 hr. To the reaction mixture was added 2 M hydrochloric acid (180 mL), and the mixture was stirred for 6 hr. The reaction mixture was partitioned between ethyl acetate and water. The organic layer was dried over magnesium sulfate, and concentrated under reduced pressure. The residue was purified by silica gel chromatography (hexane/ethyl acetate=10/1-hexane/ethyl acetate=1/4) to give the title compound (18.6 g, yield 53%) as pale-yellow prism crystals.

¹H NMR (CDCl₃) δ: 0.19 (6H, s), 0.98 (9H, s), 2.32 (6H, s), 4.58 (2H, s), 6.47 (2H, s).

Reference Example 192 methyl 4'-{[tert-butyl(dimethyl)silyl]oxy}-6-isopropoxy-2',6'-dimethylbiphenyl-3-carboxylate

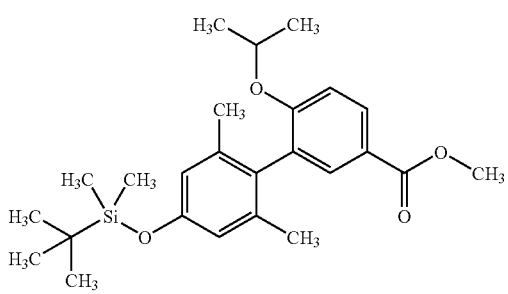

(4-{[tert-Butyl(dimethyl)silyl]oxy}-2,6-dimethylphenyl) boronic acid (500 mg, 1.83 mmol) and methyl 3-bromo-4-isopropoxybenzoate (667 mg, 2.38 mmol) were dissolved in a mixture of 2 M aqueous sodium carbonate solution (2.38 mL) and toluene (20 mL), the air was substituted with argon gas, and 2-dicyclohexylphosphino-2'-(N,N-dimethylamino)biphenyl (118 mg, 0.29 mmol) and tris(dibenzylideneacetone)dipalladium(0) (67.0 mg, 0.07 mmol) were added. The reaction mixture was heated under reflux under an argon atmosphere for one day. After cooling the reaction mixture, brine was added, and the mixture was extracted with ethyl acetate. The extract was dried over anhydrous sodium sulfate, and concentrated under reduced pressure. The residue was purified by silica gel chromatography (hexane-hexane/ethyl acetate=10/1) to give the title compound (642 mg, yield 82%) as a yellow oil.

$^1$H NMR (CDCl$_3$) δ: 0.19-0.26 (6H, m), 1.00 (9H, s), 1.17 (6H, d, J=6.0 Hz), 1.92 (6H, s), 3.87 (3H, s), 4.42-4.57 (1H, m), 6.57 (2H, s), 6.95 (1H, d, J=8.7 Hz), 7.74 (1H, d, J=2.3 Hz), 7.99 (1H, dd, J=8.7, 2.3 Hz).

Reference Example 193

(4'-{[tert-butyl(dimethyl)silyl]oxy}-6-isopropoxy-2',6'-dimethylbiphenyl-3-yl)methanol

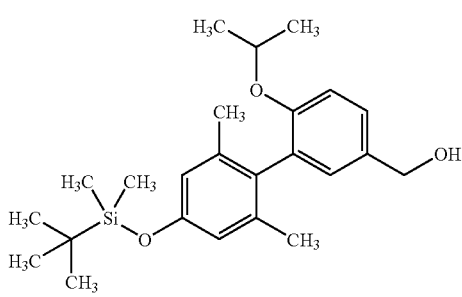

In the same manner as in Reference Example 62, the title compound was obtained as a colorless oil from methyl 4'-{[tert-butyl(dimethyl)silyl]oxy}-6-isopropoxy-2',6'-dimethylbiphenyl-3-carboxylate. yield 85%.

$^1$H NMR (CDCl$_3$) δ: 0.22 (6H, s), 1.00 (9H, s), 1.10 (6H, d, J=6.2 Hz), 1.94-1.98 (6H, m), 4.16-4.31 (1H, m), 4.64 (2H, d, J=3.6 Hz), 6.57 (2H, s), 6.94 (1H, d, J=8.5 Hz), 7.04 (1H, d, J=2.1 Hz), 7.24-7.31 (1H, m).

Reference Example 194

5-(benzyloxy)-2-bromo-1,3-dimethylbenzene

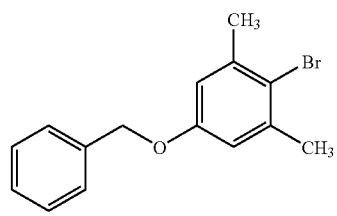

To a solution of 4-bromo-3,5-dimethylphenol (8.00 g, 39.8 mmol) and benzyl bromide (5.80 mL, 47.7 mmol) in N,N-dimethylformamide (130 mL) was added potassium carbonate (8.25 g, 59.7 mmol), and the mixture was stirred at 80° C. for 8 hr. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (hexane-hexane/ethyl acetate=97/3) to give the title compound (9.97 g, yield 86%) as a colorless oil.

$^1$H NMR (CDCl$_3$) δ: 2.38 (6H, s), 5.01 (2H, s), 6.73 (2H, s), 7.28-7.46 (5H, m).

Reference Example 195

[4-(benzyloxy)-2,6-dimethylphenyl]boronic acid

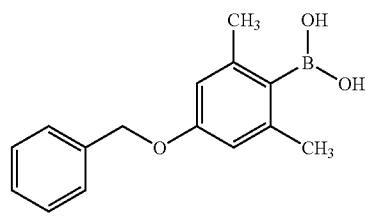

To a solution (100 mL) of 5-(benzyloxy)-2-bromo-1,3-dimethylbenzene (8.78 g, 30.2 mmol) in tetrahydrofuran was added n-butyllithium hexane solution (1.6 M, 22.6 mL, 36.2 mmol) under stirring at −78° C. The reaction mixture was stirred at the same temperature for 1.5 hr, and triisopropyl borate (20.9 mL, 90.6 mmol) was added. The mixture was allowed to warm to room temperature and stirred overnight. To the reaction mixture was added 2 M hydrochloric acid (150 mL) and the mixture was stirred for 2.5 hr. The mixture was partitioned between ethyl acetate and water. The organic layer was washed with saturated brine, dried over magnesium sulfate, and concentrated under reduced pressure. Cold hexane was added to the residue to allow crystallization. The precipitated crystals were collected by filtration, washed with cold hexane and dried to give the title compound (4.65 g, yield 60%) as colorless crystals.

$^1$H NMR (CDCl$_3$) δ: 2.36 (6H, s), 4.57 (2H, s), 5.04 (2H, s), 6.63 (2H, s), 7.28-7.47 (5H, m).

Reference Example 196 methyl 4'-(benzyloxy)-2',6,6'-trimethylbiphenyl-3-carboxylate

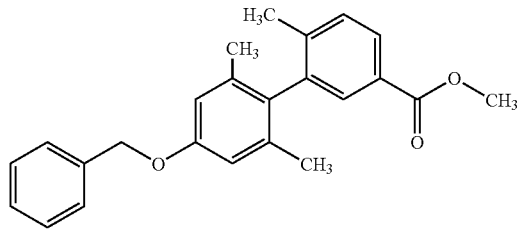

[4-(Benzyloxy)-2,6-dimethylphenyl]boronic acid (354 mg, 1.38 mmol) and methyl 3-bromo-4-methylbenzoate (229 mg, 1.00 mmol) were dissolved in a mixture of 2 M aqueous sodium carbonate solution (1.38 mL), toluene (10 mL) and 1,2-dimethoxyethane (1 mL), the air was substituted with argon gas, and dicyclohexyl(2',6'-dimethoxybiphenyl-2-yl)phosphine (32.8 mg, 0.08 mmol) and tris(dibenzylideneacetone)dipalladium(0) (18.3 mg, 0.02 mmol) were added. The reaction mixture was heated under reflux for one day. After cooling the reaction mixture, brine was added, and the mixture was extracted with ethyl acetate. The extract was dried over anhydrous sodium sulfate, and concentrated under reduced pressure. The residue was purified by silica gel chromatography (hexane-hexane/ethyl acetate=9/1) to give the title compound (255 mg, yield 71%) as a colorless oil.

MS m/z 361 (MH$^+$).

Reference Example 197 methyl 4'-hydroxy-2',6,6'-trimethylbiphenyl-3-carboxylate

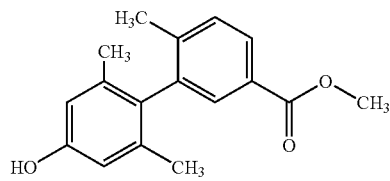

A mixture of methyl 4'-(benzyloxy)-2',6,6'-trimethylbiphenyl-3-carboxylate (255 mg, 0.71 mmol), 10% palladium-carbon (50% water-containing product, 25.5 mg) and ethanol (3 mL) was stirred overnight under a hydrogen atmosphere at room temperature. The catalyst was filtered off, and the filtrate was concentrated under reduced pressure. The residue was again subjected to the above-mentioned conditions (10% palladium-carbon (50% water-containing product, 127 mg), stirring time 2 hr) to give the title compound (199 mg, yield 100%) as a colorless oil.

MS m/z 271 (MH$^+$).

Reference Example 198 methyl 4'-[(4-hydroxytetrahydro-2H-thiopyran-4-yl)methoxy]-2',6,6'-trimethylbiphenyl-3-carboxylate

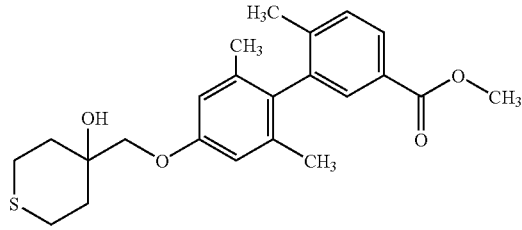

To a solution of methyl 4'-hydroxy-2',6,6'-trimethylbiphenyl-3-carboxylate (199 mg, 0.74 mmol) and 1-oxa-6-thiaspiro[2.5]octane (116 mg, 0.89 mmol) in N,N-dimethylformamide (2.5 mL) was added potassium carbonate (123 mg, 0.89 mmol) and the mixture was stirred overnight at 100° C. Brine was added to the reaction mixture, and the mixture was extracted with ethyl acetate. The extract was dried over anhydrous sodium sulfate, and concentrated under reduced pressure. The residue was purified by silica gel column chromatography (hexane/ethyl acetate=9/1-hexane/ethyl acetate=1/1) to give the title compound (191 mg, yield 64%) as a colorless oil.

MS m/z 401 (MH$^+$).

Reference Example 199

4-({[5'-(hydroxymethyl)-2,2',6-trimethylbiphenyl-4-yl]oxy}methyl)tetrahydro-2H-thiopyran-4-ol

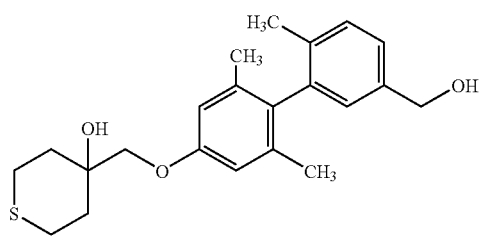

To a solution of methyl 4'-[(4-hydroxytetrahydro-2H-thiopyran-4-yl)methoxy]-2',6,6'-trimethylbiphenyl-3-carboxylate (191 mg, 0.48 mmol) in anhydrous tetrahydrofuran (3 mL) was added lithium aluminum hydride (34.2 mg, 0.72 mmol) under ice-cooling, and the mixture was stirred overnight at room temperature. Anhydrous tetrahydrofuran (10 mL) was added to the reaction solution, and the solution was ice-cooled. Sodium sulfate decahydrate (232 mg, 0.72 mmol) was added, and the mixture was stirred at room temperature for 2 hr. The precipitated insoluble material was filtered off through celite, and the filtrate was concentrated under reduced pressure to give the title compound (182 mg, yield 100%) as a colorless amorphous powder.

$^1$H NMR (CDCl$_3$) δ: 1.61 (1H, t, J=5.9 Hz), 1.76-1.99 (11H, m), 2.06-2.16 (2H, m), 2.20 (1H, s), 2.41-2.54 (2H, m), 3.04-3.17 (2H, m), 3.80 (2H, s), 4.68 (2H, d, J=5.9 Hz), 6.68 (2H, s), 6.99 (1H, s), 7.24-7.29 (2H, m).

Reference Example 200 ethyl 4-(acetylamino)-3-bromobenzoate

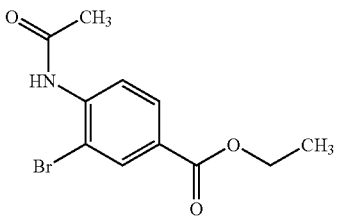

To a solution of ethyl 4-aminobenzoate (10.0 g, 59.3 mmol) and triethylamine (18.4 mL, 130 mmol) in acetic acid (30 mL) was slowly added dropwise bromine (3.04 mL, 59.3 mmol) under stirring at room temperature. The reaction mixture was stirred at room temperature for 2 hr and cold water (400 mL) was added. The precipitated solid was collected by filtration, washed with cold water and vacuum dried to give crude ethyl 4-amino-3-bromobenzoate (15.0 g) as red-pink crystals. The obtained crystals were dissolved in ethyl acetate (60 mL), and 4 M hydrogen chloride/ethyl acetate solution was added. The precipitated solid was collected by filtration, washed with a mixed solvent (1:1) of ethyl acetate-diethyl ether, and vacuum dried to give a mixture (8.99 g) of ethyl 4-aminobenzoate hydrochloride and ethyl 4-amino-3-bromobenzoate hydrochloride as colorless crystals. Successively, to a solution of the obtained mixture (1.00 g) in pyridine (12 mL) were added acetic anhydride (0.69 mL, 7.13 mmol) and 4-dimethylaminopyridine (catalytic amount) with stirring at room temperature, and the mixture was stirred overnight at the same temperature. The reaction solution was concentrated under reduced pressure, brine was added to the residue, and the mixture was extracted with ethyl acetate. The extract was dried over anhydrous sodium sulfate, and concentrated under reduced pressure. The obtained residue was purified by silica gel chromatography (hexane/ethyl acetate=9/1-hexane/ethyl acetate=1/1) to give the title compound (758 mg, yield 40%, 3 steps) as colorless crystals.

MS m/z 286 (MH$^+$).

Reference Example 201 ethyl 6-(acetylamino)-4'-(benzyloxy)-2',6'-dimethyl-biphenyl-3-carboxylate

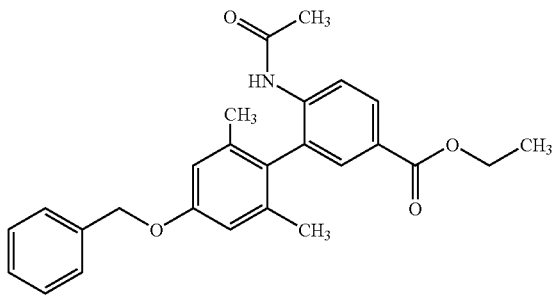

[4-(Benzyloxy)-2,6-dimethylphenyl]boronic acid (333 mg, 1.30 mmol) and ethyl 4-(acetylamino)-3-bromobenzoate (286 mg, 1.00 mmol) were dissolved in a mixture of 2 M aqueous sodium carbonate solution (1.30 mL), toluene (10 mL) and 1,2-dimethoxyethane (1 mL), the air was substituted with argon gas, and dicyclohexyl(2',6'-dimethoxybiphenyl-2-yl)phosphine (65.7 mg, 0.16 mmol) and tris(dibenzylidene-acetone)dipalladium(0) (36.6 mg, 0.04 mmol) were added. The reaction mixture was heated under reflux under an argon atmosphere for one day. After cooling the reaction mixture, brine was added, and the mixture was extracted with ethyl acetate. The extract was dried over anhydrous sodium sulfate, and concentrated under reduced pressure. The residue was purified by silica gel chromatography (hexane/ethyl acetate=9/1-hexane/ethyl acetate=13/7) to give the title compound (401 mg, yield 96%) as a colorless amorphous powder.

MS m/z 418 (MH$^+$).

Reference Example 202 ethyl 6-(acetylamino)-4'-hydroxy-2',6'-dimethylbi-phenyl-3-carboxylate

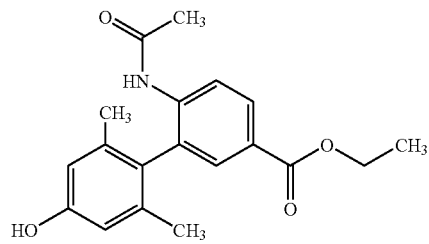

A mixture of ethyl 6-(acetylamino)-4'-(benzyloxy)-2',6'-dimethylbiphenyl-3-carboxylate (809 mg, 1.94 mmol), 10% palladium-carbon (50% water-containing product, 404 mg) and ethanol (10 mL) was stirred overnight under a hydrogen atmosphere at room temperature. The catalyst was filtered off, and the filtrate was concentrated under reduced pressure to give the title compound (544 mg, yield 86%) as colorless crystals.

MS m/z 328 (MH$^+$).

Reference Example 203 ethyl 6-(acetylamino)-4'-[(4-hydroxytetrahydro-2H-thiopyran-4-yl)methoxy]-2',6'-dimethylbiphenyl-3-carboxylate

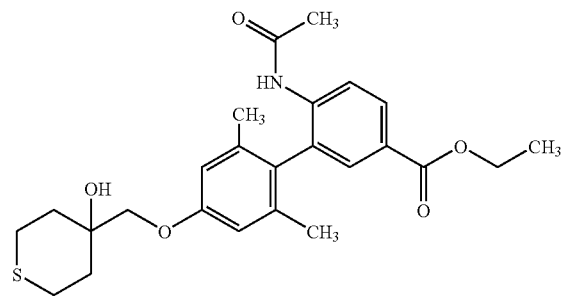

To a solution of ethyl 6-(acetylamino)-4'-hydroxy-2',6'-dimethylbiphenyl-3-carboxylate (490 mg, 1.50 mmol) and 1-oxa-6-thiaspiro[2.5]octane (224 mg, 1.72 mmol) in N,N-dimethylformamide (8 mL) was added potassium carbonate (238 mg, 1.72 mmol), and the mixture was stirred at 80° C. for 10 hr. Brine was added to the reaction mixture, and the mixture was extracted with ethyl acetate. The extract was dried over anhydrous sodium sulfate, and concentrated under reduced pressure. The residue was purified by silica gel column chromatography (hexane/ethyl acetate=9/1-hexane/ethyl acetate=2/3), and then by basic silica gel column chromatography (hexane/ethyl acetate=9/1-hexane/ethyl acetate=1/2) to give the title compound (270 mg, yield 39%) as a colorless oil.

$^1$H NMR (CDCl$_3$) δ: 1.38 (3H, t, J=7.2 Hz), 1.79-1.92 (2H, m), 1.97 (6H, s), 1.98 (3H, s), 2.07-2.19 (3H, m), 2.42-2.55 (2H, m), 3.04-3.19 (2H, m), 3.82 (2H, s), 4.35 (2H, q, J=7.1 Hz), 6.76 (2H, s), 6.86 (1H, s), 7.73 (1H, d, J=2.0 Hz), 8.06 (1H, dd, J=8.6, 2.0 Hz), 8.56 (1H, d, J=8.6 Hz).

Reference Example 204

-{5-(hydroxymethyl)-4'-[(4-hydroxytetrahydro-2H-thiopyran-4-yl)methoxy]-2',6'-dimethylbiphenyl-2-yl}acetamide

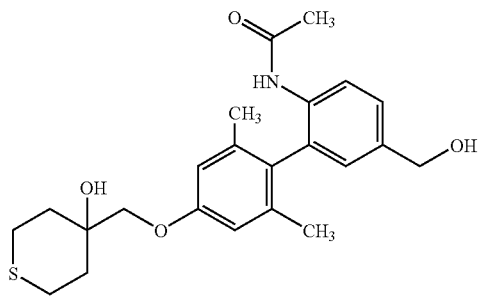

To a solution of ethyl 6-(acetylamino)-4'-[(4-hydroxytetrahydro-2H-thiopyran-4-yl)methoxy]-2',6'-dimethylbiphenyl-3-carboxylate (270 mg, 0.59 mmol) in anhydrous tetrahydrofuran (3 mL) was added lithium aluminum hydride (34.2 mg, 0.72 mmol) under ice-cooling, and the mixture was stirred at room temperature for 4 hr. The reaction solution was cooled to 0° C. again, lithium aluminum hydride (21.0 mg, 0.44 mmol) was added, and the mixture was stirred at room temperature for 2 hr. The solution was ice-cooled, sodium sulfate decahydrate (428 mg, 1.33 mmol) was added, and the mixture was stirred at room temperature for 4 days. The precipitated insoluble material was filtrated off through celite, and the filtrate was concentrated under reduced pressure. The residue was purified by silica gel chromatography (hexane/ethyl acetate=9/1-hexane/ethyl acetate=1/3) to give the title compound (148 mg, yield 60%) as colorless crystals.

MS m/z 416 (MH$^+$).

Example 1 methyl 3-(4-{[(2',6'-dimethylbiphenyl-3-yl)methyl]amino}phenyl)propanoate

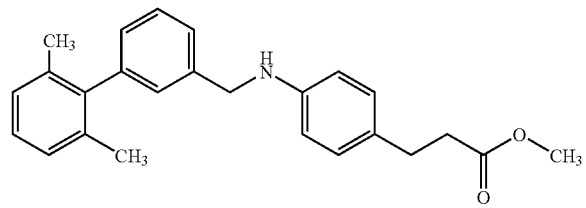

To a solution of methyl 3-(4-aminophenyl)propanoate (3.33 g, 18.6 mmol) and 2',6'-dimethylbiphenyl-3-carbaldehyde (3.91 g, 18.6 mmol) in toluene (40 mL) were added molecular sieves (0.4 nm, beads, 7.2 g), and the mixture was stirred at room temperature for 55 hr. The reaction mixture was filtered through celite, and the filtrate was concentrated under reduced pressure. The obtained residue was dissolved in tetrahydrofuran (100 mL). Sodium cyanoborohydride (2.53 g, 40.3 mmol) and acetic acid (2.31 mL, 40.3 mmol) were successively added, and the mixture was stirred under a nitrogen atmosphere at room temperature for 3 hr. Aqueous citric acid solution was added to the reaction mixture, and the mixture was extracted with ethyl acetate. The extract was washed with saturated brine, dried over anhydrous sodium sulfate, and concentrated under reduced pressure. The residue was purified by silica gel column chromatography (10%-40% ethyl acetate/hexane) to give the title compound (4.24 g, yield 61%) as a colorless oil.

MS m/z 374 (MH$^+$).

Example 2

3-(4-{[(2',6'-dimethylbiphenyl-3-yl)methyl]amino}phenyl)propanoic acid

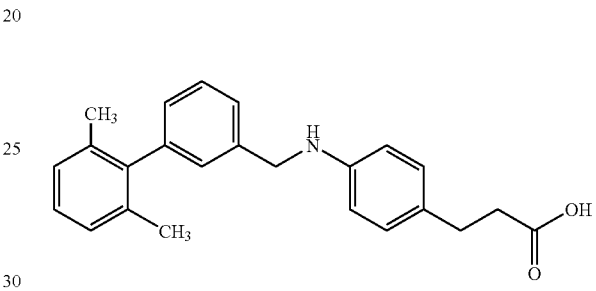

To a solution of methyl 3-(4-{[(2',6'-dimethylbiphenyl-3-yl)methyl]amino}phenyl)propanoate (0.486 g, 1.30 mmol) in a mixture of methanol (6 mL) and tetrahydrofuran (6 mL) was added 2 M aqueous sodium hydroxide solution (2 mL), and the mixture was stirred at room temperature for 21 hr. Water was added to the reaction mixture, and the mixture was weakly acidified with 10% aqueous citric acid solution and extracted with ethyl acetate. The extract was washed with saturated brine, dried over anhydrous sodium sulfate, and concentrated under reduced pressure. The residue was purified by silica gel column chromatography (30% ethyl acetate/hexane-ethyl acetate) and recrystallized from ethyl acetate-hexane to give the title compound (0.266 g, yield 57%) as colorless needle crystals.

MS m/z 360 (MH$^+$).

Example 3 methyl 3-{4-[[(2',6'-dimethylbiphenyl-3-yl)methyl](propyl)amino]phenyl}propanoate

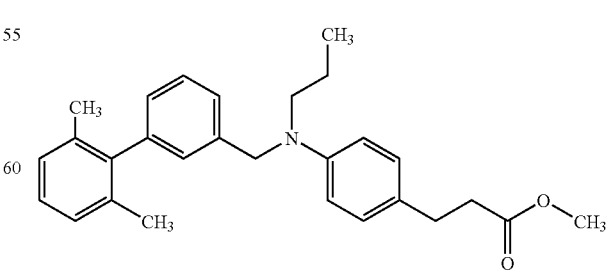

To a solution of methyl 3-(4-{[(2',6'-dimethylbiphenyl-3-yl)methyl]amino}phenyl)propanoate (0.747 g, 2.00 mmol)

and 1-iodopropane (0.585 mL, 6.00 mmol) in N,N-dimethylformamide (3 mL) was added potassium carbonate (0.415 g, 3.00 mmol), and the mixture was stirred under a nitrogen atmosphere at 90° C. for 8 hr. After cooling, the reaction mixture was concentrated under reduced pressure. Water was added to the obtained residue, and the mixture was extracted with ethyl acetate. The extract was washed with saturated brine, dried over anhydrous sodium sulfate, and concentrated under reduced pressure. The residue was purified by silica gel column chromatography (hexane-20% ethyl acetate/hexane) to give the title compound (0.740 g, yield 89%) as a yellow oil.

MS m/z 416 (MH$^+$).

Example 4

3-{4-[[(2',6'-dimethylbiphenyl-3-yl)methyl](propyl)amino]phenyl}propanoic acid

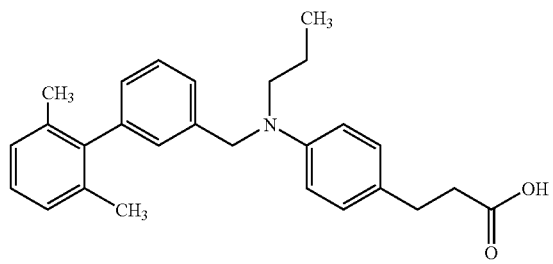

To a solution of methyl 3-{4-[[(2',6'-dimethylbiphenyl-3-yl)methyl](propyl)amino]phenyl}propanoate (0.735 g, 1.77 mmol) in a mixture of methanol (8 mL) and tetrahydrofuran (8 mL) was added 2 M aqueous sodium hydroxide solution (2.5 mL), and the mixture was stirred at room temperature for 19 hr. Water was added to the reaction mixture, and the mixture was weakly acidified with 10% aqueous citric acid solution and extracted with ethyl acetate. The extract was washed with saturated brine, dried over anhydrous sodium sulfate, and concentrated under reduced pressure. The residue was purified by silica gel column chromatography (20%-70% ethyl acetate/hexane) to give the title compound (0.710 g, yield 99%) as a yellow oil.

$^1$H NMR (CDCl$_3$) δ: 0.91 (3H, t, J=7.4 Hz), 1.59-1.72 (2H, m), 1.97 (6H, s), 2.60 (2H, t, J=7.7 Hz), 2.83 (2H, t, J=7.7 Hz), 3.32 (2H, t, J=7.4 Hz), 4.55 (2H, s), 6.60 (2H, d, J=8.7 Hz), 6.97-7.21 (8H, m), 7.36 (1H, t, J=7.4 Hz).

Example 5 methyl 3-(4-{acetyl[(2',6'-dimethylbiphenyl-3-yl)methyl]amino}phenyl)propanoate

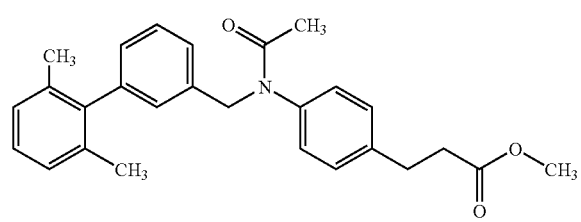

A solution of methyl 3-(4-{[(2',6'-dimethylbiphenyl-3-yl)methyl]amino}phenyl)propanoate (0.598 g, 1.60 mmol) and acetic anhydride (0.226 mL, 2.40 mmol) in pyridine (3 mL) was stirred at room temperature for 20 hr. The solvent was evaporated by concentration. The obtained residue was diluted with ethyl acetate, washed with 1 M hydrochloric acid and saturated brine, dried over anhydrous sodium sulfate, and concentrated under reduced pressure. The residue was purified by silica gel column chromatography (30%-60% ethyl acetate/hexane) to give the title compound (0.649 g, yield 98%) as a colorless oil.

MS m/z 416 (MH$^+$).

Example 6

3-(4-{acetyl[(2',6'-dimethylbiphenyl-3-yl)methyl]amino}phenyl)propanoic acid

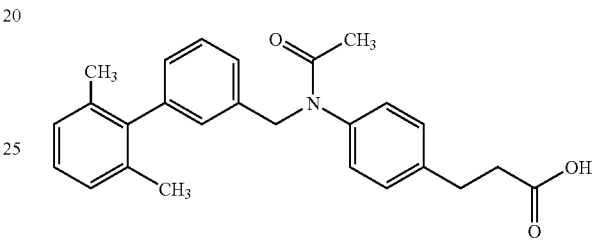

To a solution of methyl 3-(4-{acetyl[(2',6'-dimethylbiphenyl-3-yl)methyl]amino}phenyl)propanoate (0.644 g, 1.55 mmol) in a mixture of methanol (8 mL) and tetrahydrofuran (8 mL) was added 2 M aqueous sodium hydroxide solution (2.5 mL), and the mixture was stirred at room temperature for 18 hr. Water was added to the reaction mixture, and the mixture was weakly acidified with 10% aqueous citric acid solution and extracted with ethyl acetate. The extract was washed with saturated brine, dried over anhydrous magnesium sulfate, and concentrated under reduced pressure. The obtained residue was recrystallized from ethyl acetate to give the title compound (0.430 g, yield 69%) as colorless prism crystals.

MS m/z 402 (MH$^+$).

Example 7 methyl 3-{4-[[(2',6'-dimethylbiphenyl-3-yl)methyl](methyl)amino]phenyl}propanoate

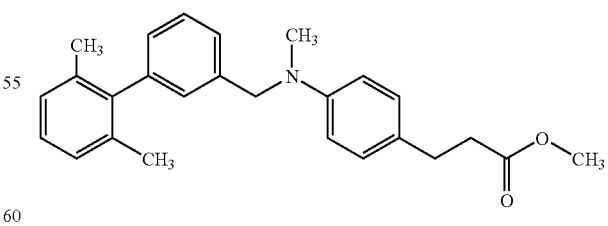

To a solution of methyl 3-(4-{[(2',6'-dimethylbiphenyl-3-yl)methyl]amino}phenyl)propanoate (0.598 g, 1.60 mmol) and iodomethane (0.498 mL, 8.00 mmol) in acetone (10 mL) was added potassium carbonate (0.332 g, 2.40 mmol), and the mixture was heated under reflux under a nitrogen atmosphere for 6 hr. After cooling, the reaction mixture was concentrated under reduced pressure. Water was added to the obtained residue, and the mixture was extracted with ethyl acetate. The extract was washed with saturated brine, dried over anhydrous sodium sulfate, and concentrated under reduced pressure. The residue was purified by silica gel column chromatography (hexane-25% ethyl acetate/hexane) to give the title compound (0.297 g, yield 48%) as a yellow oil.

MS m/z 388 (MH+).

Example 8

3-{4-[[(2',6'-dimethylbiphenyl-3-yl)methyl](methyl)amino]phenyl}propanoic acid

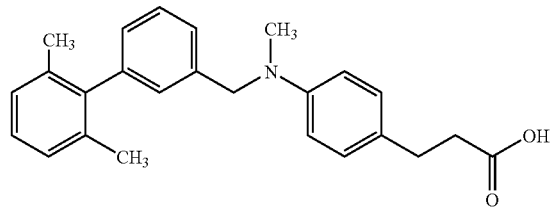

To a solution of methyl 3-{4-[[(2',6'-dimethylbiphenyl-3-yl)methyl](methyl)amino]phenyl})propanoate (0.294 g, 0.759 mmol) in a mixture of methanol (4 mL) and tetrahydrofuran (4 mL) was added 2 M aqueous sodium hydroxide solution (1.2 mL), and the mixture was stirred at room temperature for 3 days. Water was added to the reaction mixture, and the mixture was weakly acidified with 10% aqueous citric acid solution, and extracted with ethyl acetate. The extract was washed with saturated brine, dried over anhydrous sodium sulfate, and concentrated under reduced pressure. The residue was purified by preparative HPLC to give the title compound (0.198 g, yield 70%) as a brown viscous oil.

MS m/z 374 (MH+).

Example 9 methyl 3-[4-([(2-nitrophenyl)sulfonyl]{4-[(2-phenyl-1H-indol-1-yl)methyl]benzyl}amino)phenyl]propanoate

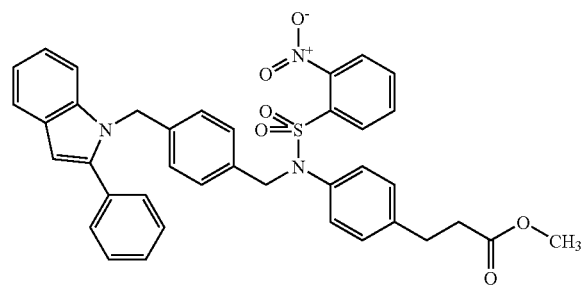

A solution of methyl 3-(4-{[(2-nitrophenyl)sulfonyl]amino}phenyl)propanoate (0.583 g, 1.60 mmol), {4-[(2-phenyl-1H-indol-1-yl)methyl]phenyl}methanol (0.470 g, 1.50 mmol) and triphenylphosphine (0.787 g, 3.00 mmol) in tetrahydrofuran (25 mL) was stirred under ice-cooling, and diethyl azodicarboxylate (40% toluene solution, 1.36 mL, 3.00 mmol) was added. The mixture was allowed to warm to room temperature and stirred for 3 hr. The reaction mixture was concentrated under reduced pressure, and the residue was purified by silica gel column chromatography (20%-60% ethyl acetate/hexane). Hexane-ethyl acetate was added to the obtained residue and the resultant insoluble material was filtered off. The filtrate was concentrated to give the title compound as a brown oil.

MS m/z 660 (MH+).

Example 10 methyl 3-[4-({4-[(2-phenyl-1H-indol-1-yl)methyl]benzyl}amino)phenyl]propanoate

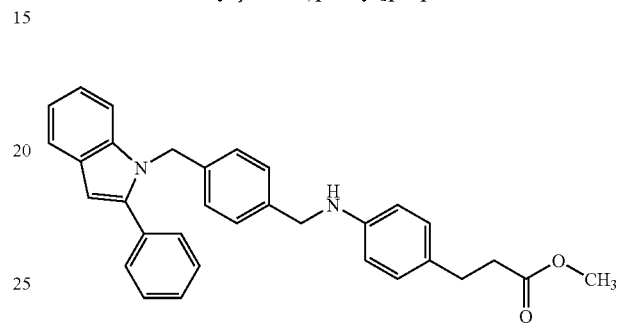

To a solution of the residue obtained in Example 9 and mercaptoacetic acid (0.209 mL, 3.00 mmol) in N,N-dimethylformamide (2 mL) was added lithium hydroxide monohydrate (0.252 g, 6.00 mmol), and the mixture was stirred at room temperature for 64 hr. Ethyl acetate was added to the residue, and the mixture was washed with saturated aqueous sodium hydrogencarbonate and saturated brine, dried over anhydrous sodium sulfate, and concentrated under reduced pressure. The residue was purified by silica gel column chromatography (hexane-25% ethyl acetate/hexane) to give the title compound (0.470 g, yield 66%, 2 steps) as a yellow oil.

MS m/z 475 (MH+).

Example 11

3-[4-({4-[(2-phenyl-1H-indol-1-yl)methyl]benzyl}amino)phenyl]propanoic acid

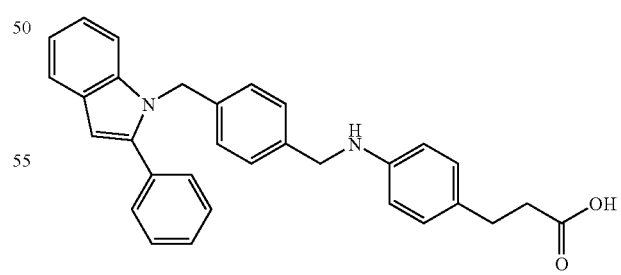

In the same manner as in Example 6, the title compound was obtained as colorless prism crystals from methyl 3-[4-({4-[(2-phenyl-1H-indol-1-yl)methyl]benzyl}amino)phenyl]propanoate. yield 82% (recrystallized from hexane-ethyl acetate).

MS m/z 461 (MH+).

Example 12

3-[4-({4-[(2-phenyl-1H-indol-1-yl)methyl]benzyl}amino)phenyl]propanoic acid hydrochloride

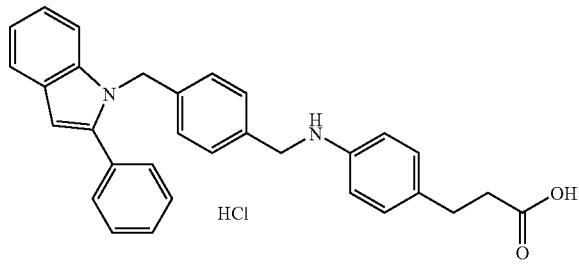

To a solution of methyl 3-[4-({4-[(2-phenyl-1H-indol-1-yl)methyl]benzyl}amino)phenyl]propanoate (0.441 g, 0.929 mmol) in a mixture of methanol (5 mL) and tetrahydrofuran (5 mL) was added 2 M aqueous sodium hydroxide solution (1.5 mL), and the mixture was stirred at room temperature for 24 hr. Water was added to the reaction mixture, and the mixture was weakly acidified with 10% aqueous citric acid solution and extracted with ethyl acetate. The extract was washed with saturated brine, dried over anhydrous sodium sulfate, and concentrated under reduced pressure. The residue was purified by silica gel column chromatography (30%-80% ethyl acetate/hexane), and the obtained residue was dissolved in ethyl acetate (2.25 mL) and treated with 4 N hydrogen chloride/ethyl acetate solution (0.75 mL) to give the title compound as colorless crystals (0.384 g, yield 83%).

$^1$H NMR (DMSO-$d_6$) δ: 2.42-2.50 (2H, m), 2.73 (2H, t, J=7.5 Hz), 4.29 (2H, s), 5.45 (2H, s), 6.65 (1H, s), 6.84-7.18 (8H, m), 7.27-7.54 (9H, m), 7.58-7.63 (1H, m).

Example 13 methyl 3-[4-([(2-nitrophenyl)sulfonyl]{4-[(2-phenyl-1H-indol-3-yl)methyl]benzyl}amino)phenyl]propanoate

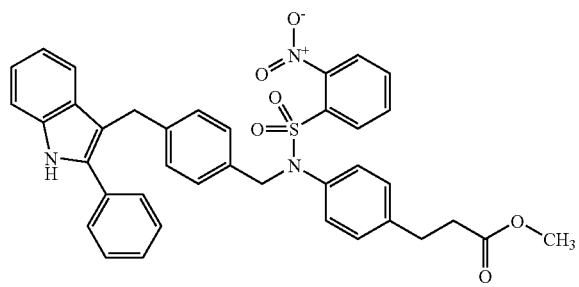

Under ice-cooling, sodium hydride (60% in oil, 0.436 g, 10.9 mmol) was added to a solution of 2-phenylindole (2.11 g, 10.9 mmol) in N,N-dimethylformamide (5 mL) by small portions, and the mixture was stirred under a nitrogen atmosphere at the same temperature for 1 hr. To the reaction mixture was added dropwise a solution of methyl 3-(4-{[4-(chloromethyl)benzyl][(2-nitrophenyl)sulfonyl]amino}phenyl)propanoate (3.65 g, 7.26 mmol) in N,N-dimethylformamide (5 mL), and the mixture was allowed to warm to room temperature and stirred for 3 hr. Water and 10% aqueous citric acid solution were added to the reaction mixture, and the mixture was extracted with ethyl acetate. The extract was washed with saturated brine, dried over anhydrous magnesium sulfate, and concentrated under reduced pressure. The obtained residue was purified by silica gel column chromatography (20%-80% ethyl acetate/hexane) to give a mixture (1.53 g, yield 32%) of the title compound and methyl 3-[4-([(2-nitrophenyl)sulfonyl]{4-[(2-phenyl-1H-indol-1-yl)methyl]benzyl}amino)phenyl]propanoate as a brown oil.

MS m/z 660 (MH$^+$).

Example 14 methyl 3-[4-({4-[(2-phenyl-1H-indol-3-yl)methyl]benzyl}amino)phenyl]propanoate

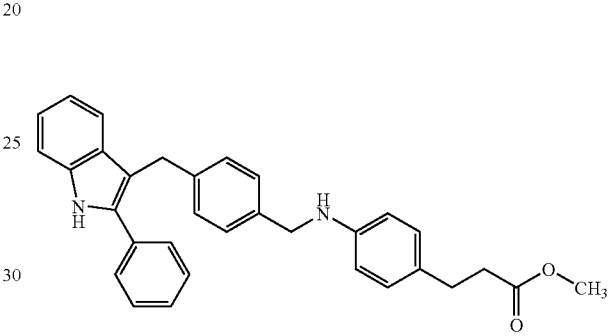

In the same manner as in Example 10, the title compound was obtained as a brown oil from a mixture of methyl 3-[4-([(2-nitrophenyl)sulfonyl]{4-[(2-phenyl-1H-indol-3-yl)methyl]benzyl}amino)phenyl]propanoate and methyl 3-[4-([(2-nitrophenyl)sulfonyl]{4-[(2-phenyl-1H-indol-1-yl)methyl]benzyl}amino)phenyl]propanoate. yield 15%.

MS m/z 475 (MH$^+$).

Example 15

3-[4-({4-[(2-phenyl-1H-indol-3-yl)methyl]benzyl}amino)phenyl]propanoic acid hydrochloride

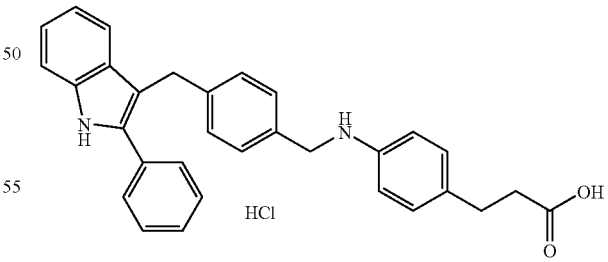

In the same manner as in Example 12, the title compound was obtained as pale-yellow crystals from methyl 3-[4-({4-[(2-phenyl-1H-indol-3-yl)methyl]benzyl}amino)phenyl]propanoate. yield 80%.

$^1$H NMR (DMSO-$d_6$) δ: 2.43-2.50 (2H, m), 2.74 (2H, t, J=7.6 Hz), 4.22 (2H, s), 4.32 (2H, s), 6.91-7.19 (8H, m), 7.28-7.35 (3H, m, J=7.9, 4.7 Hz), 7.35-7.42 (2H, m), 7.43-7.51 (2H, m), 7.56-7.62 (2H, m), 11.33 (1H, s).

Example 16 methyl 3-{4-[[(2-nitrophenyl)sulfonyl](4-{[(2-phenylethyl)(4-phenyl-1,3-thiazol-2-yl)amino]methyl}benzyl)amino]phenyl}propanoate

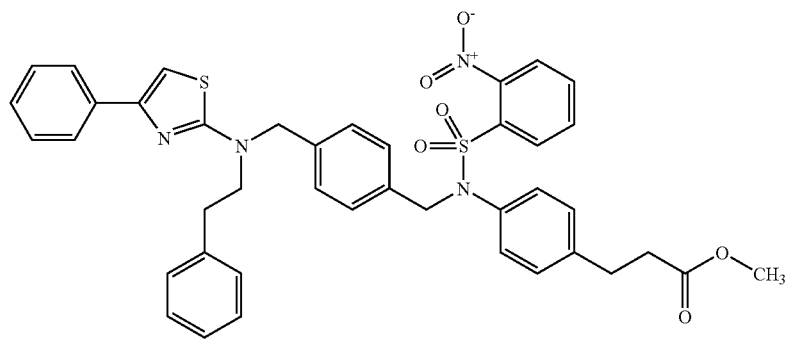

In the same manner as in Example 9, the title compound was obtained as an orange oil from methyl 3-(4-{[(2-nitrophenyl)sulfonyl]amino}phenyl)propanoate and (4-{[(2-phenylethyl)(4-phenyl-1,3-thiazol-2-yl)amino]methyl}phenyl)methanol.
MS m/z 747 (MH$^+$).

Example 17 methyl 3-{4-[(4-{[(2-phenylethyl)(4-phenyl-1,3-thiazol-2-yl)amino]methyl}benzyl)amino]phenyl}propanoate

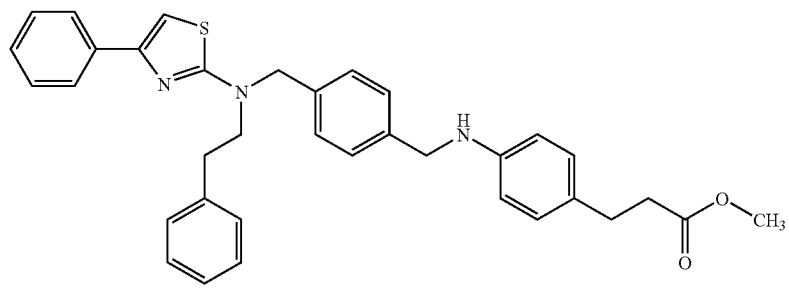

In the same manner as in Example 10, the title compound was obtained as a pale-yellow oil from methyl 3-{4-[[(2-nitrophenyl)sulfonyl](4-{[(2-phenylethyl)(4-phenyl-1,3-thiazol-2-yl)amino]methyl}benzyl)amino]phenyl}propanoate. yield 72% (2 steps).
MS m/z 562 (MH$^+$).

Example 18

3-{4-[(4-{[(2-phenylethyl)(4-phenyl-1,3-thiazol-2-yl)amino]methyl}benzyl)amino]phenyl}propanoic acid

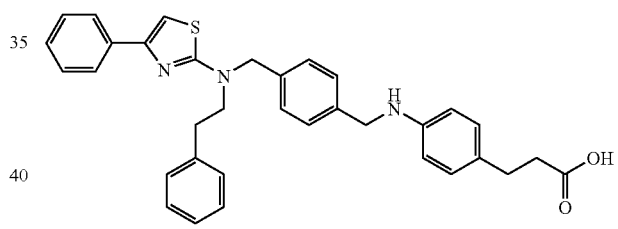

In the same manner as in Example 6, the title compound was obtained as colorless crystals from methyl 3-{4-[(4-{[(2-phenylethyl)(4-phenyl-1,3-thiazol-2-yl)amino]methyl}benzyl)amino]phenyl}propanoate. yield 90% (recrystallized from hexane-ethyl acetate).
MS m/z 548 (MH$^+$).

Example 19 methyl 3-{4-[[(2-nitrophenyl)sulfonyl](4-{[(4-phenyl-1,3-thiazol-2-yl)(propyl)amino]methyl}benzyl)amino]phenyl}propanoate

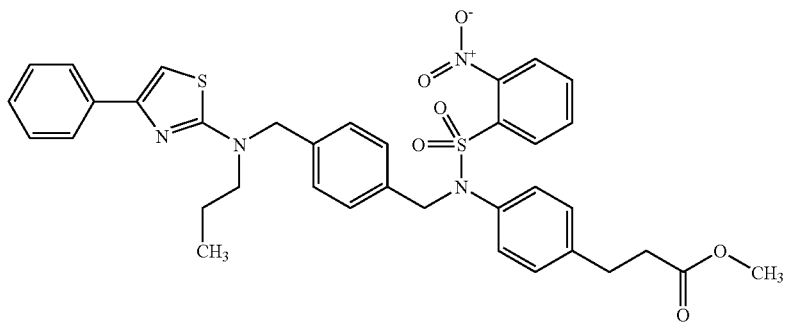

In the same manner as in Example 9, the title compound was obtained as an orange oil from methyl 3-(4-{[(2-nitrophenyl)sulfonyl]amino}phenyl)propanoate and (4-{[(4-phenyl-1,3-thiazol-2-yl)(propyl)amino]methyl}phenyl)methanol.
MS m/z 685 (MH$^+$).

Example 20 methyl 3-{4-[(4-{[(4-phenyl-1,3-thiazol-2-yl)(propyl)amino]methyl}benzyl)amino]phenyl}propanoate

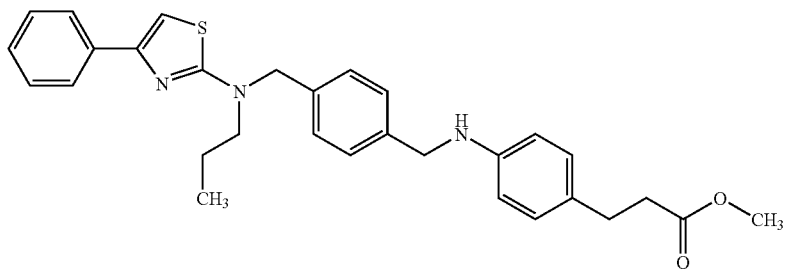

In the same manner as in Example 10, the title compound was obtained as a yellow oil from methyl 3-{4-[[(2-nitrophenyl)sulfonyl](4-{[(4-phenyl-1,3-thiazol-2-yl)(propyl)amino]methyl}benzyl)amino]phenyl}propanoate. yield 64% (2 steps).
MS m/z 500 (MH$^+$).

Example 21

3-{4-[(4-{[(4-phenyl-1,3-thiazol-2-yl)(propyl)amino]methyl}benzyl)amino]phenyl}propanoic acid

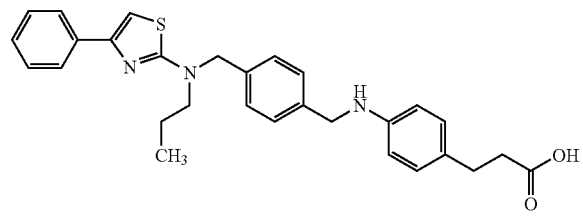

In the same manner as in Example 4, the title compound was obtained as a pale-yellow viscous oil from methyl 3-{4-[(4-{[(4-phenyl-1,3-thiazol-2-yl)(propyl)amino]methyl}benzyl)amino]phenyl}propanoate. quant.
MS m/z 486 (MH$^+$).

Example 22

3-{4-[(4-{[(4-phenyl-1,3-thiazol-2-yl)(propyl)amino]methyl}benzyl)amino]phenyl}propanoic acid dihydrochloride 4 N Hydrogen chloride/ethyl acetate solution (1.25 mL) was added to a solution of 3-{4-[(4-{[(4-phenyl-1,3-thiazol-2-yl)(propyl)amino]methyl}benzyl)amino]phenyl}propanoic acid (0.496 g, 1.02 mmol) in ethyl acetate (3.75 mL), and the resulting solid was pulverized and washed with ethyl acetate-diethyl ether to give the title compound as pale-yellow crystals (0.558 g, yield 98%).

$^1$H NMR (DMSO-d$_6$) δ: 0.88 (3H, t, J=7.3 Hz), 1.58-1.72 (2H, m), 2.44-2.50 (2H, m), 2.76 (2H, t, J=7.4 Hz), 3.40-3.47 (2H, m), 4.40 (2H, s), 4.74 (2H, s), 7.04-7.46 (12H, m), 7.80-7.86 (2H, m).

Example 23 methyl 3-(4-{[3-(2-methyl-1-naphthyl)benzyl][(2-nitrophenyl)sulfonyl]amino}phenyl)propanoate

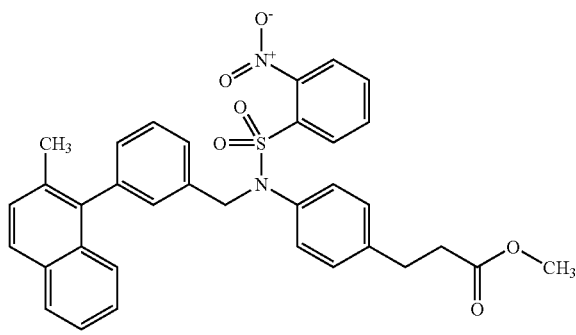

In the same manner as in Example 9, the title compound was obtained as an orange oil from methyl 3-(4-{[(2-nitrophenyl)sulfonyl]amino}phenyl)propanoate and [3-(2-methyl-1-naphthyl)phenyl]methanol.

MS m/z 595 (MH+).

Example 24 methyl 3-(4-{[3-(2-methyl-1-naphthyl)benzyl]amino}phenyl)propanoate

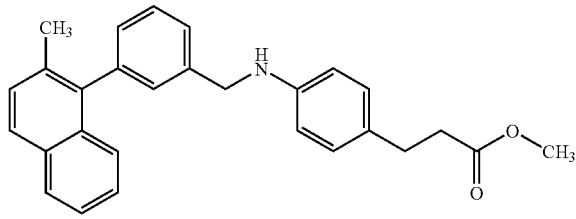

In the same manner as in Example 10, the title compound was obtained as a yellow oil from methyl 3-(4-{[3-(2-methyl-1-naphthyl)benzyl][(2-nitrophenyl)sulfonyl]amino}phenyl)propanoate. yield 87% (2 steps).

MS m/z 410 (MH+).

Example 25

3-(4-{[3-(2-methyl-1-naphthyl)benzyl]amino}phenyl)propanoic acid

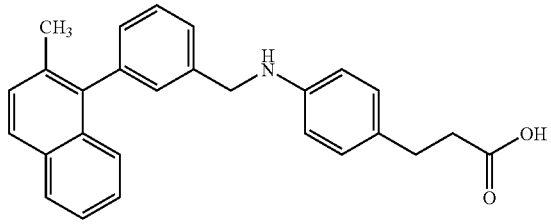

In the same manner as in Example 4, the title compound was obtained as a pale-yellow viscous oil from methyl 3-(4-{[3-(2-methyl-1-naphthyl)benzyl]amino}phenyl)propanoate. quant.

MS m/z 396 (MH+).

Example 26

3-(4-{[3-(2-methyl-1-naphthyl)benzyl]amino}phenyl)propanoic acid hydrochloride

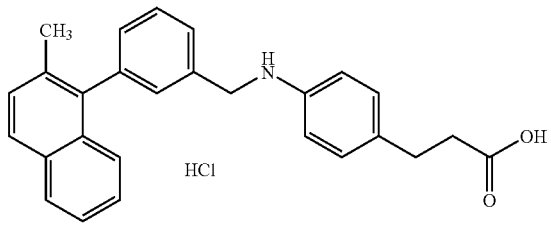

In the same manner as in Example 22, the title compound was obtained as pale-orange crystals from 3-(4-{[3-(2-methyl-1-naphthyl)benzyl]amino}phenyl)propanoic acid. yield 87%.

$^1$H NMR (DMSO-$d_6$) δ: 2.10 (3H, s), 2.46 (2H, t, J=7.7 Hz), 2.74 (2H, t, J=7.7 Hz), 4.51 (2H, s), 6.93-7.58 (12H, m), 7.86 (1H, d, J=8.5 Hz), 7.91 (1H, d, J=7.7 Hz)

Example 27 methyl 3-(4-{{[4'-(benzyloxy)-2',6'-dimethylbiphenyl-3-yl]methyl}[(2-nitrophenyl)sulfonyl]amino}phenyl)propanoate

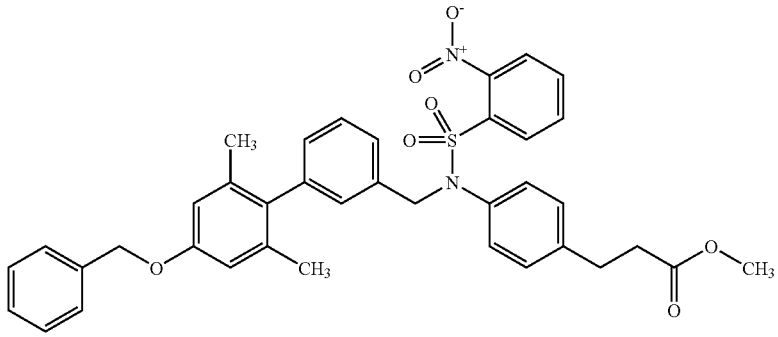

In the same manner as in Example 9, the title compound was obtained as an orange oil from methyl 3-(4-{[(2-nitrophenyl)sulfonyl]amino}phenyl)propanoate and [4'-(benzyloxy)-2',6'-dimethylbiphenyl-3-yl]methanol.
MS m/z 665 (MH$^+$).

Example 28 methyl 3-[4-({[4'-(benzyloxy)-2',6'-dimethylbiphenyl-3-yl]methyl}amino)phenyl]propanoate

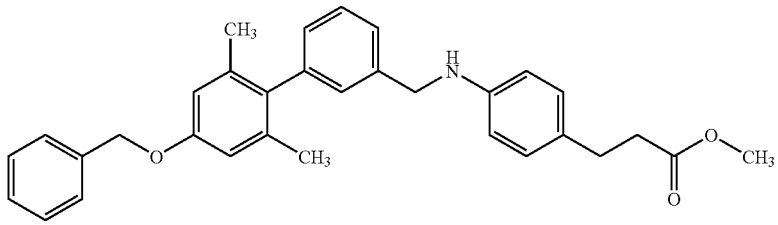

In the same manner as in Example 10, the title compound was obtained as a yellow oil from methyl 3-(4-{{[4'-(benzyloxy)-2',6'-dimethylbiphenyl-3-yl]methyl}[(2-nitrophenyl)sulfonyl]amino}phenyl)propanoate. yield 58% (2 steps).
MS m/z 480 (MH$^+$).

Example 29

3-[4-({[4'-(benzyloxy)-2',6'-dimethylbiphenyl-3-yl]methyl}amino)phenyl]propanoic acid

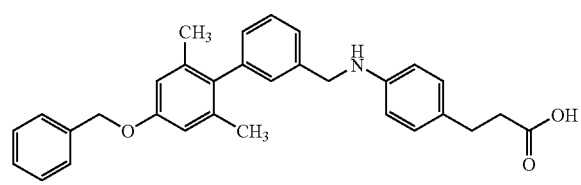

In the same manner as in Example 4, the title compound was obtained as a pale-yellow viscous oil from methyl 3-[4-({[4'-(benzyloxy)-2',6'-dimethylbiphenyl-3-yl]methyl}amino)phenyl]propanoate. quant.
MS m/z 466 (MH$^+$).

Example 30

3-[4-({[4'-(benzyloxy)-2',6'-dimethylbiphenyl-3-yl]methyl}amino)phenyl]propanoic acid hydrochloride

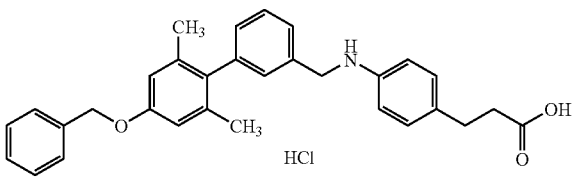

In the same manner as in Example 22, the title compound was obtained as colorless crystals from 3-[4-({[4'-(benzyloxy)-2',6'-dimethylbiphenyl-3-yl]methyl}amino)phenyl]propanoic acid. yield 84%.
$^1$H NMR (CDCl$_3$) δ: 1.80 (6H, s), 2.60-2.67 (2H, m), 2.76-2.83 (2H, m), 4.51 (2H, s), 5.03 (2H, s), 6.67 (2H, s), 6.87 (1H, s), 7.01-7.10 (3H, m), 7.11-7.17 (2H, m), 7.29-7.46 (6H, m), 7.54 (1H, d, J=7.7 Hz), 11.87 (1H, br s).

Example 31 methyl 3-(4-{{[4'-(cyclopropylmethoxy)-2',6'-dimethylbiphenyl-3-yl]methyl}[(2-nitrophenyl)sulfonyl]amino}phenyl)propanoate

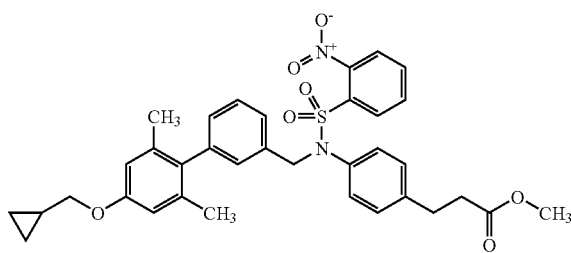

In the same manner as in Example 9, the title compound was obtained as an orange oil from methyl 3-(4-{[(2-nitrophenyl)sulfonyl]amino}phenyl)propanoate and [4'-(cyclopropylmethoxy)-2',6'-dimethylbiphenyl-3-yl]methanol.

MS m/z 629 (MH$^+$).

Example 32 methyl 3-[4-({[4'-(cyclopropylmethoxy)-2',6'-dimethylbiphenyl-3-yl]methyl}amino)phenyl]propanoate

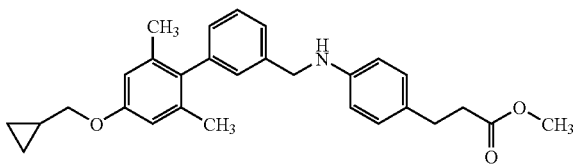

In the same manner as in Example 10, the title compound was obtained as a yellow oil from methyl 3-(4-{{[4'-(cyclopropylmethoxy)-2',6'-dimethylbiphenyl-3-yl]methyl}[(2-nitrophenyl)sulfonyl]amino}phenyl)propanoate. yield 88% (2 steps).

MS m/z 444 (MH$^+$).

Example 33

3-[4-({[4'-(cyclopropylmethoxy)-2',6'-dimethylbiphenyl-3-yl]methyl}amino)phenyl]propanoic acid hydrochloride

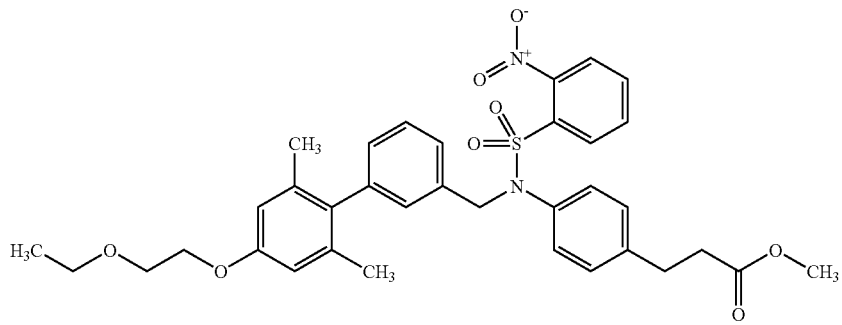

In the same manner as in Example 12, the title compound was obtained as colorless crystals from methyl 3-[4-({[4'-(cyclopropylmethoxy)-2',6'-dimethylbiphenyl-3-yl]methyl}amino)phenyl]propanoate. yield 96%.

$^1$H NMR (CDCl$_3$) δ: 0.30-0.36 (2H, m), 0.60-0.67 (2H, m), 1.19-1.32 (1H, m), 1.79 (6H, s), 2.60-2.67 (2H, m), 2.75-2.83 (2H, m), 3.77 (2H, d, J=7.0 Hz), 4.50 (2H, s), 6.59 (2H, s), 6.85 (1H, s), 7.00-7.09 (3H, m), 7.13 (2H, d, J=8.6 Hz), 7.39 (1H, t, J=7.7 Hz), 7.54 (1H, d, J=7.7 Hz), 11.86 (2H, br s).

Example 34 methyl 3-(4-{{[4'-(2-ethoxyethoxy)-2',6'-dimethylbiphenyl-3-yl]methyl}[(2-nitrophenyl)sulfonyl]amino}phenyl)propanoate A solution of methyl 3-(4-{[(2-nitrophenyl)sulfonyl]amino}phenyl)propanoate (0.802 g, 2.20 mmol), [4'-(2-ethoxyethoxy)-2',6'-dimethylbiphenyl-3-yl]methanol (0.601 g, 2.00 mmol) and triphenylphosphine (1.05 g, 4.00 mmol) in toluene (40 mL) was stirred under ice-cooling, and diethyl azodicarboxylate (40% toluene solution, 1.81 mL, 4.00 mmol) was added. The mixture was allowed to warm to room temperature and stirred for 43 hr. The reaction mixture was concentrated under reduced pressure, and the residue was purified by silica gel column chromatography (20%-60% ethyl acetate/hexane) to give the title compound as an orange oil.

MS m/z 647 (MH$^+$).

Example 35 methyl 3-[4-({[4'-(2-ethoxyethoxy)-2',6'-dimethylbiphenyl-3-yl]methyl}amino)phenyl]propanoate To a solution of methyl 3-[4-({[4'-(2-ethoxyethoxy)-2',6'-dimethylbiphenyl-3-yl]methyl}amino)phenyl]propanoate (0.755 g, 1.64 mmol) in a mixture of methanol (8 mL) and tetrahydrofuran (8 mL) was added 2 M aqueous sodium hydroxide solution (2.5 mL), and the mixture was stirred at room temperature for 18 hr. Water was added to the reaction mixture, and the mixture was weakly acidified with 10% aqueous citric acid solution, and extracted with ethyl acetate. The extract was washed with saturated brine, dried over anhydrous sodium sulfate, and concentrated under reduced pressure. The residue was purified by silica gel column chromatography (20%-80% ethyl acetate/hexane) to give the title compound (0.736 g, quant.) as a pale-yellow oil.

MS m/z 448 (MH$^+$).

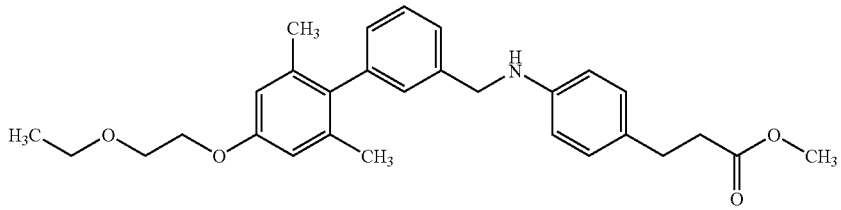

To a solution of the residue obtained in Example 34 and mercaptoacetic acid (0.278 mL, 4.00 mmol) in N,N-dimethylformamide (2 mL) was added lithium hydroxide monohydrate (0.336 g, 8.00 mmol), and the mixture was stirred at room temperature for 67 hr. Ethyl acetate was added to the residue, and the mixture was washed with saturated aqueous sodium hydrogencarbonate and saturated brine, dried over anhydrous sodium sulfate, and concentrated under reduced pressure. The residue was purified by silica gel column chromatography (10%-40% ethyl acetate/hexane) to give the title compound (0.760 g, yield 82%, 2 steps) as a yellow oil.

MS m/z 462 (MH$^+$).

Example 36

3-[4-({[4'-(2-ethoxyethoxy)-2',6'-dimethylbiphenyl-3-yl]methyl}amino)phenyl]propanoic acid

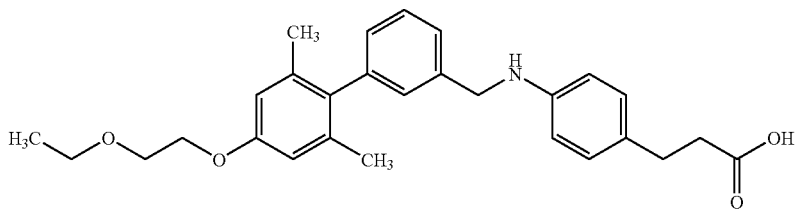

Example 37

3-[4-({[4'-(2-ethoxyethoxy)-2',6'-dimethylbiphenyl-3-yl]methyl}amino)phenyl]propanoic acid hydrochloride

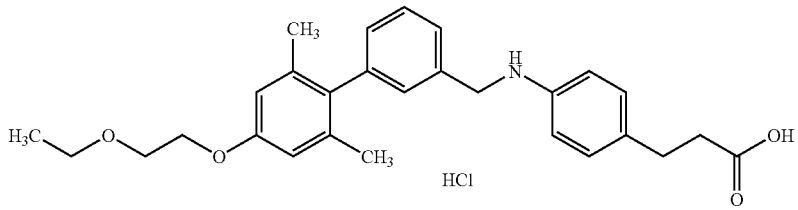

To a solution of 3-[4-({[4'-(2-ethoxyethoxy)-2',6'-dimethylbiphenyl-3-yl]methyl}amino)phenyl]propanoic acid (0.736 g, 1.64 mmol) in ethyl acetate (3.75 mL) was added 4 N hydrogen chloride/ethyl acetate solution (1.25 mL), and the resulting solid was pulverized and washed with ethyl acetate-diethyl ether to give the title compound as colorless crystals (0.762 g, yield 96%).

$^1$H NMR (CDCl$_3$) δ: 1.24 (3H, t, J=7.1 Hz), 1.79 (6H, s), 2.59-2.67 (2H, m), 2.75-2.83 (2H, m), 3.60 (2H, q, J=7.0 Hz), 3.78 (2H, t, J=4.9 Hz), 4.10 (2H, t, J=4.9 Hz), 4.50 (2H, s), 6.61 (2H, s), 6.84 (1H, s), 7.01-7.09 (3H, m), 7.14 (2H, d, J=8.4 Hz), 7.39 (1H, t, J=7.6 Hz), 7.54 (1H, d, J=7.6 Hz), 11.85 (2H, br s).

Example 38 ethyl 3-[4-({[4'-(2-ethoxyethoxy)-2',6'-dimethylbiphenyl-3-yl]methyl}amino)-2-fluorophenyl]propanoate To a solution of ethyl 3-(4-amino-2-fluorophenyl)propanoate (1.48 g, 7.00 mmol) and 4'-(2-ethoxyethoxy)-2',6'-dimethylbiphenyl-3-carbaldehyde (2.09 g, 7.00 mmol) in toluene (15 mL) were added molecular sieves (0.4 nm, beads, 3.5 g), and the mixture was stirred at room temperature for 30 hr. The reaction mixture was filtered through celite, and the filtrate was concentrated under reduced pressure. The obtained residue was dissolved in ethanol (20 mL), 10% palladium-carbon (50% water-containing product, 0.5 g) was added, and the mixture was stirred under a hydrogen atmosphere (balloon pressure) at room temperature for 12 hr. The catalyst was filtered off, and the obtained filtrate was concentrated under reduced pressure. The residue was purified by silica gel column chromatography (5%-30% ethyl acetate/hexane) to give the title compound (2.88 g, yield 83%) as a colorless oil.

MS m/z 494 (MH$^+$).

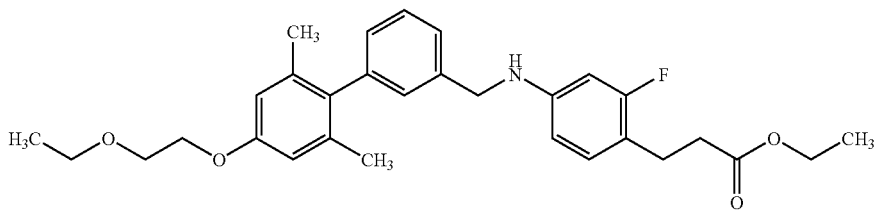

Example 39

3-[4-({[4'-(2-ethoxyethoxy)-2',6'-dimethylbiphenyl-3-yl]methyl}amino)-2-fluorophenyl]propanoic acid

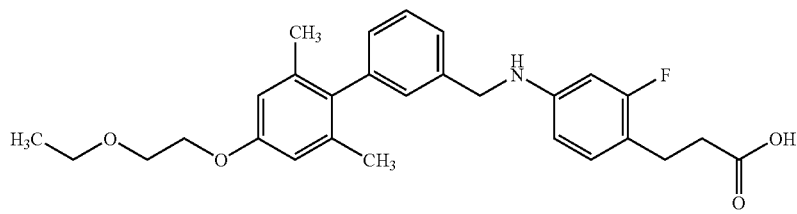

To a solution of ethyl 3-[4-({[4'-(2-ethoxyethoxy)-2',6'-dimethylbiphenyl-3-yl]methyl}amino)-2-fluorophenyl]propanoate (2.88 g, 5.83 mmol) in a mixture of ethanol (90 mL) and tetrahydrofuran (90 mL) was added 2 M aqueous sodium hydroxide solution (30 mL), and the mixture was stirred at room temperature for 16 hr. Water was added to the reaction mixture, and the mixture was weakly acidified with 10% aqueous citric acid solution, and extracted with ethyl acetate. The extract was washed with saturated brine, dried over anhydrous sodium sulfate, and concentrated under reduced pressure. The residue was purified by silica gel column chromatography (20%-80% ethyl acetate/hexane) to give the title compound (2.70 g, yield 99%) as a pale-yellow oil.

MS m/z 466 (MH$^+$).

Example 40

3-[4-({[4'-(2-ethoxyethoxy)-2',6'-dimethylbiphenyl-3-yl]methyl}amino)-2-fluorophenyl]propanoic acid hydrochloride

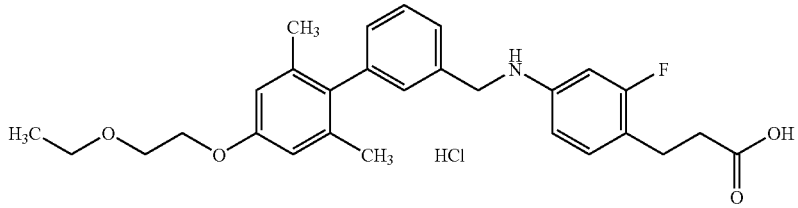

To a solution of 3-[4-({[4'-(2-ethoxyethoxy)-2',6'-dimethylbiphenyl-3-yl]methyl}amino)-2-fluorophenyl]propanoic acid (2.66 g, 5.72 mmol) in ethyl acetate (15 mL) was added 4 N hydrogen chloride/ethyl acetate solution (5 mL), and the resulting solid was pulverized and washed with ethyl acetate-diethyl ether to give the title compound as colorless crystals (2.78 g, yield 97%).

$^1$H NMR (CDCl$_3$) δ: 1.24 (3H, t, J=7.0 Hz), 1.83 (6H, s), 2.65 (2H, t, J=6.5 Hz), 2.83 (2H, t, J=6.5 Hz), 3.61 (2H, q, J=7.0 Hz), 3.78 (2H, t, J=4.8 Hz), 4.11 (2H, t, J=4.8 Hz), 4.48 (2H, s), 6.63 (2H, s), 6.82 (1H, d, J=9.8 Hz), 6.89 (1H, s), 6.94-7.01 (1H, m), 7.02-7.12 (2H, m), 7.41 (1H, t, J=7.6 Hz), 7.49-7.55 (1H, m).

Example 41 ethyl 3-[4-({3-[1-(2-ethoxyethyl)-2-phenyl-1H-indol-3-yl]benzyl}amino)-2-fluorophenyl]propanoate

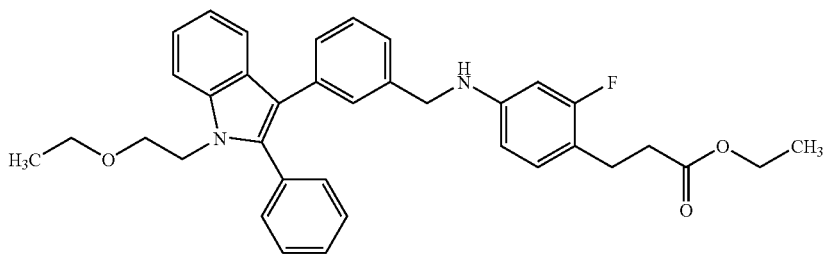

In the same manner as in Example 1, the title compound was obtained as a colorless oil from ethyl 3-(4-amino-2-fluorophenyl)propanoate and 3-[1-(2-ethoxyethyl)-2-phenyl-1H-indol-3-yl]benzaldehyde. yield 70%.

MS m/z 565 (MH$^+$).

Example 42

3-[4-({3-[1-(2-ethoxyethyl)-2-phenyl-1H-indol-3-yl]benzyl}amino)-2-fluorophenyl]propanoic acid hydrochloride

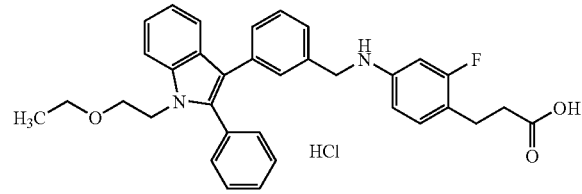

In the same manner as in Example 12, the title compound was obtained as pale-yellow prism crystals from ethyl 3-[4-({3-[1-(2-ethoxyethyl)-2-phenyl-1H-indol-3-yl]benzyl}amino)-2-fluorophenyl]propanoate. yield 93%.

$^1$H NMR (CDCl$_3$) δ: 1.09 (3H, t, J=7.0 Hz), 2.64 (2H, t, J=7.3 Hz), 2.86 (2H, t, J=7.3 Hz), 3.33 (2H, q, J=7.0 Hz), 3.61 (2H, t, J=6.4 Hz), 4.20-4.30 (4H, m), 6.43-6.64 (2H, m), 7.01 (1H, t, J=8.3 Hz), 7.10-7.40 (13H, m), 7.47 (1H, d, J=8.3 Hz), 7.57 (1H, d, J=8.1 Hz).

Example 43 methyl 3-[4-({4-[(3,5-diphenyl-1H-pyrazol-1-yl)methyl]benzyl}amino)phenyl]propanoate

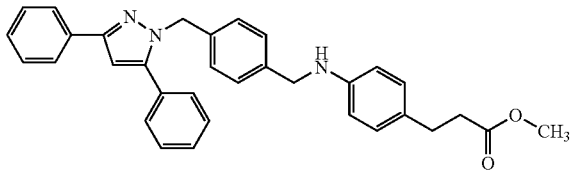

To a solution of methyl 3-(4-{[(2-nitrophenyl)sulfonyl]amino}phenyl)propanoate (180 mg, 0.5 mmol), {4-[(3,5-diphenyl-1H-pyrazol-1-yl)methyl]phenyl}methanol (178 mg, 0.5 mmol) and triphenylphosphine (262 mg, 1.0 mmol) in dichloromethane (5 mL) was added diethyl azodicarboxylate (40% toluene solution, 435 mg, 1.0 mmol) at room temperature, and the mixture was stirred at room temperature for 1 hr. The reaction mixture was purified by silica gel column chromatography (10%-80% ethyl acetate/hexane) to give a yellow oil. To a solution of the yellow oil and mercaptoacetic acid (100 mg, 1.1 mmol) in N,N-dimethylformamide (5 mL) was added lithium hydroxide monohydrate (80 mg, 1.9 mmol), and the mixture was stirred at room temperature for 14 hr. The reaction mixture was poured into 10% aqueous sodium hydrogencarbonate solution, and the mixture was extracted with ethyl acetate. The ethyl acetate layer was dried using a Presep Dehydration tube (manufactured by Wako Pure Chemical Industries, Ltd.), and concentrated. The residue was purified by silica gel column chromatography (10%-80% ethyl acetate/hexane) to give the title compound (120 mg, yield 48%, 2 steps) as a yellow oil.

$^1$H NMR (CDCl$_3$) δ: 2.56 (2H, t, J=7.8 Hz), 2.83 (2H, t, J=7.8 Hz), 3.65 (3H, s), 3.96 (1H, s), 4.26 (2H, s), 5.38 (2H, s), 6.52-6.58 (2H, m), 6.66 (1H, s), 6.99 (2H, d, J=8.5 Hz), 7.08 (2H, d, J=8.1 Hz), 7.24-7.45 (10H, m), 7.84-7.89 (2H, m).

Example 44

3-[4-({4-[(3,5-diphenyl-1H-pyrazol-1-yl)methyl]benzyl}amino)phenyl]propanoic acid

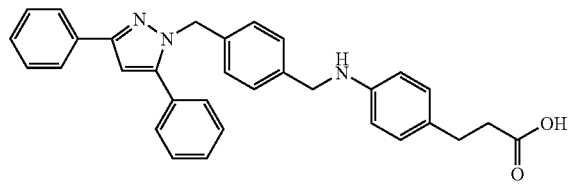

To a solution of methyl 3-[4-({4-[(3,5-diphenyl-1H-pyrazol-1-yl)methyl]benzyl}amino)phenyl]propanoate (100 mg, 0.20 mmol) in methanol (5 mL) and tetrahydrofuran (5 mL) was added 1 M aqueous sodium hydroxide solution (2 mL), and the mixture was stirred at room temperature for 2 hr. The reaction mixture was poured into water, and the mixture was weakly acidified with 10% aqueous citric acid solution and extracted with ethyl acetate. The ethyl acetate layer was dried using a Presep Dehydration tube (manufactured by Wako Pure Chemical Industries, Ltd.), and concentrated. The residue was purified by silica gel column chromatography (20%-80% ethyl acetate/hexane) to give the title compound (75 mg, yield 77%) as colorless crystals.

MS m/z 488 (MH$^+$).

Example 45 methyl 3-(4-{(4-{[5-(4-fluorophenyl)-1-methyl-1H-pyrazol-4-yl]methoxy}benzyl)[(2-nitrophenyl)sulfonyl]amino}phenyl)propanoate

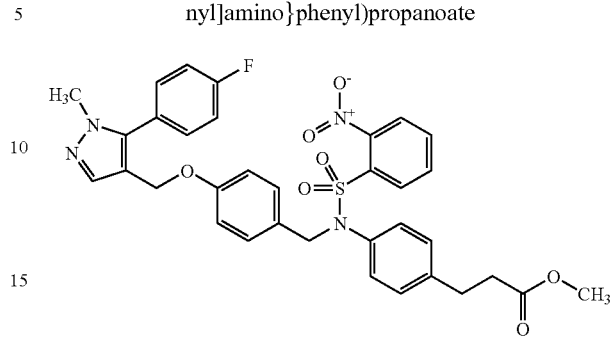

To a solution of methyl 3-(4-{[(2-nitrophenyl)sulfonyl]amino}phenyl)propanoate (182 mg, 0.5 mmol), (4-{[5-(4-fluorophenyl)-1-methyl-1H-pyrazol-4-yl]methoxy}phenyl)methanol (156 mg, 0.5 mmol) and triphenylphosphine (262 mg, 1.0 mmol) in dichloromethane (5 mL) was added diethyl azodicarboxylate (40% toluene solution, 435 mg, 1.0 mmol) at room temperature, and the mixture was stirred at room temperature for 1 hr. The reaction mixture was purified by silica gel column chromatography (10%-80% ethyl acetate/hexane) to give a yellow oil containing the title compound.

$^1$H NMR (CDCl$_3$) δ: 2.57 (2H, t, J=7.7 Hz), 2.88 (2H, t, J=7.7 Hz), 3.64 (3H, s), 3.80 (3H, s), 4.72 (2H, s), 4.84 (2H, s), 6.73-6.80 (2H, m), 6.92-6.98 (2H, m), 7.01-7.06 (2H, m), 7.08-7.18 (4H, m), 7.31-7.39 (2H, m), 7.42-7.55 (2H, m), 7.61-7.72 (3H, m).

Example 46 methyl 3-{4-[(4-{[5-(4-fluorophenyl)-1-methyl-1H-pyrazol-4-yl]methoxy}benzyl)amino]phenyl}propanoate

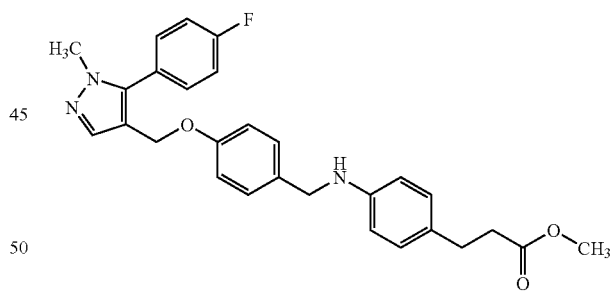

To a solution of the yellow oil obtained in Example 45 and mercaptoacetic acid (100 mg, 1.1 mmol) in N,N-dimethylformamide (5 mL) was added lithium hydroxide monohydrate (80 mg, 1.9 mmol), and the mixture was stirred at room temperature for 14 hr. The reaction mixture was poured into 10% aqueous sodium hydrogencarbonate solution, and the mixture was extracted with ethyl acetate. The ethyl acetate layer was dried using a Presep Dehydration tube (manufactured by Wako Pure Chemical Industries, Ltd.), and concentrated. The residue was purified by silica gel column chromatography (10%-80% ethyl acetate/hexane) to give the title compound (155 mg, yield 66%, 2 steps) as a yellow oil.

$^1$H NMR (CDCl$_3$) δ: 2.57 (2H, t, J=7.7 Hz), 2.84 (2H, t, J=7.7 Hz), 3.66 (3H, s), 3.81 (3H, s), 3.89 (1H, s), 4.22 (2H, s), 4.76 (2H, s), 6.57 (2H, d, J=8.7 Hz), 6.86 (2H, d, J=8.7 Hz), 7.00 (2H, d, J=8.5 Hz), 7.16 (2H, t, J=8.7 Hz), 7.22-7.30 (2H, m), 7.38 (2H, dd, J=8.9, 5.3 Hz), 7.66 (1H, s).

Example 47

3-{4-[(4-{[5-(4-fluorophenyl)-1-methyl-1H-pyrazol-4-yl]methoxy}benzyl)amino]phenyl}propanoic acid

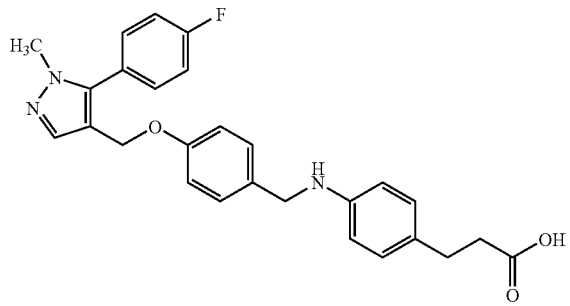

In the same manner as in Example 44, the title compound (90 mg, yield 66%) was obtained as a yellow amorphous powder from methyl 3-{4-[(4-{[5-(4-fluorophenyl)-1-methyl-1H-pyrazol-4-yl]methoxy}benzyl)amino]phenyl}propanoate.

$^1$HNMR (CDCl$_3$) δ: 2.62 (2H, t, J=7.6 Hz), 2.85 (2H, t, J=7.6 Hz), 3.80 (3H, s), 4.23 (2H, s), 4.76 (2H, s), 6.53-6.61 (2H, m), 6.83-6.90 (2H, m), 7.01 (2H, d, J=8.5 Hz), 7.12-7.21 (2H, m), 7.22-7.30 (2H, m), 7.34-7.43 (2H, m), 7.62 (1H, s).

Example 48 methyl 3-(4-{[4-({5-(2-phenylethyl)-3-[4-(trifluoromethyl)phenyl]-1H-pyrazol-1-yl}methyl)benzyl]amino}phenyl)propanoate

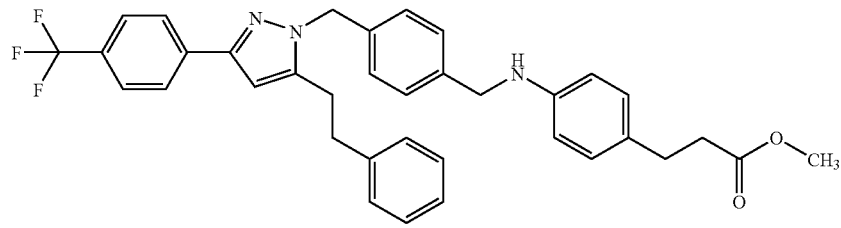

In the same manner as in Example 43, the title compound (110 mg, yield 40%, 2 steps) was obtained as a yellow oil from [4-({5-(2-phenylethyl)-3-[4-(trifluoromethyl)phenyl]-1H-pyrazol-1-yl}methyl)phenyl]methanol.

$^1$H NMR (CDCl$_3$) δ: 2.55 (2H, t, J=7.7 Hz), 2.77-2.90 (6H, m), 3.65 (3H, s), 3.96 (1H, br s), 4.27 (2H, s), 5.25 (2H, s), 6.46 (1H, s), 6.53 (2H, d, J=8.5 Hz), 6.97 (2H, d, J=8.5 Hz), 7.04-7.13 (4H, m), 7.19-7.33 (5H, m), 7.63 (2H, d, J=8.1 Hz), 7.91 (2H, d, J=8.1 Hz).

Example 49

3-(4-{[4-({5-(2-phenylethyl)-3-[4-(trifluoromethyl)phenyl]-1H-pyrazol-1-yl}methyl)benzyl]amino}phenyl)propanoic acid

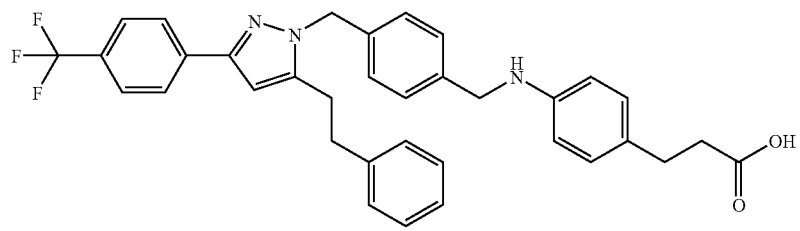

In the same manner as in Example 44, the title compound (75 mg, yield 73%) was obtained as pale-yellow crystals from methyl 3-(4-{[4-({5-(2-phenylethyl)-3-[4-(trifluoromethyl)phenyl]-1H-pyrazol-1-yl}methyl)benzyl]amino}phenyl)propanoate.

$^1$H NMR (CDCl$_3$) δ: 2.59 (2H, t, J=7.7 Hz), 2.77-2.89 (6H, m), 4.27 (2H, s), 5.25 (2H, s), 6.46 (1H, s), 6.53 (2H, d, J=8.5 Hz), 6.98 (2H, d, J=8.5 Hz), 7.03-7.13 (4H, m), 7.20-7.33 (5H, m), 7.63 (2H, d, J=8.3 Hz), 7.90 (2H, d, J=7.9 Hz).

Example 50 methyl 3-{4-[[(2-nitrophenyl)sulfonyl](4-{[(1E)-(4-phenyl-1,3-thiazol-2-yl)methylene]amino}benzyl)amino]phenyl}propanoate $^1$H NMR (CDCl$_3$) δ: 2.57 (2H, t, J=7.7 Hz), 2.88 (2H, t, J=7.7 Hz), 3.64 (3H, s), 4.95 (2H, s), 6.95-7.09 (4H, m), 7.19-7.33 (5H, m), 7.35-7.58 (5H, m), 7.63-7.71 (3H, m), 7.94 (2H, d, J=7.3 Hz).

Example 51 methyl 3-[4-([(2-nitrophenyl)sulfonyl]{4-[[(4-phenyl-1,3-thiazol-2-yl)methyl](propyl)amino]benzyl}amino)phenyl]propanoate

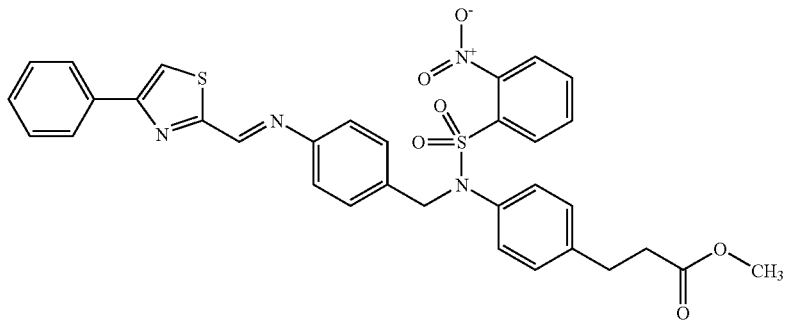

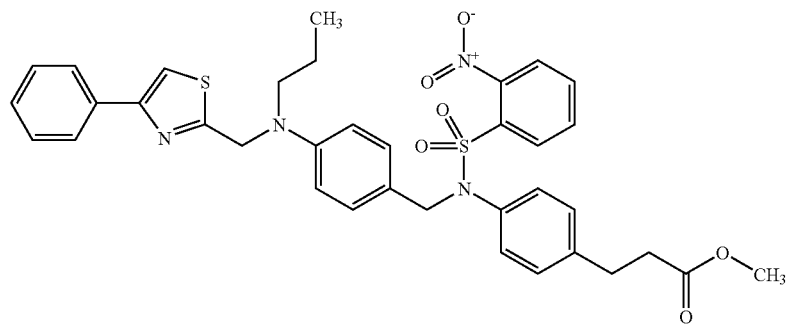

To a solution of methyl 3-(4-{[(2-nitrophenyl)sulfonyl]amino}phenyl)propanoate (364 mg, 1.0 mmol), (4-{[(1E)-(4-phenyl-1,3-thiazol-2-yl)methylene]amino}phenyl)methanol (297 mg, 1.0 mmol) and triphenylphosphine (393 mg, 1.5 mmol) in tetrahydrofuran (4 mL) was added diethyl azodicarboxylate (40% toluene solution, 660 mg, 1.5 mmol) at room temperature, and the mixture was stirred at room temperature for 1 hr. The reaction mixture was purified by silica gel column chromatography (5%-70% ethyl acetate/hexane) to give a yellow oil containing the title compound.

The yellow oil obtained in Example 50 was dissolved in 1,2-dichloroethane (20 mL), sodium triacetoxyborohydride (1.26 g, 6.0 mmol) was added at room temperature by small portions, and the mixture was stirred at room temperature for 60 hr. Propionaldehyde (200 mg, 3.0 mmol) was added to the reaction mixture at room temperature, and the mixture was stirred at room temperature for 3 hr. The reaction mixture was poured into 10% aqueous sodium hydrogencarbonate solution, and the mixture was extracted with ethyl acetate. The ethyl acetate layer was dried using a Presep Dehydration tube (manufactured by Wako Pure Chemical Industries, Ltd.), and concentrated. The residue was purified by silica gel column chromatography (5%-70% ethyl acetate/hexane) to give the title compound (549 mg, yield 80%, 2 steps) as a yellow oil.

$^1$H NMR (CDCl$_3$) δ: 0.96 (3H, t, J=7.4 Hz), 1.63-1.78 (2H, m), 2.56 (2H, t, J=7.7 Hz), 2.87 (2H, t, J=7.7 Hz), 3.34-3.45 (2H, m), 3.64 (3H, s), 4.78 (2H, s), 4.79 (2H, s), 6.63 (2H, d, J=8.9 Hz), 6.91-7.06 (6H, m), 7.29-7.35 (1H, m), 7.34-7.37 (1H, m), 7.38-7.56 (4H, m), 7.60-7.66 (2H, m), 7.85-7.90 (2H, m).

Example 52 methyl 3-[4-({4-[[(4-phenyl-1,3-thiazol-2-yl)methyl](propyl)amino]benzyl}amino)phenyl]propanoate

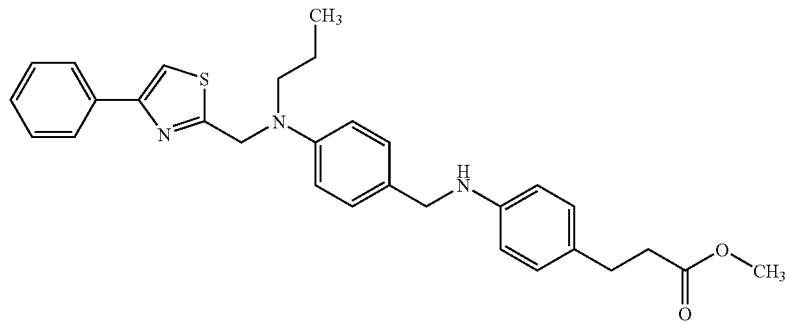

In the same manner as in Example 46, the title compound (270 mg, yield 68%) was obtained as a yellow oil from methyl 3-[4-([(2-nitrophenyl)sulfonyl]{4-[[(4-phenyl-thiazol-2-yl)methyl](propyl)amino]benzyl}amino)phenyl]propanoate.

$^1$H NMR (CDCl$_3$) δ: 0.98 (3H, t, J=7.4 Hz), 1.69-1.80 (2H, m), 2.56 (2H, t, J=7.8 Hz), 2.83 (2H, t, J=7.8 Hz), 3.40-3.48 (2H, m), 3.66 (3H, s), 3.90 (1H, br s), 4.16 (2H, s), 4.82 (2H, s), 6.75 (2H, d, J=8.7 Hz), 7.00 (2H, d, J=8.5 Hz), 7.21 (2H, d, J=8.7 Hz), 7.32-7.47 (6H, m), 7.85-7.91 (2H, m).

Example 53

3-[4-({4-[[(4-phenyl-1,3-thiazol-2-yl)methyl](propyl)amino]benzyl}amino)phenyl]propanoic acid

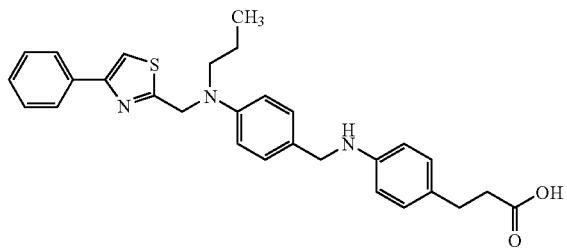

In the same manner as in Example 44, the title compound (121 mg, yield 54%) was obtained as a yellow oil from methyl 3-[4-({4-[[(4-phenyl-1,3-thiazol-2-yl)methyl](propyl)amino]benzyl}amino)phenyl]propanoate.

MS m/z 486 (MH$^+$).

Example 54 methyl 3-{6-[[(2-nitrophenyl)sulfonyl](4-{[(2-phenylethyl)(4-phenyl-1,3-thiazol-2-yl)amino]methyl}benzyl)amino]pyridin-3-yl}propanoate

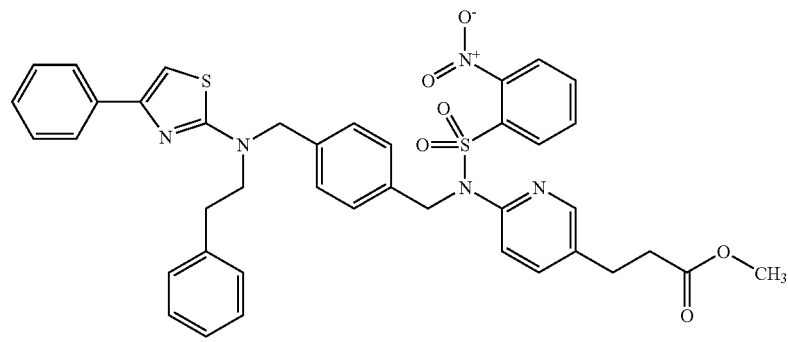

In the same manner as in Example 9, the title compound was obtained as an orange oil from methyl 3-(6-{[(2-nitrophenyl)sulfonyl]amino}pyridin-3-yl)propanoate and (4-{[(2-phenylethyl)(4-phenyl-1,3-thiazol-2-yl)amino]methyl}phenyl)methanol.

MS m/z 748 (MH$^+$).

Example 55 methyl 3-{6-[(4-{[(2-phenylethyl)(4-phenyl-1,3-thiazol-2-yl)amino]methyl}benzyl)amino]pyridin-3-yl}propanoate

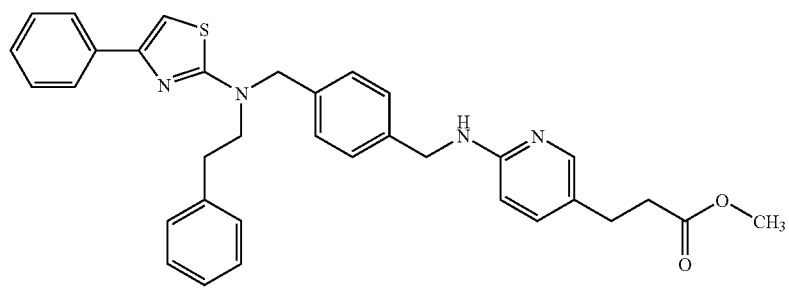

In the same manner as in Example 10, the title compound was obtained as a pale-yellow oil from methyl 3-{6-[[(2-nitrophenyl)sulfonyl](4-{[(2-phenylethyl)(4-phenyl-1,3-thiazol-2-yl)amino]methyl}benzyl)amino]pyridin-3-yl}propanoate. yield 13% (2 steps).

MS m/z 563 (M$^+$).

Example 56

3-{6-[(4-{[(2-phenylethyl)(4-phenyl-1,3-thiazol-2-yl)amino]methyl}benzyl)amino]pyridin-3-yl}propanoic acid

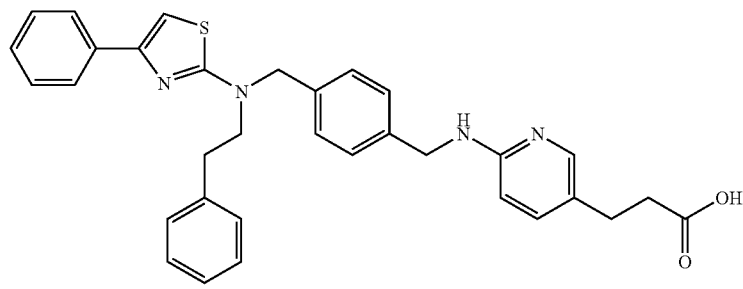

In the same manner as in Example 6, the title compound was obtained as a pale-yellow oil from methyl 3-{6-[(4-{([(2-phenylethyl)(4-phenyl-1,3-thiazol-2-yl)amino]methyl}benzyl)amino]pyridin-3-yl}propanoate. yield 82%.

MS m/z 549 (MH$^+$).

Example 57 methyl 3-(6-{[(2',6'-dimethylbiphenyl-3-yl)methyl][(2-nitrophenyl)sulfonyl]amino}pyridin-3-yl)propanoate

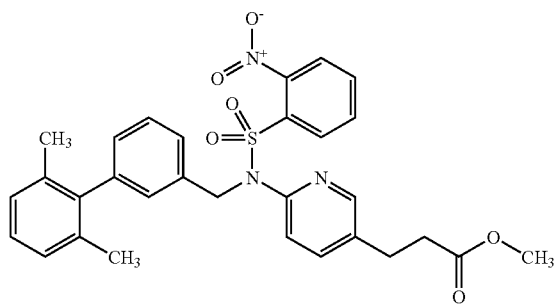

In the same manner as in Example 9, the title compound was obtained as a white powder from methyl 3-(6-{[(2-nitrophenyl)sulfonyl]amino}pyridin-3-yl)propanoate and (2',6'-dimethylbiphenyl-3-yl)methanol. yield 44%.
MS m/z 560 (MH⁺).

Example 58 methyl 3-(6-{[(2',6'-dimethylbiphenyl-3-yl)methyl]amino}pyridin-3-yl)propanoate

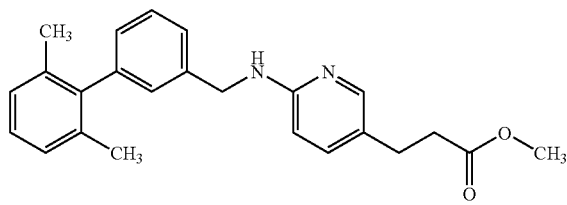

In the same manner as in Example 10, the title compound was obtained as a pale-yellow oil from methyl 3-(6-{[(2',6'-dimethylbiphenyl-3-yl)methyl][(2-nitrophenyl)sulfonyl]amino}pyridin-3-yl)propanoate. yield 15%.
MS m/z 375 (MH⁺).

Example 59

3-(6-{[(2',6'-dimethylbiphenyl-3-yl)methyl]amino}pyridin-3-yl)propanoic acid

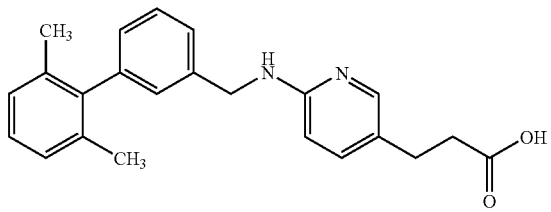

To a solution of methyl 3-(6-{[(2',6'-dimethylbiphenyl-3-yl)methyl]amino}pyridin-3-yl)propanoate (0.170 g, 0.45 mmol) in a mixture of methanol (3 mL) and tetrahydrofuran (5 mL) was added 1 M aqueous sodium hydroxide solution (1 mL), and the mixture was stirred at room temperature for 16 hr. Water was added to the reaction mixture, and the mixture was neutralized with 1 M hydrochloric acid and extracted with ethyl acetate. The extract was washed with saturated brine, dried over anhydrous magnesium sulfate, and concentrated under reduced pressure. The residue was purified by preparative HPLC to give the title compound (0.017 g, yield 10%) as a colorless oil.
MS m/z 361 (MH⁺).

Example 60 ethyl 3-[4-({[4'-(2-ethoxyethoxy)-2',6'-dimethylbiphenyl-3-yl]methyl}amino)phenyl]-2-fluoropropanoate

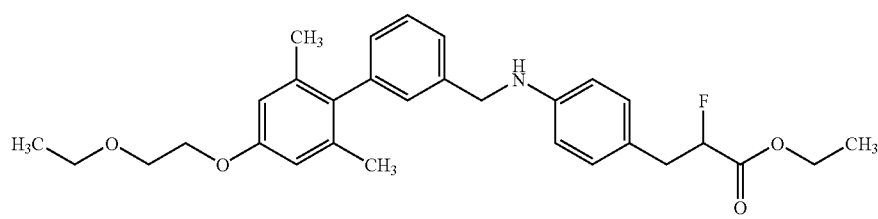

To a solution of ethyl 3-(4-aminophenyl)-2-fluoropropanoate (400 mg, 1.89 mmol) and 4'-(2-ethoxyethoxy)-2',6'-dimethylbiphenyl-3-carbaldehyde (434 mg, 1.45 mmol) in toluene (25 mL) were added molecular sieves (0.4 nm, beads, 1.6 g), and the mixture was stirred at room temperature for 16 hr. The reaction mixture was filtered through celite, and the filtrate was concentrated under reduced pressure. The obtained residue was dissolved in tetrahydrofuran (20 mL) and ethanol (20 mL), 10% palladium-carbon (50% water-containing product, 0.40 g) was added, and the mixture was stirred under a hydrogen atmosphere (balloon pressure) at room temperature for 3 hr. The catalyst was filtered off, and the filtrate was concentrated under reduced pressure. The residue was purified by silica gel column chromatography (5%-40% hexane/ethyl acetate) to give the title compound (320 mg, yield 45%) as a colorless oil.

MS m/z 494 (MH$^+$).

Example 61

3-[4-({[4'-(2-ethoxyethoxy)-2',6'-dimethylbiphenyl-3-yl]methyl}amino)phenyl]-2-Fluoropropoanoic acid

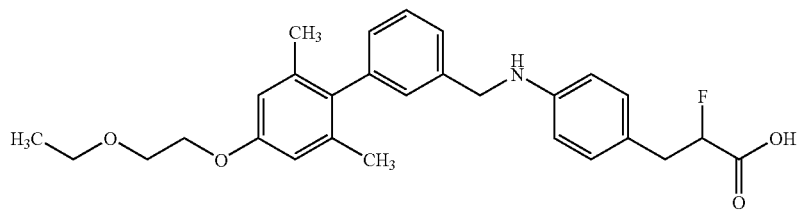

In the same manner as in Example 6, the title compound was obtained as colorless crystals from ethyl 3-[4-({[4'-(2-ethoxyethoxy)-2',6'-dimethylbiphenyl-3-yl]methyl}amino)phenyl]-2-fluoropropanoate. yield 69%.

MS m/z 466 (MH$^+$).

Example 62 ethyl 3-[4-({[4'-(2-ethoxyethoxy)-2',6'-dimethylbiphenyl-3-yl]methyl}amino)phenyl]-2,2-difluoro-3-hydroxypropanoate

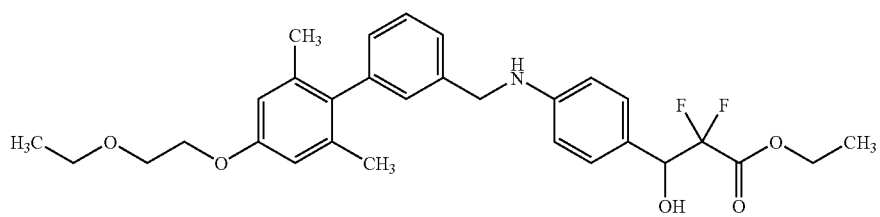

In the same manner as in Example 60, the title compound was obtained as colorless crystals from 4'-(2-ethoxyethoxy)-2',6'-dimethylbiphenyl-3-carbaldehyde and ethyl 3-(4-aminophenyl)-2,2-difluoro-3-hydroxypropanoate. yield 67%.

MS m/z 528 (MH$^+$).

Example 63

3-[4-({[4'-(2-ethoxyethoxy)-2',6'-dimethylbiphenyl-3-yl]methyl}amino)phenyl]-2,2-difluoro-3-hydroxypropanoic acid

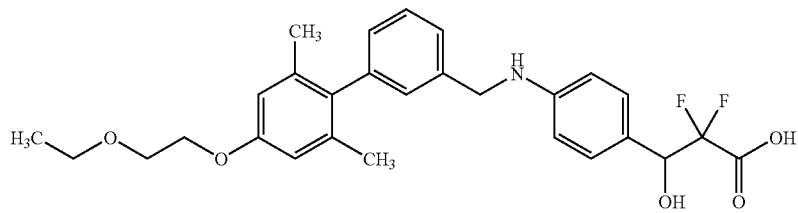

In the same manner as in Example 6, the title compound was obtained as colorless crystals from ethyl 3-[4-({[4'-(2-ethoxyethoxy)-2',6'-dimethylbiphenyl-3-yl]methyl}amino)phenyl]-2,2-difluoro-3-hydroxypropanoate. yield 51%.
MS m/z 500 (MH$^+$).

Example 64 ethyl 2-fluoro-3-{4-[(4-{[(2-phenylethyl)(4-phenyl-1,3-thiazol-2-yl)amino]methyl}benzyl)amino]phenyl}propanoate

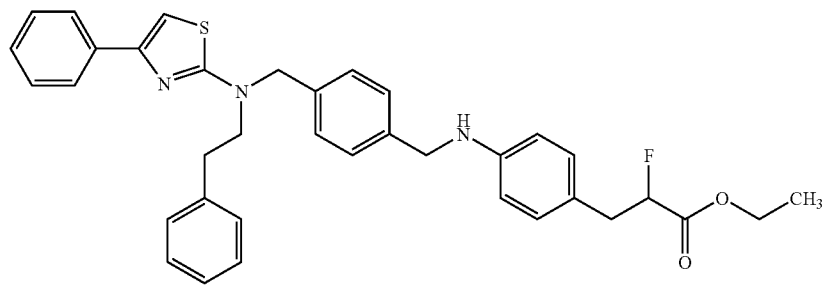

In the same manner as in Example 60, the title compound was obtained as a colorless oil from 4-{[(2-phenylethyl)(4-phenyl-1,3-thiazol-2-yl)amino]methyl}benzaldehyde and ethyl 3-(4-aminophenyl)-2-fluoropropanoate. yield 27%.
MS m/z 594 (MH$^+$).

Example 65

2-fluoro-3-{4-[(4-{[(2-phenylethyl)(4-phenyl-1,3-thiazol-2-yl)amino]methyl}benzyl)amino]phenyl}propanoic acid

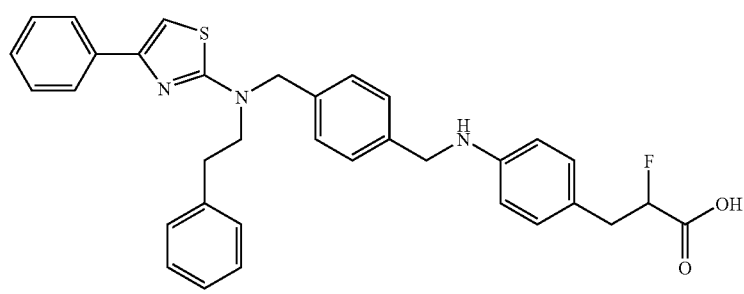

In the same manner as in Example 6, the title compound was obtained as colorless crystals from ethyl 2-fluoro-3-{4-

[(4-{[(2-phenylethyl)(4-phenyl-1,3-thiazol-2-yl)amino]methyl}benzyl)amino]phenyl}propanoate. yield 65%.
MS m/z 566 (MH+).

Example 66 ethyl [4-({[4'-(2-ethoxyethoxy)-2',6'-dimethylbiphenyl-3-yl]methyl}amino)phenoxy]acetate

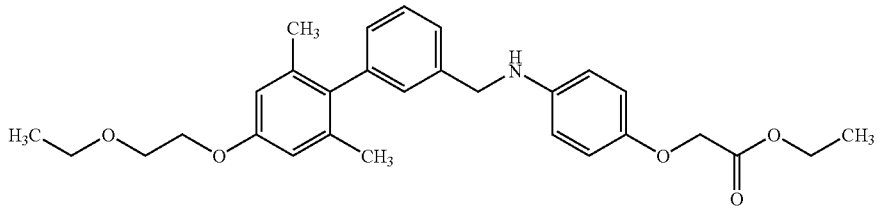

In the same manner as in Example 38, the title compound was obtained as a colorless oil from ethyl(4-aminophenoxy)acetate and 4'-(2-ethoxyethoxy)-2',6'-dimethylbiphenyl-3-carbaldehyde. yield 83%.
MS m/z 478 (MH+).

Example 67

[4-({[4'-(2-ethoxyethoxy)-2',6'-dimethylbiphenyl-3-yl]methyl}amino)phenoxy]acetic acid

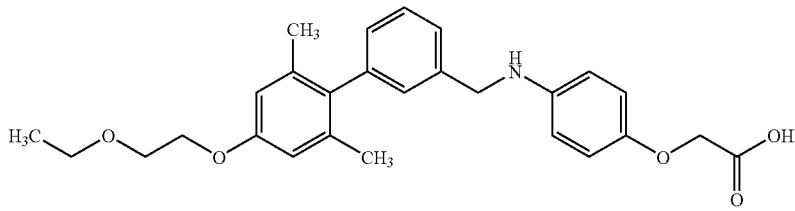

To a solution of ethyl [4-({[4'-(2-ethoxyethoxy)-2',6'-dimethylbiphenyl-3-yl]methyl}amino)phenoxy]acetate (0.37 g, 0.77 mmol) in a mixture of methanol (10 mL) and tetrahydrofuran (10 mL) was added an aqueous solution (5 mL) of potassium hydroxide (0.26 g, 3.94 mmol), and the mixture was stirred at room temperature for 18 hr. Water was added to the reaction mixture, and the mixture was weakly acidified with 10% aqueous citric acid solution and extracted with ethyl acetate. The extract was washed with saturated brine, dried over anhydrous sodium sulfate, and concentrated under reduced pressure. The obtained crystals were washed with diethyl ether-hexane to give the title compound as colorless prism crystals. yield 91%.
MS m/z 450 (MH+).

Example 68 methyl 3-(4-{{[6-(benzyloxy)-4'-(2-ethoxyethoxy)biphenyl-3-yl]methyl}[(2-nitrophenyl)sulfonyl]amino}phenyl)propanoate

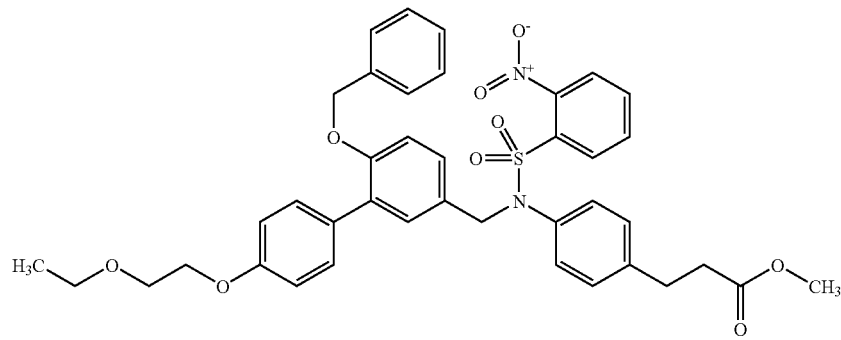

In the same manner as in Example 9, the title compound was obtained as pale-yellow needle crystals from [6-(benzyloxy)-4'-(2-ethoxyethoxy)biphenyl-3-yl]methanol and methyl 3-(4-{[(2-nitrophenyl)sulfonyl]amino}phenyl)propanoate. yield 100%.

MS (APCI–): m/z 723 (M–H).

Example 69 methyl 3-[4-({[6-(benzyloxy)-4'-(2-ethoxyethoxy)biphenyl-3-yl]methyl}amino)phenyl]propanoate

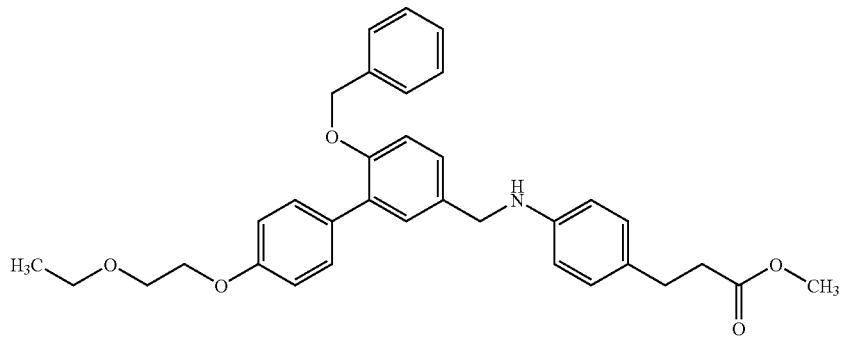

In the same manner as in Example 10, the title compound was obtained as a pale-yellow oil from methyl 3-(4-{{[6-(benzyloxy)-4'-(2-ethoxyethoxy)biphenyl-3-yl]methyl}[(2-nitrophenyl)sulfonyl]amino}phenyl)propanoate. yield 76%.

MS m/z 540 (MH$^+$).

Example 70

3-[4-({[6-(benzyloxy)-4'-(2-ethoxyethoxy)biphenyl-3-yl]methyl}amino)phenyl]propanoic acid

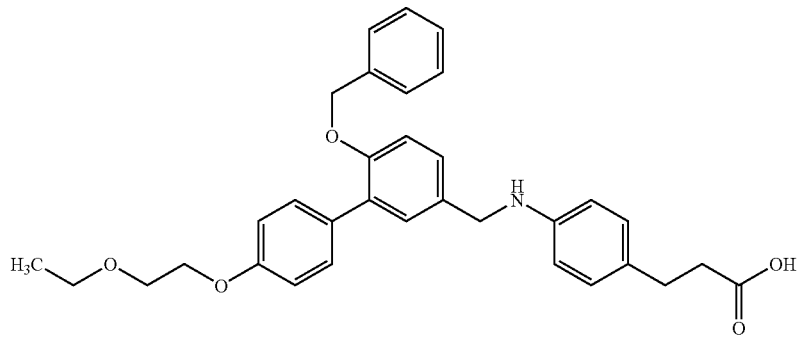

In the same manner as in Example 67, the title compound was obtained as pale-yellow needle crystals from methyl 3-[4-({[6-(benzyloxy)-4'-(2-ethoxyethoxy)biphenyl-3-yl]methyl}amino)phenyl]propanoate. yield 96%.

MS m/z 526 (MH$^+$).

Example 71 methyl 3-[4-({[4'-(2-ethoxyethoxy)-6-methoxybiphenyl-3-yl]methyl}amino)phenyl]propanoate

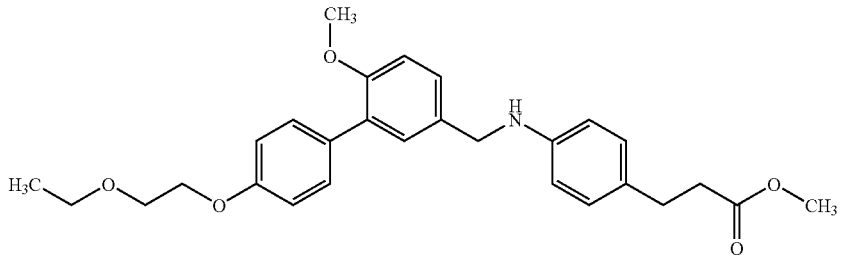

In the same manner as in Example 38, the title compound was obtained as a pale-pink oil from methyl 3-(4-aminophenyl)propanoate and 4'-(2-ethoxyethoxy)-6-methoxybiphenyl-3-carbaldehyde. yield 62%.
MS m/z 464 (MH+).

Example 72

3-[4-({[4'-(2-ethoxyethoxy)-6-methoxybiphenyl-3-yl]methyl}amino)phenyl]propanoic acid

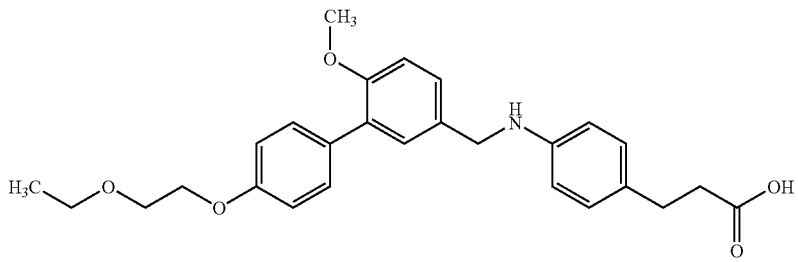

In the same manner as in Example 67, the title compound was obtained as pale-yellow needle crystals from methyl 3-[4-({[4'-(2-ethoxyethoxy)-6-methoxybiphenyl-3-yl]methyl}amino)phenyl]propanoate. yield 76%.
MS m/z 450 (MH+).

Example 73 methyl 3-(4-{{[5-isobutoxy-1-(2-methylphenyl)-1H-pyrazol-3-yl]methyl}[(2-nitrophenyl)sulfonyl]amino}phenyl)propanoate

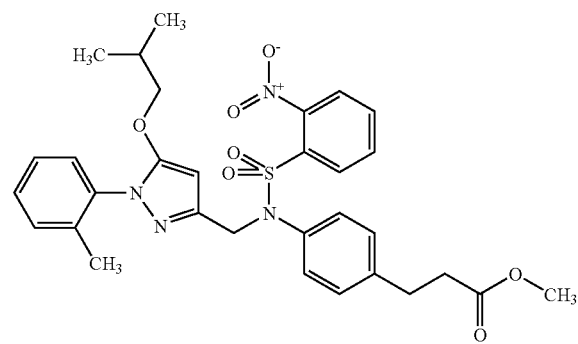

In the same manner as in Example 9, the title compound was obtained as a yellow oil from [5-isobutoxy-1-(2-methylphenyl)-1H-pyrazol-3-yl]methanol and methyl 3-(4-{[(2-nitrophenyl)sulfonyl]amino}phenyl)propanoate.
$^1$H NMR (CDCl$_3$) δ: 0.89 (6H, d, J=6.9 Hz), 1.88 (3H, s), 1.98 (1H, m), 2.56 (2H, t, J=7.8 Hz), 2.89 (2H, t, J=7.8 Hz), 3.65 (3H, s), 3.80 (2H, d, J=6.6 Hz), 4.87 (2H, s), 5.82 (1H, s), 7.00-7.32 (8H, m), 7.50 (1H, m), 7.57-7.72 (3H, s).

Example 74 methyl 3-[4-({[5-isobutoxy-1-(2-methylphenyl)-1H-pyrazol-3-yl]methyl}amino)phenyl]propanoate

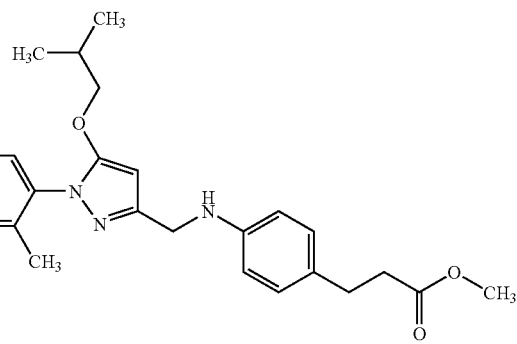

In the same manner as in Example 10, the title compound was obtained as a yellow oil from methyl 3-(4-{{[5-isobutoxy-1-(2-methylphenyl)-1H-pyrazol-3-yl]methyl}[(2-nitrophenyl)sulfonyl]amino}phenyl)propanoate.
$^1$H NMR (CDCl$_3$) δ: 0.88 (6H, d, J=6.6 Hz), 1.98 (1H, m), 2.16 (3H, s), 2.58 (2H, t, J=7.8 Hz), 2.85 (2H, t, J=7.8 Hz), 3.66 (3H, s), 3.77 (2H, d, J=6.6 Hz), 4.28 (2H, s), 5.60 (1H, s), 6.41 (1H, s), 6.66 (2H, d, J=8.4 Hz), 7.02 (2H, d, J=8.4 Hz), 7.20-7.35 (3H, m), 8.02 (1H, s).

Example 75

3-[4-({[5-isobutoxy-1-(2-methylphenyl)-1H-pyrazol-3-yl]methyl}amino)phenyl]propanoic acid

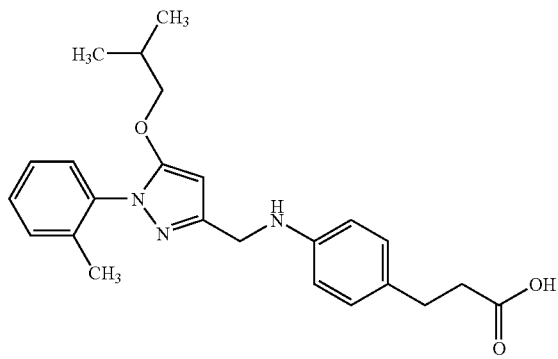

In the same manner as in Example 6, the title compound was obtained as a pale-yellow oil from methyl 3-[4-({[5-isobutoxy-1-(2-methylphenyl)-1H-pyrazol-3-yl]methyl}amino)phenyl]propanoate. (yield 77%, 3 steps).
MS (APCI-): 406 (M-H).

Example 76

3-{4-[(4-isobutoxy-3-{[(2-phenylethyl)(4-phenyl-1,3-thiazol-2-yl)amino]methyl}benzyl)amino]phenyl}propanoic acid

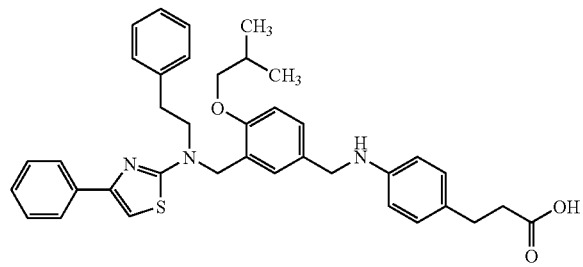

[step 1] To a mixture of methyl 3-{4-([(2-nitrophenyl)sulfonyl]amino}phenyl) propanoate (0.42 g, 1.15 mmol), (4-isobutoxy-3-{[(2-phenylethyl)(4-phenyl-1,3-thiazol-2-yl)amino]methyl}phenyl)methanol (0.54 g, 1.15 mmol), triphenylphosphine (0.60 g, 2.30 mmol) and tetrahydrofuran (20 mL) was added diethyl azodicarboxylate (40% toluene solution, 1.04 mL, 2.30 mmol) under ice-cooling, and the mixture was stirred at room temperature for 3 hr. The reaction mixture was concentrated under reduced pressure. The residue was purified by silica gel column chromatography (hexane/ethyl acetate=10/1-1/1) to give methyl 3-(4-{(4-isobutoxy-3-{[(2-phenylethyl)(4-phenyl-1,3-thiazol-2-yl)amino]methyl}benzyl)[(2-nitrophenyl)sulfonyl]amino}phenyl) propanoate as a yellow oil.

[step 2] To a solution (10 mL) of this product and mercaptoacetic acid (0.24 mL, 3.45 mmol) in N,N-dimethylformamide was added lithium hydroxide monohydrate (0.29 g, 6.90 mmol), and the mixture was stirred at room temperature for 2 hr. The reaction mixture was diluted with ethyl acetate, washed with saturated aqueous sodium hydrogencarbonate and saturated brine, dried, and concentrated under reduced pressure. The residue was purified by silica gel column chromatography (hexane/ethyl acetate=10/1-2/1) to give methyl 3-{4-[(4-isobutoxy-3-{[(2-phenylethyl)(4-phenyl-1,3-thiazol-2-yl)amino]methyl}benzyl)amino]phenyl}propanoate as a pale-yellow oil.

[step 3] To a mixture of this product, methanol (5 mL) and tetrahydrofuran (10 mL) was added 1 N aqueous sodium hydroxide solution (2.3 mL), and the mixture was stirred at room temperature for 2 hr. The reaction mixture was diluted with ethyl acetate, neutralized with 1 N hydrochloric acid, washed with saturated brine, dried, and concentrated under reduced pressure. The residue was purified by silica gel column chromatography (hexane/ethyl acetate=10/1-1/1) to give the title compound (0.38 g, yield 54%) as colorless crystals.
MS (APCI-): 618 (M-H).

Example 77

3-{4-[(4-{[(2-phenylethyl)(4-phenyl-1,3-thiazol-2-yl)amino]methyl}benzyl)amino]phenyl}propanoic acid dihydrochloride

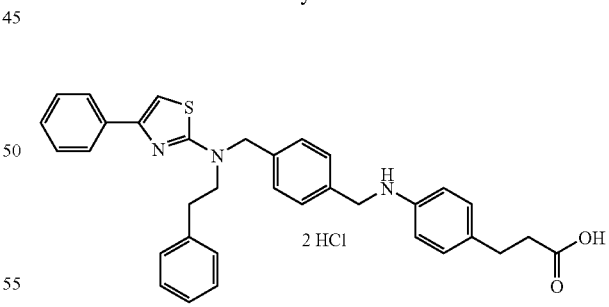

In the same manner as in Example 12, the title compound was obtained as a colorless powder from methyl 3-(4-[(4-{[(2-phenylethyl)(4-phenyl-1,3-thiazol-2-yl)amino]methyl}benzyl)amino]phenyl)propanoate. yield 81%.
$^1$H NMR (DMSO-$d_6$) δ: 2.39 (2H, t, J=7.5 Hz), 2.65 (2H, t, J=7.5 Hz), 2.94 (2H, t, J=7.7 Hz), 3.68 (2H, t, J=7.7 Hz), 4.24 (2H, s), 4.68 (2H, s), 6.33-6.45 (2H, m), 6.95 (1H, t, J=8.8 Hz), 7.15-7.44 (13H, m), 7.83-7.90 (2H, m).

Example 78 methyl(6-{{[4'-(2-ethoxyethoxy)-2',6'-dimethylbiphenyl-3-yl]methyl}[(2-nitrophenyl)sulfonyl]amino}-1-benzofuran-3-yl)acetate

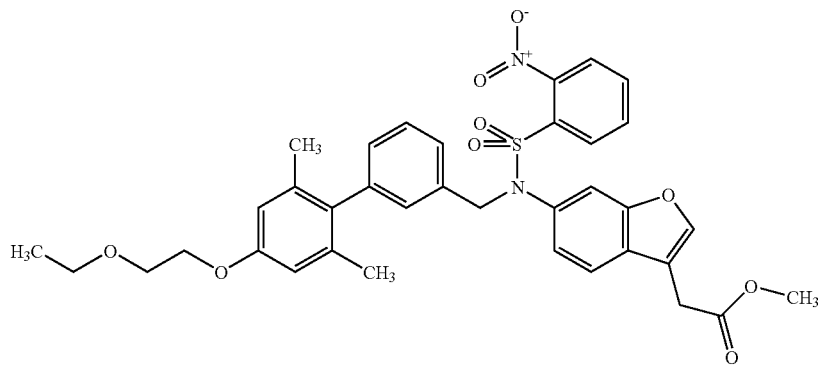

In the same manner as in Example 9, the title compound was obtained as a brown oil from methyl(6-{[(2-nitrophenyl)sulfonyl]amino}-1-benzofuran-3-yl)acetate and [4'-(2-ethoxyethoxy)-2',6'-dimethylbiphenyl-3-yl]methanol.
MS m/z 673 (MH$^+$).

Example 79 methyl [6-({[4'-(2-ethoxyethoxy)-2',6'-dimethylbiphenyl-3-yl]methyl}amino)-1-benzofuran-3-yl]acetate

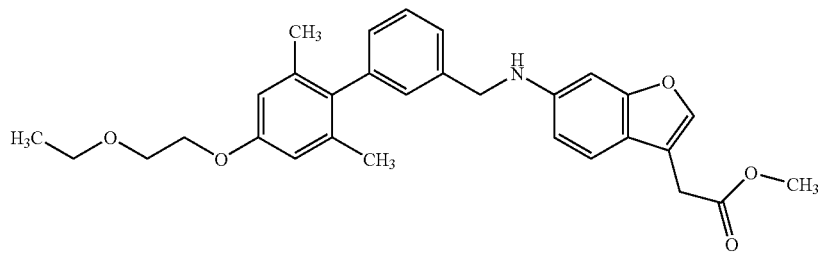

In the same manner as in Example 10, the title compound was obtained as a brown oil from methyl(6-{{[4'-(2-ethoxyethoxy)-2',6'-dimethylbiphenyl-3-yl]methyl}[(2-nitrophenyl)sulfonyl]amino}-1-benzofuran-3-yl)acetate. yield 76% (2 steps).
MS m/z 488 (MH$^+$).

Example 80

[6-({[4'-(2-ethoxyethoxy)-2',6'-dimethylbiphenyl-3-yl]methyl}amino)-1-benzofuran-3-yl]acetic acid hydrochloride

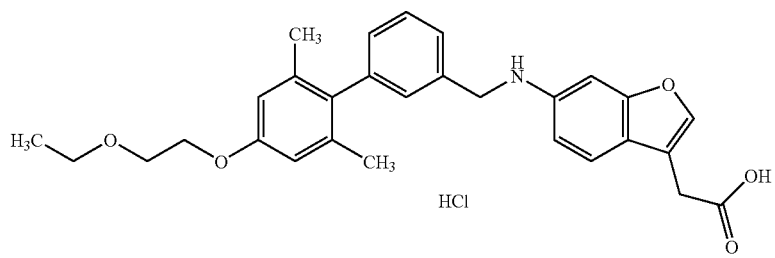

In the same manner as in Example 12, the title compound was obtained as pale-gray crystals from methyl [6-({[4'-(2-ethoxyethoxy)-2',6'-dimethylbiphenyl-3-yl]methyl}amino)-1-benzofuran-3-yl]acetate. yield 29%.

$^1$H NMR (CDCl$_3$) δ: 1.23 (3H, t, J=6.9 Hz), 1.66 (6H, s), 3.53-3.64 (4H, m), 3.77 (2H, t, J=4.8 Hz), 4.08 (2H, t, J=4.8 Hz), 4.53 (2H, s), 6.56 (2H, s), 6.71 (1H, s), 7.03 (1H, d, J=7.6 Hz), 7.09 (1H, d, J=8.3 Hz), 7.23 (1H, d, J=8.3 Hz), 7.31 (1H, s), 7.37 (1H, t, J=7.6 Hz), 7.52 (1H, s), 7.54-7.61 (1H, d, J=7.9 Hz), 11.77 (1H, s).

Example 81 methyl {6-[[(2-nitrophenyl)sulfonyl](4-{[(2-phenylethyl)(4-phenyl-1,3-thiazol-2-yl)amino]methyl}benzyl)amino]-1-benzofuran-3-yl}acetate

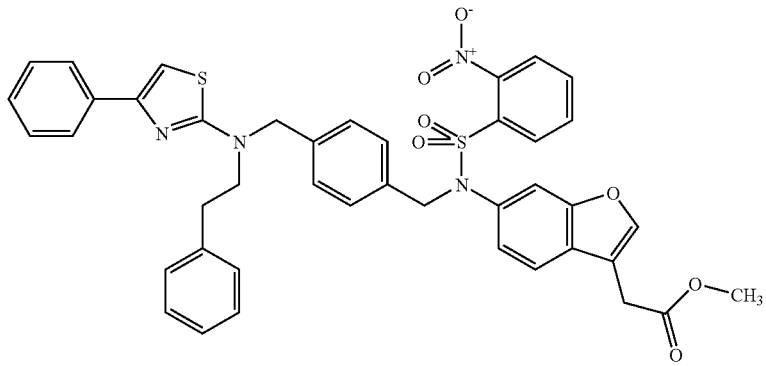

In the same manner as in Example 9, the title compound was obtained as a brown oil from methyl(6-{[(2-nitrophenyl)sulfonyl]amino}-1-benzofuran-3-yl)acetate and (4-{[(2-phenylethyl)(4-phenyl-1,3-thiazol-2-yl)amino]methyl}phenyl)methanol.

MS m/z 773 (MH$^+$).

Example 82 methyl {6-[(4-{[(2-phenylethyl)(4-phenyl-1,3-thiazol-2-yl)amino]methyl}benzyl)amino]-1-benzofuran-3-yl}acetate

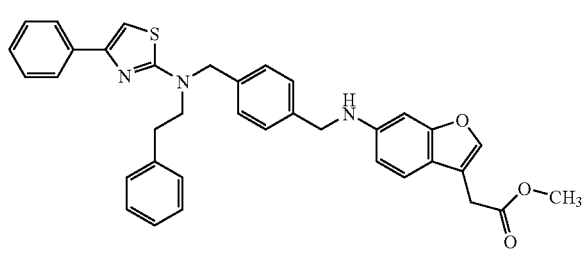

In the same manner as in Example 10, the title compound was obtained as a brown oil from methyl {6-[[(2-nitrophenyl)sulfonyl](4-{[(2-phenylethyl)(4-phenyl-1,3-thiazol-2-yl)amino]methyl}benzyl)amino]-1-benzofuran-3-yl}acetate. yield 82% (2 steps).

MS m/z 588 (MH$^+$).

Example 83

{6-[(4-{[(2-phenylethyl)(4-phenyl-1,3-thiazol-2-yl)amino]methyl}benzyl)amino]-1-benzofuran-3-yl}acetic acid

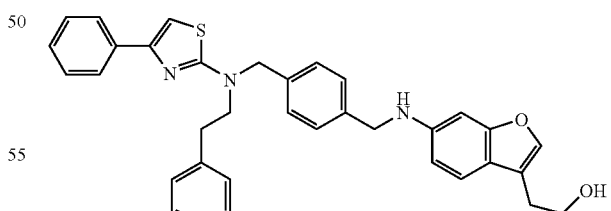

In the same manner as in Example 2, the title compound was obtained as pale-yellow prism crystals from methyl {6-[(4-{[(2-phenylethyl)(4-phenyl-1,3-thiazol-2-yl)amino]methyl}benzyl)amino]-1-benzofuran-3-yl}acetate. yield 37% (recrystallized from hexane-ethyl acetate).

MS m/z 574 (MH$^+$).

Example 84
3-[4-({[4'-(2-ethoxyethoxy)-2',6'-dimethylbiphenyl-3-yl]methyl}amino)-2-fluorophenyl]propanoic acid methanesulfonate

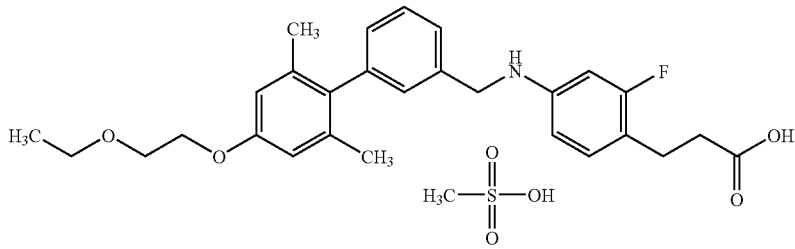

To a solution of 3-[4-({[4'-(2-ethoxyethoxy)-2',6'-dimethylbiphenyl-3-yl]methyl}amino)-2-fluorophenyl]propanoic acid (0.372 g, 0.800 mmol) in diethyl ether (5 mL) was added methanesulfonic acid (0.0519 mL, 0.800 mmol), and the resulting crystals were washed with ethyl acetate-diethyl ether to give the title compound as colorless crystals (0.402 g, yield 90%).

$^1$H NMR (CDCl$_3$) δ: 1.25 (3H, t, J=7.0 Hz), 1.82 (6H, s), 2.61 (2H, t, J=6.7 Hz), 2.77 (3H, s), 2.83 (2H, t, J=6.7 Hz), 3.61 (2H, q, J=7.0 Hz), 3.79 (2H, t, J=4.8 Hz), 4.11 (2H, t, J=4.8 Hz), 4.51 (2H, s), 6.63 (2H, s), 6.80-6.90 (2H, m), 6.98-7.04 (1H, m), 7.07-7.16 (2H, m), 7.35-7.43 (2H, m), 10.97 (1H, br s).

Example 85
methyl [6-({[4'-(2-ethoxyethoxy)-2',6'-dimethylbiphenyl-3-yl]methyl}amino)-2,3-dihydro-1-benzofuran-3-yl]acetate

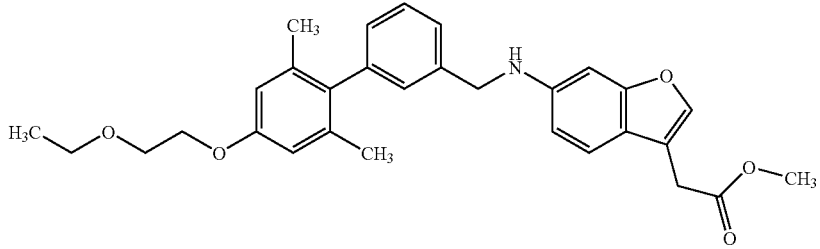

In the same manner as in Reference Example 21, the title compound was obtained as a colorless oil from methyl [6-({[4'-(2-ethoxyethoxy)-2',6'-dimethylbiphenyl-3-yl]methyl}amino)-1-benzofuran-3-yl]acetate. yield 66%.
MS m/z 490 (MH$^+$).

Example 86
[6-({[4'-(2-ethoxyethoxy)-2',6'-dimethylbiphenyl-3-yl]methyl}amino)-2,3-dihydro-1-benzofuran-3-yl]acetic acid hydrochloride

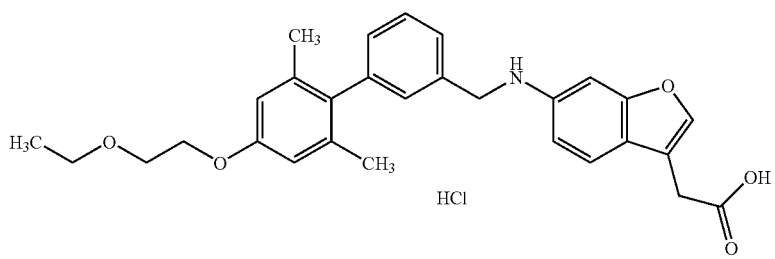

In the same manner as in Example 12, the title compound was obtained as colorless crystals from methyl [6-({[4'-(2-ethoxyethoxy)-2',6'-dimethylbiphenyl-3-yl]methyl}amino)-2,3-dihydro-1-benzofuran-3-yl]acetate. yield 85%.

$^1$H NMR (CDCl$_3$) δ: 1.25 (3H, t, J=7.1 Hz), 1.81 (6H, s), 2.44-2.55 (1H, m), 2.59-2.69 (1H, m), 3.58-3.75 (3H, m), 3.79 (2H, t, J=6.1 Hz), 4.10 (2H, t, J=6.1 Hz), 4.23 (1H, dd, J=9.2, 6.5 Hz), 4.46 (2H, s), 4.64 (1H, t, J=9.2 Hz), 6.61 (2H, s), 6.68 (1H, d, J=1.3 Hz), 6.75-6.83 (2H, m), 7.00 (1H, d, J=7.9 Hz), 7.07 (1H, d, J=7.7 Hz), 7.39 (1H, t, J=7.7 Hz), 7.60 (1H, d, J=7.0 Hz), 11.70 (1H, br s).

mp 140° C.

Example 87

3-[4-({[4'-(2-ethoxyethoxy)-2',6'-dimethylbiphenyl-3-yl]methyl}amino)-2-fluorophenyl]propanoic acid p-toluenesulfonate

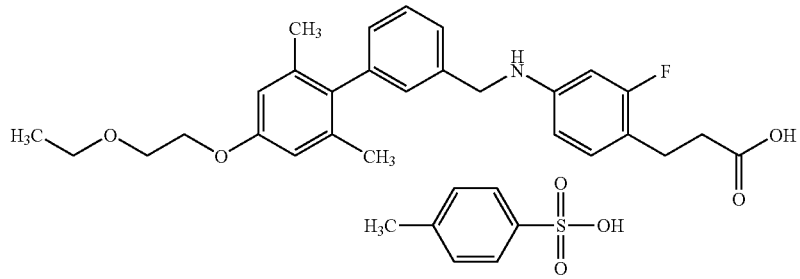

To a solution of 3-[4-({[4'-(2-ethoxyethoxy)-2',6'-dimethylbiphenyl-3-yl]methyl}amino)-2-fluorophenyl]propanoic acid (0.372 g, 0.800 mmol) in diethyl ether (5 mL) was added a solution of p-toluenesulfonic acid monohydrate (0.152 g, 0.800 mmol) in ethyl acetate (5 mL), and the resulting crystals were washed with ethyl acetate-diethyl ether to give the title compound as colorless crystals (0.456 g, yield 89%).

$^1$H NMR (CDCl$_3$) δ: 1.25 (3H, t, J=7.1 Hz), 1.75 (6H, s), 2.38 (3H, s), 2.63 (2H, t, J=6.5 Hz), 2.81 (2H, t, J=6.5 Hz), 3.61 (2H, q, J=7.0 Hz), 3.79 (2H, t, J=5.1 Hz), 4.11 (2H, t, J=5.1 Hz), 4.47 (2H, s), 6.61 (2H, s), 6.71-6.78 (2H, m), 6.98-7.10 (3H, m), 7.15 (2H, d, J=8.0 Hz), 7.23-7.32 (2H, m), 7.71 (2H, d, J=8.0 Hz), 11.05 (1H, br s).

Example 88

3-[4-({[4'-(2-ethoxyethoxy)-2',6'-dimethylbiphenyl-3-yl]methyl}amino)-2-fluorophenyl]propanoic acid benzenesulfonate

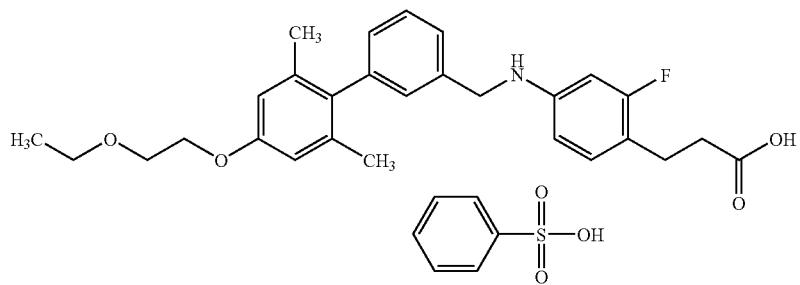

To a solution of 3-[4-({[4'-(2-ethoxyethoxy)-2',6'-dimethylbiphenyl-3-yl]methyl}amino)-2-fluorophenyl]propanoic acid (0.372 g, 0.800 mmol) in diethyl ether (5 mL) was added a solution of benzenesulfonic acid monohydrate (0.141 g, 0.800 mmol) in ethyl acetate (3 mL), and the resulting crystals were washed with ethyl acetate-diethyl ether to give the title compound as colorless crystals (0.474 g, yield 95%).

$^1$H NMR (CDCl$_3$) δ: 1.25 (3H, t, J=7.0 Hz), 1.75 (6H, s), 2.64 (2H, t, J=6.4 Hz), 2.82 (2H, t, J=6.4 Hz), 3.61 (2H, q, J=7.0 Hz), 3.79 (2H, t, J=4.9 Hz), 4.11 (2H, t, J=4.9 Hz), 4.47 (2H, s), 6.60 (2H, s), 6.72-6.79 (2H, m), 6.97-7.10 (3H, m), 7.23-7.46 (5H, m), 7.79-7.85 (2H, m), 11.06 (1H, br s).

Example 89 ethyl 3-(2-fluoro-4-{[3-(2-methyl-1-naphthyl)benzyl]amino}phenyl)propanoate

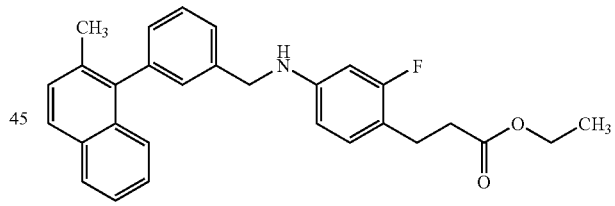

In the same manner as in Example 38, the title compound was obtained as a pale-yellow oil from ethyl 3-(4-amino-2-fluorophenyl)propanoate and 3-(2-methyl-1-naphthyl)benzaldehyde. yield 87%.

MS m/z 442 (MH$^+$).

Example 90

3-(2-fluoro-4-{[3-(2-methyl-1-naphthyl)benzyl]amino}phenyl)propanoic acid methanesulfonate

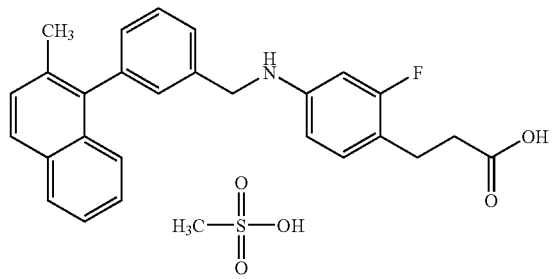

In the same manner as in Example 4 and Example 84, the title compound was obtained as a pale-yellow viscous oil from ethyl 3-(2-fluoro-4-{[3-(2-methyl-1-naphthyl)benzyl]amino}phenyl)propanoate. yield 91%.

MS m/z 414 (MH$^+$, as free form).

Example 91

3-[4-({[4'-(2-ethoxyethoxy)-2',6'-dimethylbiphenyl-3-yl]methyl}amino)-2-fluorophenyl]propanamide A solution of 3-[4-({[4'-(2-ethoxyethoxy)-2',6'-dimethylbiphenyl-3-yl]methyl}amino)-2-fluorophenyl]propanoic acid (0.251 g, 0.500 mmol), 7 M ammonia/methanol (0.4 mL, 2.80 mmol) solution, 1-ethyl-3-(3-aminopropyl)carbodiimide hydrochloride (288 g, 1.50 mmol), 1-hydroxybenzotriazole (0.230 g, 1.50 mmol), 1,8-diazabicyclo[5.4.0]-7-undecene (0.448 mL, 3.00 mmol) and triethylamine (0.502 mL, 3.60 mmol) in acetonitrile (3 mL) was stirred at room temperature for 24 hr. The reaction mixture was poured into saturated aqueous sodium hydrogencarbonate solution, and the mixture was extracted with ethyl acetate. The extract was washed with saturated brine, dried over anhydrous sodium sulfate, and concentrated under reduced pressure. The residue was purified by basic silica gel column chromatography (50% ethyl acetate/hexane-ethyl acetate) to give the title compound (0.206 g, yield 89%) as a colorless oil.

MS m/z 465 (MH$^+$).

Example 92

N-{[4'-(2-ethoxyethoxy)-2',6'-dimethylbiphenyl-3-yl]methyl}-3-fluoro-4-[3-oxo-3-(1-pyrrolidinyl)propyl]aniline

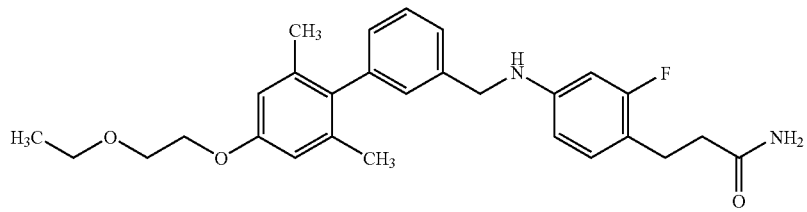

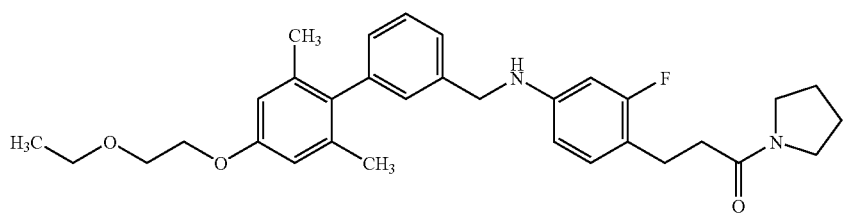

In the same manner as in Example 91, the title compound was obtained as a yellow oil from 3-[4-({[4'-(2-ethoxyethoxy)-2',6'-dimethylbiphenyl-3-yl]methyl}amino)-2-fluorophenyl]propanoic acid and pyrrolidine. yield 93%.

MS m/z 519 (MH+).

Example 93

N-(benzylsulfonyl)-3-[4-({[4'-(2-ethoxyethoxy)-2',6'-dimethylbiphenyl-3-yl]methyl}amino)-2-fluorophenyl]propanamide

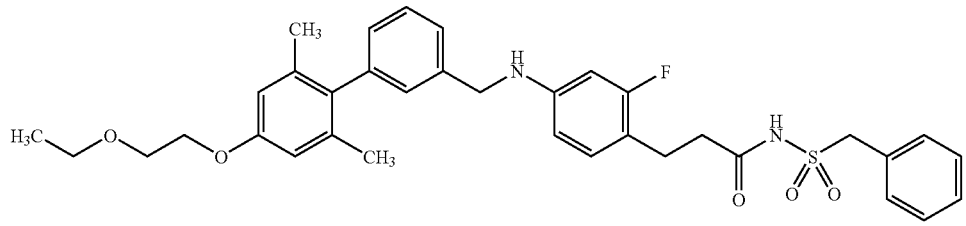

To a solution of 3-[4-({[4'-(2-ethoxyethoxy)-2',6'-dimethylbiphenyl-3-yl]methyl}amino)-2-fluorophenyl]propanoic acid (0.186 g, 0.400 mmol) in tetrahydrofuran (5 mL) was added 1,1'-carbonyldiimidazole (97.3 mg, 0.600 mmol), and the mixture was heated under reflux under a nitrogen atmosphere for 1 hr. After cooling the reaction mixture, 1-phenylmethanesulfonamide (91.5 mg, 0.480 mmol) and 1,8-diazabicyclo[5.4.0]-7-undecene (0.0897 mL, 0.600 mmol) were added, and the mixture was stirred under a nitrogen atmosphere at room temperature for 24 hr. The reaction mixture was concentrated under reduced pressure, 10% aqueous citric acid solution was added to the residue, and the mixture was extracted with ethyl acetate. The extract was washed with saturated brine, dried over anhydrous sodium sulfate, and concentrated under reduced pressure. The residue was purified by silica gel column chromatography (20%-60% ethyl acetate/hexane) to give the title compound (0.189 g, yield 76%) as a colorless oil.

MS m/z 619 (MH+).

Example 94

3-[4-({[4'-(2-ethoxyethoxy)-2',6'-dimethylbiphenyl-3-yl]methyl}amino)-2-fluorophenyl]-N-(propylsulfonyl)propanamide

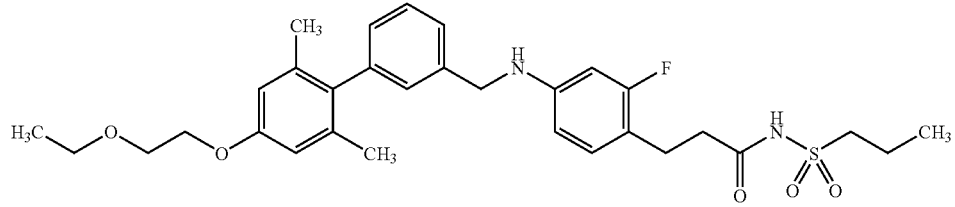

In the same manner as in Example 93, the title compound was obtained as a colorless oil from 3-[4-({[4'-(2-ethoxyethoxy)-2',6'-dimethylbiphenyl-3-yl]methyl}amino)-2-fluorophenyl]propanoic acid and propane-1-sulfonamide. yield 43%.

MS m/z 571 (MH+).

Example 95

3-[4-({[4'-(2-ethoxyethoxy)-2',6'-dimethylbiphenyl-3-yl]methyl}amino)-2-fluorophenyl]-N-(methylsulfonyl)propanamide

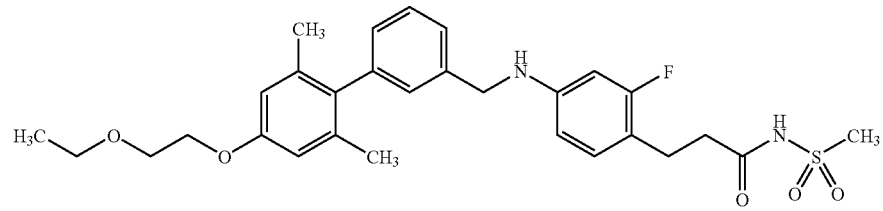

In the same manner as in Example 93, the title compound was obtained as a colorless oil from 3-[4-({[4'-(2-ethoxyethoxy)-2',6'-dimethylbiphenyl-3-yl]methyl}amino)-2-fluorophenyl]propanoic acid and methanesulfonamide. yield 85%.

MS m/z 543 (MH+).

Example 96

3-[4-({[4'-(2-ethoxyethoxy)-2',6'-dimethylbiphenyl-3-yl]methyl}amino)-2-fluorophenyl]-N-[(trifluoromethyl)sulfonyl]propanamide

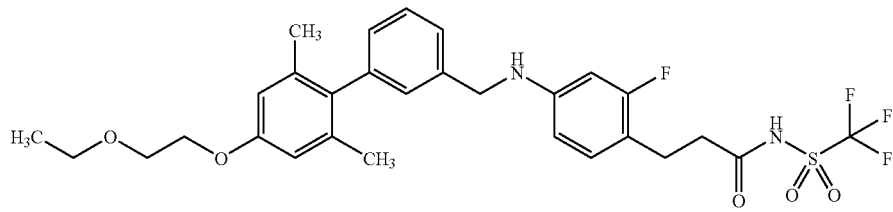

In the same manner as in Example 93, the title compound was obtained as a brown oil from 3-[4-({[4'-(2-ethoxyethoxy)-2',6'-dimethylbiphenyl-3-yl]methyl}amino)-2-fluorophenyl]propanoic acid and 1,1,1-trifluoromethanesulfonamide. yield 48%.

MS m/z 597 (MH+).

Example 97 ethyl 3-{4-[({4'-[2-(diethylamino)-2-oxoethoxy]-2',6'-dimethylbiphenyl-3-yl}methyl)amino]-2-fluorophenyl}propanoate

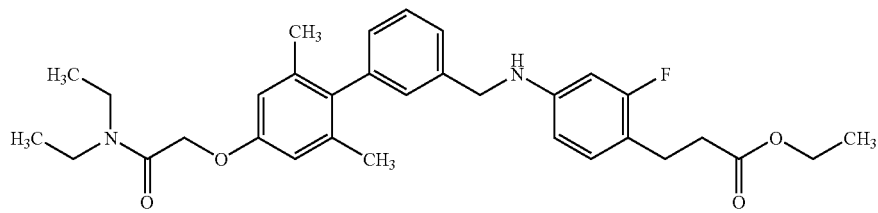

To a solution of ethyl 3-(4-amino-2-fluorophenyl)propanoate (0.496 g, 2.35 mmol) and N,N-diethyl-2-[(3'-formyl-2,6-dimethylbiphenyl-4-yl)oxy]acetamide (0.725 g, 2.14 mmol) in 1,2-dichloroethane (10 mL) was added acetic acid (0.245 mL, 4.28 mmol), and the mixture was stirred at room temperature for 3 hr. Sodium triacetoxyborohydride (0.907 q, 4.28 mmol) was added to the reaction mixture, and the mixture was stirred at room temperature for 15 hr. Water and 10% aqueous citric acid solution were added to the reaction mixture, and the mixture was extracted with ethyl acetate. The extract was washed with saturated brine, dried over anhydrous sodium sulfate, and concentrated under reduced pressure. The residue was purified by silica gel column chromatography (20%-70% ethyl acetate/hexane) to give the title compound (0.978 g, yield 86%) as a yellow oil.

MS m/z 535 (MH+).

Example 98

3-{4-[({4'-[2-(diethylamino)-2-oxoethoxy]-2',6'-dimethylbiphenyl-3-yl}methyl)amino]-2-fluorophenyl}propanoic acid

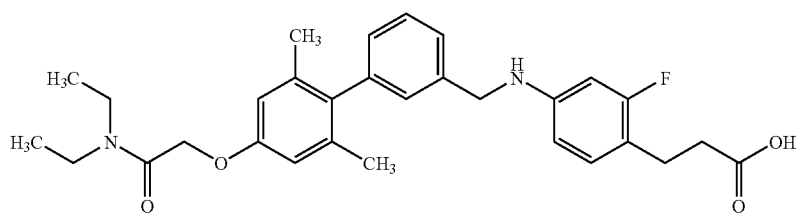

In the same manner as in Example 8, the title compound was obtained as a pale-yellow oil from ethyl 3-{4-[({4'-[2-(diethylamino)-2-oxoethoxy]-2',6'-dimethylbiphenyl-3-yl}methyl)amino]-2-fluorophenyl}propanoate. yield 89%.
MS m/z 507 (MH⁺).

Example 99 ethyl 3-[4-({[2',6'-dimethyl-4'-(2-morpholin-4-yl-2-oxoethoxy)biphenyl-3-yl]methyl}amino)-2-fluorophenyl]propanoate

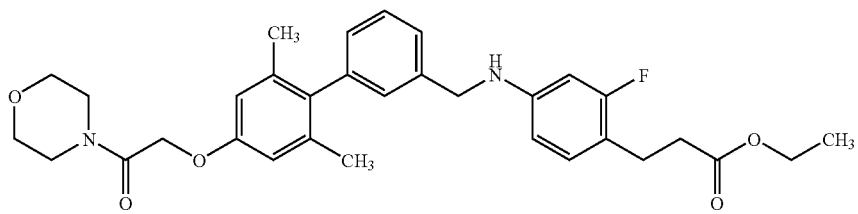

In the same manner as in Example 97, the title compound was obtained as a yellow oil from ethyl 3-(4-amino-2-fluorophenyl)propanoate and 2',6'-dimethyl-4'-(2-morpholin-4-yl-2-oxoethoxy)biphenyl-3-carbaldehyde. yield 84%.
MS m/z 549 (MH⁺).

Example 100

3-[4-({[4'-(carboxymethoxy)-2',6'-dimethylbiphenyl-3-yl]methyl}amino)-2-fluorophenyl]propanoic acid

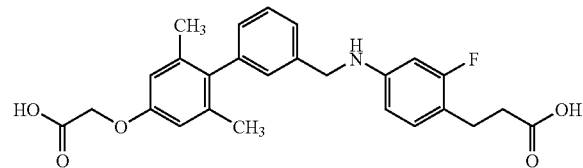

In the same manner as in Example 2, the title compound was obtained as colorless prism crystals from ethyl 3-[4-({[2',6'-dimethyl-4'-(2-morpholin-4-yl-2-oxoethoxy)biphenyl-3-yl]methyl}amino)-2-fluorophenyl]propanoate. yield 45%.

MS m/z 507 (MH⁺).

Example 101 ethyl 3-[4-({3-[1-(2-ethoxyethyl)-2-methyl-1H-indol-3-yl]benzyl}amino)-2-fluorophenyl]propanoate

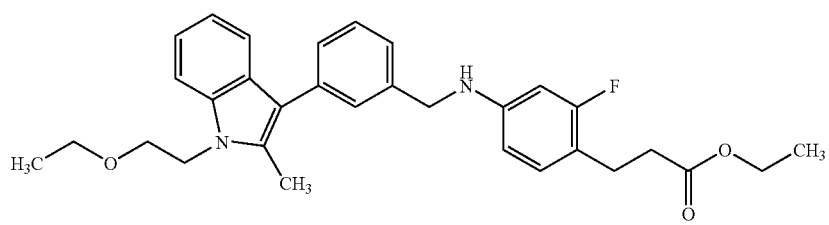

In the same manner as in Example 38, the title compound was obtained as a colorless oil from ethyl 3-(4-amino-2-fluorophenyl)propanoate and 3-[1-(2-ethoxyethyl)-2-methyl-1H-indol-3-yl]benzaldehyde. yield 53%.

MS m/z 503 (MH⁺).

Example 102

3-[4-({3-[1-(2-ethoxyethyl)-2-methyl-1H-indol-3-yl]benzyl}amino)-2-fluorophenyl]propanoic acid hydrochloride

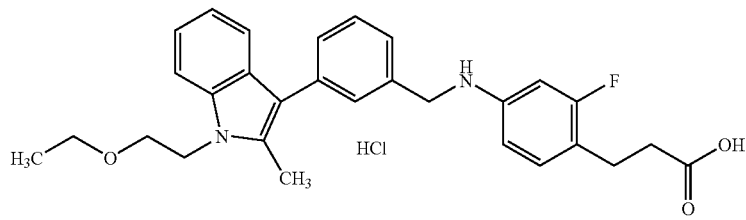

In the same manner as in Example 12, the title compound was obtained as colorless crystals from ethyl 3-[4-({3-[1-(2-ethoxyethyl)-2-methyl-1H-indol-3-yl]benzyl}amino)-2-fluorophenyl]propanoate. yield 85%.

$^1$H NMR (DMSO-$d_6$) δ: 1.04 (3H, t, J=7.0 Hz), 2.37-2.47 (5H, m), 2.69 (2H, t, J=7.6 Hz), 3.38 (2H, q, J=7.0 Hz), 3.66 (2H, t, J=5.4 Hz), 4.30-4.41 (4H, m), 6.46-6.57 (2H, m), 6.94-7.06 (2H, m), 7.07-7.15 (1H, m), 7.25-7.34 (2H, m), 7.38-7.49 (4H, m).

Example 103 ethyl 3-(4-({[5-(benzyloxy)-2',6'-dimethylbiphenyl-3-yl]methyl}[(2-nitrophenyl)sulfonyl]amino}-2-fluorophenyl)propanoate

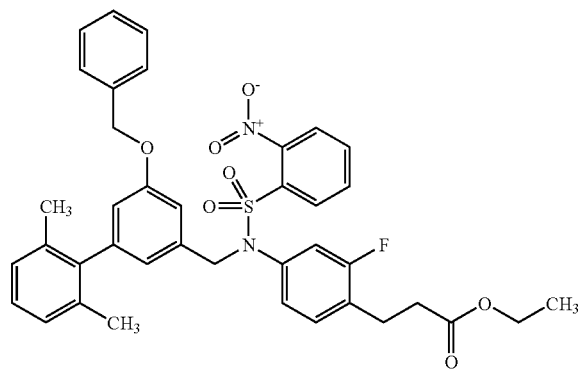

In the same manner as in Example 9, the title compound was obtained as an orange oil from ethyl 3-(2-fluoro-4-{[(2-nitrophenyl)sulfonyl]amino}phenyl)propanoate and [5-(benzyloxy)-2',6'-dimethylbiphenyl-3-yl]methanol.

MS m/z 697 (MH⁺).

Example 104 ethyl 3-[4-({[5-(benzyloxy)-2',6'-dimethylbiphenyl-3-yl]methyl}amino)-2-fluorophenyl]propanoate

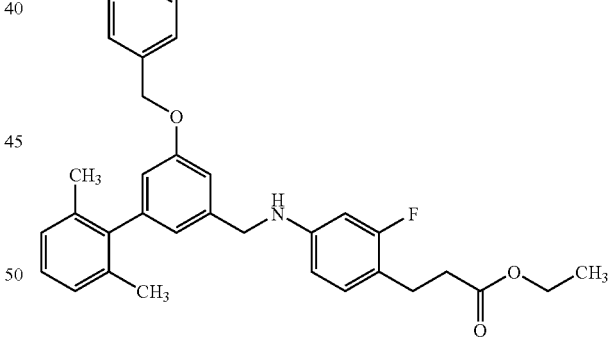

In the same manner as in Example 10, the title compound was obtained as a colorless oil from ethyl 3-(4-{{[5-(benzyloxy)-2',6'-dimethylbiphenyl-3-yl]methyl}[(2-nitrophenyl)sulfonyl]amino}-2-fluorophenyl)propanoate. yield 76% (2 steps).

MS m/z 512 (MH⁺).

Example 105

3-[4-({[5-(benzyloxy)-2',6'-dimethylbiphenyl-3-yl]methyl}amino)-2-fluorophenyl]propanoic acid methanesulfonate

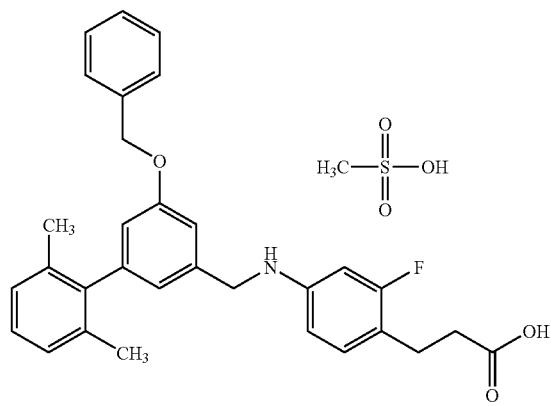

In the same manner as in Example 4 and Example 84, the title compound was obtained as colorless crystals from ethyl 3-[4-({[5-(benzyloxy)-2',6'-dimethylbiphenyl-3-yl]methyl}amino)-2-fluorophenyl]propanoate. yield 95%.

$^1$H NMR (CDCl$_3$) δ: 1.83 (6H, s), 2.65 (2H, t, J=6.5 Hz), 2.79 (3H, s), 2.84 (2H, t, J=6.5 Hz), 4.48 (2H, s), 5.10 (2H, s), 6.42 (1H, s), 6.72 (1H, s), 6.81-6.89 (1H, m), 6.95-7.18 (6H, m), 7.28-7.45 (5H, m).

Example 106 ethyl 3-[4-({4-[(3-tert-butyl-5-phenyl-1H-pyrazol-1-yl)methyl]benzyl}amino)-2-fluorophenyl]propanoate

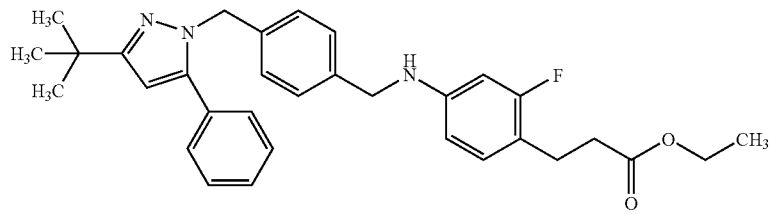

To a solution of ethyl 3-(2-fluoro-4-{[(2-nitrophenyl)sulfonyl]amino}phenyl)propanoate (435 mg, 1.1 mmol) {4-[(3-tert-butyl-5-phenyl-1H-pyrazol-1-yl)methyl]phenyl}methanol (360 mg, 1.1 mmol) and triphenylphosphine (393 mg, 1.5 mmol) in dichloromethane (5 mL) was added diethyl azodicarboxylate (40% toluene solution, 660 mg, 1.5 mmol) at room temperature, and the mixture was stirred at room temperature for 1 hr. The reaction mixture was purified by silica gel column chromatography (10%-80% ethyl acetate/hexane) to give a yellow oil. To a solution of the yellow oil and mercaptoacetic acid (360 mg, 3.9 mmol) in N,N-dimethylformamide (5 mL) was added lithium hydroxide monohydrate (320 mg, 7.6 mmol), and the mixture was stirred at room temperature for 14 hr. The reaction mixture was poured into 10% aqueous sodium hydrogencarbonate solution, and the mixture was extracted with ethyl acetate. The ethyl acetate layer was dried using a Presep Dehydration tube (manufactured by Wako Pure Chemical Industries, Ltd.), and concentrated under reduced pressure. The residue was purified by silica gel column chromatography (10%-80% ethyl acetate/hexane) to give the title compound (160 mg, yield 28%) as a yellow oil.

$^1$H NMR (CDCl$_3$) δ: 1.23-1.29 (3H, m), 1.37 (9H, s), 2.55 (2H, t, J=7.7 Hz), 2.84 (2H, t, J=7.7 Hz), 4.10-4.16 (2H, m), 4.24 (2H, s), 5.30 (2H, s), 6.20 (1H, s), 6.24-6.35 (2H, m), 6.92-7.01 (3H, m), 7.21-7.37 (7H, m).

Example 107

3-[4-({4-[(3-tert-butyl-5-phenyl-1H-pyrazol-1-yl)methyl]benzyl}amino)-2-fluorophenyl]propanoic acid

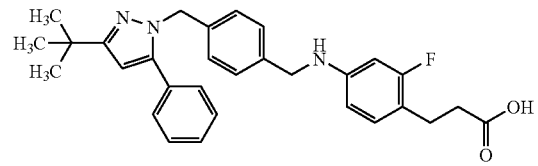

To a solution of ethyl 3-[4-({4-[(3-tert-butyl-5-phenyl-1H-pyrazol-1-yl)methyl]benzyl}amino)-2-fluorophenyl]propanoate (150 mg, 0.29 mmol) in ethanol (5 mL) and tetrahydrofuran (5 mL) was added 1 M aqueous sodium hydroxide solution (2 mL), and the mixture was stirred at room temperature for 2 hr. The reaction mixture was poured into water, and the mixture was weakly acidified with 10% aqueous citric acid solution and extracted with ethyl acetate. The ethyl acetate layer was dried using a Presep Dehydration tube (manufactured by Wako Pure Chemical Industries, Ltd.), and concentrated under reduced pressure. The residue was purified by silica gel column chromatography (20%-80% ethyl acetate/hexane) to give the title compound (91 mg, yield 65%) as a yellow oil.

$^1$H NMR (CDCl$_3$) δ: 1.36 (9H, s), 2.60 (2H, t, J=7.6 Hz), 2.84 (2H, t, J=7.7 Hz), 4.23 (2H, s), 5.31 (2H, s), 6.20 (1H, s), 6.24-6.34 (2H, m), 6.93-7.00 (3H, m), 7.21-7.37 (7H, m).

Example 108 ethyl 3-(2-fluoro-4-{[4-({5-(2-phenylethyl)-3-[4-(trifluoromethyl)phenyl]-1H-pyrazol-1-yl}methyl)benzyl]amino}phenyl)propanoate

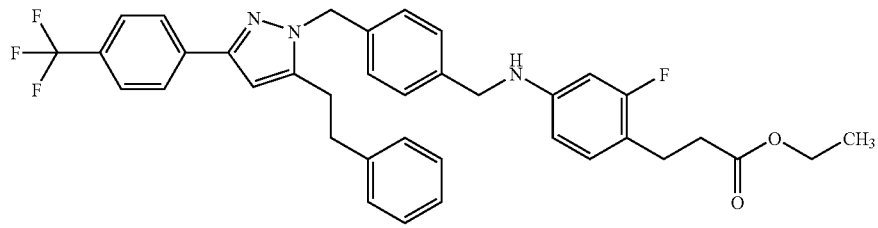

To a mixture of 4-({5-(2-phenylethyl)-3-[4-(trifluoromethyl)phenyl]-1H-pyrazol-1-yl}methyl)benzaldehyde (868 mg, 2.0 mmol), ethyl 3-(4-amino-2-fluorophenyl)propanoate (420 mg, 2.0 mmol), acetic acid (300 mg, 5.0 mmol) and 1,2-dichloroethane (15 mL) was added sodium triacetoxyborohydride (1.20 g, 6.0 mmol) by small portions at room temperature and the mixture was stirred for 1 hr. The reaction mixture was poured into 10% aqueous sodium hydrogencarbonate solution, and the mixture was extracted with ethyl acetate. The extract was dried over anhydrous magnesium sulfate, and concentrated under reduced pressure. The residue was purified by silica gel column chromatography (20%-60% ethyl acetate/hexane) to give the title compound as a yellow oil.

$^1$H NMR (CDCl$_3$) δ: 1.26 (3H, t, J=7.1 Hz), 2.53 (2H, t, J=7.7 Hz), 2.78-2.91 (6H, m), 4.12 (2H, q, J=7.0 Hz), 4.25 (2H, s), 5.25 (2H, s), 6.22-6.32 (2H, m), 6.47 (1H, s), 6.94 (1H, t, J=8.4 Hz), 7.05-7.13 (4H, m), 7.20-7.35 (5H, m), 7.63 (2H, d, J=8.1 Hz), 7.91 (2H, d, J=8.1 Hz).

Example 109

3-(2-fluoro-4-{[4-({5-(2-phenylethyl)-3-[4-(trifluoromethyl)phenyl]-1H-pyrazol-1-yl}methyl)benzyl]amino}phenyl)propanoic acid

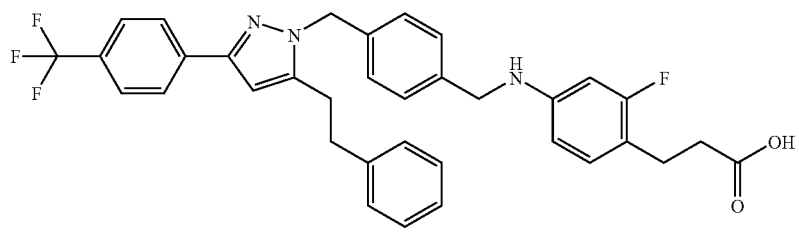

To a solution of ethyl 3-(2-fluoro-4-{[4-({5-(2-phenylethyl)-3-[4-(trifluoromethyl)phenyl]-1H-pyrazol-1-yl}methyl)benzyl]amino}phenyl)propanoate in ethanol (10 mL) and tetrahydrofuran (10 mL) was added 1 M aqueous sodium hydroxide solution (4 mL), and the mixture was stirred at room temperature for 2 hr. The reaction mixture was poured into water, and the mixture was weakly acidified with 10% aqueous citric acid solution and extracted with ethyl acetate. The ethyl acetate layer was dried using a Presep Dehydration tube (manufactured by Wako Pure Chemical Industries, Ltd.), and concentrated under reduced pressure. The residue was purified by silica gel column chromatography (20%-80% ethyl acetate/hexane) to give the title compound (620 mg, yield 51%, 2 steps) as a yellow oil.

$^1$H NMR (CDCl$_3$) δ: 2.58 (2H, t, J=7.6 Hz), 2.76-2.93 (6H, m), 4.24 (2H, s), 5.25 (2H, s), 6.21-6.33 (2H, m), 6.46 (1H, s), 6.93 (1H, t, J=8.5 Hz), 7.04-7.13 (4H, m), 7.18-7.32 (6H, m), 7.63 (2H, d, J=8.1 Hz), 7.90 (2H, d, J=7.9 Hz).

Example 110

3-(2-fluoro-4-{[4-({5-(2-phenylethyl)-3-[4-(trifluoromethyl)phenyl]-1H-pyrazol-1-yl}methyl)benzyl]amino}phenyl)propanoic acid methanesulfonate

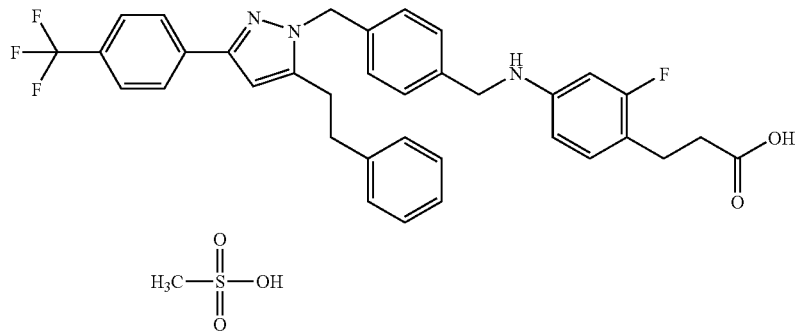

To a solution of 3-(2-fluoro-4-{[4-({5-(2-phenylethyl)-3-[4-(trifluoromethyl)phenyl]-1H-pyrazol-1-yl}methyl)benzyl]amino}phenyl)propanoic acid (500 mg, 0.83 mmol) in ethyl acetate (20 mL) was added methanesulfonic acid (95 mg, 1.0 mmol) at room temperature, and the mixture was stirred for 1 hr. The reaction mixture was concentrated, isopropyl ether was added and the precipitated crystals were collected by filtration, washed with isopropyl ether and dried to give the title compound as colorless crystals (348 mg, yield 60%).

$^1$H NMR (CDCl$_3$) δ: 2.57 (2H, t, J=6.7 Hz), 2.76 (3H, s), 2.77-2.88 (6H, m), 4.43 (2H, s), 5.24 (2H, s), 6.45 (1H, s), 6.78-7.09 (7H, m), 7.14-7.32 (6H, m), 7.64 (2H, d, J=8.3 Hz), 7.86 (2H, d, J=8.1 Hz).

Example 111 ethyl 3-{4-[(4-{[3-tert-butyl-5-(2-phenylethyl)-1H-pyrazol-1-yl]methyl}benzyl)amino]-2-fluorophenyl}propanoate

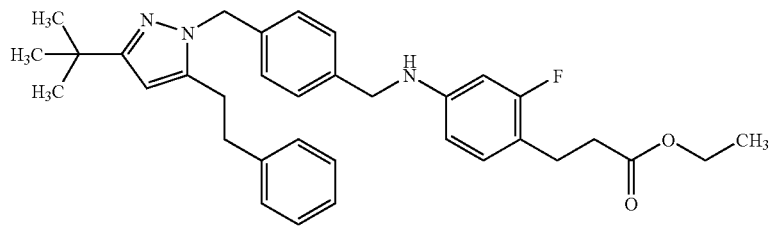

In the same manner as in Example 108, the title compound was obtained as a yellow oil from 4-{[3-tert-butyl-5-(2-phenylethyl)-1H-pyrazol-1-yl]methyl}benzaldehyde and ethyl 3-(4-amino-2-fluorophenyl)propanoate.

$^1$H NMR (CDCl$_3$) δ: 1.26 (3H, t, J=7.2 Hz), 1.32 (9H, s), 2.53 (2H, t, J=7.7 Hz), 2.67-2.87 (6H, m), 4.12 (2H, q, J=7.2 Hz), 4.24 (2H, s), 5.20 (2H, s), 5.97 (1H, s), 6.23-6.32 (2H, m), 6.90-7.00 (3H, m), 7.05-7.11 (2H, m), 7.18-7.30 (5H, m).

Example 112

3-{4-[(4-{[3-tert-butyl-5-(2-phenylethyl)-1H-pyrazol-1-yl]methyl}benzyl)amino]-2-fluorophenyl}propanoic acid

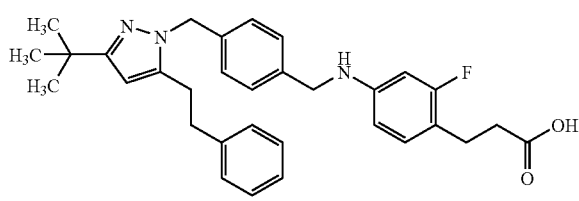

In the same manner as in Example 109, the title compound was obtained as a yellow oil from ethyl 3-(4-[(4-{[3-tert-butyl-5-(2-phenylethyl)-1H-pyrazol-1-yl]methyl}benzyl)amino]-2-fluorophenyl)propanoate. yield 68% (2 steps).

$^1$H NMR (CDCl$_3$) δ: 1.32 (9H, s), 2.59 (2H, t, J=7.6 Hz), 2.68-2.88 (6H, m), 4.24 (2H, s), 5.20 (2H, s), 5.97 (1H, s), 6.23-6.33 (2H, m), 6.90-7.00 (3H, m), 7.05-7.10 (2H, m), 7.18-7.31 (6H, m).

Example 113

3-{4-[(4-{[3-tert-butyl-5-(2-phenylethyl)-1H-pyrazol-1-yl]methyl}benzyl)amino]-2-fluorophenyl}propanoic acid methanesulfonate

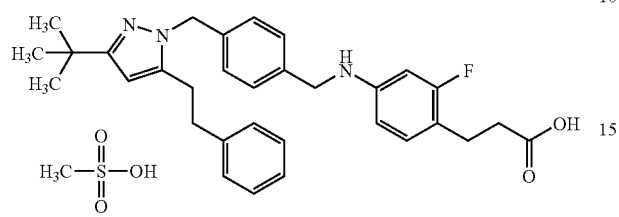

In the same manner as in Example 110, the title compound was obtained as a pale-yellow amorphous powder from 3-{4-[(4-{[3-tert-butyl-5-(2-phenylethyl)-1H-pyrazol-1-yl]methyl}benzyl)amino]-2-fluorophenyl}propanoic acid. yield 82%.

$^1$H NMR (CDCl$_3$) δ: 1.37 (9H, s), 2.57 (2H, t, J=6.8 Hz), 2.75-2.87 (9H, m), 4.39 (2H, s), 5.48 (2H, s), 6.04 (1H, s), 6.61 (1H, dd, J=8.1, 1.7 Hz), 6.82 (1H, d, J=10.5 Hz), 6.97-7.09 (5H, m), 7.14-7.31 (6H, m).

Example 114 ethyl 3-{4-[(4-{[5-tert-butyl-3-(2-phenylethyl)-1H-pyrazol-1-yl]methyl}benzyl)amino]-2-fluorophenyl}propanoate

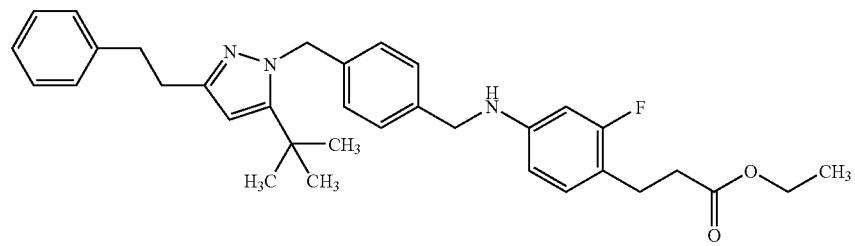

In the same manner as in Example 108, the title compound was obtained as a yellow oil from 4-{[5-tert-butyl-3-(2-phenylethyl)-1H-pyrazol-1-yl]methyl}benzaldehyde and ethyl 3-(4-amino-2-fluorophenyl)propanoate.

$^1$H NMR (CDCl$_3$) δ: 1.23 (3H, t, J=7.1 Hz), 1.35 (9H, s), 2.56 (2H, t, J=7.6 Hz), 2.87 (2H, t, J=7.6 Hz), 2.93-3.05 (4H, m), 4.12 (2H, q, J=7.2 Hz), 4.31 (2H, s), 5.65 (2H, s), 6.02 (1H, s), 6.46-6.56 (2H, m), 6.88 (2H, d, J=8.1 Hz), 7.05 (1H, s), 7.13-7.33 (8H, m).

Example 115

3-{4-[(4-{[5-tert-butyl-3-(2-phenylethyl)-1H-pyrazol-1-yl]methyl}benzyl)amino]-2-fluorophenyl}propanoic acid

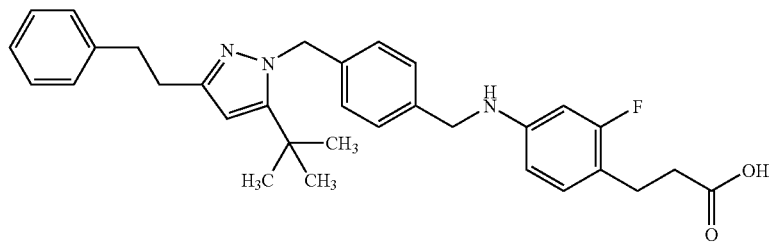

In the same manner as in Example 109, the title compound was obtained as a yellow oil from ethyl 3-{4-[(4-{[5-tert-butyl-3-(2-phenylethyl)-1H-pyrazol-1-yl]methyl}benzyl)amino]-2-fluorophenyl}propanoate. yield 49% (2 steps).

$^1$H NMR (CDCl$_3$) δ: 1.28 (9H, s), 2.59 (2H, t, J=7.5 Hz), 2.76-3.01 (6H, m), 4.24 (2H, s), 5.45 (2H, s), 5.88 (1H, s), 6.23-6.34 (2H, m), 6.95 (1H, t, J=8.7 Hz), 7.13-7.31 (10H, m).

Example 116 ethyl 3-[4-({[4'-(2-ethoxyethoxy)-2',6'-dimethylbiphenyl-3-yl]methyl}amino)phenyl]-2,2-difluoropropanoate

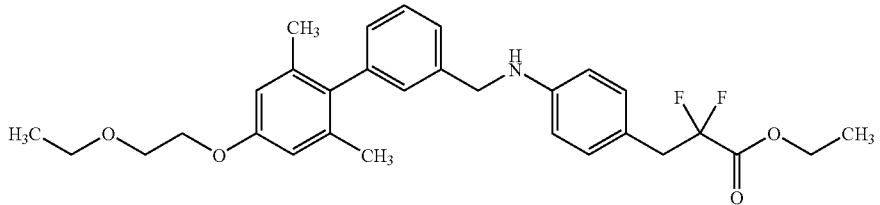

In the same manner as in Example 97, the title compound was obtained as a colorless oil from 4'-(2-ethoxyethoxy)-2',6'-dimethylbiphenyl-3-carbaldehyde and ethyl 3-(4-aminophenyl)-2,2-difluoropropanoate. yield 90%.

MS m/z 512 (MH$^+$).

Example 117

3-[4-({[4'-(2-ethoxyethoxy)-2',6'-dimethylbiphenyl-3-yl]methyl}amino)phenyl]-2,2-difluoropropanoic acid

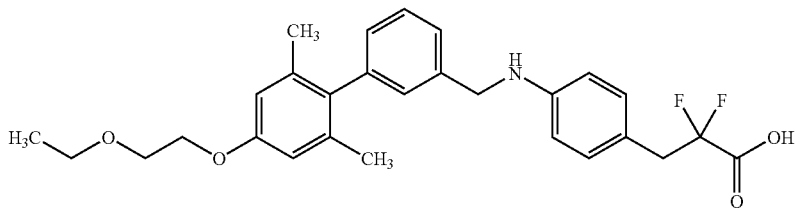

A mixture of ethyl 3-[4-({[4'-(2-ethoxyethoxy)-2',6'-dimethylbiphenyl-3-yl]methyl}amino)phenyl]-2,2-difluoropropanoate (665 mg, 1.30 mmol), tetrahydrofuran (15 mL), ethanol (10 mL), water (10 mL) and lithium hydroxide monohydrate (162 mg, 3.89 mmol) was stirred at room temperature for 3 hr. The reaction mixture was neutralized with 1 M hydrochloric acid, and the mixture was extracted with ethyl acetate. The organic layer was washed with saturated brine, dried over anhydrous magnesium sulfate, and the solvent was evaporated under reduced pressure. The residue was purified by silica gel column chromatography (20%-100% ethyl acetate/hexane), and the residue was recrystallized from ethyl acetate-hexane to give the title compound (415 mg, yield 66%) as colorless crystals.

MS m/z 484 (MH$^+$).

Example 118 methyl 3-[6-({[4'-(2-ethoxyethoxy)-2',6'-dimethylbiphenyl-3-yl]methyl}amino)pyridin-3-yl]propanoate

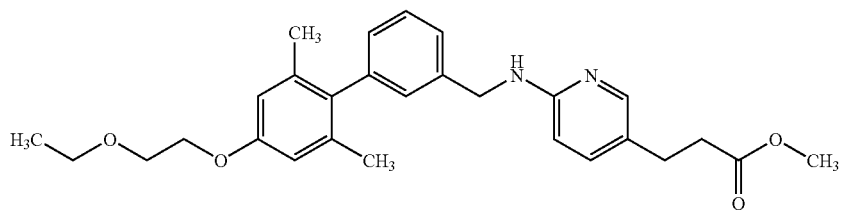

In the same manner as in Example 97, the title compound was obtained as a colorless oil from 4'-(2-ethoxyethoxy)-2',6'-dimethylbiphenyl-3-carbaldehyde and methyl 3-(6-aminopyridin-3-yl)propanoate. yield 83%.
MS m/z 463 (MH+).

Example 119

3-[6-({[4'-(2-ethoxyethoxy)-2',6'-dimethylbiphenyl-3-yl]methyl}amino)pyridin-3-yl]propanoic acid

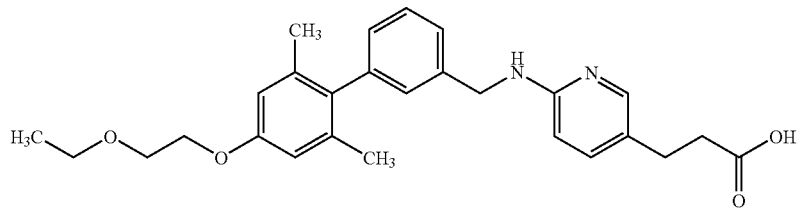

In the same manner as in Example 117, the title compound was obtained as a colorless oil from methyl 3-[6-({[4'-(2-ethoxyethoxy)-2',6'-dimethylbiphenyl-3-yl]methyl}amino)pyridin-3-yl]propanoate. yield 83%.
MS m/z 449 (MH+).

Example 120

3-[6-({[4'-(2-ethoxyethoxy)-2',6'-dimethylbiphenyl-3-yl]methyl}amino)pyridin-3-yl]propanoic acid methanesulfonate

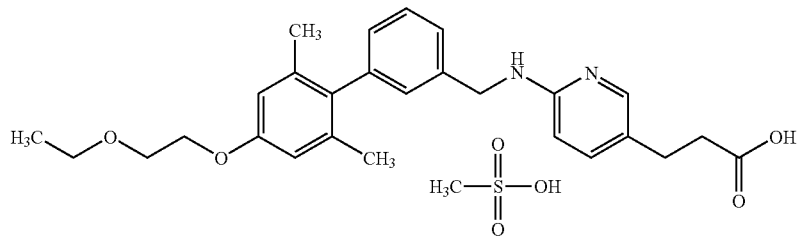

To a solution of 3-[6-({[4'-(2-ethoxyethoxy)-2',6'-dimethylbiphenyl-3-yl]methyl}amino)pyridin-3-yl]propanoic acid (0.729 g, 1.63 mmol) in diethyl ether (5 mL) and ethyl acetate (5 mL) was added methanesulfonic acid (0.157 g, 1.63 mmol), and the resulting crystals were washed with diethyl ether to give the title compound (0.740 g, yield 83%) as colorless crystals.

$^1$H NMR (CDCl$_3$) δ: 1.24 (3H, t, J=7.0 Hz), 1.94 (6H, s), 2.51 (2H, t, J=6.8 Hz), 2.79 (2H, t, J=6.7 Hz), 3.61 (2H, q, J=7.0 Hz), 3.76-3.82 (2H, m), 4.08-4.17 (2H, m), 4.44 (2H, s), 6.40 (1H, d, J=8.9 Hz), 6.66 (2H, s), 7.01 (1H, d, J=7.4 Hz), 7.07 (1H, s), 7.28 (1H, s), 7.34 (1H, d, J=7.5 Hz), 7.37-7.45 (1H, m), 7.90 (1H, d, J=1.9 Hz).

Example 121 ethyl 3-(4-{({2',6'-dimethyl-4'-[(methylsulfonyl)oxy]biphenyl-3-yl}methyl)[(2-nitrophenyl)sulfonyl]amino}-2-fluorophenyl)propanoate

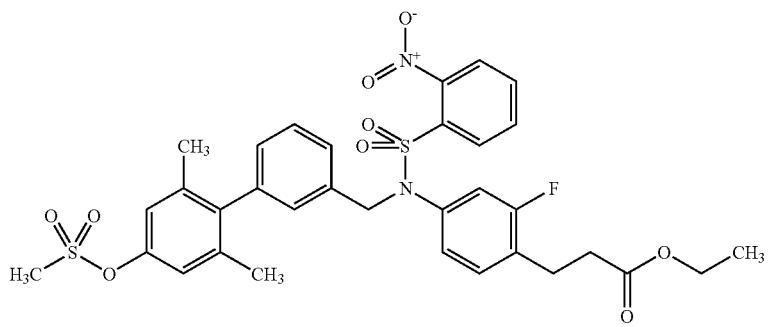

217

To an ice-cooled solution of ethyl 3-(2-fluoro-4-{[(4'-hydroxy-2',6'-dimethylbiphenyl-3-yl)methyl][(2-nitrophenyl)sulfonyl]amino}phenyl)propanoate (600 mg, 0.989 mmol) in pyridine (10 mL) was added dropwise methanesulfonyl chloride (227 mg, 1.98 mmol). The mixture was stirred at room temperature for 16 hr. To the mixture was added water, and the mixture was extracted with ethyl acetate. The extract was washed with saturated brine, dried over anhydrous magnesium sulfate, and concentrated under reduced pressure. The residue was purified by silica gel column chromatography (hexane/ethyl acetate=10/1-1/1) to give the title compound (670 mg, yield 98%) as a colorless oil.

$^1$H NMR (CDCl$_3$) δ: 1.17-1.29 (3H, m), 1.89 (6H, s), 2.53 (2H, t, J=7.7 Hz), 2.88 (2H, t, J=7.5 Hz), 3.18 (3H, s), 4.05-4.16 (2H, m), 4.94 (2H, s), 6.72-6.82 (2H, m), 6.90-7.09 (5H, m), 7.23-7.31 (1H, m), 7.36 (1H, t, J=7.5 Hz), 7.48-7.74 (4H, m).

Example 122 ethyl 3-{4-[({2',6'-dimethyl-4'-[(methylsulfonyl)oxy]biphenyl-3-yl}methyl)amino]-2-fluorophenyl}propanoate

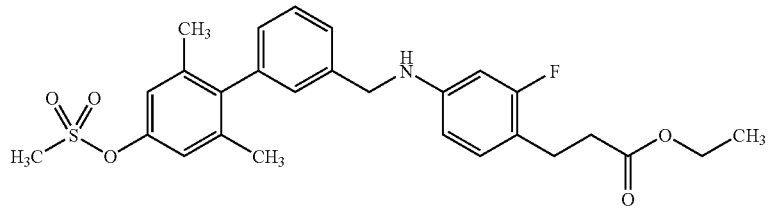

In the same manner as in Example 10, the title compound was obtained as a colorless oil from ethyl 3-(4-{({2',6'-dimethyl-4'-[(methylsulfonyl)oxy]biphenyl-3-yl}methyl)[(2-nitrophenyl)sulfonyl]amino}-2-fluorophenyl)propanoate. yield 52%.

MS m/z 500 (MH$^+$).

218

Example 123

3-{4-[({2',6'-dimethyl-4'-[(methylsulfonyl)oxy]biphenyl-3-yl}methyl)amino]-2-fluorophenyl}propanoic acid

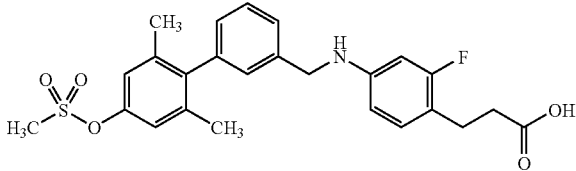

In the same manner as in Example 2, the title compound was obtained as a colorless oil from ethyl 3-{4-[({2',6'-dimethyl-4'-[(methylsulfonyl)oxy]biphenyl-3-yl}methyl)amino]-2-fluorophenyl}propanoate. yield 74%.

MS m/z 473 (MH$^+$).

Example 124 ethyl 3-[4-({[4'-(2-ethoxyethoxy)-2',6'-dimethylbiphenyl-3-yl]methyl}amino)-2-methylphenyl]propanoate

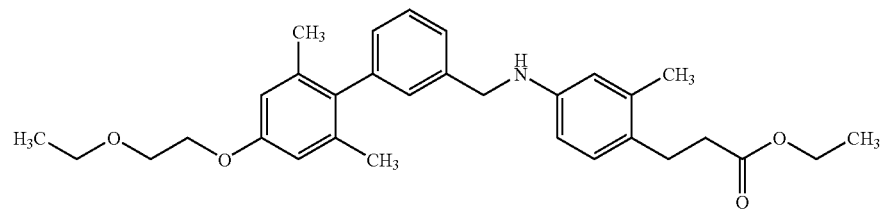

In the same manner as in Example 1, the title compound was obtained as a colorless oil from 4'-(ethoxyethoxy)-2',6'-dimethylbiphenyl-3-carbaldehyde and ethyl 3-(4-amino-2-methylphenyl)propanoate. yield 45%. MS m/z 490 (MH$^+$).

Example 125

3-[4-({[4'-(2-ethoxyethoxy)-2',6'-dimethylbiphenyl-3-yl]methyl}amino)-2-methylphenyl]propanoic acid methanesulfonate

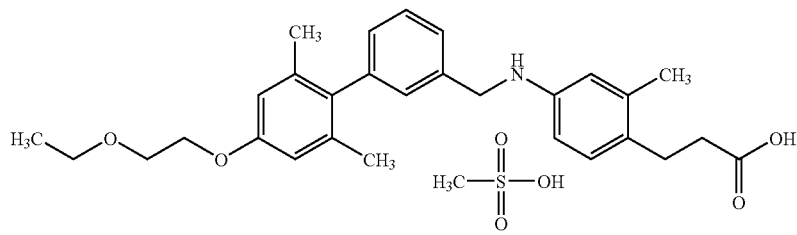

In the same manner as in Example 67, 3-[4-({[4'-(2-ethoxyethoxy)-2',6'-dimethylbiphenyl-3-yl]methyl}amino)-2-methylphenyl]propanoic acid was obtained as a pale-yellow oil from ethyl 3-[4-({[4'-(2-ethoxyethoxy)-2',6'-dimethylbiphenyl-3-yl]methyl}amino)-2-methylphenyl]propanoate. The obtained oil was dissolved in ethyl acetate (4 mL), and methanesulfonic acid (1 equivalent amount) was added to this solution. The solution was diluted with hexane, and the precipitated crystals were collected by filtration to give the title compound as pale-yellow crystals. yield 91%.
MS m/z 462 (MH$^+$).

Example 126 methyl 3-[4-({[4'-(2-ethoxyethoxy)-6-isopropoxybiphenyl-3-yl]methyl}amino)phenyl]propanoate

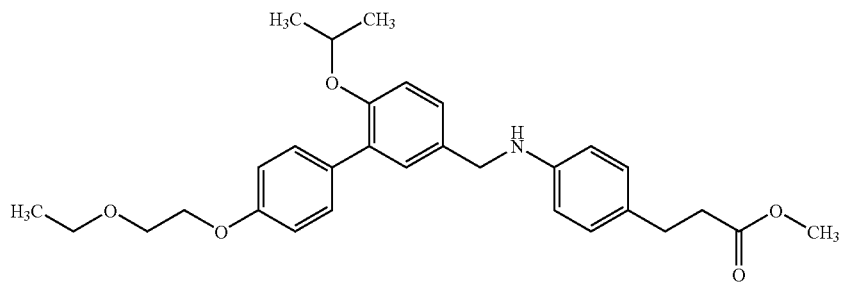

In the same manner as in Example 1, the title compound was obtained as a colorless oil from 4'-(2-ethoxyethoxy)-6-isopropoxybiphenyl-3-carbaldehyde and methyl 3-(4-aminophenyl)propanoate. yield 61%.
MS m/z 492 (MH$^+$).

Example 127

3-[4-({[4'-(2-ethoxyethoxy)-6-isopropoxybiphenyl-3-yl]methyl}amino)phenyl]propanoic acid

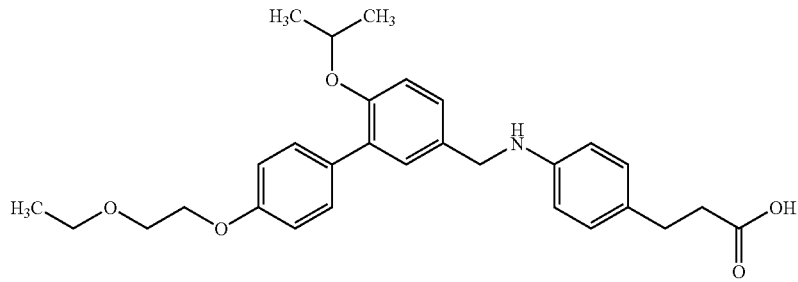

In the same manner as in Example 67, the title compound was obtained as a colorless oil from methyl 3-[4-({[4'-(2-ethoxyethoxy)-6-isopropoxybiphenyl-3-yl]methyl}amino)phenyl]propanoate. yield 90%.

MS m/z 478 (MH$^+$).

Example 128

2-[4-({[4'-(2-ethoxyethoxy)-2',6'-dimethylbiphenyl-3-yl]methyl}amino)phenoxy]-N-methoxy-N-methylacetamide

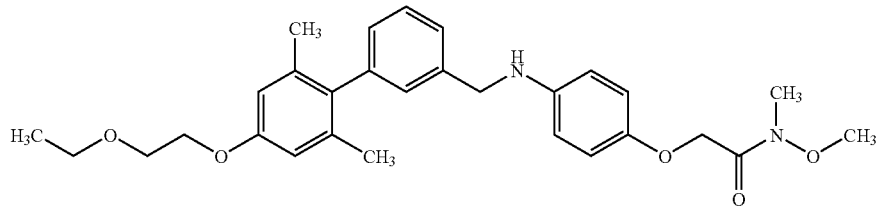

To a solution of [4-({[4'-(2-ethoxyethoxy)-2',6'-dimethylbiphenyl-3-yl]methyl}amino)phenoxy]acetic acid (0.22 g, 0.49 mmol), N,O-dimethylhydroxylamine hydrochloride (72 mg, 0.74 mmol), triethylamine (0.12 mL, 0.86 mmol) and 1-hydroxybenzotriazole (98 mg, 0.64 mmol) in N,N-dimethylformamide (15 mL) was added 1-ethyl-3-(3-dimethylaminopropyl)carbodiimide hydrochloride (122 mg, 0.64 mmol) under ice-cooling, and the mixture was stirred at room temperature for 18 hr. The reaction solution was diluted with ethyl acetate, washed successively with aqueous citric acid solution, water and aqueous sodium chloride solution, dried over magnesium sulfate, and concentrated under reduced pressure. The residue was purified by silica gel column chromatography (ethyl acetate:hexane=1:5-2:1) to give the title compound (160 mg, yield 66%) as a colorless oil.

MS m/z 493 (MH$^+$).

Example 129 ethyl 3-(2-fluoro-4-{[4-[(4-methylbenzyl)oxy]-3-(2-methylprop-2-en-1-yl)benzyl][(2-nitrophenyl)sulfonyl]amino}phenyl)propanoate

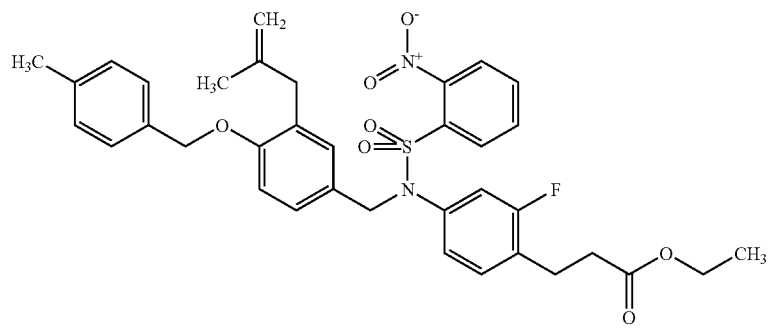

In the same manner as in Example 9, the title compound was obtained as a pale-brown oil from [4-[(4-methylbenzyl)oxy]-3-(2-methylprop-2-en-1-yl)phenyl]methanol and ethyl 3-(2-fluoro-4-{[(2-nitrophenyl)sulfonyl]amino}phenyl)propanoate. yield 98%.

MS APCI (−) 659 (M−H).

Example 130 ethyl 3-[2-fluoro-4-({3-isobutyl-4-[(4-methylbenzyl)oxy]benzyl}amino)phenyl]propanoate

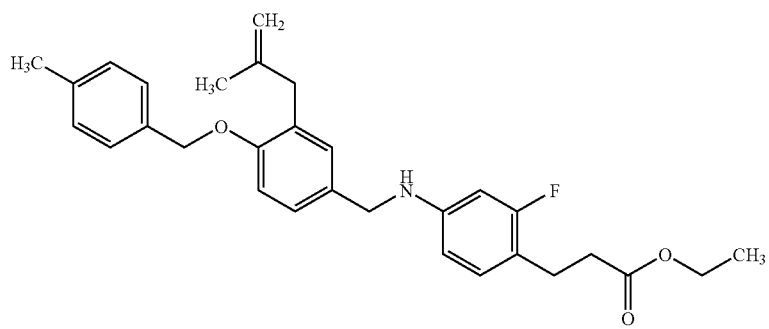

In the same manner as in Example 10, ethyl 3-(2-fluoro-4-{[4-[(4-methylbenzyl)oxy]-3-(2-methylprop-2-en-1-yl)benzyl]amino}phenyl)propanoate was obtained as a colorless oil from ethyl 3-(2-fluoro-4-{[4-[(4-methylbenzyl)oxy]-3-(2-methylprop-2-en-1-yl)benzyl][(2-nitrophenyl)sulfonyl]amino}phenyl)propanoate. The obtained oil (570 mg, 1.20 mmol) was dissolved in ethanol (30 mL), 10% palladium-carbon (50% water-containing product, 0.18 g) and 2,2'-bipyridyl (94 mg, 0.60 mmol) were added, and the mixture was stirred under a hydrogen atmosphere for 4 hr. The catalyst was filtered off, and the filtrate was concentrated under reduced pressure. The obtained residue was subjected to silica gel column chromatography (ethyl acetate:hexane=1:19-3:7) to give the title compound (457 mg, yield 56%, 2 steps) as a colorless oil.

MS m/z 478 (MH⁺).

Example 131

3-[2-fluoro-4-({3-isobutyl-4-[(4-methylbenzyl)oxy]benzyl}amino)phenyl]propanoic acid

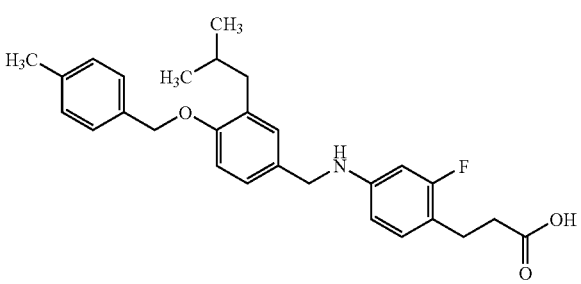

In the same manner as in Example 67, the title compound was obtained as colorless needle crystals from ethyl 3-[2-fluoro-4-({3-isobutyl-4-[(4-methylbenzyl)oxy]benzyl}amino)phenyl]propanoate. yield 80%.

MS APCI (−) 448 (M−H).

Example 132 ethyl 3-[2-fluoro-4-({[4'-(methoxymethoxy)-2',6'-dimethylbiphenyl-3-yl]methyl}amino)phenyl]propanoate

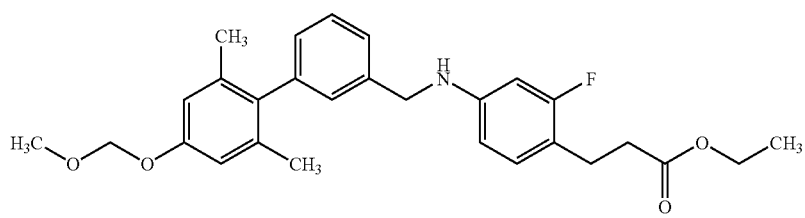

In the same manner as in Example 1, the title compound was obtained as a colorless oil from 4'-(methoxymethoxy)-2',6'-dimethylbiphenyl-3-carbaldehyde and ethyl 3-(4-amino-2-fluorophenyl)propanoate. yield 82%.

MS m/z 466 (MH$^+$).

Example 133

3-[2-fluoro-4-({[4'-(methoxymethoxy)-2',6'-dimethylbiphenyl-3-yl]methyl}amino)phenyl]propanoic acid

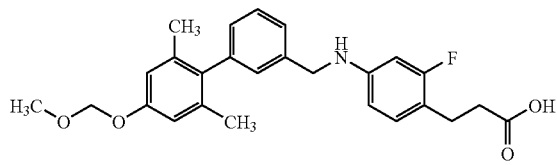

In the same manner as in Example 67, the title compound was obtained as a pale-yellow oil from ethyl 3-[2-fluoro-4-({[4'-(methoxymethoxy)-2',6'-dimethylbiphenyl-3-yl]methyl}amino)phenyl]propanoate. yield 17%.

MS m/z 438 (MH$^+$).

Example 134

3-(2-fluoro-4-{[(4'-hydroxy-2',6'-dimethylbiphenyl-3-yl)methyl]amino}phenyl)propanoic acid

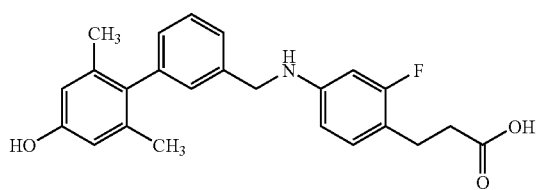

3-[2-Fluoro-4-({[4'-(methoxymethoxy)-2',6'-dimethylbiphenyl-3-yl]methyl}amino)phenyl]propanoic acid (1.0 g, 2.29 mmol) was dissolved in ethyl acetate (2 mL) and diethyl ether (4 mL). To this solution was added methanesulfonic acid (0.16 mL, 2.47 mmol) and the solution was concentrated under reduced pressure. Aqueous sodium hydrogencarbonate solution was added to the residue, and the mixture was extracted with ethyl acetate. The extract was dried over magnesium sulfate, concentrated under reduced pressure. The residue was purified by preparative HPLC to give the title compound (85 mg, yield 9%) as a colorless oil.

MS m/z 394 (MH$^+$).

Example 135 ethyl 3-(4-[({7-[4-(2-ethoxyethoxy)phenyl]-2,2-dimethyl-2,3-dihydro-1-benzofuran-5-yl}methyl)amino]-2-fluorophenyl)propanoate

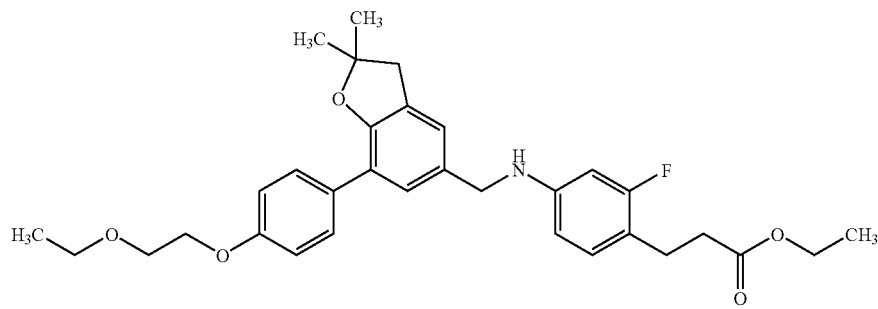

In the same manner as in Example 97, the title compound was obtained as a colorless oil from 7-[4-(2-ethoxyethoxy)phenyl]-2,2-dimethyl-2,3-dihydro-1-benzofuran-5-carbaldehyde and ethyl 3-(4-amino-2-fluorophenyl)propanoate. yield 100%.

$^1$H NMR (CDCl$_3$) δ: 1.23 (3H, t, J=7.2 Hz), 1.26 (3H, t, J=7.2 Hz), 1.50 (6H, s), 2.55 (2H, t, J=7.8 Hz), 2.85 (2H, t, J=7.8 Hz), 3.02 (2H, s), 3.61 (2H, q, J=7.2 Hz), 3.80 (2H, t, J=4.8 Hz), 3.95 (1H, br t, J=4.2 Hz), 4.11 (2H, q, J=7.2 Hz), 4.14 (2H, t, J=4.8 Hz), 4.19 (2H, br d, J=4.2 Hz), 6.30-6.40 (2H, m), 6.90-7.00 (3H, m), 7.05 (1H, d, J=1.5 Hz), 7.21 (1H, d, J=1.5 Hz), 7.63 (2H, d, J=9.0 Hz).

Example 136

3-{4-[({7-[4-(2-ethoxyethoxy)phenyl]-2,2-dimethyl-2,3-dihydro-1-benzofuran-5-yl}methyl)amino]-2-fluorophenyl}propanoic acid methanesulfonate

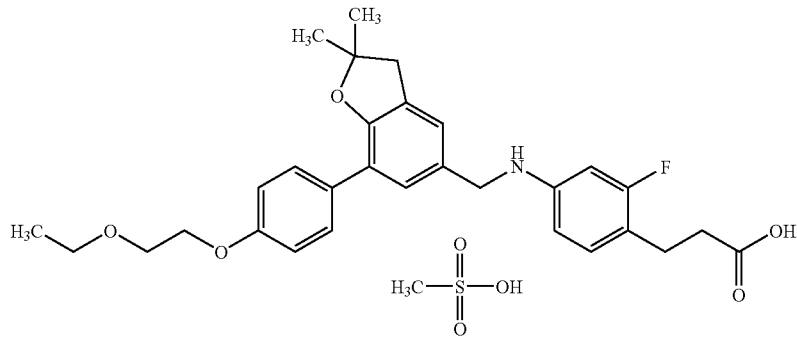

In the same manner as in Example 125, the title compound was obtained as pale-yellow crystals from ethyl 3-{4-[({7-[4-(2-ethoxyethoxy)phenyl]-2,2-dimethyl-2,3-dihydro-1-benzofuran-5-yl}methyl)amino]-2-fluorophenyl}propanoate. yield 87%.
MS APCI (−) 506 (M−H).

Example 137

3-[4-({3-[(dibenzylamino)methyl]-4-isobutoxybenzyl}amino)phenyl]propanoic acid trifluoroacetate

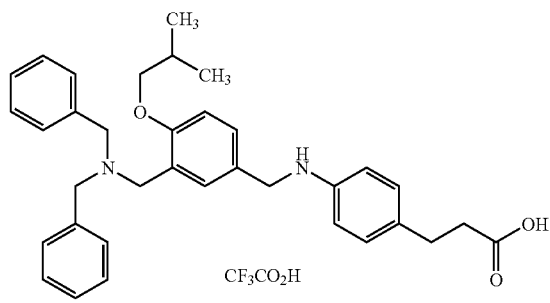

In the same manner as in Example 76, the title compound was obtained as a yellow powder from methyl 3-(4-{[(2-nitrophenyl)sulfonyl]amino}phenyl)propanoate and {3-[(dibenzylamino)methyl]-4-isobutoxyphenyl}methanol. yield 37% (3 steps). The present compound was purified by preparative HPLC (gradient cycle A).
MS (APCI−): 535 (M−H, as free form).

Example 138

3-[4-({3-[(2,2-dimethylquinolin-1(2H)-yl)methyl]-4-isobutoxybenzyl}amino)phenyl]propanoic acid

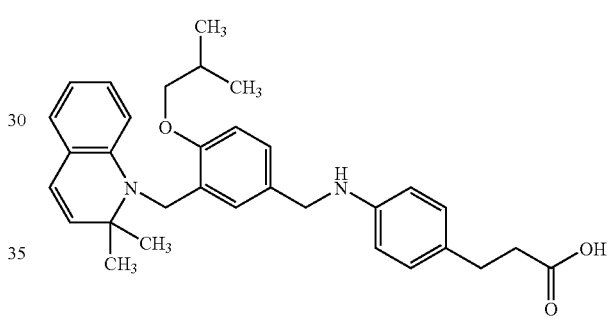

In the same manner as in Example 76, the title compound was obtained as a beige powder from methyl 3-(4-{[(2-nitrophenyl)sulfonyl]amino}phenyl)propanoate and {3-[(2,2-dimethylquinolin-1(2H)-yl)methyl]-4-isobutoxyphenyl}methanol. yield 39% (3 steps).
MS (APCI−): 497 (M−H).

Example 139 ethyl 3-(4-{[(4'-{[tert-butyl(dimethyl)silyl]oxy}-2',6'-dimethylbiphenyl-3-yl)methyl][(2-nitrophenyl)sulfonyl]amino}-2-fluorophenyl)propanoate

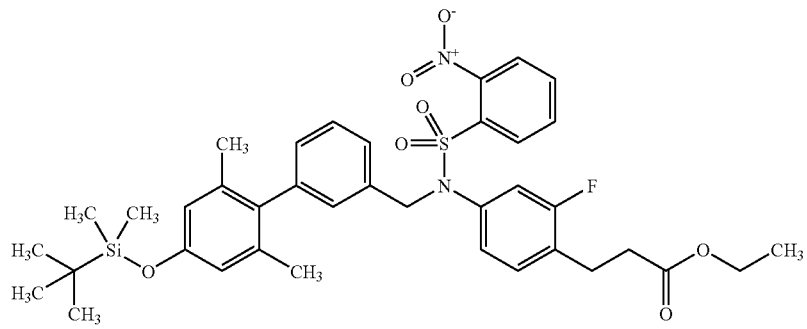

In the same manner as in Example 9, the title compound was obtained as an orange oil from ethyl 3-(2-fluoro-4-{[(2-nitrophenyl)sulfonyl]amino}phenyl)propanoate and (4'-{[tert-butyl(dimethyl)silyl]oxy}-2',6'-dimethylbiphenyl-3-yl)methanol. yield 100%.

$^1$H NMR (CDCl$_3$) δ: 0.22 (6H, s), 1.00 (9H, s), 1.21 (3H, t, J=7.2 Hz), 1.81 (6H, s), 2.53 (2H, t, J=7.8 Hz), 2.87 (2H, t, J=7.8 Hz), 4.10 (2H, q, J=7.2 Hz), 4.92 (2H, s), 6.54 (2H, s), 6.71-6.81 (2H, m), 6.90 (1H, s), 6.96-7.08 (2H, m), 7.22-7.36 (2H, m), 7.52 (1H, m), 7.60 (1H, m), 7.63-7.73 (2H, m).

Example 140 ethyl 3-(2-fluoro-4-{[(4'-hydroxy-2',6'-dimethylbiphenyl-3-yl)methyl][(2-nitrophenyl)sulfonyl]amino}phenyl)propanoate

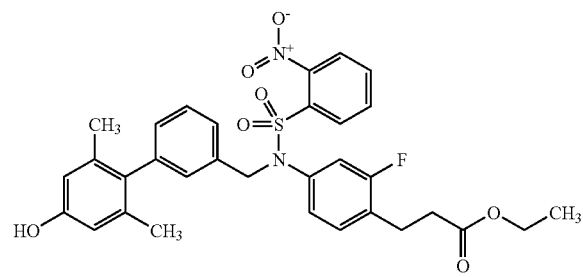

To a solution of ethyl 3-(4-{[(4'-{[tert-butyl(dimethyl)silyl]oxy}-2',6'-dimethylbiphenyl-3-yl)methyl][(2-nitrophenyl)sulfonyl]amino}-2-fluorophenyl)propanoate (6.32 g, 8.76 mmol) in tetrahydrofuran (60 mL) was added tetrabutylammonium fluoride (1 M solution, 9.64 mL, 9.64 mmol) under stirring at room temperature, and the mixture was stirred at room temperature for 2 hr. The reaction mixture was concentrated under reduced pressure. The residue was purified by silica gel column chromatography (hexane/ethyl acetate=10/1-hexane/ethyl acetate=1/1) to give the title compound (4.0 g, yield 75%) as colorless crystals.

$^1$H NMR (CDCl$_3$) δ: 1.21 (3H, t, J=7.2 Hz), 1.82 (6H, s), 2.53 (2H, t, J=7.8 Hz), 2.87 (2H, t, J=7.8 Hz), 4.10 (2H, q, J=7.2 Hz), 4.58 (1H, s), 4.93 (2H, s), 6.55 (2H, s), 6.71-6.81 (2H, m), 6.88 (1H, s), 6.96-7.09 (2H, m), 7.23-7.37 (2H, m), 7.52 (1H, m), 7.60 (1H, m), 7.64-7.73 (2H, m).

Example 141 tert-butyl 3-(4-{[(4'-{[tert-butyl(dimethyl)silyl]oxy}-2',6'-dimethylbiphenyl-3-yl)methyl][(2-nitrophenyl)sulfonyl]amino}-2-fluorophenyl)propanoate

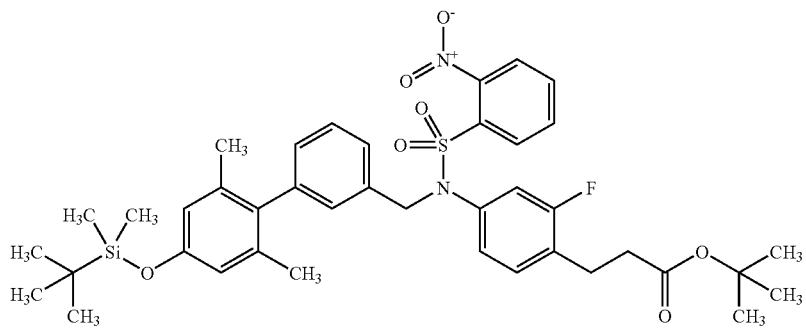

In the same manner as in Example 9, the title compound was obtained as a yellow oil from tert-butyl 3-(2-fluoro-4-{[(2-nitrophenyl)sulfonyl]amino}phenyl)propanoate and (4'-{[tert-butyl(dimethyl)silyl]oxy}-2',6'-dimethylbiphenyl-3-yl)methanol. yield 92%.

$^1$H NMR (CDCl$_3$) δ: 0.20-0.24 (6H, m), 0.96-1.02 (9H, m), 1.36-1.41 (9H, m), 1.81 (6H, s), 2.45 (2H, t, J=7.7 Hz, 2.89 (2H, t, J=7.7 Hz), 4.92 (2H, s), 6.54 (2H, s), 6.71-6.80 (2H, m), 6.90-7.07 (3H, m), 7.19-7.33 (2H, m), 7.46-7.54 (1H, m), 7.56-7.61 (1H, m), 7.63-7.72 (2H, m).

Example 142 tert-butyl 3-(2-fluoro-4-{[(4'-hydroxy-2',6'-dimethylbiphenyl-3-yl)methyl][(2-nitrophenyl)sulfonyl]amino}phenyl)propanoate

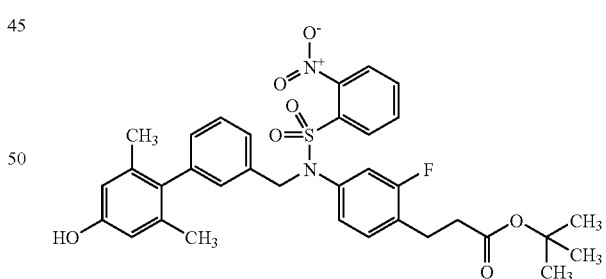

In the same manner as in Example 140, the title compound was obtained as a yellow oil from tert-butyl 3-(4-{[(4'-{[tert-butyl(dimethyl)silyl]oxy}-2',6'-dimethylbiphenyl-3-yl)methyl][(2-nitrophenyl)sulfonyl]amino}-2-fluorophenyl)propanoate. yield 79%.

$^1$H NMR (CDCl$_3$) δ: 1.39 (9H, s), 1.83 (6H, s), 2.45 (2H, t, J=7.8 Hz), 2.82 (2H, t, J=7.8 Hz), 4.70 (1H, s), 4.93 (2H, s), 6.55 (2H, s), 6.71-6.81 (2H, m), 6.90 (1H, s), 6.96-7.07 (2H, m), 7.23 (1H, m), 7.31 (1H, t, J=7.5 Hz), 7.50 (1H, m), 7.59 (1H, m), 7.63-7.72 (2H, m).

Example 143 tert-butyl 3-(4-{({4'-[2-(ethylthio)ethoxy]-2',6'-dimethylbiphenyl-3-yl}methyl)[(2-nitrophenyl)sulfonyl]amino}-2-fluorophenyl)propanoate

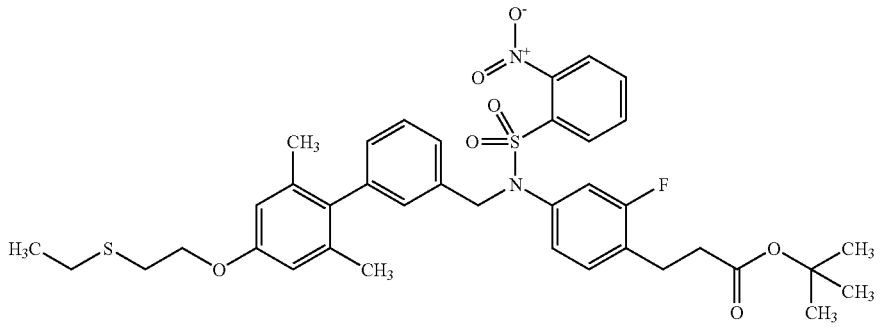

To a solution of tert-butyl 3-(2-fluoro-4-{[(4'-hydroxy-2',6'-dimethylbiphenyl-3-yl)methyl][(2-nitrophenyl)sulfonyl]amino}phenyl)propanoate (2.0 g, 3.15 mmol), 2-(ethylthio)ethanol (0.37 mL, 3.47 mmol) and tributylphosphine (1.18 mL, 4.73 mmol) in tetrahydrofuran (40 mL) was added 1,1'-(azodicarbonyl)dipiperidine (1.19 g, 4.73 mmol) under stirring at room temperature, and the mixture was stirred for 16 hr. To the reaction mixture were added reagents (2-(ethylthio)ethanol, tributylphosphine and 1,1'-(azodicarbonyl)dipiperidine) in a half amount as above, and the mixture was further stirred for 8 hr. The reaction mixture was diluted with diethyl ether, the insoluble material was filtered off, and the filtrate was concentrated under reduced pressure. The residue was purified by silica gel column chromatography (hexane/ethyl acetate=10/1-hexane/ethyl acetate=2/1) to give the title compound (1.96 g, yield 86%) as a yellow oil.

MS (ESI+): 723 (M+H).

To a solution of tert-butyl 3-(4-{({4'-[2-(ethylthio)ethoxy]-2',6'-dimethylbiphenyl-3-yl}methyl)[(2-nitrophenyl)sulfonyl]amino}-2-fluorophenyl)propanoate (1.96 g, 2.71 mmol) in dichloromethane (40 mL) was added m-chloroperbenzoic acid (70%, 1.47 g, 5.96 mmol) under stirring at 0° C., and the mixture was stirred at the same temperature for 2 hr. The reaction mixture was washed with 1 M aqueous sodium hydroxide solution and saturated brine, dried over anhydrous magnesium sulfate, and concentrated under reduced pressure. The residue was purified by silica gel column chromatography (hexane/ethyl acetate=2/1-hexane/ethyl acetate=1/2) to give the title compound (1.67 g, yield 81%) as a pale-yellow oil.

$^1$H NMR (CDCl$_3$) δ: 1.38 (9H, s), 1.47 (3H, t, J=7.5 Hz), 1.87 (6H, s), 2.46 (2H, t, J=7.8 Hz), 2.83 (2H, t, J=7.8 Hz), 3.18 (2H, q, J=7.5 Hz), 3.41 (2H, t, J=5.1 Hz), 4.43 (2H, t, J=5.1 Hz), 4.93 (2H, s), 6.61 (2H, s), 6.72-6.81 (2H, m), 6.90-7.08 (3H, m), 7.20-7.36 (2H, m), 7.45-7.62 (2H, m), 7.64-7.73 (2H, m).

Example 144 tert-butyl 3-(4-{({4'-[2-(ethylsulfonyl)ethoxy]-2',6'-dimethylbiphenyl-3-yl}methyl)[(2-nitrophenyl)sulfonyl]amino}-2-fluorophenyl)propanoate

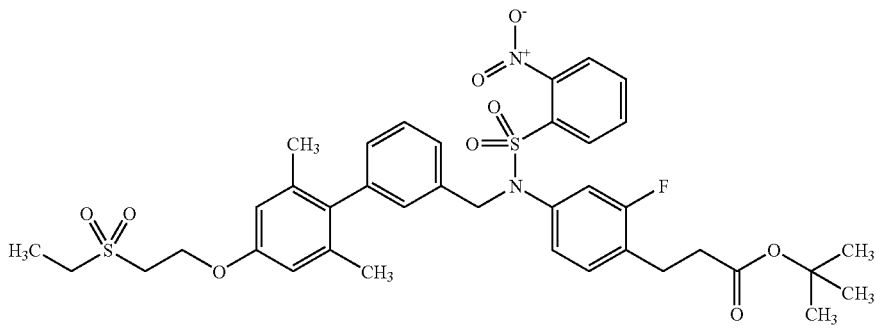

Example 145 tert-butyl 3-{4-[({4'-[2-(ethylsulfonyl)ethoxy]-2',6'-dimethylbiphenyl-3-yl}methyl)amino]-2-fluorophenyl}propanoate

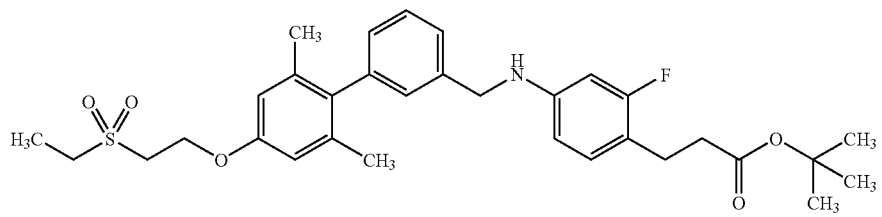

To a solution of tert-butyl 3-(4-{({4'-[2-(ethylsulfonyl)ethoxy]-2',6'-dimethylbiphenyl-3-yl}methyl)[(2-nitrophenyl)sulfonyl]amino}-2-fluorophenyl)propanoate (1.67 g, 2.21 mmol) and mercaptoacetic acid (0.51 mL, 6.64 mmol) in N,N-dimethylformamide (17 mL) was added lithium hydroxide monohydrate (0.56 g, 13.3 mmol) under stirring at room temperature, and the mixture was stirred at the same temperature for 2 hr. The reaction mixture was diluted with ethyl acetate, washed with saturated aqueous sodium hydrogencarbonate. and saturated brine, dried, and concentrated under reduced pressure. The residue was purified by silica gel column chromatography (hexane/ethyl acetate=4/1-hexane/ethyl acetate=1/1) to give the title compound (1.17 g, yield 93%) as a colorless oil.

MS (ESI+): 570 (M+H).

Example 146

3-{4-[({4'-[2-(ethylsulfonyl)ethoxy]-2',6'-dimethylbiphenyl-3-yl}methyl)amino]-2-fluorophenyl}propanoic acid methanesulfonate To a solution of tert-butyl 3-{4-[({4'-[2-(ethylsulfonyl)ethoxy]-2',6'-dimethylbiphenyl-3-yl}methyl)amino]-2-fluorophenyl}propanoate (1.17 g, 2.05 mmol) in toluene (20 mL) was added trifluoroacetic acid (20 mL) under stirring at 0° C., and the mixture was stirred at room temperature for 1.5 hr. The reaction mixture was concentrated under reduced pressure, the residue was neutralized with saturated aqueous sodium hydrogencarbonate, and extracted with ethyl acetate. The organic layer was washed with saturated brine, dried over anhydrous magnesium sulfate, and concentrated under reduced pressure. The residue was purified by silica gel column chromatography (hexane/ethyl acetate=2/1-hexane/ethyl acetate=1/4) to give a colorless oil. The obtained oil was diluted with ethyl acetate, and methanesulfonic acid (0.12 mL) was added. The precipitated crystals were collected by filtration, washed and dried to give the title compound (1.00 g, yield 80%) as colorless crystals.

MS (ESI+): 514 (M+H, as free form).

$^1$H NMR (CDCl$_3$) δ: 1.47 (3H, t, J=7.5 Hz), 1.84 (6H, s), 2.66 (2H, t, J=6.0 Hz), 2.80 (3H, s), 2.85 (2H, t, J=6.0 Hz), 3.17 (2H, q, J=7.5 Hz), 3.41 (2H, t, J=5.4 Hz), 4.42 (2H, t, J=5.4 Hz), 4.52 (2H, s), 6.60 (2H, s), 6.79-6.86 (2H, m), 7.02 (1H, dd, J=1.5, 7.8 Hz), 7.07-7.18 (2H, m), 7.34-7.45 (2H, m).

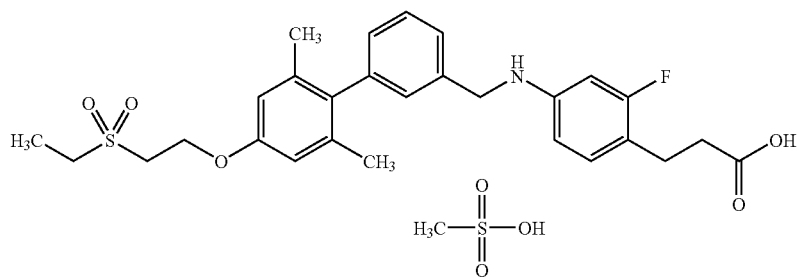

Example 147 ethyl 3-(4-{({2',6'-dimethyl-4'-[3-(2-oxopyrrolidin-1-yl)propoxy]biphenyl-3-yl}methyl)[(2-nitrophenyl)sulfonyl]amino}-2-fluorophenyl)propanoate

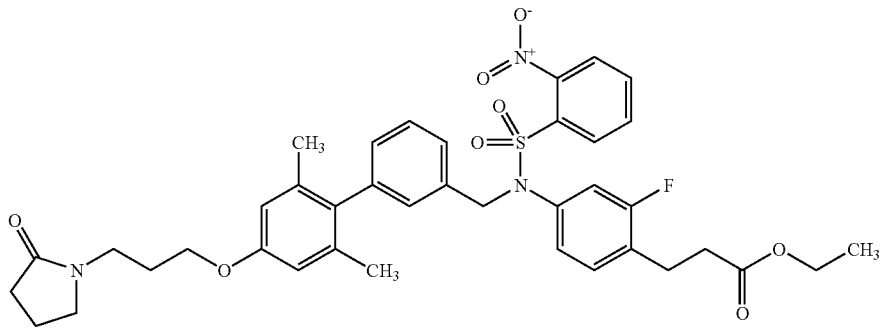

In the same manner as in Example 143, the title compound was obtained as a yellow oil from ethyl 3-(2-fluoro-4-{[(4'-hydroxy-2',6'-dimethylbiphenyl-3-yl)methyl][(2-nitrophenyl)sulfonyl]amino}phenyl)propanoate and 1-(3-hydroxypropyl)-2-pyrrolidone. yield 91%.
MS (ESI+): 732 (M+H).

Example 148 ethyl 3-{4-[({2',6'-dimethyl-4'-[3-(2-oxopyrrolidin-1-yl)propoxy]biphenyl-3-yl}methyl)amino]-2-fluorophenyl}propanoate

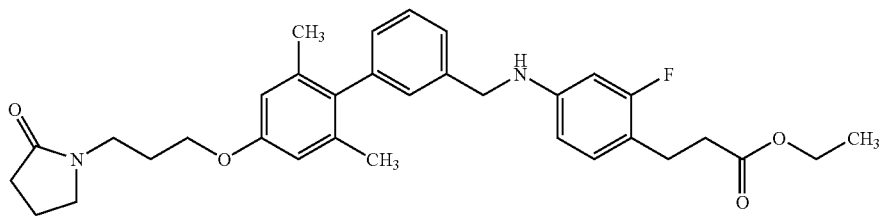

In the same manner as in Example 145, the title compound was obtained as a colorless oil from ethyl 3-(4-{({2',6'-dimethyl-4'-[3-(2-oxopyrrolidin-1-yl)propoxy]biphenyl-3-yl}methyl)[(2-nitrophenyl)sulfonyl]amino}-2-fluorophenyl)propanoate. yield 97%.
MS (ESI+): 547 (M+H).

Example 149

3-{4-[({2',6'-dimethyl-4'-[3-(2-oxopyrrolidin-1-yl)propoxy]biphenyl-3-yl}methyl)amino]-2-fluorophenyl}propanoic acid benzenesulfonate

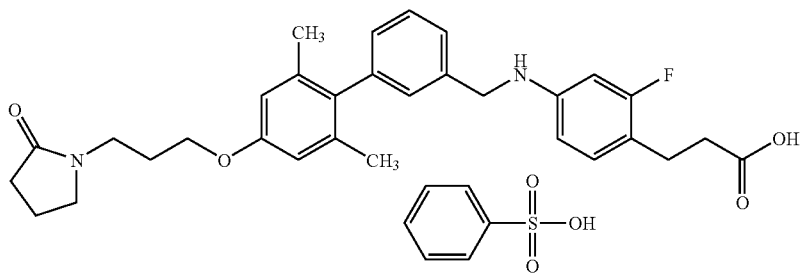

To a mixture of ethyl 3-{4-[({2',6'-dimethyl-4'-[3-(2-oxopyrrolidin-1-yl)propoxy]biphenyl-3-yl}methyl)amino]-2-fluorophenyl}propanoate (1.13 g, 2.07 mmol), methanol (5 mL) and tetrahydrofuran (10 mL) was added 1 M aqueous sodium hydroxide solution (4.14 mL), and the mixture was stirred at room temperature for 2 hr. The reaction mixture was neutralized with 1M hydrochloric acid, and diluted with ethyl acetate, and the organic layer was washed with saturated brine, dried, and concentrated under reduced pressure. The residue was purified by silica gel column chromatography (hexane/ethyl acetate=4/1-hexane/ethyl acetate=1/2) to give a colorless oil. The obtained oil was diluted with ethyl acetate, and benzenesulfonic acid was added. The precipitated crystals were collected by filtration, washed, and dried to give the title compound (0.78 g, yield 56%) as colorless crystals.

MS (ESI+): 519 (M+H, as free form).

$^1$H NMR (DMSO-$d_6$) δ: 1.83-1.99 (4H, m), 1.87 (6H, s), 2.21 (2H, t, J=8.1 Hz), 2.39 (2H, t, J=7.8 Hz), 2.64 (2H, t, J=7.8 Hz), 3.29-3.40 (4H, m), 3.94 (2H, t, J=6.3 Hz), 4.30 (2H, s), 6.25-6.42 (2H, m), 6.66 (2H, s), 6.87-7.00 (2H, m), 7.05 (1H, s), 7.25-7.42 (5H, m), 7.55-7.64 (2H, m).

Example 150 ethyl 3-(4-{({2',6'-dimethyl-4'-[(3-methyloxetan-3-yl)methoxy]biphenyl-3-yl}methyl)[(2-nitrophenyl)sulfonyl]amino}-2-fluorophenyl)propanoate

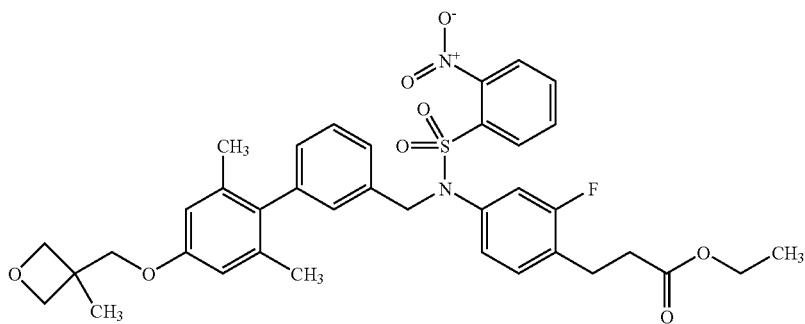

In the same manner as in Example 143, the title compound was obtained as a pale-yellow oil from ethyl 3-(2-fluoro-4-{[(4'-hydroxy-2',6'-dimethylbiphenyl-3-yl)methyl][(2-nitrophenyl)sulfonyl]amino}phenyl)propanoate and 3-methyl-3-oxetanemethanol. yield 61%.

MS (ESI+): 691 (M+H).

Example 151

3-{4-[({2',6'-dimethyl-4'-[(3-methyloxetan-3-yl)methoxy]biphenyl-3-yl}methyl)amino]-2-fluorophenyl}propanoic acid methanesulfonate

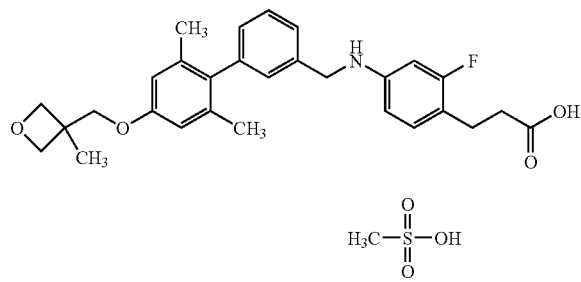

To a solution of ethyl 3-(4-{({2',6'-dimethyl-4'-[(3-methyloxetan-3-yl)methoxy]biphenyl-3-yl}methyl)[(2-nitrophenyl)sulfonyl]amino}-2-fluorophenyl)propanoate (0.33 g, 0.48 mmol) and mercaptoacetic acid (0.11 mL, 1.45 mmol) in N,N-dimethylformamide (2 mL) was added lithium hydroxide monohydrate (0.12 g, 2.90 mmol) under stirring at room temperature, and the mixture was stirred at the same temperature for 2 hr. The reaction mixture was diluted with ethyl acetate, washed with saturated aqueous sodium hydrogencarbonate and saturated brine, dried, and concentrated under reduced pressure. To a mixture of the residue, methanol (5 mL) and tetrahydrofuran (10 mL) was added 1 M aqueous sodium hydroxide solution (1.45 mL), and the mixture was stirred at room temperature for 2 hr. The reaction mixture was neutralized with 1M hydrochloric acid, and diluted with ethyl acetate, and the organic layer was washed with saturated brine, dried, and concentrated under reduced pressure. The residue was purified by silica gel column chromatography (hexane/ethyl acetate=2/1-hexane/ethyl acetate=1/4) to give a colorless oil (0.21 g). The obtained oil was diluted with ethyl acetate, and methanesulfonic acid was added. The precipitated crystals were collected by filtration, washed, and dried to give the title compound (0.23 g, yield 83%) as colorless crystals.

MS (ESI+): 478 (M+H, as free form).

Example 152 ethyl 3-{4-{(((2',6'-dimethyl-4'-[(5-methylisoxazol-3-yl)methoxy]biphenyl-3-yl}methyl)[(2-nitrophenyl)sulfonyl]amino}-2-fluorophenyl)propanoate

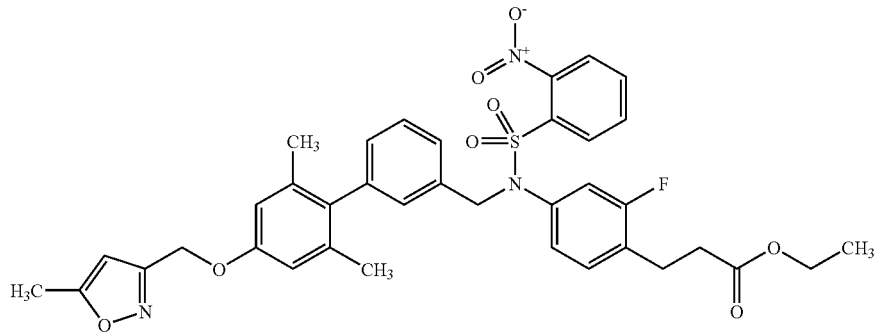

In the same manner as in Example 143, the title compound as obtained as a pale-yellow oil from ethyl 3-(2-fluoro-4-{[(4'-hydroxy-2',6'-dimethylbiphenyl-3-yl)methyl][(2-nitrophenyl)sulfonyl]amino}phenyl)propanoate and (5-methylisoxazol-3-yl)methanol. yield 85%.

MS (ESI+): 702 (M+H).

Example 153

3-{4-[({2',6'-dimethyl-4'-[(5-methylisoxazol-3-yl)methoxy]biphenyl-3-yl}methyl)amino]-2-fluorophenyl}propanoic acid methanesulfonate

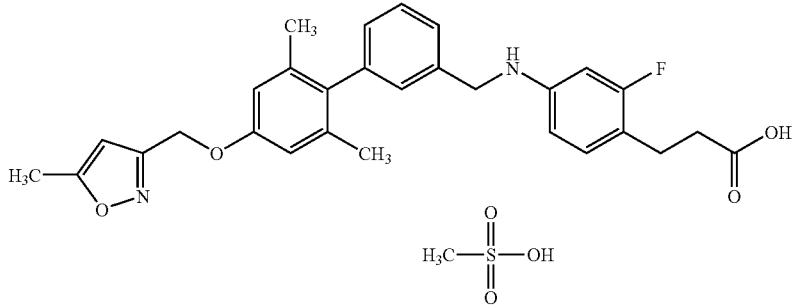

In the same manner as in Example 151, the title compound was obtained as colorless crystals from ethyl 3-(4-{({2',6'-dimethyl-4'-[(5-methylisoxazol-3-yl)methoxy]biphenyl-3-yl}methyl)[(2-nitrophenyl)sulfonyl]amino}-2-fluorophenyl)propanoate. yield 66%.
MS (ESI+): 489 (M+H, as free form).

Example 154 ethyl 3-(4-{({4'-[(3,5-dimethylisoxazol-4-yl)methoxy]-2',6'-dimethylbiphenyl-3-yl}methyl)[(2-nitrophenyl)sulfonyl]amino}-2-fluorophenyl)propanoate

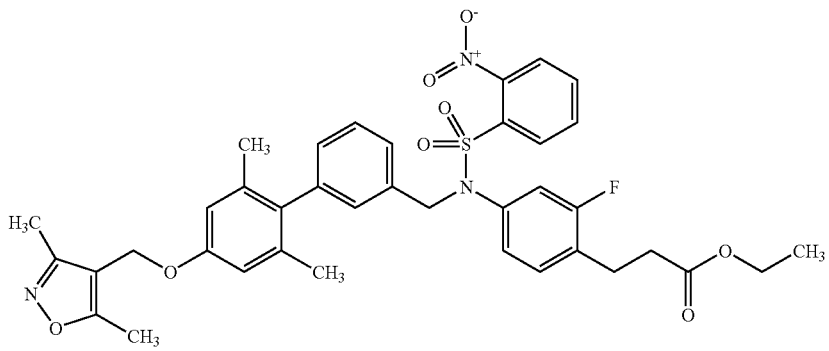

In the same manner as in Example 143, the title compound was obtained as a pale-yellow oil from ethyl 3-(2-fluoro-4-{[(4'-hydroxy-2',6'-dimethylbiphenyl-3-yl)methyl][(2-nitrophenyl)sulfonyl]amino}phenyl)propanoate and (3,5-dimethylisoxazol-4-yl)methanol. yield 85%.
MS (ESI+): 716 (M+H).

Example 155

3-{4-[({4'-[(3,5-dimethylisoxazol-4-yl)methoxy]-2',6'-dimethylbiphenyl-3-yl}methyl)amino]-2-fluorophenyl}propanoic acid benzenesulfonate

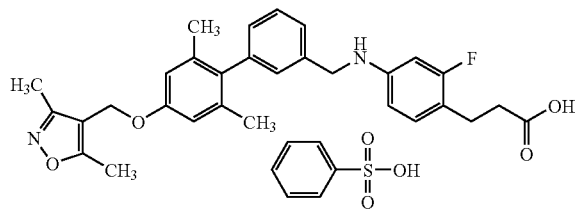

In the same manner as in Example 151, the title compound was obtained as colorless crystals from ethyl 3-(4-{({4'-[(3,5-dimethylisoxazol-4-yl)methoxy]-2',6'-dimethylbiphenyl-3-yl}methyl)[(2-nitrophenyl)sulfonyl]amino}-2-fluorophenyl)propanoate and benzenesulfonic acid. yield 44%.

MS (ESI+): 503 (M+H, as free form).

Example 156 ethyl 3-[4-({3-[(3,5-di-tert-butyl-1H-pyrazol-1-yl)methyl]-4-isobutoxybenzyl}amino)-2-fluorophenyl]propanoate

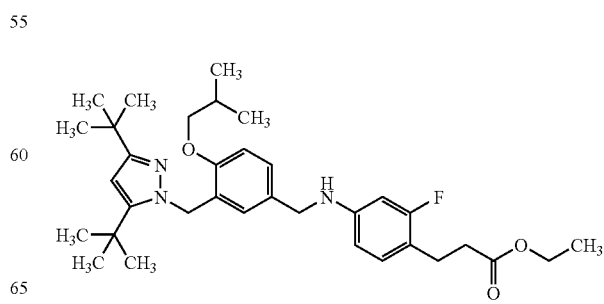

To a solution of 3-[(3,5-di-tert-butyl-1H-pyrazol-1-yl)methyl]-4-isobutoxybenzaldehyde (0.43 g, 1.16 mmol) and ethyl 3-(4-amino-2-fluorophenyl)propanoate (0.25 g, 1.16 mmol) in 1,2-dichloroethane (8.6 mL) was added acetic acid (0.20 mL, 3.48 mmol), and the mixture was stirred at room temperature for 3 hr. Sodium triacetoxyborohydride (0.74 g, 3.48 mmol) was added, and the mixture was further stirred for 5 hr. The reaction mixture was diluted with ethyl acetate, washed with saturated aqueous sodium hydrogencarbonate and saturated brine, dried, and concentrated under reduced pressure to give the title compound (0.62 g, yield 100%) as a colorless oil.
MS (ESI+): 566 (M+H).

Example 157

3-[4-({3-[(3,5-di-tert-butyl-1H-pyrazol-1-yl)methyl]-4-isobutoxybenzyl}amino)-2-fluorophenyl]propanoic acid

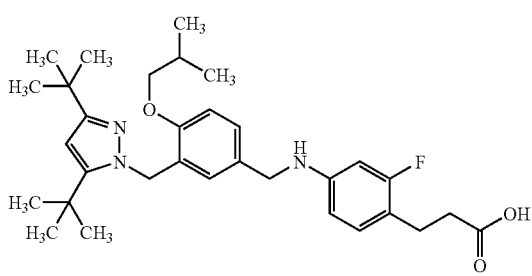

To a mixture of ethyl 3-[4-({3-[(3,5-di-tert-butyl-1H-pyrazol-1-yl)methyl]-4-isobutoxybenzyl}amino)-2-fluorophenyl]propanoate (0.62 g, 1.16 mmol), methanol (6 mL) and tetrahydrofuran (12 mL) was added 1 M aqueous sodium hydroxide solution (2.32 mL), and the mixture was stirred at room temperature for 2 hr. The reaction mixture was neutralized with 1M hydrochloric acid, and diluted with ethyl acetate, and the organic layer was washed with saturated brine, dried, and concentrated under reduced pressure. The residue was purified by silica gel column chromatography (hexane/ethyl acetate=4/1-hexane/ethyl acetate=1/4) to give the title compound (0.52 g, yield 83%) as colorless crystals.
MS (ESI+): 538 (M+H).

Example 158 ethyl 3-{4-[({2',6'-dimethyl-4'-[(6-methylpyridin-2-yl)oxy]biphenyl-3-yl}methyl)amino]-2-fluorophenyl}propanoate

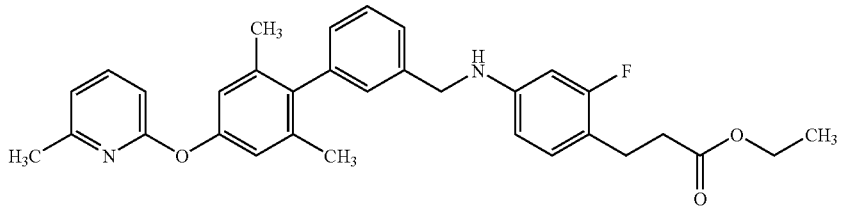

In the same manner as in Example 156, the title compound was obtained as a colorless oil from ethyl 3-(4-amino-2-fluorophenyl)propanoate and 2',6'-dimethyl-4'-[(6-methylpyridin-2-yl)oxy]biphenyl-3-carbaldehyde. yield 85%.
MS (ESI+): 513 (M+H).

Example 159

3-{4-[({2',6'-dimethyl-4'-[(6-methylpyridin-2-yl)oxy]biphenyl-3-yl}methyl)amino]-2-fluorophenyl}propanoic acid dihydrochloride

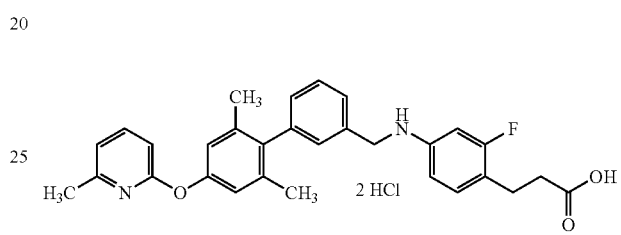

In the same manner as in Example 149, the title compound was obtained as colorless crystals from ethyl 3-{4-[({2',6'-dimethyl-4'-[(6-methylpyridin-2-yl)oxy]biphenyl-3-yl}methyl)amino]-2-fluorophenyl}propanoate and 4 M hydrogen chloride/ethyl acetate solution. yield 66%.

MS (ESI+): 485 (M+H, as free form).

Example 160 tert-butyl 3-(4-{{[4'-(2-ethoxyethoxy)-6-methoxy-2',6'-dimethylbiphenyl-3-yl]methyl}[(2-nitrophenyl)sulfonyl]amino}-2-fluorophenyl)propanoate

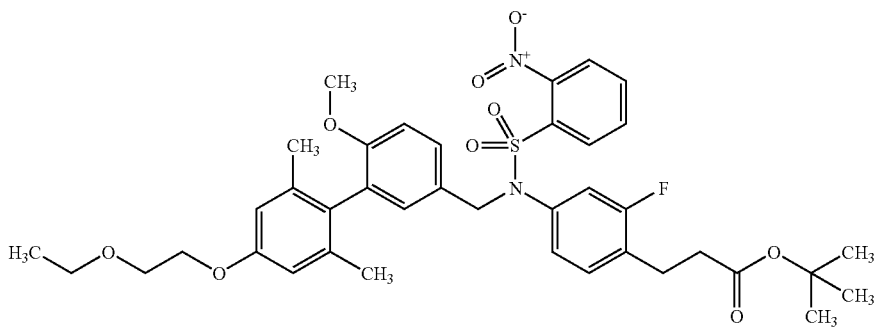

In the same manner as in Example 9, the title compound was obtained as a pale-yellow oil from [4'-(2-ethoxyethoxy)-6-methoxy-2',6'-dimethylbiphenyl-3-yl]methanol and tert-butyl 3-(2-fluoro-4-{[(2-nitrophenyl)sulfonyl]amino}phenyl)propanoate. yield 95%.

$^1$H NMR (CDCl$_3$) δ: 1.24 (3H, t, J=7.2 Hz), 1.39 (9H, s), 1.82 (6H, s), 2.46 (2H, t, J=7.8 Hz), 2.83 (2H, t, J=7.8 Hz), 3.60 (2H, q, J=7.2 Hz), 3.69 (3H, s), 3.78 (2H, t, J=5.4 Hz), 4.11 (2H, t, J=4.8 Hz), 4.82-4.89 (2H, m), 6.61-6.79 (5H, m), 6.86 (1H, d, J=8.7 Hz), 7.03 (1H, t, J=8.4 Hz), 7.20-7.30 (1H, m), 7.43-7.73 (4H, m).

Example 161 tert-butyl 3-[4-({[4'-(2-ethoxyethoxy)-6-methoxy-2',6'-dimethylbiphenyl-3-yl]methyl}amino)-2-fluorophenyl]propanoate

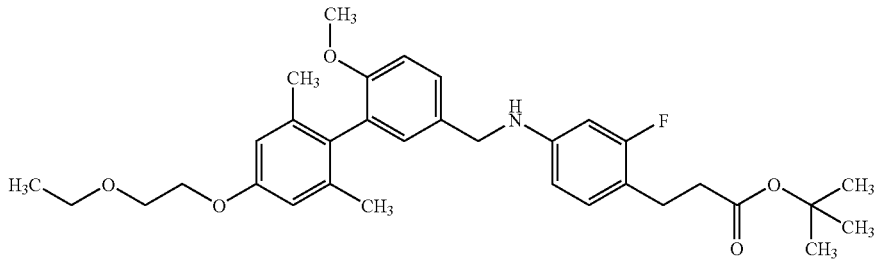

In the same manner as in Example 145, the title compound was obtained as a colorless oil from tert-butyl 3-(4-{{[4'-(2-ethoxyethoxy)-6-methoxy-2',6'-dimethylbiphenyl-3-yl]methyl}[(2-nitrophenyl)sulfonyl]amino}-2-fluorophenyl)propanoate. yield 76%.

$^1$H NMR (CDCl$_3$) δ: 1.24 (3H, t, J=6.9 Hz), 1.41 (9H, s), 1.96 (6H, s), 2.46 (2H, t, J=7.8 Hz), 2.79 (2H, t, J=7.8 Hz), 3.61 (2H, q, J=6.9 Hz), 3.72 (3H, s), 3.79 (2H, t, J=5.1 Hz), 4.12 (2H, t, J=5.1 Hz), 4.24 (2H, s), 6.24-6.36 (2H, m), 6.68 (2H, s), 6.89-7.02 (3H, m), 7.29 (1H, dd, J=2.4, 8.4 Hz).

Example 162

3-[4-({[4'-(2-ethoxyethoxy)-6-methoxy-2',6'-dimethylbiphenyl-3-yl]methyl}amino)-2-fluorophenyl]propanoic acid

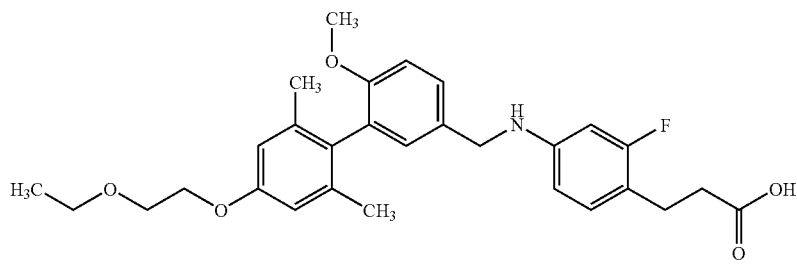

To a solution of tert-butyl 3-[4-({[4'-(2-ethoxyethoxy)-6-ethoxy-2',6'-dimethylbiphenyl-3-yl]methyl})amino)-2-fluorophenyl]propanoate (0.42 g, 0.76 mmol) in toluene (10 mL) was added trifluoroacetic acid (10 mL) under stirring at 0° C. and the mixture was stirred at room temperature for 1 hr. The reaction mixture was concentrated under reduced pressure, the residue was neutralized with saturated aqueous sodium hydrogencarbonate, and extracted with ethyl acetate. The organic layer was washed with saturated brine, dried over magnesium sulfate, and concentrated under reduced pressure. The residue was purified by silica gel column chromatography (hexane/ethyl acetate=3/1-hexane/ethyl acetate=1/2) to give the title compound (0.34 g, yield 91%) as a yellow oil.
MS (APCI−): 494 (M−H).

Example 163 ethyl 3-{2-fluoro-4-[({4'-[(6-methoxypyridin-2-yl)oxy]-2',6'-dimethylbiphenyl-3-yl}methyl)amino]phenyl}propanoate

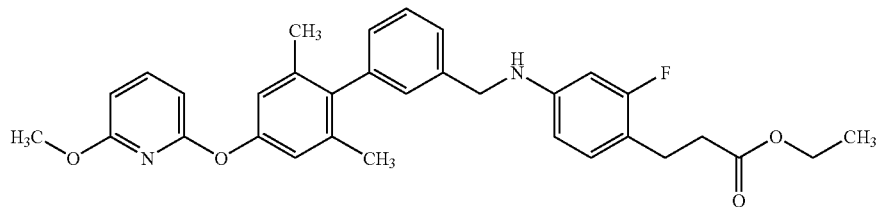

In the same manner as in Example 156, the title compound was obtained as a colorless oil from ethyl 3-(4-amino-2-fluorophenyl)propanoate and 4'-[(6-methoxypyridin-2-yl)oxy]-2',6'-dimethylbiphenyl-3-carbaldehyde. yield 28%.
MS (ESI+): 529 (M+H).

Example 164

3-{2-fluoro-4-[({4'-[(6-methoxypyridin-2-yl)oxy]-2',6'-dimethylbiphenyl-3-yl}methyl)amino]phenyl}propanoic acid dihydrochloride

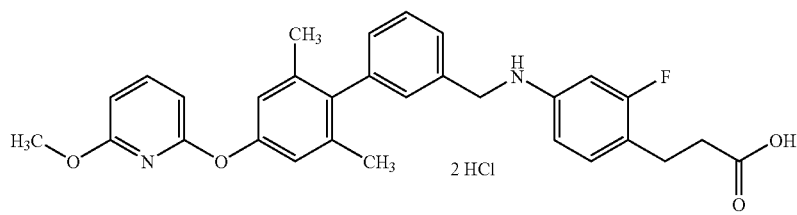

In the same manner as in Example 149, the title compound as obtained as colorless crystals from ethyl 3-{2-fluoro-4-[({4'-[(6-methoxypyridin-2-yl)oxy]-2',6'-dimethylbiphenyl-3-yl}methyl)amino]phenyl}propanoate and 4 M hydrogen chloride/ethyl acetate solution. yield 66%.

MS (ESI+): 501 (M+H, as free form).

Example 165 ethyl 3-(4-{[4-({3-tert-butyl-5-[(6-methylpyridin-2-yl)methoxy]-1H-pyrazol-1-yl}methyl)benzyl][(2-nitrophenyl)sulfonyl]amino}-2-fluorophenyl)propanoate

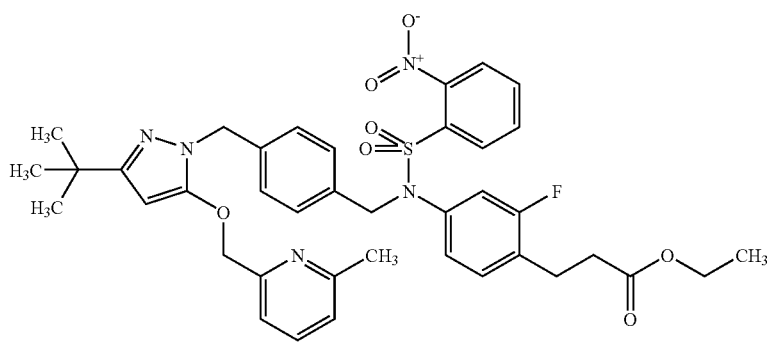

In the same manner as in Example 9, the title compound was obtained as a pale-yellow powder from [4-({3-tert-butyl-5-[(6-methylpyridin-2-yl)methoxy]-1H-pyrazol-1-yl}methyl)phenyl]methanol and ethyl 3-(2-fluoro-4-{[(2-nitrophenyl)sulfonyl]amino}phenyl)propanoate. yield 100%.

MS (ESI+): 744 (M+H).

Example 166 ethyl 3-(4-{[4-({3-tert-butyl-5-[(6-methylpyridin-2-yl)methoxy]-1H-pyrazol-1-yl}methyl)benzyl]amino}-2-fluorophenyl)propanoate

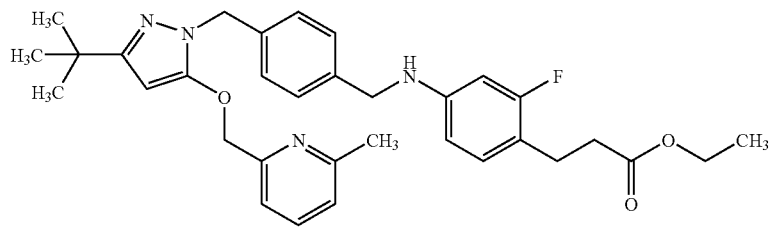

In the same manner as in Example 145, the title compound was obtained as a colorless oil from ethyl 3-(4-{[4-({3-tert-butyl-5-[(6-methylpyridin-2-yl)methoxy]-1H-pyrazol-1-yl}methyl)benzyl][(2-nitrophenyl)sulfonyl]amino}-2-fluorophenyl)propanoate. yield 88%.

MS (ESI+): 559 (M+H).

Example 167

3-(4-{[4-({3-tert-butyl-5-[(6-methylpyridin-2-yl)methoxy]-1H-pyrazol-1-yl}methyl)benzyl]amino}-2-fluorophenyl)propanoic acid dimethanesulfonate

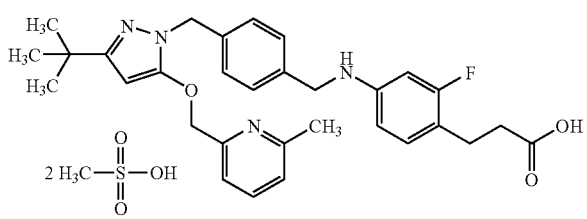

In the same manner as in Example 149, the title compound was obtained as a yellow powder from ethyl 3-(4-{[4-({3-tert-butyl-5-[(6-methylpyridin-2-yl)methoxy]-1H-pyrazol-1-yl}methyl)benzyl]amino}-2-fluorophenyl)propanoate and methanesulfonic acid. yield 66%.

MS (ESI+): 531 (M+H, as free form).

Example 168 tert-butyl 3-{4-[(4-{[3-tert-butyl-5-(phenoxymethyl)-1H-pyrazol-1-yl]methyl}benzyl)amino]-2-fluorophenyl}propanoate

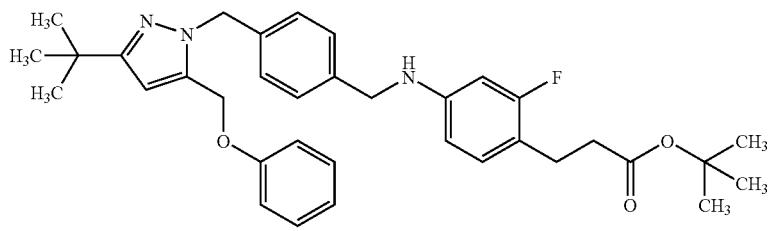

A solution of (4-{[3-tert-butyl-5-(phenoxymethyl)-1H-pyrazol-1-yl]methyl}phenyl)methanol (0.71 g, 2.0 mmol), tert-butyl 3-(2-fluoro-4-{[(2-nitrophenyl)sulfonyl]amino}phenyl)propanoate (0.77 g, 2.1 mmol) and triphenylphosphine (1.06 g, 4.04 mmol) in tetrahydrofuran (30 mL) was stirred under ice-cooling, and diethyl azodicarboxylate (40% toluene solution, 1.76 g, 4.04 mmol) was added. The mixture was allowed to warm to room temperature and stirred for 1 hr. The reaction mixture was concentrated under reduced pressure, and the residue was purified by silica gel column chromatography (30% ethyl acetate/hexane) to give an oil (1.70 g). To a solution of the obtained oil (1.70 g) and mercaptoacetic acid (0.42 mL, 6.0 mmol) in N,N-dimethylformamide (20 mL) was added lithium hydroxide monohydrate (0.50 g, 12 mmol), and the mixture was stirred overnight at room temperature. Ethyl acetate was added to the residue, and the mixture was washed with saturated aqueous sodium hydrogencarbonate and saturated brine, dried over anhydrous magnesium sulfate, and concentrated under reduced pressure. The residue was purified by silica gel column chromatography (20% ethyl acetate/hexane) to give the title compound (0.80 g, yield 70%, 2 steps) as a colorless oil.
$^1$H NMR (CDCl$_3$) δ: 1.33 (9H, s), 1.41 (9H, s), 2.41-2.52 (2H, m), 2.74-2.85 (2H, m), 4.04 (1H, br s), 4.24 (2H, br s), 4.83 (2H, s), 5.36 (2H, s), 6.20-6.35 (3H, m), 6.78-7.07 (6H, m), 7.20-7.32 (4H, m).

Example 169

3-{4-[(4-{[3-tert-butyl-5-(phenoxymethyl)-1H-pyrazol-1-yl]methyl}benzyl)amino]-2-fluorophenyl}propanoic acid dimethanesulfonate

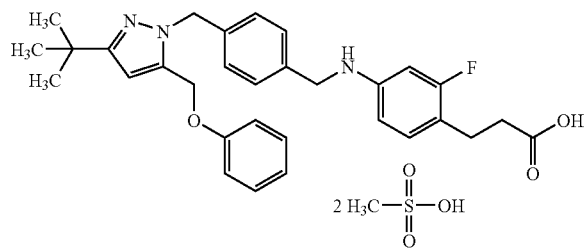

A mixture of tert-butyl 3-{4-[(4-{[3-tert-butyl-5-(phenoxymethyl)-1H-pyrazol-1-yl]methyl}benzyl)amino]-2-fluorophenyl}propanoate (0.80 g, 1.4 mmol) and 4 M hydrogen chloride/ethyl acetate solution (30 mL) was stirred overnight at room temperature. The reaction mixture was concentrated, and the residue was neutralized with saturated aqueous sodium hydrogencarbonate. The mixture was weakly acidified with 10% aqueous citric acid solution and extracted with ethyl acetate. The extract was washed with saturated brine, dried over anhydrous magnesium sulfate, and concentrated under reduced pressure. The residue was purified by silica gel column chromatography (70% ethyl acetate/hexane) to give a yellow oil (0.58 g). To a solution of the obtained oil (0.58 g) in ethyl acetate (20 mL) was added methanesulfonic acid (0.11 g, 1.1 mmol), and the precipitated crystals were collected by filtration to give the title compound (0.39 g, yield 39%) as colorless crystals.
mp 158-160° C.

Example 170 tert-butyl 3-{4-[(4-{[5-(benzyloxy)-3-tert-butyl-1H-pyrazol-1-yl]methyl}benzyl)amino]-2-fluorophenyl}propanoate

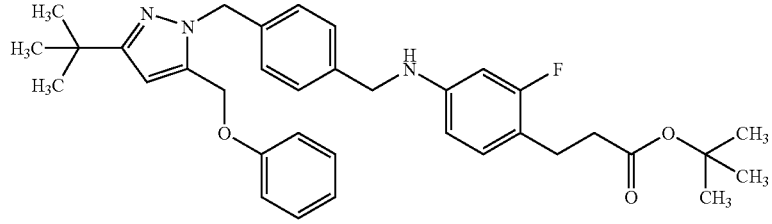

A solution of (4-{[5-(benzyloxy)-3-tert-butyl-1H-pyrazol-1-yl]methyl}phenyl)methanol (1.34 g, 3.82 mmol), tert-butyl 3-(2-fluoro-4-{[(2-nitrophenyl)sulfonyl]amino}phenyl)propanoate (1.45 g, 4.02 mmol) and triphenylphosphine (2.00 g, 7.63 mmol) in tetrahydrofuran (60 mL) was stirred under ice-cooling, and diethyl azodicarboxylate (40% toluene solution, 3.33 g, 7.65 mmol) was added. The mixture was allowed to warm to room temperature and stirred for 1 hr. The reaction mixture was concentrated under reduced pressure, and the residue was purified by silica gel column chromatography (30% ethyl acetate/hexane) to give an oil (2.74 g). To a solution of the obtained oil (2.74 g) and mercaptoacetic acid (0.80 mL, 12 mmol) in N,N-dimethylformamide (20 mL) was added lithium hydroxide monohydrate (0.96 g, 23 mmol), and the mixture was stirred overnight at room temperature. Ethyl acetate was added to the residue, and the mixture was washed with saturated aqueous sodium hydrogencarbonate and saturated brine, dried over anhydrous magnesium sulfate, and concentrated under reduced pressure. The residue was purified by silica gel column chromatography (20% ethyl acetate/hexane) to give the title compound (1.16 g, yield 53%, 2 steps) as a colorless oil.
$^1$H NMR (CDCl$_3$) δ: 1.28 (9H, s), 1.41 (9H, s), 2.40-2.52 (2H, m), 2.73-2.85 (2H, m), 4.02 (1H, br s), 4.24 (2H, br s), 5.00 (2H, s), 5.13 (2H, s), 5.47 (1H, s), 6.23-6.35 (2H, m), 6.89-7.37 (10H, m).

Example 171

3-{4-[(4-{[5-(benzyloxy)-3-tert-butyl-1H-pyrazol-1-yl]methyl}benzyl)amino]-2-fluorophenyl}propanoic acid dimethanesulfonate

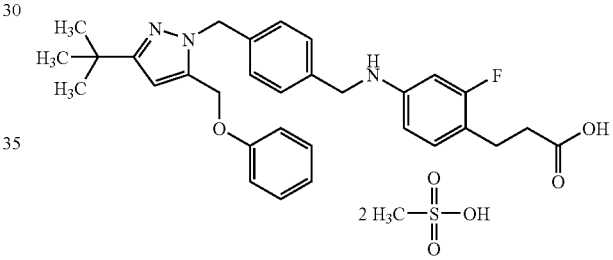

A mixture of tert-butyl 3-{4-[(4-{[5-(benzyloxy)-3-tert-butyl-1H-pyrazol-1-yl]methyl}benzyl)amino]-2-fluorophenyl}propanoate (1.16 g, 2.03 mmol) and 4 M hydrogen chloride/ethyl acetate solution (30 mL) was stirred overnight at room temperature. The reaction mixture was concentrated, and the residue was neutralized with saturated aqueous sodium hydrogencarbonate. The mixture was weakly acidified with 10% aqueous citric acid solution and extracted with ethyl acetate. The extract was washed with saturated brine, dried over anhydrous magnesium sulfate, and concentrated under reduced pressure. The residue was purified by silica gel column chromatography (70% ethyl acetate/

Example 173 ethyl 3-{2-fluoro-4-[({4'-[(3-methoxy-1-methyl-1H-pyrazol-5-yl)methoxy]-2',6'-dimethylbiphenyl-3-yl}methyl)amino]phenyl}propanoate

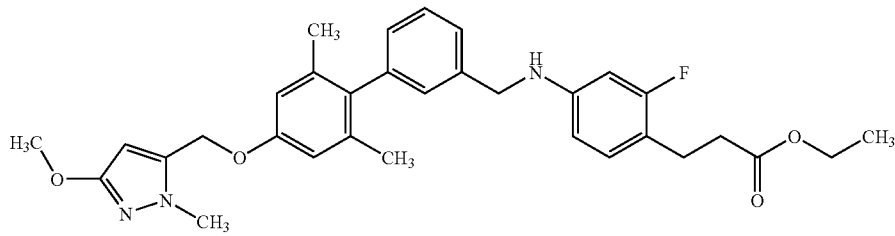

To a solution of ethyl 3-(2-fluoro-4-{[(4'-hydroxy-2',6'-dimethylbiphenyl-3-yl)methyl]amino}phenyl)propanoate (0.50 g, 1.2 mmol), (3-methoxy-1-methyl-1H-pyrazol-5-yl)methanol (0.17 g, 1.2 mmol) and tributylphosphine (0.59 mL, 2.4 mmol) in tetrahydrofuran (30 mL) was added 1,1'-(azodicarbonyl)dipiperidine (0.60 g, 2.4 mmol), and the mixture was stirred at room temperature for 2 hr. The reaction solution was concentrated, diisopropyl ether was added to the residue, and the resultant insoluble material was filtered off. The filtrate was concentrated and the residue was purified by silica gel column chromatography (40% ethyl acetate/hexane) to give the title compound (0.44 g, yield 68%) as a colorless oil.

$^1$H NMR (CDCl$_3$) δ: 1.23 (3H, t, J=7.1 Hz), 1.98 (6H, s), 2.50-2.60 (2H, m), 2.78-2.90 (2H, m), 3.77 (3H, s), 3.88 (3H, s), 4.04-4.20 (3H, s), 4.33 (2H, br s), 4.94 (2H, s), 5.73 (1H, s), 6.23-7.37 (2H, m), 6.71 (2H, s), 6.90-7.12 (3H, m), 7.26-7.45 (2H, m).

Example 174

3-{2-fluoro-4-[({4'-[(3-methoxy-1-methyl-1H-pyrazol-5-yl)methoxy]-2',6'-dimethylbiphenyl-3-yl}methyl)amino]phenyl}propanoic acid dimethanesulfonate

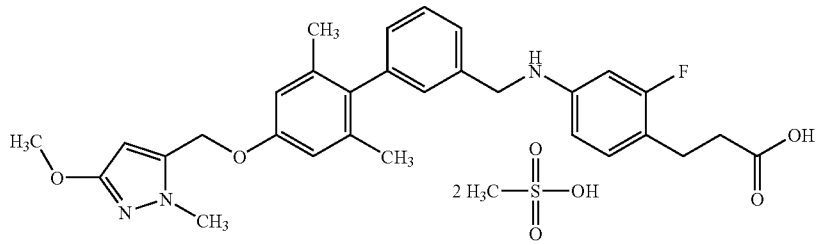

To a solution of ethyl 3-{2-fluoro-4-[({4'-[(3-methoxy-1-methyl-1H-pyrazol-5-yl)methoxy]-2',6'-dimethylbiphenyl-3-yl}methyl)amino]phenyl}propanoate (1.19 g, 2.18 mmol) in a mixture of methanol (6 mL) and tetrahydrofuran (6 mL) was added 1 M aqueous sodium hydroxide solution (4.4 mL), and the mixture was stirred at room temperature for 2 hr. Water was added to the reaction mixture, and the mixture was weakly acidified with 10% aqueous citric acid solution and

--- hexane) to give a yellow oil (0.58 g). To a solution of the obtained oil (0.58 g) in ethyl acetate (20 mL) was added methanesulfonic acid (0.18 g, 1.9 mmol), and the precipitated crystals were collected by filtration to give the title compound (0.53 g, yield 37%) as colorless crystals.

mp 151-153° C.

Example 172 ethyl 3-(2-fluoro-4-{[(4'-hydroxy-2',6'-dimethylbiphenyl-3-yl)methyl]amino}phenyl)propanoate

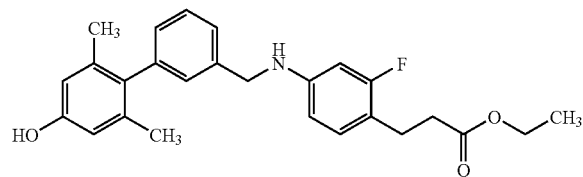

A mixture of 4'-hydroxy-2',6'-dimethylbiphenyl-3-carbaldehyde (1.05 g, 4.64 mmol), ethyl 3-(4-amino-2-fluorophenyl)propanoate. (1.00 g, 4.73 mol), acetic acid (0.80 mL, 14 mmol) and 1,2-dichloroethane (20 mL) was stirred at room temperature for 2 hr, and sodium triacetoxyborohydride (3.00 g, 14.2 mmol) was added. The mixture was stirred overnight at room temperature and concentrated. Ethyl acetate was added to the residue, and the mixture was washed with water and saturated brine, dried over anhydrous magnesium sulfate, and concentrated under reduced pressure. The mixture was purified by silica gel column chromatography (30% ethyl acetate/hexane) to give the title compound (1.29 g, yield 66%) as a yellow oil.

$^1$H NMR (CDCl$_3$) δ: 1.23 (3H, t, J=7.1 Hz), 1.95 (6H, s), 2.50-2.60 (2H, m), 2.77-2.90 (2H, m), 4.11 (2H, q, J=7.1 Hz), 4.32 (2H, s), 4.70 (1H, br s), 6.23-7.38 (2H, m), 6.58 (2H, s), 6.89-7.12 (3H, m), 7.26-7.43 (2H, m).

extracted with ethyl acetate. The extract was washed with saturated brine, dried over anhydrous magnesium sulfate, and concentrated under reduced pressure. The residue was purified by silica gel column chromatography (80% ethyl acetate/hexane) to give a colorless oil (1.35 g). To a solution of the obtained oil (1.35 g) in ethyl acetate (40 mL) was added methanesulfonic acid (0.42 g, 4.4 mmol), and the precipitated crystals were collected by filtration to give the title compound (1.38 g, yield 89%) as colorless crystals.

mp 129-130° C.

Example 175 tert-butyl 3-{4-[({2',6'-dimethyl-4'-[(2-methyl-1,3-thiazol-4-ylmethoxy)biphenyl-3-yl]methyl}amino)-2-fluoromethyl]propanoate hexane) to give the title compound (1.38 g, yield 79%, 2 steps) as a colorless oil.

¹H NMR (CDCl₃) δ: 1.41 (9H, s), 1.97 (6H, s), 2.40-2.52 (2H, m), 2.70-2.88 (5H, m), 4.10 (1H, br s), 4.32 (2H, br s), 5.16 (2H, s), 6.23-6.33 (2H, m), 6.74 (2H, s), 6.90-7.09 (3H, m), 7.26-7.43 (2H, m).

Example 176

3-{4-[({2',6'-dimethyl-4'-[(2-methyl-1,3-thiazol-4-yl)methoxy]biphenyl-3-yl}methyl)amino]-2-fluorophenyl}propanoic acid dibenzenesulfonate

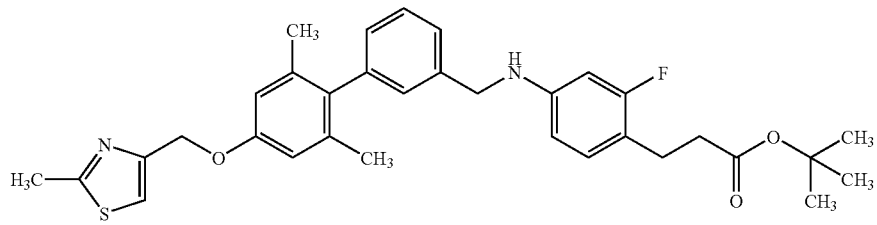

To a solution of tert-butyl 3-(2-fluoro-4-{[(4'-hydroxy-2',6'-dimethylbiphenyl-3-yl)methyl][(2-nitrophenyl)sulfonyl]amino}phenyl)propanoate (2.00 g, 3.15 mmol), (2-methyl-1,

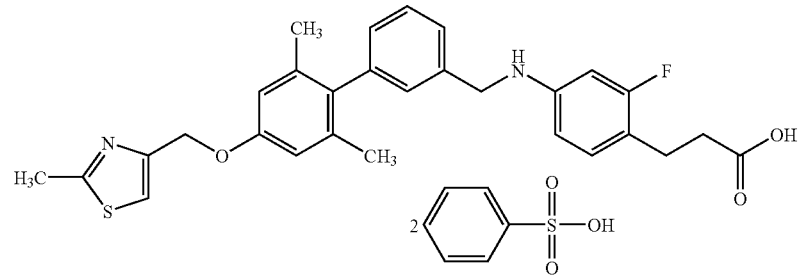

3-thiazol-4-yl)methanol (0.40 g, 3.1 mmol) and tributylphosphine (1.54 mL, 6.18 mmol) in tetrahydrofuran (50 mL) was added 1,1'-(azodicarbonyl)dipiperidine (1.56 g, 6.18 mmol), and the mixture was stirred at room temperature for 2 hr. The reaction solution was concentrated, and diisopropyl ether was added to the residue. The resultant insoluble material was filtered off and the filtrate was concentrated. The residue was purified by silica gel column chromatography (40% ethyl acetate/hexane) to give an oil (2.32 h). To a solution of the obtained oil (2.32 g) and mercaptoacetic acid (0.66 mL, 9.5 mmol) in N,N-dimethylformamide (15 mL) was added lithium hydroxide monohydrate (0.79 g, 19 mmol), and the mixture was stirred overnight at room temperature. Ethyl acetate was added to the residue, and the mixture was washed with saturated aqueous sodium hydrogencarbonate and saturated brine, dried over anhydrous magnesium sulfate, and concentrated under reduced pressure. The residue was purified by silica gel column chromatography (40% ethyl acetate/

A mixture of tert-butyl 3-{4-[({2',6'-dimethyl-4'-[(2-methyl-1,3-thiazol-4-yl)methoxy]biphenyl-3-yl}methyl)amino]-2-fluorophenyl}propanoate (1.38 g, 2.46 mmol), trifluoroacetic acid (6 mL) and toluene (6 mL) was stirred at room temperature for 2 hr. The reaction mixture was concentrated, and the residue was neutralized with saturated aqueous sodium hydrogencarbonate. The mixture was weakly acidified with 10% aqueous citric acid solution and extracted with ethyl acetate. The extract was washed with saturated brine, dried over anhydrous magnesium sulfate, and concentrated under reduced pressure. The residue was purified by silica gel column chromatography (80% ethyl acetate/hexane) to give a colorless oil (1.37 g). To a solution of the obtained oil (1.37 g) in ethyl acetate (20 mL) was added benzenesulfonic acid (0.47 g, 4.9 mmol), and the precipitated crystals were collected by filtration to give the title compound (1.11 g, yield 33%) as colorless crystals.

mp 103-105° C.

Example 177 ethyl 3-[4-({4-[(3,5-di-tert-butyl-1H-pyrazol-1-yl)methyl]benzyl}amino)-2-fluorophenyl]propanoate

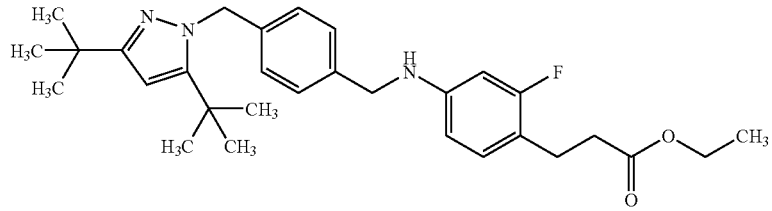

A solution of {4-[(3,5-di-tert-butyl-1H-pyrazol-1-yl)methyl]phenyl}methanol (0.70 g, 2.3 mmol), ethyl 3-(2-fluoro-4-{[(2-nitrophenyl)sulfonyl]amino}phenyl)propanoate (0.93 g, 2.3 mmol) and triphenylphosphine (1.22 g, 4.65 mmol) in tetrahydrofuran (20 mL) was stirred under ice-cooling, diethyl azodicarboxylate (40% toluene solution, 2.03 g, 4.66 mmol) was added, and the mixture was allowed to warm to room temperature and stirred for 1 hr. The reaction mixture was concentrated under reduced pressure, and the residue was purified by silica gel column chromatography (50% ethyl acetate/hexane) to give an oil (2.23 g). To a solution of the obtained oil (2.23 g) and mercaptoacetic acid (0.49 mL, 7.0 mmol) in N,N-dimethylformamide (15 mL) was added lithium hydroxide monohydrate (0.60 g, 14 mmol), and the mixture was stirred overnight at room temperature. Ethyl acetate was added to the residue, and the mixture was washed with saturated aqueous sodium hydrogencarbonate and saturated brine, dried over anhydrous magnesium sulfate, and concentrated under reduced pressure. The residue was purified by silica gel column chromatography (30% ethyl acetate/hexane) to give the title compound (0.96 g, yield 83%, 2 steps) as a colorless oil.

$^1$H NMR (CDCl$_3$) δ: 1.23 (3H, t, J=7.4 Hz), 1.25 (9H, s), 1.31 (9H, s), 2.50-2.60 (2H, m), 2.79-2.90 (2H, m), 4.11 (2H, q, J=7.4 Hz), 4.23 (2H, s), 5.45 (2H, s), 5.91 (1H, s), 6.22-7.35 (2H, m), 6.82-7.00 (3H, m), 7.20-7.27 (2H, m).

Example 178

3-[4-({4-[(3,5-di-tert-butyl-1H-pyrazol-1-yl)methyl]benzyl}amino)-2-fluorophenyl]propanoic acid

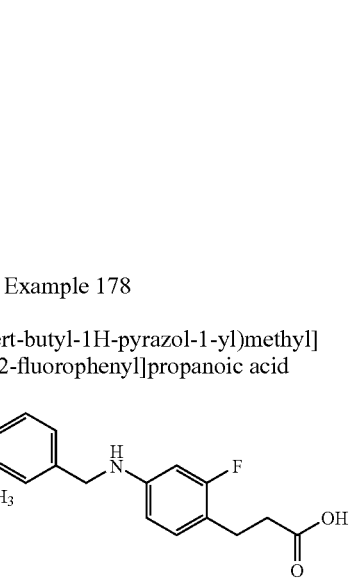

To a solution of ethyl 3-[4-({4-[(3,5-di-tert-butyl-1H-pyrazol-1-yl)methyl]benzyl}amino)-2-fluorophenyl]propanoate (0.96 g, 1.9 mmol) in a mixture of methanol (8 mL) and tetrahydrofuran (8 mL) was added 1 M aqueous sodium hydroxide solution (4.0 mL), and the mixture was stirred at 60° C. for 2 hr. Water was added to the reaction mixture, and the mixture was weakly acidified with 10% aqueous citric acid solution and extracted with ethyl acetate. The extract was washed with saturated brine, dried over anhydrous magnesium sulfate, and concentrated under reduced pressure. The residue was purified by silica gel column chromatography (60% ethyl acetate/hexane), and recrystallized from ethyl acetate-hexane to give the title compound (0.77 g, yield 89%) as colorless crystals.

mp 146-147° C.

Example 179 tert-butyl 3-(4-{({2',6'-dimethyl-4'-[2-(2-oxopyrrolidin-1-yl)ethoxy]biphenyl-3-yl}methyl)[(2-nitrophenyl)sulfonyl]amino}-2-fluorophenyl)propanoate

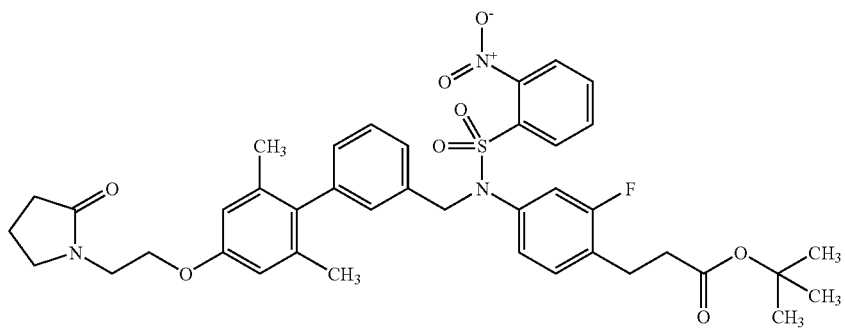

To a solution of tert-butyl 3-(2-fluoro-4-{[(4'-hydroxy-2',6'-dimethylbiphenyl-3-yl)methyl][(2-nitrophenyl)sulfonyl]amino}phenyl)propanoate (1.2 g, 1.89 mmol), 1-(2-hydroxyethyl)pyrrolidin-2-one (0.23 mL, 2.08 mmol) and tributylphosphine (0.75 mL, 2.84 mmol) in tetrahydrofuran (25 mL) was added 1,1'-(azodicarbonyl)dipiperidine (0.74 g, 2.84 mmol) under stirring at room temperature, and the mixture was stirred for 14 hr. The resulting precipitate was filtered off, and the filtrate was concentrated under reduced pressure. The residue was purified by silica gel column chromatography (hexane/ethyl acetate=10/1-ethyl acetate) to give the title compound (0.91 g, yield 65%) as a colorless oil.

MS m/z 746 (MH+).

Example 180 tert-butyl 3-{4-[({2',6'-dimethyl-4'-[2-(2-oxopyrrolidin-1-yl)ethoxy]biphenyl-3-yl}methyl)amino]-2-fluorophenyl}propanoate mixture was extracted with ethyl acetate. The extract was dried over anhydrous sodium sulfate, and concentrated under reduced pressure. The residue was purified by silica gel column chromatography (hexane/ethyl acetate-=5/1-ethyl acetate) to give the title compound (0.51 g, yield 74%) as a colorless amorphous powder.

$^1$H NMR (CDCl$_3$) δ: 1.41 (9H, s), 1.90-2.12 (8H, m), 2.34-2.54 (4H, m), 2.79 (2H, t, J=7.6 Hz), 3.61 (2H, t, J=7.1 Hz), 3.69 (2H, t, J=5.0 Hz), 4.12 (2H, t, J=5.0 Hz), 4.33 (2H, s), 6.23-6.40 (2H, m), 6.63 (2H, s), 6.94 (1H, t, J=8.5 Hz), 7.03 (1H, d, J=7.3 Hz), 7.09 (1H, s), 7.30 (1H, d, J=7.9 Hz), 7.38 (1H, t, J=7.4 Hz).

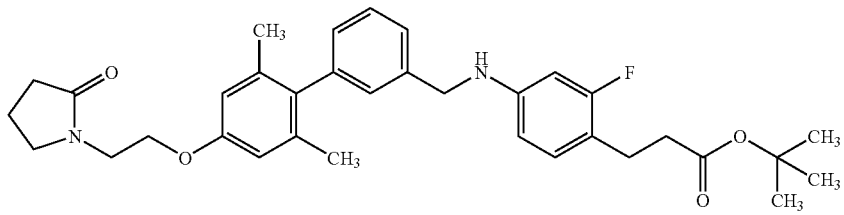

To a solution of tert-butyl 3-(4-{({2',6'-dimethyl-4'-[2-(2-oxopyrrolidin-1-yl)ethoxy]biphenyl-3-yl}methyl)[(2-nitrophenyl)sulfonyl]amino}-2-fluorophenyl)propanoate (0.91 g, 1.23 mmol) and mercaptoacetic acid (0.26 mL, 3.68 mmol) in N,N-dimethylformamide (9 mL) was added lithium hydroxide monohydrate (0.31 g, 7.38 mmol) under stirring at room temperature, and the mixture was stirred at the same temperature for 4 hr. The reaction mixture was concentrated under reduced pressure, and to the residue was added brine. The

Example 181

3-{4-[({2',6'-dimethyl-4'-[2-(2-oxopyrrolidin-1-yl)ethoxy]biphenyl-3-yl}methyl)amino]-2-fluorophenyl}propanoic acid methanesulfonate

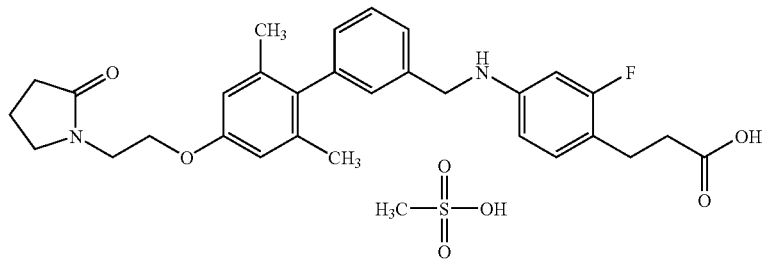

To a solution of tert-butyl 3-{4-[({2',6'-dimethyl-4'-[2-(2-oxopyrrolidin-1-yl)ethoxy]biphenyl-3-yl}methyl)amino]-2-fluorophenyl}propanoate (0.51 g, 0.91 mmol) in toluene (5 mL) was added trifluoroacetic acid (5 mL) under stirring at room temperature, and the mixture was stirred for 3 hr. The reaction mixture was concentrated under reduced pressure, and the residue was neutralized with saturated aqueous sodium hydrogencarbonate. The mixture was extracted with ethyl acetate. The organic layer was dried over anhydrous sodium sulfate, and concentrated under reduced pressure. The residue was purified by silica gel column chromatography (hexane/ethyl acetate=1/1-ethyl acetate-ethyl acetate/methanol=10/1) to give a colorless amorphous powder. The obtained amorphous powder was dissolved in ethyl acetate, and methanesulfonic acid (0.82 mL) was added. The precipitated crystals were collected by filtration, washed, and dried to give the title compound (0.44 g, yield 88%) as colorless crystals.

MS m/z 505 (MH$^+$, as free form).

Example 182 tert-butyl 3-(4-{({4'-[(2-ethoxyethyl)sulfonyl]-2',6'-dimethylbiphenyl-3-yl}methyl)[(2-nitrophenyl)sulfonyl]amino}-2-fluorophenyl)propanoate subjected to silica gel column chromatography (hexane/ethyl acetate=5/1-hexane/ethyl acetate=3/1) to give a mixture (1.96 g) of tert-butyl 3-(4-{({4'-[(2-ethoxyethyl)thio]-2',6'-dimethylbiphenyl-3-yl}methyl)[(2-nitrophenyl)sulfonyl]amino}-2-fluorophenyl)propanoate, {4'-[(2-ethoxyethyl)thio]-2',6'-dimethylbiphenyl-3-yl}methanol and tert-butyl 3-(2-fluoro-4-{[(2-nitrophenyl)sulfonyl]amino}phenyl)propanoate as a yellow oil. In the same manner as in Example 144, the title compound (1.25 g, yield 55%, 2 steps) was obtained as a colorless amorphous powder from the above-mentioned mixture (1.96 g).

$^1$H NMR (CDCl$_3$) δ: 1.09 (3H, t, J=7.0 Hz), 1.39 (9H, s), 1.96 (6H, s), 2.46 (2H, t, J=7.5 Hz), 2.83 (2H, t, J=7.5 Hz), 3.38-3.50 (4H, m), 3.82 (2H, t, J=6.2 Hz), 4.96 (2H, s), 6.71-6.86 (2H, m), 6.91-7.01 (2H, m), 7.05 (1H, t, J=8.0 Hz), 7.23-7.33 (1H, m), 7.37 (1H, t, J=7.6 Hz), 7.46-7.75 (6H, m).

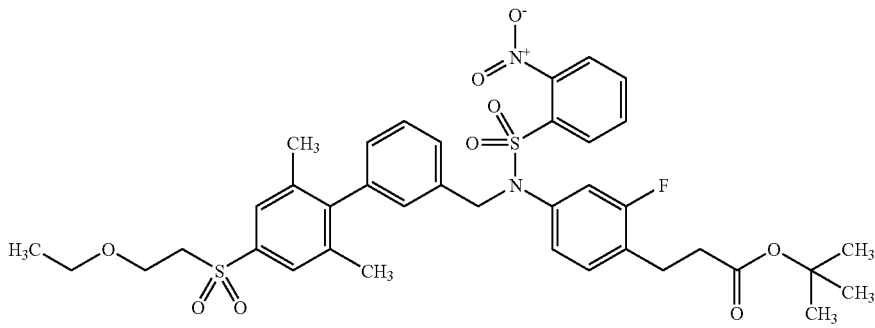

Example 183 tert-butyl 3-{4-[({4'-[(2-ethoxyethyl)sulfonyl]-2',6'-dimethylbiphenyl-3-yl}methyl)amino]-2-fluorophenyl}propanoate

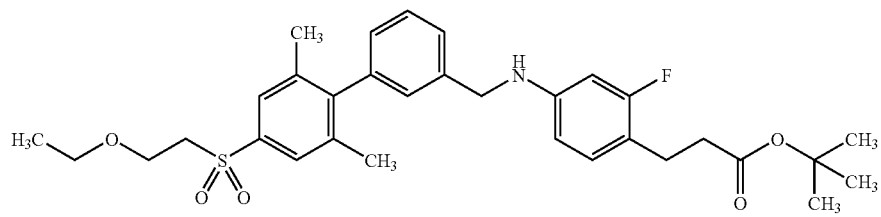

To a solution of {4'-[(2-ethoxyethyl)thio]-2',6'-dimethylbiphenyl-3-yl}methanol (0.94 g, 2.98 mmol), tert-butyl 3-(2-fluoro-4-{[(2-nitrophenyl)sulfonyl]amino}phenyl)propanoate (1.13 g, 3.13 mmol) and tributylphosphine (1.03 mL, 3.87 mmol) in tetrahydrofuran (25 mL) was added 1,1'-(azodicarbonyl)dipiperidine (1.01 g, 3.87 mmol) under stirring at room temperature, and the mixture was stirred for 3 days. The resulting precipitate was filtered off, and the filtrate was concentrated under reduced pressure. The residue was In the same manner as in Example 180, the title compound was obtained as a colorless amorphous powder from tert-butyl 3-(4-{({4'-[(2-ethoxyethyl)sulfonyl]-2',6'-dimethylbiphenyl-3-yl}methyl)[(2-nitrophenyl)sulfonyl]amino}-2-fluorophenyl)propanoate. yield 93%.

$^1$H NMR (CDCl$_3$) δ: 1.08 (3H, t, J=7.1 Hz), 1.41 (9H, s), 2.02-2.14 (6H, m), 2.46 (2H, t, J=7.7 Hz), 2.79 (2H, t, J=7.7 Hz), 3.37-3.52 (4H, m), 3.82 (2H, t, J=6.3 Hz), 4.36 (2H, s), 6.22-6.42 (2H, m), 6.90-7.04 (2H, m), 7.07 (1H, s), 7.33-7.41 (1H, m), 7.44 (1H, t, J=7.4 Hz), 7.63 (2H, s).

Example 184

3-{4-[({4'-[(2-ethoxyethyl)sulfonyl]-2',6'-dimethyl-biphenyl-3-yl}methyl)amino]-2-fluorophenyl}propanoic acid

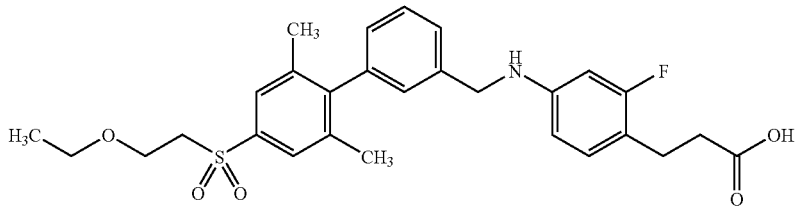

In the same manner as in Example 162, the title compound was obtained as a colorless amorphous powder from tert-butyl 3-{4-[({4'-[(2-ethoxyethyl)sulfonyl]-2',6'-dimethylbiphenyl-3-yl}methyl)amino]-2-fluorophenyl}propanoate. yield 90%.

MS m/z 514 (MH$^+$).

Example 185 ethyl 3-(2-fluoro-4-{({4'-[(4-hydroxytetrahydro-2H-thiopyran-4-yl)methoxy]-2',6'-dimethylbiphenyl-3-yl}methyl)[(2-nitrophenyl)sulfonyl]amino}phenyl) propanoate To a solution of 4-({[3'-(hydroxymethyl)-2,6-dimethylbiphenyl-4-yl]oxy}methyl)tetrahydro-2H-thiopyran-4-ol (0.90 g, 2.51 mmol), ethyl 3-(2-fluoro-4-{[(2-nitrophenyl)sulfonyl]amino}phenyl)propanoate (1.05 g, 2.64 mmol) and tributylphosphine (0.86 mL, 3.26 mmol) in tetrahydrofuran (15 mL) was added 1,1'-(azodicarbonyl)dipiperidine (0.85 g, 3.26 mmol) under stirring at room temperature, and the mixture was stirred for 10 hr. The resulting precipitate was filtered off, and the filtrate was concentrated under reduced pressure. The residue was purified by silica gel column chromatography (hexane/ethyl acetate=10/1-hexane/ethyl acetate=2/1) to give the title compound (1.71 g, yield 92%) as a pale-yellow amorphous powder.

MS m/z 737 (MH$^+$).

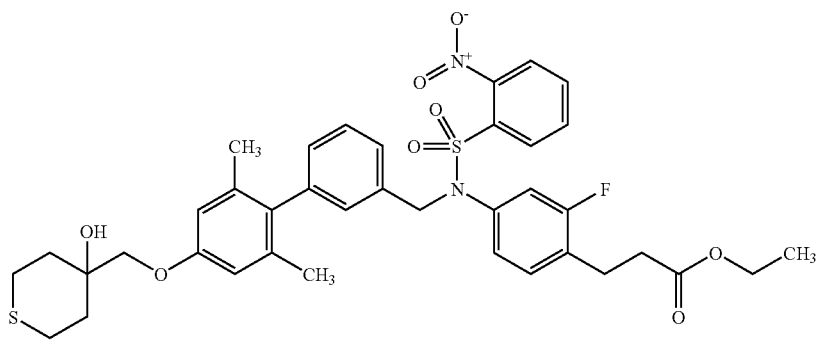

Example 186 ethyl 3-(2-fluoro-4-{({4'-[(4-hydroxy-1,1-dioxidotetrahydro-2H-thiopyran-4-yl)methoxy]-2',6'-dimethylbiphenyl-3-yl}methyl)[(2-nitrophenyl)sulfonyl]amino}phenyl)propanoate

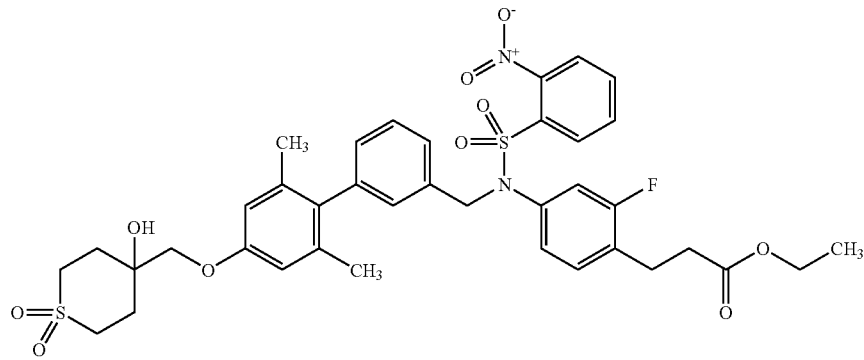

In the same manner as in Example 144, the title compound was obtained as a colorless amorphous powder from ethyl 3-(2-fluoro-4-{({4'-[(4-hydroxytetrahydro-2H-thiopyran-4-yl)methoxy]-2',6'-dimethylbiphenyl-3-yl}methyl)[(2-nitrophenyl)sulfonyl]amino}phenyl)propanoate. yield 86%.

MS m/z 769 (MH$^+$).

Example 187 ethyl 3-{2-fluoro-4-[({4'-[(4-hydroxy-1,1-dioxidotetrahydro-2H-thiopyran-4-yl)methoxy]-2',6'-dimethylbiphenyl-3-yl}methyl)amino]phenyl}propanoate

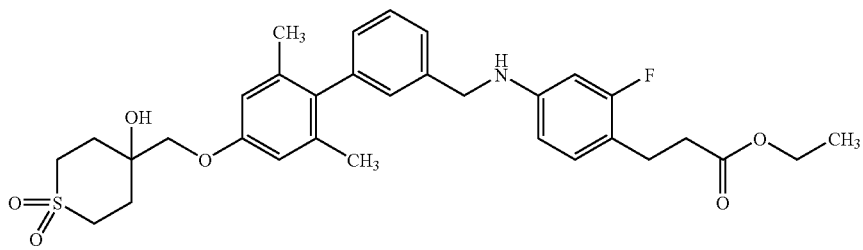

In the same manner as in Example 180, the title compound was obtained as a colorless amorphous powder from ethyl 3-(2-fluoro-4-{({4'-[(4-hydroxy-1,1-dioxidotetrahydro-2H-thiopyran-4-yl)methoxy]-2',6'-dimethylbiphenyl-3-yl}methyl)[(2-nitrophenyl)sulfonyl]amino}phenyl)propanoate. yield 99%.

MS m/z 584 (MH$^+$).

Example 188

3-{2-fluoro-4-[({4'-[(4-hydroxy-1,1-dioxidotetrahydro-2H-thiopyran-4-yl)methoxy]-2',6'-dimethylbiphenyl-3-yl}methyl)amino]phenyl}propanoic acid

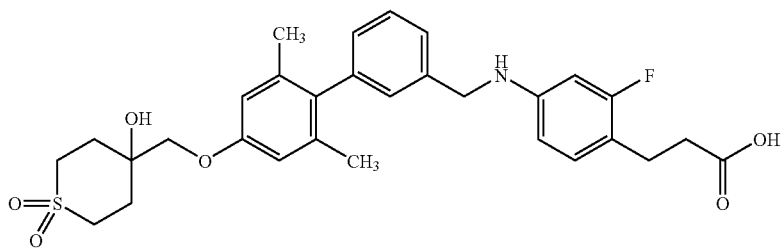

To a mixture of ethyl 3-(2-fluoro-4-[({4'-[(4-hydroxy-1,1-dioxidotetrahydro-2H-thiopyran-4-yl)methoxy]-2',6'-dimethylbiphenyl-3-yl)methyl)amino]phenyl}propanoate (1.99 g, 3.40 mmol), methanol (24 mL) and tetrahydrofuran (7 mL) was. added 1 M aqueous sodium hydroxide solution (10.2 mL), and the mixture was stirred at room temperature for 4 hr. The reaction mixture was neutralized with 1 M hydrochloric acid, and concentrated under reduced pressure to evaporate the organic solvent. The residue was extracted with ethyl acetate, and the organic layer was dried over anhydrous sodium sulfate, and concentrated under reduced pressure. The obtained residue was purified by silica gel column chromatography (hexane/ethyl acetate=5/1-hexane/ethyl acetate=1/1) and recrystallized from ethyl acetate-hexane to give the title compound (1.47 g, yield 78%) as colorless crystals.

MS m/z 556 (MH$^+$).

mp 178° C.

Example 189 tert-butyl 3-(4-{{[2',6'-dimethyl-4'-(2-morpholin-4-ylethoxy)biphenyl-3-yl]methyl}[(2-nitrophenyl)sulfonyl]amino}-2-fluorophenyl)propanoate

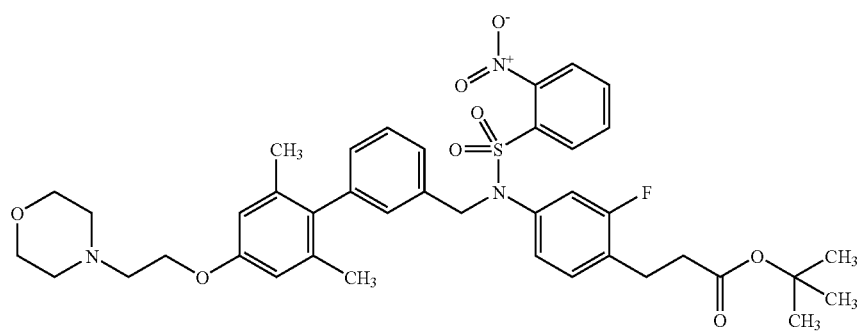

In the same manner as in Example 179, the title compound was obtained as a colorless oil from tert-butyl 3-(2-fluoro-4-{[(4'-hydroxy-2',6'-dimethylbiphenyl-3-yl)methyl][(2-nitrophenyl)sulfonyl]amino}phenyl)propanoate and 2-morpholin-4-ylethanol. yield 71%.

MS m/z 748 (MH$^+$).

Example 190 tert-butyl 3-[4-({[2',6'-dimethyl-4'-(2-morpholin-4-ylethoxy)biphenyl-3-yl]methyl}amino)-2-fluorophenyl]propanoate

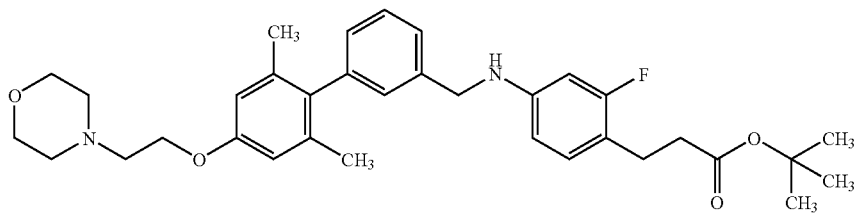

In the same manner as in Example 180, the title compound was obtained as a colorless amorphous powder from tert-butyl 3-(4-{{[2',6'-dimethyl-4'-(2-morpholin-4-ylethoxy)biphenyl-3-yl]methyl}[(2-nitrophenyl)sulfonyl]amino}-2-fluorophenyl)propanoate. yield 87%.

$^1$H NMR (CDCl$_3$) δ: 1.41 (9H, s), 1.97 (6H, s), 2.46 (2H, t, J=7.8 Hz), 2.59 (4H, t, J=4.7 Hz), 2.72-2.86 (4H, m), 3.74 (4H, t, J=4.7 Hz), 4.12 (2H, t, J=5.7 Hz), 4.32 (2H, d, J=3.2 Hz), 6.24-6.37 (2H, m), 6.66 (2H, s), 6.94 (1H, t, J=8.4 Hz), 7.03 (1H, d, J=7.3 Hz), 7.10 (1H, s), 7.27-7.33 (1H, m), 7.38 (1H, t, J=7.4 Hz).

Example 191

3-[4-({[2',6'-dimethyl-4'-(2-morpholin-4-ylethoxy)biphenyl-3-yl]methyl}amino)-2-fluorophenyl]propanoic acid

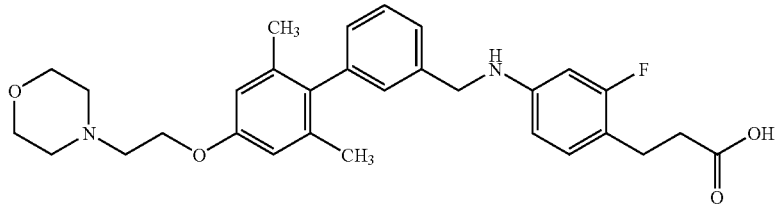

In the same manner as in Example 181, the title compound was obtained as a colorless amorphous powder from tert-butyl 3-[4-({[2',6'-dimethyl-4'-(2-morpholin-4-ylethoxy)biphenyl-3-yl]methyl}amino)-2-fluorophenyl]propanoate. yield 96%.

MS m/z 507 (MH$^+$).

Example 192

3-[4-({[2',6'-dimethyl-4'-(2-morpholin-4-ylethoxy)biphenyl-3-yl]methyl}amino)-2-fluorophenyl]propanoic acid dimethanesulfonate

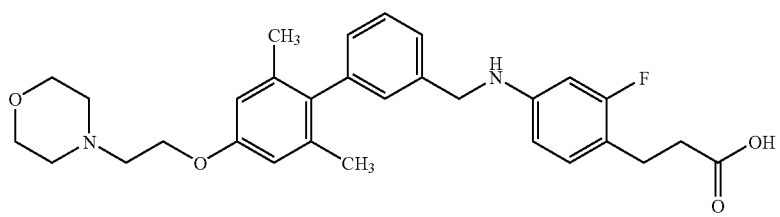

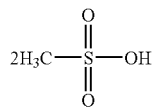

3-[4-({[2',6'-Dimethyl-4'-(2-morpholin-4-ylethoxy)biphenyl-3-yl]methyl}amino)-2-fluorophenyl]propanoic acid (0.58 g, 1.14 mmol) was dissolved in ethyl acetate (5 mL), and methanesulfonic acid (0.08 mL) was added. The precipitated crystals were collected by filtration, washed, and dried to give the title compound as colorless crystals. yield 73%.

$^1$H NMR (DMSO-$d_6$) δ: 1.89 (6H, s), 2.31-2.45 (8H, m), 2.65 (2H, t, J=7.6 Hz), 3.12-3.33 (2H, m), 3.44-3.64 (4H, m), 3.73 (2H, t, J=11.6 Hz), 4.00 (2H, d, J=12.4 Hz), 4.25-4.43 (4H, m), 6.29-6.46 (2H, m), 6.76 (2H, s), 6.90-7.00 (2H, m), 7.02 (1H, s), 7.32 (1H, d, J=7.8 Hz), 7.40 (1H, t, J=7.5 Hz), 9.92 (1H, s).

Example 193 tert-butyl 3-(4-{({4'-[2-(2,5-dioxopyrrolidin-1-yl)ethoxy]-2',6'-dimethylbiphenyl-3-yl}methyl) [(2-nitrophenyl)sulfonyl]amino}-2-fluorophenyl)propanoate In the same manner as in Example 180, the title compound was obtained as a colorless amorphous powder from tert-butyl 3-(4-{({4'-[2-(2,5-dioxopyrrolidin-1-yl)ethoxy]-2',6'-dimethylbiphenyl-3-yl}methyl)[(2-nitrophenyl)sulfonyl]amino}-2-fluorophenyl)propanoate. yield 79%.

$^1$H NMR (CDCl$_3$) δ: 1.41 (9H, s), 1.95 (6H, s), 2.46 (2H, t, J=7.7 Hz), 2.72 (4H, s), 2.79 (2H, t, J=7.7 Hz), 3.95 (2H, t, J=5.8 Hz), 4.15 (2H, t, J=5.8 Hz), 4.32 (2H, s), 6.23-6.38 (2H, m), 6.62 (2H, s), 6.94 (1H, t, J=8.4 Hz), 7.01 (1H, d, J=7.3 Hz), 7.08 (1H, s), 7.26-7.34 (1H, m), 7.37 (1H, t, J=7.5 Hz).

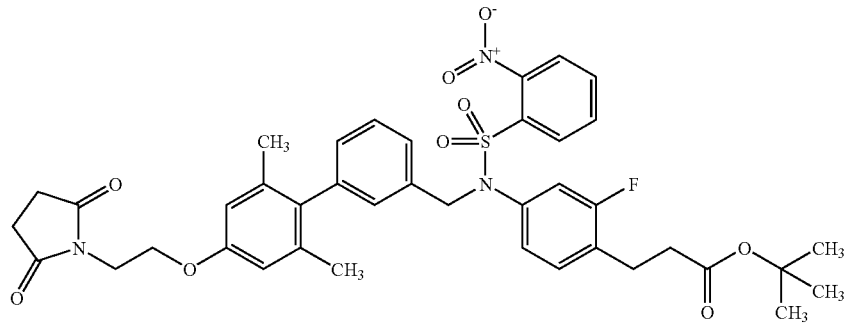

In the same manner as in Example 179, the title compound was obtained as a colorless oil from tert-butyl 3-(2-fluoro-4-{[(4'-hydroxy-2',6'-dimethylbiphenyl-3-yl)methyl][(2-nitrophenyl)sulfonyl]amino}phenyl)propanoate and 1-(2-hydroxyethyl)pyrrolidine-2,5-dione. yield 25%.

$^1$H NMR (CDCl$_3$) δ: 1.38 (9H, s), 1.84 (6H, s), 2.45 (2H, t, J=7.5 Hz), 2.72 (4H, s), 2.82 (2H, t, J=7.5 Hz), 3.94 (2H, t, J=5.6 Hz), 4.15 (2H, t, J=5.6 Hz), 4.92 (2H, s), 6.59 (2H, s), 6.69-6.84 (2H, m), 6.90 (1H, s), 6.93-7.10 (2H, m), 7.19-7.36 (2H, m), 7.46-7.74 (4H, m).

Example 194 tert-butyl 3-{4-[({4'-[2-(2,5-dioxopyrrolidin-1-yl)ethoxy]-2',6'-dimethylbiphenyl-3-yl}methyl)amino]-2-fluorophenyl}propanoate

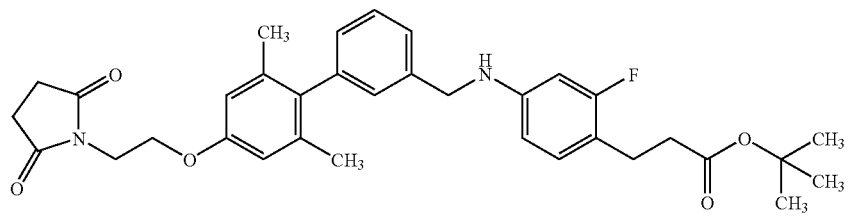

Example 195

3-{4-[({4'-[2-(2,5-dioxopyrrolidin-1-yl)ethoxy]-2',6'-dimethylbiphenyl-3-yl}methyl)amino]-2-fluorophenyl}propanoic acid

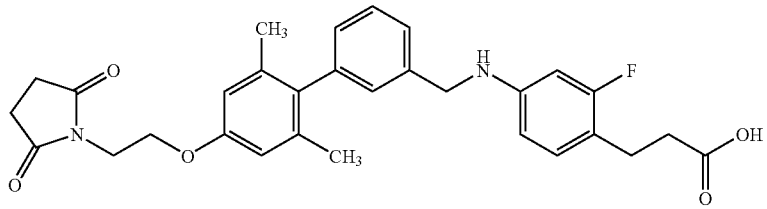

In the same manner as in Example 162, the title compound was obtained as a colorless amorphous powder from tert-butyl 3-{4-[({4'-[2-(2,5-dioxopyrrolidin-1-yl)ethoxy]-2',6'-dimethylbiphenyl-3-yl}methyl)amino]-2-fluorophenyl}propanoate. yield 61%.
MS m/z 519 (MH$^+$).

Example 196 tert-butyl 3-(4-{[(4'-{2-[ethyl(isobutyryl)amino]ethoxy}-2',6'-dimethylbiphenyl-3-yl)methyl][(2-nitrophenyl)sulfonyl]amino}-2-fluorophenyl)propanoate

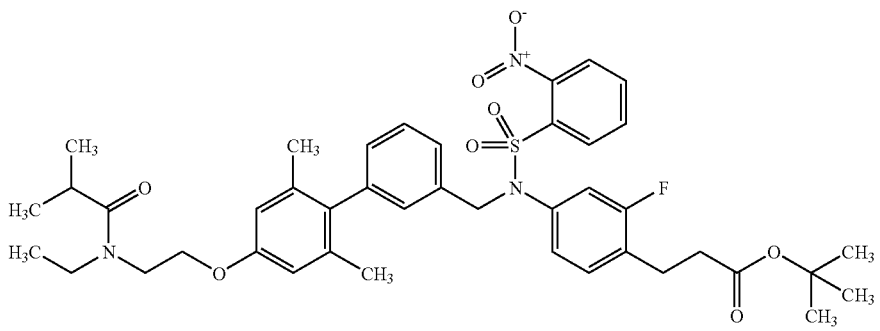

To a solution of tert-butyl 3-(2-fluoro-4-{[(4'-hydroxy-2',6'-dimethylbiphenyl-3-yl)methyl][(2-nitrophenyl)sulfonyl]amino}phenyl)propanoate (3.60 g, 5.67 mmol), 2-(ethylamino)ethanol (0.61 mL, 6.24 mmol) and tributylphosphine (2.26 mL, 8.51 mmol) in tetrahydrofuran (100 mL) was added 1,1'-(azodicarbonyl)dipiperidine (2.21 g, 8.53 mmol) under stirring at room temperature, and the mixture was stirred for 16 hr. The resulting precipitate was filtered off, and the filtrate was concentrated under reduced pressure. The residue was subjected to silica gel column chromatography (hexane/ethyl acetate=5/1-hexane/ethyl acetate=1/3) to give a mixture (6.11 g) of tert-butyl 3-(4-{({4'-[2-(ethylamino)ethoxy]-2',6'-dimethylbiphenyl-3-yl}methyl)[(2-nitrophenyl)sulfonyl]amino}-2-fluorophenyl)propanoate and tributylphosphine oxide as a yellow oil. To a solution of the obtained oil (0.57 g) in pyridine (3 mL) were added 2-methylpropanoyl chloride (0.17 mL, 1.62 mmol) and a small amount of N,N-dimethylpyridine-4-amine under stirring at room temperature, and the mixture was stirred for 1 hr. The reaction mixture was concentrated under reduced pressure, and the residue was partitioned between ethyl acetate and saturated aqueous sodium hydrogencarbonate, and the mixture was extracted with ethyl acetate. The organic layer was dried over anhydrous sodium sulfate, and concentrated under reduced pressure. The obtained residue was purified by silica gel column chromatography (hexane/ethyl acetate=10/1-hexane/ethyl acetate=2/5) to give the title compound (0.35 g) as a colorless oil.
MS m/z 777 (MH$^+$).

Example 197

3-(4-{[(4'-{2-[ethyl(isobutyryl)amino]ethoxy}-2',6'-dimethylbiphenyl-3-yl)methyl]amino}-2-fluorophenyl)propanoic acid

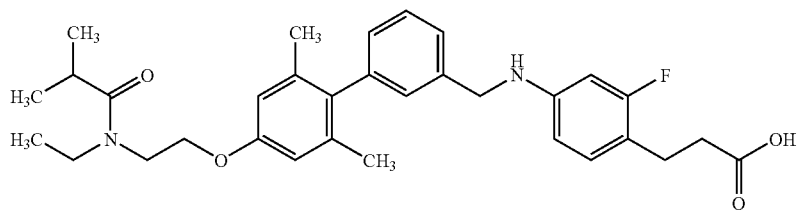

In the same manner as in Example 180 and Example 162, the title compound was obtained as a colorless amorphous powder from tert-butyl 3-(4-{[(4'-{2-[ethyl(isobutyryl)amino]ethoxy}-2',6'-dimethylbiphenyl-3-yl)methyl][(2-nitrophenyl)sulfonyl]amino}-2-fluorophenyl)propanoate. yield 73% (2 steps).

MS m/z 535 (MH$^+$).

Example 198 tert-butyl 3-(4-{[(4'-{2-[acetyl(ethyl)amino]ethoxy}-2',6'-dimethylbiphenyl-3-yl)methyl][(2-nitrophenyl)sulfonyl]amino}-2-fluorophenyl)propanoate

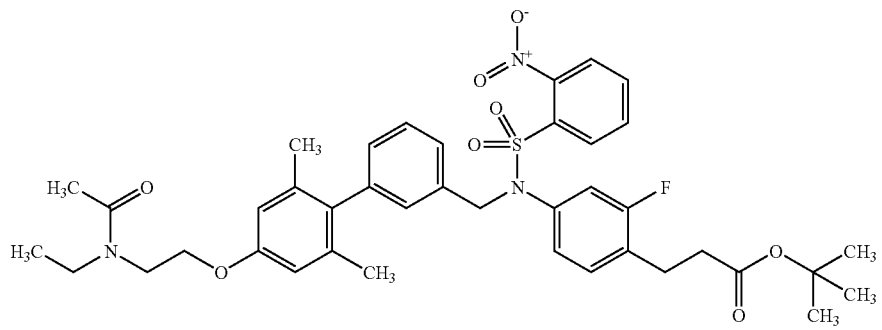

In the same manner as in Example 196, the title compound (0.19 g) was obtained as a colorless amorphous powder from tert-butyl 3-(2-fluoro-4-{[(4'-hydroxy-2',6'-dimethylbiphenyl-3-yl)methyl][(2-nitrophenyl)sulfonyl]amino}phenyl)propanoate, 2-(ethylamino)ethanol and acetic anhydride MS m/z 748 (MH$^+$).

Example 199

3-(4-{[(4'-{2-[acetyl(ethyl)amino]ethoxy}-2',6'-dimethylbiphenyl-3-yl)methyl]amino}-2-fluorophenyl)propanoic acid

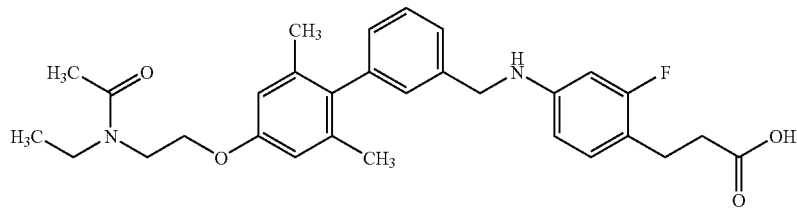

In the same manner as in Example 180 and Example 162, the title compound was obtained as a colorless amorphous powder from tert-butyl 3-(4-{[(4'-{2-[acetyl(ethyl)amino]ethoxy}-2',6'-dimethylbiphenyl-3-yl)methyl][(2-nitrophenyl)sulfonyl]amino}-2-fluorophenyl)propanoate. yield 81% (2 steps).

MS m/z 507 (MH$^+$).

Example 200

3-(4-{[(4'-{2-[acetyl(ethyl)amino]ethoxy}-2',6'-dimethylbiphenyl-3-yl)methyl]amino}-2-fluorophenyl)propanoic acid methanesulfonate

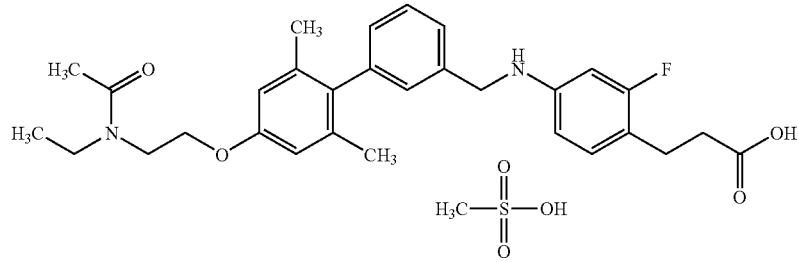

In the same manner as in Example 84, the title compound was obtained as colorless crystals from 3-(4-{[(4'-{2-[acetyl (ethyl)amino]ethoxy}-2',6'-dimethylbiphenyl-3-yl)methyl] amino}-2-fluorophenyl)propanoic acid. yield 94%.

¹H NMR (CDCl₃) δ: 1.10-1.31 (3H, m), 1.69-1.88 (6H, m), 2.09-2.28 (3H, m), 2.56 (2H, t, J=6.5 Hz), 2.72-2.93 (5H, m), 3.48 (2H, q, J=7.0 Hz), 3.69 (2H, t, J=5.3 Hz), 4.03-4.20 (2H, m), 4.52 (2H, s), 6.53-6.68 (2H, m), 6.69-6.83 (1H, m), 6.92 (1H, d, J=9.6 Hz), 6.98-7.23 (3H, m), 7.35-7.51 (2H, m).

Example 201 tert-butyl 3-(4-{{[2',6'-dimethyl-4'-(tetrahydro-2H-thiopyran-4-yloxy)biphenyl-3-yl]methyl}[(2-nitrophenyl)sulfonyl]amino}-2-fluorophenyl)propanoate

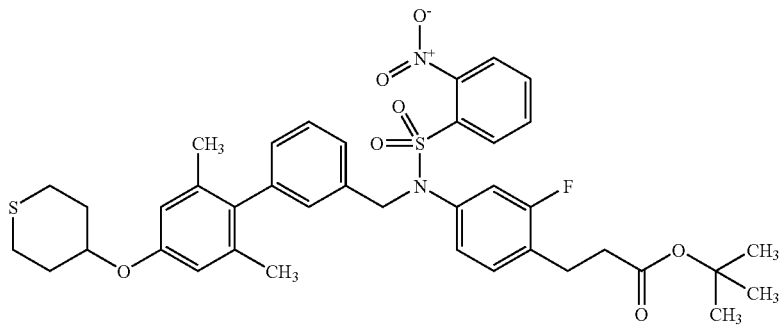

reduced pressure and the residue was purified by silica gel column chromatography (hexane/ethyl acetate=10/1-hexane/ethyl acetate=2/1) to give the title compound (3.5 g, yield 100%) as a pale-yellow oil.

MS m/z 735 (MH⁺).

Example 202 tert-butyl 3-(4-{({4'-[(1,1-dioxidotetrahydro-2H-thiopyran-4-yl)oxy]-2',6'-dimethylbiphenyl-3-yl}methyl)[(2-nitrophenyl)sulfonyl]amino}-2-fluorophenyl)propanoate

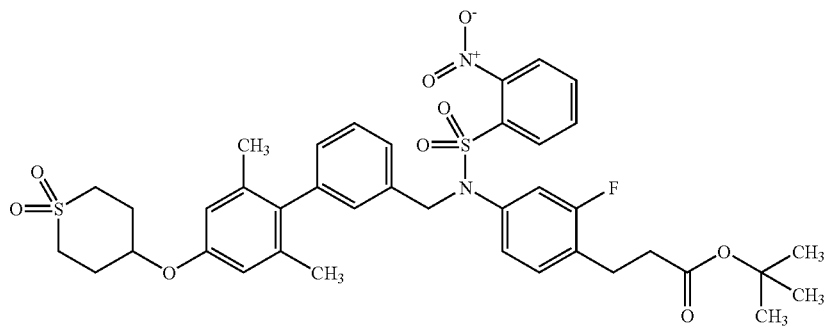

To a solution of tert-butyl 3-(2-fluoro-4-{[(4'-hydroxy-2', 6'-dimethylbiphenyl-3-yl)methyl][(2-nitrophenyl)sulfonyl] amino}phenyl)propanoate (3.0 g, 4.73 mmol), tetrahydro-2H-thiopyran-4-ol (0.62 g, 5.20 mmol) and triphenylphosphine (1.36 g, 5.20 mmol) in tetrahydrofuran (60 mL) was added diethyl azodicarboxylate (40% toluene solution, 2.79 mL, 6.15 mmol) under stirring at room temperature, and the mixture was stirred for 16 hr. To the reaction mixture were added reagents (tetrahydro-2H-thiopyran-4-ol, triphenylphosphine and diethyl azodicarboxylate) in a half amount as mentioned above, and the mixture was further stirred for 8 hr. The reaction mixture was concentrated under In the same manner as in Example 144, the title compound was obtained as a colorless amorphous powder from tert-butyl 3-(4-{{[2',6'-dimethyl-4'-(tetrahydro-2H-thiopyran-4-yloxy)biphenyl-3-yl]methyl}[(2-nitrophenyl)sulfonyl] amino}-2-fluorophenyl)propanoate. yield 68%.

¹H NMR (CDCl₃) δ: 1.38 (9H, s), 1.87 (6H, s), 2.28-2.58 (6H, m), 2.83 (2H, t, J=7.6 Hz), 2.88-3.02 (2H, m), 3.36-3.53 (2H, m), 4.61-4.70 (1H, m), 4.94 (2H, s), 6.65 (2H, s), 6.70-6.84 (2H, m), 6.93-7.10 (3H, m), 7.20 (1H, d, J=7.7 Hz), 7.31 (1H, t, J=7.8 Hz), 7.46-7.54 (1H, m), 7.54-7.62 (1H, m), 7.63-7.74 (2H, m).

Example 203 tert-butyl 3-{4-[({4'-[(1,1-dioxidotetrahydro-2H-thiopyran-4-yl)oxy]-2',6'-dimethylbiphenyl-3-yl}methyl)amino]-2-fluorophenyl}propanoate

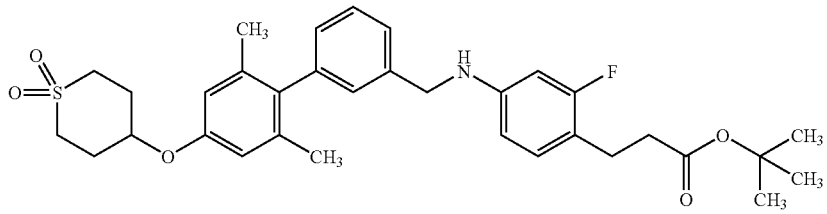

In the same manner as in Example 180, the title compound was obtained as a colorless amorphous powder from tert-butyl 3-(4-{({4'-[(1,1-dioxidotetrahydro-2H-thiopyran-4-yl)oxy]-2',6'-dimethylbiphenyl-3-yl}methyl)[(2-nitrophenyl)sulfonyl]amino}-2-fluorophenyl)propanoate. yield 82%.
MS m/z 582 (MH$^+$).

Example 204

3-{4-[({4'-[(1,1-dioxidotetrahydro-2H-thiopyran-4-yl)oxy]-2',6'-dimethylbiphenyl-3-yl}methyl)amino]-2-fluorophenyl}propanoic acid methanesulfonate

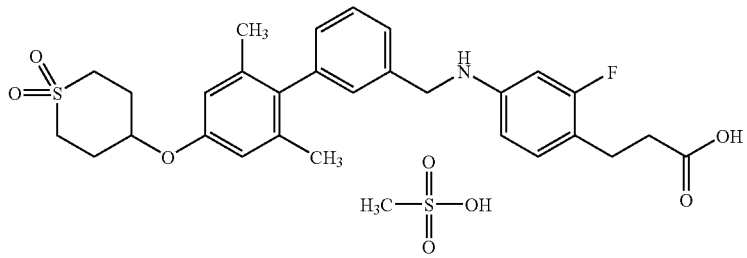

In the same manner as in Example 181, the title compound was obtained as colorless crystals from tert-butyl 3-{4-[({4'-[(1,1-dioxidotetrahydro-2H-thiopyran-4-yl)oxy]-2',6'-dimethylbiphenyl-3-yl}methyl)amino]-2-fluorophenyl}propanoate. yield 84%.

$^1$H NMR (DMSO-d$_6$) δ: 1.87 (6H, s), 2.10-2.30 (4H, m), 2.34-2.46 (5H, m), 2.67 (2H, t, J=7.5 Hz), 3.06-3.28 (4H, m), 4.35 (2H, s), 4.63-4.77 (1H, m), 6.35-6.53 (2H, m), 6.78 (2H, s), 6.92-7.10 (3H, m), 7.32 (1H, d, J=7.8 Hz), 7.39 (1H, t, J=7.5 Hz).

mp 174° C.

Example 205 ethyl 3-(2-fluoro-4-{({4'-[(4-methoxy-1,1-dioxidotetrahydro-2H-thiopyran-4-yl)methoxy]-2',6'-dimethylbiphenyl-3-yl}methyl)[(2-nitrophenyl)sulfonyl]amino}phenyl)propanoate

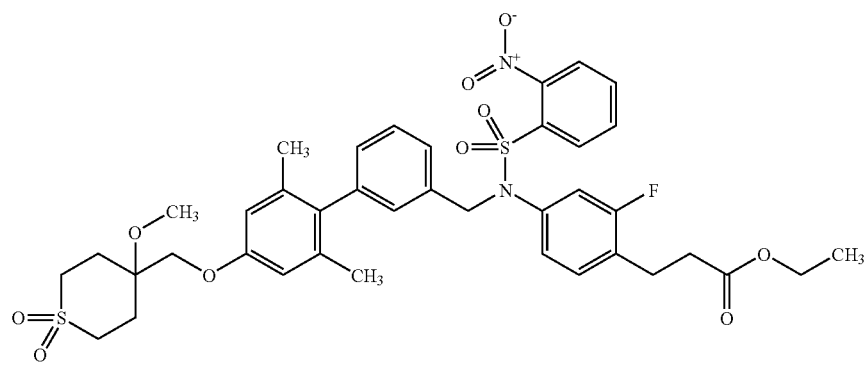

To a solution of ethyl 3-(2-fluoro-4-{({4'-[(4-hydroxytetrahydro-2H-thiopyran-4-yl)methoxy]-2',6'-dimethylbiphenyl-3-yl}methyl)[(2-nitrophenyl)sulfonyl]amino}phenyl)propanoate (1.24 g, 1.62 mmol) and iodomethane (0.50 mL, 8.1 mmol) in tetrahydrofuran (10 mL) was added sodium hydride (60% in oil, 0.10 g, 2.42 mmol) under stirring at 0° C., and the mixture was stirred at room temperature for 5 hr. The reaction mixture was partitioned between ethyl acetate and saturated brine. The organic layer was dried over anhydrous sodium sulfate, and concentrated under reduced pressure. The residue was purified by silica gel column chromatography (hexane/ethyl acetate=10/1-hexane/ethyl acetate=5/6) to give the title compound (0.81 g, yield 64%) as a yellow amorphous powder.

MS m/z 783 (MH$^+$).

Example 206 ethyl 3-{2-fluoro-4-[({4'-[(4-methoxy-1,1-dioxidotetrahydro-2H-thiopyran-4-yl)methoxy]-2',6'-dimethylbiphenyl-3-yl}methyl)amino]phenyl}propanoate

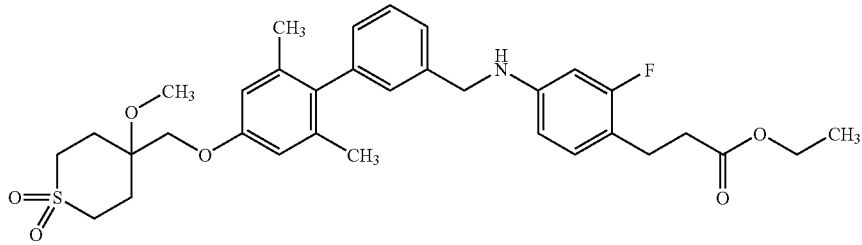

In the same manner as in Example 180, the title compound was obtained as colorless crystals from ethyl 3-(2-fluoro-4-{({4'-[(4-methoxy-1,1-dioxidotetrahydro-2H-thiopyran-4-yl)methoxy]-2',6'-dimethylbiphenyl-3-yl}methyl)[(2-nitrophenyl)sulfonyl]amino}phenyl)propanoate. yield 44%.

MS m/z 598 (MH$^+$).

Example 207

3-{2-fluoro-4-[({4'-[(4-methoxy-1,1-dioxidotetrahydro-2H-thiopyran-4-yl)methoxy]-2',6'-dimethylbiphenyl-3-yl}methyl)amino]phenyl}propanoic acid

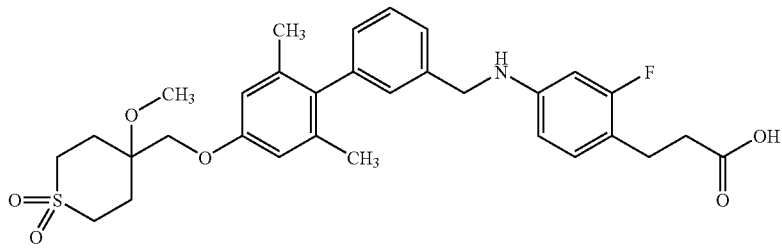

In the same manner as in Example 188, the title compound was obtained as colorless crystals from ethyl 3-{2-fluoro-4-[({4'-[(4-methoxy-1,1-dioxidotetrahydro-2H-thiopyran-4-yl)methoxy]-2',6'-dimethylbiphenyl-3-yl}methyl)amino]phenyl}propanoate. yield 60%.

MS m/z 570 (MH$^+$).

Example 208

3-(4-{[5-(2,6-dimethylphenyl)-2,3-dihydro-1H-inden-1-yl]amino}phenyl)propanoic acid

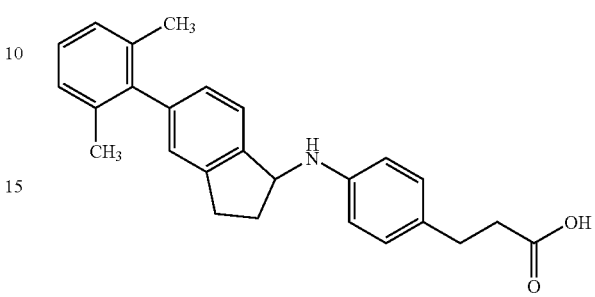

5-(2,6-Dimethylphenyl)indan-1-one (690 mg, 2.92 mmol), methyl 3-(4-aminophenyl)propanoate (937 mg, 4.09 mmol) and acetic acid (526 mg, 8.76 mmol) were dissolved in 1,2-dichloroethane (20 mL), sodium triacetoxyborohydride (1.86 g, 8.76 mmol) was added by small portions at room temperature, and the mixture was stirred at room temperature for 16 hr. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (5%-40% ethyl acetate/hexane). The obtained oil was dissolved in tetrahydrofuran (10 mL), methanol (6 mL), and water (6 mL), and lithium hydroxide monohydrate (133 mg, 3.18 mmol) was added. The mixture was stirred at room temperature for 3 hr. The reaction mixture was neutralized with 1 M hydrochloric acid, and the mixture was extracted

Example 209

3-{4-[(5-phenoxy-2,3-dihydro-1H-inden-1-yl)amino]phenyl}propanoic acid

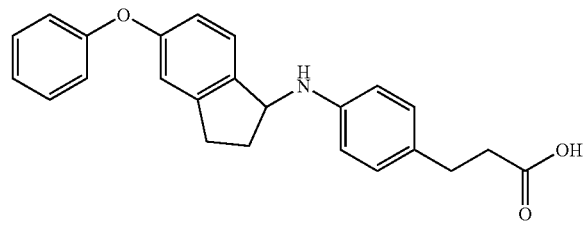

In the same manner as in Example 208, the title compound was obtained as a colorless oil from 5-phenoxyindan-1-one and methyl 3-(4-aminophenyl)propanoate. yield 26%.

$^1$H NMR (CDCl$_3$) δ: 1.85-2.00 (1H, m), 2.51-2.70 (3H, m), 2.78-3.05 (4H, m), 4.96 (1H, t, J=6.6 Hz), 6.62-6.70 (2H, m), 6.83-6.92 (2H, m), 6.98-7.15 (5H, m), 7.24-7.39 (3H, m).

Example 210

3-(4-{[5-(benzyloxy)-2,3-dihydro-1H-inden-1-yl]amino}phenyl)propanoic acid

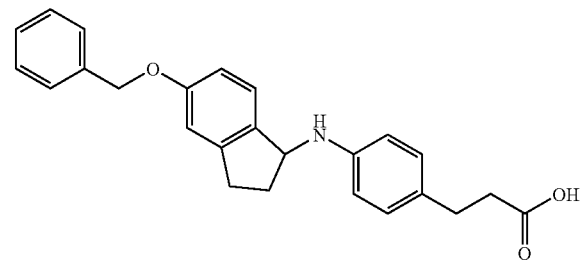

In the same manner as in Example 208, the title compound was obtained as colorless crystals from 5-(benzyloxy)indan-1-one and methyl 3-(4-aminophenyl)propanoate. yield 18%.

$^1$H NMR (CDCl$_3$) δ: 1.84-2.00 (1H, m), 2.48-2.70 (3H, m), 2.78-3.05 (4H, m), 4.92 (1H, t, J=6.3 Hz), 5.06 (2H, s), 6.64 (2H, d, J=8.5 Hz), 6.80-6.91 (2H, m), 7.04 (2H, d, J=8.3 Hz), 7.22-7.48 (6H, m).

Example 211

3-(4-{[4-(benzyloxy)-2,3-dihydro-1H-inden-1-yl]amino}phenyl)propanoic acid

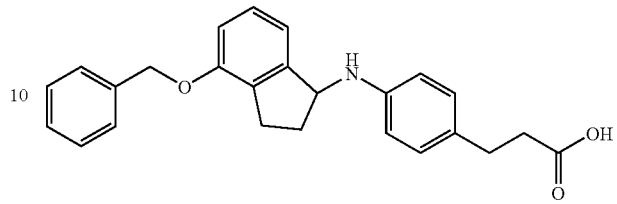

In the same manner as in Example 208, the title compound was obtained as colorless crystals from 4-(benzyloxy)indan-1-one and methyl 3-(4-aminophenyl)propanoate. yield 5%.

$^1$H NMR (CDCl$_3$) δ: 1.81-1.97 (1H, m), 2.51-2.70 (3H, m), 2.79-2.92 (3H, m), 2.99-3.12 (1H, m), 4.99 (1H, t, J=6.7 Hz), 5.11 (2H, s), 6.64 (2H, d, J=8.3 Hz), 6.81 (1H, d, J=8.1 Hz), 6.98 (1H, d, J=7.5 Hz), 7.04 (2H, d, J=8.3 Hz), 7.16 (1H, t, J=7.8 Hz), 7.28-7.49 (5H, m).

Example 212

3-{4-[(4-phenoxy-2,3-dihydro-1H-inden-1-yl)amino]phenyl}propanoic acid

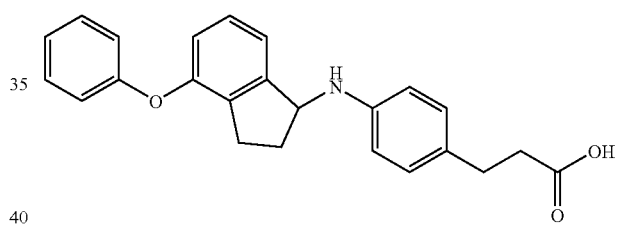

In the same manner as in Example 208, the title compound was obtained as colorless crystals from 4-phenoxyindan-1-one and methyl 3-(4-aminophenyl)propanoate. yield 26%.

$^1$H NMR (CDCl$_3$) δ: 1.81-1.96 (1H, m), 2.52-2.81 (4H, m), 2.83-3.01 (3H, m), 5.03 (1H, t, J=6.9 Hz), 6.67 (2H, d, J=8.5 Hz), 6.84 (1H, dd, J=7.4, 1.5 Hz), 6.93-7.01 (2H, m), 7.02-7.23 (5H, m), 7.27-7.39 (2H, m).

Example 213

3-(4-{[4-(2,6-dimethylphenyl)-2,3-dihydro-1H-inden-1-yl]amino}phenyl)propanoic acid

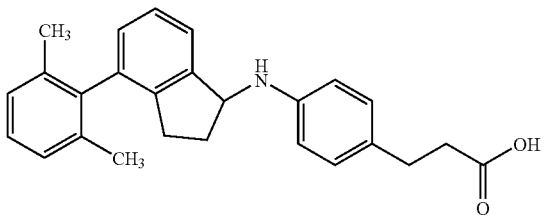

In the same manner as in Example 208, the title compound was obtained as colorless crystals from 4-(2,6-dimethylphenyl)indan-1-one and methyl 3-(4-aminophenyl)propanoate. yield 21%.

$^1$H NMR (CDCl$_3$) δ: 1.72-1.90 (1H, m), 1.98 (3H, s), 1.99 (3H, s), 2.43-2.60 (3H, m), 2.66 (2H, t, J=7.7 Hz), 2.88 (2H, t, J=7.7 Hz), 5.05 (1H, t, J=6.8 Hz), 6.69 (2H, d, J=8.5 Hz), 6.97-7.20 (6H, m), 7.24-7.32 (1H, m), 7.35 (1H, d, J=7.5 Hz).

Example 214

3-[4-({4-[4-(2-ethoxyethoxy)-2,6-dimethylphenyl]-2,3-dihydro-1H-inden-1-yl}amino)-2-fluorophenyl]propanoic acid In the same manner as in Example 120, the title compound was obtained as colorless crystals from 3-[4-({4-[4-(2-ethoxyethoxy)-2,6-dimethylphenyl]-2,3-dihydro-1H-inden-1-yl}amino)-2-fluorophenyl]propanoic acid. yield 63%.

$^1$H NMR (DMSO-d$_6$) δ: 1.06-1.19 (3H, m), 1.70-1.79 (1H, m), 1.87 (3H, s), 1.89 (3H, s), 2.36-2.56 (4H, m), 2.65-2.78 (3H, m), 3.51 (2H, q, J=7.0 Hz), 3.66-3.73 (2H, m), 4.05-4.12 (2H, m), 5.04 (1H, t, J=6.7 Hz), 5.04 (1H, t, J=6.7 Hz), 6.50-6.59 (2H, m), 6.71 (2H, s), 6.90-7.07 (2H, m), 7.23-7.32 (2H, m).

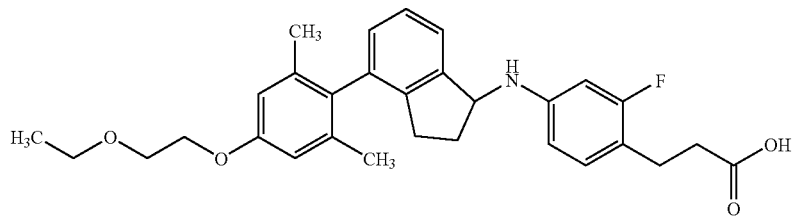

In the same manner as in Example 208, the title compound was obtained as a colorless oil from 4-[4-(2-ethoxyethoxy)-2,6-dimethylphenyl]indan-1-one and ethyl 3-(4-amino-2-fluorophenyl)propanoate. yield 18%.

$^1$H NMR (CDCl$_3$) δ: 1.25 (3H, t, J=7.0 Hz), 1.72-1.88 (1H, m), 1.94 (3H, s), 1.94-1.96 (3H, m), 2.39-2.61 (3H, m), 2.65 (2H, t, J=7.5 Hz), 2.89 (2H, t, J=7.5 Hz), 3.62 (2H, q, J=7.0 Hz), 3.78-3.83 (2H, m), 4.10-4.17 (2H, m), 5.00 (1H, t, J=6.7 Hz), 6.39-6.46 (2H, m), 6.69 (2H, s), 6.97-7.05 (2H, m), 7.23-7.35 (2H, m).

Example 215

3-[4-({4-[4-(2-ethoxyethoxy)-2,6-dimethylphenyl]-2,3-dihydro-1H-inden-1-yl}amino)-2-fluorophenyl]propanoic acid methanesulfonate

Example 216 ethyl 3-(4-{[4-(2,6-dimethylphenyl)-2,3-dihydro-1H-inden-1-yl][(2-nitrophenyl)sulfonyl]amino}-2-fluorophenyl)propanoate

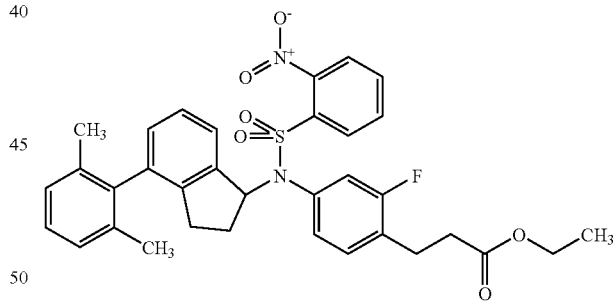

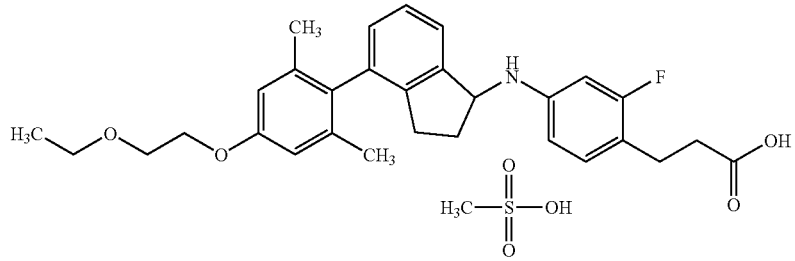

In the same manner as in Example 9, the title compound was obtained as a pale-yellow oil from 4-(2,6-dimethylphenyl)indan-1-ol and ethyl 3-(2-fluoro-4-{[(2-nitrophenyl)sulfonyl]amino}phenyl)propanoate. yield 76%.

MS m/z 617 (MH+).

Example 217 ethyl 3-(4-{[4-(2,6-dimethylphenyl)-2,3-dihydro-1H-inden-1-yl]amino}-2-fluorophenyl)propanoate

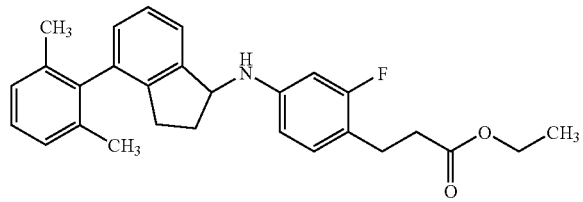

In the same manner as in Example 10, the title compound was obtained as a colorless oil from ethyl 3-(4-{[4-(2,6-dimethylphenyl)-2,3-dihydro-1H-inden-1-yl][(2-nitrophenyl)sulfonyl]amino}-2-fluorophenyl)propanoate. yield 63%.

$^1$H NMR (CDCl$_3$) δ: 1.73-1.89 (1H, m), 1.97 (3H, s), 1.98 (3H, s), 2.47-2.63 (5H, m), 2.87 (2H, t, J=7.7 Hz), 4.02 (1H, br s), 4.08-4.18 (2H, m), 5.01 (1H, br s), 6.38-6.46 (2H, m), 6.96-7.05 (2H, m), 7.07-7.20 (3H, m), 7.23-7.37 (2H, m).

Example 218

3-(4-{[4-(2,6-dimethylphenyl)-2,3-dihydro-1H-inden-1-yl]amino}-2-fluorophenyl)propanoic acid

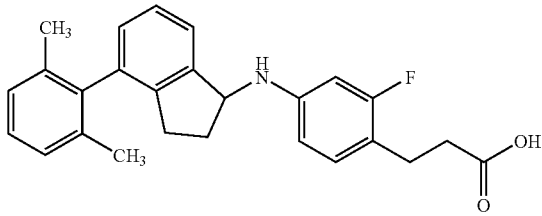

In the same manner as in Example 117, the title compound was obtained as colorless crystals from ethyl 3-(4-{[4-(2,6-dimethylphenyl)-2,3-dihydro-1H-inden-1-yl]amino}-2-fluorophenyl)propanoate. yield 58%.

$^1$H NMR (CDCl$_3$) δ: 1.73-1.90 (1H, m), 1.97 (3H, s), 1.98 (3H, s), 2.41-2.62 (3H, m), 2.65 (2H, t, J=7.5 Hz), 2.89 (2H, t, J=7.5 Hz), 5.01 (1H, t, J=6.6 Hz), 6.38-6.47 (2H, m), 6.97-7.06 (2H, m), 7.07-7.21 (3H, m), 7.27-7.37 (2H, m).

Example 219

3-[4-({[4'-(2-ethoxyethoxy)-6-isopropoxy-2',6'-dimethylbiphenyl-3-yl]methyl}amino)-2-fluorophenyl]propanoic acid hydrochloride

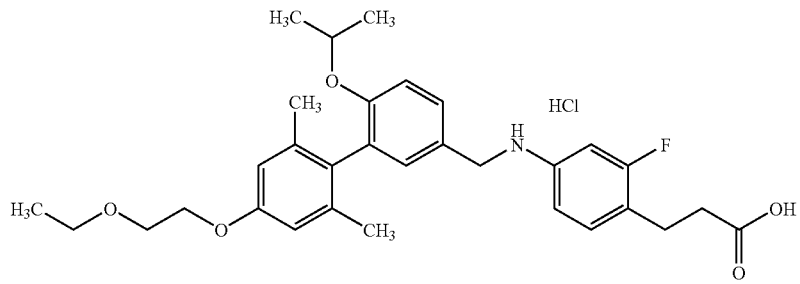

[step 1] A mixture of 3-bromo-4-isopropoxybenzaldehyde (0.42 g, 1.72 mmol), [4-(2-ethoxyethoxy)-2,6-dimethylphenyl]boronic acid (0.45 g, 1.89 mmol), tris(dibenzylideneacetone)dipalladium(0) (63 mg, 0.069 mmol), 2-(dicyclohexylphosphino)biphenyl (37 mg, 0.10 mmol), tripotassium phosphate (0.73 g, 3.44 mmol) and toluene (20 mL) was stirred under a nitrogen atmosphere at 90° C. for 18 hr. After cooling the reaction mixture, the insoluble material was filtered off, and the filtrate was concentrated under reduced pressure. The residue was crudely purified by silica gel column chromatography (hexane/ethyl acetate=9/1-hexane/ethyl acetate=1/1) to give crude 4'-(2-ethoxyethoxy)-6-isopropoxy-2',6'-dimethylbiphenyl-3-carbaldehyde (0.22 g) as a yellow oil.

[step 2] To a solution of the obtained oil and ethyl 3-(4-amino-2-fluorophenyl)propanoate (0.14 g, 0.67 mmol) in 1,2-dichloroethane (4.4 mL) was added acetic acid (0.12 mL, 2.01 mmol), and the mixture was stirred at room temperature for 3 hr. Sodium triacetoxyborohydride (0.43 g, 2.01 mmol) was added to the reaction mixture, and the mixture was stirred at room temperature for 3 hr. The reaction mixture was washed with water and saturated brine, dried over anhydrous sodium sulfate, and concentrated under reduced pressure. The residue was crudely purified by silica gel column chromatography (hexane/ethyl acetate=10/1-hexane/ethyl acetate=2/1) to give crude ethyl 3-[4-({[4'-(2-ethoxyethoxy)-6-isopropoxy-2',6'-dimethylbiphenyl-3-yl]methyl}amino)-2-fluorophenyl]propanoate (0.26 g) as a colorless oil.

[step 3] To a solution of the obtained oil in a mixture of methanol (2.6 mL) and tetrahydrofuran (5.2 mL) was added 1 N aqueous sodium hydroxide solution (0.94 mL, 0.94 mmol), and the mixture was stirred at room temperature for 2 hr. The reaction mixture was neutralized with 1 N hydrochloric acid, and diluted with ethyl acetate, and the organic layer was washed with water and saturated brine, dried over anhydrous magnesium sulfate, and concentrated under reduced pressure. The residue was purified by silica gel column chromatography (hexane/ethyl acetate=4/1-hexane/ethyl acetate=1/2) to give a colorless oil. The obtained oil was dissolved in ethyl acetate, and 4 N hydrogen chloride/ethyl acetate solution was added. The precipitated crystals were collected by filtration, washed with ethyl acetate and dried to give the title compound (93 mg, yield 10%, 3 steps) as beige crystals.

$^1$H NMR (CDCl$_3$) δ: 1.12 (6H, d, J=6.0 Hz), 1.24 (3H, t, J=6.9 Hz), 1.77 (6H, s), 2.66 (2H, t, J=6.3 Hz), 2.82 (2H, t, J=6.3 Hz), 3.61 (2H, q, J=6.9 Hz), 3.78 (2H, t, J=4.8 Hz), 4.10 (2H, t, J=4.8 Hz), 4.37 (1H, m), 4.43 (2H, s), 6.59 (2H, s), 6.64 (1H, d, J=2.4 Hz), 6.84 (1H, m), 6.92-7.12 (3H, m), 7.55 (1H, dd, J=2.4, 8.7 Hz).

Example 220

3-[4-({[4'-(2-ethoxyethoxy)-2',6'-dimethyl-6-propoxybiphenyl-3-yl]methyl}amino)-2-fluorophenyl]propanoic acid hydrochloride

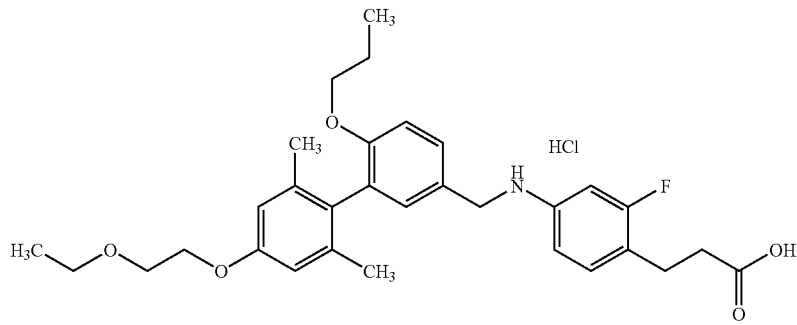

In the same manner as in Example 219, the title compound was obtained as beige crystals from 3-bromo-4-propoxybenzaldehyde, [4-(2-ethoxyethoxy)-2,6-dimethylphenyl]boronic acid and ethyl 3-(4-amino-2-fluorophenyl)propanoate. yield 17%.

MS (APCI−): 522 (M−H, as free form).

Example 221

3-[4-({[6-(cyclopropylmethoxy)-4'-(2-ethoxyethoxy)-2',6'-dimethylbiphenyl-3-yl]methyl}amino)-2-fluorophenyl]propanoic acid hydrochloride In the same manner as in Example 219, the title compound was obtained as beige crystals from 3-bromo-4-cyclopropylmethoxybenzaldehyde, [4-(2-ethoxyethoxy)-2,6-dimethylphenyl]boronic acid and ethyl 3-(4-amino-2-fluorophenyl)propanoate. yield 25%.

MS (APCI−): 534 (M−H, as free form).

Example 222 ethyl 3-[4-({3-[(3,5-diphenyl-1H-pyrazol-1-yl)methyl]-4-isobutoxybenzyl}amino)-2-fluorophenyl]propanoate

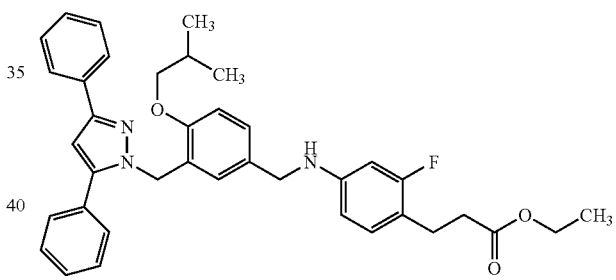

In the same manner as in Example 156, the title compound was obtained as colorless crystals from 3-[(3,5-diphenyl-1H-pyrazol-1-yl)methyl]-4-isobutoxybenzaldehyde and ethyl 3-(4-amino-2-fluorophenyl)propanoate. yield 70%.

MS (ESI+): 606 (M+H).

Example 223

3-[4-({3-[(3,5-diphenyl-1H-pyrazol-1-yl)methyl]-4-isobutoxybenzyl}amino)-2-fluorophenyl]propanoic acid

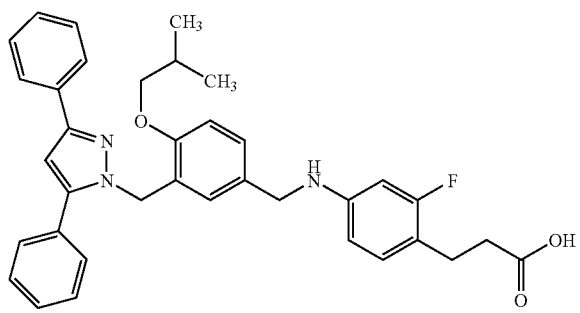

In the same manner as in Example 157, the title compound was obtained as colorless crystals from ethyl 3-[4-({3-[(3,5-diphenyl-1H-pyrazol-1-yl)methyl]-4-isobutoxybenzyl}amino)-2-fluorophenyl]propanoate. yield 70%.

MS (ESI+): 578 (M+H).

Example 224 ethyl 3-[4-({4-[(3,5-diphenyl-1H-pyrazol-1-yl)methyl]-3-isopropoxybenzyl}amino)-2-fluorophenyl]propanoate

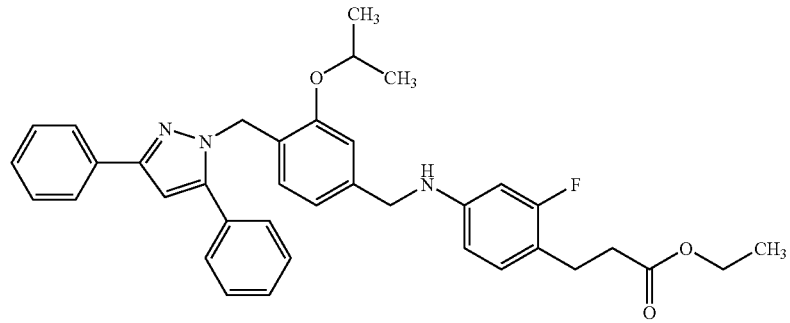

To a solution of 4-[(3,5-diphenyl-1H-pyrazol-1-yl)methyl]-3-isopropoxybenzaldehyde (0.38 g, 0.95 mmol) and ethyl 3-(4-amino-2-fluorophenyl)propanoate (0.20 g, 0.95 mmol) in 1,2-dichloroethane (7.0 mL) was added acetic acid (0.16 mL, 2.86 mmol) and the mixture was stirred at room temperature for 3 hr. Sodium triacetoxyborohydride (0.61 g, 2.86 mmol) was added, and the mixture was further stirred for 3 hr. The reaction mixture was diluted with ethyl acetate, washed with water and saturated brine, dried over anhydrous sodium sulfate, and concentrated under reduced pressure. The residue was purified by silica gel column chromatography (hexane/ethyl acetate=4/1-hexane/ethyl acetate=1/1) to give the title compound (0.52 g, yield 92%) as a colorless oil.

$^1$H NMR (CDCl$_3$) δ: 1.19-1.27 (9H, m), 2.54 (2H, t, J=7.8 Hz), 2.84 (2H, t, J=7.8 Hz), 4.11 (2H, t, J=7.2 Hz), 4.22 (2H, s), 4.53 (1H, m), 5.38 (2H, s), 6.25-6.35 (2H, m), 6.70 (1H, s), 6.74-6.85 (3H, m), 6.96 (1H, t, J=8.4 Hz), 7.25-7.45 (8H, m), 7.87 (2H, dd, J=1.5, 8.4 Hz).

Example 225

3-[4-({4-[(3,5-diphenyl-1H-pyrazol-1-yl)methyl]-3-isopropoxybenzyl}amino)-2-fluorophenyl]propanoic acid

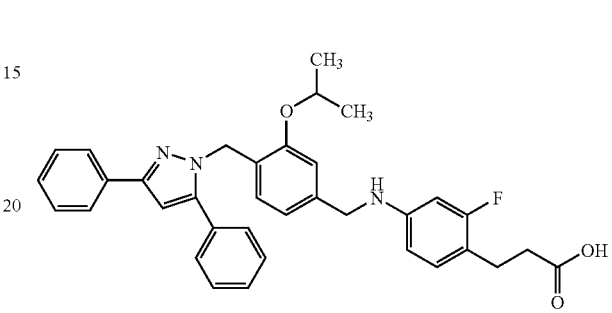

In the same manner as in Example 157, the title compound was obtained as a colorless powder from ethyl 3-[4-({4-[(3,5-diphenyl-1H-pyrazol-1-yl)methyl]-3-isopropoxybenzyl}amino)-2-fluorophenyl]propanoate. yield 99%.

MS (ESI+): 564 (M+H).

Example 226

3-[4-({4-[(3,5-diphenyl-1H-pyrazol-1-yl)methyl]-3-isopropoxybenzyl}amino)-2-fluorophenyl]propanoic acid dihydrochloride

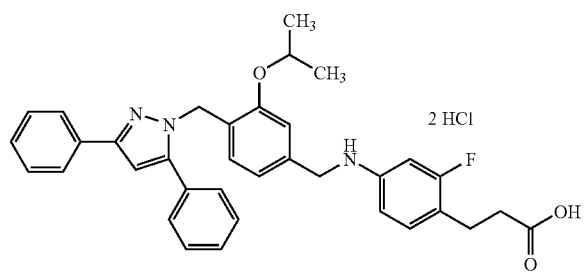

3-[4-({4-[(3,5-Diphenyl-1H-pyrazol-1-yl)methyl]-3-isopropoxybenzyl}amino)-2-fluorophenyl]propanoic acid (0.40 g, 0.71 mmol) was dissolved in ethyl acetate (4.0 mL), and 4 N hydrogen chloride/ethyl acetate solution (0.53 mL, 2.1 mmol) was added. The precipitated crystals were collected by filtration, washed with ethyl acetate and dried to give the title compound (0.41 g, yield 90%) as colorless crystals.

MS (ESI+): 564 (M+H, as free form).

Example 227 ethyl 3-[4-({[4'-(2-ethoxyethoxy)-2',3',6'-trimethylbiphenyl-3-yl]methyl}amino)-2-fluorophenyl]propanoate

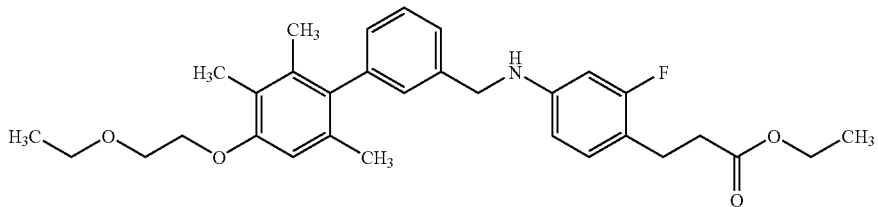

In the same manner as in Example 224, the title compound was obtained as a colorless oil from 4'-(2-ethoxyethoxy)-2',3',6'-trimethylbiphenyl-3-carbaldehyde and ethyl 3-(4-amino-2-fluorophenyl)propanoate. yield 100%.

$^1$H NMR (CDCl$_3$) δ: 1.19-1.29 (6H, m), 1.90 (3H, s), 1.95 (3H, s), 2.17 (3H, s), 2.54 (2H, t, J=7.8 Hz), 2.84 (2H, t, J=7.8 Hz), 3.64 (2H, q, J=6.9 Hz), 3.83 (2H, t, J=5.1 Hz), 4.07-4.18 (5H, m), 4.32 (2H, s), 6.25-6.37 (2H, m), 6.64 (1H, s), 6.95 (1H, t, J=8.4 Hz), 7.03 (1H, d, J=7.5 Hz), 7.08 (1H, s), 7.29 (1H, d, J=7.5 Hz), 7.38 (1H, t, J=7.5 Hz).

Example 228

3-[4-({[4'-(2-ethoxyethoxy)-2',3',6'-trimethylbiphenyl-3-yl]methyl}amino)-2-fluorophenyl]propanoic acid

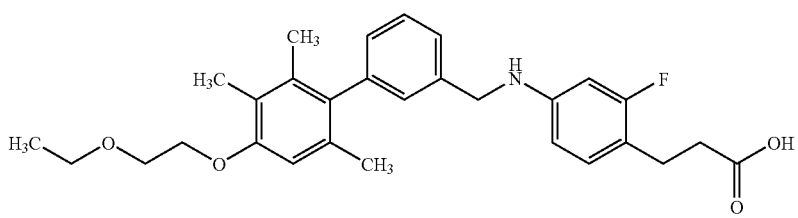

In the same manner as in Example 157, the title compound was obtained as a colorless oil from ethyl 3-[4-({[4'-(2-ethoxyethoxy)-2',3',6'-trimethylbiphenyl-3-yl]methyl}amino)-2-fluorophenyl]propanoate. yield 95%.

MS (ESI+): 480 (M+H).

Example 229

3-[4-({[4'-(2-ethoxyethoxy)-2',3',6'-trimethylbiphenyl-3-yl]methyl}amino)-2-fluorophenyl]propanoic acid hydrochloride

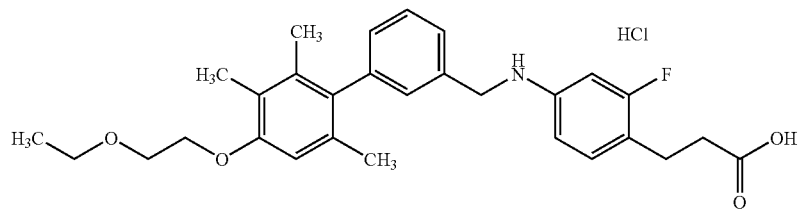

In the same manner as in Example 226, the title compound was obtained as colorless crystals from 3-[4-({[4'-(2-ethoxyethoxy)-2',3',6'-trimethylbiphenyl-3-yl]methyl}amino)-2-fluorophenyl]propanoic acid. yield 79%.

MS (ESI+): 480 (M+H, as free form).

Example 230 ethyl 3-[4-({[4'-(2-ethoxyethoxy)-2',3',5',6'-tetramethylbiphenyl-3-yl]methyl}amino)-2-fluorophenyl]propanoate

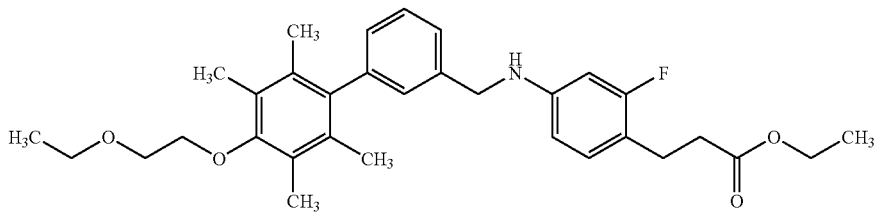

To a solution of 4'-(2-ethoxyethoxy)-2',3',5',6'-tetramethylbiphenyl-3-carbaldehyde (0.300 g, 0.99 mmol) and ethyl 3-(4-amino-2-fluorophenyl)propanoate (0.194 g, 0.99 mmol) in 1,2-dichloroethane (7.0 mL) was added acetic acid (0.158 mL, 2.76 mmol), and the mixture was stirred at room temperature for 3 hr. Sodium triacetoxyborohydride (0.585 g, 2.76 mmol) was added, and the mixture was further stirred for 3 hr. The reaction mixture was diluted with ethyl acetate, washed with saturated aqueous sodium hydrogencarbonate and saturated brine, dried over anhydrous sodium sulfate, and concentrated under reduced pressure. The residue was purified by silica gel column chromatography (hexane/ethyl acetate=10/1-hexane/ethyl acetate=2/1) to give the title compound (0.400 g, yield 84%) as a colorless oil.

$^1$H NMR (CDCl$_3$) δ: 1.23 (3H, t, J=7.2 Hz), 1.28 (3H, t, J=7.2 Hz), 1.86 (6H, s), 2.23 (6H, s), 2.54 (2H, t, J=7.8 Hz), 2.84 (2H, t, J=7.8 Hz), 3.64 (2H, q, J=7.2 Hz), 3.77-3.83 (2H, m), 3.88-3.94 (2H, m), 4.11 (2H, q, J=7.2 Hz), 4.32 (2H, s), 6.26-6.36 (2H, m), 6.95 (1H, t, J=8.4 Hz), 7.02 (1H, m), 7.08 (1H, s), 7.29 (1H, d, J=7.5 Hz), 7.38 (1H, t, J=7.5 Hz).

Example 231

3-[4-({[4'-(2-ethoxyethoxy)-2',3',5',6'-tetramethylbiphenyl-3-yl]methyl}amino)-2-fluorophenyl]propanoic acid hydrochloride

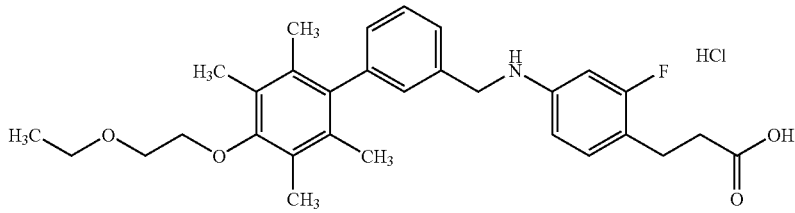

To a solution of ethyl 3-[4-({[4'-(2-ethoxyethoxy)-2',3',5',6'-tetramethylbiphenyl-3-yl]methyl}amino)-2-fluorophenyl]propanoate (0.40 g, 0.77 mmol) in a mixture of methanol (4.0 mL) and tetrahydrofuran (8.0 mL) was added 1 N aqueous sodium hydroxide solution (1.53 mL, 1.53 mmol), and the mixture was stirred at 50° C. for 2 hr. The reaction mixture was neutralized with 1 N hydrochloric acid, and diluted with ethyl acetate, and the organic layer was washed with water and saturated brine, dried over anhydrous magnesium sulfate, and concentrated under reduced pressure. The residue was purified by silica gel column chromatography (hexane/ethyl acetate=4/1-hexane/ethyl acetate=1/2) to give a colorless oil. The obtained oil was dissolved in ethyl acetate, and 4 N hydrogen chloride/ethyl acetate solution was added. The precipitated crystals were collected by filtration, washed with ethyl acetate, and dried to give the title compound (0.28 g, yield 70%) as colorless crystals.

MS (ESI+): 494 (M+H, as free form).
elemental analysis for C$_{30}$H$_{37}$NO$_4$ClF
Calculated: C, 67.98; H, 7.04; N, 2.64.
Found: C, 68.00; H, 7.07; N, 2.42.

Example 232 ethyl 3-[4-({4-[(2,2-dimethylquinolin-1(2H)-yl)methyl]-3-isopropoxybenzyl}amino)-2-fluorophenyl]propanoate

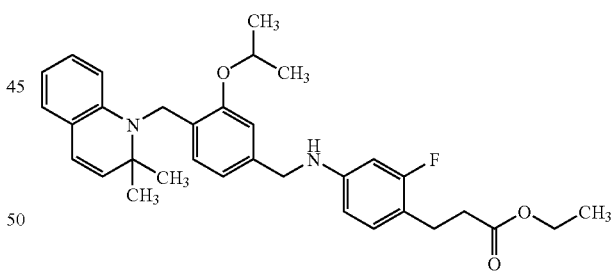

In the same manner as in Example 224, the title compound was obtained as a colorless oil from 4-[(2,2-dimethylquinolin-1(2H)-yl)methyl]-3-isopropoxybenzaldehyde and ethyl 3-(4-amino-2-fluorophenyl)propanoate. yield 90%.

MS (ESI+): 531 (M+H).

Example 233

3-[4-({4-[(2,2-dimethylquinolin-1(2H)-yl)methyl]-3-isopropoxybenzyl}amino)-2-fluorophenyl]propanoic acid

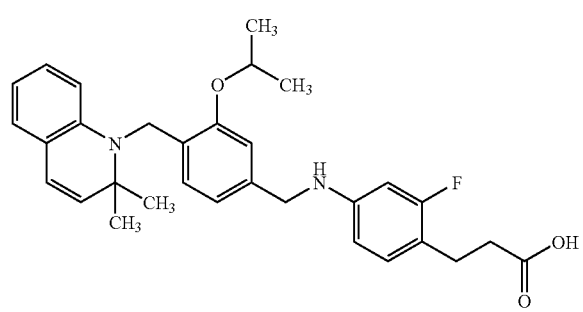

In the same manner as in Example 157, the title compound was obtained as a yellow oil from ethyl 3-[4-({4-[(2,2-dimethylquinolin-1(2H)-yl)methyl]-3-isopropoxybenzyl}amino)-2-fluorophenyl]propanoate. yield 95%.

MS (ESI+): 503 (M+H).

Example 234

3-[4-({4-[(2,2-dimethylquinolin-1(2H)-yl)methyl]-3-isopropoxybenzyl}amino)-2-fluorophenyl]propanoic acid calcium salt

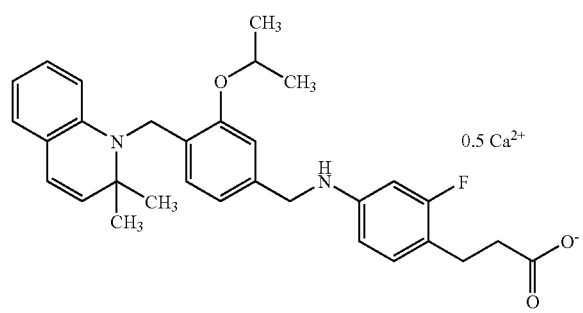

3-[4-({4-[(2,2-Dimethylquinolin-1(2H)-yl)methyl]-3-isopropoxybenzyl}amino)-2-fluorophenyl]propanoic acid (0.12 g, 0.24 mmol) was dissolved in methanol (2 mL), and 1 N aqueous sodium hydroxide solution (0.24 mL, 0.24 mmol) was added. A solution of calcium chloride (13 mg, 0.12 mmol) in water (1 mL) was added, and the precipitated solid was collected by filtration, washed with water and methanol and dried to give the title compound (53 mg, yield 43%) as a colorless powder.

MS (ESI+): 503 (M+H, as free form).

Example 235 ethyl 3-[2-fluoro-4-({3-isopropoxy-4-[(2-methyl-3,4-dihydroquinolin-1(2H)-yl)methyl]benzyl}amino)phenyl]propanoate

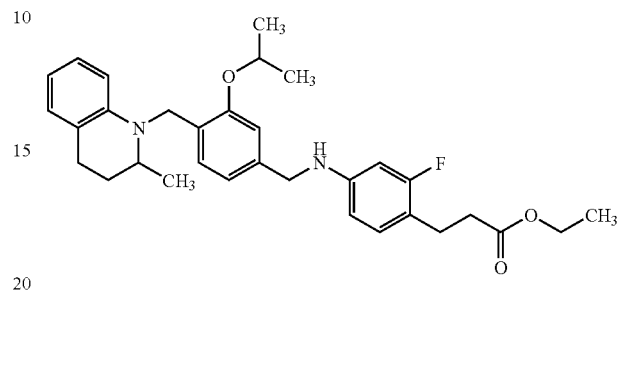

In the same manner as in Example 224, the title compound was obtained as a colorless oil from 3-isopropoxy-4-[(2-methyl-3,4-dihydroquinolin-1(2H)-yl)methyl]benzaldehyde and ethyl 3-(4-amino-2-fluorophenyl)propanoate. yield 82%.

MS (ESI+): 519 (M+H).

Example 236

3-[2-fluoro-4-({3-isopropoxy-4-[(2-methyl-3,4-dihydroquinolin-1(2H)-yl)methyl]benzyl}amino)phenyl]propanoic acid

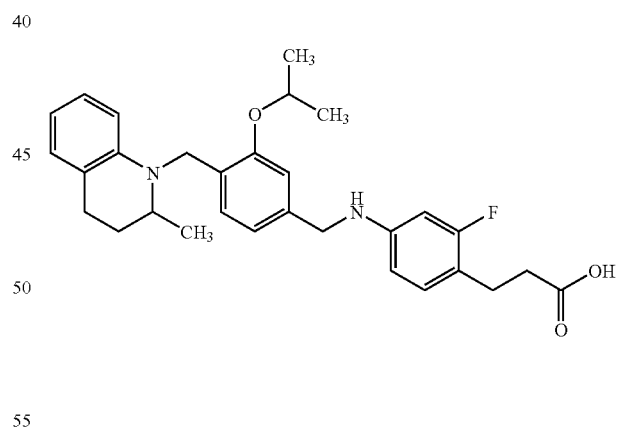

In the same manner as in Example 157, the title compound was obtained as a yellow oil from ethyl 3-[2-fluoro-4-({3-isopropoxy-4-[(2-methyl-3,4-dihydroquinolin-1(2H)-yl)methyl]benzyl}amino)phenyl]propanoate. yield 88%.

$^1$H NMR (CDCl$_3$) δ: 1.19 (3H, d, J=6.3 Hz), 1.36 (6H, dd, J=6.0, 2.4 Hz), 1.83 (1H, m), 2.03 (1H, m), 2.61 (2H, t, J=7.8 Hz), 2.75 (1H, m), 2.81-3.00 (3H, m), 3.56 (1H, m), 4.22 (2H, s), 4.36 (1H, d, J=18.0 Hz), 4.49 (1H, d, J=18.0 Hz), 4.60 (1H, m), 6.26-6.38 (3H, m), 6.54 (1H, m), 6.78 (1H, d, J=7.8 Hz), 6.85-7.02 (4H, m), 7.09 (1H, d, J=7.8 Hz).

Example 237

3-[2-fluoro-4-({3-isopropoxy-4-[(2-methyl-3,4-dihydroquinolin-1(2H)-yl)methyl]benzyl}amino)phenyl]propanoic acid calcium salt

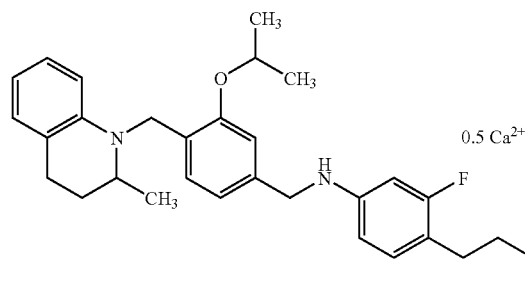

In the same manner as in Example 234, the title compound was obtained as a beige powder from 3-[2-fluoro-4-({3-isopropoxy-4-[(2-methyl-3,4-dihydroquinolin-1(2H)-yl)methyl]benzyl}amino)phenyl]propanoic acid. yield 68%.

$^1$H NMR (DMSO-d$_6$) δ: 1.09 (3H, d, J=6.6 Hz), 1.29 (6H, dd, J=5.1, 2.1 Hz), 1.77 (1H, m), 1.91 (1H, m), 2.06-2.17 (2H, m), 2.54-2.90 (4H, m), 3.55 (1H, m), 4.14 (2H, d, J=5.7 Hz), 4.25 (1H, d, J=17.7 Hz), 4.39 (1H, d, J=17.7 Hz), 4.61 (1H, m), 6.15 (1H, d, J=7.8 Hz), 6.19-6.35 (3H, m), 6.41 (1H, t, J=7.2 Hz), 6.74-6.85 (2H, m), 6.85-6.97 (3H, m), 7.00 (1H, s).

Example 238 ethyl 3-{4-[(4-{[4-(2,6-dimethylphenoxy)piperidin-1-yl]methyl}-3-isopropoxybenzyl)amino]-2-fluorophenyl}propanoate

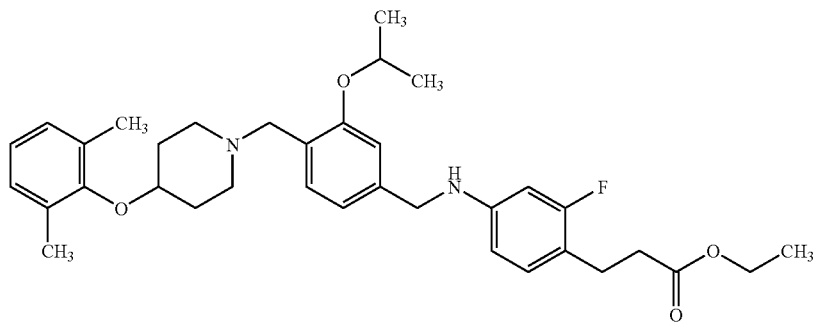

In the same manner as in Example 224, the title compound was obtained as a colorless oil from 4-{[4-(2,6-dimethylphenoxy)piperidin-1-yl]methyl}-3-isopropoxybenzaldehyde and ethyl 3-(4-amino-2-fluorophenyl)propanoate. yield 67%.

MS (ESI+): 577 (M+H).

Example 239

3-{4-[(4-{[4-(2,6-dimethylphenoxy)piperidin-1-yl]methyl}-3-isopropoxybenzyl)amino]-2-fluorophenyl}propanoic acid

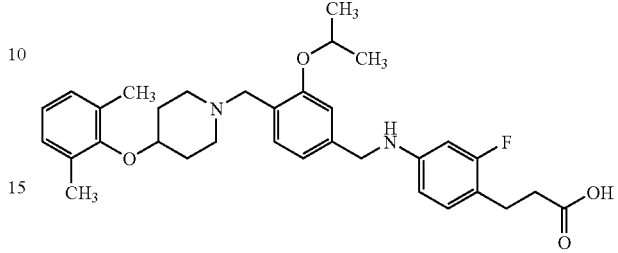

In the same manner as in Example 157, the title compound was obtained as a colorless oil from ethyl 3-{4-[(4-{[4-(2,6-dimethylphenoxy)piperidin-1-yl]methyl}-3-isopropoxybenzyl)amino]-2-fluorophenyl}propanoate. yield 99%.

MS (ESI+): 549 (M+H).

Example 240 ethyl 3-[2-fluoro-4-({3-isopropoxy-4-[(2-methyl-1H-indol-1-yl)methyl]benzyl}amino)phenyl]propanoate

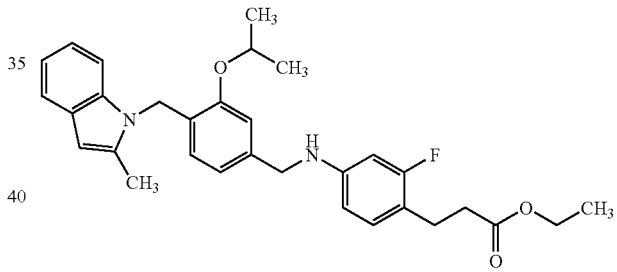

In the same manner as in Example 224, the title compound was obtained as a colorless oil from 3-isopropoxy-4-[(2-methyl-1H-indol-1-yl)methyl]benzaldehyde and ethyl 3-(4-amino-2-fluorophenyl)propanoate. yield 16%.

MS (ESI+): 503 (M+H).

Example 241

3-[2-fluoro-4-({3-isopropoxy-4-[(2-methyl-1H-indol-1-yl)methyl]benzyl}amino)phenyl]propanoic acid

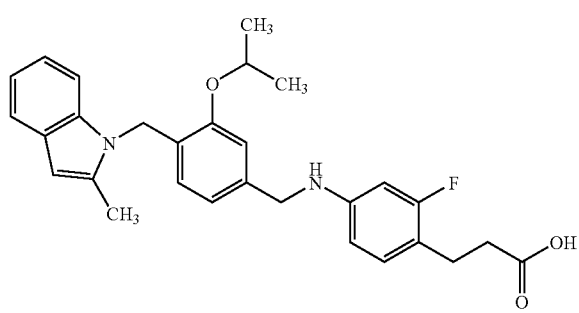

In the same manner as in Example 157, the title compound was obtained as an orange powder from ethyl 3-[2-fluoro-4-({3-isopropoxy-4-[(2-methyl-1H-indol-1-yl)methyl]benzyl}amino)phenyl]propanoate. yield 81%.

MS (APCI+): 475 (M+H).

Example 242 ethyl 3-[2-fluoro-4-({4-[(2-methyl-3,4-dihydroquinolin-1(2H)-yl)methyl]-3-[(methylsulfonyl)oxy]benzyl}amino)phenyl]propanoate

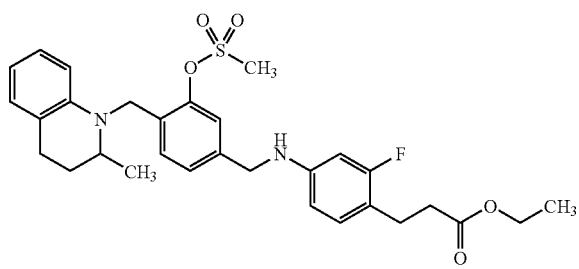

In the same manner as in Example 177, the title compound was obtained as a colorless oil from 5-(hydroxymethyl)-2-[(2-methyl-3,4-dihydroquinolin-1(2H)-yl)methyl]phenyl methanesulfonate and ethyl 3-(2-fluoro-4-{[(2-nitrophenyl)sulfonyl]amino}phenyl)propanoate. yield 83%.

MS (ESI+): 555 (M+H).

Example 243

3-[2-fluoro-4-({4-[(2-methyl-3,4-dihydroquinolin-1(2H)-yl)methyl]-3-[(methylsulfonyl)oxy]benzyl}amino)phenyl]propanoic acid

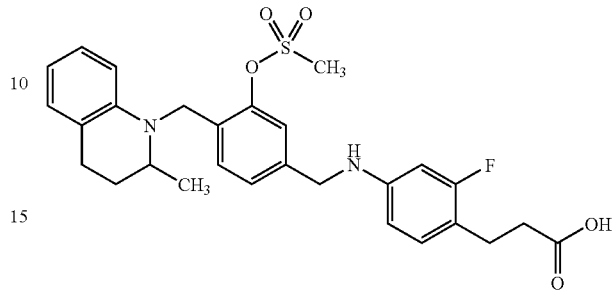

To a solution of ethyl 3-[2-fluoro-4-({4-[(2-methyl-3,4-dihydroquinolin-1(2H)-yl)methyl]-3-[(methylsulfonyl)oxy]benzyl}amino)phenyl]propanoate (0.60 g, 1.07 mmol) in a mixture of methanol (3.0 mL) and tetrahydrofuran (6.0 mL) was added 1 N aqueous sodium hydroxide solution (2.14 mL, 2.14 mmol), and the mixture was stirred at 50° C. for 1 hr. The reaction mixture was diluted with ethyl acetate, and the organic layer was washed with 10% aqueous citric acid solution and saturated brine, dried over anhydrous magnesium sulfate, and concentrated under reduced pressure. The residue was purified by preparative HPLC (gradient cycle A) to give a colorless oil. The obtained oil was dissolved in ethyl acetate, and the solution was neutralized with saturated aqueous sodium hydrogencarbonate solution, washed with saturated brine and dried to give the title compound (0.25 g, yield 56%) as a colorless oil.

MS (ESI+): 527 (M+H).

Example 244

3-[2-fluoro-4-({4-[(2-methyl-3,4-dihydroquinolin-1(2H)-yl)methyl]-3-[(methylsulfonyl)oxy]benzyl}amino)phenyl]propanoic acid calcium salt

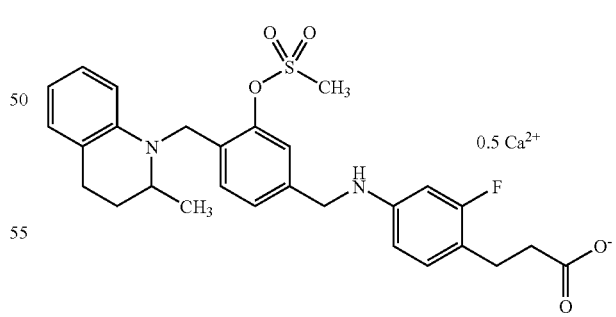

In the same manner as in Example 234, the title compound was obtained as a colorless powder from 3-[2-fluoro-4-({4-[(2-methyl-3,4-dihydroquinolin-1(2H)-yl)methyl]-3-[(methylsulfonyl)oxy]benzyl}amino)phenyl]propanoic acid. yield 66%.

MS (ESI+): 527 (M+H, as free form).

Example 245 ethyl 3-[4-({4-[(3,5-diphenyl-1H-pyrazol-1-yl)methyl]-3-methoxybenzyl}amino)-2-fluorophenyl]propanoate

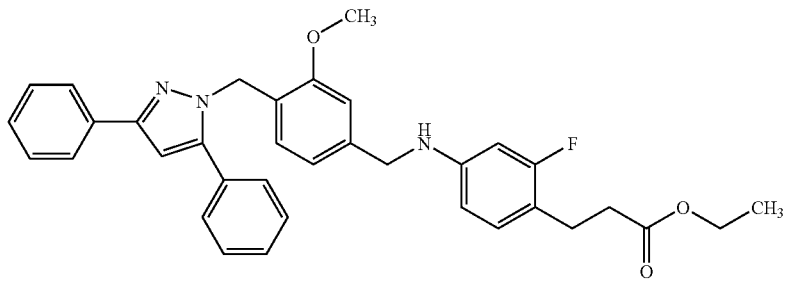

In the same manner as in Example 177, the title compound was obtained as a pale-yellow oil from {4-[(3,5-diphenyl-1H-pyrazol-1-yl)methyl]-3-methoxyphenyl}methanol and ethyl 3-(2-fluoro-4-{[(2-nitrophenyl)sulfonyl]amino}phenyl)propanoate. yield 82%.

MS (ESI+): 564 (M+H).

Example 246

3-[4-({4-[(3,5-diphenyl-1H-pyrazol-1-yl)methyl]-3-methoxybenzyl}amino)-2-fluorophenyl]propanoic acid dihydrochloride

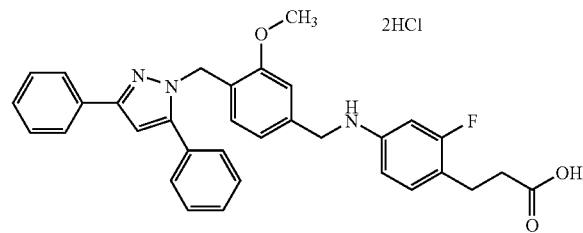

To a solution of ethyl 3-[4-({4-[(3,5-diphenyl-1H-pyrazol-1-yl)methyl]-3-methoxybenzyl}amino)-2-fluorophenyl]propanoate (0.57 g, 1.01 mmol) in a mixture of methanol (4.0 mL) and tetrahydrofuran (8.0 mL) was added 1 N aqueous sodium hydroxide solution (2.02 mL, 2.02 mmol), and the mixture was stirred at room temperature for 3 hr. The reaction mixture was diluted with ethyl acetate, and the organic layer was washed with 10% aqueous citric acid solution and saturated brine, dried over anhydrous magnesium sulfate, and concentrated under reduced pressure. The residue was purified by silica gel column chromatography (hexane/ethyl acetate=2/1-hexane/ethyl acetate=1/2) to give a colorless oil. The obtained oil was dissolved in ethyl acetate, and 4 N hydrogen chloride/ethyl acetate solution was added. The precipitated crystals were collected by filtration, washed with ethyl acetate and dried to give the title compound (0.48 g, yield 77%) as colorless crystals.

MS (ESI+): 536 (M+H, as free form).

Example 247 ethyl 3-(4-{[4-(diphenylmethoxy)-3-isobutylbenzyl][(2-nitrophenyl)sulfonyl]amino}-2-fluorophenyl)propanoate

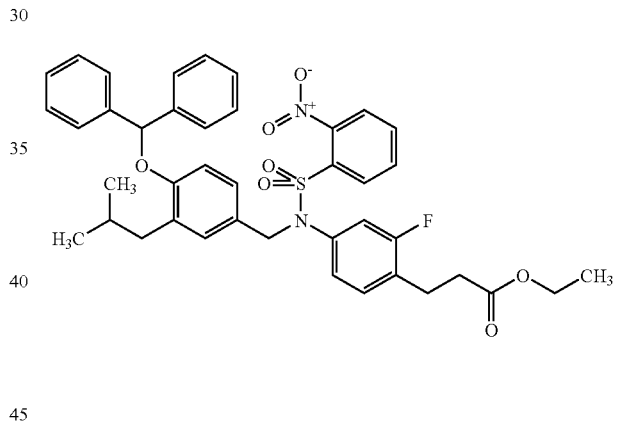

To a solution of [4-(diphenylmethoxy)-3-isobutylphenyl]methanol (0.49 g, 1.41 mmol), ethyl 3-(2-fluoro-4-{[(2-nitrophenyl)sulfonyl]amino}phenyl)propanoate (0.62 g, 1.56 mmol) and triphenylphosphine (0.55 g, 2.10 mmol) in tetrahydrofuran (25 mL) was added diethyl azodicarboxylate (40% toluene solution, 0.93 mL, 2.13 mmol) at room temperature, and the mixture was stirred at room temperature for 18 hr. The reaction mixture was concentrated, and the residue was subjected to silica gel column chromatography (ethyl acetate/hexane=3/97-15/85) to give the title compound (800 mg, yield 78%) as a colorless oil.

MS m/z 747 ((M+Na)$^+$).

$^1$H NMR (CDCl$_3$) δ: 0.83 (6H, d, J=6.6 Hz), 1.20 (3H, t, J=7.0 Hz), 1.80-2.00 (1H, m), 2.45-2.60 (4H, m), 2.87 (2H, t, J=7.8 Hz), 4.10 (2H, q, J=7.0 Hz), 4.77 (2H, s), 6.12 (1H, s), 6.62 (1H, d, J=7.6 Hz), 6.68-7.70 (19H, m).

Example 248 ethyl 3-(4-{[4-(diphenylmethoxy)-3-isobutylbenzyl]amino}-2-fluorophenyl)propanoate

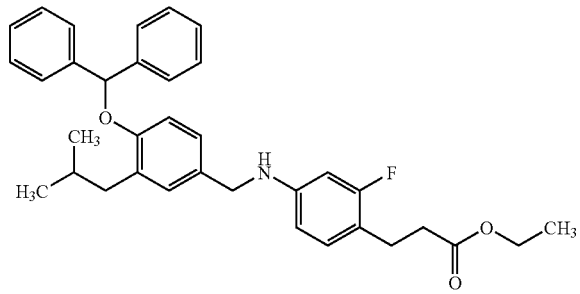

To a solution of ethyl 3-(4-{[4-(diphenylmethoxy)-3-isobutylbenzyl][(2-nitrophenyl)sulfonyl]amino}-2-fluorophenyl)propanoate (0.80 g, 1.10 mmol) and mercaptoacetic acid (0.17 mL, 2.45 mmol) in N,N-dimethylformamide (15 mL) was added lithium hydroxide monohydrate (0.20 g, 4.77 mmol), and the mixture was stirred at room temperature for 18 hr. The reaction mixture was poured into 10% aqueous sodium hydrogencarbonate solution, and the mixture was extracted with ethyl acetate. The ethyl acetate layer was washed successively with water and saturated brine, dried over anhydrous magnesium sulfate, and concentrated under reduced pressure. The residue was subjected to silica gel column chromatography (ethyl acetate/hexane=3/97-15/85) to give the title compound (552 mg, yield 93%) as a pale-yellow oil.

MS m/z 562 ((M+Na)$^+$).

$^1$H NMR (CDCl$_3$) δ: 0.91 (6H, d, J=6.3 Hz), 1.22 (3H, t, J=7.2 Hz), 1.94-2.08 (1H, m), 2.50-2.64 (4H, m), 2.83 (2H, t, J=7.8 Hz), 3.88 (1H, br s), 4.10 (2H, q, J=7.2 Hz), 4.12 (2H, s), 6.15 (1H, s), 6.23-6.32 (2H, m), 6.70 (1H, d, J=8.4 Hz), 6.90-7.45 (12H, m).

Example 249

3-(4-{[4-(diphenylmethoxy)-3-isobutylbenzyl]amino}-2-fluorophenyl)propanoic acid

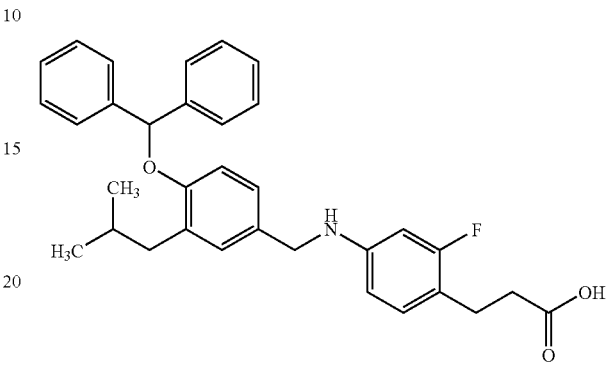

To a solution of ethyl 3-(4-{[4-(diphenylmethoxy)-3-isobutylbenzyl]amino}-2-fluorophenyl)propanoate (0.50 g, 0.93 mmol) in a mixture of methanol (8 mL) and tetrahydrofuran (8 mL) was added an aqueous solution (4 mL) of 85% potassium hydroxide (0.20 g, 3.03 mmol), and the mixture was stirred at room temperature for 18 hr. Water was added to the reaction mixture, and the mixture was weakly acidified with 10% aqueous citric acid solution and extracted with ethyl acetate. The extract was washed with saturated brine, dried over anhydrous magnesium sulfate, and concentrated under reduced pressure. The obtained residue was recrystallized from ethyl acetate-diethyl ether to give the title compound (354 mg, yield 75%) as colorless prism crystals.

$^1$H NMR (CDCl$_3$) δ: 0.92 (6H, d, J=6.3 Hz), 1.92-2.12 (1H, m), 2.58 (2H, d, J=7.2 Hz), 2.60 (2H, t, J=7.8 Hz), 2.85 (2H, t, J=7.8 Hz), 4.12 (2H, s), 6.16 (1H, s), 6.25-6.36 (2H, m), 6.71 (1H, d, J=8.2 Hz), 6.90-7.48 (12H, m).

Example 250 methyl {6-[({4'-[(4-hydroxy-1,1-dioxidotetrahydro-2H-thiopyran-4-yl)methoxy]-2',6'-dimethylbiphenyl-3-yl}methyl)amino]-1-benzofuran-3-yl}acetate

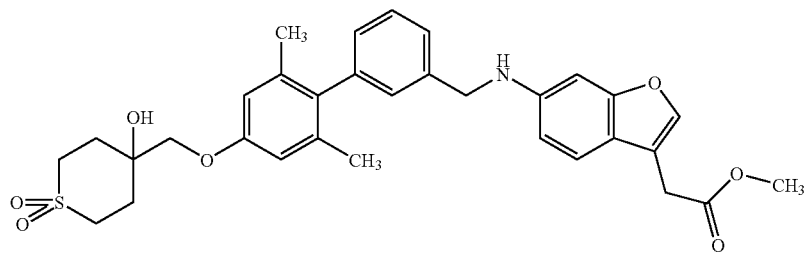

To a solution of methyl(6-{[(2-nitrophenyl)sulfonyl]amino}-1-benzofuran-3-yl)acetate (1.95 g, 5.00 mmol), 4-({[3'-(hydroxymethyl)-2,6-dimethylbiphenyl-4-yl]oxy}methyl)tetrahydro-2H-thiopyran-4-ol (1.79 g, 5.00 mmol) and triphenylphosphine (2.63 g, 10.0 mmol) in toluene (75 mL) was added diethyl azodicarboxylate (40% toluene solution, 4.55 mL, 10.0 mmol), and the mixture was stirred at room temperature for 24 hr. The reaction mixture was concentrated under reduced pressure, and the residue was purified by silica gel column chromatography (ethyl acetate/hexane=20/80-60/40) to give methyl(6-{({4-[(4-hydroxytetrahydro-2H-thiopyran-4-yl)methoxy]-2',6'-dimethylbiphenyl-3-yl}methyl)[(2-nitrophenyl)sulfonyl]amino}-1-benzofuran-3-yl)acetate as an orange oil. The obtained oil was dissolved in ethyl acetate (20 mL), and m-chloroperbenzoic acid (72%, 2.39 g, 9.99 mmol) was added under ice-cooling. The mixture was gradually warmed to room temperature and stirred for 24 hr. The reaction mixture was diluted with water, basified with 1 M aqueous sodium hydroxide solution, and extracted with ethyl acetate. The extract was washed with saturated brine, dried over anhydrous magnesium sulfate, and concentrated under reduced pressure. The residue was purified by silica gel column chromatography (ethyl acetate/hexane=70/30-100/0) to give methyl(6-{({4'-[(4-hydroxy-1,1-dioxidotetrahydro-2H-thiopyran-4-yl)methoxy]-2',6'-dimethylbiphenyl-3-yl}methyl)[(2-nitrophenyl)sulfonyl]amino}-1-benzofuran-3-yl)acetate as an orange oil. To a solution of the obtained oil and mercaptoacetic acid (0.694 mL, 9.99 mmol) in N,N-dimethylformamide (5 mL) was added lithium hydroxide monohydrate (0.838 g, 20.0 mmol), and the mixture was stirred at room temperature for 2 hr. Ethyl acetate was added to the residue, and the mixture was washed with saturated aqueous sodium hydrogencarbonate and saturated brine, dried over anhydrous sodium sulfate, and concentrated under reduced pressure. The residue was purified by silica gel column chromatography (ethyl acetate/hexane=40/60-80/20) and recrystallized from hexane-ethyl acetate to give the title compound (1.13 g, yield 39%, 3 steps) as pale-yellow crystals.

MS m/z 578 (MH+).

Example 251

{6-[({4'-[(4-hydroxy-1,1-dioxidotetrahydro-2H-thiopyran-4-yl)methoxy]-2',6'-dimethylbiphenyl-3-yl}methyl)amino]-1-benzofuran-3-yl}acetic acid

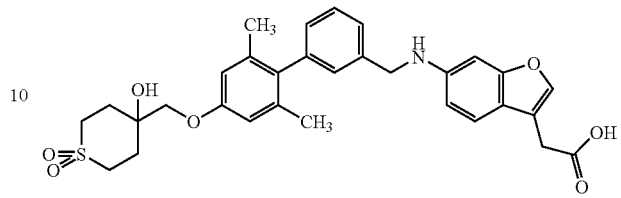

In the same manner as in Example 6, the title compound was obtained as pale-green crystals from methyl {6-[({4'-[(4-hydroxy-1,1-dioxidotetrahydro-2H-thiopyran-4-yl)methoxy]-2',6'-dimethylbiphenyl-3-yl}methyl)amino]-1-benzofuran-3-yl}acetate. yield 89%.

MS m/z 564 (MH+).

Example 252 methyl {6-[({4'-[(4-hydroxy-1,1-dioxidotetrahydro-2H-thiopyran-4-yl)methoxy]-2',6'-dimethylbiphenyl-3-yl}methyl)amino]-2,3-dihydro-1-benzofuran-3-yl}acetate

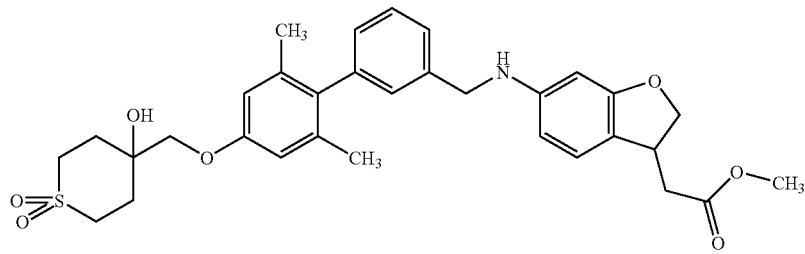

In the same manner as in Reference Example 21, the title compound was obtained as a colorless amorphous powder from methyl {6-[({4'-[(4-hydroxy-1,1-dioxidotetrahydro-2H-thiopyran-4-yl)methoxy]-2',6'-dimethylbiphenyl-3-yl}methyl)amino]-1-benzofuran-3-yl}acetate. yield 80%.

MS m/z 580 (MH+).

Example 253

{6-[({4'-[(4-hydroxy-1,1-dioxidotetrahydro-2H-thiopyran-4-yl)methoxy]-2',6'-dimethylbiphenyl-3-yl}methyl)amino]-2,3-dihydro-1-benzofuran-3-yl}acetic acid

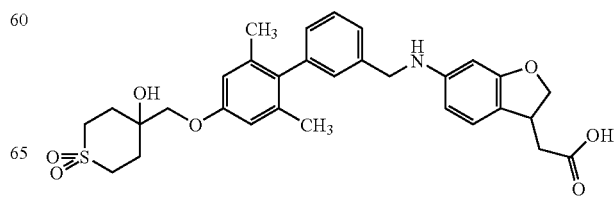

In the same manner as in Example 6, the title compound was obtained as beige crystals from methyl {6-[({4'-[(4-hydroxy-1,1-dioxidotetrahydro-2H-thiopyran-4-yl)methoxy]-2',6'-dimethylbiphenyl-3-yl}methyl)amino]-2,3-dihydro-1-benzofuran-3-yl}acetate. yield 83%.

MS m/z 566 (MH⁺).

Example 254 ethyl 3-{2-fluoro-4-[(4-{1-[(4-phenyl-1,3-thiazol-2-yl)methyl]butyl}benzyl)amino]phenyl}propanoate

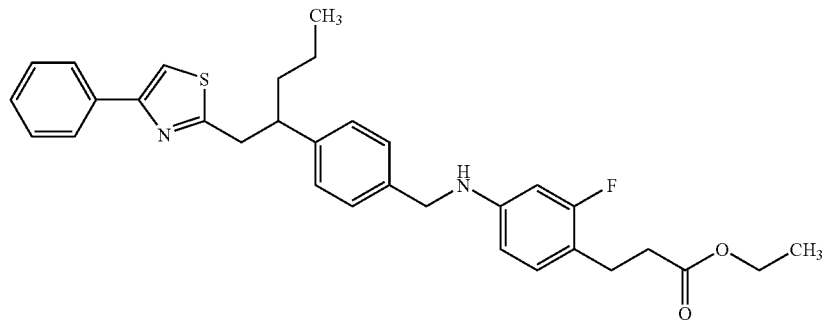

A solution of ethyl 3-(2-fluoro-4-{[(2-nitrophenyl)sulfonyl]amino}phenyl)propanoate (0.686 g, 1.73 mmol), (4-{1-[(4-phenyl-1,3-thiazol-2-yl)methyl]butyl}phenyl)methanol (0.389 g, 1.15 mmol) and triphenylphosphine (0.603 g, 2.30 mmol) in tetrahydrofuran (15 mL) was stirred under ice-cooling, and diethyl azodicarboxylate (40% toluene solution, 1.05 mL, 2.3 mmol) was added. The mixture was allowed to warm to room temperature and stirred for 16 hr. The reaction mixture was concentrated under reduced pressure, and the residue was purified by silica gel column chromatography (10%-80% ethyl acetate/hexane) to give ethyl 3-{2-fluoro-4-[[(2-nitrophenyl)sulfonyl](4-{1-[(4-phenyl-1,3-thiazol-2-yl)methyl]butyl}benzyl)amino]phenyl}propanoate as a yellow oil. To a solution of the obtained oil and mercaptoacetic acid (0.291 g, 3.16 mmol) in N,N-dimethylformamide (15 mL) was added lithium hydroxide monohydrate (0.265 g, 6.32 mmol), and the mixture was stirred at room temperature for 2 hr. Ethyl acetate was added to the reaction mixture, and the mixture was washed with saturated aqueous sodium hydrogencarbonate and saturated brine, dried over anhydrous magnesium sulfate, and concentrated under reduced pressure. The residue was purified by silica gel column chromatography (5%-40% ethyl acetate/hexane) to give the title compound (0.420 g, yield 69%, 2 steps) as a colorless oil.

MS m/z 531 (MH⁺).

Example 255

3-{2-fluoro-4-[(4-{1-[(4-phenyl-1,3-thiazol-2-yl)methyl]butyl}benzyl)amino]phenyl}propanoic acid

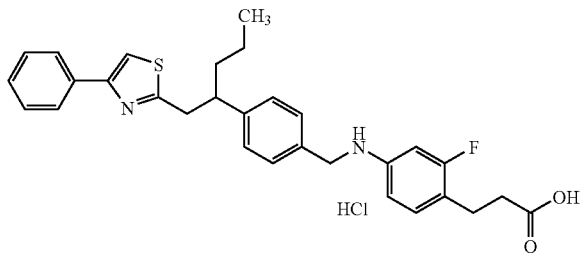

To a solution of ethyl 3-{2-fluoro-4-[(4-{1-[(4-phenyl-1,3-thiazol-2-yl)methyl]butyl}benzyl)amino]phenyl}propanoate (0.420 g, 0.790 mmol) in a mixture of ethanol (6 mL), tetrahydrofuran (12 mL) and water (6 mL) was added lithium hydroxide monohydrate (0.198 g, 4.74 mmol), and the mixture was stirred at room temperature for 2.5 hr. The reaction mixture was neutralized with 1 N hydrochloric acid and extracted with ethyl acetate. The organic layer was washed with saturated brine, dried over anhydrous magnesium sulfate, and concentrated under reduced pressure. The residue was purified by silica gel column chromatography (15%-60% ethyl acetate/hexane) to give the title compound (330 mg, yield 83%) as a colorless oil.

MS m/z 503 (MH⁺).

Example 256

3-{2-fluoro-4-[(4-{1-[(4-phenyl-1,3-thiazol-2-yl)methyl]butyl}benzyl)amino]phenyl}propanoic acid hydrochloride

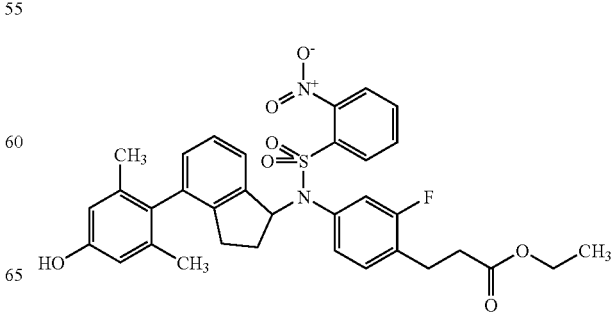

In the same manner as in Example 40, the title compound was obtained as colorless crystals from 3-{2-fluoro-4-[(4-{1-[(4-phenyl-1,3-thiazol-2-yl)methyl]butyl}benzyl)amino]phenyl}propanoic acid. yield 66%.

MS m/z 503 (MH⁺, as free form).

Example 257 ethyl 3-(2-fluoro-4-{[4-(4-hydroxy-2,6-dimethylphenyl)-2,3-dihydro-1H-inden-1-yl][(2-nitrophenyl)sulfonyl]amino}phenyl)propanoate Ethyl 3-{2-fluoro-4-[[(2-nitrophenyl)sulfonyl](4-{[(trifluoromethyl)sulfonyl]oxy}-2,3-dihydro-1H-inden-1-yl)amino]phenyl}propanoate (3.14 g, 4.76 mmol), (4-{[tert-butyl(dimethyl)silyl]oxy}-2,6-dimethylphenyl)boronic acid (2.0 g, 7.14 mmol) and sodium carbonate (1.51 g, 14.3 mmol) were dissolved in a mixture of water (10 mL), ethanol (10 mL) and toluene (30 mL), and the air was substituted with argon gas. Tetrakis(triphenylphosphine)palladium(0) (0.275 g, 0.24 mmol) was added. The reaction mixture was stirred under an argon atmosphere at 120° C. for 16 hr. After cooling, the reaction mixture was diluted with water, and the mixture was extracted with ethyl acetate. The extract was washed with saturated brine, dried over anhydrous magnesium sulfate, and concentrated under reduced pressure. The residue was purified by silica gel column chromatography (3%-60% ethyl acetate/hexane) to give ethyl 3-(4-{[4-(4-{[tert-butyl(dimethyl)silyl]oxy}-2,6-dimethylphenyl)-2,3-dihydro-1H-inden-1-yl][(2-nitrophenyl)sulfonyl]amino}-2-fluorophenyl)propanoate as a yellow oil. The obtained oil was dissolved in tetrahydrofuran (30 mL), tetrabutylammonium fluoride (1 M THF solution, 2.43 mL, 2.43 mmol) was added under stirring at room temperature, and the mixture was stirred at room temperature for 16 hr. The reaction mixture was diluted with ethyl acetate, washed with saturated brine, dried over anhydrous magnesium sulfate, and concentrated under reduced pressure. The residue was purified by silica gel column chromatography (10%-60% ethyl acetate/hexane) to give the title compound (1.46 g, yield 78%, 2 steps) as a yellow oil.

MS m/z 633 (MH$^+$).

Example 258 ethyl 3-(4-{{4-[2,6-dimethyl-4-(tetrahydro-2H-thiopyran-4-yloxy)phenyl]-2,3-dihydro-1H-inden-1-yl}[(2-nitrophenyl)sulfonyl]amino}-2-fluorophenyl)propanoate

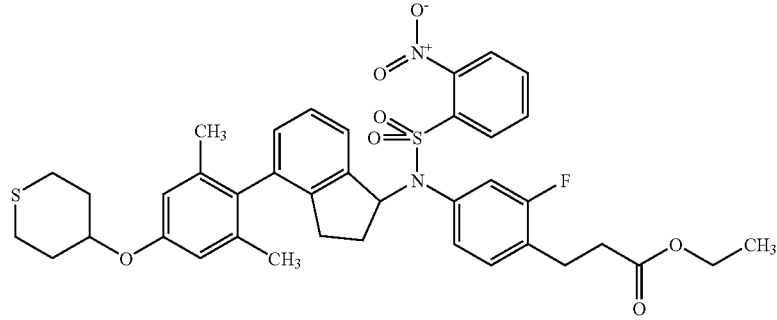

In the same manner as in Example 201, the title compound was obtained as a yellow oil from ethyl 3-(2-fluoro-4-{[4-(4-hydroxy-2,6-dimethylphenyl)-2,3-dihydro-1H-inden-1-yl][(2-nitrophenyl)sulfonyl]amino}phenyl)propanoate. yield 100%.

MS m/z 733 (MH$^+$).

Example 259 ethyl 3-(4-{(4-{4-[(1,1-dioxidotetrahydro-2H-thiopyran-4-yl)oxy]-2,6-dimethylphenyl}-2,3-dihydro-1H-inden-1-yl)[(2-nitrophenyl)sulfonyl]amino}-2-fluorophenyl)propanoate

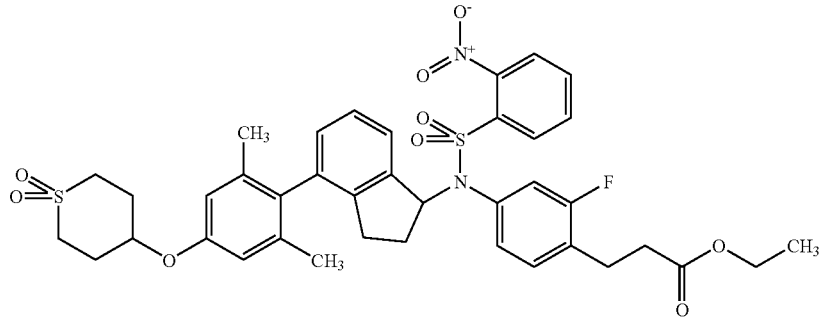

In the same manner as in Example 144, the title compound was obtained as a yellow oil from ethyl 3-(4-{{4-[2,6-dimethyl-4-(tetrahydro-2H-thiopyran-4-yloxy)phenyl]-2,3-dihydro-1H-inden-1-yl}[(2-nitrophenyl)sulfonyl]amino}-2-fluorophenyl)propanoate. yield 24%.

MS m/z 765 (MH⁺).

Example 260 ethyl 3-{4-[(4-{4-[(1,1-dioxidotetrahydro-2H-thiopyran-4-yl)oxy]-2,6-dimethylphenyl}-2,3-dihydro-1H-inden-1-yl)amino]-2-fluorophenyl}propanoate

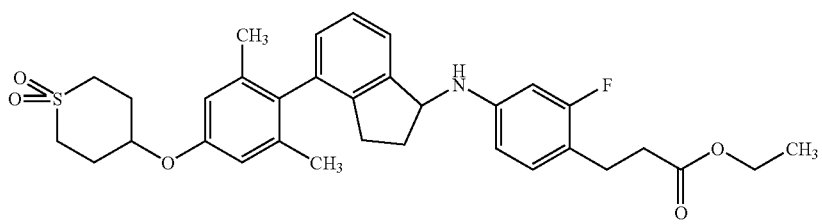

In the same manner as in Example 10, the title compound was obtained as a yellow oil from ethyl 3-(4-{(4-{4-[(1,1-dioxidotetrahydro-2H-thiopyran-4-yl)oxy]-2,6-dimethylphenyl}-2,3-dihydro-1H-inden-1-yl)[(2-nitrophenyl)sulfonyl]amino}-2-fluorophenyl)propanoate. yield 42%.

MS m/z 580 (MH⁺).

Example 261

3-{4-[(4-{4-[(1,1-dioxidotetrahydro-2H-thiopyran-4-yl)oxy]-2,6-dimethylphenyl}-2,3-dihydro-1H-inden-1-yl)amino]-2-fluorophenyl}propanoic acid

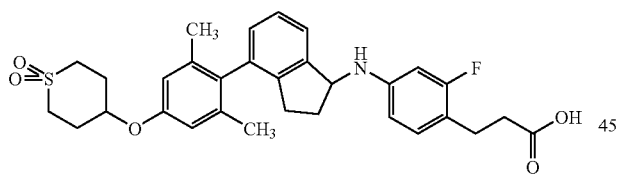

In the same manner as in Example 188, the title compound was obtained as colorless crystals from ethyl 3-{4-[(4-{4-[(1,1-dioxidotetrahydro-2H-thiopyran-4-yl)oxy]-2,6-dimethylphenyl}-2,3-dihydro-1H-inden-1-yl)amino]-2-fluorophenyl}propanoate. yield 75%.

MS m/z 552 (MH⁺).

Example 262 ethyl 3-(2-fluoro-4-{(4-{4-[(4-hydroxy-1,1-dioxidotetrahydro-2H-thiopyran-4-yl)methoxy]-2,6-dimethylphenyl}-2,3-dihydro-1H-inden-1-yl)[(2-nitrophenyl)sulfonyl]amino}phenyl)propanoate

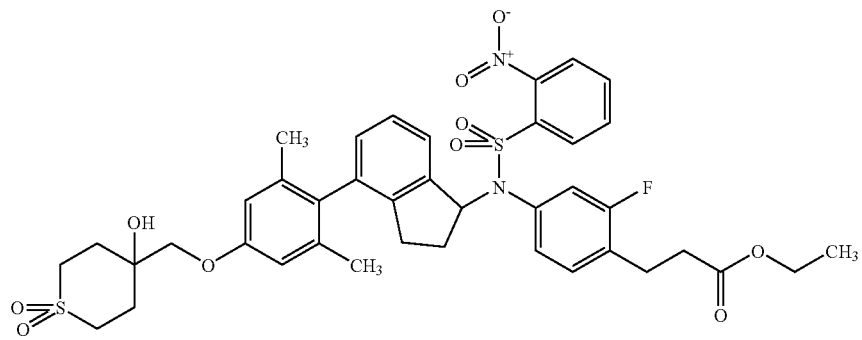

To a solution of ethyl 3-(2-fluoro-4-{[4-(4-hydroxy-2,6-dimethylphenyl)-2,3-dihydro-1H-inden-1-yl][(2-nitrophenyl)sulfonyl]amino}phenyl)propanoate (0.698 g, 1.1 mmol) in N,N-dimethylformamide (8 mL) were added 1-oxa-6-thiaspiro[2.5]octane (0.286 g, 2.20 mmol) and potassium carbonate (0.304 g, 2.20 mmol) under stirring at room temperature, and the mixture was stirred at 80° C. for 16 hr. To the reaction mixture were added reagents (1-oxa-6-thiaspiro[2.5]octane and potassium carbonate) in the same amount as mentioned above. After stirring for 8 hr, reagents (1-oxa-6-thiaspiro[2.5]octane and potassium carbonate) in twice the above-mentioned amount were added and the mixture was stirred for 16 hr. After cooling the reaction mixture, water was added to the reaction mixture and the mixture was extracted with ethyl acetate. The extract was washed with saturated brine, dried over anhydrous magnesium sulfate, and concentrated under reduced pressure. The residue was purified by silica gel column chromatography (10%-80% ethyl acetate/hexane) to give ethyl 3-(2-fluoro-4-{(4-{4-[(4-hydroxytetrahydro-2H-thiopyran-4-yl)methoxy]-2,6-dimethylphenyl}-2,3-dihydro-1H-inden-1-yl)[(2-nitrophenyl)sulfonyl]amino}phenyl)propanoate as a yellow oil. To the obtained oil dissolved in ethyl acetate (15 mL) was added m-chloroperbenzoic acid (70%, 0.459 g, 1.86 mmol) under stirring at 0° C., and the mixture was stirred at the same temperature for 3 hr. The reaction mixture was washed with saturated brine and saturated brine, dried over anhydrous magnesium sulfate, and concentrated under reduced pressure. The residue was purified by silica gel column chromatography (15%-90% ethyl acetate/hexane) to give the title compound (0.426 g, yield 72%, 2 steps) as a colorless oil.

MS m/z 795 (MH$^+$).

Example 263 ethyl 3-{2-fluoro-4-[(4-{4-[(4-hydroxy-1,1-dioxidotetrahydro-2H-thiopyran-4-yl)methoxy]-2,6-dimethylphenyl}-2,3-dihydro-1H-inden-1-yl)amino]phenyl}propanoate

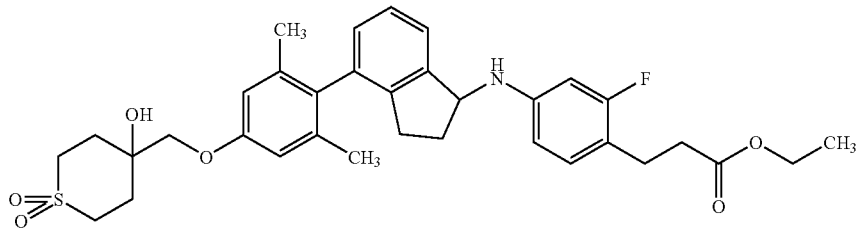

In the same manner as in Example 10, the title compound was obtained as a colorless oil from ethyl 3-(2-fluoro-4-{(4-{4-[(4-hydroxy-1,1-dioxidotetrahydro-2H-thiopyran-4-yl)methoxy]-2,6-dimethylphenyl}-2,3-dihydro-1H-inden-1-yl)[(2-nitrophenyl)sulfonyl]amino}phenyl)propanoate. yield 61%.

MS m/z 610 (MH$^+$).

Example 264

3-{2-fluoro-4-[(4-{4-[(4-hydroxy-1,1-dioxidotetrahydro-2H-thiopyran-4-yl)methoxy]-2,6-dimethylphenyl}-2,3-dihydro-1H-inden-1-yl)amino]phenyl}propanoic acid

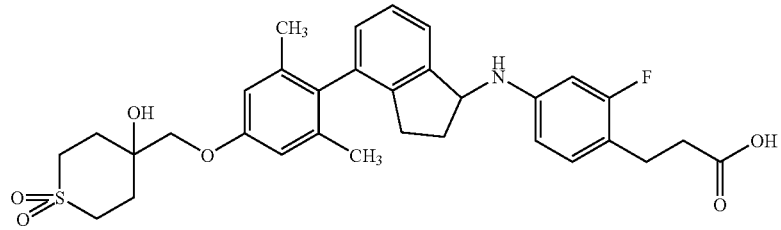

In the same manner as in Example 188, the title compound was obtained as colorless crystals from ethyl 3-{2-fluoro-4-[(4-{4-[(4-hydroxy-1,1-dioxidotetrahydro-2H-thiopyran-4-yl)methoxy]-2,6-dimethylphenyl}-2,3-dihydro-1H-inden-1-yl)amino]phenyl}propanoate. yield 57%.
MS m/z 582 (MH$^+$).

Example 265 ethyl 3-(4-{(4-{4-[2-(ethylthio)ethoxy]-2,6-dimethylphenyl}-2,3-dihydro-1H-inden-1-yl)[(2-nitrophenyl)sulfonyl]amino}-2-fluorophenyl)propanoate

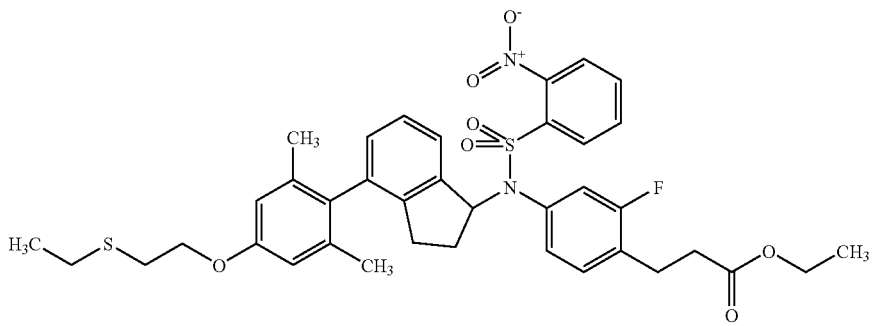

To a solution of ethyl 3-(2-fluoro-4-{[4-(4-hydroxy-2,6-dimethylphenyl)-2,3-dihydro-1H-inden-1-yl][(2-nitrophenyl)sulfonyl]amino}phenyl)propanoate (1.00 g, 1.58 mmol), 2-(ethylthio)ethanol (0.219 mg, 2.06 mmol) and tributylphosphine (0.417 mg, 2.06 mmol) in tetrahydrofuran (25 mL) was added 1,1'-(azodicarbonyl)dipiperidine (0.520 g, 2.06 mmol) under stirring at room temperature, and the mixture was stirred for 16 hr. The reaction mixture was diluted with diisopropyl ether, the insoluble material was filtered off, and the filtrate was concentrated under reduced pressure. The residue was purified by silica gel column chromatography (10%-80% ethyl acetate/hexane) to give the title compound (1.06 g, yield 93%) as a colorless oil.
MS m/z 721 (MH$^+$).

Example 266

3-(4-{(4-{4-[2-(ethylthio)ethoxy]-2,6-dimethylphenyl}-2,3-dihydro-1H-inden-1-yl)[(2-nitrophenyl)sulfonyl]amino}-2-fluorophenyl)propanoic acid To a mixture of ethyl 3-(4-{(4-{4-[2-(ethylthio)ethoxy]-2,6-dimethylphenyl}-2,3-dihydro-1H-inden-1-yl)[(2-nitrophenyl)sulfonyl]amino}-2-fluorophenyl)propanoate (1.06 g, 1.47 mmol), ethanol (5 mL) and tetrahydrofuran (5 mL) was added 1 N aqueous sodium hydroxide solution (2.94 mL, 2.94 mmol), and the mixture was stirred at room temperature for 4 hr. The reaction mixture was neutralized with 1 N hydrochloric acid, and concentrated under reduced pressure to evaporate the organic solvent. The residue was extracted with ethyl acetate, and the organic layer was dried over anhydrous magnesium sulfate, and concentrated under reduced pressure. The obtained residue was purified by silica gel column chromatography (20%-100% ethyl acetate/hexane) to give the title compound (0.804 g, yield 79%) as a colorless oil.

$^1$H NMR (CDCl$_3$) δ: 1.22-1.32 (3H, m), 1.52 (3H, s), 1.66-1.82 (1H, m), 1.84 (3H, s), 2.06-2.20 (2H, m), 2.43-2.69 (5H, m), 2.87 (4H, q, J=7.2 Hz), 4.06-4.17 (2H, m), 6.06 (1H, dd, J=8.7, 2.1 Hz), 6.46 (1H, dd, J=10.6, 1.9 Hz), 6.51-6.60 (3H, m), 6.92-7.00 (2H, m), 7.34 (1H, t, J=7.5 Hz), 7.53-7.63 (2H, m), 7.68-7.76 (3H, m).

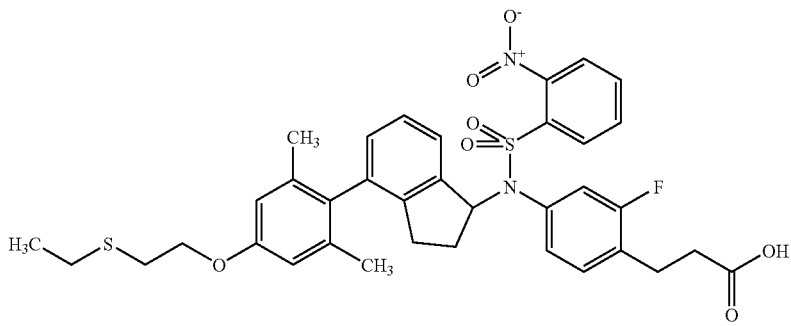

Example 267

3-(4-{(4-{4-[2-(ethylsulfonyl)ethoxy]-2,6-dimethylphenyl}-2,3-dihydro-1H-inden-1-yl)[(2-nitrophenyl)sulfonyl]amino}-2-fluorophenyl)propanoic acid

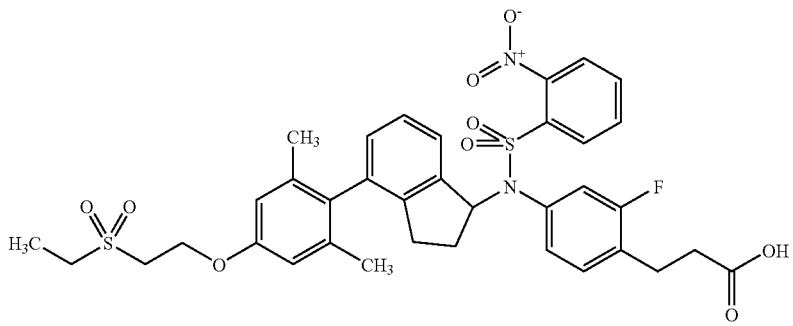

To a solution of 3-(4-{(4-{4-[2-(ethylthio)ethoxy]-2,6-dimethylphenyl}-2,3-dihydro-1H-inden-1-yl)[(2-nitrophenyl)sulfonyl]amino}-2-fluorophenyl)propanoic acid (0.804 g, 1.16 mmol) in ethyl acetate (20 mL) was added m-chloroperbenzoic acid (70%, 0.716 g, 2.90 mmol) under stirring at 0° C., and the mixture was stirred at the same temperature for 3 hr. The reaction mixture was diluted with ethyl acetate, washed with water and saturated brine, dried over anhydrous magnesium sulfate, and concentrated under reduced pressure. The residue was purified by silica gel column chromatography (40%-100% ethyl acetate/hexane) to give the title compound (0.620 g, yield 74%) as a colorless oil.

$^1$H NMR (CDCl$_3$) δ: 1.44 (3H, t, J=7.5 Hz), 1.53 (3H, s), 1.65-1.80 (1H, m), 1.86 (3H, s), 2.02-2.19 (2H, m), 2.42-2.56 (1H, m), 2.59 (2H, t, J=7.7 Hz), 2.86 (2H, t, J=7.7 Hz), 3.15 (2H, q, J=7.5 Hz), 3.38 (2H, t, J=5.1 Hz), 4.38 (2H, t, J=5.4 Hz), 6.07 (1H, dd, J=8.8, 2.0 Hz), 6.45 (1H, dd, J=10.6, 2.0 Hz), 6.51-6.60 (3H, m), 6.90-7.00 (2H, m), 7.35 (1H, t, J=7.5 Hz), 7.54-7.66 (2H, m), 7.68-7.77 (3H, m).

MS m/z 747 ((M+Na)$^+$).

Example 268

3-{4-[(4-{4-[2-(ethylsulfonyl)ethoxy]-2,6-dimethylphenyl}-2,3-dihydro-1H-inden-1-yl)amino]-2-fluorophenyl}propanoic acid hydrochloride To a solution of 3-(4-{(4-{4-[2-(ethylsulfonyl)ethoxy]-2,6-dimethylphenyl}-2,3-dihydro-1H-inden-1-yl)[(2-nitrophenyl)sulfonyl]amino}-2-fluorophenyl)propanoic acid (0.620 g, 0.856 mmol) and mercaptoacetic acid (0.181 mg, 1.97 mmol) in N,N-dimethylformamide (20 mL) was added lithium hydroxide monohydrate (0.143 g, 3.42 mmol), and the mixture was stirred at room temperature for 2.5 hr. The reaction mixture was diluted with water, neutralized with 1 N hydrochloric acid and extracted with ethyl acetate. The extract was washed with saturated brine, dried over anhydrous magnesium sulfate, and concentrated under reduced pressure. The residue was purified by silica gel column chromatography (hexane-25% ethyl acetate/hexane), and the obtained residue was dissolved in ethyl acetate (10 mL) and treated with 4 N hydrogen chloride/ethyl acetate solution (0.170 mL) to give the title compound as colorless crystals (0.127 g, yield 26%).

$^1$H NMR (DMSO-d$_6$) δ: 1.27 (3H, t, J=7.4 Hz), 1.72-1.85 (1H, m), 1.88 (6H, s), 2.35-2.53 (5H, m), 2.72 (2H, t, J=7.5 Hz), 3.20 (2H, q, J=7.4 Hz), 3.60 (2H, t, J=5.6 Hz), 4.34 (2H, t, J=5.6 Hz), 5.06 (1H, t, J=6.9 Hz), 6.54-6.67 (2H, m), 6.76 (2H, s), 6.90-6.97 (1H, m), 7.06 (1H, t, J=8.5 Hz), 7.24-7.32 (2H, m).

MS m/z 540 (MH$^+$, as free form).

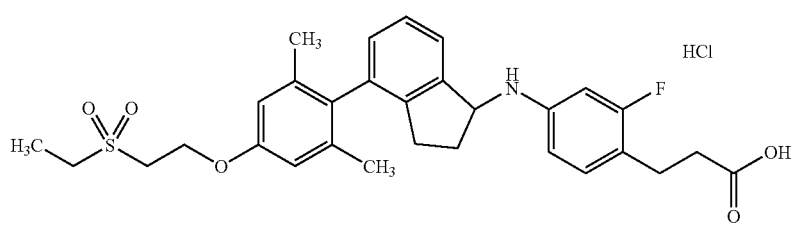

Example 269 methyl 3-[6-({[4'-(2-ethoxyethoxy)-2',6'-dimethylbiphenyl-3-yl]methyl}amino)-2-methylpyridin-3-yl]propanoate

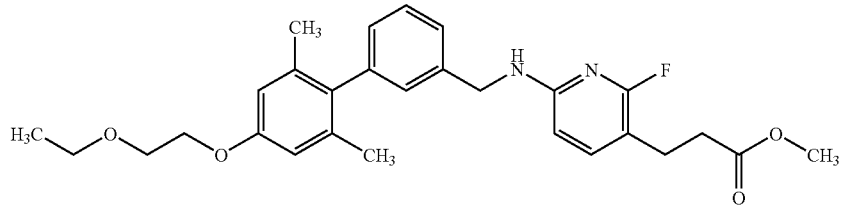

In the same manner as in Example 97, the title compound was obtained as a colorless oil from 4'-(2-ethoxyethoxy)-2',6'-dimethylbiphenyl-3-carbaldehyde and methyl 3-(6-amino-2-methylpyridin-3-yl)propanoate. yield 72%.
MS m/z 477 (MH+).

Example 270

3-[6-({[4'-(2-ethoxyethoxy)-2',6'-dimethylbiphenyl-3-yl]methyl}amino)-2-methylpyridin-3-yl]propanoic acid

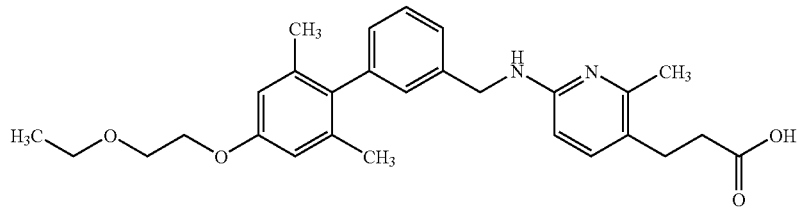

In the same manner as in Example 188, the title compound was obtained as colorless crystals from methyl 3-[6-({[4'-(2-ethoxyethoxy)-2',6'-dimethylbiphenyl-3-yl]methyl}amino)-2-methylpyridin-3-yl]propanoate. yield 64%.
MS m/z 463 (MH+).

Example 271 methyl 3-[2-({[4'-(2-ethoxyethoxy)-2',6'-dimethylbiphenyl-3-yl]methyl}amino)pyrimidin-5-yl]propanoate

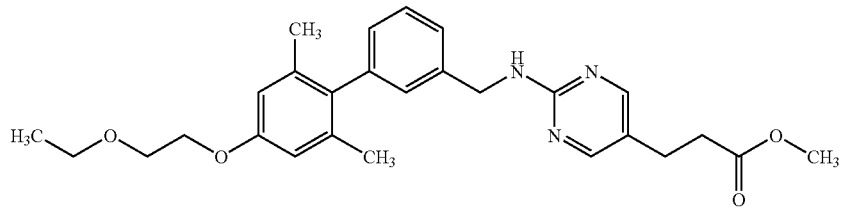

In the same manner as in Example 97, the title compound was obtained as a colorless oil from 4'-(2-ethoxyethoxy)-2',6'-dimethylbiphenyl-3-carbaldehyde and methyl 3-(2-aminopyrimidin-5-yl)propanoate. yield 33%.
MS m/z 464 (MH+).

Example 272

3-[2-({[4'-(2-ethoxyethoxy)-2',6'-dimethylbiphenyl-3-yl]methyl}amino)pyrimidin-5-yl]propanoic acid

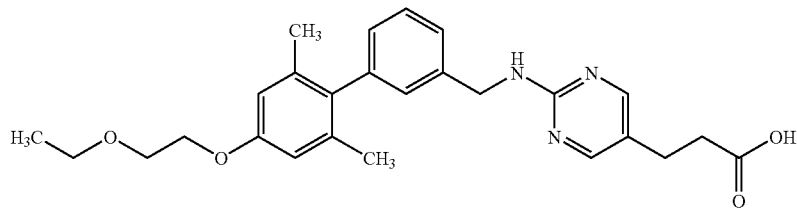

In the same manner as in Example 188, the title compound was obtained as colorless crystals from methyl 3-[2-({[4'-(2-ethoxyethoxy)-2',6'-dimethylbiphenyl-3-yl]methyl}amino)pyrimidin-5-yl]propanoate. yield 39%.

$^1$H NMR (CDCl$_3$) δ: 1.20-1.31 (3H, m), 1.97 (6H, s), 2.56 (2H, t, J=7.0 Hz), 2.75 (2H, t, J=7.0 Hz), 3.61 (2H, q, J=7.0 Hz), 3.76-3.82 (2H, m), 4.08-4.18 (2H, m), 4.64 (2H, d, J=5.3 Hz), 6.50 (1H, s), 6.66 (2H, s), 7.01 (1H, d, J=7.4 Hz), 7.10 (1H, s), 7.24-7.43 (1H, m), 8.16 (2H, s).

Example 273 ethyl 3-[2-fluoro-4-({4-[((3-methylbutyl){4-[4-(trifluoromethyl)phenyl]-1,3-thiazol-2-yl}amino)methyl]benzyl}amino)phenyl]propanoate boxylate (40% toluene solution, 1.50 mL, 3.29 mmol) was added and the concentrated under reduced pressure, and the residue was purified by silica gel column chromatography (3%-60% ethyl acetate/hexane) to give ethyl 3-(2-fluoro-4-{{4-[((3-methylbutyl){4-[4-(trifluoromethyl)phenyl]-1,3-thiazol-2-yl}amino)methyl]benzyl}[(2-nitrophenyl)sulfonyl]amino}phenyl)propanoate as a yellow oil. To a solution of the obtained oil and mercaptoacetic acid (0.365 g, 3.96 mmol) in N,N-dimethylformamide (20 mL) was added lithium hydroxide monohydrate (0.332 g, 7.92 mmol), and the mixture was stirred at room temperature for 2 hr. Ethyl acetate was added to the residue, and the mixture was washed with saturated aqueous sodium hydrogencarbonate and saturated brine, dried over anhydrous magnesium sulfate, and concentrated under reduced pressure. The residue was purified by silica gel column chromatography (5%-45% ethyl acetate/hexane) to give the title compound (0.450 g, yield 33%, 2 steps) as a colorless oil.

$^1$H NMR (CDCl$_3$) δ: 0.94 (6H, d, J=6.0 Hz), 1.18-1.30 (3H, m), 1.49-1.67 (3H, m), 2.54 (2H, t, J=7.7 Hz), 2.84 (2H, t, J=7.7 Hz), 3.43-3.49 (2H, m), 4.06-4.17 (2H, m), 4.28 (2H, s), 4.75 (2H, s), 6.24-6.36 (2H, m), 6.80 (1H, s), 6.96 (1H, t, J=8.4 Hz), 7.29-7.36 (4H, m), 7.60 (2H, d, J=8.4 Hz), 7.94 (2H, d, J=8.4 Hz).

MS m/z 628 (MH$^+$).

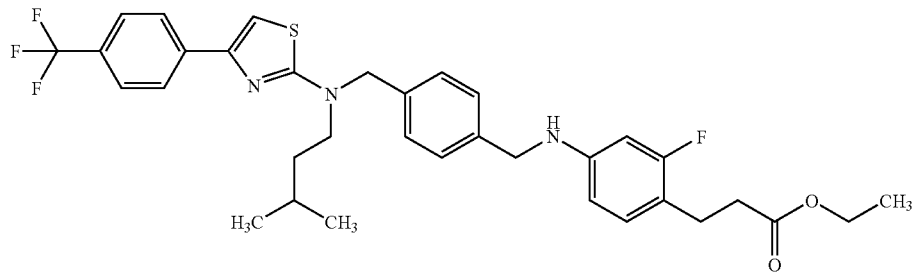

A solution of ethyl 3-(2-fluoro-4-{[(2-nitrophenyl)sulfonyl]amino}phenyl)propanoate (1.04 g, 2.63 mmol), 4-[((3-methylbutyl){4-[4-(trifluoromethyl)phenyl]-1,3-thiazol-2-yl)amino)methyl]phenyl}methanol (0.950 g, 2.19 mmol) and triphenylphosphine (0.862 g, 3.20 mmol) in tetrahydrofuran (10 mL) was stirred at room temperature. Diethyl azodicar-

Example 274

3-[2-fluoro-4-({4-[((3-methylbutyl){4-[4-(trifluoromethyl)phenyl]-1,3-thiazol-2-yl}amino)methyl]benzyl}amino)phenyl]propanoic acid

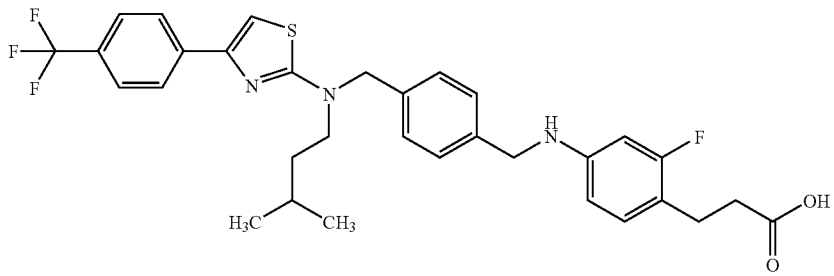

To a solution of ethyl 3-[2-fluoro-4-({4-[((3-methylbutyl){4-[4-(trifluoromethyl)phenyl]-1,3-thiazol-2-yl}amino)methyl]benzyl}amino)phenyl]propanoate (0.450 g, 0.720 mmol) in a mixture of ethanol (6 mL) and tetrahydrofuran (15 mL) was added 1 N sodium hydroxide (4.32 mL, 4.32 mmol), and the mixture was stirred at 60° C. for 1 hr. The reaction mixture was neutralized with 1 N hydrochloric acid, and the mixture was extracted with ethyl acetate. The extract was washed with saturated brine, dried over anhydrous magnesium sulfate, and concentrated under reduced pressure. The residue was recrystallized from diethyl ether-hexane to give the title compound (0.274 g, yield 64%) as colorless crystals.

$^1$H NMR (CDCl$_3$) δ: 0.94 (6H, d, J=6.0 Hz), 1.50-1.68 (3H, m), 2.61 (2H, t, J=7.7 Hz), 2.85 (2H, t, J=7.7 Hz), 3.42-3.50 (2H, m), 4.28 (2H, s), 4.75 (2H, s), 6.25-6.37 (2H, m), 6.80 (1H, s), 6.97 (1H, t, J=8.4 Hz), 7.31 (4H, s), 7.60 (2H, d, J=8.1 Hz), 7.94 (2H, d, J=8.1 Hz).

MS m/z 600 (MH$^+$).

Example 275

3-[2-fluoro-4-({4-[((3-methylbutyl){4-[4-(trifluoromethyl)phenyl]-1,3-thiazol-2-yl}amino)methyl]benzyl}amino)phenyl]propanoic acid dihydrochloride

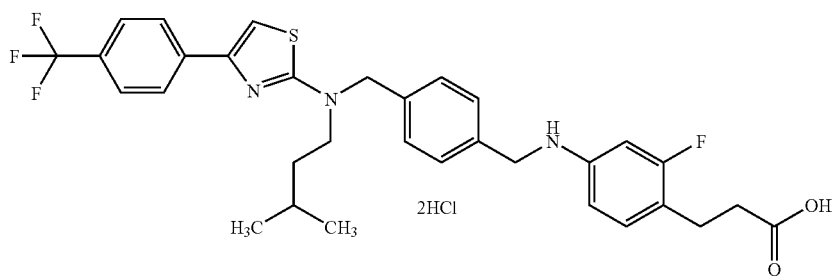

In the same manner as in Example 40, the title compound was obtained as colorless crystals from 3-[2-fluoro-4-({4-[((3-methylbutyl){4-[4-(trifluoromethyl)phenyl]-1,3-thiazol-2-yl}amino)methyl]benzyl}amino)phenyl]propanoic acid. yield 66%.

MS m/z 600 (MH$^+$, as free form).

Example 276 ethyl 3-[4-({[4'-(2-ethoxyethoxy)-2',6'-dimethylbiphenyl-3-yl]methyl}amino)-2,6-difluorophenyl]propanoate

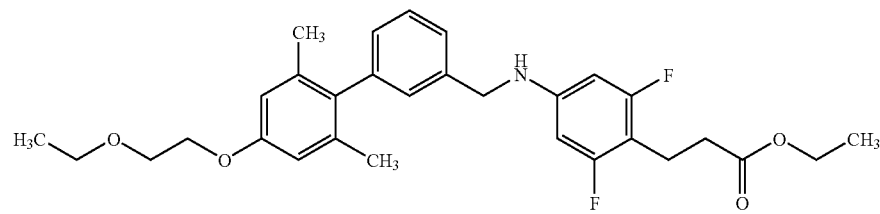

In the same manner as in Example 97, the title compound was obtained as a colorless oil from 4'-(2-ethoxyethoxy)-2',6'-dimethylbiphenyl-3-carbaldehyde and ethyl 3-(4-amino-2,6-difluorophenyl)propanoate. yield 78%.

MS m/z 512 (MH⁺).

Example 277

3-[4-({[4'-(2-ethoxyethoxy)-2',6'-dimethylbiphenyl-3-yl]methyl}amino)-2,6-difluorophenyl]propanoic acid

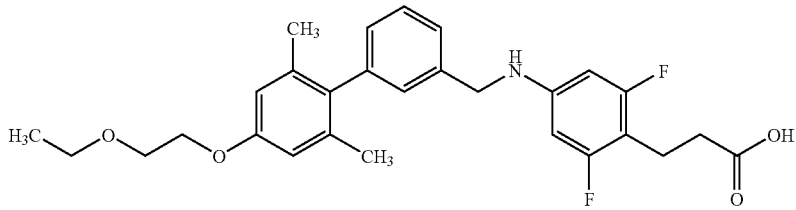

In the same manner as in Example 188, the title compound was obtained as colorless crystals from ethyl 3-[4-({[4'-(2-ethoxyethoxy)-2',6'-dimethylbiphenyl-3-yl]methyl}amino)-2,6-difluorophenyl]propanoate. yield 72%.

MS m/z 484 (MH⁺).

Example 278 ethyl 3-{2,6-difluoro-4-[(4-{[(2-phenylethyl)(4-phenyl-1,3-thiazol-2-yl)amino]methyl}benzyl)amino]phenyl}propanoate

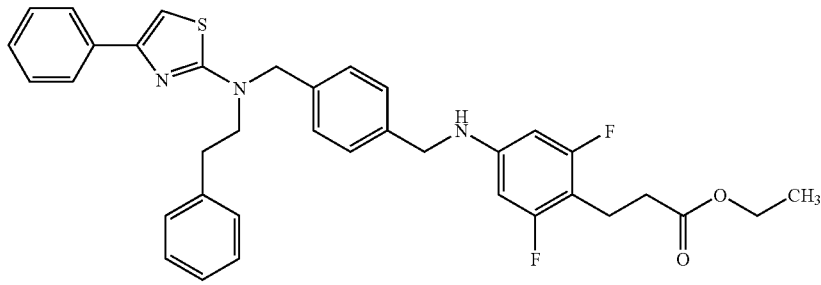

In the same manner as in Example 97, the title compound was obtained as a colorless oil from 4-{[(2-phenylethyl)(4-phenyl-1,3-thiazol-2-yl)amino]methyl}benzaldehyde and ethyl 3-(4-amino-2,6-difluorophenyl)propanoate. yield 24%.

MS m/z 612 (MH⁺).

Example 279

3-{2,6-difluoro-4-[(4-{[(2-phenylethyl)(4-phenyl-1,3-thiazol-2-yl)amino]methyl}benzyl)amino]phenyl}propanoic acid

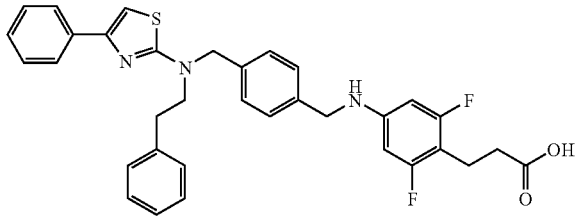

In the same manner as in Example 188, the title compound was obtained as colorless crystals from ethyl 3-{2,6-difluoro-4-[(4-{[(2-phenylethyl)(4-phenyl-1,3-thiazol-2-yl)amino]methyl}benzyl)amino]phenyl}propanoate. yield 67%.

MS m/z 584 (MH⁺).

Example 280 ethyl 3-(2-fluoro-4-{[4-(4-methoxy-2,6-dimethylphenyl)-2,3-dihydro-1H-inden-1-yl]amino}phenyl)propanoate

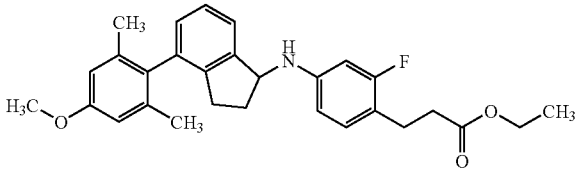

In the same manner as in Example 254, the title compound was obtained as a yellow oil from ethyl 3-(2-fluoro-4-{[4-(4-hydroxy-2,6-dimethylphenyl)-2,3-dihydro-1H-inden-1-yl][(2-nitrophenyl)sulfonyl]amino}phenyl)propanoate and methanol. yield 53%.

MS m/z 462 (MH⁺).

Example 281

3-(2-fluoro-4-{[4-(4-methoxy-2,6-dimethylphenyl)-2,3-dihydro-1H-inden-1-yl]amino}phenyl)propanoic acid

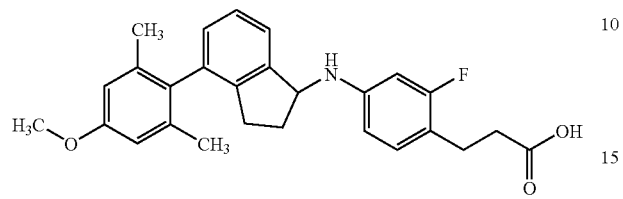

In the same manner as in Example 188, the title compound was obtained as a colorless oil from ethyl 3-(2-fluoro-4-{[4-(4-methoxy-2,6-dimethylphenyl)-2,3-dihydro-1H-inden-1-yl]amino}phenyl)propanoate. yield 100%.

$^1$H NMR (CDCl$_3$) δ: 1.76-1.89 (1H, m), 1.95 (3H, s), 1.96-1.97 (3H, m), 2.41-2.61 (3H, m), 2.65 (2H, t, J=7.7 Hz), 2.89 (2H, t, J=7.7 Hz), 3.82 (3H, s), 5.01 (1H, t, J=6.7 Hz), 6.38-6.46 (2H, m), 6.67 (2H, s), 7.02 (2H, t, J=8.4 Hz), 7.23-7.36 (2H, m).

Example 282

3-(2-fluoro-4-{[4-(4-methoxy-2,6-dimethylphenyl)-2,3-dihydro-1H-inden-1-yl]amino}phenyl)propanoic acid hydrochloride

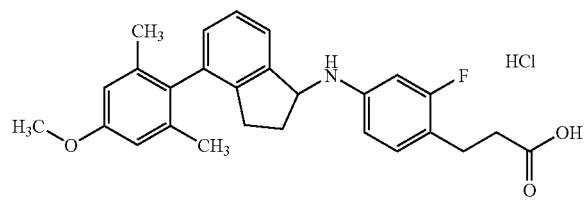

In the same manner as in Example 40, the title compound was obtained as colorless crystals from 3-(2-fluoro-4-{[4-(4-methoxy-2,6-dimethylphenyl)-2,3-dihydro-1H-inden-1-yl]amino}phenyl)propanoic acid. yield 66%.

$^1$H NMR (DMSO-d$_6$) δ: 1.77-1.93 (7H, m), 2.31-2.53 (5H, m), 2.68-2.78 (2H, m), 3.75 (3H, s), 5.04-5.12 (1H, m), 6.55-6.80 (4H, m), 6.95 (1H, d, J=6.2 Hz), 7.10 (1H, br s), 7.23-7.36 (2H, m).

Example 283 ethyl 3-[4-({4-[(3,5-diphenyl-1H-pyrazol-1-yl)methyl]-3-isopropoxybenzyl}amino)-2,6-difluorophenyl]propanoate

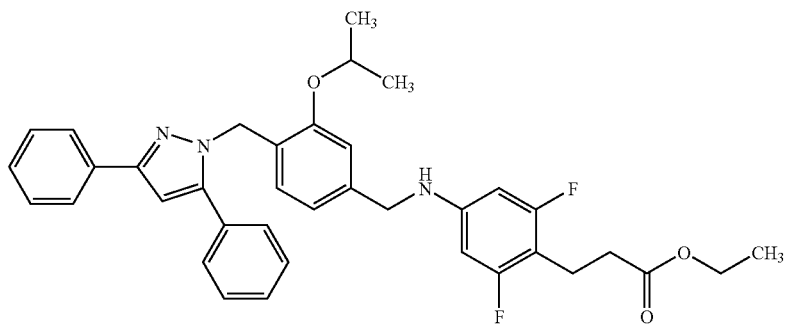

A solution of ethyl 3-(2,6-difluoro-4-{[(2-nitrophenyl)sulfonyl]amino}phenyl)propanoate (0.425 g, 1.03 mmol), {4-[(3,5-diphenyl-1H-pyrazol-1-yl)methyl]-3-isopropoxyphenyl}methanol (0.315 g, 0.790 mmol) and triphenylphosphine (0.312 g, 1.19 mmol) in tetrahydrofuran (15 mL) was stirred at room temperature, diethyl azodicarboxylate (40% toluene solution, 0.540 mL, 1.19 mmol) was added and the mixture was stirred for 16 hr. The reaction mixture was concentrated under reduced pressure, and the residue was purified by silica gel column chromatography (20%-80% ethyl acetate/hexane) to give ethyl 3-(4-{{4-[(3,5-diphenyl-1H-pyrazol-1-yl)methyl]-3-isopropoxybenzyl}[(2-nitrophenyl)sulfonyl]amino}-2,6-difluorophenyl)propanoate as a yellow oil. To a solution of the obtained oil and mercaptoacetic acid (0.169 g, 1.84 mmol) in N,N-dimethylformamide (15 mL) was added lithium hydroxide monohydrate (0.154 g, 3.68 mmol), and the mixture was stirred at room temperature for 2 hr. Ethyl acetate was added to the residue, and the mixture was washed with saturated aqueous sodium hydrogencarbonate and saturated brine, dried over anhydrous magnesium sulfate, and concentrated under reduced pressure. The residue was purified by silica gel column chromatography (5%-40% ethyl acetate/hexane) to give the title compound (0.431 g, yield 90%, 2 steps) as a yellow oil.

$^1$H NMR (CDCl$_3$) δ: 1.18-1.27 (9H, m), 2.47-2.55 (2H, m), 2.82-2.89 (2H, m), 4.12 (2H, q, J=7.1 Hz), 4.20 (2H, d, J=4.2

Hz), 4.47-4.59 (1H, m), 5.38 (2H, s), 6.02-6.17 (2H, m), 6.70 (1H, s), 6.76-6.82 (3H, m), 7.27-7.45 (8H, m), 7.83-7.90 (2H, m).
MS m/z 610 (MH$^+$).

Example 284

3-[4-({4-[(3,5-diphenyl-1H-pyrazol-1-yl)methyl]-3-isopropoxybenzyl}amino)-2,6-difluorophenyl]propanoic acid

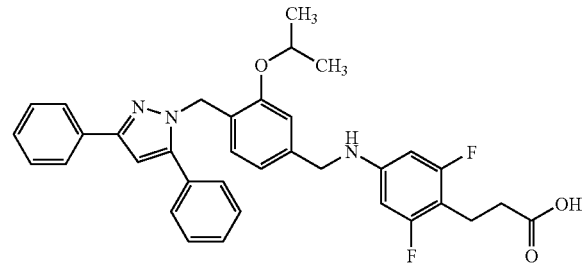

To a solution of ethyl 3-[4-({4-[(3,5-diphenyl-1H-pyrazol-1-yl)methyl]-3-isopropoxybenzyl}amino)-2,6-difluorophenyl]propanoate (0.431 g, 0.710 mmol) in a mixture of ethanol (5 mL) and tetrahydrofuran (8 mL) was added 1 N sodium hydroxide (2.12 mL, 2.12 mmol) and the mixture was stirred at 60° C. for 1 hr. The reaction mixture was neutralized with 1 N hydrochloric acid and extracted with ethyl acetate. The organic layer was washed with saturated brine, dried over anhydrous magnesium sulfate, and concentrated under reduced pressure. The residue was recrystallized from diethyl ether-hexane to give the title compound (0.310 g, yield 75%) as colorless crystals.
$^1$H NMR (DMSO-d$_6$) δ: 1.14 (6H, d, J=6.0 Hz), 2.33 (2H, t, J=7.8 Hz), 2.65 (2H, t, J=7.8 Hz), 4.18 (2H, d, J=5.7 Hz), 4.49-4.63 (1H, m), 5.30 (2H, s), 6.19 (2H, d, J=10.7 Hz), 6.65 (1H, t, J=5.8 Hz), 6.71-6.77 (1H, m), 6.78-6.85 (1H, m), 6.92-7.03 (2H, m), 7.25-7.35 (1H, m), 7.37-7.51 (7H, m), 7.79-7.88 (2H, m), 12.13 (1H, s).
MS m/z 582 (MH$^+$).

Example 285 ethyl 3-(4-{[4-(2,6-dimethylphenoxy)-2,3-dihydro-1H-inden-1-yl]amino}-2-fluorophenyl)propanoate

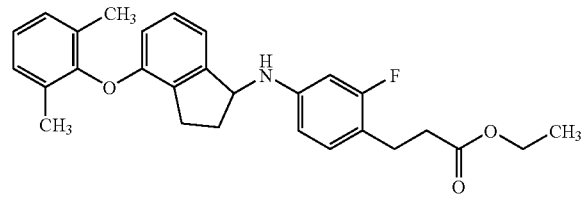

In the same manner as in Example 254, the title compound was obtained as a colorless oil from 4-(2,6-dimethylphenoxy)indan-1-ol and ethyl 3-(2-fluoro-4-{[(2-nitrophenyl)sulfonyl]amino}phenyl)propanoate. yield 40%.
MS m/z 448 (MH$^+$).

Example 286

3-(4-{[4-(2,6-dimethylphenoxy)-2,3-dihydro-1H-inden-1-yl]amino}-2-fluorophenyl)propanoic acid

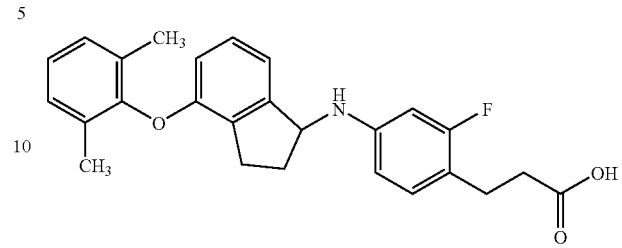

In the same manner as in Example 188, the title compound was obtained as colorless crystals from ethyl 3-(4-{[4-(2,6-dimethylphenoxy)-2,3-dihydro-1H-inden-1-yl]amino}-2-fluorophenyl)propanoate. yield 47%.
$^1$H NMR (CDCl$_3$) δ: 1.90-2.05 (1H, m), 2.13 (6H, s), 2.60-2.74 (3H, m), 2.89 (2H, t, J=7.6 Hz), 2.93-3.05 (1H, m), 3.12-3.24 (1H, m), 5.01 (1H, t, J=6.7 Hz), 6.22 (1H, dd, J=7.6 Hz, 1.0 Hz), 6.42 (2H, d, J=10.6 Hz), 6.91-7.19 (6H, m).

Example 287 ethyl 3-{2-fluoro-4-[(4-{[5-(trifluoromethyl)pyridin-2-yl]oxy}-2,3-dihydro-1H-inden-1-yl)amino]phenyl}propanoate

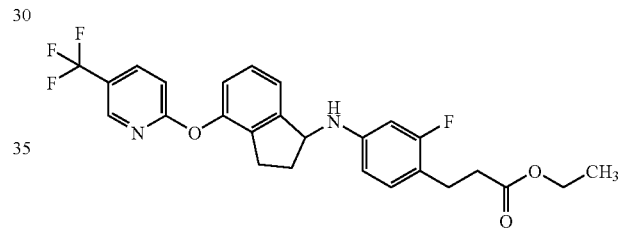

In the same manner as in Example 254, the title compound was obtained as a colorless oil from 4-{[5-(trifluoromethyl)pyridin-2-yl]oxy}indan-1-ol and ethyl 3-(2-fluoro-4-{[(2-nitrophenyl)sulfonyl]amino}phenyl)propanoate. yield 39%.
MS m/z 489 (MH$^+$).

Example 288

3-{2-fluoro-4-[(4-{[5-(trifluoromethyl)pyridin-2-yl]oxy}-2,3-dihydro-1H-inden-1-yl)amino]phenyl}propanoic acid

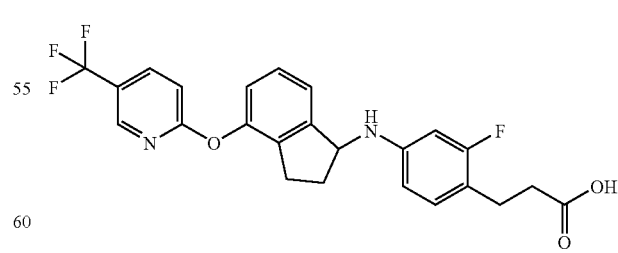

In the same manner as in Example 188, the title compound was obtained as colorless crystals from ethyl 3-{2-fluoro-4-[(4-{[5-(trifluoromethyl)pyridin-2-yl]oxy}-2,3-dihydro-1H-inden-1-yl)amino]phenyl}propanoate. yield 65%.

$^1$H NMR (CDCl$_3$) δ: 1.81-1.96 (1H, m), 2.50-2.75 (4H, m), 2.77-2.95 (3H, m), 5.02 (1H, t, J=6.8 Hz), 6.36-6.48 (2H, m), 6.94-7.12 (3H, m), 7.24-7.36 (2H, m), 7.91 (1H, dd, J=8.7, 2.5 Hz), 8.43 (1H, s).

Example 289 ethyl 3-(2,6-difluoro-4-{[4-(4-methoxy-2,6-dimethylphenyl)-2,3-dihydro-1H-inden-1-yl]amino}phenyl)propanoate

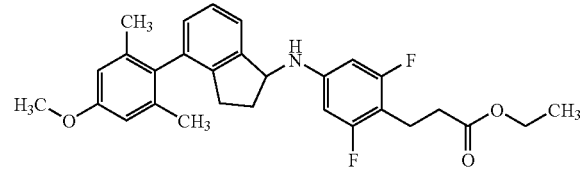

In the same manner as in Example 254, the title compound was obtained as a yellow oil from 4-(4-methoxy-2,6-dimethylphenyl)indan-1-ol and ethyl 3-(2,6-difluoro-4-{[(2-nitrophenyl)sulfonyl]amino}phenyl)propanoate. yield 66%.
MS m/z 502 ((M+Na)$^+$).

Example 290

3-(2,6-difluoro-4-{[4-(4-methoxy-2,6-dimethylphenyl)-2,3-dihydro-1H-inden-1-yl]amino}phenyl)propanoic acid

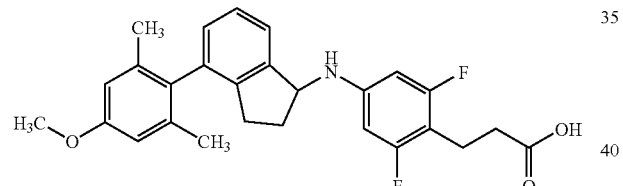

In the same manner as in Example 188, the title compound was obtained as a colorless amorphous powder from ethyl 3-(2,6-difluoro-4-{[4-(4-methoxy-2,6-dimethylphenyl)-2,3-dihydro-1H-inden-1-yl]amino}phenyl)propanoate. yield 54%.

elemental analysis for C$_{27}$H$_{27}$NO$_3$F$_2$
Calculated: C, 71.82; H, 6.03; N, 3.10.
Found: C, 71.76; H, 6.28; N, 2.91.

Example 291

3-(2,6-difluoro-4-{[4-(4-methoxy-2,6-dimethylphenyl)-2,3-dihydro-1H-inden-1-yl]amino}phenyl)propanoic acid hydrochloride

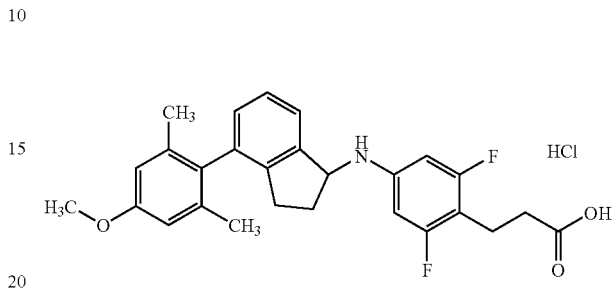

In the same manner as in Example 40, the title compound was obtained as colorless crystals from 3-(2,6-difluoro-4-{[4-(4-methoxy-2,6-dimethylphenyl)-2,3-dihydro-1H-inden-1-yl]amino}phenyl)propanoic acid. yield 79%.

elemental analysis for C$_{27}$H$_{28}$NO$_3$F$_2$Cl
Calculated: C, 66.46; H, 5.78; N, 2.87.
Found: C, 66.43; H, 5.81; N, 2.58.

Example 292 tert-butyl 3-{4-[({4'-[(1,1-dioxidotetrahydro-2H-thiopyran-4-yl)methoxy]-2',6'-dimethylbiphenyl-3-yl}methyl)amino]-2-fluorophenyl}propanoate

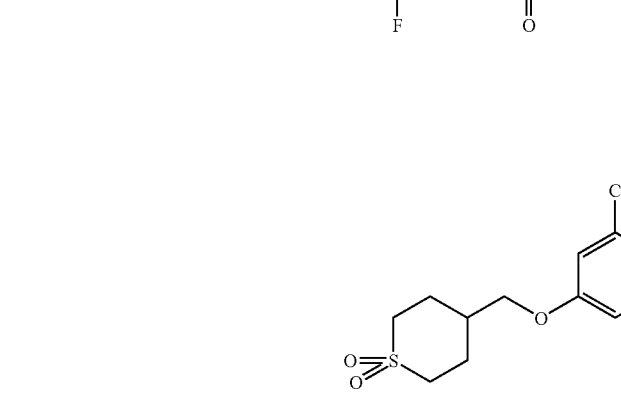

To a solution of tert-butyl 3-(2-fluoro-4-{[(4'-hydroxy-2',6'-dimethylbiphenyl-3-yl)methyl][(2-nitrophenyl)sulfonyl]amino}phenyl) propanoate (0.60 g, 0.95 mmol), tetrahydro-2H-thiopyran-4-ylmethanol (0.14 g, 1.05 mmol) and triphenylphosphine (0.28 g, 1.05 mmol) in tetrahydrofuran (5 mL) was added diethyl azodicarboxylate (40% toluene solution, 0.56 mL, 1.24 mmol) under stirring at room temperature, and the mixture was stirred for 2 hr. To the reaction mixture were added reagents (tetrahydro-2H-thiopyran-4-ylmethanol, triphenylphosphine and diethyl azodicarboxylate) in the same amount as mentioned above, and the mixture was further stirred for 24 hr. The reaction mixture was concentrated under reduced pressure and the residue was purified by silica gel column chromatography (hexane/ethyl acetate=9/1-hexane/ethyl acetate=3/2) to give an oil (0.23 g). To a solution of the obtained oil in ethyl acetate (2 mL) was added m-chloroperbenzoic acid (70%, 0.16 g, 0.64 mmol) under stirring at 0° C., and the mixture was stirred at room temperature for 3 days. The reaction mixture was washed with 1 M aqueous sodium hydroxide solution and saturated brine, dried over anhydrous sodium sulfate, and concentrated under reduced pressure. The residue was purified by silica gel column chromatography (hexane/ethyl acetate=9/1-hexane/ethyl acetate=3/2) to give tert-butyl 3-(4-{({4'-[(1,1-dioxidotetrahydro-2H-thiopyran-4-yl)methoxy]-2',6'-dimethylbiphenyl-3-yl}methyl)[(2-nitrophenyl)sulfonyl]amino}-2-fluorophenyl)propanoate (0.13 g, yield 17%, 2 steps) as a pale-yellow oil. To a solution of the obtained tert-butyl 3-(4-{({4'-[(1,1-dioxidotetrahydro-2H-thiopyran-4-yl)methoxy]-2',6'-dimethylbiphenyl-3-yl}methyl)[(2-nitrophenyl)sulfonyl]amino}-2-fluorophenyl)propanoate (0.13 g, 0.16 mmol) and mercaptoacetic acid (0.03 mL, 0.49 mmol) in N,N-dimethylformamide (2 mL) was added lithium hydroxide monohydrate (0.04 g, 0.98 mmol) under stirring at room temperature, and the mixture was stirred overnight at the same temperature. The reaction mixture was diluted with ethyl acetate, washed with saturated aqueous sodium hydrogencarbonate and saturated brine, dried over anhydrous sodium sulfate, and concentrated under reduced pressure. The residue was purified by silica gel column chromatography (hexane/ethyl acetate=9/1-hexane/ethyl acetate=1/1) to give the title compound (0.08 g, yield 85%) as colorless crystals.

MS m/z 596 (MH+).

Example 293

3-{4-[({4'-[(1,1-dioxidotetrahydro-2H-thiopyran-4-yl)methoxy]-2',6'-dimethylbiphenyl-3-yl}methyl)amino]-2-fluorophenyl}propanoic acid

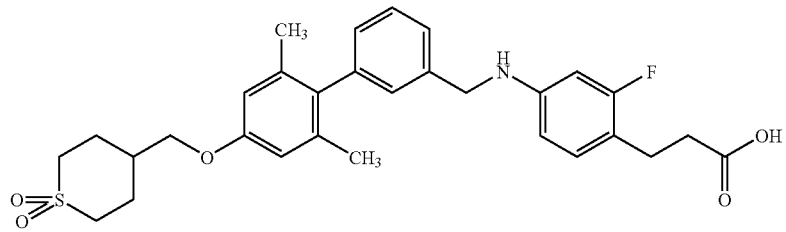

To a solution of tert-butyl 3-{4-[({4'-[(1,1-dioxidotetrahydro-2H-thiopyran-4-yl)methoxy]-2',6'-dimethylbiphenyl-3-yl}methyl)amino]-2-fluorophenyl}propanoate (0.08 g, 0.14 mmol) in methylene chloride (2 mL) was added trifluoroacetic acid (2 mL) under stirring at 0° C., and the mixture was stirred at room temperature for 2 hr. The reaction mixture was concentrated under reduced pressure, and the residue was neutralized with saturated aqueous sodium hydrogencarbonate, and the mixture was extracted with ethyl acetate. The organic layer was washed with saturated brine, dried over anhydrous sodium sulfate, and concentrated under reduced pressure. The residue was recrystallized from ethyl acetate-hexane to give the title compound (0.06 g, yield 78%) as colorless crystals.

MS m/z 540 (MH+).

Example 294 ethyl 3-{2-fluoro-4-[({4'-[(4-hydroxytetrahydro-2H-thiopyran-4-yl)methoxy]-2',6'-dimethylbiphenyl-3-yl}methyl)amino]phenyl}propanoate

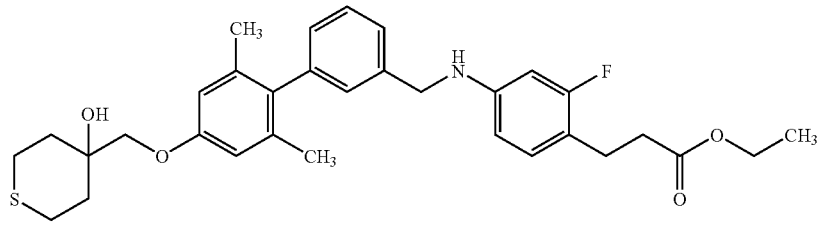

In the same manner as in Example 10, the title compound was obtained as a colorless oil from ethyl 3-(2-fluoro-4-{({4'-[(4-hydroxytetrahydro-2H-thiopyran-4-yl)methoxy]-2',6'-dimethylbiphenyl-3-yl}methyl)[(2-nitrophenyl)sulfonyl]amino}phenyl)propanoate. yield 62%.

MS m/z 552 (MH+).

Example 295

3-{2-fluoro-4-[({4'-[(4-hydroxytetrahydro-2H-thiopyran-4-yl)methoxy]-2',6'-dimethylbiphenyl-3-yl}methyl)amino]phenyl}propanoic acid methanesulfonate

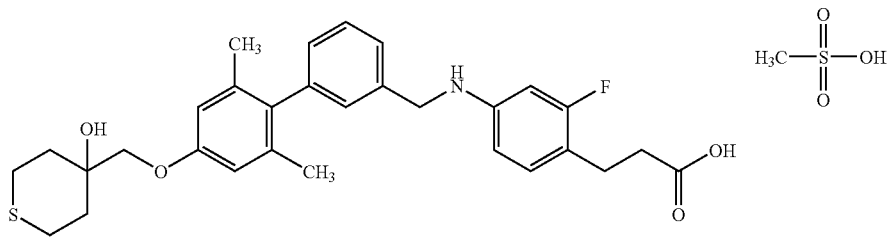

To a mixture of ethyl 3-{2-fluoro-4-[({4'-[(4-hydroxytetrahydro-2H-thiopyran-4-yl)methoxy]-2',6'-dimethylbiphenyl-3-yl}methyl)amino]phenyl}propanoate (0.81 g, 1.47 mmol) in methanol (8 mL) and tetrahydrofuran (4 mL) was added 1 M aqueous sodium hydroxide solution (4.41 mL), and the mixture was stirred at 50° C. for 1.5 hr. The reaction mixture was neutralized with 1 M hydrochloric acid, and diluted with ethyl acetate, and the organic layer was washed with saturated brine, dried, and concentrated under reduced pressure. The residue was purified by silica gel column chromatography (hexane/ethyl acetate=9/1-hexane/ethyl acetate=2/3) to give a colorless oil (0.79 g). The obtained oil was diluted with ethyl acetate (6 mL), and methanesulfonic acid (0.15 mL, 1.52 mmol) was added. Thereto was added diethyl ether and the precipitated crystals were collected by filtration, washed, and dried to give the title compound (0.81 g, yield 89%) as colorless crystals.

MS m/z 524 (MH$^+$) (as free form).

Example 296 ethyl 3-{2-fluoro-4-[({4'-[(4-hydroxy-1-oxidotetrahydro-2H-thiopyran-4-yl)methoxy]-2',6'-dimethylbiphenyl-3-yl}methyl)amino]phenyl}propanoate To a solution of ethyl 3-(2-fluoro-4-{({4'-[(4-hydroxytetrahydro-2H-thiopyran-4-yl)methoxy]-2',6'-dimethylbiphenyl-3-yl}methyl) [(2-nitrophenyl)sulfonyl]amino}phenyl)propanoate (2.24 g, 3.04 mmol) in ethyl acetate (15 mL) was added m-chloroperbenzoic acid (70%, 0.46 g, 1.88 mmol) under stirring at 0° C., and the mixture was stirred at room temperature for 3 days. The reaction mixture was washed with 1 M aqueous sodium hydroxide solution and saturated brine, dried over anhydrous magnesium sulfate, and concentrated under reduced pressure. The residue was purified by silica gel column chromatography (hexane/ethyl acetate=9/1-ethyl acetate-ethyl acetate/methanol=17/3) to give ethyl 3-(2-fluoro-4-{({4'-[(4-hydroxy-1-oxidotetrahydro-2H-thiopyran-4-yl)methoxy]-2',6'-dimethylbiphenyl-3-yl}methyl)[(2-nitrophenyl)sulfonyl]amino}phenyl)propanoate (1.36 g, yield 60%) as a colorless amorphous powder. To a solution of the obtained ethyl 3-(2-fluoro-4-{({4'-[(4-hydroxy-1-oxidotetrahydro-2H-thiopyran-4-yl)methoxy]-2',6'-dimethylbiphenyl-3-yl}methyl)[(2-nitrophenyl)sulfonyl]amino}phenyl)propanoate (1.36 g, 1.81 mmol) and mercaptoacetic acid (0.38 mL, 5.43 mmol) in N,N-dimethylformamide (10 mL) was added lithium hydroxide monohydrate (0.46 g, 10.86 mmol) under stirring at room temperature, and the mixture was stirred at the same temperature for 3 hr. The reaction mixture was diluted with ethyl acetate, washed with saturated aqueous sodium hydrogencarbonate and saturated brine, dried over anhydrous sodium sulfate, and concentrated under reduced pressure. The residue was purified by silica gel column chromatography (hexane/ethyl acetate=9/1-ethyl acetate) to give the title compound (0.52 g, yield 50%) as a colorless oil.

MS m/z 568 (MH$^+$).

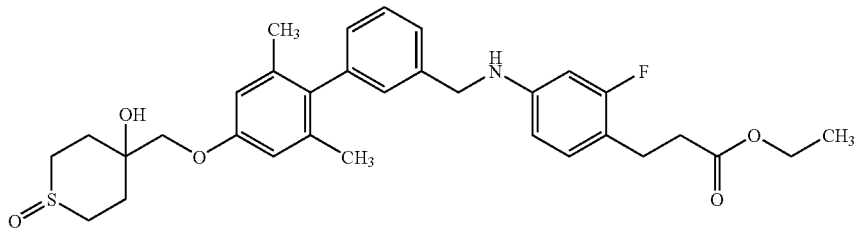

Example 297

3-{2-fluoro-4-[({4'-[(4-hydroxy-1-oxidotetrahydro-2H-thiopyran-4-yl)methoxy]-2',6'-dimethylbiphenyl-3-yl}methyl)amino]phenyl}propanoic acid

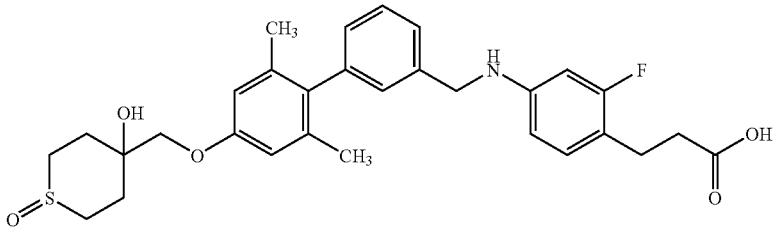

In the same manner as in Example 10, the title compound was obtained as colorless crystals from ethyl 3-{2-fluoro-4-[({4'-[(4-hydroxy-1-oxidotetrahydro-2H-thiopyran-4-yl)methoxy]-2',6'-dimethylbiphenyl-3-yl}methyl)amino]phenyl}propanoate. yield 85%.
MS m/z 540 (MH$^+$).

Example 298 tert-butyl 3-(2-fluoro-4-{[(4'-hydroxy-2',6'-dimethylbiphenyl-3-yl)methyl]amino}phenyl)propanoate

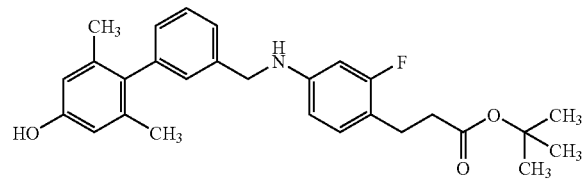

In the same manner as in Example 224, the title compound was obtained as a pale-yellow oil from 4'-hydroxy-2',6'-dimethylbiphenyl-3-carbaldehyde and tert-butyl 3-(4-amino-2-fluorophenyl)propanoate. yield 92%.
MS m/z 450 (MH$^+$).

Example 299

3-{4-[({4'-[3-(diethylphosphono)propoxy]-2',6'-dimethylbiphenyl-3-yl}methyl)amino]-2-fluorophenyl}propanoic acid To a solution of tert-butyl 3-(2-fluoro-4-{[(4'-hydroxy-2',6'-dimethylbiphenyl-3-yl)methyl]amino}phenyl)propanoate (0.67 g, 1.49 mmol) in N,N-dimethylformamide (7.5 mL) was added sodium hydride (60%, 0.06 g, 1.49 mmol) with stirring at 0° C., and the mixture was stirred at room temperature for 1 hr. Diethyl(3-bromopropyl)phosphonate (0.60 mL, 2.97 mmol) and potassium iodide (0.05 g, 0.30 mmol) were added and the reaction solution was stirred at 50° C. for 5 hr, and thereafter stirred overnight at room temperature, and concentrated under reduced pressure. The residue was diluted with ethyl acetate, washed with saturated brine, dried over anhydrous sodium sulfate, and concentrated under reduced pressure. The residue was purified by silica gel column chromatography (hexane/ethyl acetate=9/1-hexane/ethyl acetate=3/7) to give a yellow oil (1.05 g). To a solution of the obtained oil in toluene (5 mL) was added trifluoroacetic acid (5 mL) at room temperature, and the mixture was stirred for 1 hr. The reaction mixture was concentrated under reduced pressure, and the residue was neutralized with saturated aqueous sodium hydrogencarbonate, and the mixture was extracted with ethyl acetate. The organic layer was washed with saturated brine, dried over anhydrous sodium sulfate, and concentrated under reduced pressure. The residue was purified by preparative HPLC to give the title compound (0.29 g, yield 34%, 2 steps) as a colorless oil.

MS m/z 572 (MH$^+$).

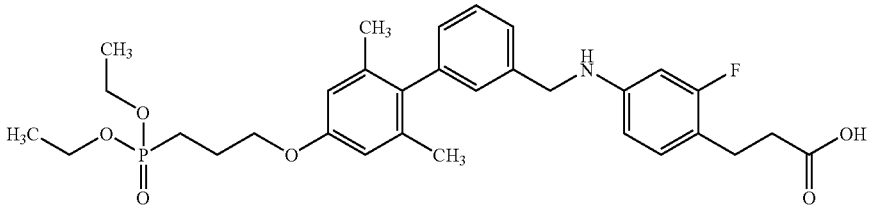

Example 300 ethyl 3-(4-{[(4'-{[tert-butyl(dimethyl)silyl]oxy}-6-isopropoxy-2',6'-dimethylbiphenyl-3-yl)methyl][(2-nitrophenyl)sulfonyl]amino}-2-fluorophenyl)propanoate

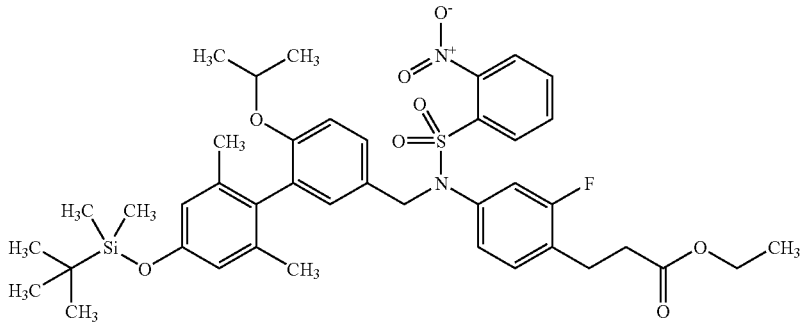

In the same manner as in Example 50, the title compound was obtained as a yellow oil from (4'-{[tert-butyl(dimethyl)silyl]oxy}-6-isopropoxy-2',6'-dimethylbiphenyl-3-yl)methanol and ethyl 3-(2-fluoro-4-{[(2-nitrophenyl)sulfonyl]amino}phenyl)propanoate. yield 77%.

$^1$H NMR (CDCl$_3$) δ: 0.21 (6H, s), 0.99 (9H, s), 1.08 (6H, d, J=6.0 Hz), 1.21 (3H, t, J=7.2 Hz), 1.79 (6H, s), 2.53 (2H, t, J=7.7 Hz), 2.87 (2H, t, J=7.7 Hz), 4.10 (2H, q, J=7.1 Hz), 4.18-4.28 (1H, m), 4.84 (2H, s), 6.51 (2H, s), 6.68-6.79 (3H, m), 6.85 (1H, d, J=8.5 Hz), 7.03 (1H, t, J=8.2 Hz), 7.19 (1H, dd, J=8.4, 2.4 Hz), 7.47-7.55 (1H, m), 7.57-7.72 (3H, m).

Example 301 ethyl 3-(2-fluoro-4-{[(4'-hydroxy-6-isopropoxy-2',6'-dimethylbiphenyl-3-yl)methyl][(2-nitrophenyl)sulfonyl]amino}phenyl)propanoate

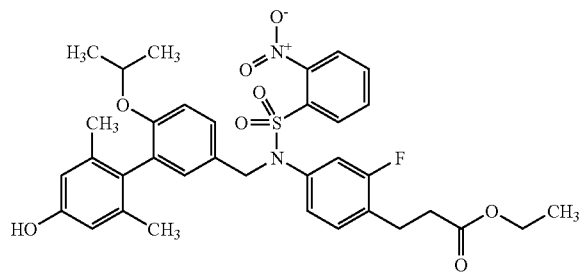

In the same manner as in Example 140, the title compound was obtained as a pale-yellow amorphous powder from ethyl 3-(4-{[(4'-{[tert-butyl(dimethyl)silyl]oxy}-6-isopropoxy-2',6'-dimethylbiphenyl-3-yl)methyl][(2-nitrophenyl)sulfonyl]amino}-2-fluorophenyl)propanoate. yield 89%.

MS m/z 665 (MH$^+$).

Example 302 ethyl 3-(4-{({4'-[(1,1-dioxidotetrahydro-2H-thiopyran-4-yl)oxy]-6-isopropoxy-2',6'-dimethylbiphenyl-3-yl}methyl)[(2-nitrophenyl)sulfonyl]amino}-2-fluorophenyl)propanoate

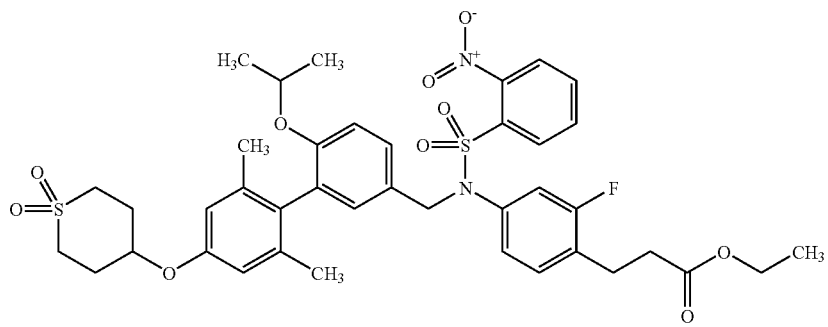

To a solution of ethyl 3-(2-fluoro-4-{[(4'-hydroxy-6-isopropoxy-2',6'-dimethylbiphenyl-3-yl)methyl][(2-nitrophenyl)sulfonyl]amino}phenyl)propanoate (0.59 g, 0.89 mmol), tetrahydro-2H-thiopyran-4-ol (0.12 g, 0.98 mmol) and triphenylphosphine (0.30 g, 1.16 mmol) in tetrahydrofuran (8 mL) was added diethyl azodicarboxylate (40% toluene solution, 0.53 mL, 1.16 mmol) under stirring at room temperature, and the mixture was stirred for 1 hr. To the reaction mixture were added reagents (tetrahydro-2H-thiopyran-4-ol, triphenylphosphine and diethyl azodicarboxylate) in the same amount as mentioned above, and the mixture was further stirred for 24 hr. The reaction mixture was concentrated under reduced pressure. The residue was purified by silica gel column chromatography (hexane/ethyl acetate=9/1-hexane/ethyl acetate=2/1) to give an oil (0.64 g). To a solution of the obtained oil in ethyl acetate (9 mL) was added m-chloroperbenzoic acid (70%, 0.44 g, 1.78 mmol) under stirring at 0° C., and the mixture was stirred at the same temperature for 2 hr. The reaction mixture was washed with 1 M aqueous sodium hydroxide solution and saturated brine, dried over anhydrous sodium sulfate, and concentrated under reduced pressure. The residue was purified by silica gel column chromatography (hexane/ethyl acetate=9/1-ethyl acetate) to give ethyl 3-(2-fluoro-4-{({6-isopropoxy-2',6'-dimethyl-4'-[(1-oxidotetrahydro-2H-thiopyran-4-yl)oxy]biphenyl-3-yl}methyl)[(2-nitrophenyl)sulfonyl]amino}phenyl)propanoate (0.42 g, yield 61%, 2 steps) as a pale-yellow oil. To a solution of the obtained ethyl 3-(2-fluoro-4-{({6-isopropoxy-2',6'-dimethyl-4'-[(1-oxidotetrahydro-2H-thiopyran-4-yl)oxy]biphenyl-3-yl}methyl)[(2-nitrophenyl)sulfonyl]amino}phenyl)propanoate (0.42 g, 0.54 mmol) in ethyl acetate (6 mL) was added m-chloroperbenzoic acid (70%, 0.15 g, 0.59 mmol) under stirring at 0° C., and the mixture was stirred at the same temperature for 1.5 hr. The reaction mixture was washed with 1 M aqueous sodium hydroxide solution and saturated brine, dried over anhydrous sodium sulfate, and concentrated under reduced pressure. The residue was purified by silica gel column chromatography (hexane/ethyl acetate=9/1-hexane/ethyl acetate=1/1) to give the title compound (0.40 g, yield 93%) as a colorless oil.

MS m/z 797 (MH$^+$).

Example 303 ethyl 3-{4-[({4'-[(1,1-dioxidotetrahydro-2H-thiopyran-4-yl)oxy]-6-isopropoxy-2',6'-dimethylbiphenyl-3-yl}methyl)amino]-2-fluorophenyl}propanoate In the same manner as in Example 10, the title compound was obtained as a colorless amorphous powder from ethyl 3-(4-{({4'-[(1,1-dioxidotetrahydro-2H-thiopyran-4-yl)oxy]-6-isopropoxy-2',6'-dimethylbiphenyl-3-yl}methyl)[(2-nitrophenyl)sulfonyl]amino}-2-fluorophenyl)propanoate. yield 86%.

$^1$H NMR (CDCl$_3$) δ: 1.13 (6H, d, J=6.0 Hz), 1.23 (3H, t, J=7.2 Hz), 1.97 (6H, s), 2.28-2.43 (2H, m), 2.44-2.60 (4H, m), 2.84 (2H, t, J=7.7 Hz), 2.88-3.01 (2H, m), 3.38-3.54 (2H, m), 4.11 (2H, q, J=7.2 Hz), 4.23 (2H, s), 4.26-4.37 (1H, m), 4.62-4.70 (1H, m), 6.24-6.37 (2H, m), 6.65 (2H, s), 6.89-7.01 (3H, m), 7.22-7.31 (1H, m).

Example 304

3-{4-[({4'-[(1,1-dioxidotetrahydro-2H-thiopyran-4-yl)oxy]-6-isopropoxy-2',6'-dimethylbiphenyl-3-yl}methyl)amino]-2-fluorophenyl}propanoic acid methanesulfonate

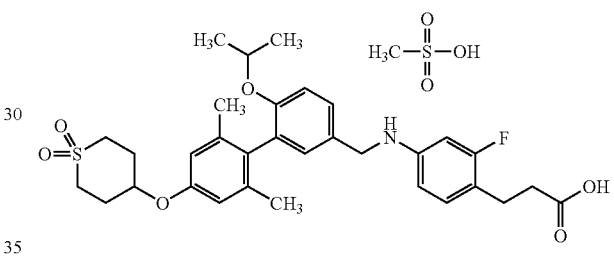

In the same manner as in Example 295, the title compound was obtained as colorless crystals from ethyl 3-{4-[({4'-[(1,1-dioxidotetrahydro-2H-thiopyran-4-yl)oxy]-6-isopropoxy-2',6'-dimethylbiphenyl-3-yl}methyl)amino]-2-fluorophenyl}propanoate. yield 77%.

$^1$H NMR (CDCl$_3$) δ: 1.13 (6H, d, J=6.0 Hz), 1.81 (6H, s), 2.27-2.57 (6H, m), 2.79 (3H, s), 2.82-3.01 (4H, m), 3.35-3.52 (2H, m), 4.33-4.47 (3H, m), 4.60-4.69 (1H, m), 6.57-6.71 (3H, m), 6.86-6.95 (2H, m), 6.99 (1H, dd, J=8.3, 1.7 Hz), 7.18 (1H, t, J=8.0 Hz), 7.36 (1H, dd, J=8.5, 2.3 Hz).

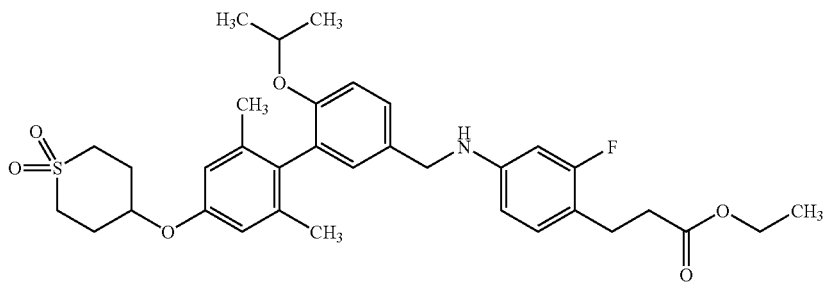

Example 305 ethyl 3-(2-fluoro-4-{[({4'-[(4-hydroxytetrahydro-2H-thiopyran-4-yl)methoxy]-6-isopropoxy-2',6'-dimethylbiphenyl-3-yl}methyl)[(2-nitrophenyl)sulfonyl]amino}phenyl)propanoate

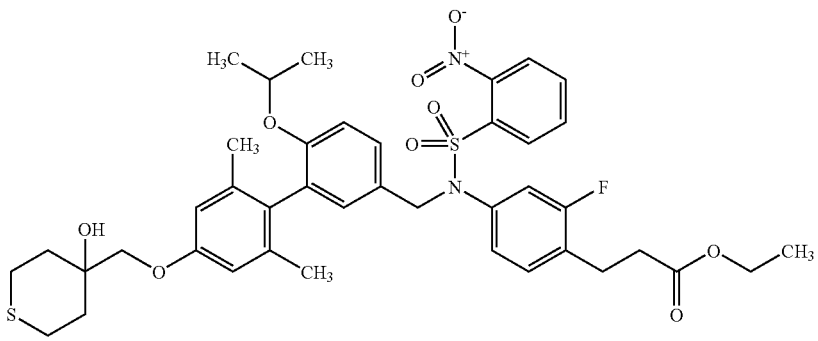

To a solution of ethyl 3-(2-fluoro-4-{[(4'-hydroxy-6-isopropoxy-2',6'-dimethylbiphenyl-3-yl)methyl][(2-nitrophenyl)sulfonyl]amino}phenyl)propanoate (993 mg, 1.49 mmol) and 1-oxa-6-thiaspiro[2.5]octane (779 mg, 5.98 mmol) in N,N-dimethylformamide (10 mL) was added potassium carbonate (827 mg, 5.98 mmol), and the mixture was stirred overnight at 80° C. Brine was added to the reaction mixture, and the mixture was extracted with ethyl acetate. The extract was dried over anhydrous sodium sulfate, and concentrated under reduced pressure. The residue was purified by silica gel column chromatography (hexane/ethyl acetate=9/1-hexane/ethyl acetate=1/1) to give the title compound (605 mg, yield 51%) as a yellow oil.

$^1$H NMR (CDCl$_3$) δ: 1.11 (6H, d, J=6.2 Hz), 1.26 (3H, t, J=7.1 Hz), 1.75-1.92 (8H, m), 2.01-2.16 (2H, m), 2.21 (1H, s), 2.39-2.59 (4H, m), 2.87 (2H, t, J=7.6 Hz), 3.02-3.17 (2H, m), 3.78 (2H, s), 4.12 (2H, q, J=7.2 Hz), 4.27-4.38 (1H, m), 4.83 (2H, s), 6.60 (2H, s), 6.67-6.79 (3H, m), 6.86 (1H, d, J=8.5 Hz), 7.02 (1H, t, J=8.2 Hz), 7.22 (1H, dd, J=8.5, 2.4 Hz), 7.47-7.72 (4H, m).

Example 306 ethyl 3-(2-fluoro-4-{[({4'-[(4-hydroxy-1,1-dioxidotetrahydro-2H-thiopyran-4-yl)methoxy]-6-isopropoxy-2',6'-dimethylbiphenyl-3-yl}methyl)[(2-nitrophenyl)sulfonyl]amino}phenyl)propanoate To a solution of ethyl 3-(2-fluoro-4-{[({4'-[(4-hydroxytetrahydro-2H-thiopyran-4-yl)methoxy]-6-isopropoxy-2',6'-dimethylbiphenyl-3-yl}methyl)[(2-nitrophenyl)sulfonyl]amino}phenyl)propanoate (605 mg, 0.76 mmol) in ethyl acetate (5 mL) was added m-chloroperbenzoic acid (70%, 413 mg, 1.67 mmol) under stirring at 0° C., and the mixture was stirred at room temperature for 4 days. The reaction mixture was washed with 1 M aqueous sodium hydroxide solution and saturated brine, dried over anhydrous sodium sulfate, and concentrated under reduced pressure. The residue was purified by silica gel column chromatography (hexane/ethyl acetate=9/1-hexane/ethyl acetate=1/2) to give the title compound (400 mg, yield 63%) as a pale-yellow oil.

$^1$H NMR (CDCl$_3$) δ: 1.12 (6H, d, J=6.0 Hz), 1.22 (3H, t, J=7.2 Hz), 1.84 (6H, s), 2.16-2.34 (4H, m), 2.47-2.58 (3H, m), 2.81-3.02 (4H, m), 3.41-3.57 (2H, m), 3.87 (2H, s), 4.11 (2H, q, J=7.2 Hz), 4.28-4.40 (1H, m), 4.84 (2H, s), 6.60 (2H, s), 6.68-6.79 (3H, m), 6.86 (1H, d, J=8.7 Hz), 7.03 (1H, t, J=8.2 Hz), 7.20 (1H, dd, J=8.5, 2.3 Hz), 7.47-7.73 (4H, m).

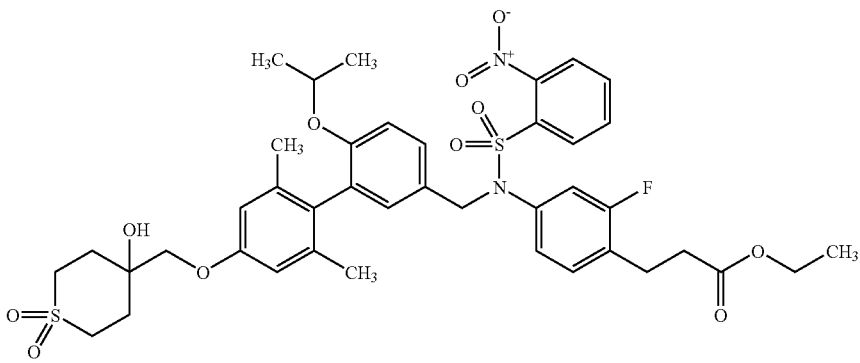

Example 307 ethyl 3-{2-fluoro-4-[({4'-[(4-hydroxy-1,1-dioxidotetrahydro-2H-thiopyran-4-yl)methoxy]-6-isopropoxy-2',6'-dimethylbiphenyl-3-yl}methyl)amino]phenyl}propanoate

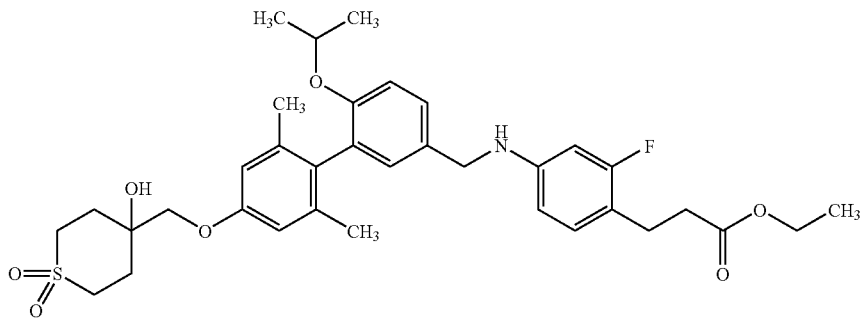

In the same manner as in Example 10, the title compound was obtained as a pale-yellow amorphous powder from ethyl 3-(2-fluoro-4-{({4'-[(4-hydroxy-1,1-dioxidotetrahydro-2H-thiopyran-4-yl)methoxy]-6-isopropoxy-2',6'-dimethylbiphenyl-3-yl}methyl)[(2-nitrophenyl)sulfonyl]amino}phenyl)propanoate. yield 90%.

$^1$H NMR (CDCl$_3$) δ: 1.14 (6H, d, J=6.0 Hz), 1.23 (3H, t, J=7.2 Hz), 1.97 (6H, s), 2.16-2.34 (4H, m), 2.48-2.58 (3H, m), 2.84 (2H, t, J=7.6 Hz), 2.90-3.01 (2H, m), 3.42-3.57 (2H, m), 3.88 (2H, s), 4.11 (2H, q, J=7.2 Hz), 4.23 (2H, s), 4.28-4.39 (1H, m), 6.25-6.36 (2H, m), 6.63 (2H, s), 6.90-7.00 (3H, m), 7.22-7.29 (1H, m).

Example 308

3-{2-fluoro-4-[({4'-[(4-hydroxy-1,1-dioxidotetrahydro-2H-thiopyran-4-yl)methoxy]-6-isopropoxy-2',6'-dimethylbiphenyl-3-yl}methyl)amino]phenyl}propanoic acid

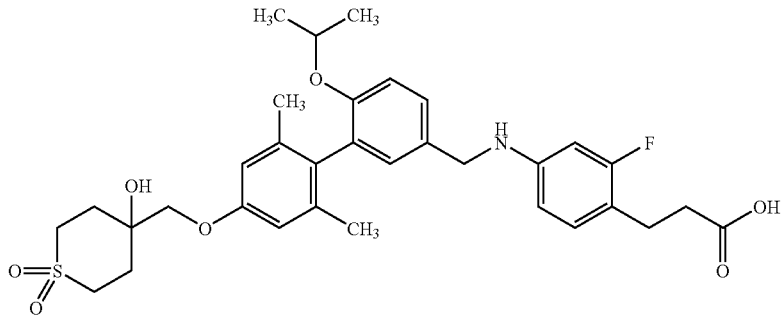

In the same manner as in Example 4, the title compound was obtained as a pale-yellow oil from ethyl 3-{2-fluoro-4-[({4'-[(4-hydroxy-1,1-dioxidotetrahydro-2H-thiopyran-4-yl)methoxy]-6-isopropoxy-2',6'-dimethylbiphenyl-3-yl}methyl)amino]phenyl}propanoate. yield 79%

$^1$H NMR (CDCl$_3$) δ: 1.14 (6H, d, J=6.0 Hz), 1.97 (6H, s), 2.17 (1H, s), 2.20-2.33 (4H, m), 2.60 (2H, t, J=7.6 Hz), 2.84 (2H, t, J=7.6 Hz), 2.89-3.01 (2H, m), 3.41-3.56 (2H, m), 3.87 (2H, s), 4.23 (2H, s), 4.28-4.40 (1H, m), 6.24-6.37 (2H, m), 6.63 (2H, s), 6.89-7.01 (3H, m), 7.22-7.29 (1H, m).

Example 309 ethyl 3-{2-fluoro-4-[({6-isopropoxy-2',6'-dimethyl-4'-[(2-methyl-1,3-thiazol-4-yl)methoxy]biphenyl-3-yl}methyl)amino]phenyl}propanoate

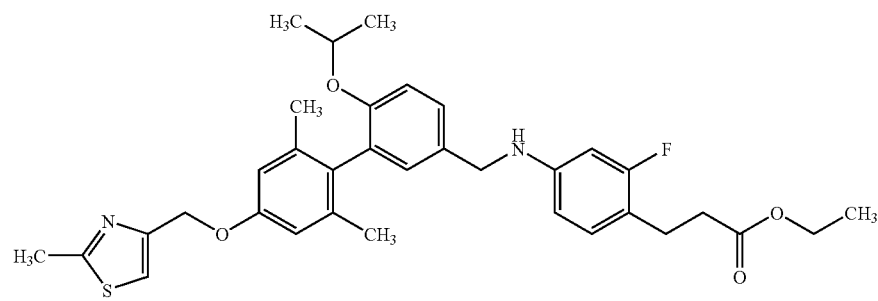

To a solution of ethyl 3-(2-fluoro-4-{[(4'-hydroxy-6-isopropoxy-2',6'-dimethylbiphenyl-3-yl)methyl][(2-nitrophenyl)sulfonyl]amino}phenyl)propanoate (0.61 g, 0.91 mmol), (2-methyl-1,3-thiazol-4-yl)methanol (0.13 g, 1.00 mmol) and tributylphosphine (0.36 mL, 1.37 mmol) in tetrahydrofuran (10 mL) was added 1,1'-(azodicarbonyl)dipiperidine (0.36 g, 1.37 mmol) under stirring at room temperature, and the mixture was stirred for 1.5 hr. To the reaction mixture were added reagents ((2-methyl-1,3-thiazol-4-yl)methanol, tributylphosphine and 1,1'-(azodicarbonyl)dipiperidine) in the same amount as mentioned above, and the mixture was further stirred for 2 hr. The insoluble material was filtered off, and the filtrate was concentrated under reduced pressure. The residue was purified by basic silica gel column chromatography (hexane/ethyl acetate=9/1-hexane/ethyl acetate=1/1) to give an oil (0.75 g). To a solution of the obtained oil and mercaptoacetic acid (0.20 mL, 2.91 mmol) in N,N-dimethylformamide (5 mL) was added lithium hydroxide monohydrate (0.24 g, 5.82 mmol) under stirring at room temperature, and the mixture was stirred at the same temperature overnight. The reaction mixture was diluted with ethyl acetate, washed with saturated aqueous sodium hydrogencarbonate and saturated brine, dried over anhydrous sodium sulfate, and concentrated under reduced pressure. The residue was purified by silica gel column chromatography (hexane/ethyl acetate=9/1-hexane/ethyl acetate=1/1) to give the title compound (0.40 g, yield 75%, 2 steps) as a colorless oil.

MS m/z 591 (MH⁺).

Example 310

3-{2-fluoro-4-[({6-isopropoxy-2',6'-dimethyl-4'-[(2-methyl-1,3-thiazol-4-yl)methoxy]biphenyl-3-yl}methyl)amino]phenyl}propanoic acid

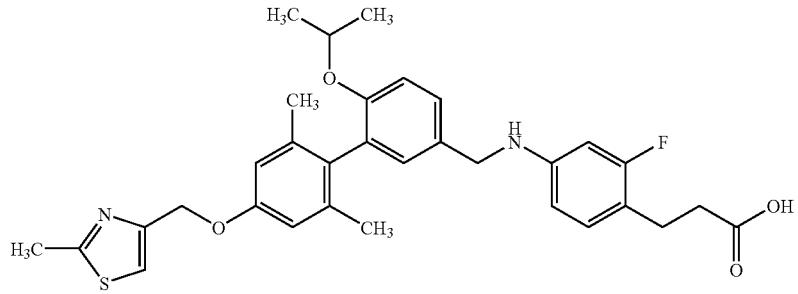

In the same manner as in Example 4, the title compound was obtained as a colorless oil from ethyl 3-{2-fluoro-4-[({6-isopropoxy-2',6'-dimethyl-4'-[(2-methyl-1,3-thiazol-4-yl)methoxy]biphenyl-3-yl}methyl)amino]phenyl}propanoate.
yield 98%

MS m/z 563 (MH⁺).

Example 311 ethyl 3-(2-fluoro-4-{({4'-[(4-hydroxy-1,1-dioxidotetrahydro-2H-thiopyran-4-yl)methoxy]-2',6,6'-trimethylbiphenyl-3-yl}methyl)[(2-nitrophenyl)sulfonyl]amino}phenyl)propanoate

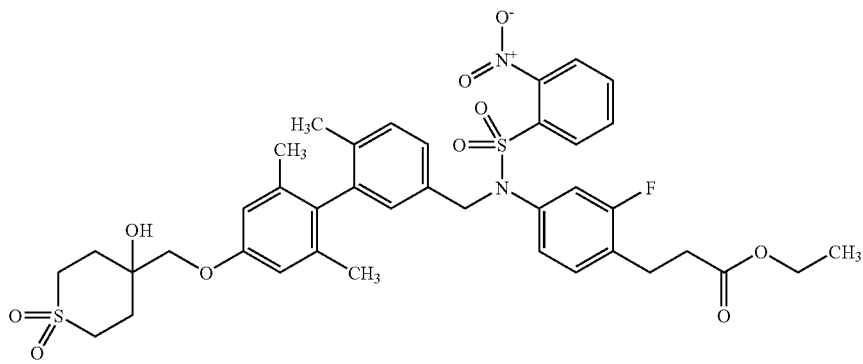

To a solution of 4-({[5'-(hydroxymethyl)-2,2',6-trimethylbiphenyl-4-yl]oxy}methyl)tetrahydro-2H-thiopyran-4-ol (182 mg, 0.49 mmol), ethyl 3-(2-fluoro-4-{[(2-nitrophenyl)sulfonyl]amino}phenyl)propanoate (214 mg, 0.54 mmol) and triphenylphosphine (257 mg, 0.98 mmol) in tetrahydrofuran (3 mL) was added diethyl azodicarboxylate (40% toluene solution, 0.45 mL, 0.98 mmol) under stirring at room temperature, and the mixture was stirred overnight. The reaction mixture was concentrated under reduced pressure and the residue was purified by silica gel column chromatography (hexane/ethyl acetate=9/1-hexane/ethyl acetate=2/1) to give an oil (373 mg). To a solution of the obtained oil in ethyl acetate (4 mL) was added m-chloroperbenzoic acid (70%, 266 mg, 1.08 mmol) under stirring at 0° C., and the mixture was stirred at room temperature for one day. The reaction mixture was washed with 1 M aqueous sodium hydroxide solution and saturated brine, dried over anhydrous sodium sulfate, and concentrated under reduced pressure. The residue was purified by silica gel column chromatography (hexane/ethyl acetate=9/1-hexane/ethyl acetate=1/2), and then by basic silica gel column chromatography (hexane/ethyl acetate=9/1-hexane/ethyl acetate=1/3) to give the title compound (189 mg, yield 49%) as a colorless oil.

MS m/z 783 (MH+).

Example 312 ethyl 3-{2-fluoro-4-[({4'-[(4-hydroxy-1,1-dioxidotetrahydro-2H-thiopyran-4-yl)methoxy]-2',6,6'-trimethylbiphenyl-3-yl}methyl)amino]phenyl}propanoate

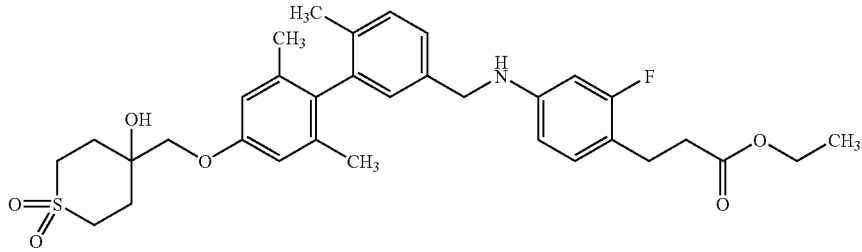

To a solution of ethyl 3-(2-fluoro-4-{({4'-[(4-hydroxy-1,1-dioxidotetrahydro-2H-thiopyran-4-yl)methoxy]-2',6,6'-trimethylbiphenyl-3-yl}methyl)[(2-nitrophenyl)sulfonyl]amino}phenyl)propanoate (189 mg, 0.24 mmol) and mercaptoacetic acid (50.1 μL, 0.72 mmol) in N,N-dimethylformamide (2 mL) was added lithium hydroxide monohydrate (60.4 mg, 1.44 mmol), and the mixture was stirred at room temperature for 2 days. Brine was added, and the mixture was extracted with ethyl acetate. The organic layer was dried over anhydrous sodium sulfate, and concentrated under reduced pressure. The residue was purified by silica gel column chromatography (hexane/ethyl acetate=9/1-hexane/ethyl acetate=1/2) to give the title compound (133 mg, yield 93%) as a colorless oil.

MS m/z 598 (MH+).

Example 313

3-{2-fluoro-4-[({4'-[(4-hydroxy-1,1-dioxidotetrahydro-2H-thiopyran-4-yl)methoxy]-2',6,6'-trimethylbiphenyl-3-yl}methyl)amino]phenyl}propanoic acid

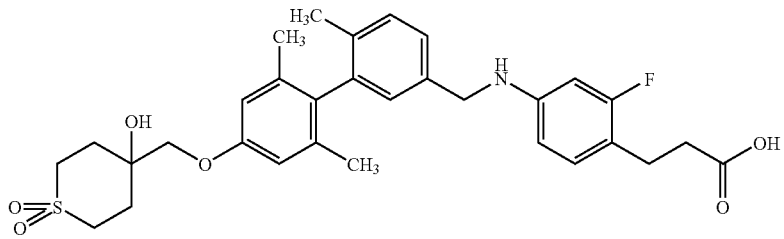

To a solution of ethyl 3-{2-fluoro-4-[({4'-[(4-hydroxy-1,1-dioxidotetrahydro-2H-thiopyran-4-yl)methoxy]-2',6,6'-trimethylbiphenyl-3-yl}methyl)amino]phenyl}propanoate (133 mg, 0.22 mmol) in a mixture of methanol (0.5 mL) and tetrahydrofuran (1 mL) was added 1 M aqueous sodium hydroxide solution (0.66 mL), and the mixture was stirred at room temperature for 2 hr. The reaction mixture was neutralized with 1 M hydrochloric acid, and brine was added. The mixture was extracted with ethyl acetate. The extract was dried over anhydrous sodium sulfate, and concentrated under reduced pressure. The residue was purified by silica gel column chromatography (hexane/ethyl acetate=9/1-ethyl acetate) to give the title compound (72.7 mg, yield 58%) as a colorless amorphous powder.

$^1$H NMR (CDCl$_3$) δ: 1.89 (6H, s), 1.94 (3H, s), 2.17-2.33 (4H, m), 2.60 (2H, t, J=7.6 Hz), 2.84 (2H, t, J=7.7 Hz), 2.89-3.01 (2H, m), 3.42-3.57 (2H, m), 3.87 (2H, s), 4.28 (2H, s), 6.22-6.35 (2H, m), 6.66 (2H, s), 6.90-6.99 (2H, m), 7.19-7.30 (2H, m).

MS m/z 570 (MH+).

Example 314

3-{2-fluoro-4-[({4'-[(4-hydroxy-1,1-dioxidotetrahydro-2H-thiopyran-4-yl)methoxy]-2',6,6'-trimethylbiphenyl-3-yl}methyl)amino]phenyl}propanoic acid calcium salt

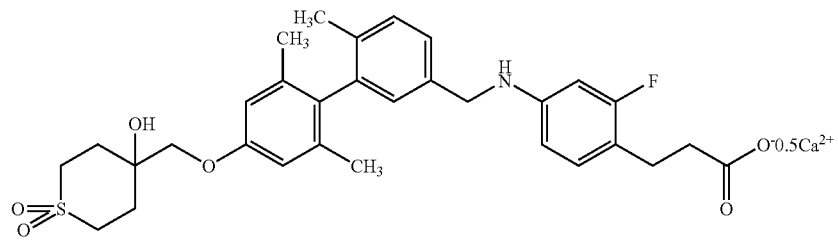

To a solution of 3-{2-fluoro-4-[({4'-[(4-hydroxy-1,1-di-oxidotetrahydro-2H-thiopyran-4-yl)methoxy]-2',6,6'-trimethylbiphenyl-3-yl}methyl)amino]phenyl}propanoic acid (57.0 mg, 0.10 mmol) in methanol (1 mL) was added 1 M aqueous sodium hydroxide solution (0.10 mL). Successively, an aqueous solution of calcium chloride (6.2 mg, 0.05 mmol) was gradually added. The precipitated solid was collected by filtration, washed with water and vacuum dried to give the title compound (32.2 mg, yield 55%) as a colorless amorphous powder.

$^1$H NMR (DMSO-$d_6$) δ: 1.79 (6H, s), 1.86 (3H, s), 1.95-2.23 (6H, m), 2.58 (2H, t, J=8.1 Hz), 2.94-3.08 (2H, m), 3.17-3.33 (2H, m), 3.83 (2H, s), 4.21 (2H, d, J=5.8 Hz), 5.29 (1H, s), 6.16-6.34 (3H, m), 6.71 (2H, s), 6.83-6.95 (2H, m), 7.16-7.29 (2H, m).

elemental analysis for $C_{62}H_{70}N_2O_{12}S_2F_2Ca \cdot 3.5H_2O$
Calculated: C, 60.03; H, 6.26; N, 2.26.
Found: C, 60.19; H, 6.23; N, 2.09.

Example 315 ethyl 3-(4-{({6-(acetylamino)-4'-[(4-hydroxytetrahydro-2H-thiopyran-4-yl)methoxy]-2',6'-dimethylbiphenyl-3-yl}methyl)[(2-nitrophenyl)sulfonyl]amino}-2-fluorophenyl)propanoate To a solution of N-{5-(hydroxymethyl)-4'-[(4-hydroxytetrahydro-2H-thiopyran-4-yl)methoxy]-2',6'-dimethylbiphenyl-2-yl}acetamide (148 mg, 0.36 mmol), ethyl 3-(2-fluoro-4-{[(2-nitrophenyl)sulfonyl]amino}phenyl)propanoate (157 mg, 0.40 mmol) and triphenylphosphine (189 mg, 0.72 mmol) in tetrahydrofuran (4 mL) was added diethyl azodicarboxylate (40% toluene solution, 0.33 mL, 0.72 mmol) under stirring at room temperature, and the mixture was stirred for one day. The reaction mixture was concentrated under reduced pressure, and the residue was purified by silica gel column chromatography (hexane/ethyl acetate=9/1-hexane/ethyl acetate=1/3) to give the title compound (262 mg, yield 83%) as a colorless amorphous powder.

MS m/z 794 (MH$^+$).

Example 316 ethyl 3-(4-{({6-(acetylamino)-4'-[(4-hydroxy-1,1-dioxidotetrahydro-2H-thiopyran-4-yl)methoxy]-2',6'-

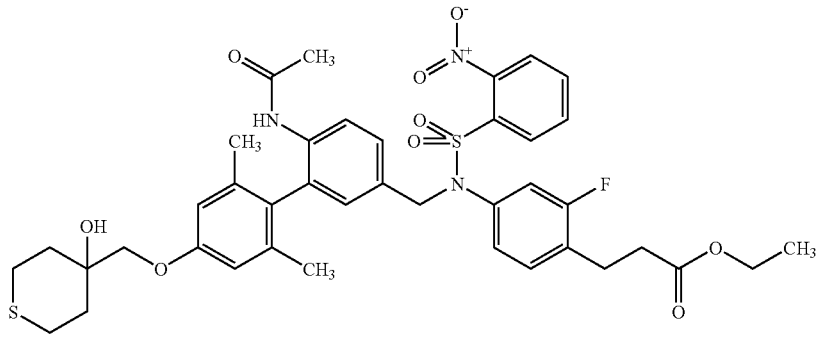

dimethylbiphenyl-3-yl}methyl)[(2-nitrophenyl)sulfonyl]amino}-2-fluorophenyl)propanoate

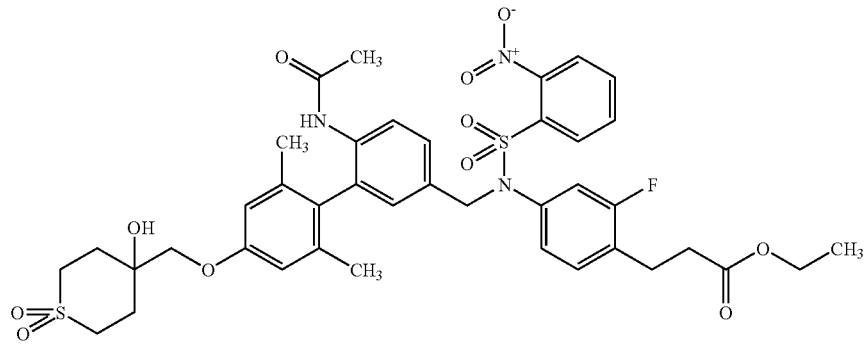

To a solution of ethyl 3-(4-{({6-(acetylamino)-4'-[(4-hydroxytetrahydro-2H-thiopyran-4-yl}methoxy]-2',6'-dimethylbiphenyl-3-yl)methyl][(2-nitrophenyl)sulfonyl]amino}-2-fluorophenyl)propanoate in ethyl acetate (3 mL) was added m-chloroperbenzoic acid (70%, 179 mg, 0.73 mmol) under stirring at 0° C., and the mixture was stirred at room temperature for 5 hr. The reaction mixture was washed with 1 M aqueous sodium hydroxide solution and saturated brine, dried over anhydrous sodium sulfate, and concentrated under reduced pressure. The residue was purified by silica gel column chromatography (hexane/ethyl acetate=7/3-ethyl acetate) to give the title compound (246 mg, yield 90%) as a colorless amorphous powder.

MS m/z 826 (MH$^+$).

Example 317 ethyl 3-{4-[({6-(acetylamino)-4'-[(4-hydroxy-1,1-dioxidotetrahydro-2H-thiopyran-4-yl)methoxy]-2',6'-dimethylbiphenyl-3-yl}methyl)amino]-2-fluorophenyl}propanoate

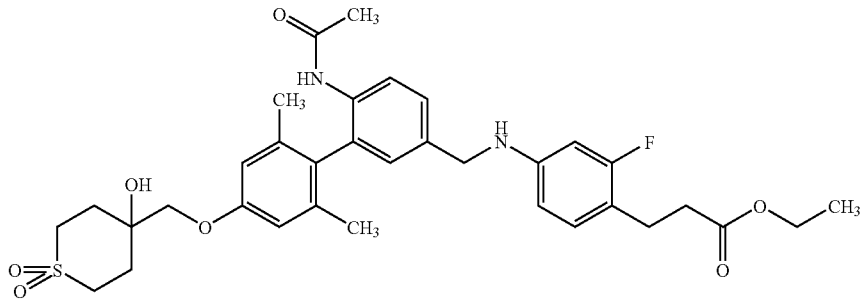

To a solution of ethyl 3-(4-{({6-(acetylamino)-4'-[(4-hydroxy-1,1-dioxidotetrahydro-2H-thiopyran-4-yl)methoxy]-2',6'-dimethylbiphenyl-3-yl}methyl)[(2-nitrophenyl)sulfonyl]amino}-2-fluorophenyl)propanoate (246 mg, 0.30 mmol) and mercaptoacetic acid (62.6 μL, 0.90 mmol) in N,N-dimethylformamide (2 mL) was added lithium hydroxide monohydrate (75.5 mg, 1.80 mmol), and the mixture was stirred at room temperature for 3 days. Brine was added to the reaction mixture, and the mixture was extracted with ethyl acetate. The organic layer was dried over anhydrous sodium sulfate, and concentrated under reduced pressure. The residue was purified by silica gel column chromatography (hexane/ethyl acetate=7/3-ethyl acetate) to give the title compound (176 mg, yield 92%) as a colorless oil.

$^1$H NMR (CDCl$_3$) δ: 1.23 (3H, t, J=7.2 Hz), 1.94 (6H, s), 1.95 (3H, s), 2.23-2.34 (4H, m), 2.45 (1H, s), 2.53 (2H, t, J=7.7 Hz), 2.83 (2H, t, J=7.7 Hz), 2.91-3.03 (2H, m), 3.43-3.58 (2H, m), 3.90 (2H, s), 4.11 (2H, q, J=7.2 Hz), 4.29 (2H, s), 6.21-6.34 (2H, m), 6.64 (1H, s), 6.72 (2H, s), 6.89-7.02 (2H, m), 7.35 (1H, dd, J=8.4, 2.0 Hz), 8.37 (1H, d, J=8.5 Hz).

Example 318

3-{4-[({6-(acetylamino)-4'-[(4-hydroxy-1,1-dioxidotetrahydro-2H-thiopyran-4-yl)methoxy]-2',6'-dimethylbiphenyl-3-yl}methyl)amino]-2-fluorophenyl}propanoic acid

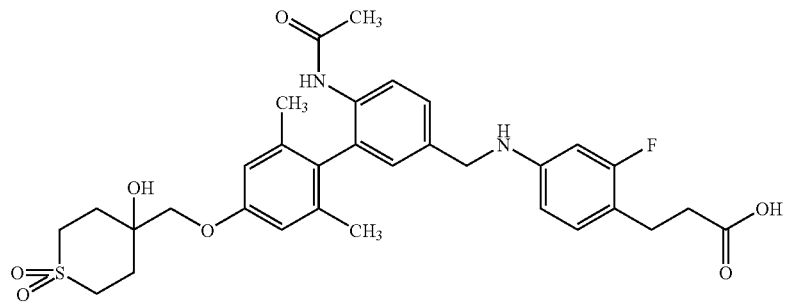

To a solution of ethyl 3-{4-[({6-(acetylamino)-4'-[(4-hydroxy-1,1-dioxidotetrahydro-2H-thiopyran-4-yl)methoxy]-2',6'-dimethylbiphenyl-3-yl}methyl)amino]-2-fluorophenyl}propanoate (173 mg, 0.27 mmol) in a mixture of methanol (1 mL) and tetrahydrofuran (2 mL) was added 1 M aqueous sodium hydroxide solution (0.81 mL), and the mixture was stirred overnight at room temperature. The reaction mixture was neutralized with 1 M hydrochloric acid, and brine was added. The mixture was extracted with ethyl acetate. The extract was dried over anhydrous sodium sulfate, and concentrated under reduced pressure. The residue was purified by silica gel column chromatography (ethyl acetate-ethyl acetate/methanol=9/1) to give the title compound (103 mg, yield 62%) as a yellow amorphous powder.

$^1$H NMR (CDCl$_3$) δ: 1.93 (6H, s), 1.95 (3H, s), 2.20-2.34 (4H, m), 2.59 (2H, t, J=7.6 Hz), 2.83 (2H, t, J=7.6 Hz), 2.89-3.02 (2H, m), 3.41-3.60 (2H, m), 3.89 (2H, s), 4.29 (2H, s), 6.21-6.35 (2H, m), 6.66 (1H, s), 6.72 (2H, s), 6.89-7.02 (2H, m), 7.34 (1H, dd, J=8.5, 1.9 Hz), 8.36 (1H, d, J=8.3 Hz).

MS m/z 613 (MH$^+$).

Example 319

3-{4-[({6-(acetylamino)-4'-[(4-hydroxy-1,1-dioxi-dotetrahydro-2H-thiopyran-4-yl)methoxy]-2',6'-dimethylbiphenyl-3-yl}methyl)amino]-2-fluorophenyl}propanoic acid calcium salt

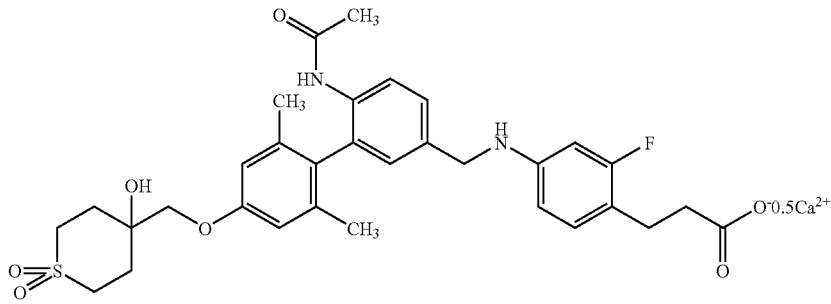

To a solution of 3-{4-[({6-(acetylamino)-4'-[(4-hydroxy-1,1-dioxidotetrahydro-2H-thiopyran-4-yl)methoxy]-2',6'-dimethylbiphenyl-3-yl}methyl)amino]-2-fluorophenyl}propanoic acid (86.3 mg, 0.14 mmol) in methanol (1 mL) was added 1 M sodium hydroxide solution (0.14 mL). Successively, an aqueous solution of calcium chloride (8.7 mg, 0.07 mmol) was gradually added. The precipitated solid was collected by filtration, washed with water, and vacuum dried to give the title compound (39.2 mg, yield 44%) as a colorless amorphous powder.

$^1$H NMR (DMSO-d$_6$) δ: 1.82 (6H, s), 1.83 (12H, s), 1.95-2.07 (4H, m), 2.08-2.25 (8H, m), 2.60 (4H, t, J=7.7 Hz), 2.92-3.08 (4H, m), 3.15-3.36 (4H, m), 3.83 (4H, s), 4.22 (4H, d, J=5.5 Hz), 5.31 (2H, s), 6.17-6.35 (6H, m), 6.69 (4H, s), 6.84-6.95 (4H, m), 7.26 (2H, d, J=8.5 Hz), 7.60 (2H, d, J=8.5 Hz), 8.47 (2H, s).

elemental analysis for C$_{64}$H$_{72}$N$_4$O$_{14}$S$_2$F$_2$Ca.2.5H$_2$O

Calculated: C, 58.74; H, 5.93; N, 4.28.

Found: C, 58.67; H, 5.88; N, 4.20.

Formulation Example 1

Production of Capsule

| 1) compound of Example 1 | 30 mg |
| 2) microcrystalline cellulose | 10 mg |
| 3) lactose | 19 mg |
| 4) magnesium stearate | 1 mg |
| total | 60 mg |

The above-mentioned 1), 2), 3) and 4) are mixed and filled in a gelatin capsule.

Formulation Example 2

Production of Tablet

| 1) compound of Example 1 | 30 g |
| 2) lactose | 50 g |
| 3) corn starch | 15 g |
| 4) carboxymethylcellulose calcium | 44 g |
| 5) magnesium stearate | 1 g |
| 1000 tablets total | 140 g |

The total amount of the above-mentioned 1), 2) and 3) and 30 g of 4) are kneaded with water, vacuum dried and granulated. The granulated powder is mixed with 14 g of 4) and 1 g of 5) and tableted with a tableting machine. In this way, 1000 tablets containing 30 mg of the compound of Example 1 per tablet are obtained.

Experimental Example 1

Determination of EC$_{50}$ of the Compound of the Present Invention for Human GPR40

For determination of EC$_{50}$, CHO cell line that stably expressed human GPR40 was used. Unless otherwise indicated, the CHO cell line was cultured using α-MEM medium (Invitrogen) containing 10% fetal calf serum (Invitrogen).

The cells cultured to nearly confluent were rinsed with PBS (Invitrogen) on the previous day of the assay, peeled off with 0.05% Trypsin-EDTA solution (Invitrogen) and recovered by centrifugation. The number of the obtained cells was counted, and the cells were diluted such that 3×10$^5$ cells were contained per 1 mL of the medium, dispensed to a black welled 96-well plate (coster) by 100 μL per well and cultured overnight in a CO$_2$ incubator. Various test compounds were added to the CHO cells thus prepared, and the changes in the intracellular calcium concentration were measured using FLIPR (Molecular Device). The below-mentioned pre-treatment was applied to measure changes in the intracellular calcium concentration by FLIPR.

First, an assay buffer for adding a fluorescence dye Fluo3-AM (DOJIN) to the cells, or for washing the cells immediately before FLIPR assay was prepared. To a solution of HBSS (Invitrogen, 1000 mL) to which 1M HEPES (pH 7.4, DOJIN, 20 mL) added (hereinafter HBSS/HEPES solution)

was added a solution (10 mL) obtained by dissolving probenecid (Sigma, 710 mg) in 1N NaOH (5 mL), and adding and mixing an HBSS/HEPES solution (5 mL), and the resulting solution was used as an assay buffer. Next, Fluo3-AM (50 µg) was dissolved in dimethylsulfoxide (Wako, 21 µL), and an equivalent amount of 20% pluronic acid (Molecular Probes) was added and mixed. The solution was added to the assay buffer (10.6 mL) supplemented with fetal vovine serum (105 µL) to give a fluorescence dye solution. The medium of the CHO cells inoculated to the black welled 96-well plate on the previous day of assay was removed, the fluorescence dye solution was immediately dispensed by 100 µL per well and the cells were cultured in a $CO_2$ incubator for 1 hr to allow intake of the fluorescence dye by the cells. The cells after the culture were washed with the above-mentioned assay buffer and set on FLIPR. The test compound was diluted with dimethylsulfoxide in advance, dispensed to polypropylene 96-well plate (sample plate) by 2 mL, and cryopreserved at −20° C. To the thawed sample plate was added an assay buffer containing 0.015% CHAPS (DOJIN) by 198 µL, and simultaneously set on FLIPR together with the cell plate. After the aforementioned pre-treatment, changes in the intracellular calcium concentration upon addition of various test compounds as measured by FLIPR. Based on the results, a dose-response curve of each test compound was formed and $EC_{50}$ was calculated. The results are shown in Table 1.

TABLE 1

Receptor Function Modulating Action On GPR40

| Compound No. | $EC_{50}$ (nM) |
|---|---|
| Example 2 | <10 |
| Example 12 | <100 |
| Example 18 | <100 |
| Example 21 | <100 |
| Example 26 | <100 |
| Example 30 | <100 |
| Example 33 | <100 |
| Example 37 | <100 |
| Example 40 | <100 |
| Example 44 | <100 |
| Example 47 | <1000 |
| Example 67 | <100 |
| Example 70 | <100 |
| Example 86 | <100 |
| Example 98 | <100 |
| Example 100 | <1000 |
| Example 105 | <100 |
| Example 107 | <100 |
| Example 113 | <100 |
| Example 117 | <100 |
| Example 120 | <100 |
| Example 123 | <100 |
| Example 127 | <100 |
| Example 131 | <100 |
| Example 136 | <100 |
| Example 138 | <1000 |
| Example 146 | <100 |
| Example 149 | <100 |
| Example 151 | <100 |
| Example 164 | <100 |
| Example 169 | <100 |
| Example 171 | <100 |
| Example 184 | <100 |
| Example 188 | <100 |
| Example 200 | <100 |
| Example 204 | <100 |
| Example 210 | <100 |
| Example 212 | <100 |
| Example 218 | <100 |

INDUSTRIAL APPLICABILITY

The compound (I), a salt thereof and a prodrug thereof have a superior GPR40 receptor function modulating action and can be used as an agent for the prophylaxis or treatment of diabetes and the like.

This application is based on patent application Nos. 2004-73576 and 2004-247339 filed in Japan, the contents of which are incorporated in full herein by this reference.

The invention claimed is:
1. A compound represented by formula (I):

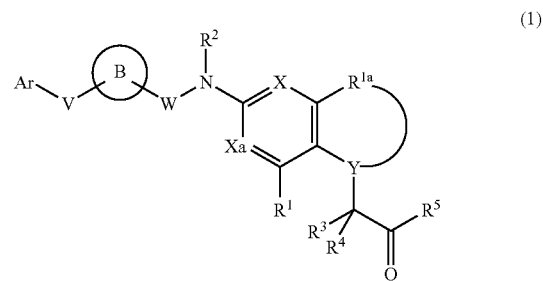

wherein:
partial structural formula

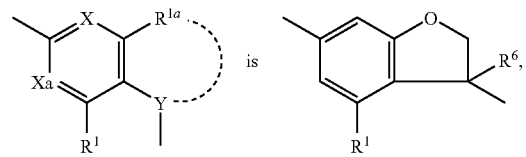

Ar is an optionally substituted cyclic group, provided that the cyclic group is not a 4-piperidinyl group,
ring B is an optionally substituted ring, provided that the ring is not a thiazole ring and an oxazole ring,
V is a bond; —O—; —CH=N—; or —$CH_2$—, —$CH_2CH_2$—, —$CH_2O$—, —NH—$CH_2$—, —$CH_2$—NH— or —$CH_2$—NH—$CH_2$—, each of which optionally has substituent(s) selected from the group consisting of a $C_{1-6}$ alkyl group, a $C_{7-16}$ aralkyl group and a $C_{6-14}$ aryl group,
W is a bond or a $C_{1-6}$ alkylene group optionally substituted by $C_{1-6}$ alkoxy group(s),
$R^6$ is a hydrogen atom, a halogen atom, a $C_{1-6}$ alkyl group or an optionally substituted hydroxy group,
$R^1$ is a hydrogen atom, a halogen atom, a $C_{1-6}$ alkyl group or a $C_{1-6}$ alkoxy group,
$R^2$ is a hydrogen atom, a $C_{1-6}$ alkyl group or an optionally substituted acyl group,
$R^3$ and $R^4$ are the same or different and each is a hydrogen atom or a halogen atom, and
$R^5$ is an optionally substituted hydroxy group or an optionally substituted amino group, provided that when W is a bond, then ring B is an optionally substituted non-aromatic ring condensed with a benzene ring, not being an optionally substituted tetrahydroquinoline ring, or a salt thereof.
2. The compound of claim 1, wherein W is a $C_{1-6}$ alkylene group optionally substituted by $C_{1-6}$ alkoxy group(s).
3. The compound of claim 1, wherein $R^5$ is a hydroxy group.

4. The compound of claim 1, wherein the cyclic group for Ar is phenyl, naphthyl, thiazolyl, pyrazolyl, indolyl or dihydroquinolinyl.

5. The compound of claim 1, wherein the ring for ring B is a benzene ring, a pyrazole ring or an indane ring.

6. The compound of claim 1, wherein $R^2$ is a hydrogen atom.

7. [6-({[4'-(2-ethoxyethoxy)-2',6'-dimethylbiphenyl-3-yl]methyl}amino)-2,3-dihydro-1-benzofuran-3-yl]acetic acid or a salt thereof.

8. A pharmaceutical agent comprising the compound of claim 1 and a pharmacologically acceptable carrier.

* * * * *